US010689707B2

(12) United States Patent
Guilford et al.

(10) Patent No.: US 10,689,707 B2
(45) **Date of Patent: *Jun. 23, 2020**

(54) TREATMENT OF RECURRENT GASTRIC CANCER IDENTIFIED USING GENETIC BIOMARKERS

(71) Applicant: Pacific Edge Limited, Dunedin (NZ)

(72) Inventors: Parry John Guilford, Dunedin (NZ); Andrew John Holyoake, Christchurch (NZ)

(73) Assignee: Pacific Edge Limited, Dunedin (NZ)

( * ) Notice: Subject to any disclaimer, the term of this patent is extended or adjusted under 35 U.S.C. 154(b) by 15 days.

This patent is subject to a terminal disclaimer.

(21) Appl. No.: 15/252,869

(22) Filed: Aug. 31, 2016

(65) Prior Publication Data

US 2016/0369355 A1 Dec. 22, 2016

Related U.S. Application Data

(63) Continuation of application No. 10/565,068, filed as application No. PCT/US2004/022959 on Jul. 16, 2004, now Pat. No. 10,179,935.

(60) Provisional application No. 60/487,906, filed on Jul. 17, 2003.

(51) Int. Cl.

| | |
|---|---|
| ***C12Q 1/6886*** | (2018.01) |
| ***G01N 33/574*** | (2006.01) |
| ***C12Q 1/6837*** | (2018.01) |

(52) U.S. Cl.

CPC ..... *C12Q 1/6886* (2013.01); *G01N 33/57446* (2013.01); *C12Q 1/6837* (2013.01); *C12Q 2600/112* (2013.01); *C12Q 2600/158* (2013.01); *C12Q 2600/16* (2013.01)

(58) Field of Classification Search

None

See application file for complete search history.

(56) References Cited

U.S. PATENT DOCUMENTS

| | | | | |
|---|---|---|---|---|
| 2003/0232350 A1* | 12/2003 | Afar | C12Q 1/6886 | 435/6.14 |
| 2006/0019256 A1* | 1/2006 | Clarke | C12N 5/0695 | 435/6.14 |

FOREIGN PATENT DOCUMENTS

| | | | | |
|---|---|---|---|---|
| EP | 1074617 A2 * | 2/2001 | C07K 14/47 |
| WO | WO 02/086443 A2 * | 10/2002 | |
| WO | WO-2004048938 A2 * | 6/2004 | C07H 21/04 |
| WO | WO 2004/071530 A2 * | 8/2004 | |

OTHER PUBLICATIONS

Pfaffl et al. A new mathematical model for relative quantification in real-time RT-PCR. Nucleic Acids Research 29(9): 2002-2007, 2001.*

* cited by examiner

*Primary Examiner* — Alana Harris Dent

(74) *Attorney, Agent, or Firm* — D. Benjamin Borson; Borson Law Group PC

(57) ABSTRACT

Early detection of tumors is a major determinant of survival of patients suffering from tumors, including gastric tumors. Members of the GTM gene family can be over-expressed in gastric tumor tissue and other tumor tissue, and thus can be used as markers for gastric and other types of cancer. GTM proteins can be released from cancer cells, and can reach sufficiently high concentrations in the serum and/or other fluids to permit their detection. Thus, methods and test kits for detection and quantification of GTM can provide a valuable tool for diagnosis of gastric cancer.

13 Claims, 104 Drawing Sheets

Specification includes a Sequence Listing.

| name | symbol | Applied Biosystems "assay on demand" assay # | forward primer | Seq ID No. | reverse primer | Seq ID No. | probe | Seq ID No. |
|---|---|---|---|---|---|---|---|---|
| asporin (lrr class 1) | ASPN | | AAATACAAAAGGACACATTCAAAGGA | 1 | TGCTTCTGCAATTCTGATATGGA | 23 | TTGGAAATGAGTGCAAACCCTCTTGATAATAATG | 45 |
| chondroitin sulfate proteoglycan 2 (versican) | CSPG2 | | GCCAGTGGAATGATGTTCCC | 2 | TCTTGGCATTTTCTACAACAGGG | 24 | AGGAACAGTTGCTTGCGGCCAGC | 46 |
| cystatins SN, SA & S | CST1, 2, 4 | | AGTCCCAGCCCAACTTGGA | 3 | GGGAACTTCGTAGATCTGGAAAGA | 25 | AGCCAGAACTGCAGAAGAAACAGTTGTGC | 47 |
| gamma-glutamyl hydrolase | GGH | | GTGGCAATGCCGCTGAA | 4 | TGACAGCAACAACTCAGTAGGAAAA | 26 | TTCACTGGAGGTCAATTGCACAGCAGAAT | 48 |
| insulin-like growth factor binding protein 7 | IGFBP7 | | CAGGTCAGCAAGGGCACC | 5 | TCACAGCTCAAGTACACCTGGG | 27 | AGCAAGGTCCTTCCATAGTGACGCCC | 49 |
| kallikrein 10 | KLK10 | | ACAACATGATATGTGCTGGACTGG | 6 | GAGAGGATGCCTTGGAGGGT | 28 | CTTGCCAGAGTGACTCTGGAGGCCC | 50 |
| leucine proline-enriched proteoglycan 1(leprecan 1) | LEPRE1 | | CTTGAGTACAACGCTGACCTCTTC | 7 | CCGTGACACAGTTCTGCTTACAG | 29 | CCATCACAGATCATTACATCCAGGTCCTCA | 51 |
| lumican | LUM | | GATTCTTGTCCATAGTGCATCTGC | 8 | CCAATCAATGCCAGGAAGAGA | 30 | TAAGGATTCAAACCATTTGCCAAAAATGAGTCTAA G | 52 |
| lysyl oxidase-like 2 | LOXL2 | | AGGCCAGCTTCTGCTTGGA | 9 | CCCTGATCGCCGAGTTG | 31 | CGTAATTCTTCTGGATGTCTCCTTCACATTCTG | 53 |
| matrix metalloproteinase 12 | MMP12 | | GCCTCTCTGCTGATGACATACGT | 10 | AGTGACAGCATCAAAACTCAAATTG | 32 | TCAGTCCCTGTATGGAGACCCAAAAGAGAA | 54 |
| metalloproteinase inhibitor 1 | TIMP1 | | CCAGACCACCTTATACCAGCG | 11 | GGACCTGTGGAAGTATCCGC | 33 | CAAGATGACCAAGATGTATAAAGGGTTCCAAGC | 55 |
| n-acylsphingosine amidohydrolase | ASAH1 | | CGCAGAACGCCTGCAAA | 12 | ACAGGACATCATACATGGTTTCAAA | 34 | TGTCTGAACCGCACCAGCCAAGAGAATA | 56 |
| secreted frizzled-related protein 2 | SFRP2 | | CGCTAGCAGCGACCACCT | 13 | TTTTGCAGGCTTCACATACCTTT | 35 | CTGCCAGCCACCGAGGAAGCTC | 57 |
| secreted protein, acidic, cysteine rich | SPARC | | TCTTCCCTGTACACTGGCAGTTC | 14 | GAAAAAGCGGGTGGTGCA | 36 | TGGACCAGCACCCCATTGACGG | 58 |
| serine protease 11 (IGF binding) | PRSS11 | | TCGGGAGGCCCGTTAGTAA | 15 | AAGGAGATTCCAGCTGTCACTTTC | 37 | AGTGTTAATTCCAATCACTTCACCGTCCAGG | 59 |
| thrombospondin 2 | THBS2 | | TGGAAGGACTACACGGCCTATAG | 16 | TAGGTTTGGTCATAGATAGGTCCTGAGT | 38 | AGGCCCAAGACCGGCTACATCAGAGTC | 60 |
| thyroglobulin | TG | | GACGGTTCCTCGCAGTTCAA | 17 | TGTAAAGCCGCTCCACTTCACAT | 39 | TCTGGCAGATTCCGATGCCCCACAA | 61 |
| human cell growth regulator with EF hand domain 1 | CGR11 | | CTGCCCACCCCTTCCA | 18 | TTCTGTCCTTCCTAGTCCCTTTAGG | 40 | CCAGGCCAGGAGCAGCTCGG | 62 |
| human serine or cysteine proteinase inhibitor clade B | SERPINB5 | | TCCACGCATTTTCCAGGATAA | 19 | AAGCCGAATTTGCTAGTTGCA | 41 | TGACTCCAGGCCCGCAATGGA | 63 |
| transforming growth factor β1 | TGFB1 | | GGTCCATGTCATCACCAATGTT | 20 | TCTGCAAGTTCATCCCCTCTTT | 42 | CAGCCTCCAGCCAACAGACCTCAGG | 64 |
| human proprotein convertase subtilisin/kexin type 5 | PCSK5 | | AAAAATCTTTGCCGGAAATGC | 21 | AGTCCTGGCCGTTGAAATACC | 43 | ACAGAATGTAGGGATGGGTTAAGCCTGCA | 65 |
| matrix metalloproteinase 2 | MMP2 | | TTGATGGCATCGCTCAGATC | 22 | TGTCACGTGGCGTCACAGT | 44 | TTCAAGGACCGGTTCATTTGGCG | 66 |
| human serine or cysteine proteinase inhibitor clade H | SERPINH1 | Hs00241844_m1 | | | | | | |
| adlican | | Hs00377849_m1 | | | | | | |
| egf-containing fibulin-like extracellular matrix protein 2 | EFEMP2 | Hs00213545_m1 | | | | | | |
| secreted frizzled-related protein 4 | SFRP4 | Hs00180066_m1 | | | | | | |
| inhibin beta A chain | INHBA | Hs00170103_m1 | | | | | | |
| osteopontin | SPP1 | Hs00167093_m1 | | | | | | |
| transforming growth factor B-induced | TGFBI | Hs00165908_ml | | | | | | |
| | | | | | | | | |

Figure 1

Microarray - Identification of Markers for Gastric Malignancy

| name | symbol | MWG oligo # | NCBI mRNA ref sequence | protein ref sequence | fold change | fold change rank | original t-test | Bonferroni-adjusted p value | 2 sample Wilcoxon test |
|---|---|---|---|---|---|---|---|---|---|
| adlican | | C:0531 | NM_015419 | NP_056234 | 1.8 | -17818 | 1.0E-28 | 3.04E-24 | 0.0E+00 |
| asporin (lrr class 1) | ASPN | A:07749 | NM_017680 | NP_060150 | 2.6 | -22292 | 6.4E-23 | 1.9E-18 | 0.0E+00 |
| carboxypeptidase N | CPN2 | B:4922 | | P22792 | 2.7 | -22367.5 | 2.3E-42 | 7.0E-38 | 0.0E+00 |
| cell growth regulatory factor with EF-hand domain | CGR11 | A:07876 | NM_006569 | NP_006560 | 3.0 | -21188.5 | 4.33E-42 | 1.3E-37 | 0.0E+00 |
| chondroitin sulfate proteoglycan 2 (versican) | CSPG2 | A:10008 | NM_004385 | NP_004376 | 2.3 | -21606.5 | 2.23E-33 | 6.65E-29 | 0.00E+00 |
| cystatin SN | CST1 | A:06089 | NM_001898 | NP_001889 | 2.1 | -17475 | 1.3E-18 | 3.8E-14 | 0.0E+00 |
| cystatin SA | CST2 | A:06089 | NM_001322 | NP_001313 | 2.1 | -17475 | 1.3E-18 | 3.8E-14 | 0.0E+00 |
| cystatin S | CST4 | A:06089 | NM_001899 | NP_001890 | 2.1 | -17475 | 1.3E-18 | 3.8E-14 | 0.0E+00 |
| egf-containing fibulin-like extracellular matrix protein 2 | EFEMP2 | A:09072 | NM_016938 | NP_058634 | 2.4 | -22761 | 2.0E-35 | 5.9E-31 | 0.0E+00 |
| gamma-glutamyl hydrolase | GGH | A:03601 | NM_003878 | NP_003869 | 1.6 | -18092 | 1.6E-07 | 4.8E-03 | 5.7E-11 |
| inhibin beta A chain | INHBA | A:02189 | NM_002192 | NP_002183 | 2.1 | -21247 | 1.4E-30 | 4.3E-26 | 0.0E+00 |
| insulin-like growth factor binding protein 7 | IGFBP7 | A:03385 | NM_001553 | NP_001544 | 3.0 | -25854 | 5.4E-31 | 1.6E-26 | 0.0E+00 |
| kallikrein 10 | KLK10 | A:07907 | NM_002776 | NP_002767 | 2.3 | -17986.5 | 5.0E-10 | 1.5E-05 | 4.9E-06 |
| leucine proline-enriched proteoglycan 1(leprecan 1) | LEPRE1 | A:04646 | NM_022356 | NP_071751 | 1.7 | -18019 | 8.2E-14 | 2.4E-09 | 1.1E-12 |
| lumican | LUM | A:09199 | NM_002345 | NP_002336 | 2.9 | -24927 | 4.2E-24 | 1.3E-19 | 0.0E+00 |
| lysyl oxidase-like 2 | LOXL2 | A:06085 | NM_002318 | NP_002309 | 1.6 | -16994.5 | 5.9E-10 | 1.7E-05 | 7.9E-10 |
| matrix metalloproteinase 2 | MMP2 | A:06749 | NM_004530 | P08253 | 1.8 | -18710 | 1.2E-11 | 3.6E-07 | 1.5E-10 |
| matrix metalloproteinase 12 | MMP12 | A:01762 | NM_002426 | NP_002417 | 2.1 | -20209.5 | 2.2E-12 | 6.6E-08 | 4.9E-11 |
| metalloproteinase inhibitor 1 | TIMP1 | A:08048 | NM_003254 | NP_003245 | 3.2 | -24177 | 7.5E-38 | 2.3E-33 | 0.0E+00 |
| n-acylsphingosine amidohydrolase | ASAH1 | A:10030 | NM_004315 | NP_004306 | 1.7 | -19636.5 | 9.6E-16 | 2.9E-11 | 0.0E+00 |
| olfactomedin | OLFM1 | B:3555 | NM_014279 | NP_055094 | 3.9 | -25782.5 | 6.5E-46 | 1.9E-41 | 0.0E+00 |
| osteopontin | SPP1 | A:09441 | NM_000582 | NP_000573 | 7.0 | -26668 | 4.0E-32 | 1.2E-27 | 0.0E+00 |
| human proprotein convertase subtilisin/kexin type 5 | PCSK5 | A:00704 | NM_006200 | Q92824 | 1.7 | -18736 | 2.0E-11 | 6.0E-07 | 7.3E-11 |
| group xiii secreted phospholipase a2 | PLA2G12b | B:1811 | NM_032562 | NP_115951 | 3.0 | -23212 | 7.92E-39 | 2.36E-34 | 0.00E+00 |
| secreted frizzled-related protein 2 | SFRP2 | B:1634 | XM_050625 | XP_050625 | 2.1 | -19217 | 2.7E-10 | 8.1E-06 | 4.1E-08 |
| secreted frizzled-related protein 4 | SFRP4 | A:07398 | NM_003014 | NP_003005 | 3.0 | -22153 | 6.0E-24 | 1.8E-19 | 0.0E+00 |
| serine (or cysteine) proteinase inhibitor clade H | SERPINH1 | A:08615 | NM_001235 | NP_001226 | 1.9 | -20252 | 2.8E-34 | 8.2E-30 | 0.0E+00 |
| human serine or cysteine proteinase inhibitor clade B | SERPINB5 | A:10485 | NM_002639 | P36952 | 1.5 | -17026 | 4.6E-06 | 1.4E-01 | 5.6E-06 |
| serine protease 11 (IGF binding) | PRSS11 | B:1274 | NM_002775 | NP_002766 | 1.6 | -17184.5 | 9.3E-18 | 2.8E-13 | 0.0E+00 |
| secreted protein, acidic, cysteine rich | SPARC | A:08092 | NM_003118 | NP_003109 | 2.5 | -22947.5 | 1.5E-44 | 4.6E-40 | 0.0E+00 |
| spondin 2 | SPON2 | B:2543 | NM_012445 | NP_036577 | 2.4 | -20390.5 | 2.9E-31 | 8.5E-27 | 0.0E+00 |
| stannin | SNN | A:09316 | NM_003498 | NP_003489 | 2.1 | -20162.5 | 3.25E-24 | 9.71E-20 | 0.00E+00 |
| thrombospondin 2 | THBS2 | B:9017 | NM_003247 | NP_003238 | 2.6 | -22095 | 5.8E-29 | 1.7E-24 | 0.0E+00 |
| thrombospondin repeat containing 1 | TSRC1 | B:7686 | NM_019032 | NP_061905 | 2.6 | -22608 | 1.38E-45 | 4.1E-41 | 0.0E+00 |
| thyroglobulin | TG | B:5402 | NM_003235 | NP_003226 | 2.4 | -23644 | 4.39E-36 | 1.3E-31 | 0.0E+00 |
| transforming growth factor β-induced | TGFBI | A:08124 | NM_000358 | NP_000349 | 2.5 | -23339.5 | 1.96E-24 | 9.71E-20 | 0.0E+00 |
| transforming growth factor β1 | TGFB1 | A:07050 | NM_000660 | P01137 | 1.6 | -17214 | 2.30E-18 | 6.86E-14 | 0.0E+00 |
| hyaluronan and proteoglycan link protein 4 | HAPLN4 | C:6300 | NM_023002 | NP_075378 | 3.4 | -23516.5 | 7.32E-44 | 2.2E-39 | 0.0E+00 |

Figure 2

Quantitative RT-PCR - Quantification of Expression of Selected Gastric Cancer Candidate Genes

| name | symbol | median T:N fold change | Maximum T:N fold change | % T >95th percentile N[1] |
|---|---|---|---|---|
| adlican | | 5 | 37 | 74 |
| asporin (lrr class 1) | ASPN | 12 | 73 | 91 |
| chondroitin sulfate proteoglycan 2 (versican) | CSPG2 | 6 | 24 | 78 |
| cystatins SN, SA & S | CST1, 2, 4 | 525 | 25532 | 100 |
| egf-containing fibulin-like extracellular matrix protein 2 | EFEMP2 | 3 | 15 | 56 |
| gamma-glutamyl hydrolase | GGH | 5 | 36 | 67 |
| inhibin beta A chain | INHBA | 34 | 357 | 98 |
| insulin-like growth factor binding protein 7 | IGFBP7 | 4 | 19 | 80 |
| kallikrein 10 | KLK10 | 5 | 633 | 70 |
| leucine proline-enriched proteoglycan 1(leprecan 1) | LEPRE1 | 4 | 17 | 72 |
| lumican | LUM | 5 | 47 | 80 |
| lysyl oxidase-like 2 | LOXL2 | 6 | 26 | 93 |
| matrix metalloproteinase 12 | MMP12 | 9 | 586 | 67 |
| metalloproteinase inhibitor 1 | TIMP1 | 8 | 19 | 91 |
| n-acylsphingosine amidohydrolase | ASAH1 | 3 | 7 | 63 |
| osteopontin | SPP1 | 40 | 481 | 96 |
| secreted frizzled-related protein 2 | SFRP2 | 5 | 85 | 63 |
| secreted frizzled-related protein 4 | SFRP4 | 56 | 600 | 100 |
| secreted protein, acidic, cysteine rich | SPARC | 9 | 56 | 93 |
| serine protease 11 (IGF binding) | PRSS11 | 4 | 25 | 54 |
| thrombospondin 2 | THBS2 | 25 | 239 | 91 |
| thyroglobulin | TG | 5 | 153 | 54 |
| transforming growth factor B-induced | TGFBI | 7 | 204 | 82 |

[1] percentage of tumors with expression levels greater than the 95th percentile of non-malignant samples.

Figure 3

Fig.7a Relative expression of markers in tumor and normal samples compared to CEA
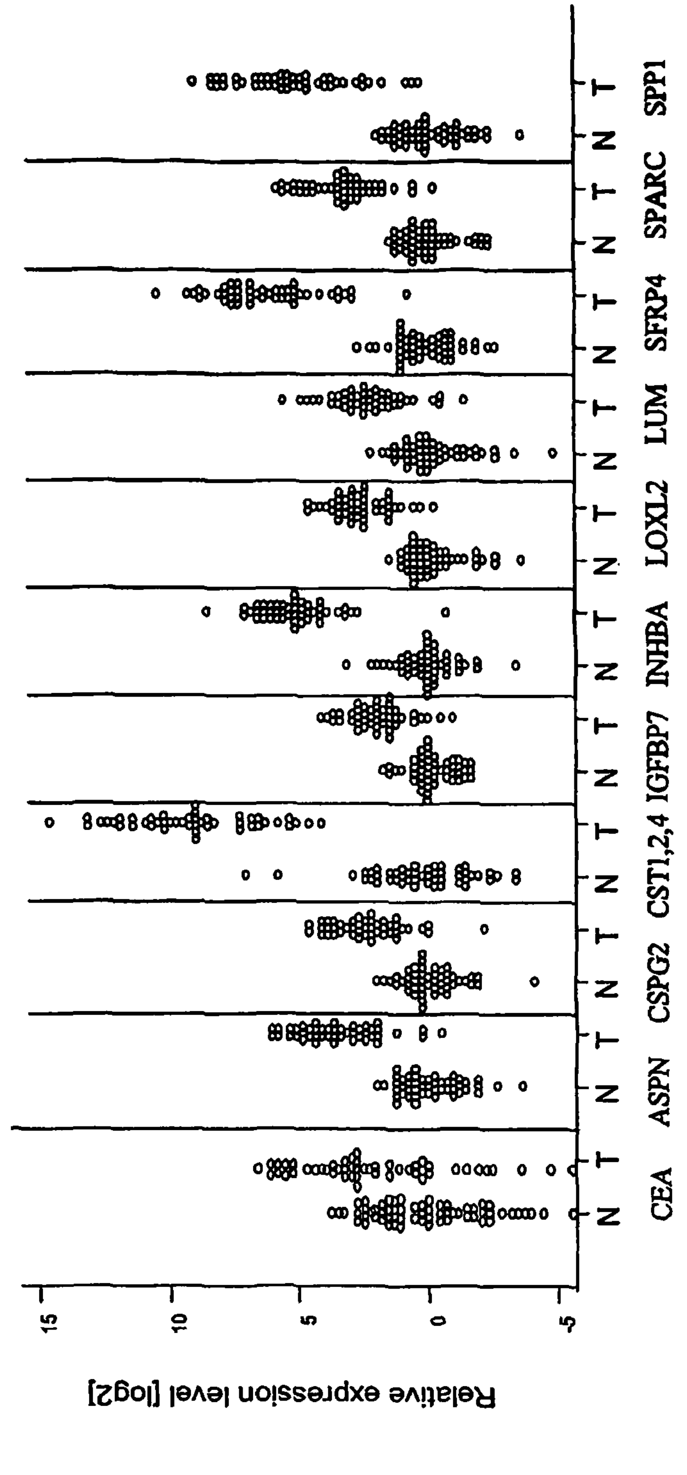

Fig. 8. Quantitative RT-PCR: expression in paired tumor and non-malignant samples of selected gastric cancer markers

| name | symbol | median T:N fold change | maximum T:N fold change | % tumor samples with expression >paired non-malignant sample |
|---|---|---|---|---|
| adlican | | 5 | 146 | 88 |
| asporin (lrr class 1) | ASPN | 11 | 198 | 100 |
| chondroitin sulfate proteoglycan 2 (versican) | CSPG2 | 5 | 68 | 93 |
| cystatins SN, SA & S | CST1, 2, 4 | 498 | 11911 | 100 |
| egf-containing fibulin-like extracellular matrix protein 2 | EFEMP2 | 3 | 17 | 93 |
| gamma-glutamyl hydrolase | GGH | 4 | 34 | 83 |
| inhibin beta A chain | INHBA | 27 | 630 | 95 |
| insulin-like growth factor binding protein 7 | IGFBP7 | 5 | 38 | 93 |
| kallikrein 10 | KLK10 | 7 | 519 | 78 |
| leucine proline-enriched proteoglycan 1(leprecan 1) | LEPRE1 | 4 | 23 | 85 |
| lumican | LUM | 5 | 68 | 90 |
| lysyl oxidase-like 2 | LOXL2 | 7 | 53 | 95 |
| matrix metalloproteinase 12 | MMP12 | 9 | 468 | 85 |
| metalloproteinase inhibitor 1 | TIMP1 | 6 | 103 | 95 |
| n-acylsphingosine amidohydrolase | ASAH1 | 3 | 15 | 88 |
| osteopontin | SPP1 | 36 | 626 | 98 |
| secreted frizzled-related protein 2 | SFRP2 | 5 | 48 | 83 |
| secreted frizzled-related protein 4 | SFRP4 | 54 | 375 | 100 |
| secreted protein, acidic, cysteine rich | SPARC | 10 | 66 | 95 |
| serine protease 11 (IGF binding) | PRSS11 | 4 | 63 | 90 |
| thrombospondin 2 | THBS2 | 23 | 452 | 98 |
| thyroglobulin | TG | 4 | 174 | 93 |
| transforming growth factor B-induced | TGFBI | 5 | 78 | 95 |
| cell growth regulatory factor with EF-hand domain | CGR11 | 3 | 33 | 75 |
| serine (or cysteine) proteinase inhibitor H1 | SERPINH1 | 10 | 51 | 98 |
| matrix metalloproteinase 12 | MMP2 | 2 | 46 | 83 |
| proprotein convertase subtilisin/kexin type 5 | PCSK5 | 2 | 63 | 80 |
| serine (or cysteine) proteinase inhibitor B5 | SERPINB5 | 5 | 861 | 73 |
| transforming growth factor β1 | TGFB1 | 3 | 16 | 88 |
| | | | | |
| carcinoembryonic antigen (CEA) | CEACAM5 | 3 | 177 | 68 |

Fig. 9a Relative tumor:normal fold changes in paired tumor/normal gastric samples
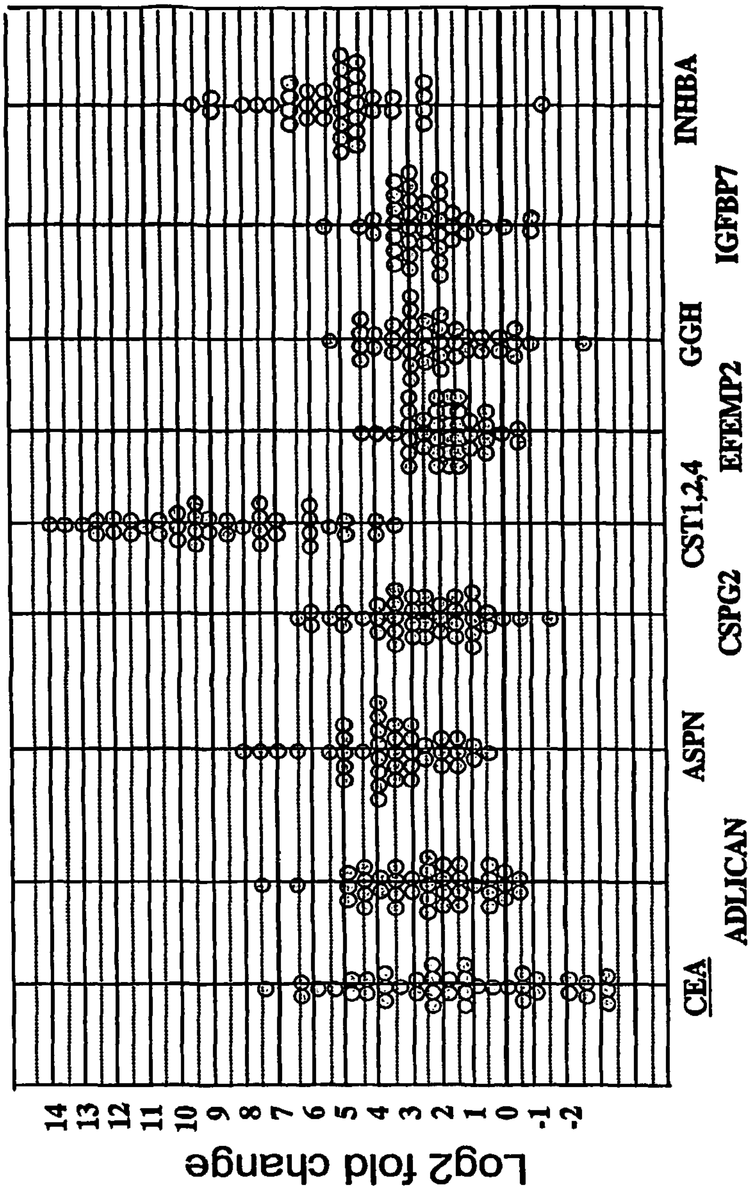

Fig. 10a adlican
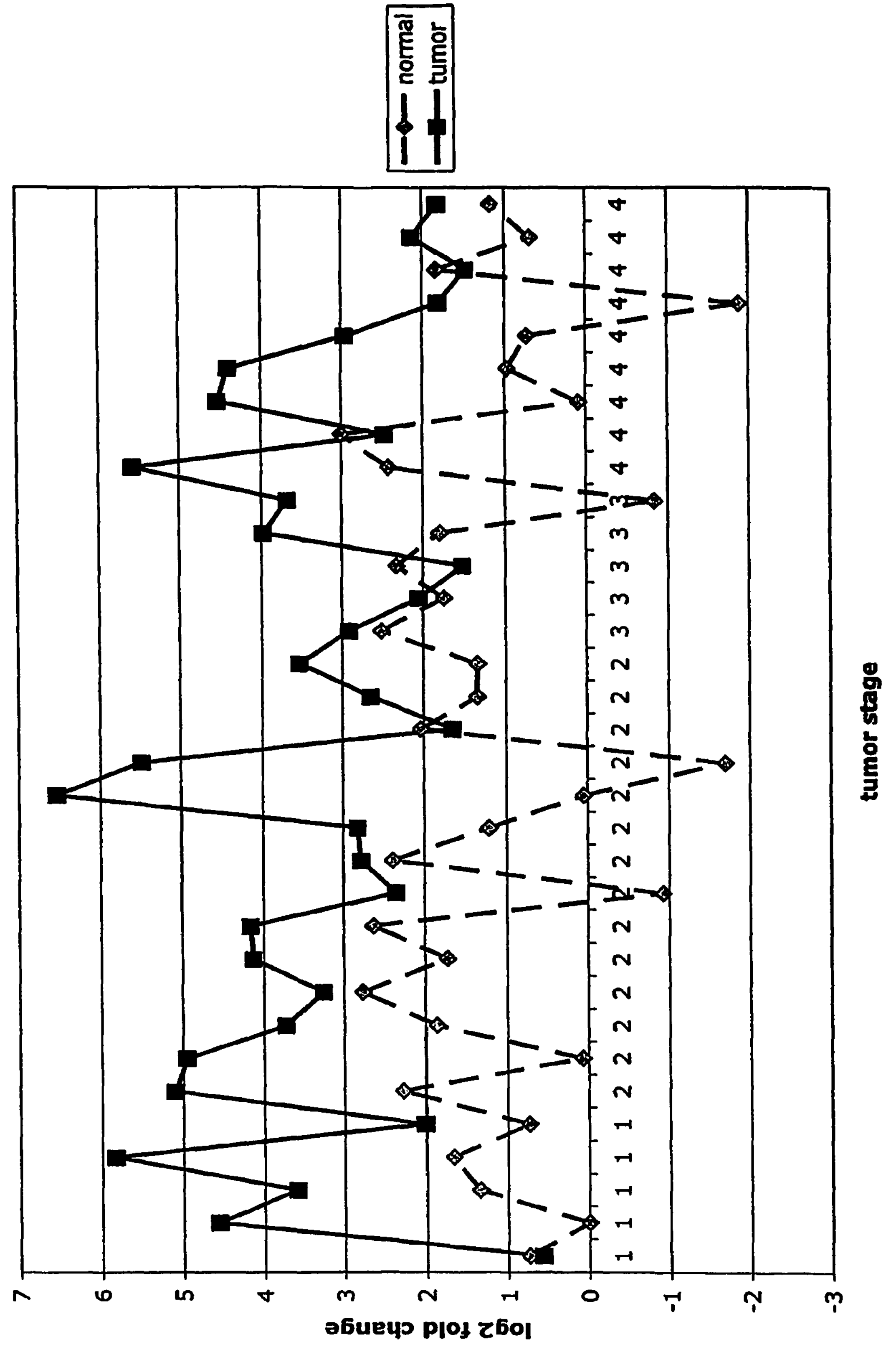

Fig. 10b ASPN
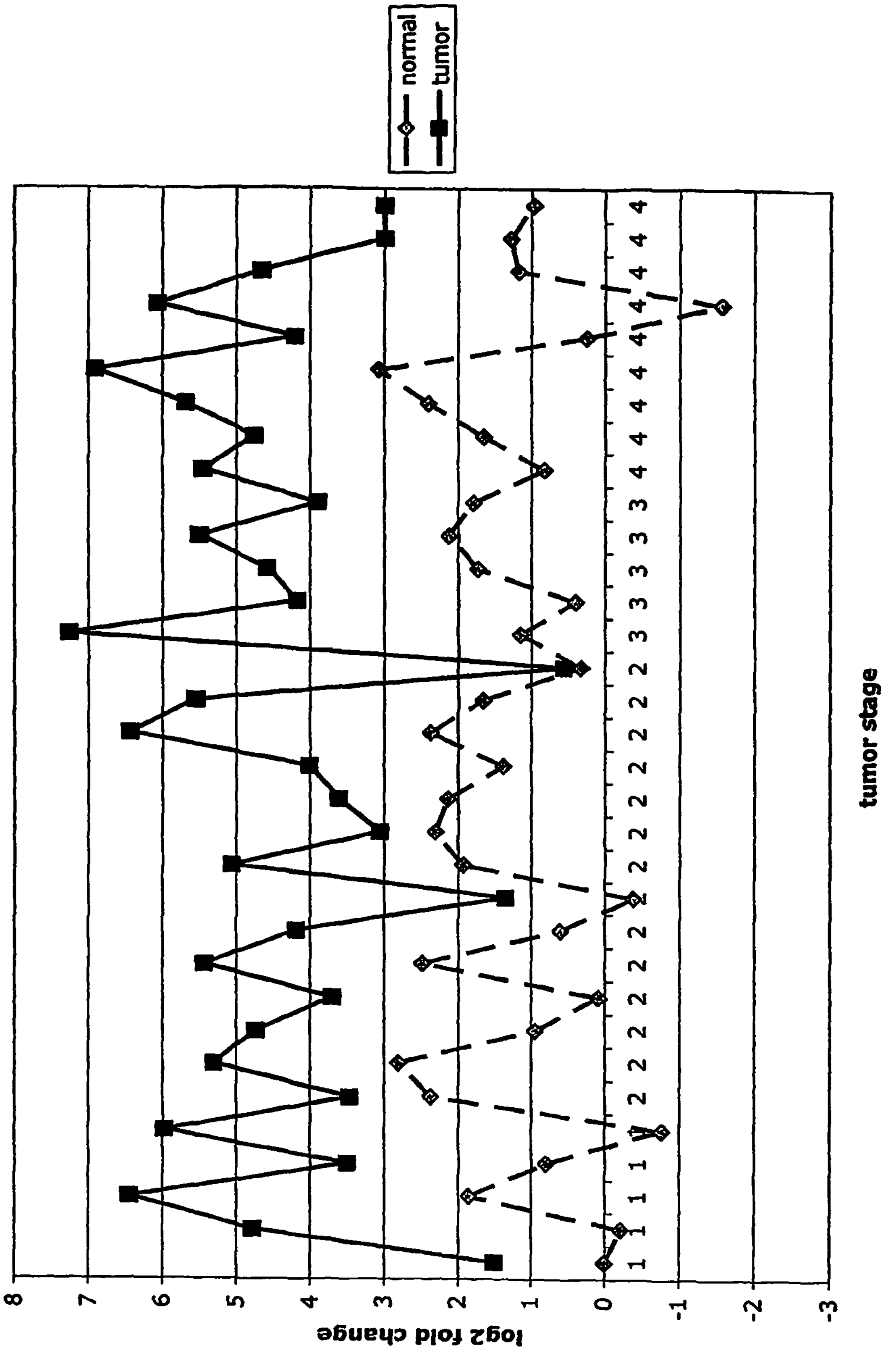

Fig. 10c CSPG2
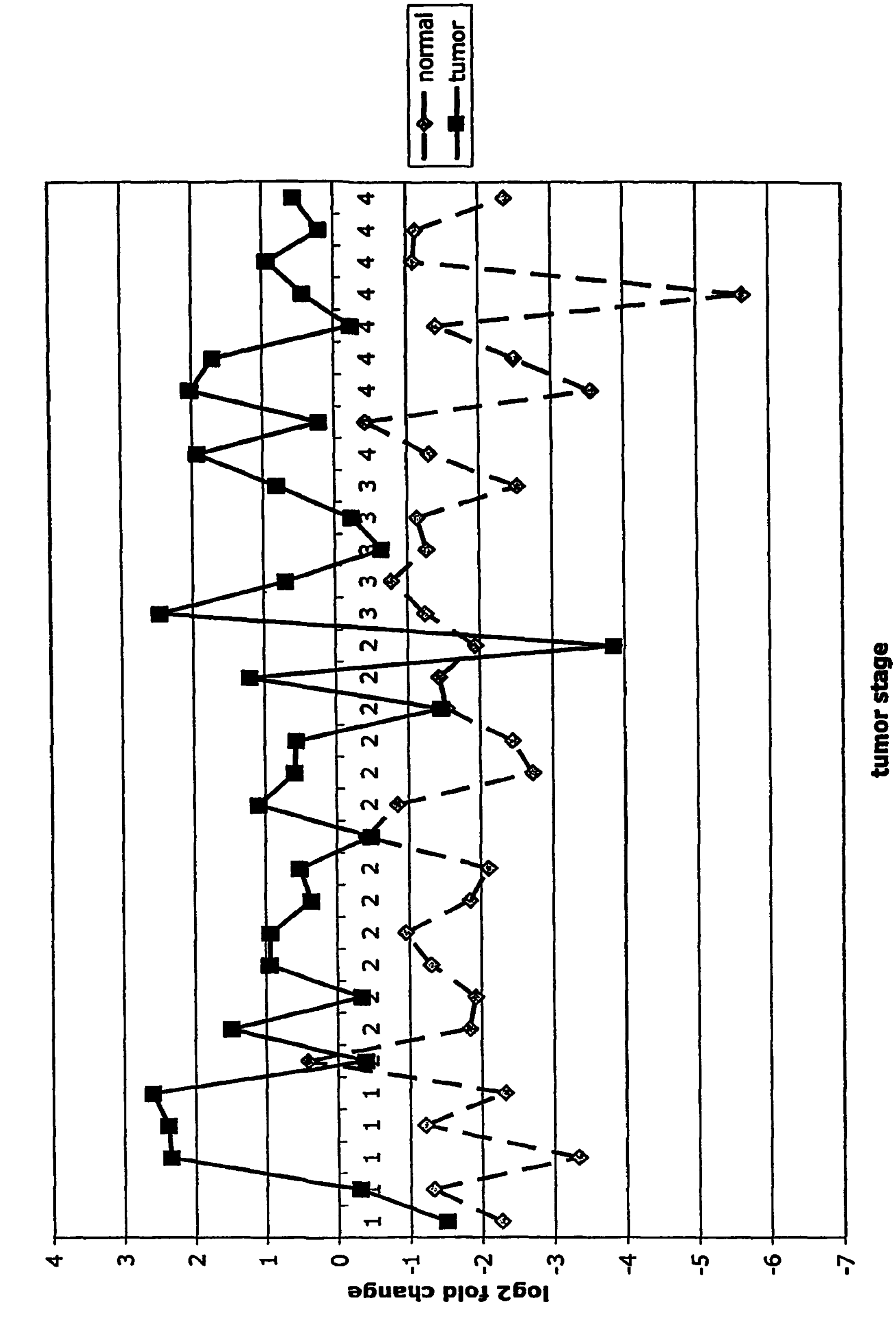

Fig. 10d CST1,2,4
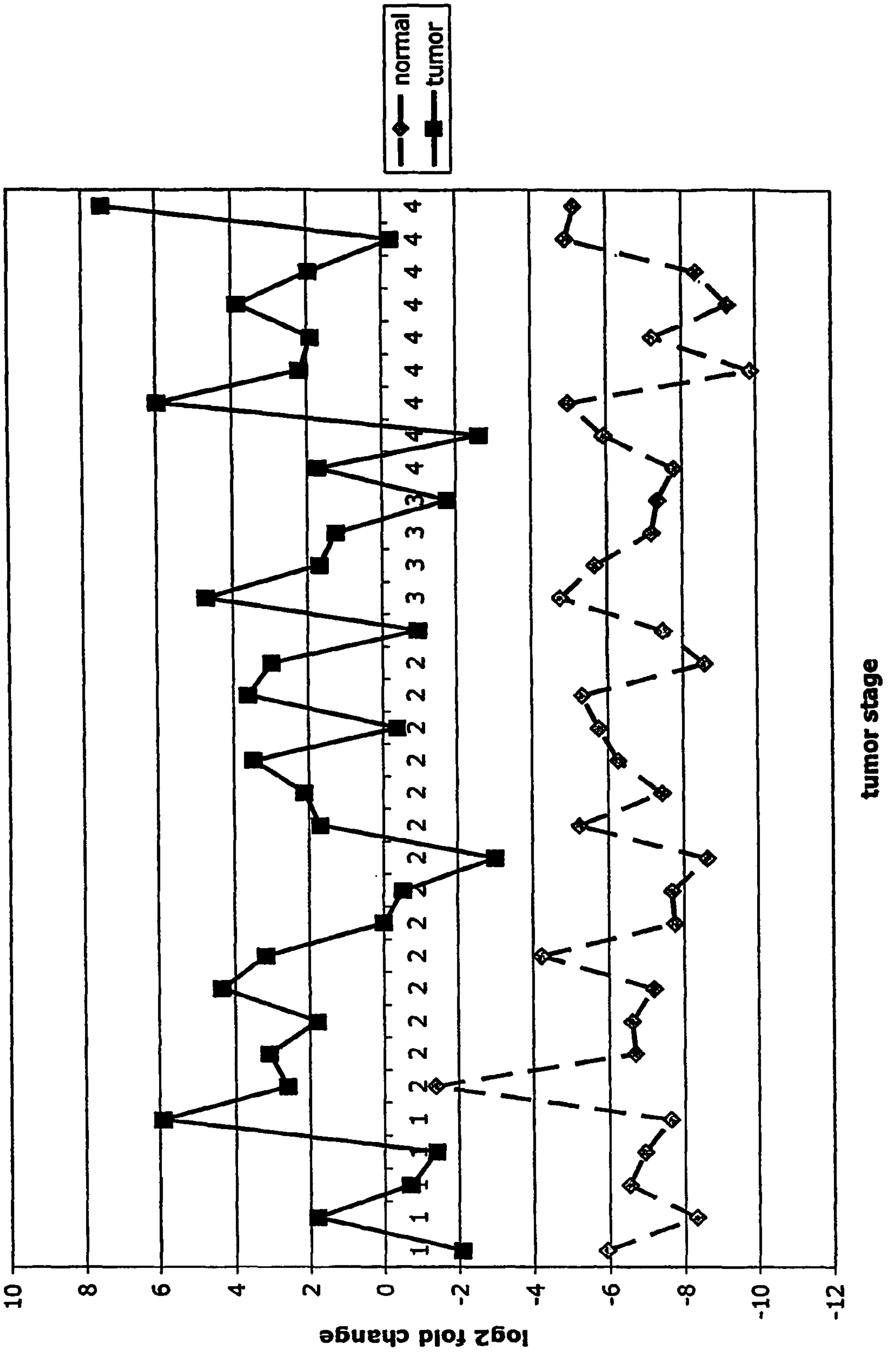

Fig. 10e EFEMP2
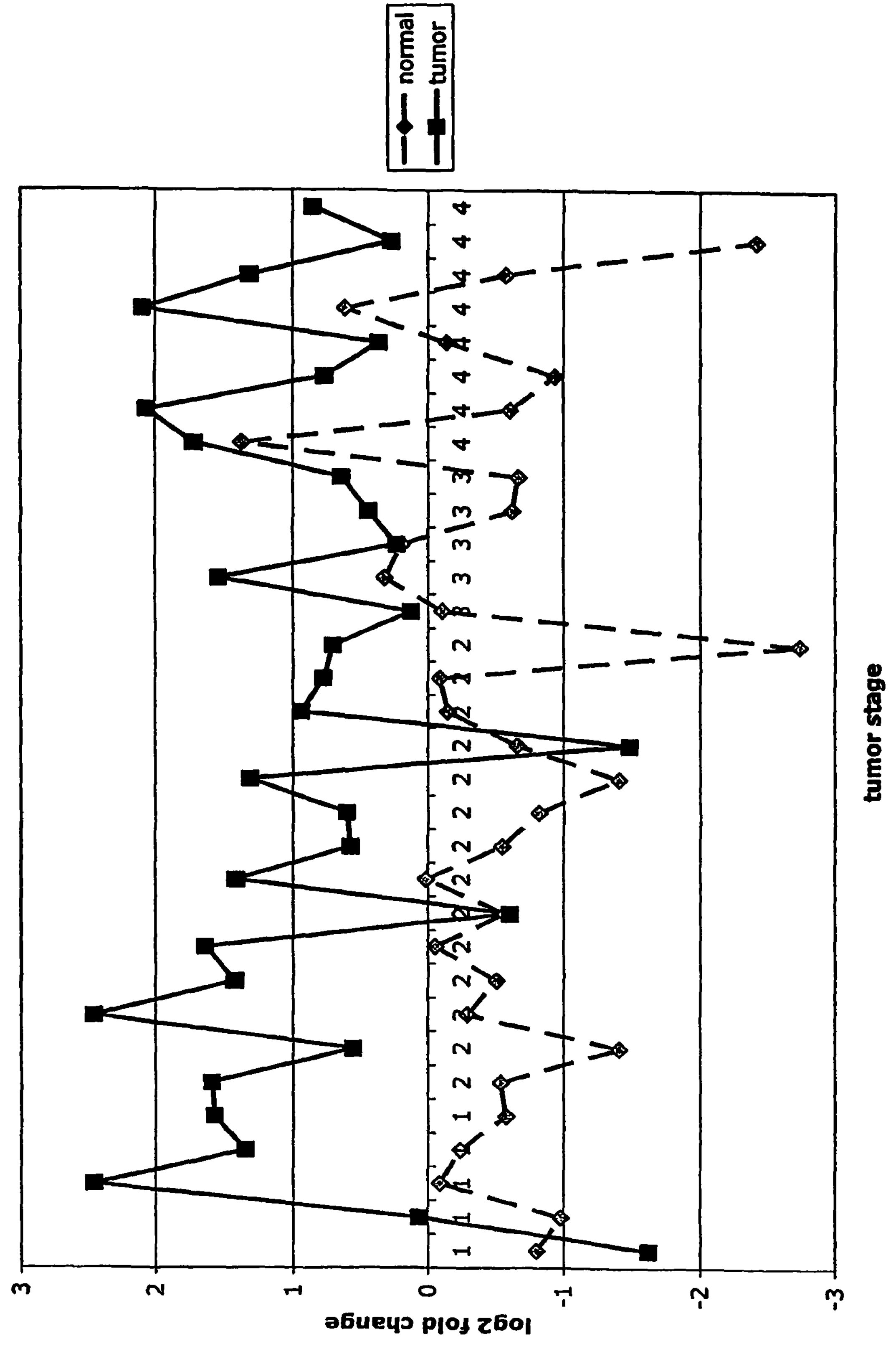

Fig. 10f GGH
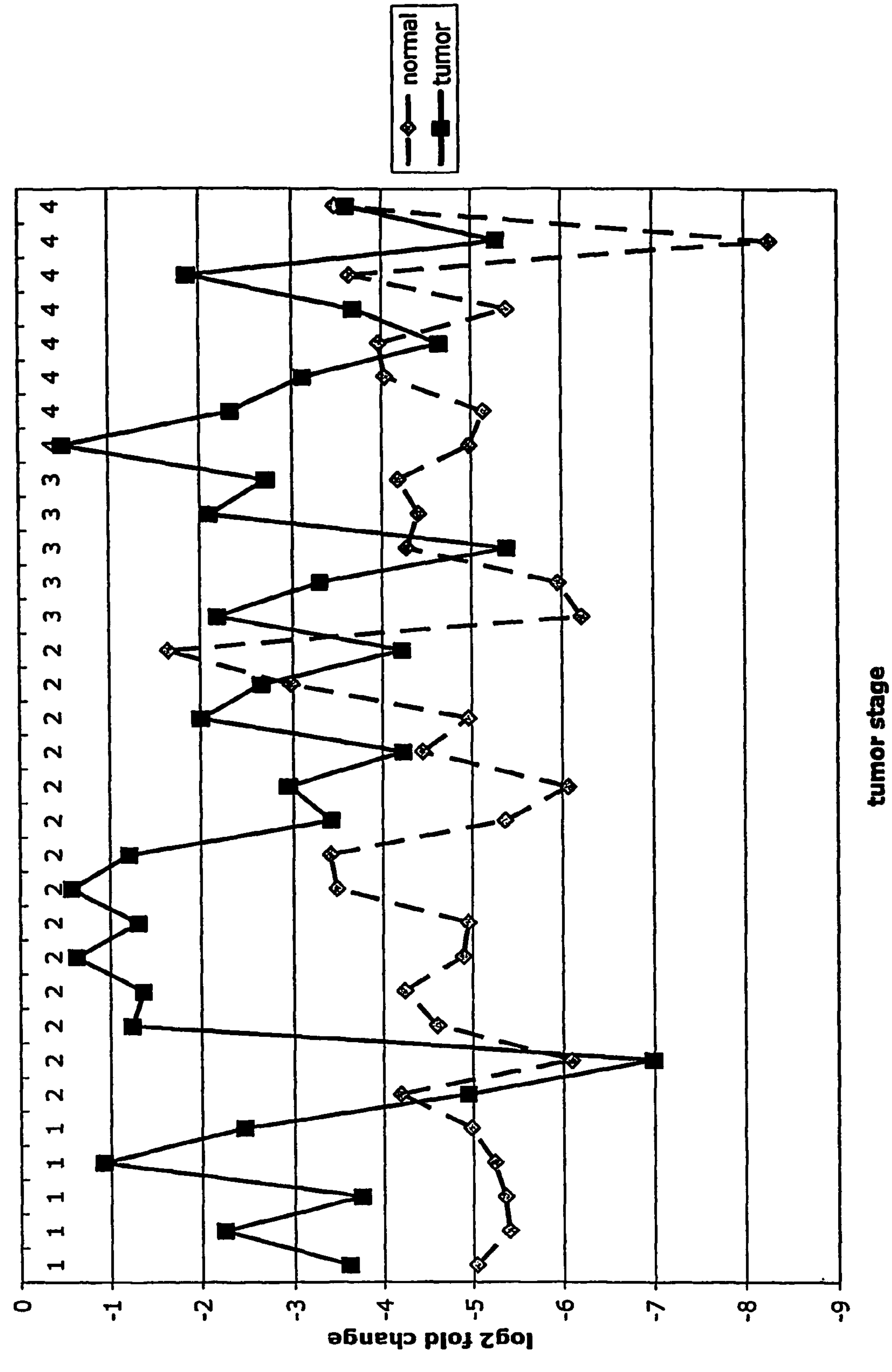

Fig. 10g INHBA
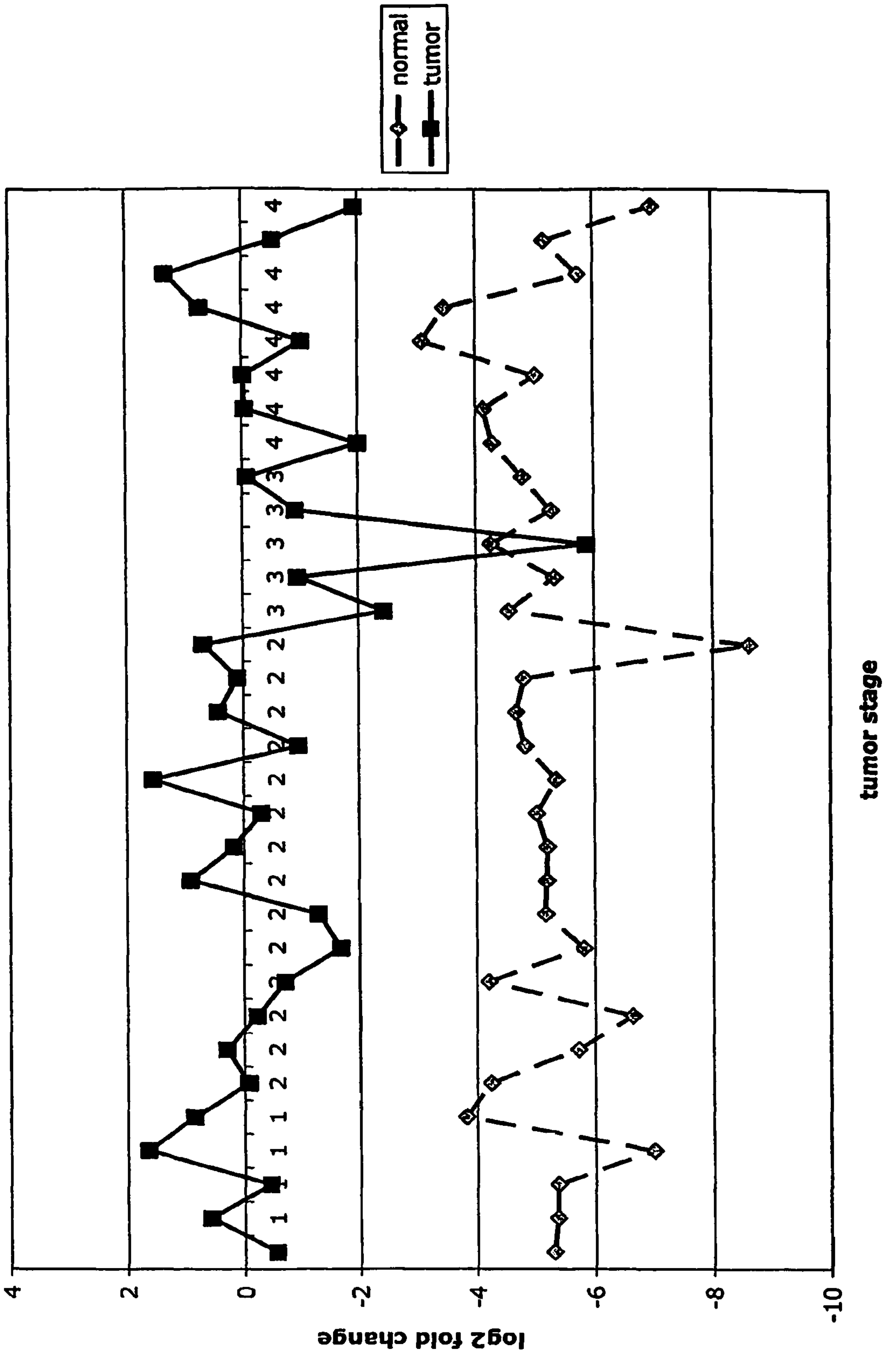

Fig. 10h IGFBP7
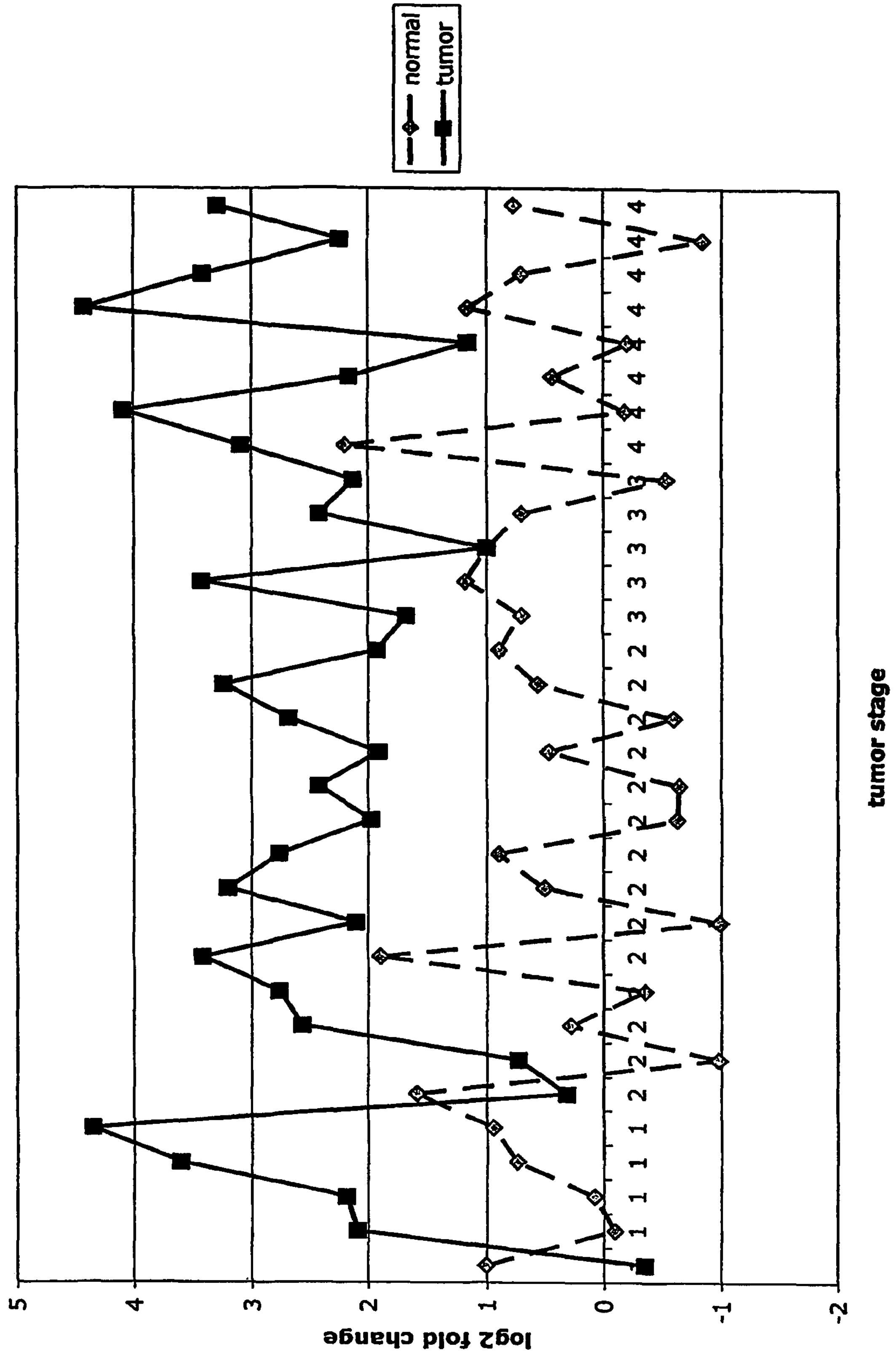

Fig. 10i KLK10
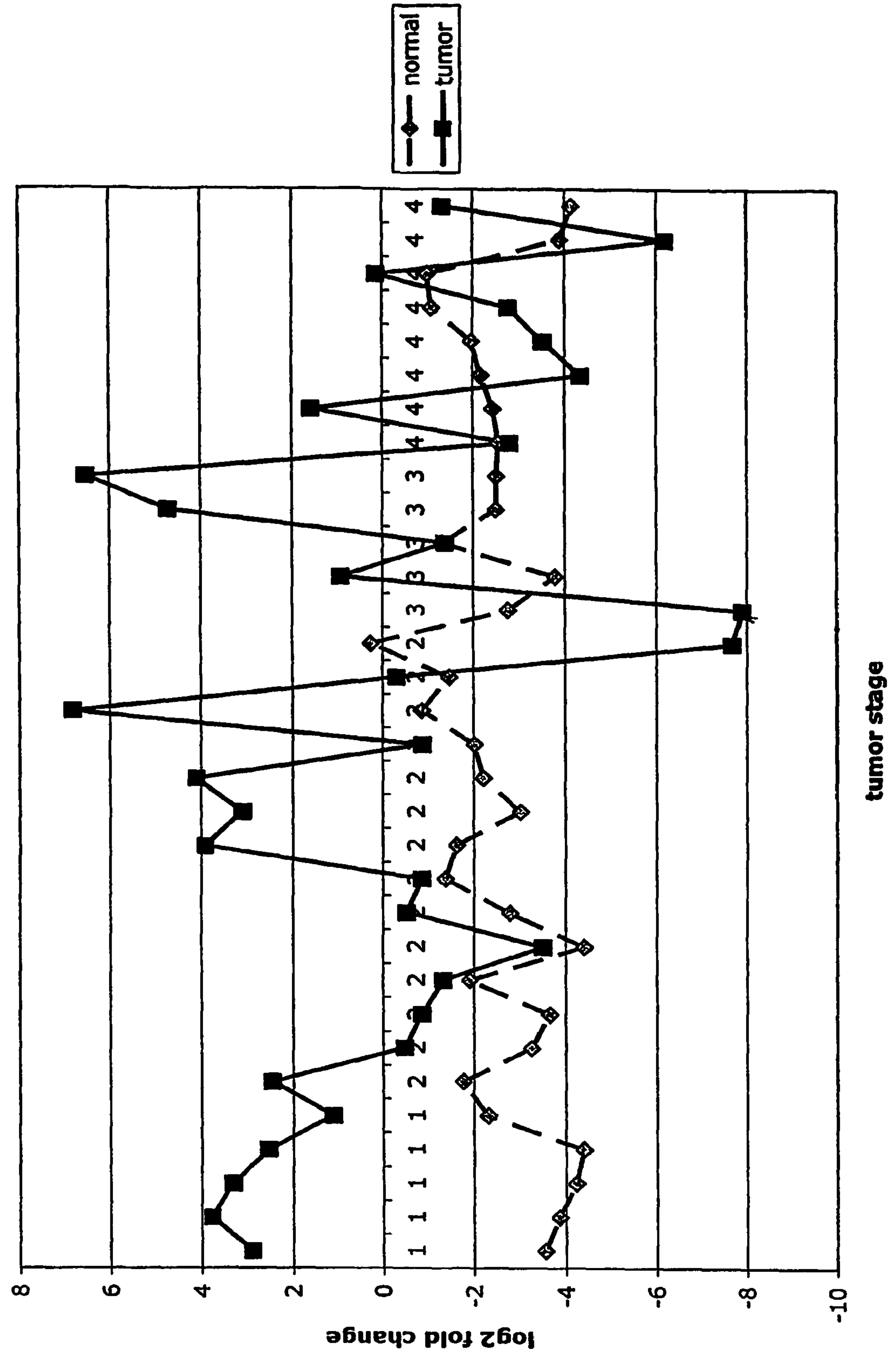

Fig. 10j LEPRE1
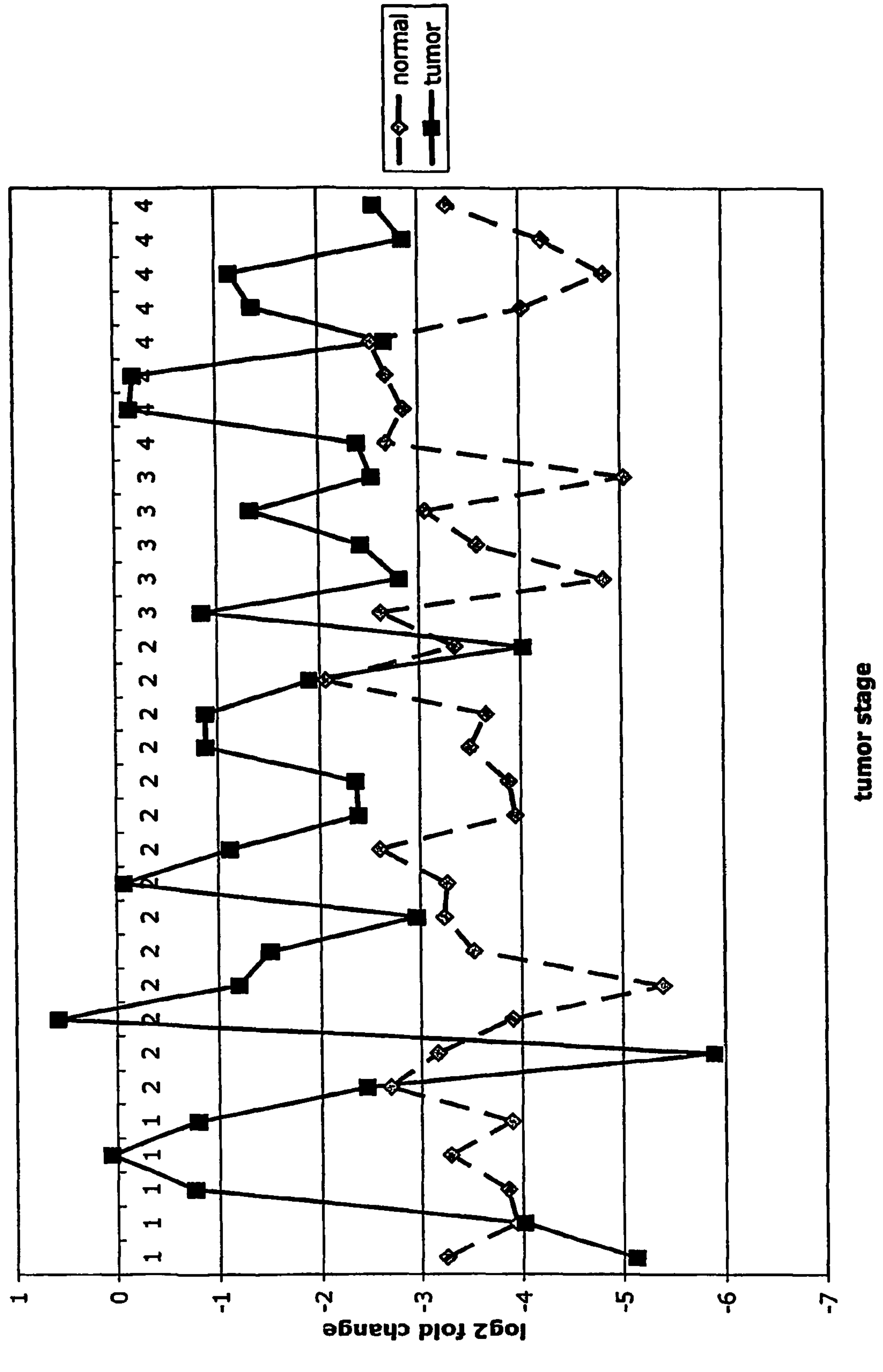

Fig. 10k LUM
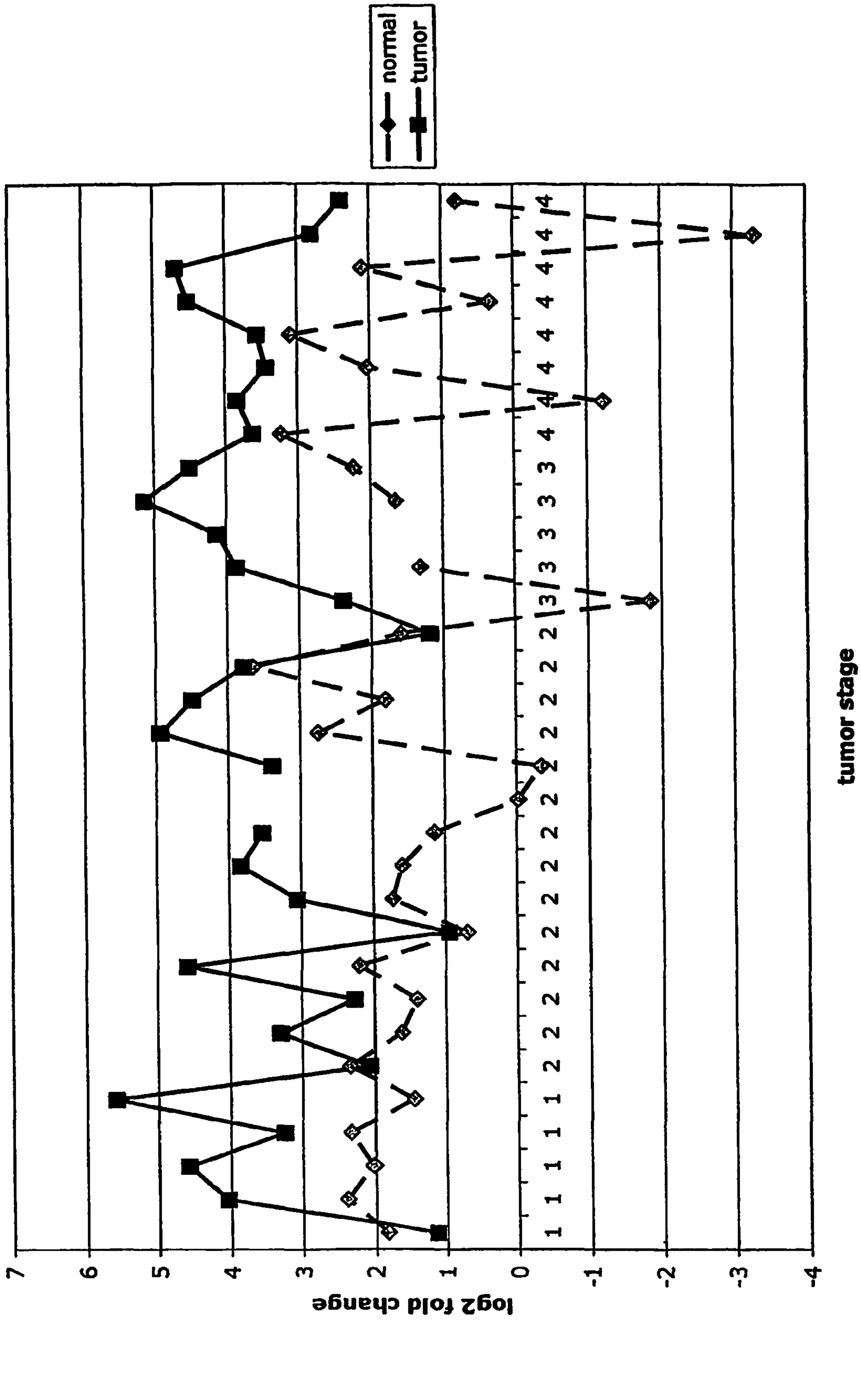

Fig. 10I LOXL2
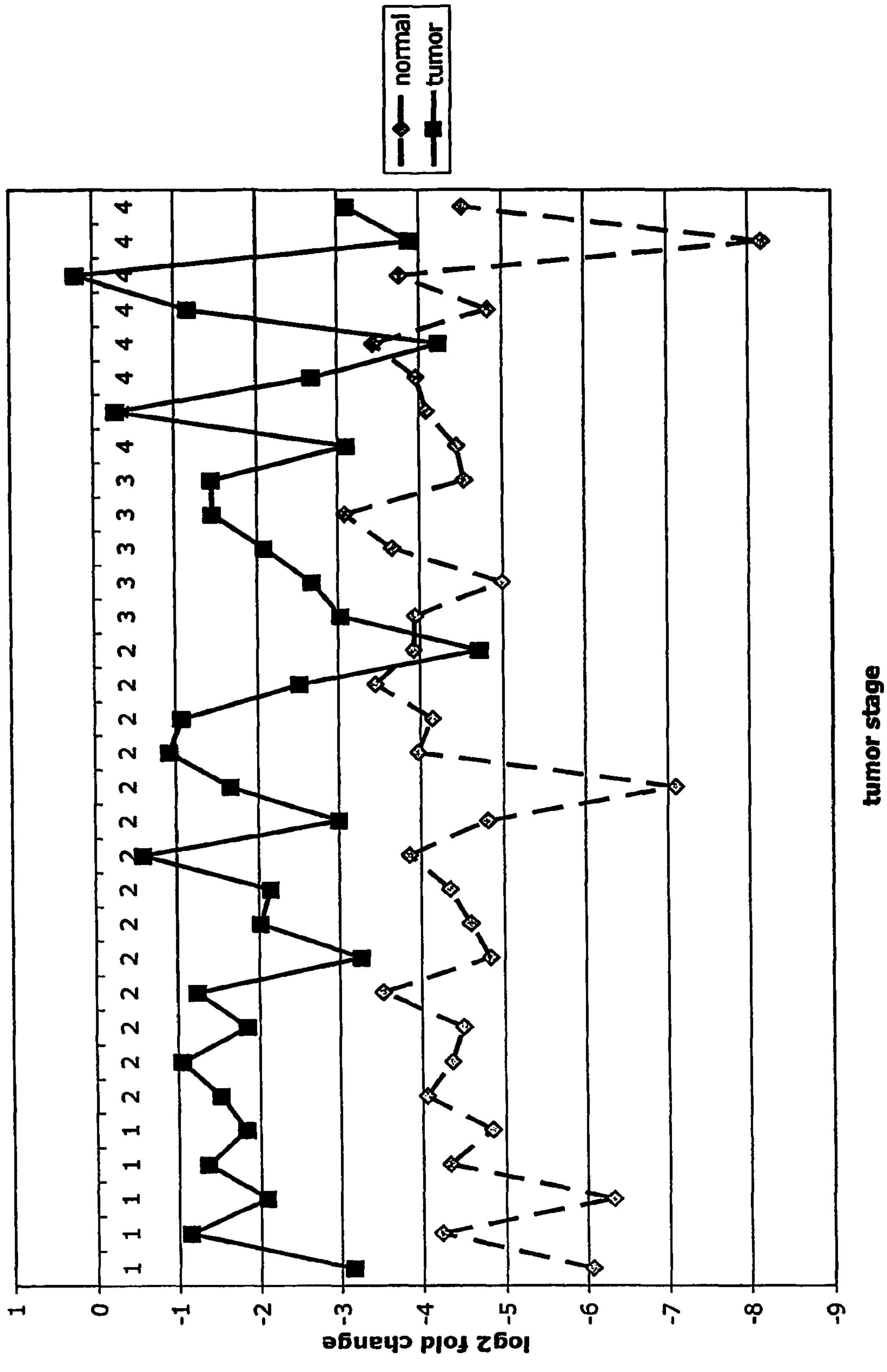

Fig. 10m MMP12
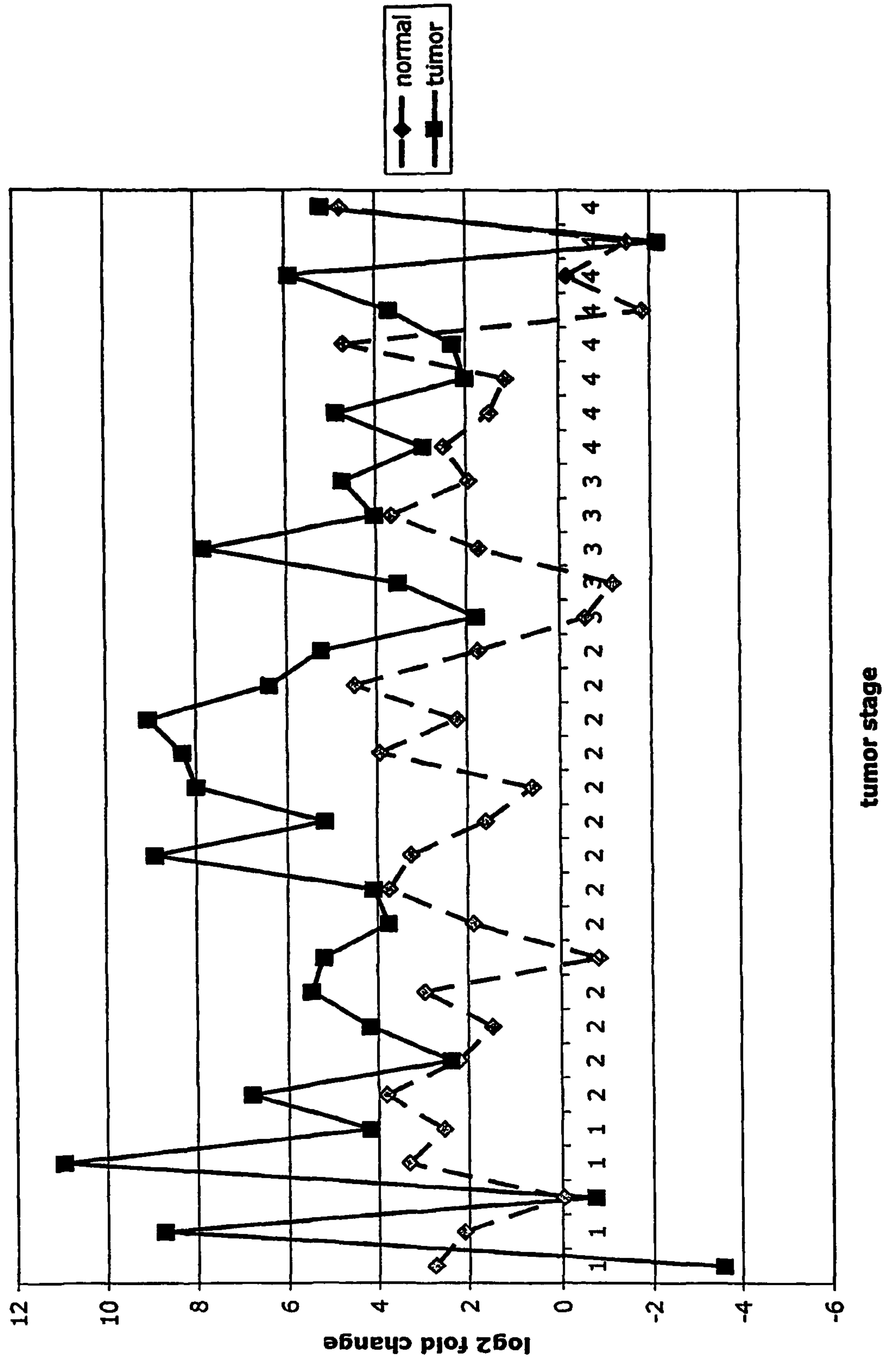

Fig.10n TIMP1
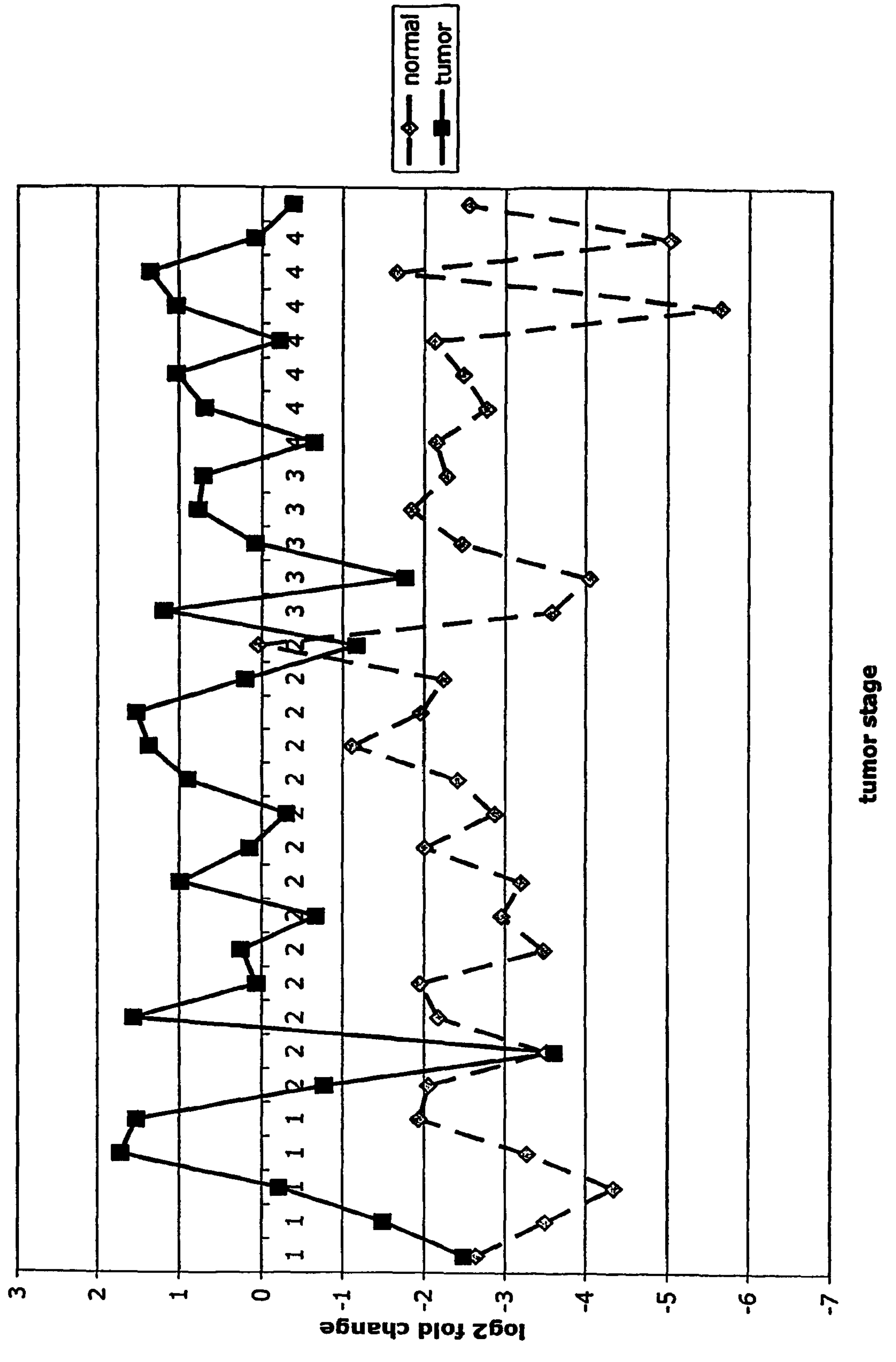

Fig. 10o ASAH1
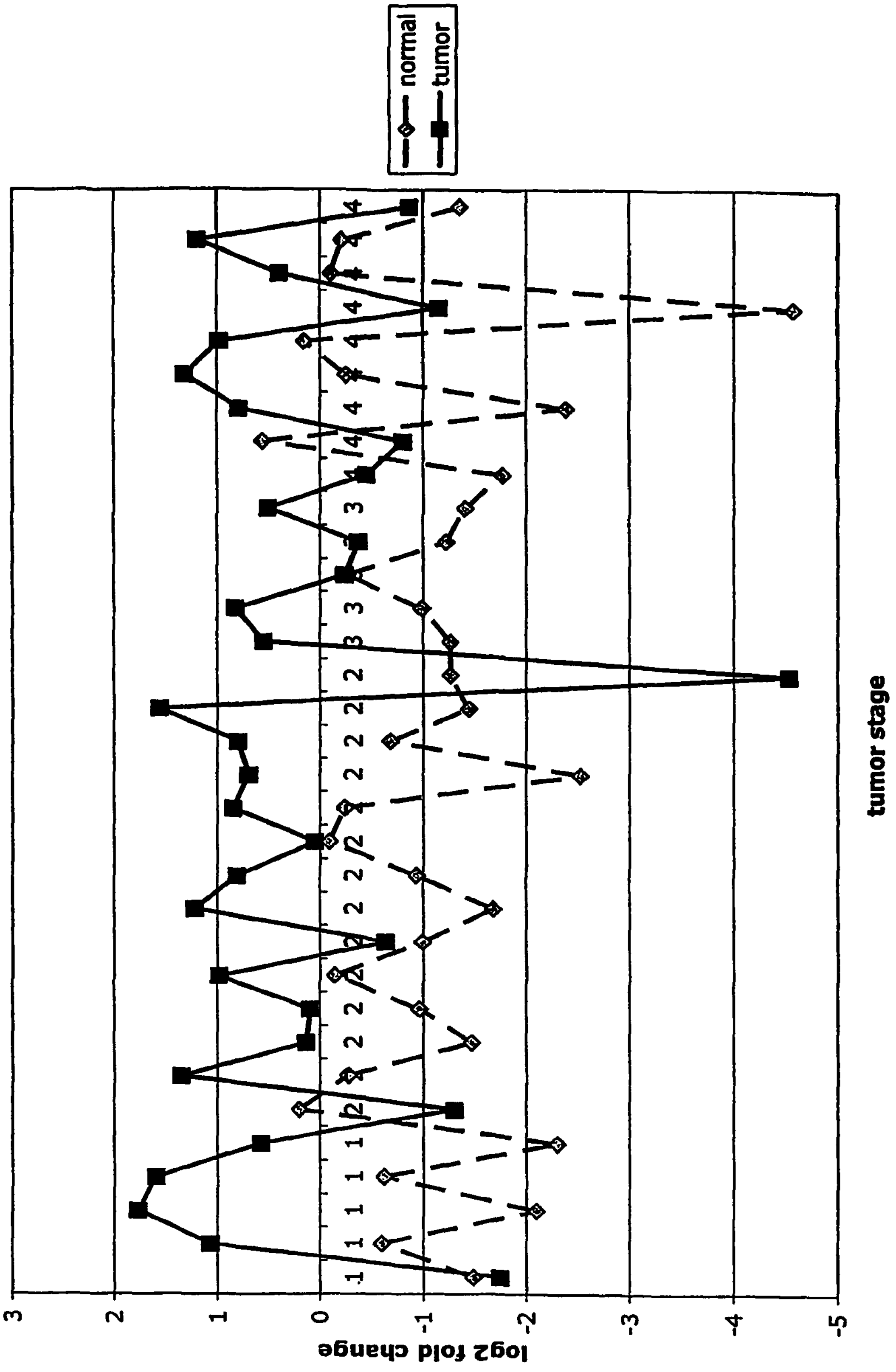

Fig. 10p SPP1
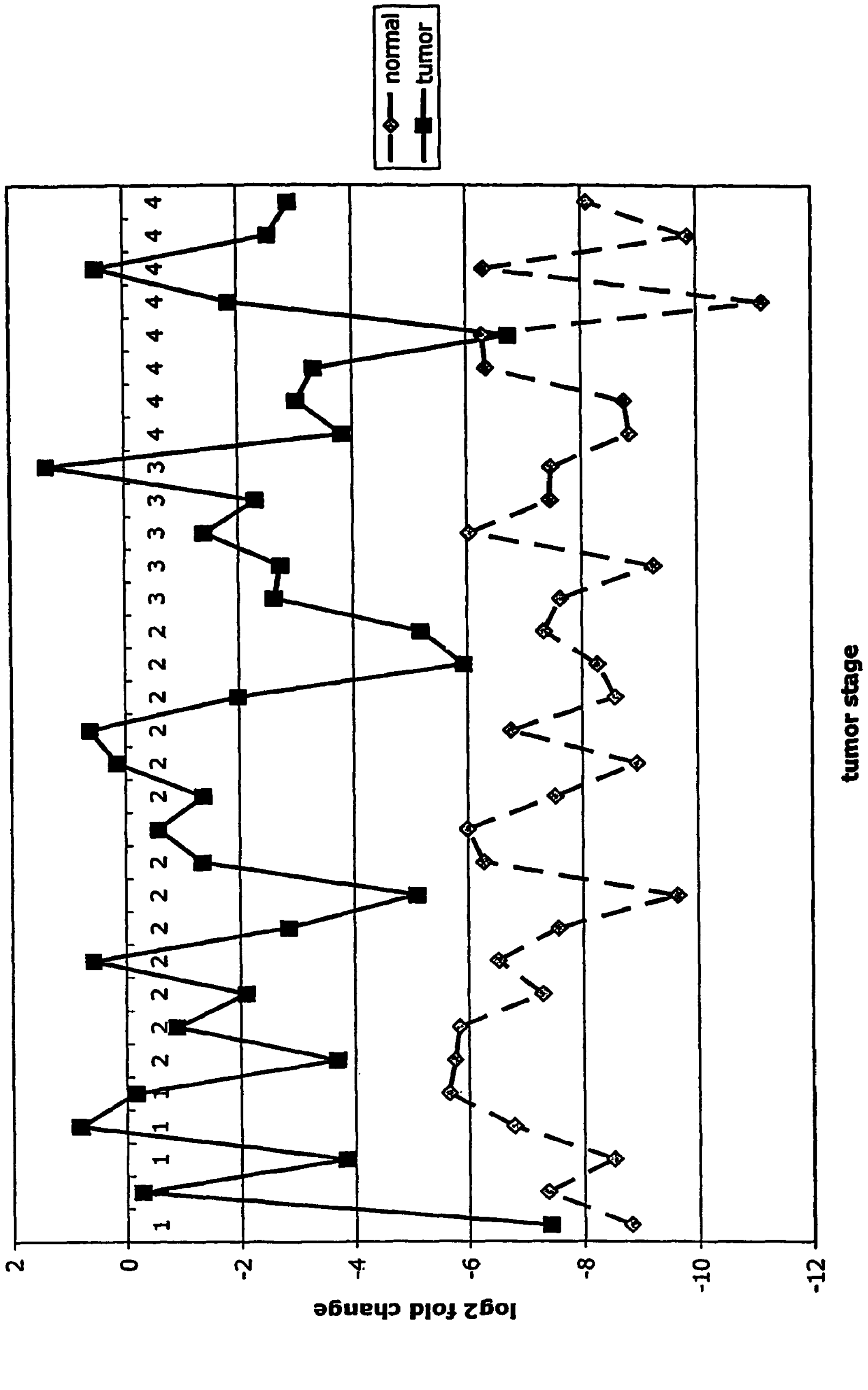

Fig. 10q SFRP2
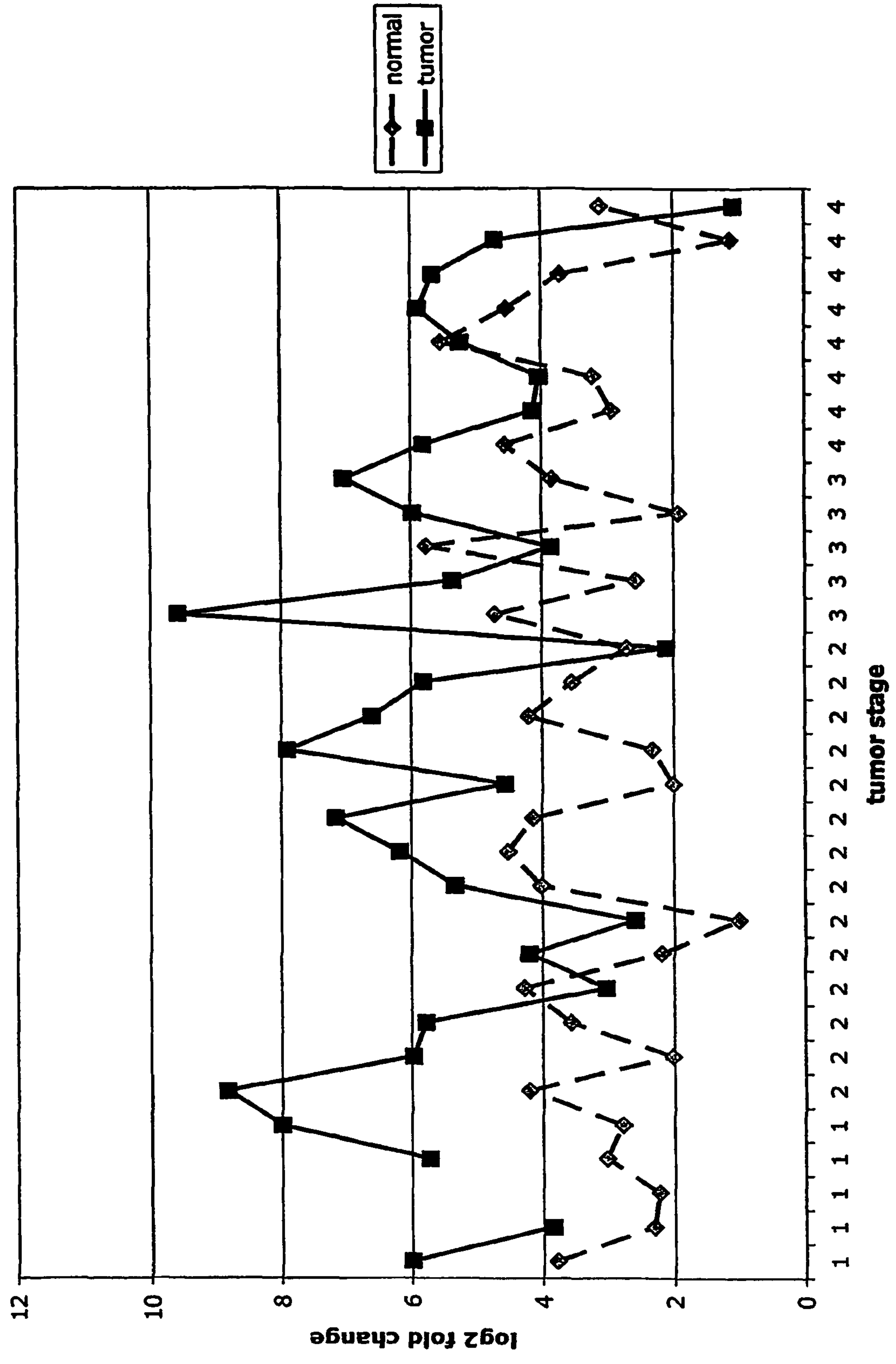

Fig. 10r SFRP4
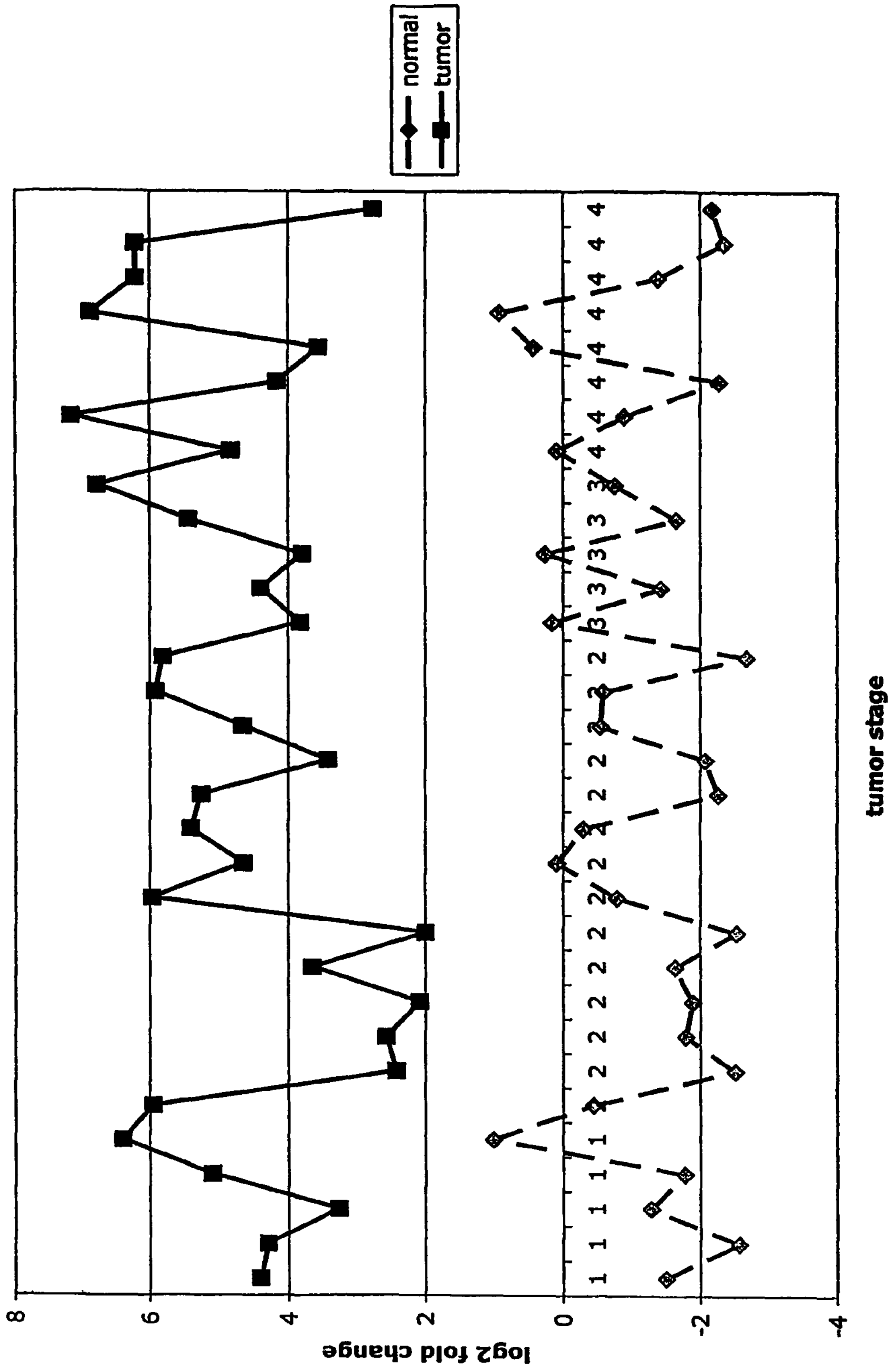

Fig. 10s SPARC
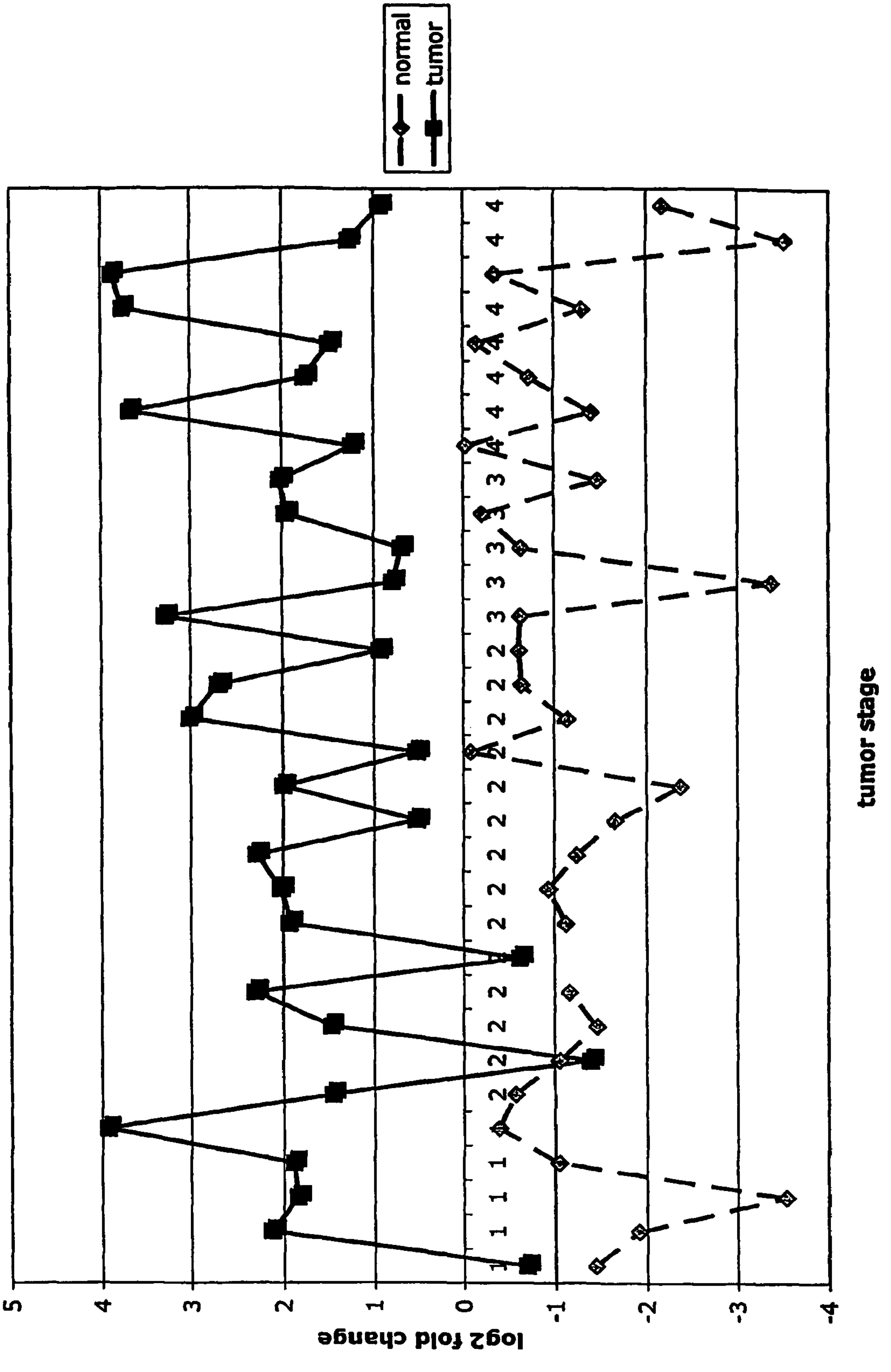

Fig. 10t PRSS11
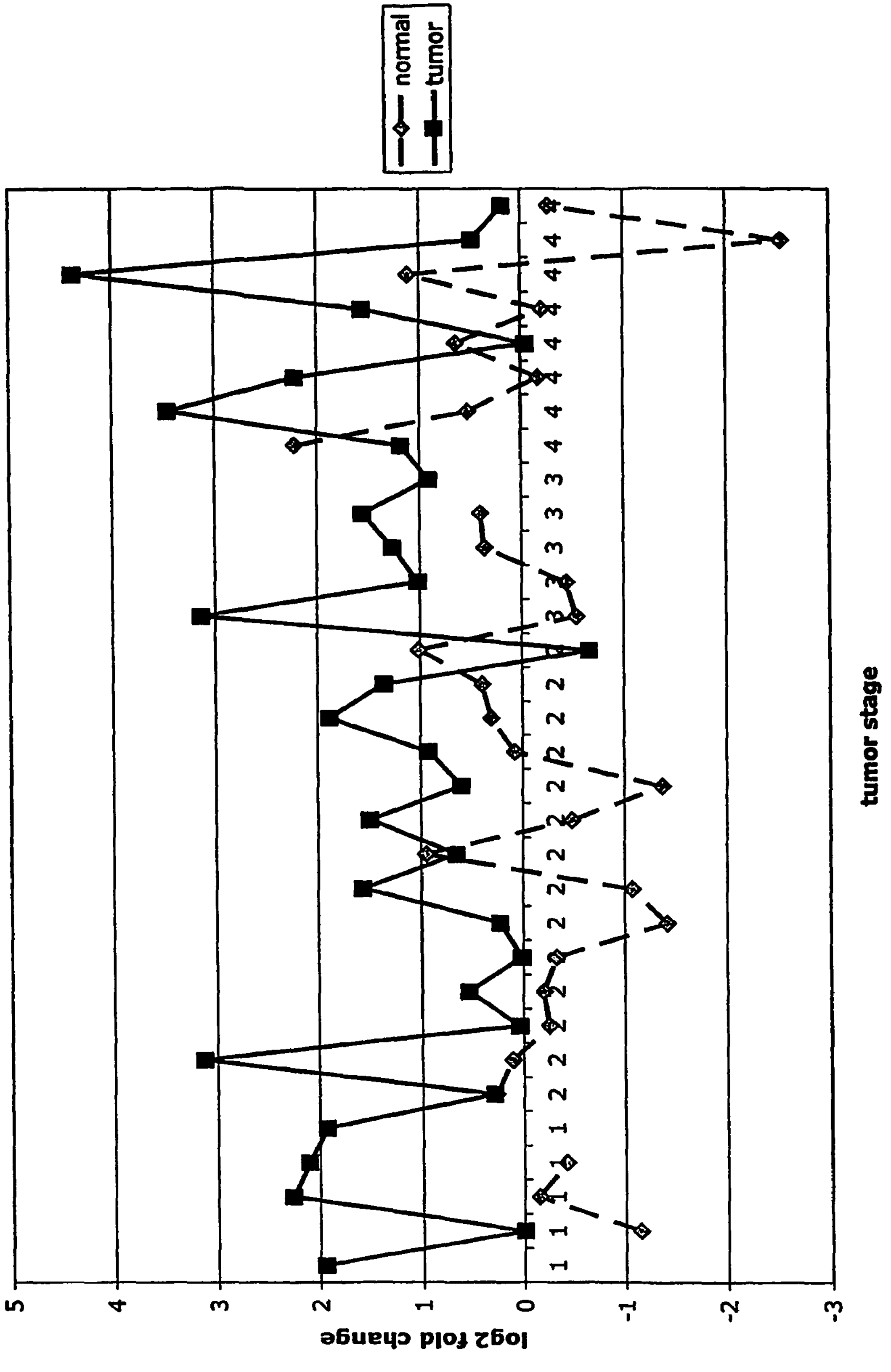

Fig. 10u THBS2
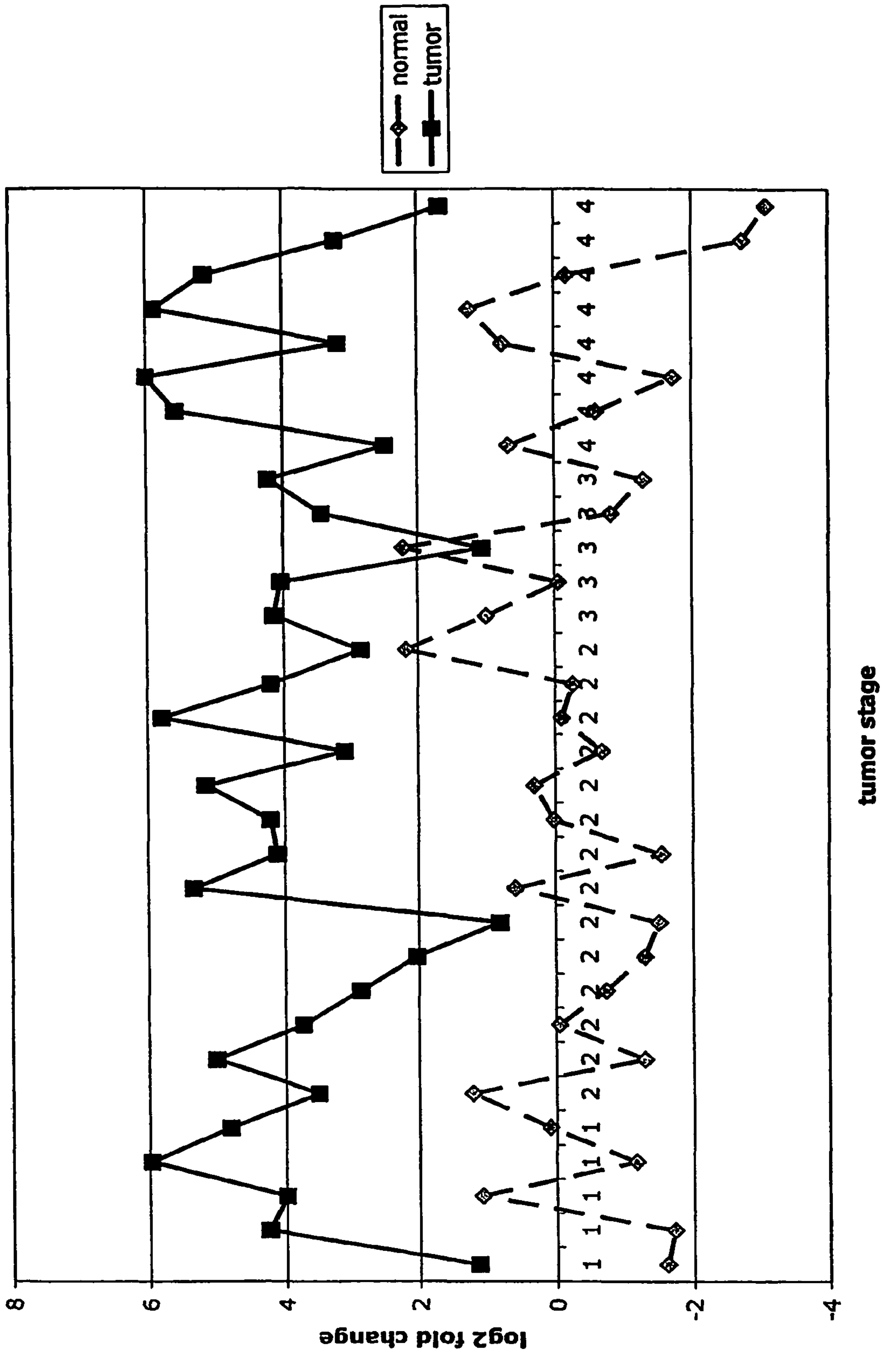

Fig. 10v TG
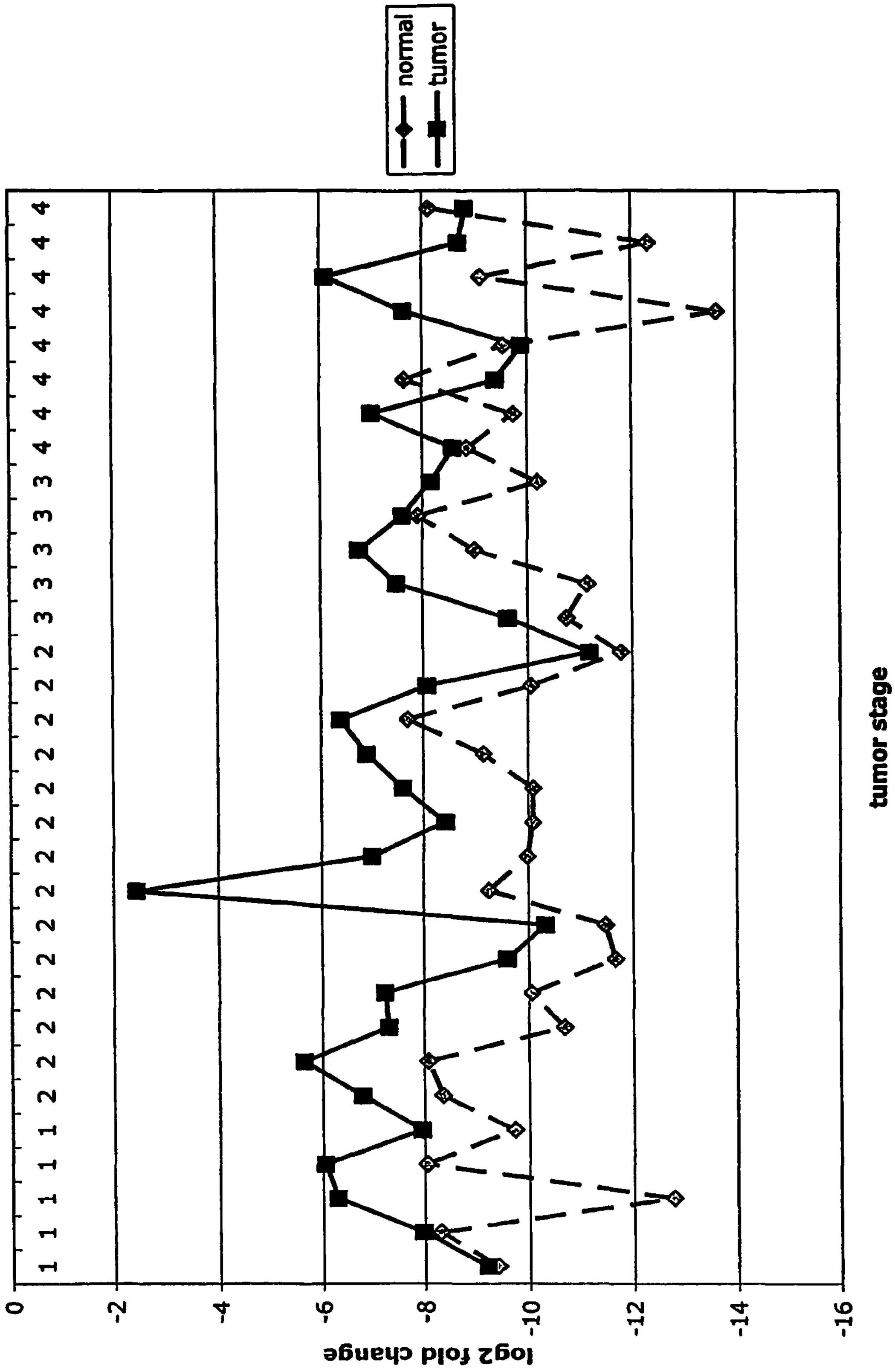

Fig. 10w TGFBI
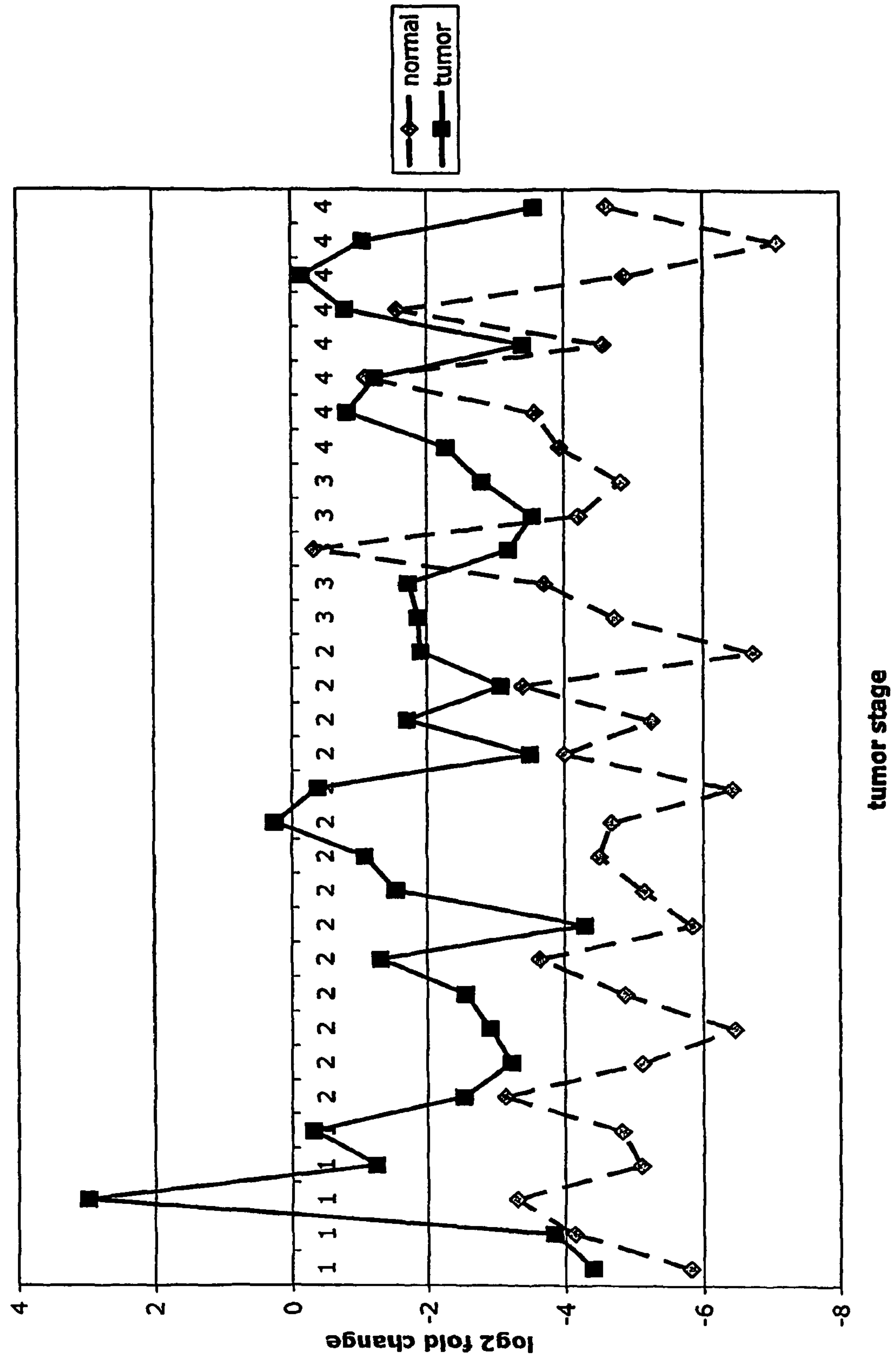

Fig. 10x CGR11
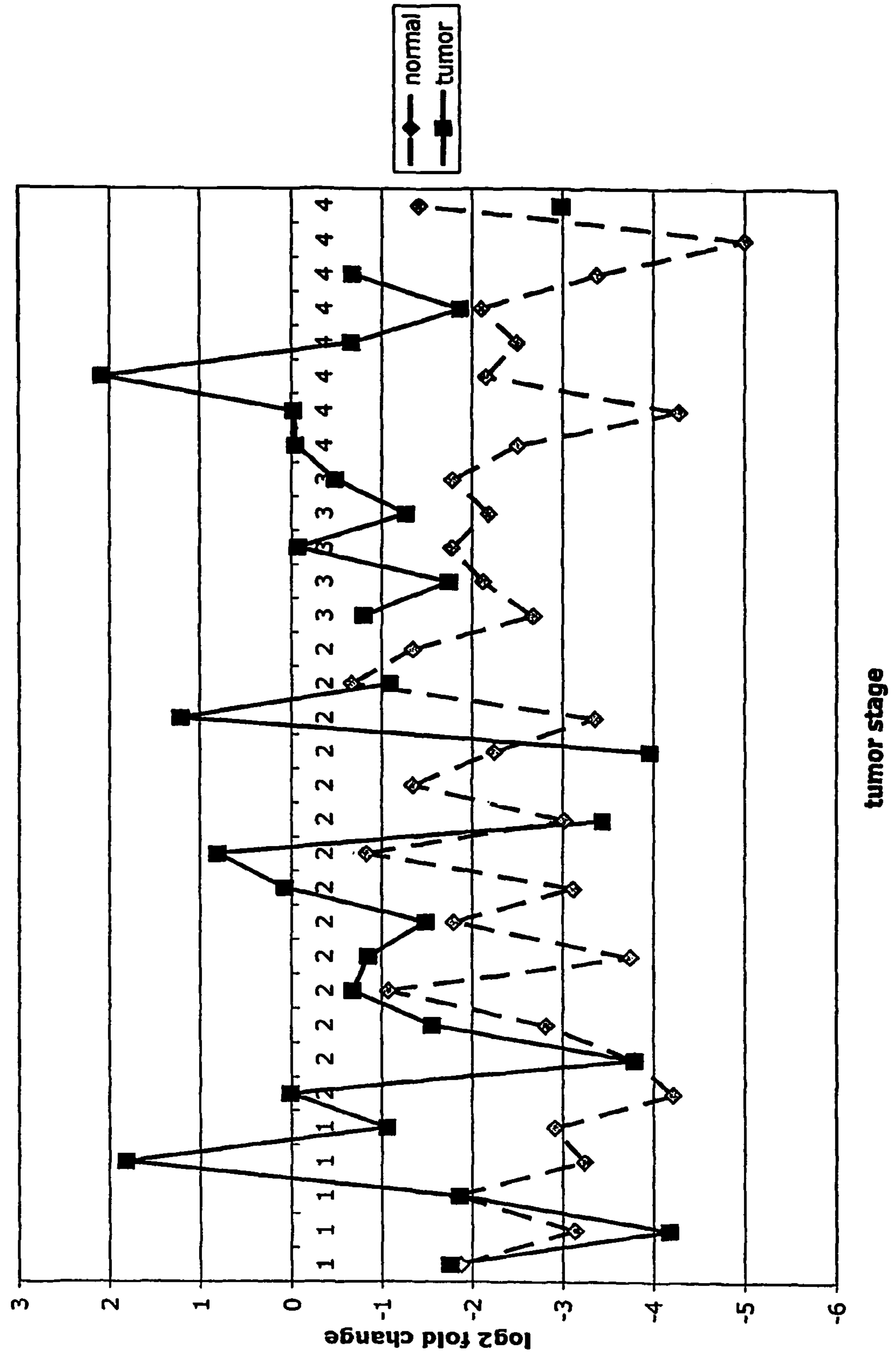

Fig. 10y SERPINH1
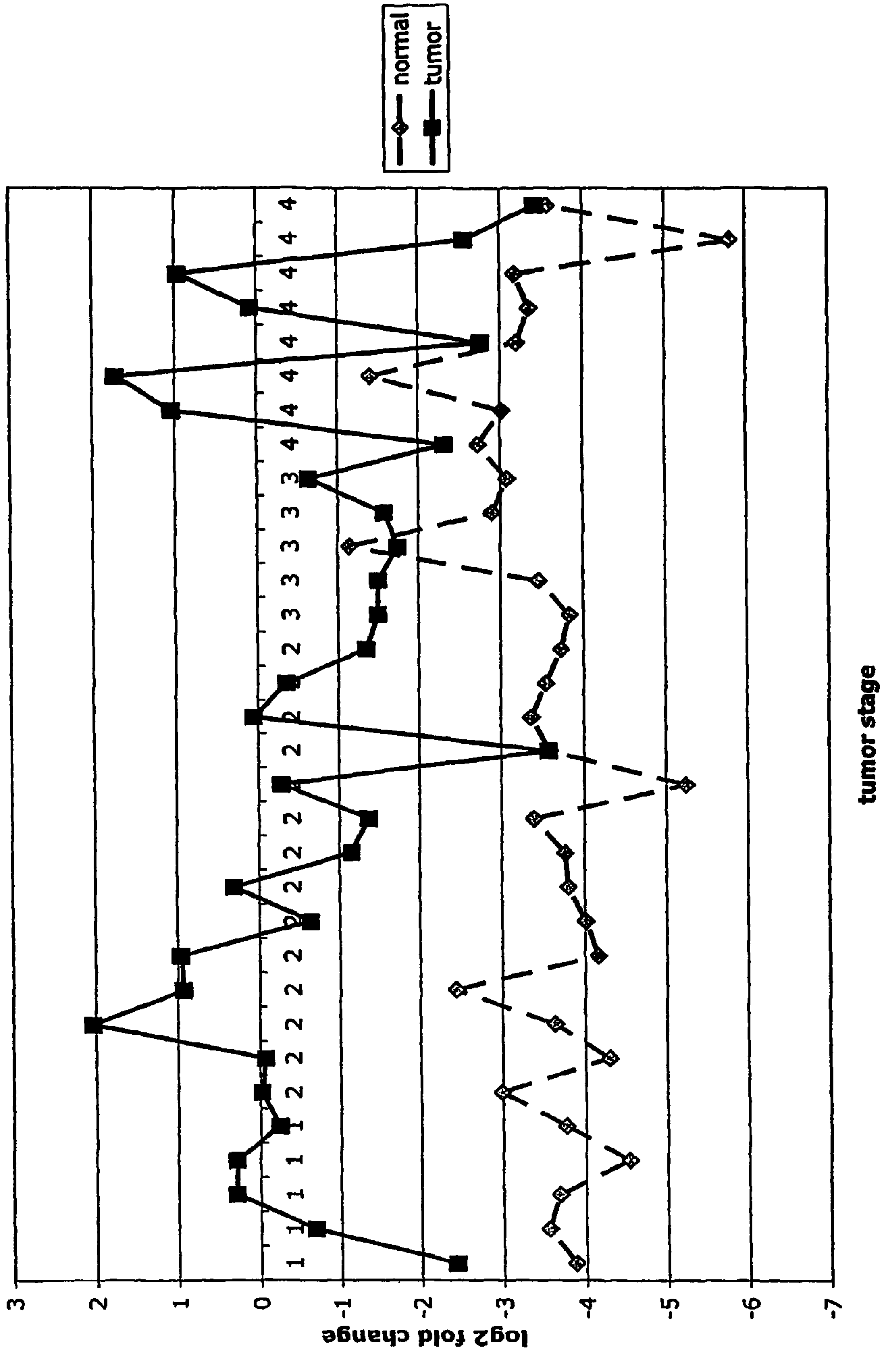

Fig. 10z MMP2
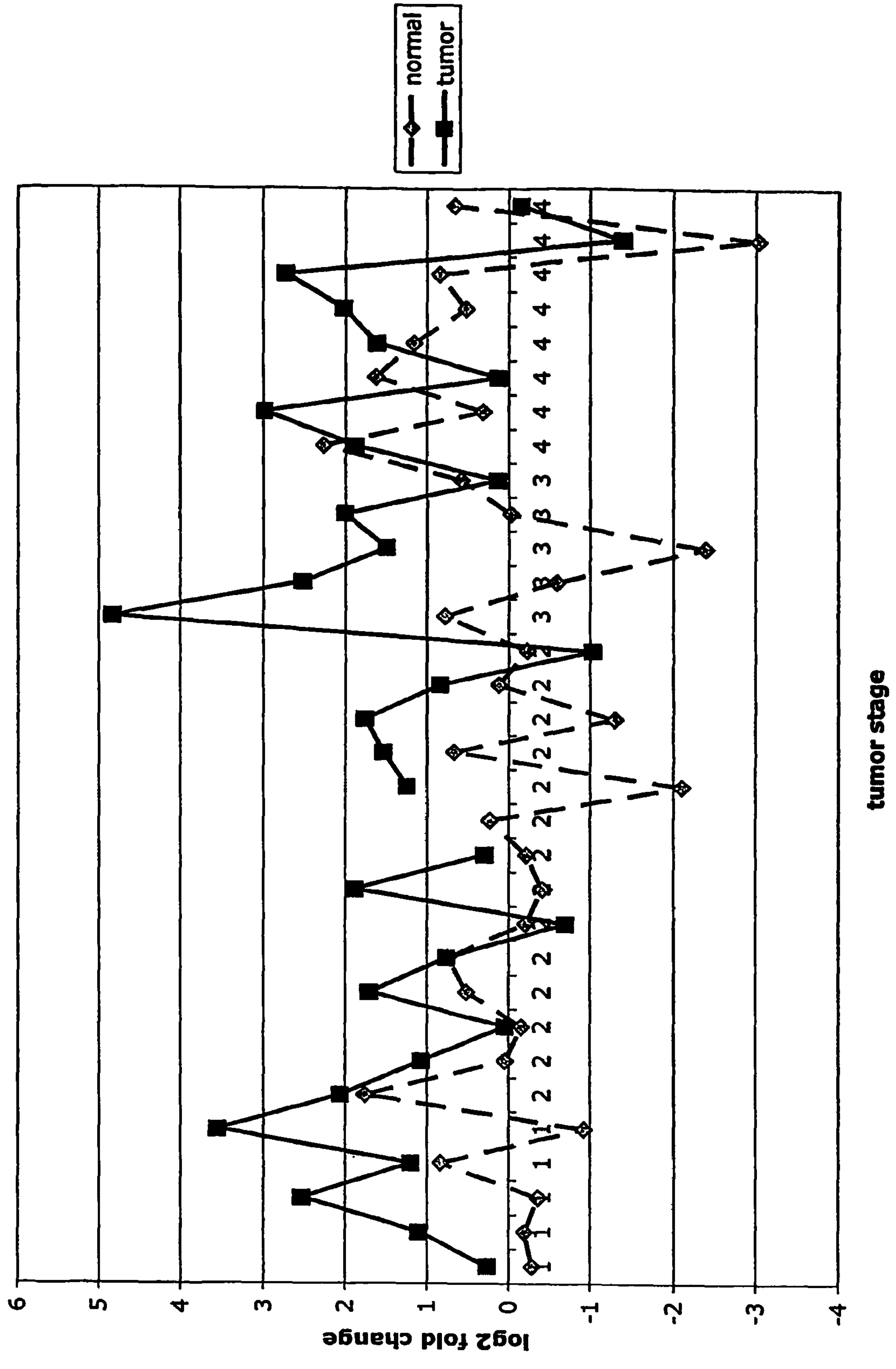

Fig. 10aa PCSK5
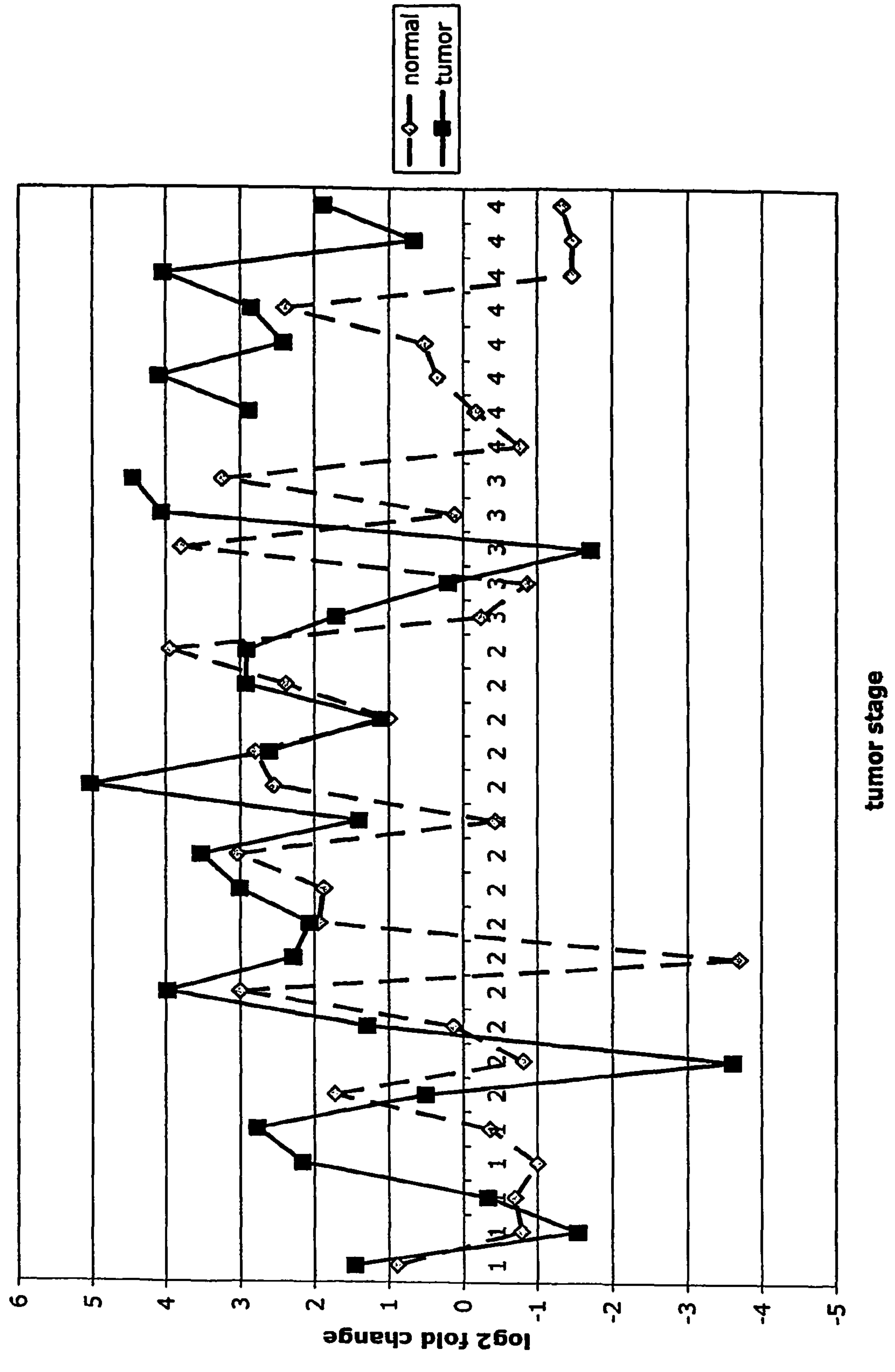

Fig. 10ab SERPINB5
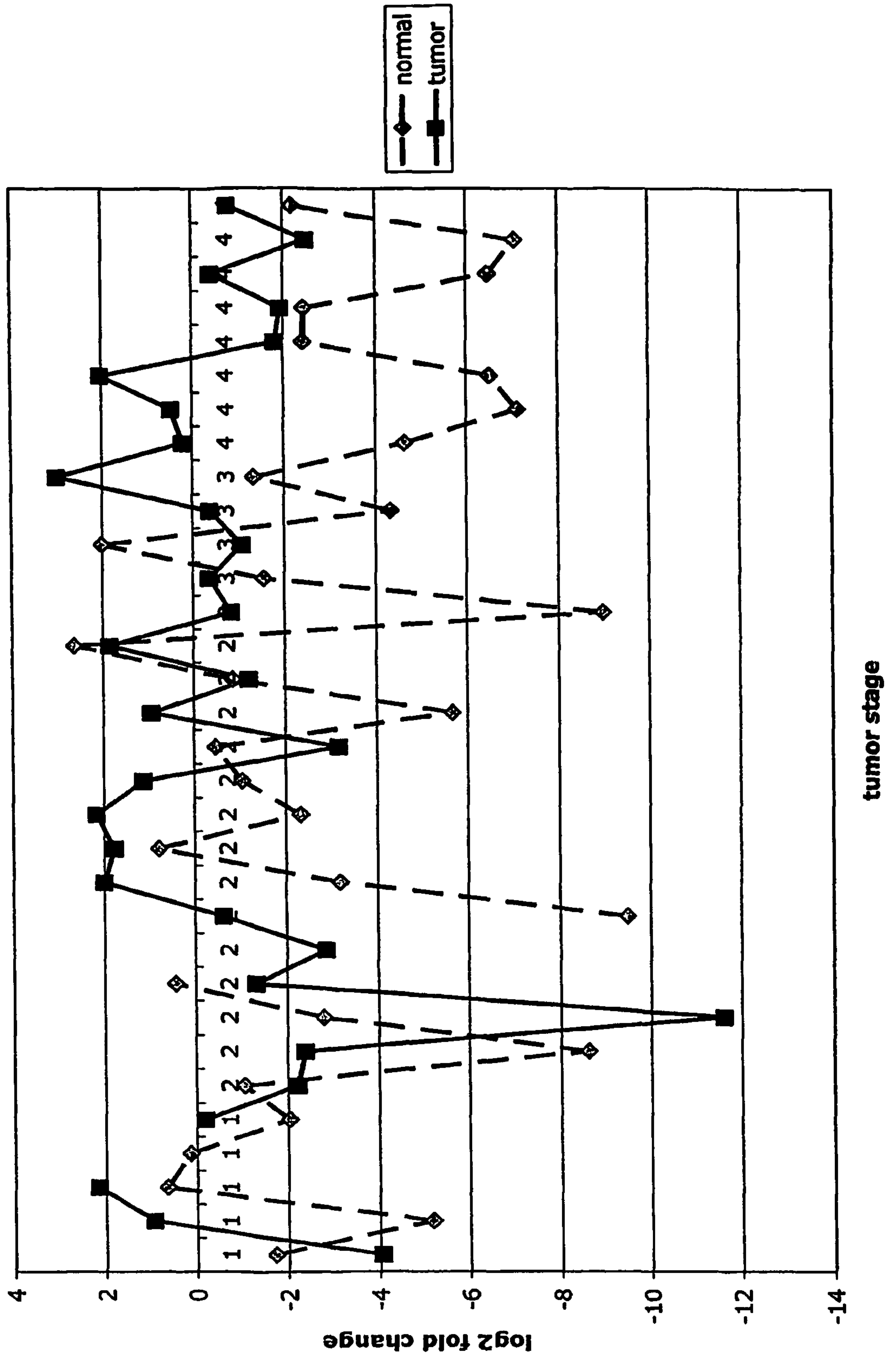

Fig. 10ac TGFb1
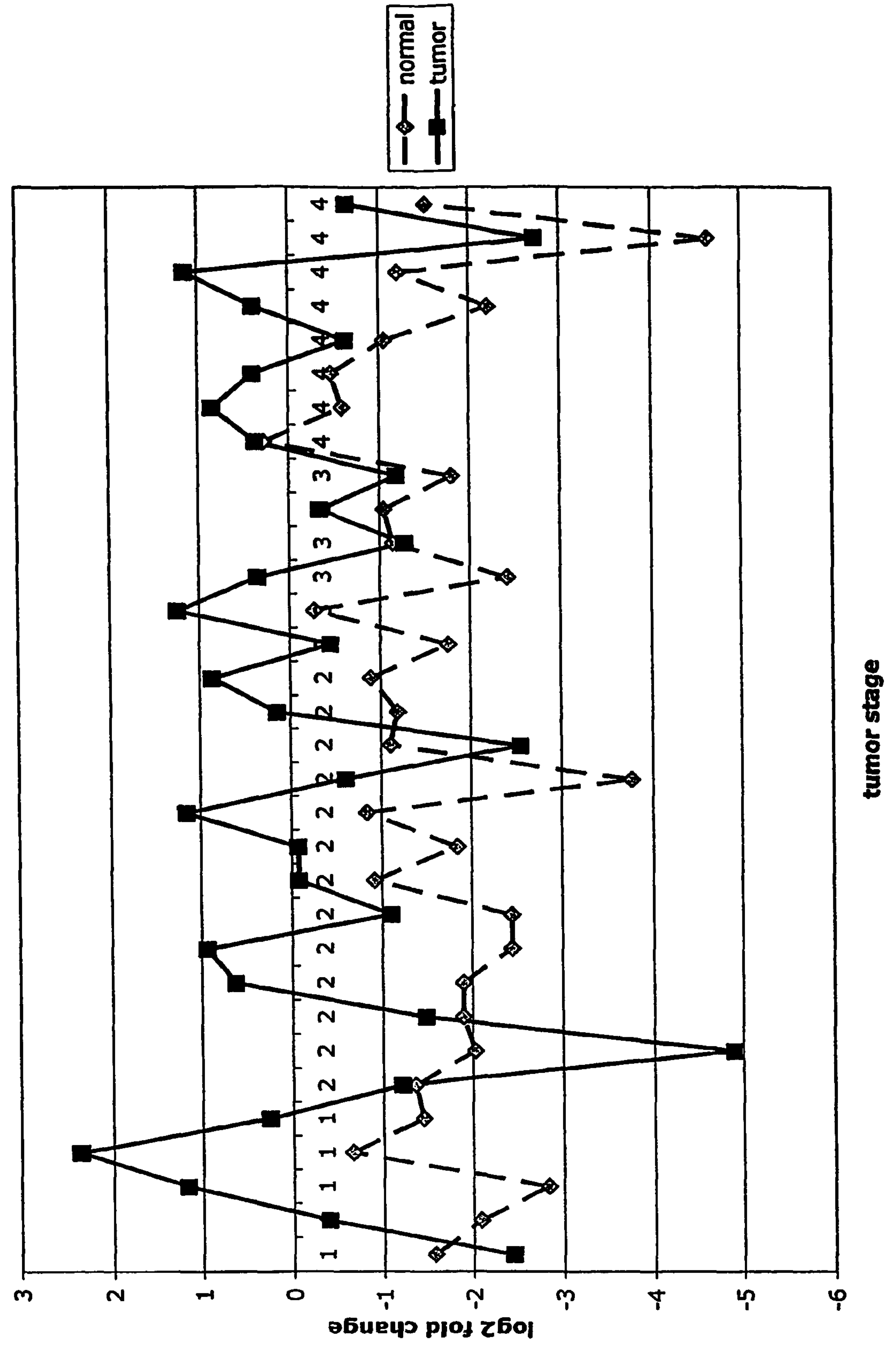

Fig. 10ad CEA
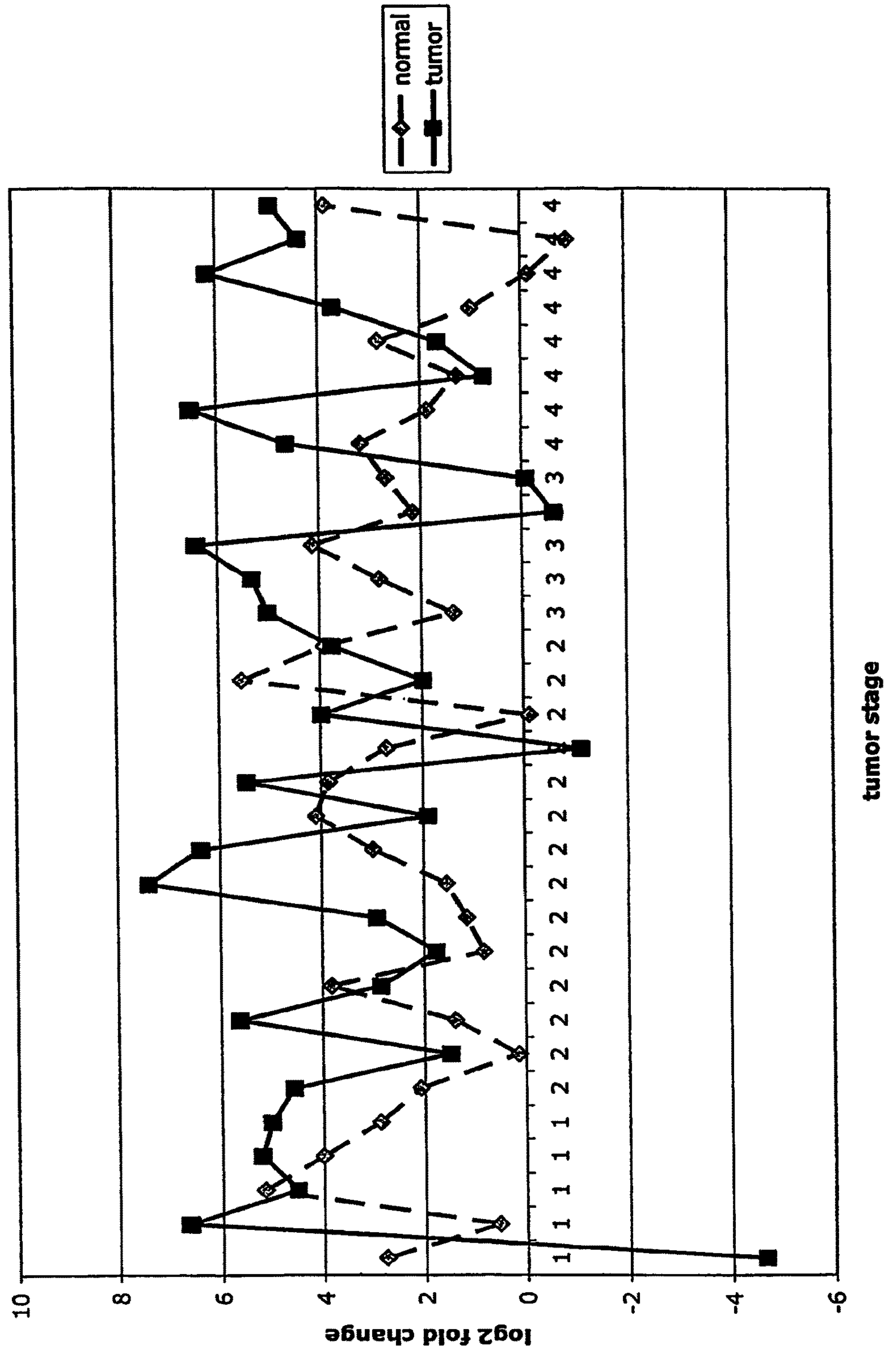

Fig. 11a Adlican
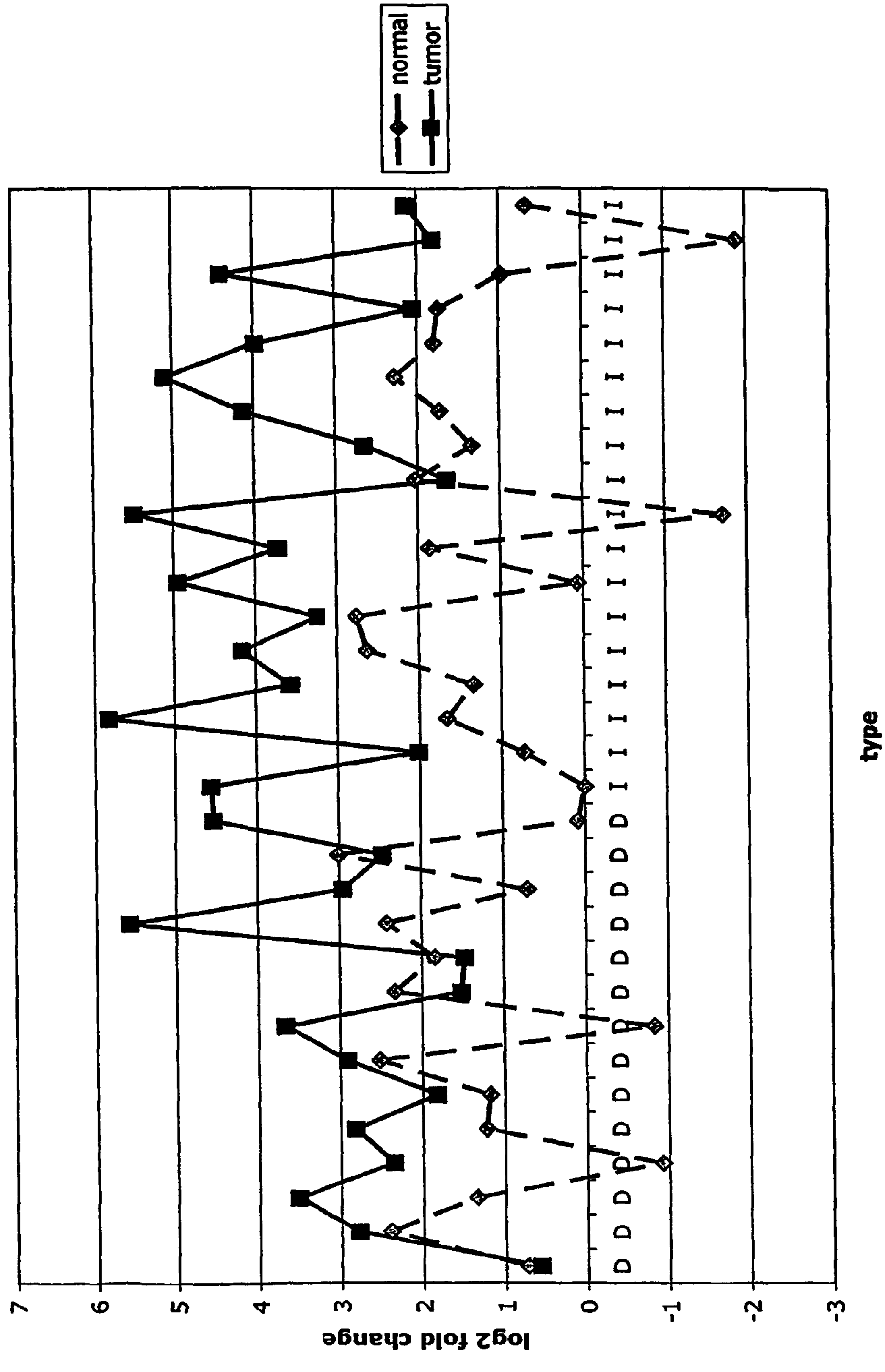

Fig. 11b ASPN
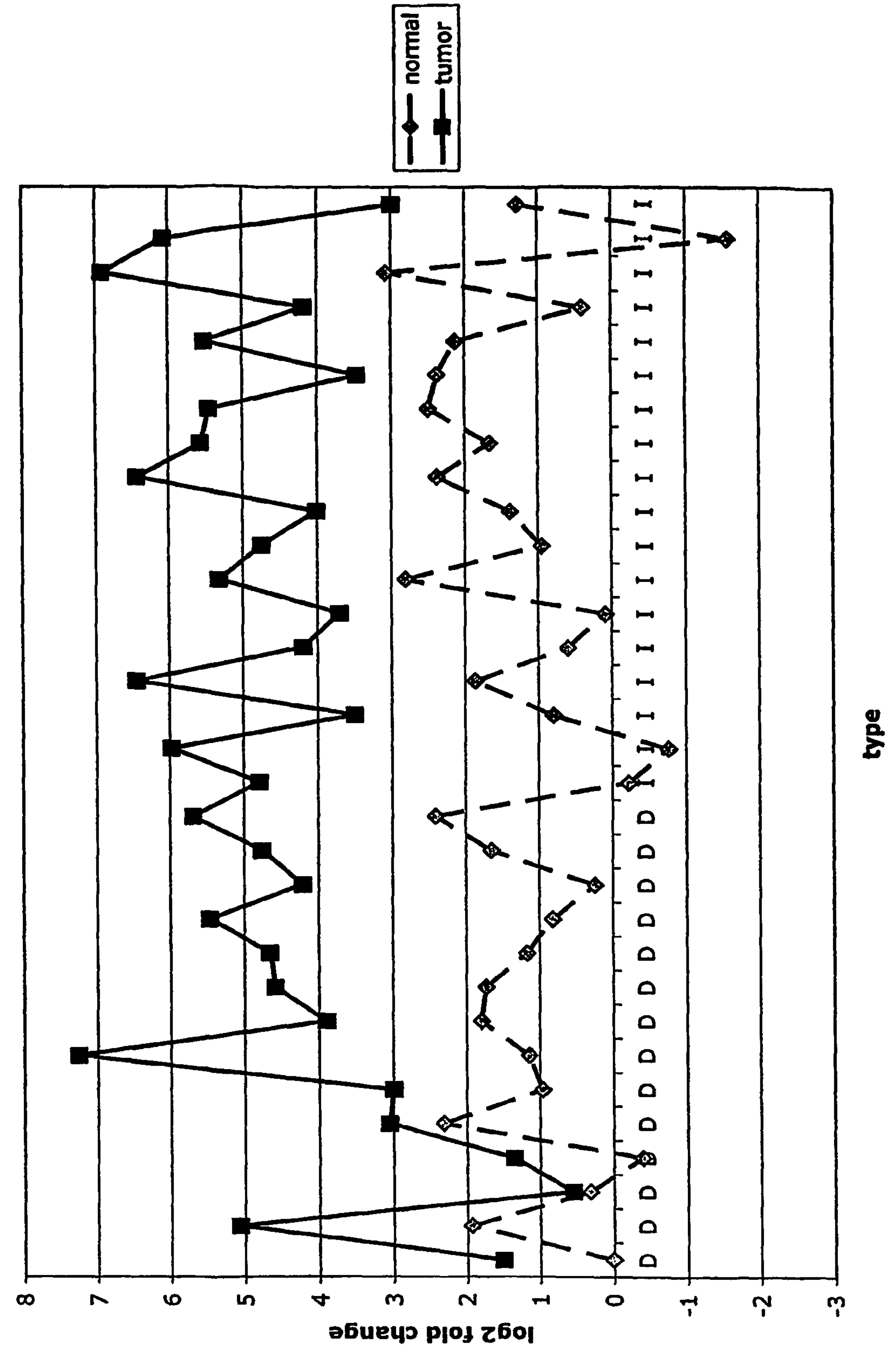

Fig. 11c CSPG2
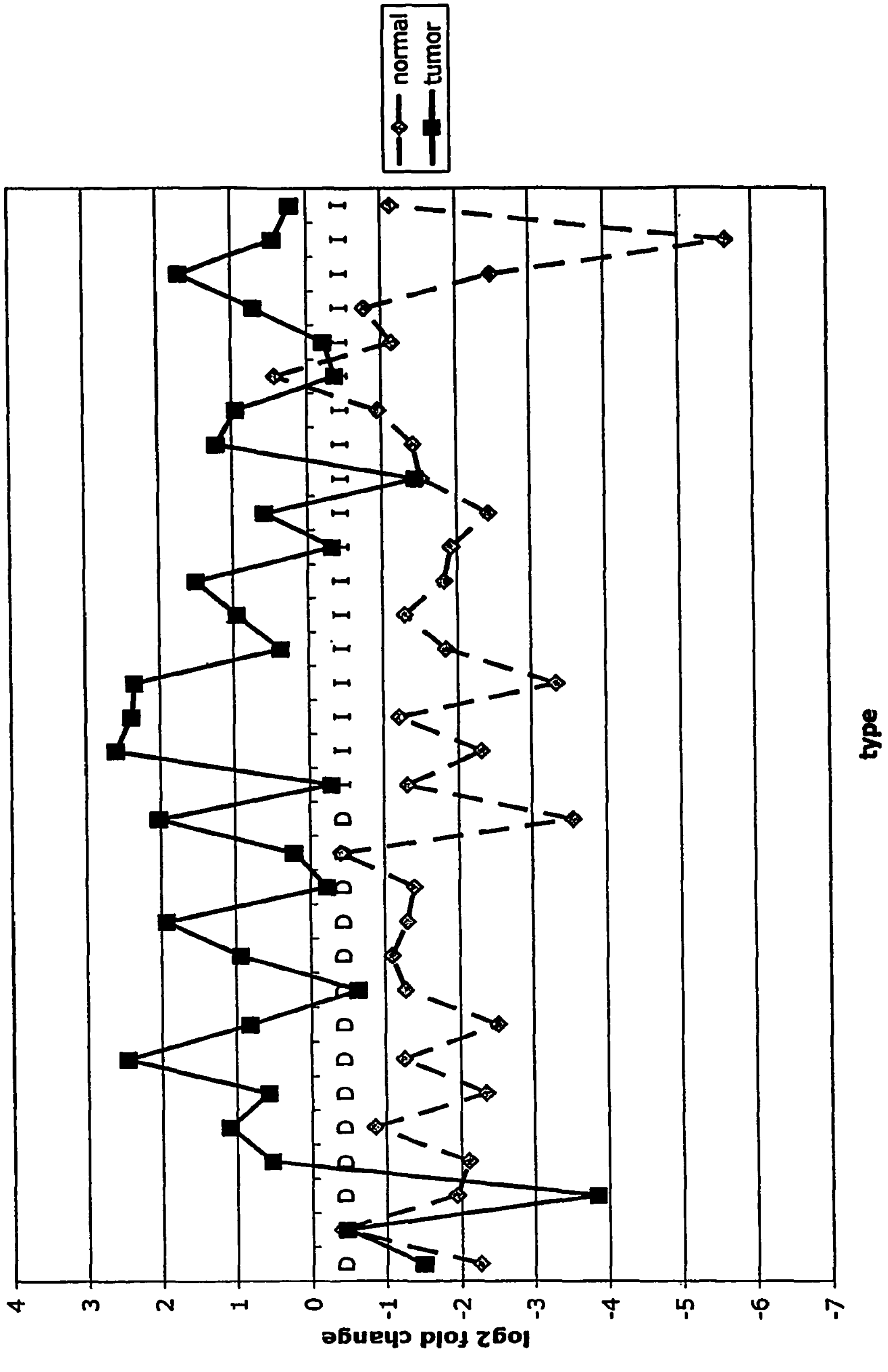

Fig. 11d CST1,2,4
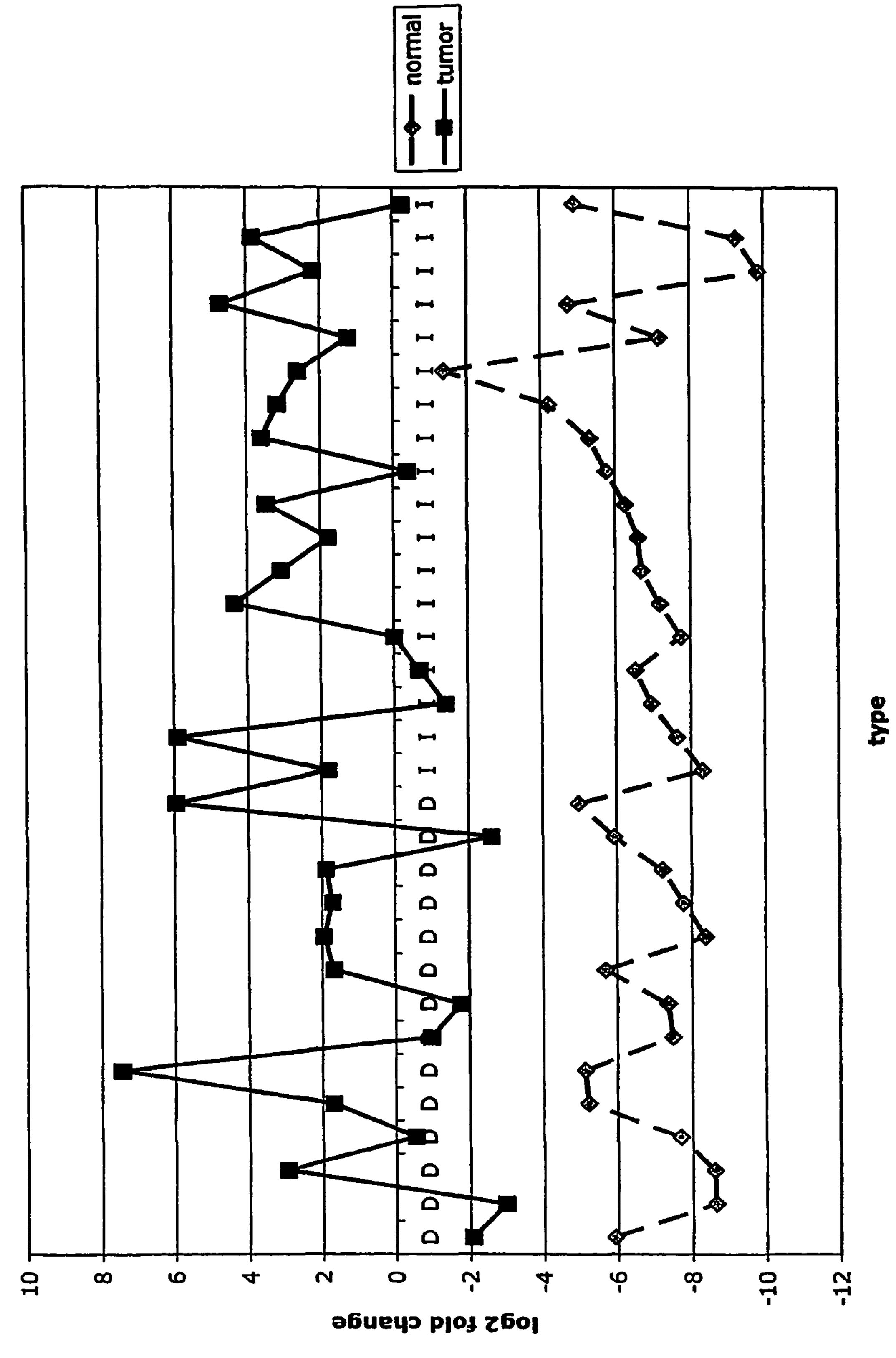

Fig. 11e EFEMP2
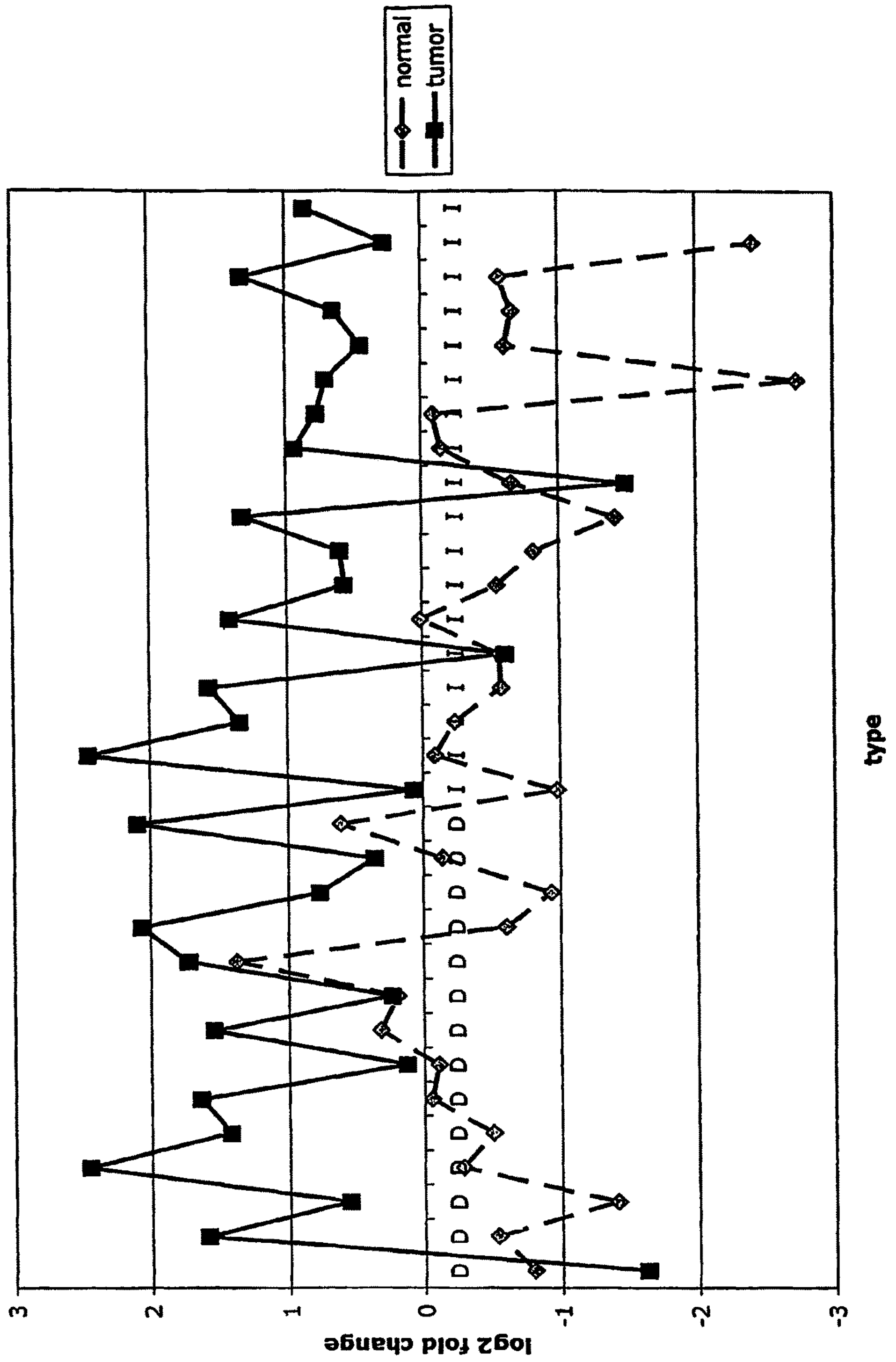

Fig. 11f GGH
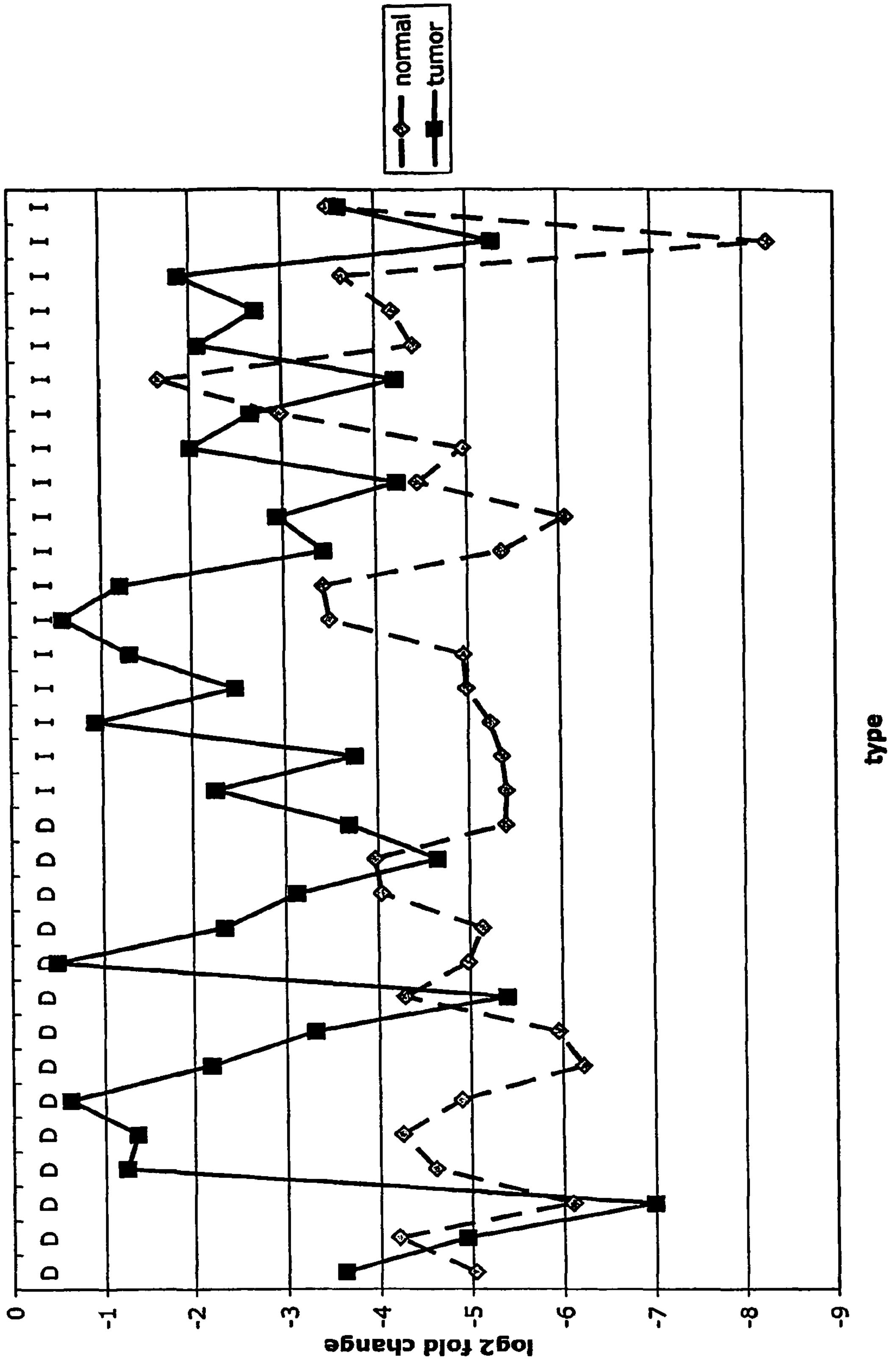

Fig. 11g INHBA
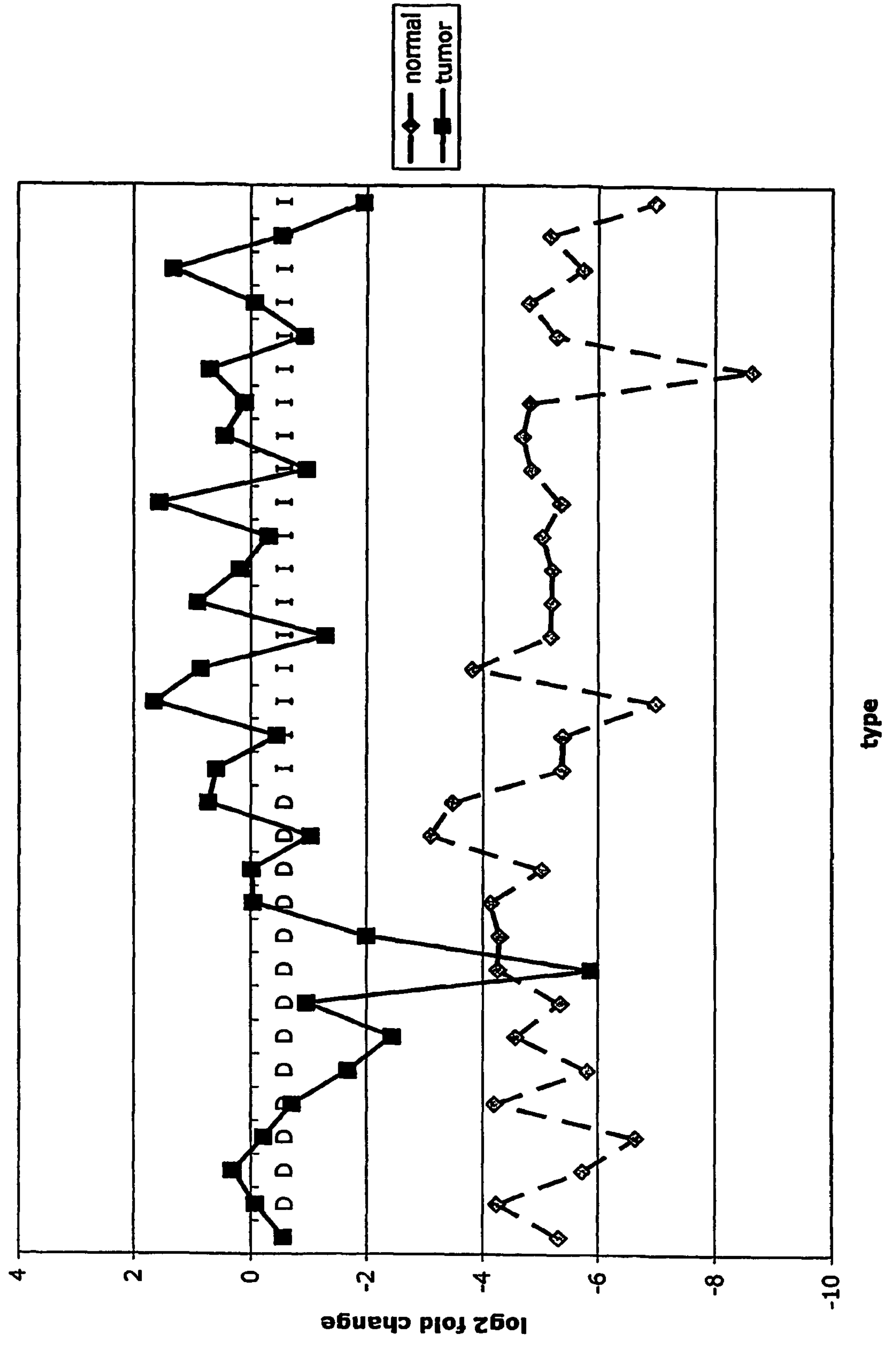

Fig. 11h IGFBP7
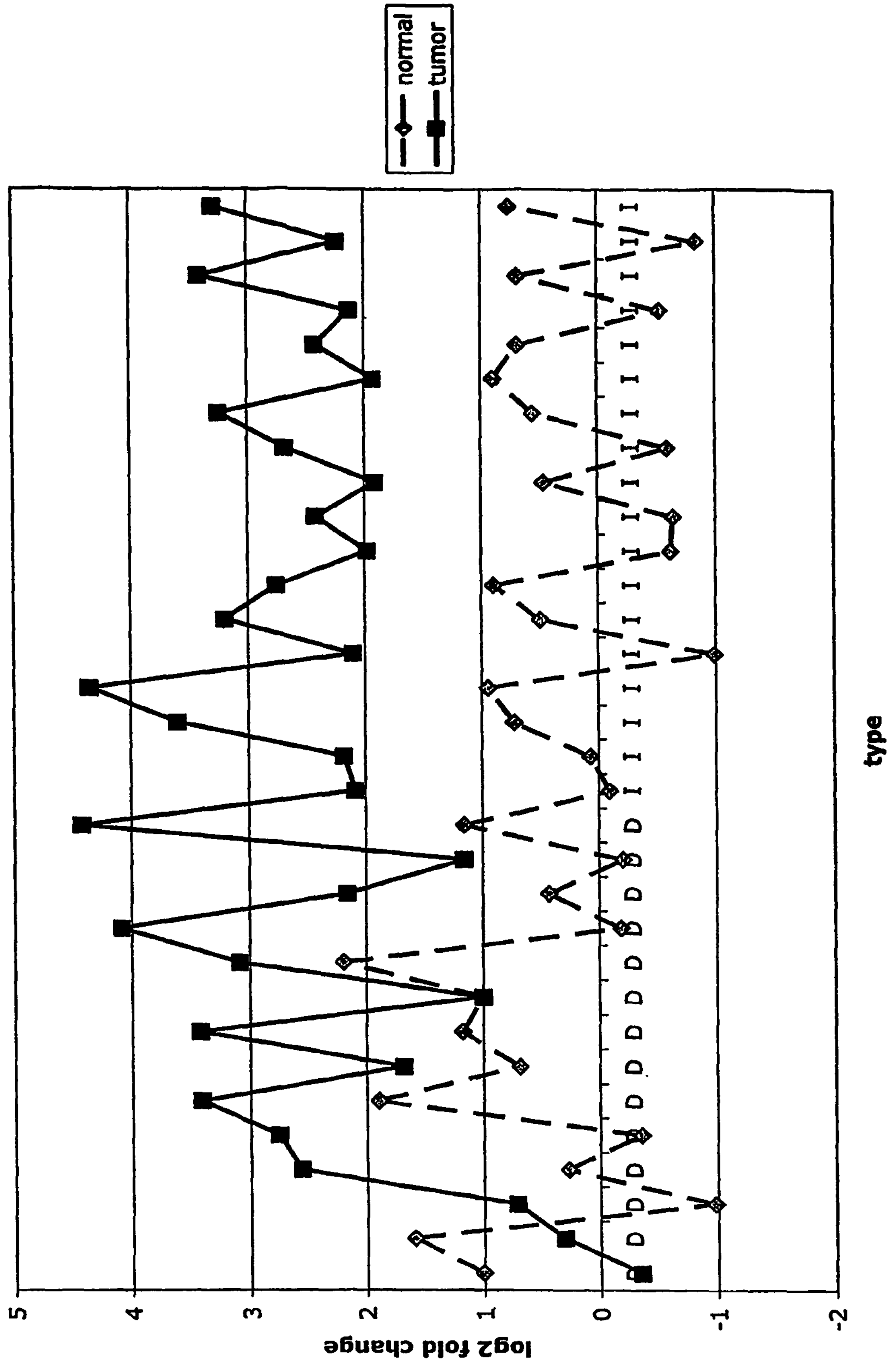

Fig. 11i KLK10
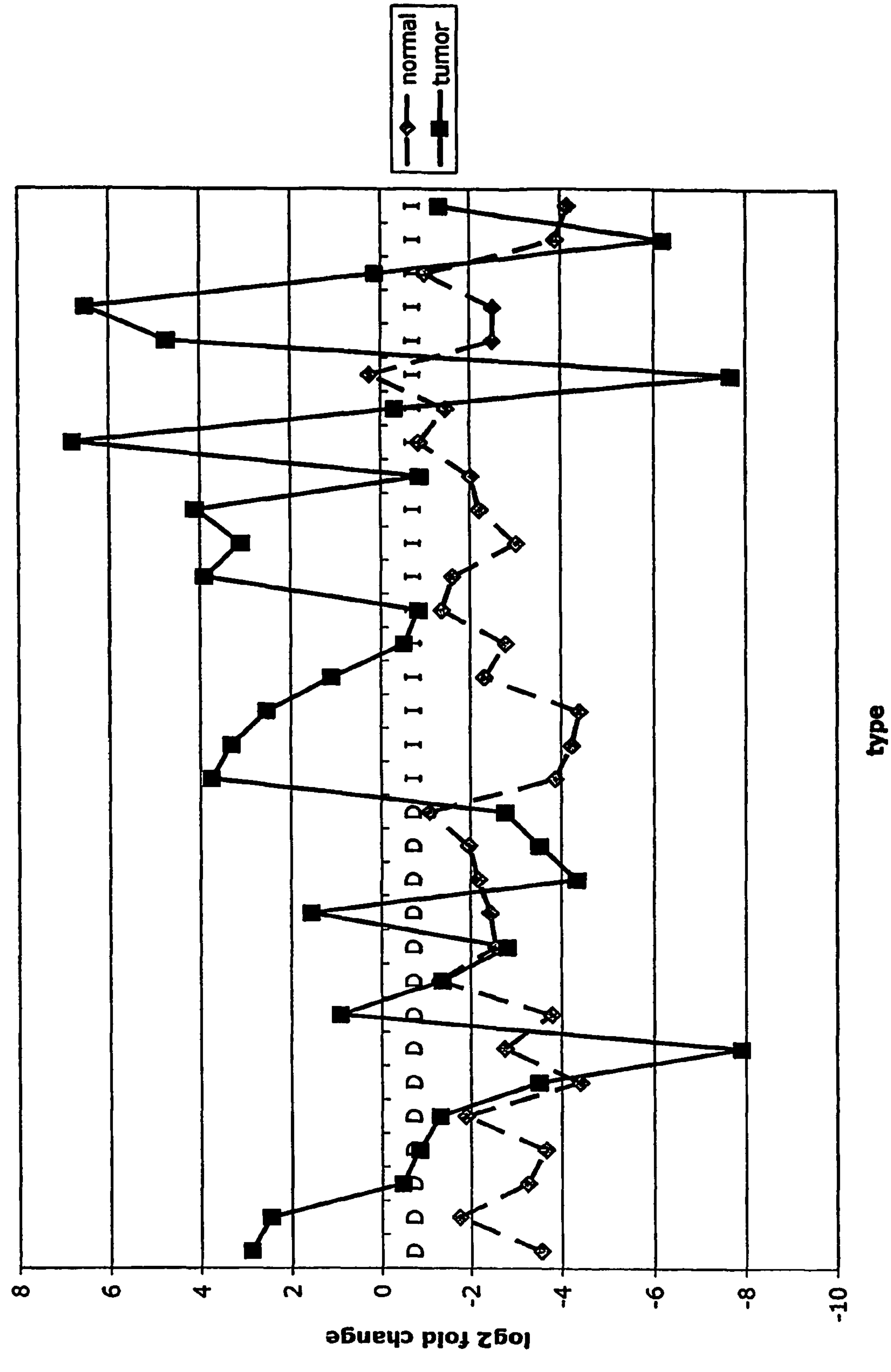

Fig. 11j LEPRE1
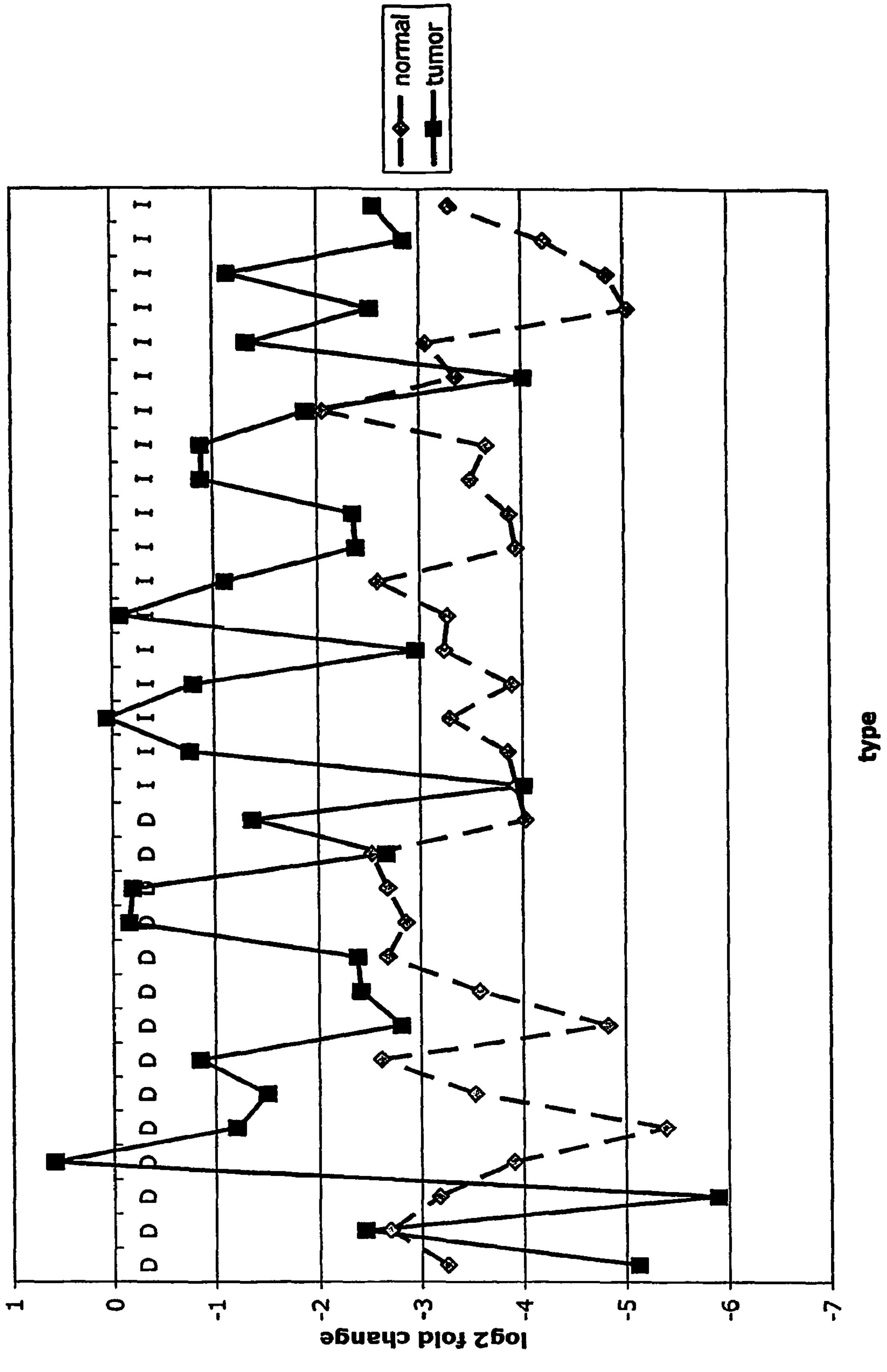

Fig. 11k LUM
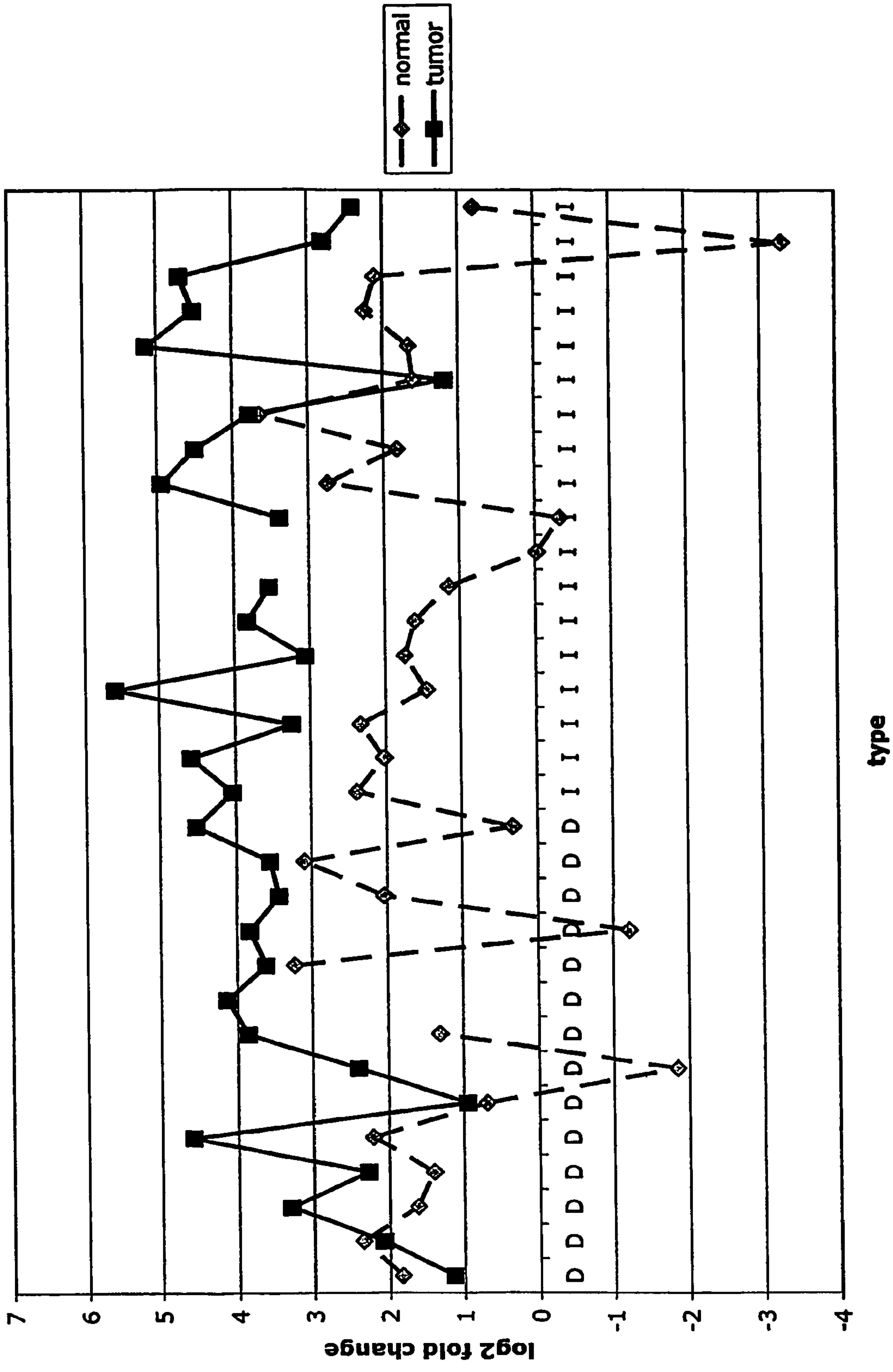

Fig. 11I LOXL2
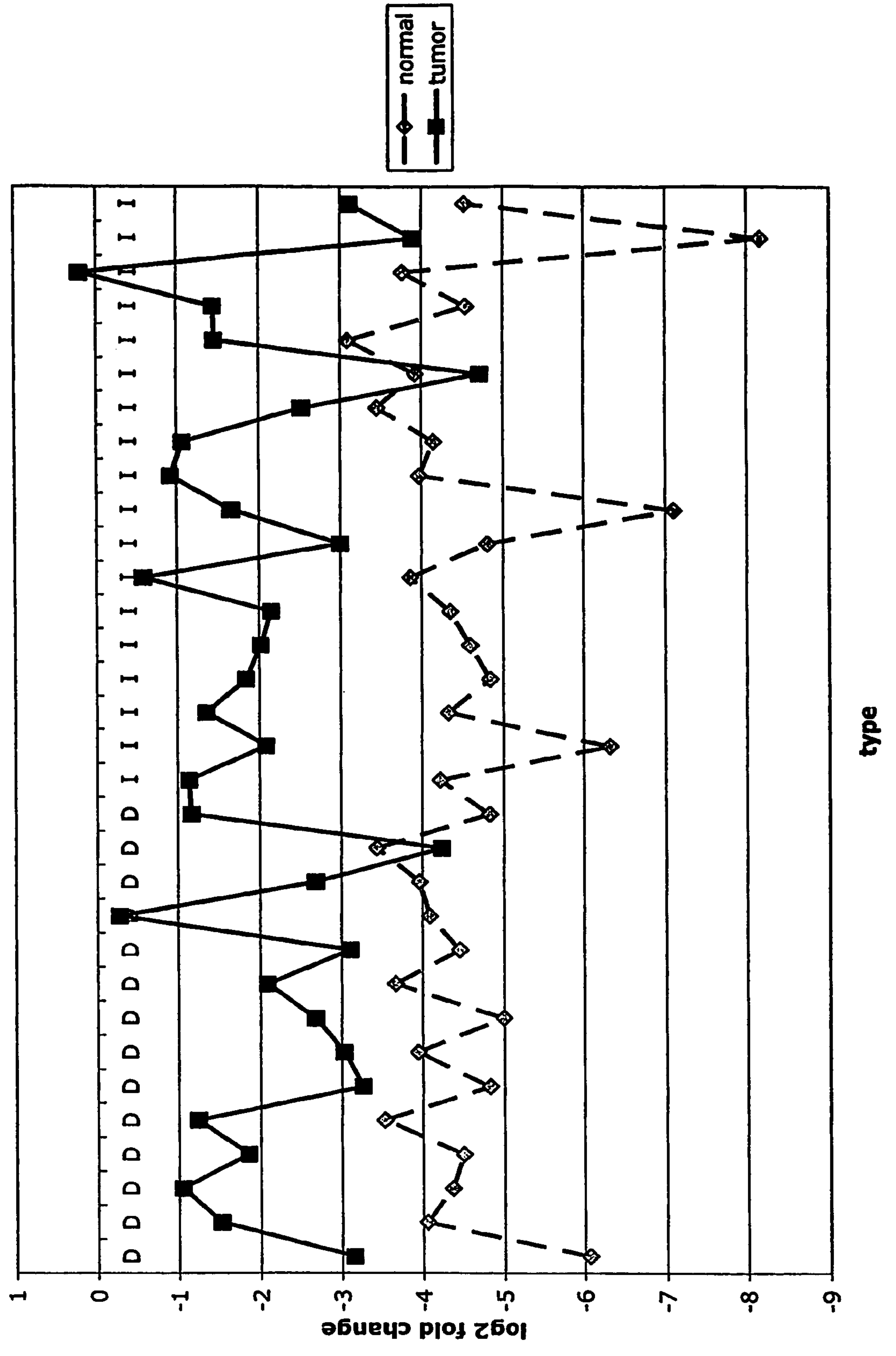

Fig. 11m MMP12
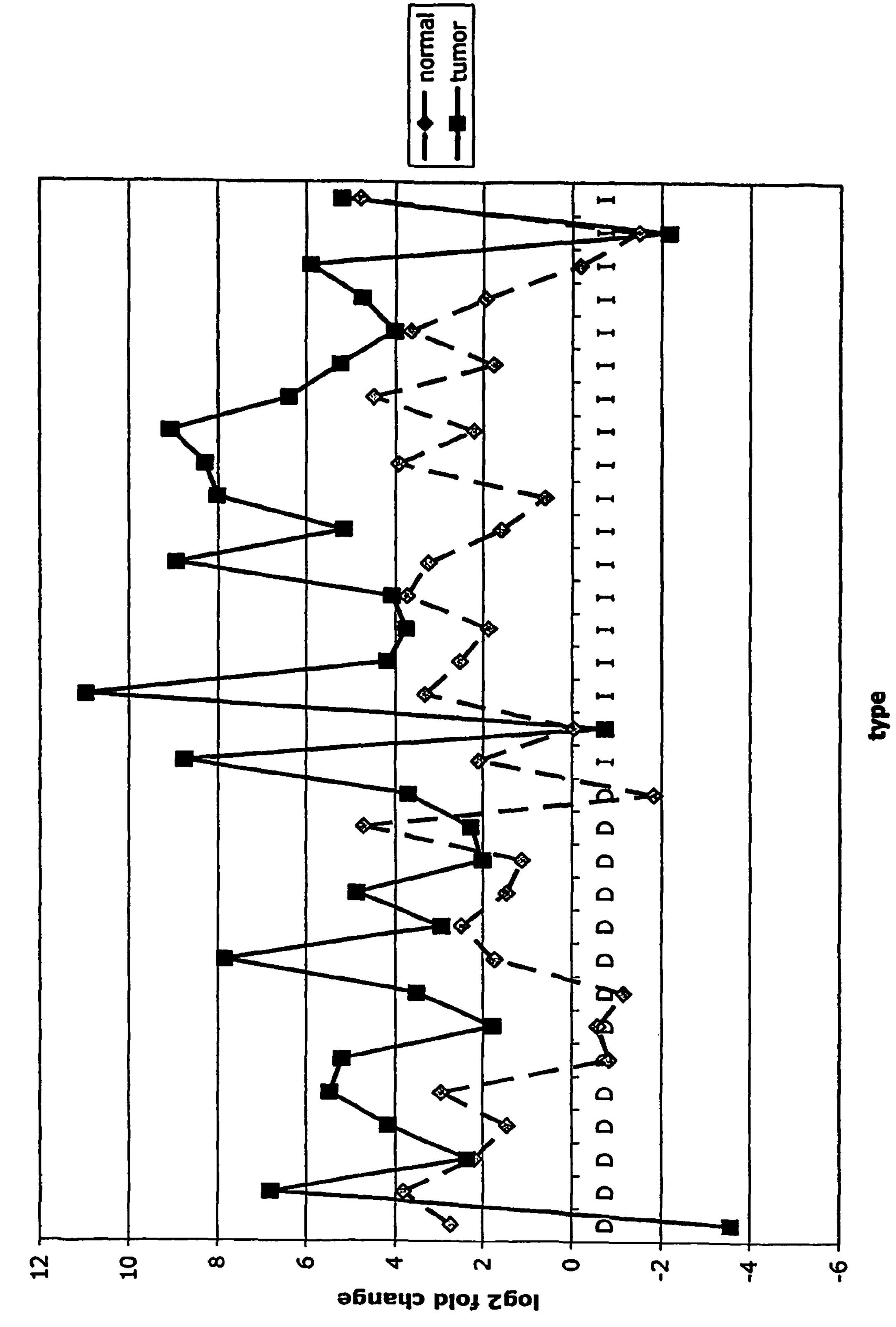

Fig. 11n TIMP1
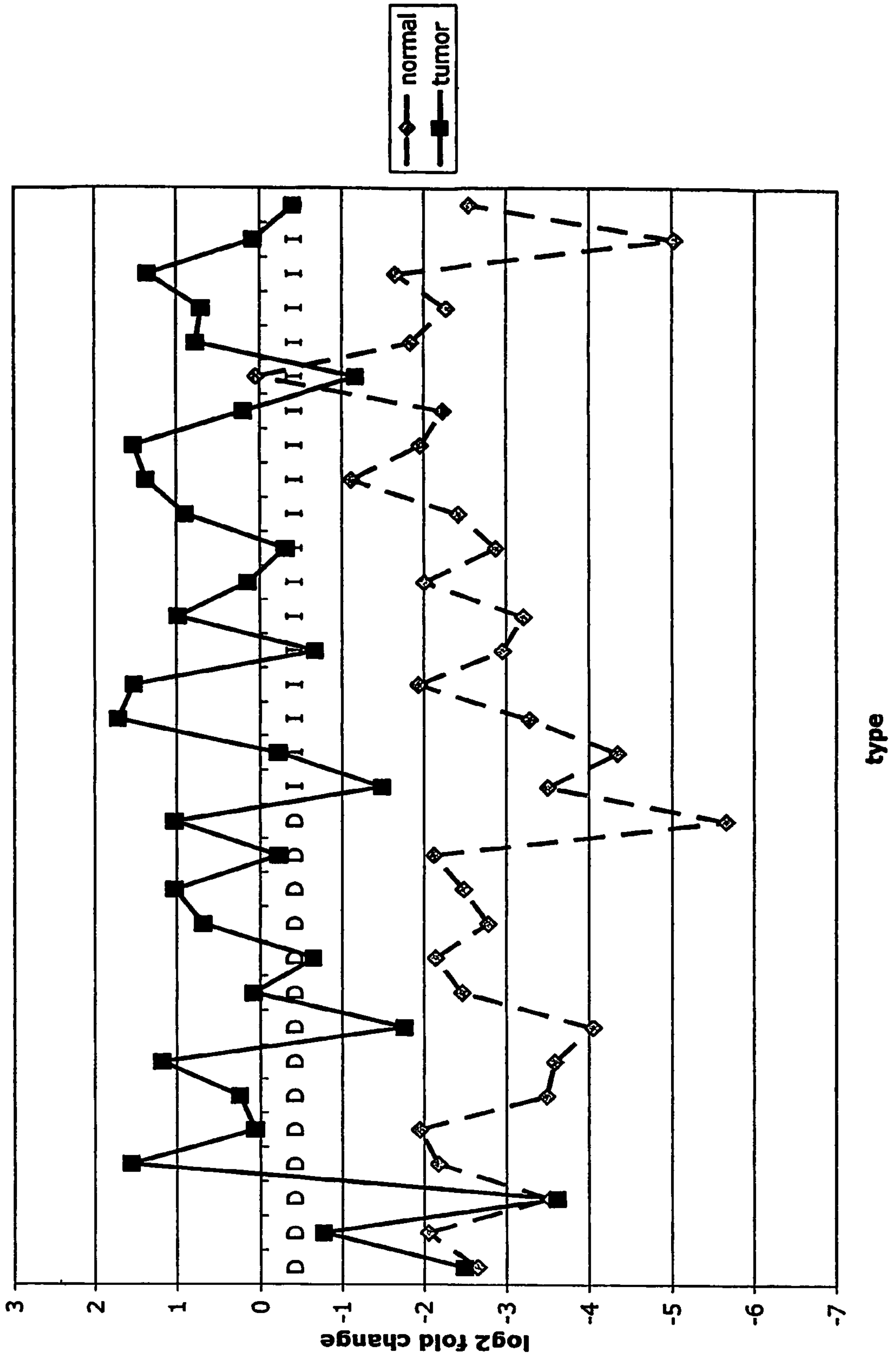

Fig. 11o ASAH1
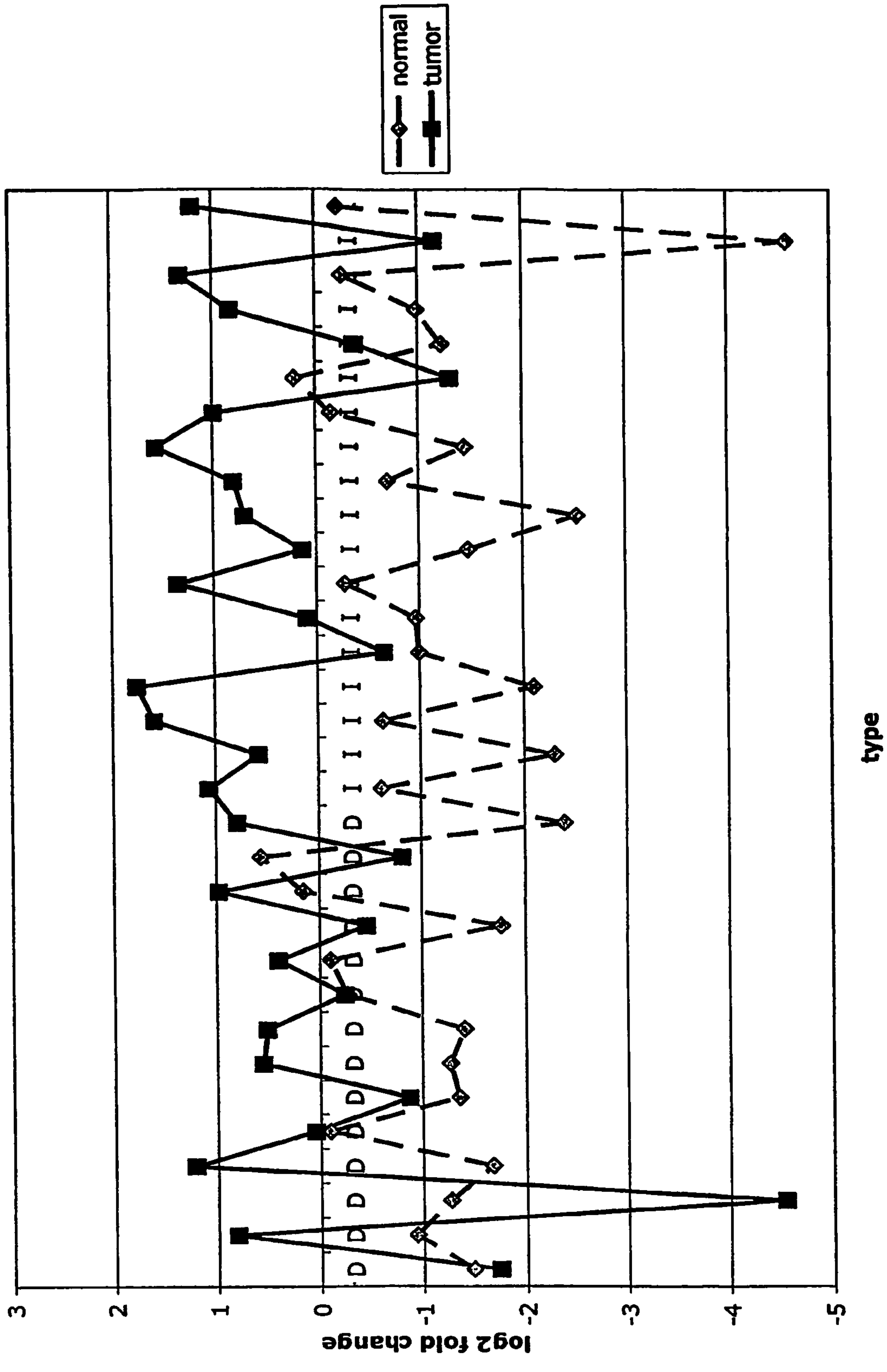

Fig. 11p SPP1
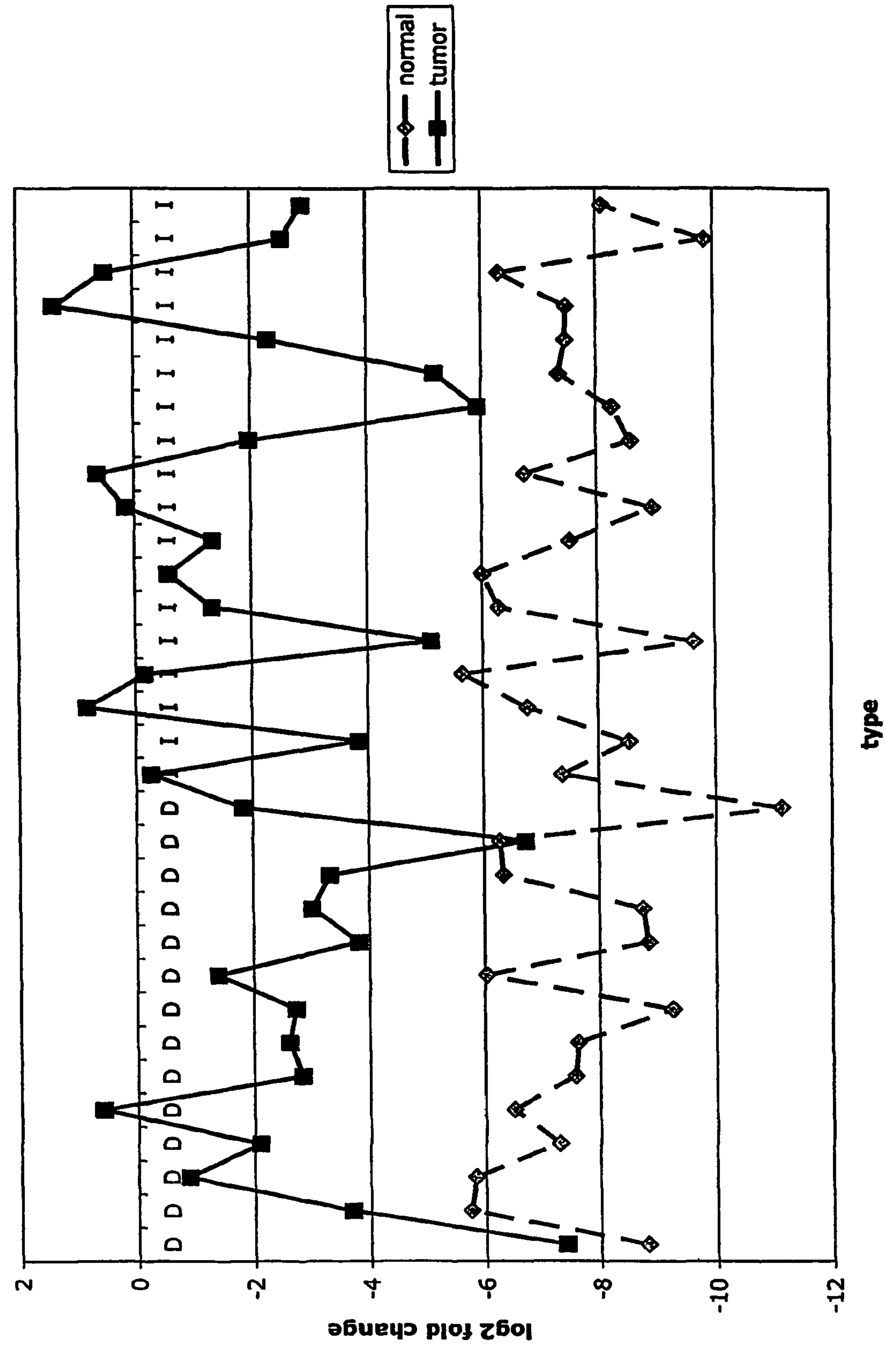

Fig. 11q SFRP2
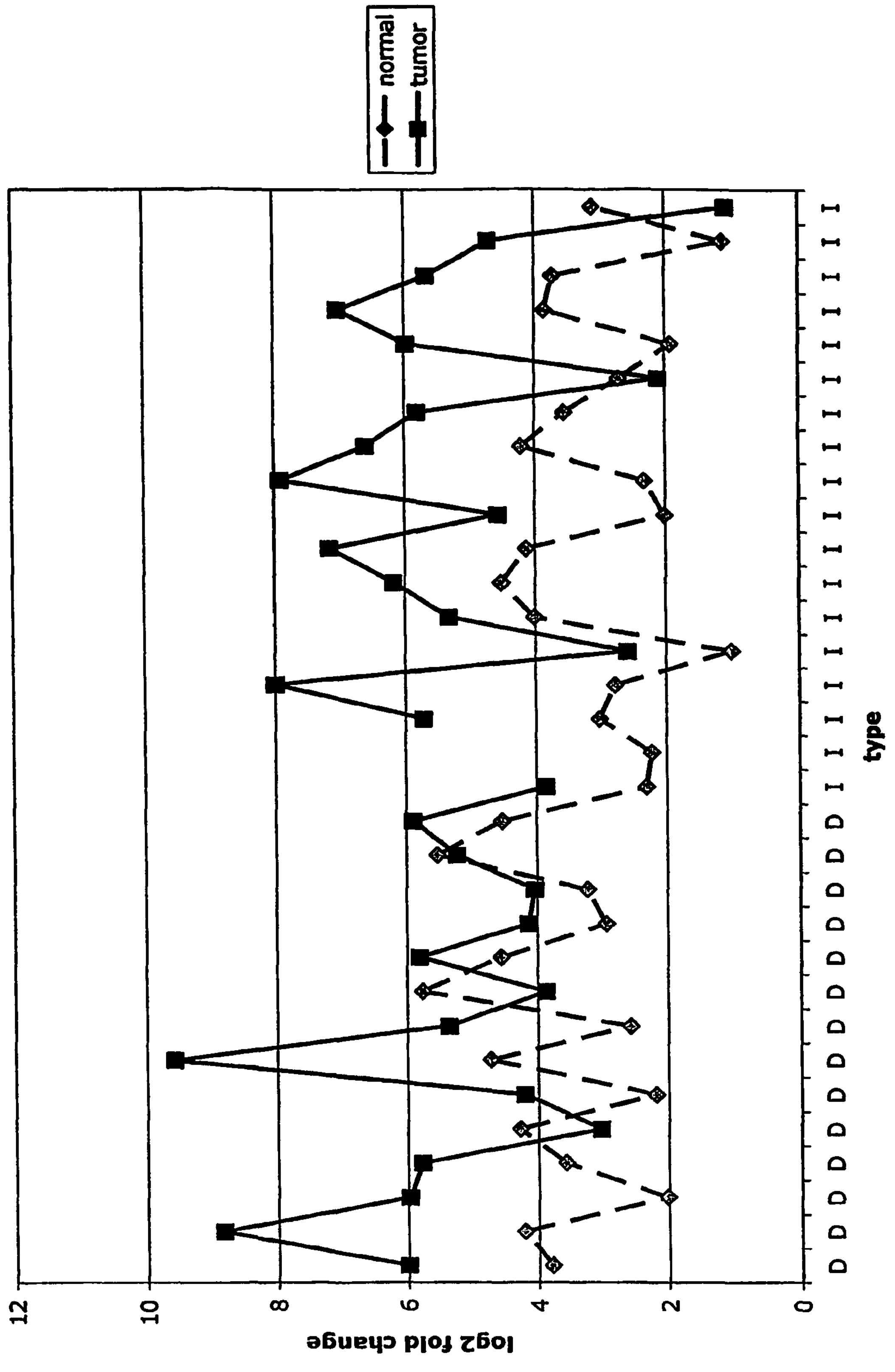

Fig. 11r SFRP4
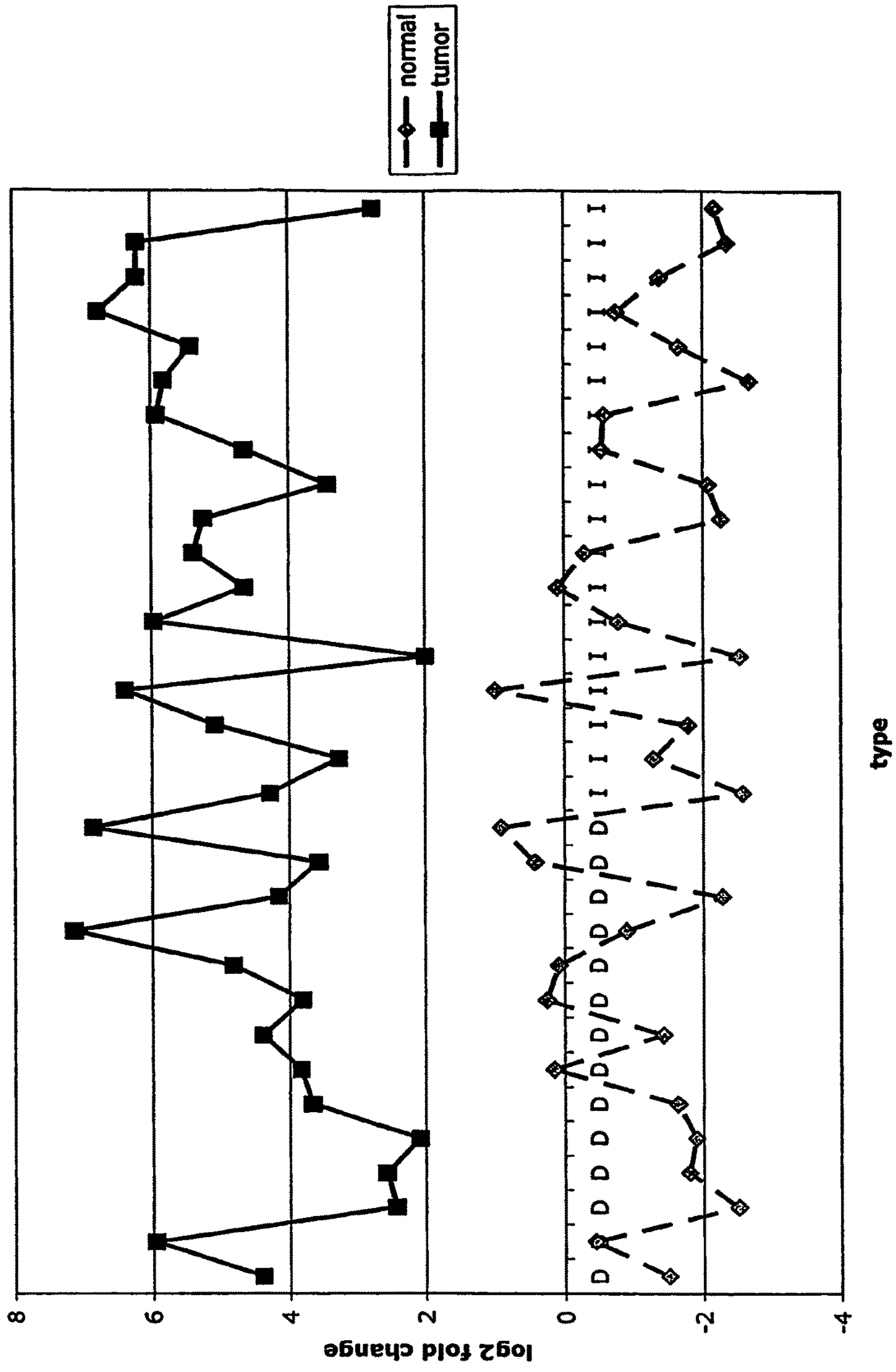

Fig. 11s SPARC
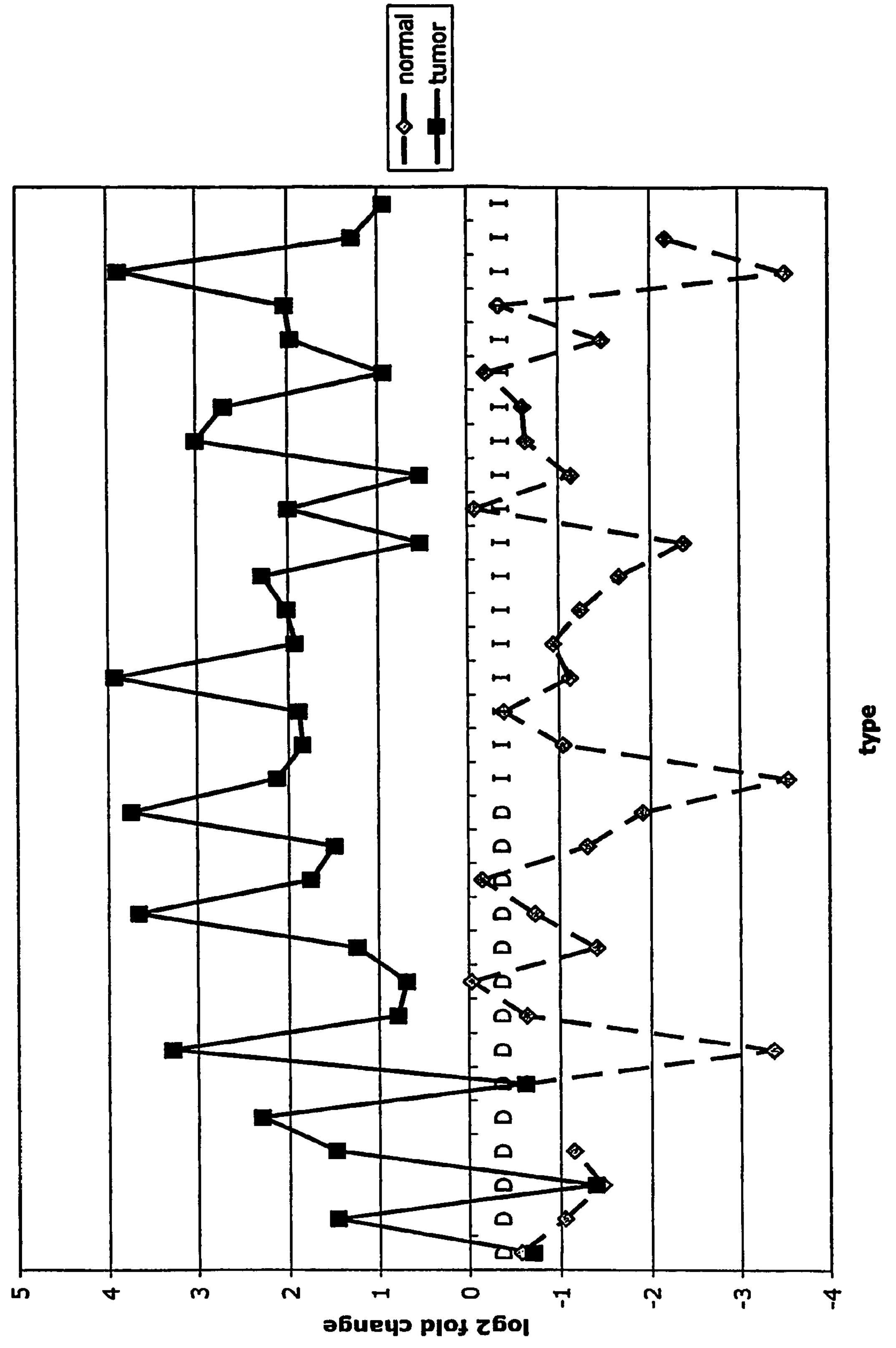

Fig. 11t PRSS11
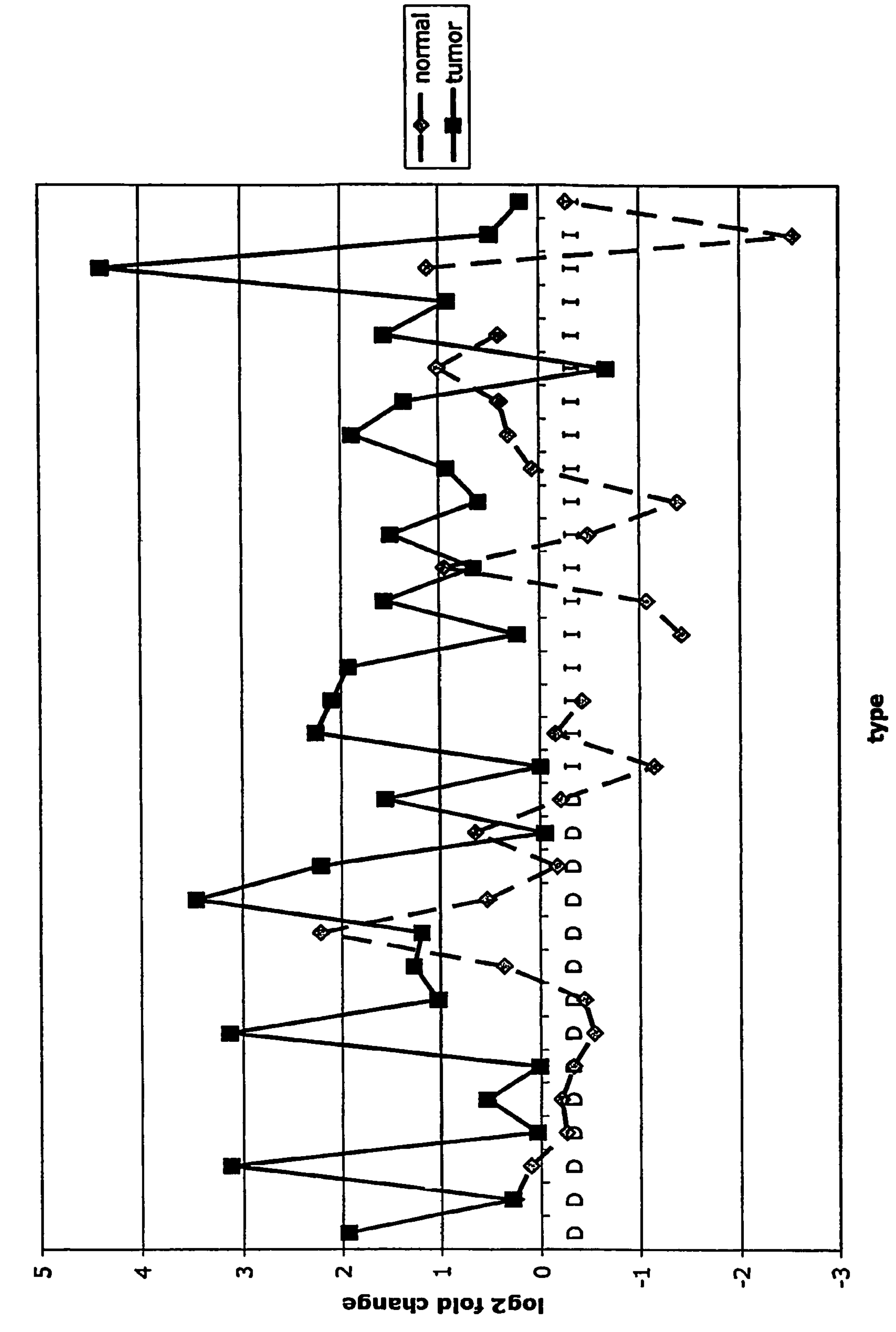

Fig. 11u THBS2
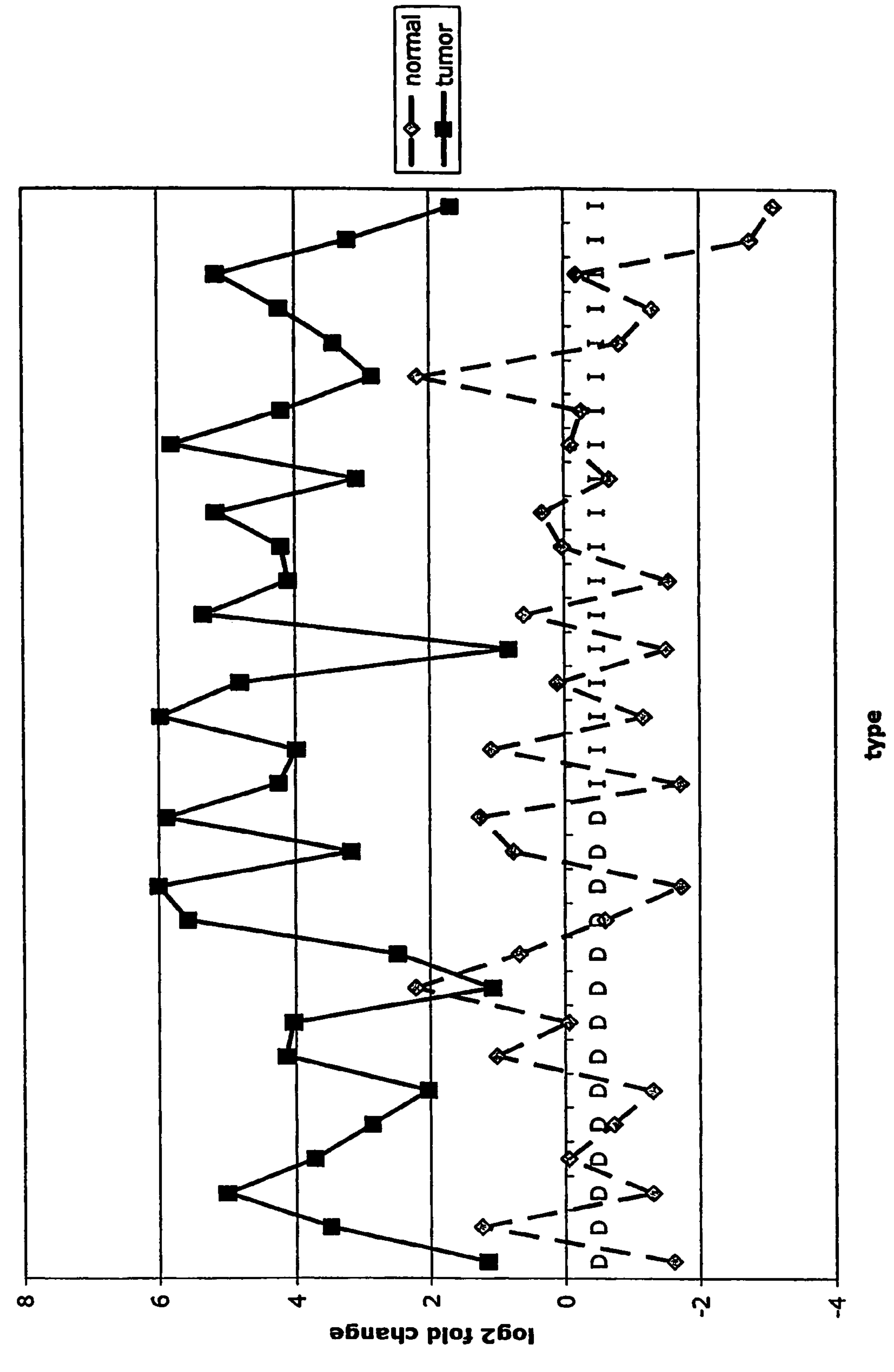

Fig. 11v TG
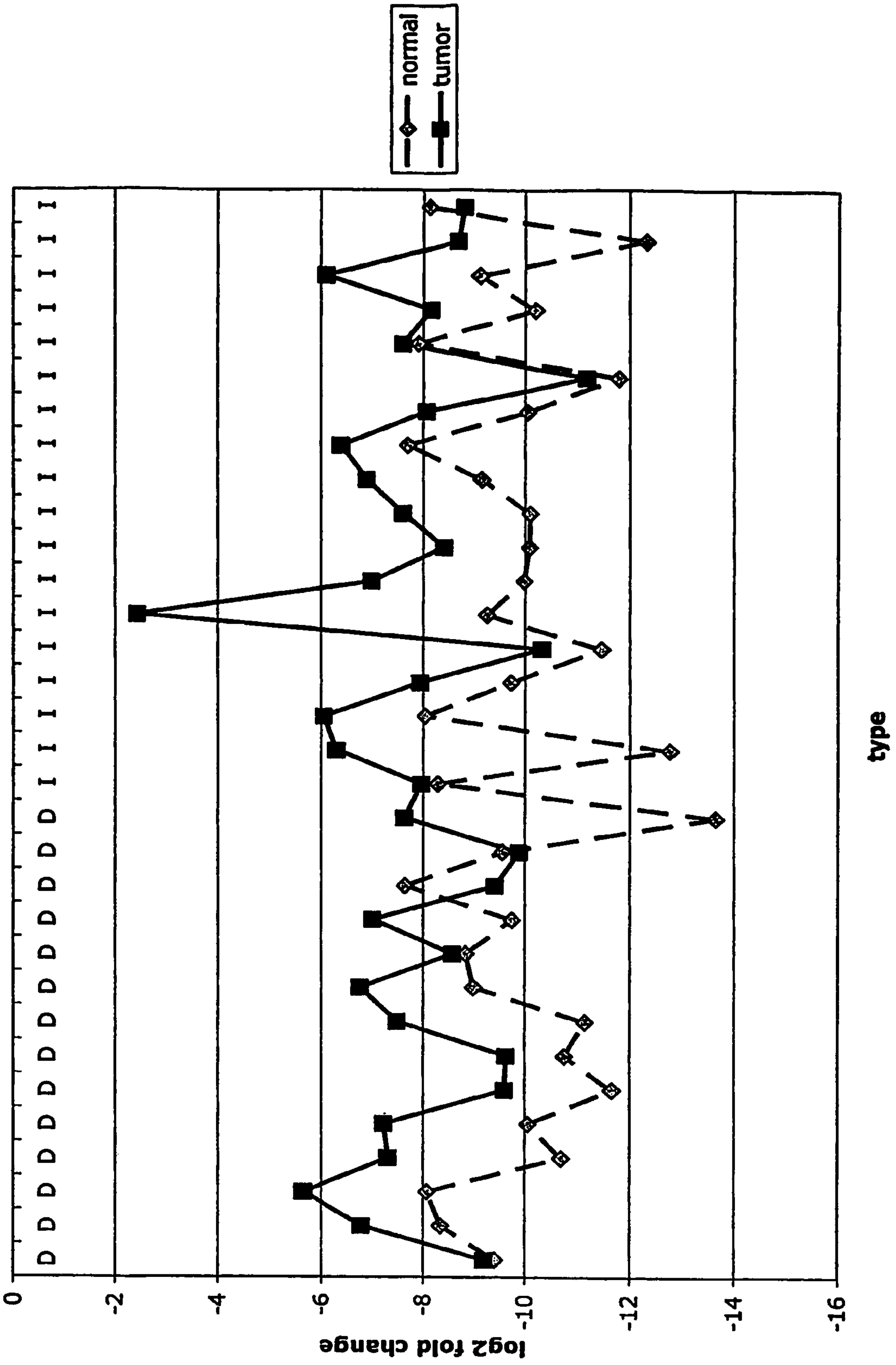

Fig. 11w TGFBI
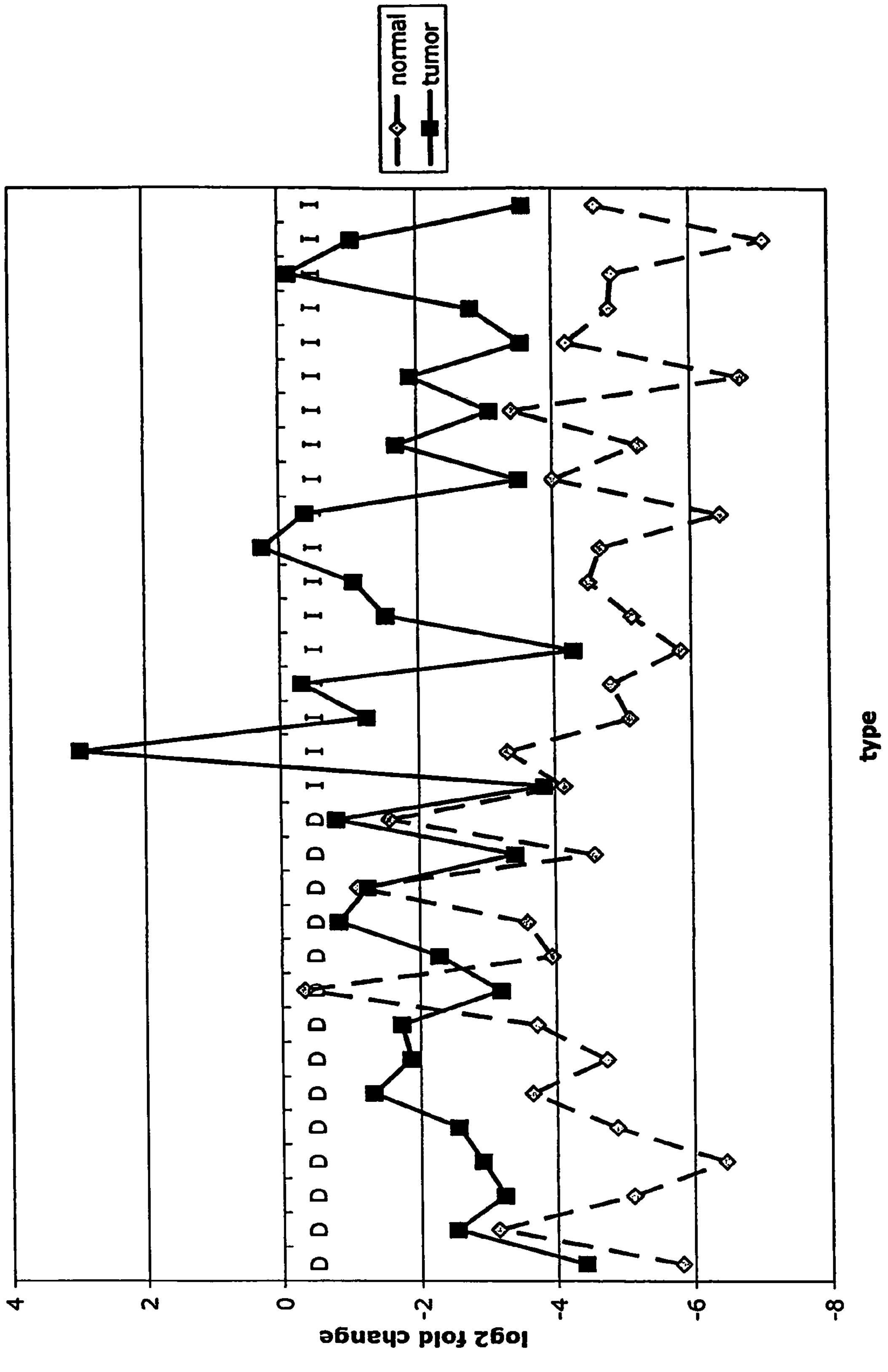

Fig. 11x CGR11
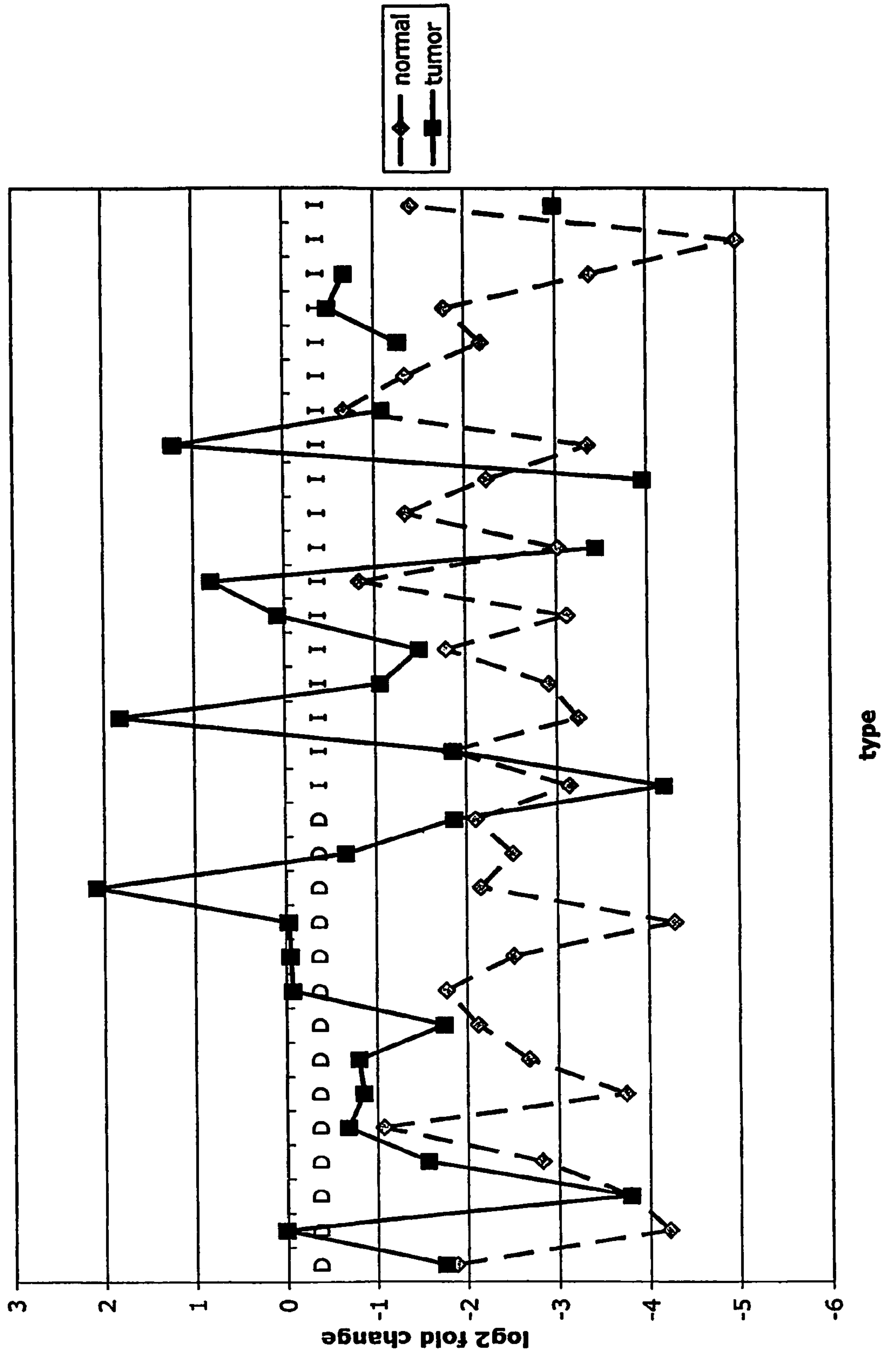

Fig. 11y SERPINH1
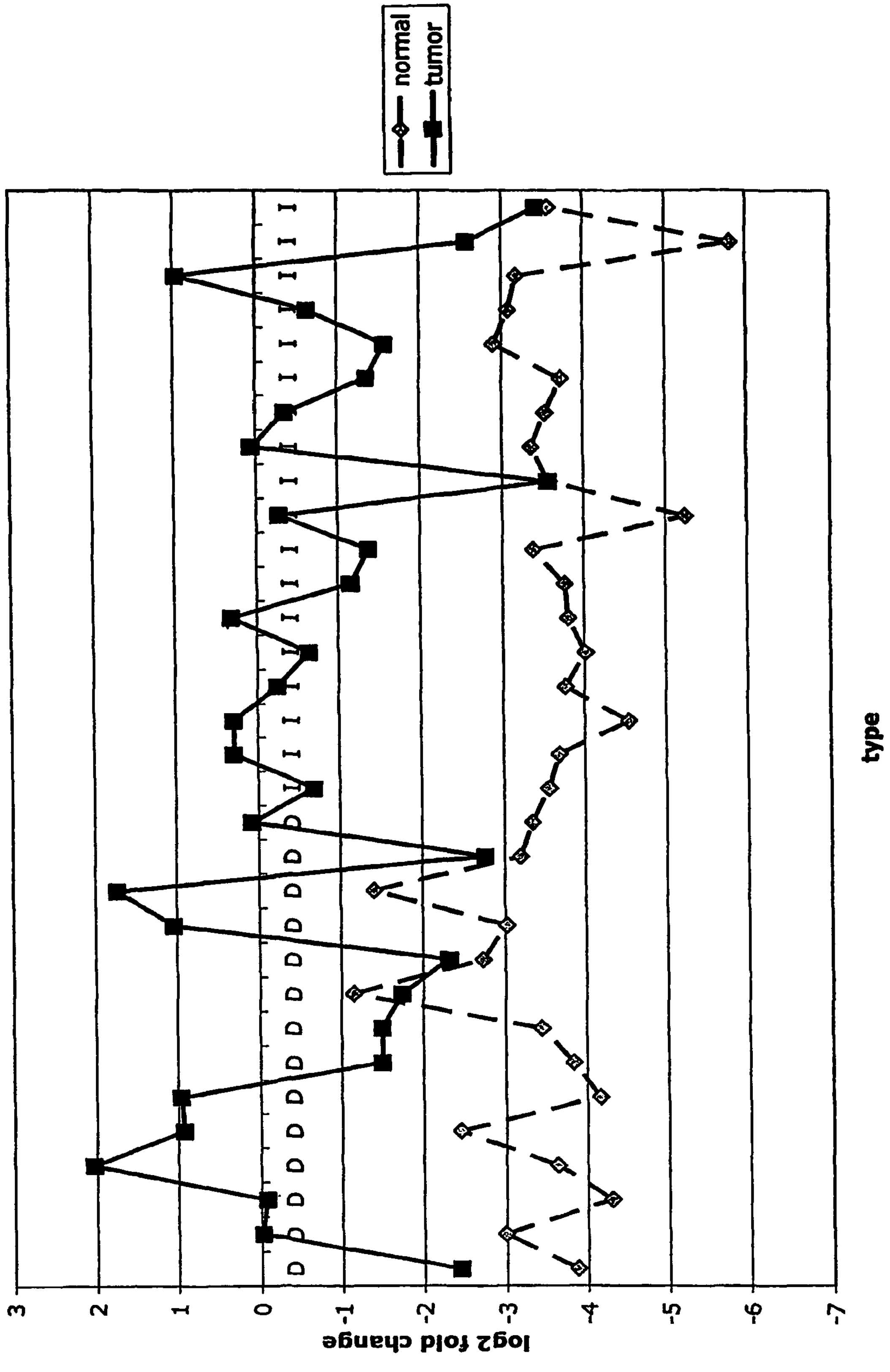

Fig. 11z MMP2
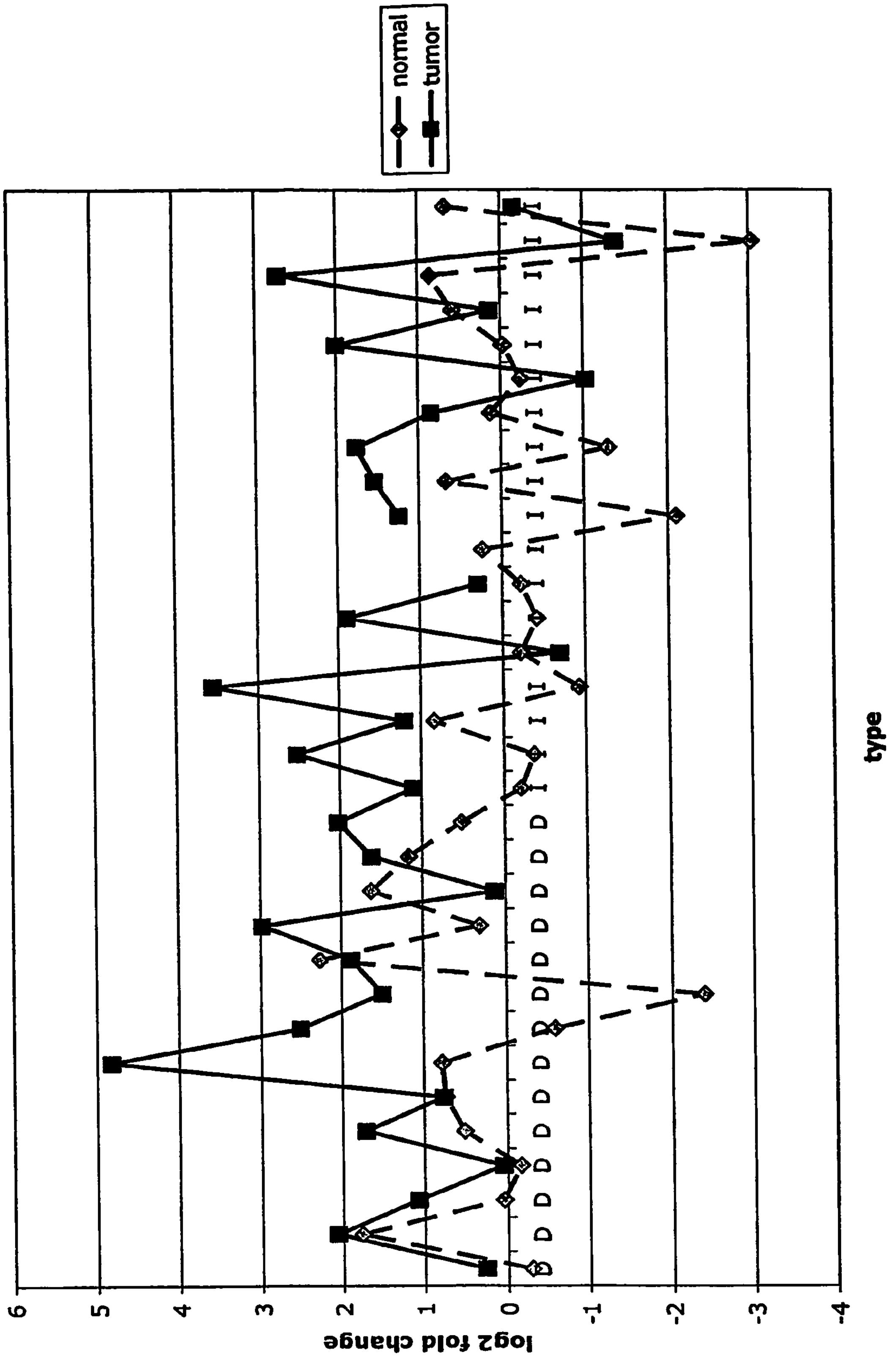

Fig. 11aa PCSK5
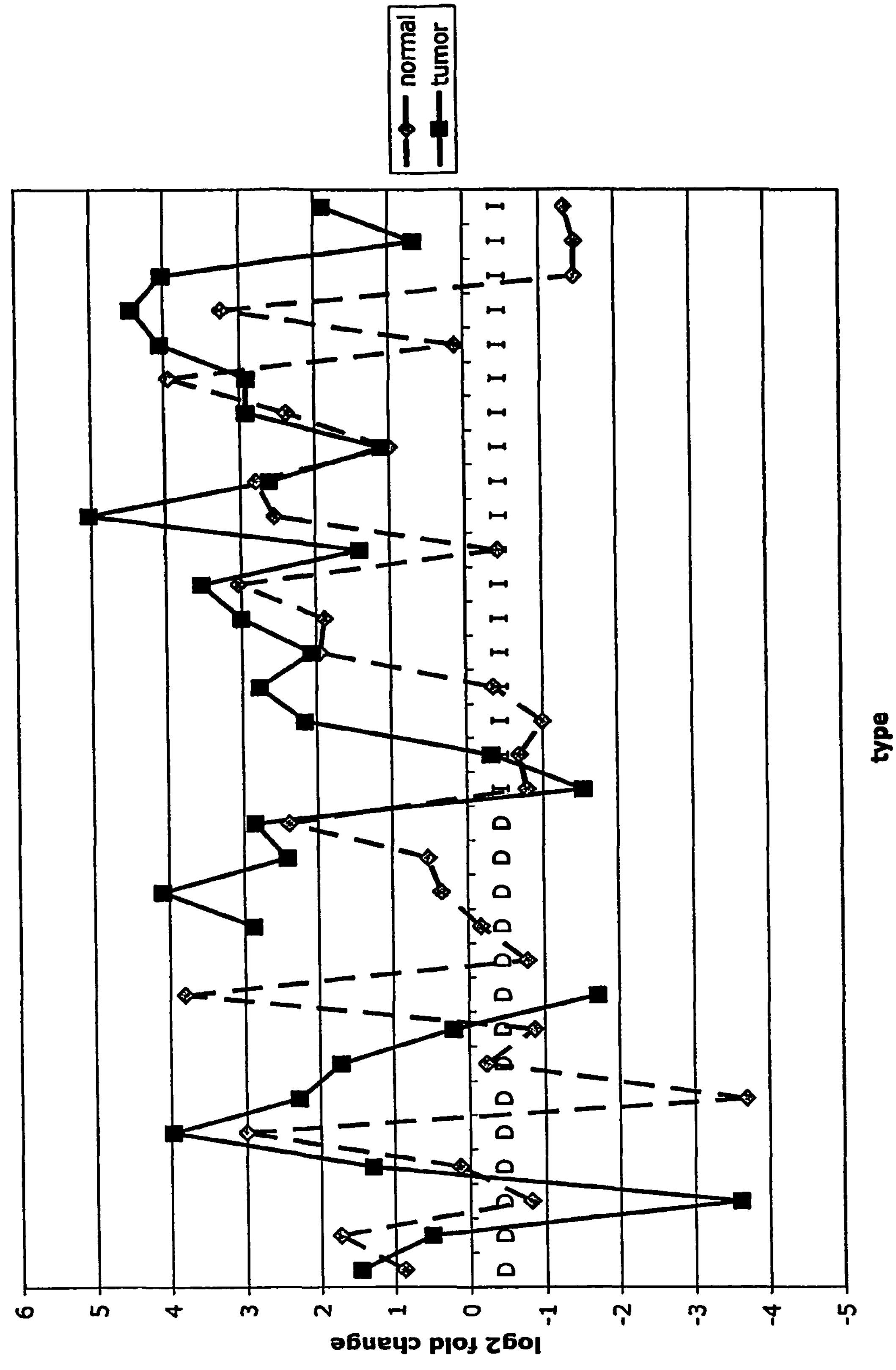

Fig. 11ab SERPINB5
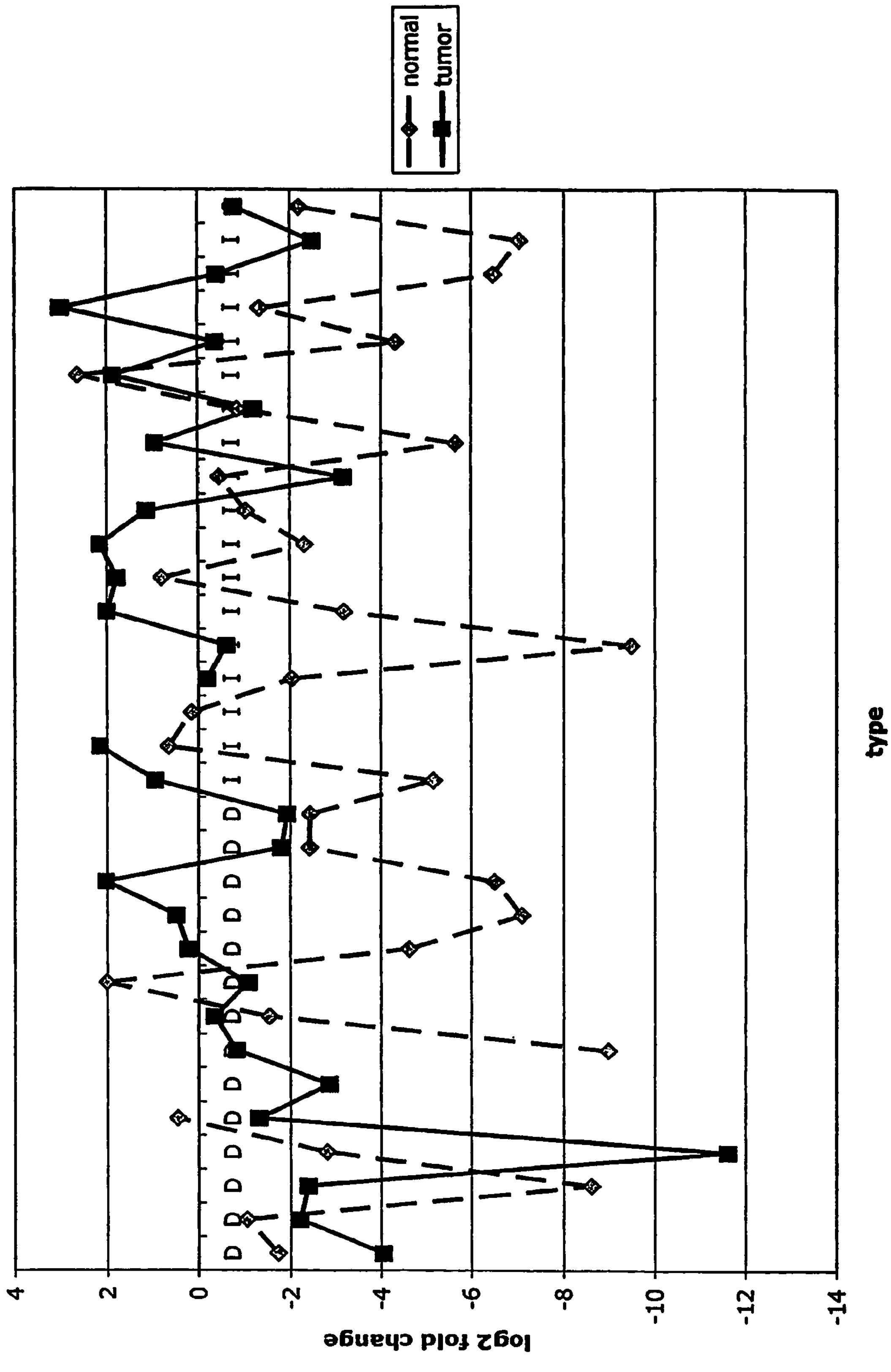

Fig. 11ac TGFB1
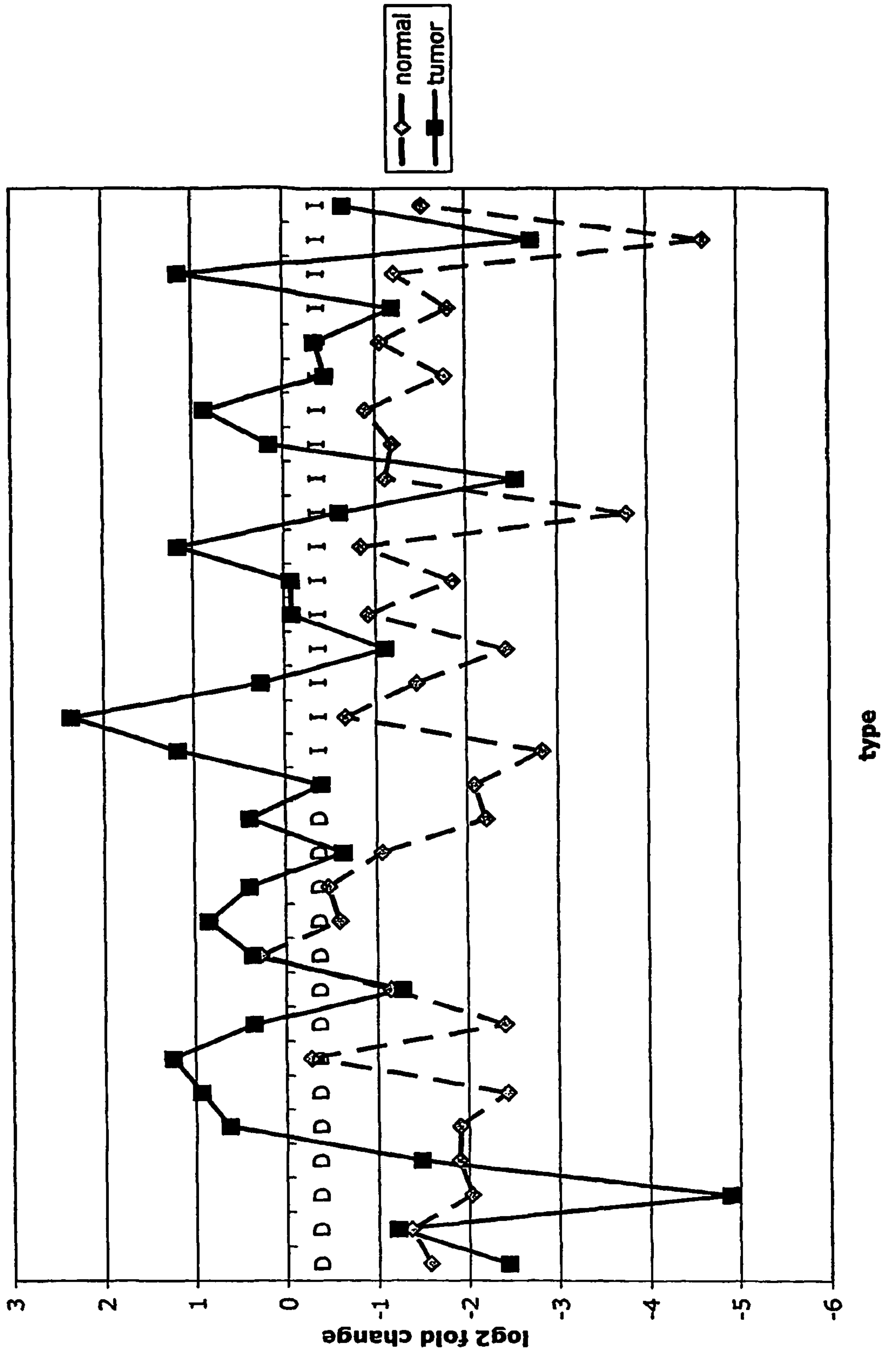

Fig. 11ad CEACAM5
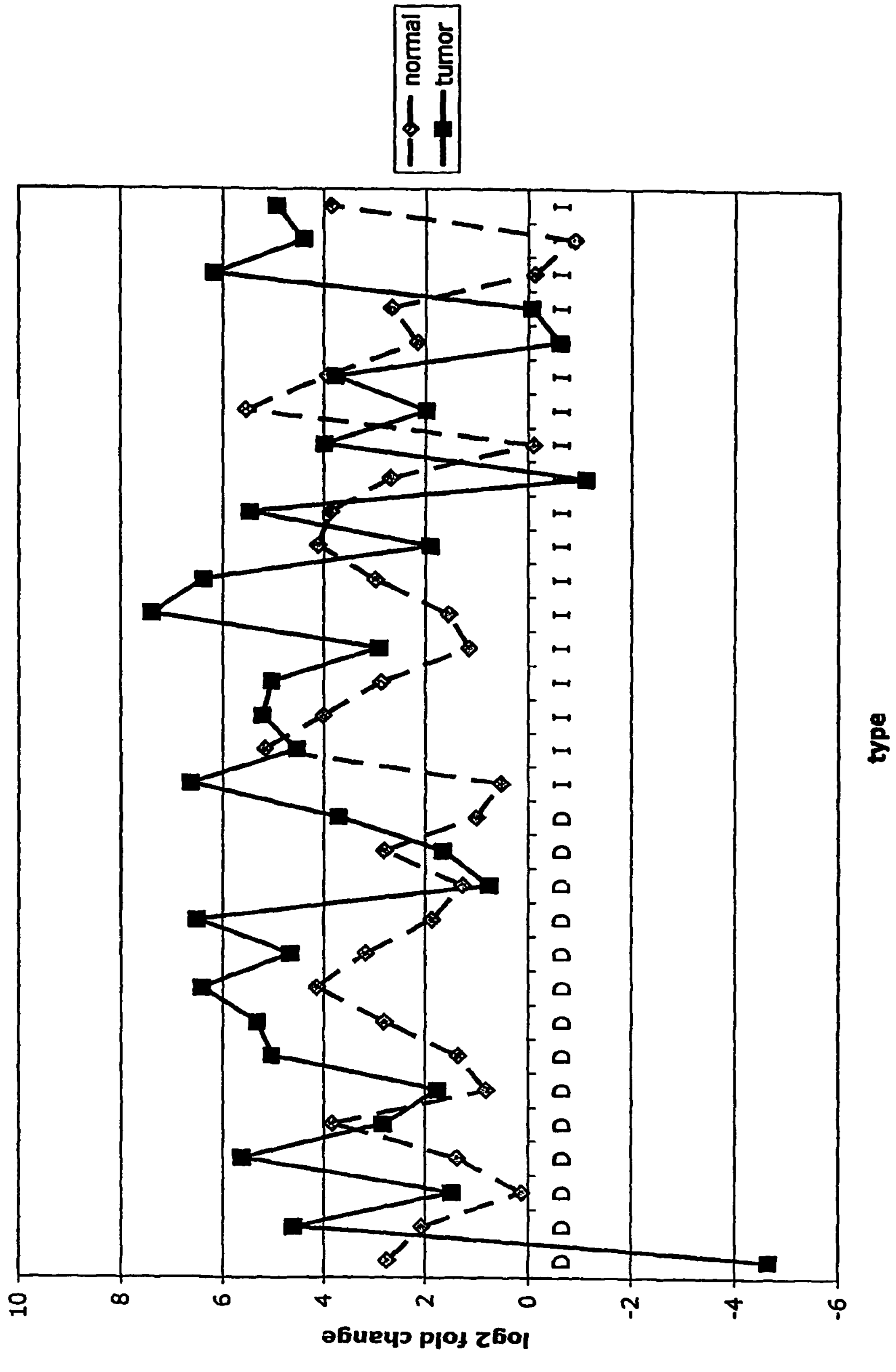

Fig. 12 The separation of gastric tumor samples from non-malignant samples using three markers
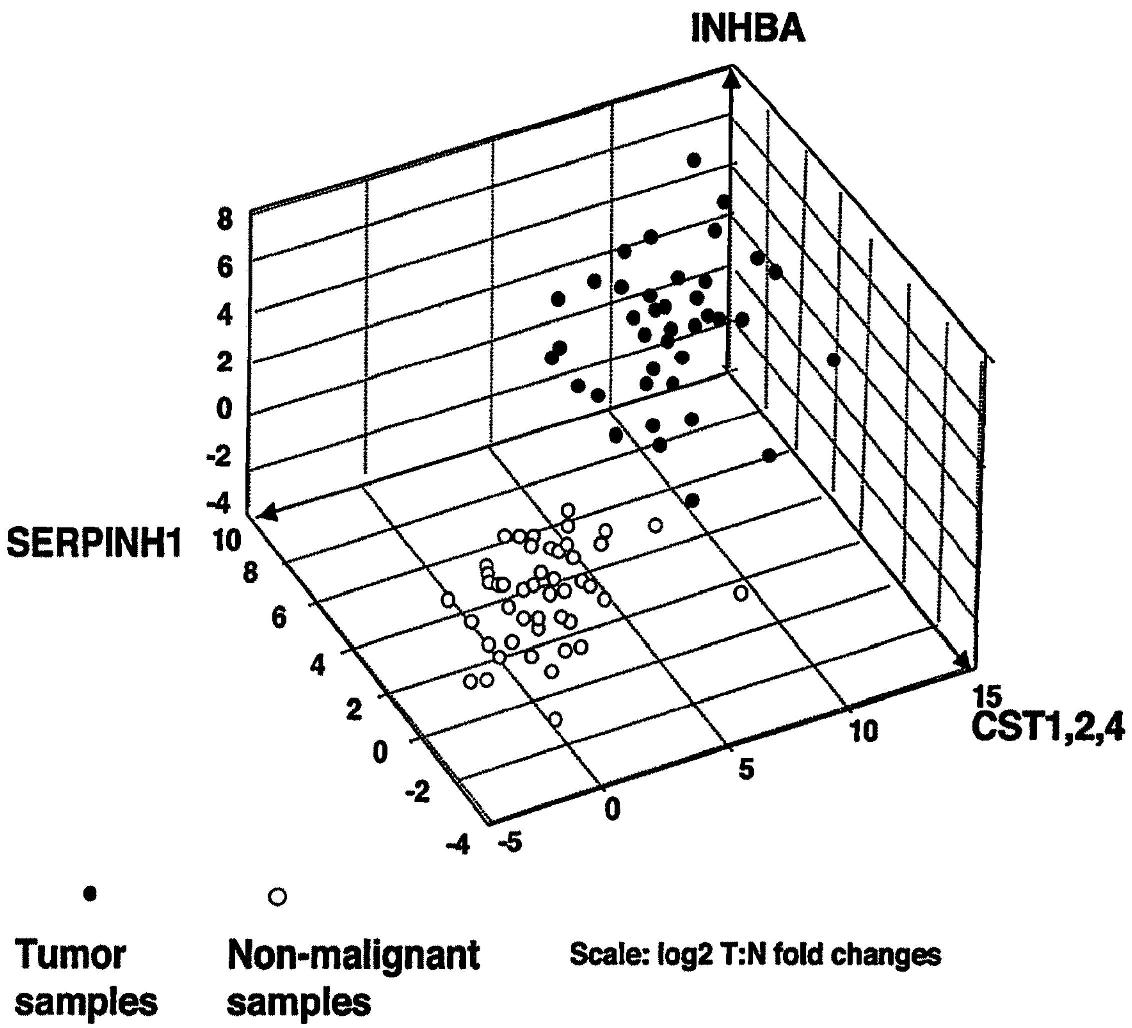

| Number of markers in test | Total possible tests | Number of tests with sensitivity | | | Proportion of tests with sensitivity | | |
|---|---|---|---|---|---|---|---|
| | | >=90% | >=95% | >=99% | >=90% | >=95% | >=99% |
| 1 | 29 | 2 | 1 | 0 | 6.9% | 3.4% | 0% |
| 2 | 406 | 33 | 27 | 1 | 8.1% | 6.7% | 0.2% |
| 3 | 3654 | 796 | 457 | 50 | 21.8% | 12.5% | 1.4% |

Fig. 13. The effect of multiple markers on the ability to accurately discriminate between tumor tissue and non-malignant tissue.

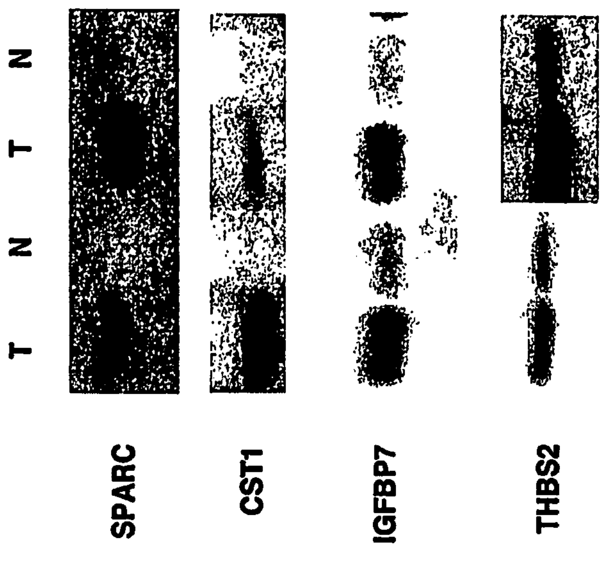
Fig. 14. Western analysis of markers in tumor and non-malignant tissue

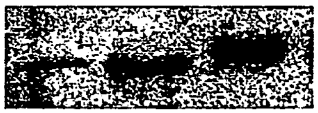
Fig. 15. Western analysis of SPARC in gastric tumor material and serum.

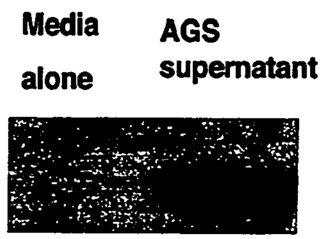
Fig. 16. Immunodetection of cystatin SN in the supernatant of the gastric cancer cell line, AGS.

SEQUENCE LISTING

<160> NUMBER OF SEQ ID NOS: 108

<210> SEQ ID NO 1
<211> LENGTH: 26
<212> TYPE: DNA
<213> ORGANISM: homo sapiens

<400> SEQUENCE: 1
aaatacaaaa ggacacattc aaagga 26

<210> SEQ ID NO 2
<211> LENGTH: 20
<212> TYPE: DNA
<213> ORGANISM: homo sapiens

<400> SEQUENCE: 2
gccagtggaa tgatgttccc 20

<210> SEQ ID NO 3
<211> LENGTH: 19
<212> TYPE: DNA
<213> ORGANISM: homo sapiens

<400> SEQUENCE: 3
agtcccagcc caacttgga 19

<210> SEQ ID NO 4
<211> LENGTH: 17
<212> TYPE: DNA
<213> ORGANISM: homo sapiens

<400> SEQUENCE: 4
gtggcaatgc cgctgaa 17

<210> SEQ ID NO 5
<211> LENGTH: 18
<212> TYPE: DNA
<213> ORGANISM: homo sapiens

<400> SEQUENCE: 5
caggtcagca agggcacc 18

<210> SEQ ID NO 6
<211> LENGTH: 24
<212> TYPE: DNA
<213> ORGANISM: homo sapiens

<400> SEQUENCE: 6

-continued acaacatgat atgtgctgga ctgg 24

<210> SEQ ID NO 7
<211> LENGTH: 24
<212> TYPE: DNA
<213> ORGANISM: homo sapiens

<400> SEQUENCE: 7
cttgagtaca acgctgacct cttc 24

<210> SEQ ID NO 8
<211> LENGTH: 24
<212> TYPE: DNA
<213> ORGANISM: homo sapiens

<400> SEQUENCE: 8
gattcttgtc catagtgcat ctgc 24

<210> SEQ ID NO 9
<211> LENGTH: 19
<212> TYPE: DNA
<213> ORGANISM: homo sapiens

<400> SEQUENCE: 9
aggccagctt ctgcttgga 19

<210> SEQ ID NO 10
<211> LENGTH: 23
<212> TYPE: DNA
<213> ORGANISM: homo sapiens

<400> SEQUENCE: 10
gcctctctgc tgatgacata cgt 23

<210> SEQ ID NO 11
<211> LENGTH: 21
<212> TYPE: DNA
<213> ORGANISM: homo sapiens

<400> SEQUENCE: 11
ccagaccacc ttataccagc g 21

<210> SEQ ID NO 12
<211> LENGTH: 17
<212> TYPE: DNA
<213> ORGANISM: homo sapiens

<400> SEQUENCE: 12
cgcagaacgc ctgcaaa 17

<210> SEQ ID NO 13
<211> LENGTH: 18
<212> TYPE: DNA
<213> ORGANISM: homo sapiens

<400> SEQUENCE: 13
cgctagcagc gaccacct 18

<210> SEQ ID NO 14
<211> LENGTH: 23
<212> TYPE: DNA
<213> ORGANISM: homo sapiens

<400> SEQUENCE: 14
tcttccctgt acactggcag ttc 23

<210> SEQ ID NO 15
<211> LENGTH: 19
<212> TYPE: DNA
<213> ORGANISM: homo sapiens

<400> SEQUENCE: 15
tcgggaggcc cgttagtaa 19

<210> SEQ ID NO 16
<211> LENGTH: 23
<212> TYPE: DNA
<213> ORGANISM: homo sapiens

<400> SEQUENCE: 16
tggaaggact acacggccta tag 23

<210> SEQ ID NO 17
<211> LENGTH: 20
<212> TYPE: DNA
<213> ORGANISM: homo sapiens

<400> SEQUENCE: 17
gacggttcct cgcagttcaa 20

<210> SEQ ID NO 18
<211> LENGTH: 16
<212> TYPE: DNA
<213> ORGANISM: homo sapiens

<400> SEQUENCE: 18
ctgcccaccc cttcca 16

<210> SEQ ID NO 19
<211> LENGTH: 21
<212> TYPE: DNA
<213> ORGANISM: homo sapiens

<400> SEQUENCE: 19
tccacgcatt ttccaggata a 21

<210> SEQ ID NO 20
<211> LENGTH: 22
<212> TYPE: DNA
<213> ORGANISM: homo sapiens

<400> SEQUENCE: 20
ggtccatgtc atcaccaatg tt 22

<210> SEQ ID NO 21
<211> LENGTH: 21
<212> TYPE: DNA
<213> ORGANISM: homo sapiens

<400> SEQUENCE: 21
aaaaatcttt gccggaaatg c 21

<210> SEQ ID NO 22
<211> LENGTH: 20
<212> TYPE: DNA
<213> ORGANISM: homo sapiens

<400> SEQUENCE: 22
ttgatggcat cgctcagatc 20

<210> SEQ ID NO 23
<211> LENGTH: 23
<212> TYPE: DNA
<213> ORGANISM: homo sapiens

<400> SEQUENCE: 23
tgcttctgca attctgatat gga 23

<210> SEQ ID NO 24
<211> LENGTH: 23
<212> TYPE: DNA
<213> ORGANISM: homo sapiens

<400> SEQUENCE: 24
tcttggcatt ttctacaaca ggg 23

<210> SEQ ID NO 25
<211> LENGTH: 24
<212> TYPE: DNA
<213> ORGANISM: homo sapiens

<400> SEQUENCE: 25
gggaacttcg tagatctgga aaga 24

<210> SEQ ID NO 26
<211> LENGTH: 25
<212> TYPE: DNA
<213> ORGANISM: homo sapiens

<400> SEQUENCE: 26
tgacagcaac aactcagtag gaaaa 25

<210> SEQ ID NO 27
<211> LENGTH: 22
<212> TYPE: DNA
<213> ORGANISM: homo sapiens

<400> SEQUENCE: 27
tcacagctca agtacacctg gg 22

<210> SEQ ID NO 28
<211> LENGTH: 20
<212> TYPE: DNA
<213> ORGANISM: homo sapiens

<400> SEQUENCE: 28
gagaggatgc cttggagggt 20

<210> SEQ ID NO 29
<211> LENGTH: 23
<212> TYPE: DNA
<213> ORGANISM: homo sapiens

<400> SEQUENCE: 29
ccgtgacaca gttctgctta cag 23

<210> SEQ ID NO 30
<211> LENGTH: 21
<212> TYPE: DNA

-continued

<213> ORGANISM: homo sapiens

<400> SEQUENCE: 30
ccaatcaatg ccaggaagag a 21

<210> SEQ ID NO 31
<211> LENGTH: 17
<212> TYPE: DNA
<213> ORGANISM: homo sapiens

<400> SEQUENCE: 31
ccctgatcgc cgagttg 17

<210> SEQ ID NO 32
<211> LENGTH: 25
<212> TYPE: DNA
<213> ORGANISM: homo sapiens

<400> SEQUENCE: 32
agtgacagca tcaaaactca aattg 25

<210> SEQ ID NO 33
<211> LENGTH: 20
<212> TYPE: DNA
<213> ORGANISM: homo sapiens

<400> SEQUENCE: 33
ggacctgtgg aagtatccgc 20

<210> SEQ ID NO 34
<211> LENGTH: 25
<212> TYPE: DNA
<213> ORGANISM: homo sapiens

<400> SEQUENCE: 34
acaggacatc atacatggtt tcaaa 25

<210> SEQ ID NO 35
<211> LENGTH: 23
<212> TYPE: DNA
<213> ORGANISM: homo sapiens

<400> SEQUENCE: 35
ttttgcaggc ttcacatacc ttt 23

<210> SEQ ID NO 36
<211> LENGTH: 18
<212> TYPE: DNA
<213> ORGANISM: homo sapiens

<400> SEQUENCE: 36
gaaaaagcgg gtggtgca 18

<210> SEQ ID NO 37
<211> LENGTH: 24
<212> TYPE: DNA
<213> ORGANISM: homo sapiens

<400> SEQUENCE: 37
aaggagattc cagctgtcac tttc 24

<210> SEQ ID NO 38
<211> LENGTH: 28

-continued

<212> TYPE: DNA
<213> ORGANISM: homo sapiens

<400> SEQUENCE: 38
taggtttggt catagatagg tcctgagt 28

<210> SEQ ID NO 39
<211> LENGTH: 22
<212> TYPE: DNA
<213> ORGANISM: homo sapiens

<400> SEQUENCE: 39
tgtaaaccgc tccacttcac at 22

<210> SEQ ID NO 40
<211> LENGTH: 25
<212> TYPE: DNA
<213> ORGANISM: homo sapiens

<400> SEQUENCE: 40
ttctgtcctt cctagtccct ttagg 25

<210> SEQ ID NO 41
<211> LENGTH: 21
<212> TYPE: DNA
<213> ORGANISM: homo sapiens

<400> SEQUENCE: 41
aagccgaatt tgctagttgc a 21

<210> SEQ ID NO 42
<211> LENGTH: 22
<212> TYPE: DNA
<213> ORGANISM: homo sapiens

<400> SEQUENCE: 42
tctgcaagtt catcccctct tt 22

<210> SEQ ID NO 43
<211> LENGTH: 21
<212> TYPE: DNA
<213> ORGANISM: homo sapiens

<400> SEQUENCE: 43
agtcctggcc gttgaaatac c 21

<210> SEQ ID NO 44
<211> LENGTH: 19
<212> TYPE: DNA
<213> ORGANISM: homo sapiens

<400> SEQUENCE: 44
tgtcacgtgg cgtcacagt 19

<210> SEQ ID NO 45
<211> LENGTH: 34
<212> TYPE: DNA
<213> ORGANISM: homo sapiens

<400> SEQUENCE: 45
ttggaaatga gtgcaaaccc tcttgataat aatg 34

<210> SEQ ID NO 46

-continued

<211> LENGTH: 23
<212> TYPE: DNA
<213> ORGANISM: homo sapiens

<400> SEQUENCE: 46
aggaacagtt gcttgcggcc agc 23

<210> SEQ ID NO 47
<211> LENGTH: 29
<212> TYPE: DNA
<213> ORGANISM: homo sapiens

<400> SEQUENCE: 47
agccagaact gcagaagaaa cagttgtgc 29

<210> SEQ ID NO 48
<211> LENGTH: 29
<212> TYPE: DNA
<213> ORGANISM: homo sapiens

<400> SEQUENCE: 48
ttcactggag gtcaattgca cagcagaat 29

<210> SEQ ID NO 49
<211> LENGTH: 26
<212> TYPE: DNA
<213> ORGANISM: homo sapiens

<400> SEQUENCE: 49
agcaaggtcc ttccatagtg acgccc 26

<210> SEQ ID NO 50
<211> LENGTH: 25
<212> TYPE: DNA
<213> ORGANISM: homo sapiens

<400> SEQUENCE: 50
cttgccagag tgactctgga ggccc 25

<210> SEQ ID NO 51
<211> LENGTH: 30
<212> TYPE: DNA
<213> ORGANISM: homo sapiens

<400> SEQUENCE: 51
ccatcacaga tcattacatc caggtcctca 30

<210> SEQ ID NO 52
<211> LENGTH: 36
<212> TYPE: DNA
<213> ORGANISM: homo sapiens

<400> SEQUENCE: 52
taaggattca aaccatttgc caaaaatgag tctaag 36

<210> SEQ ID NO 53
<211> LENGTH: 33
<212> TYPE: DNA
<213> ORGANISM: homo sapiens

<400> SEQUENCE: 53
cgtaattctt ctggatgtct ccttcacatt ctg 33

<210> SEQ ID NO 54
<211> LENGTH: 30
<212> TYPE: DNA
<213> ORGANISM: homo sapiens

<400> SEQUENCE: 54
tcagtccctg tatggagacc caaaagagaa 30

<210> SEQ ID NO 55
<211> LENGTH: 33
<212> TYPE: DNA
<213> ORGANISM: homo sapiens

<400> SEQUENCE: 55
caagatgacc aagatgtata aagggttcca agc 33

<210> SEQ ID NO 56
<211> LENGTH: 28
<212> TYPE: DNA
<213> ORGANISM: homo sapiens

<400> SEQUENCE: 56
tgtctgaacc gcaccagcca agagaata 28

<210> SEQ ID NO 57
<211> LENGTH: 22
<212> TYPE: DNA
<213> ORGANISM: homo sapiens

<400> SEQUENCE: 57
ctgccagcca ccgaggaagc tc 22

<210> SEQ ID NO 58
<211> LENGTH: 22
<212> TYPE: DNA
<213> ORGANISM: homo sapiens

<400> SEQUENCE: 58
tggaccagca ccccattgac gg 22

<210> SEQ ID NO 59
<211> LENGTH: 31
<212> TYPE: DNA
<213> ORGANISM: homo sapiens

<400> SEQUENCE: 59
agtgttaatt ccaatcactt caccgtccag g 31

<210> SEQ ID NO 60
<211> LENGTH: 27
<212> TYPE: DNA
<213> ORGANISM: homo sapiens

<400> SEQUENCE: 60
aggcccaaga ccggctacat cagagtc 27

<210> SEQ ID NO 61
<211> LENGTH: 25
<212> TYPE: DNA
<213> ORGANISM: homo sapiens

<400> SEQUENCE: 61
tctggcagat tccgatgccc cacaa 25

<210> SEQ ID NO 62
<211> LENGTH: 20
<212> TYPE: DNA
<213> ORGANISM: homo sapiens

<400> SEQUENCE: 62
ccaggccagg agcagctcgg 20

<210> SEQ ID NO 63
<211> LENGTH: 21
<212> TYPE: DNA
<213> ORGANISM: homo sapiens

<400> SEQUENCE: 63
tgactccagg cccgcaatgg a 21

<210> SEQ ID NO 64
<211> LENGTH: 25
<212> TYPE: DNA
<213> ORGANISM: homo sapiens

<400> SEQUENCE: 64
cagcctccag ccaacagacc tcagg 25

<210> SEQ ID NO 65
<211> LENGTH: 29
<212> TYPE: DNA
<213> ORGANISM: homo sapiens

<400> SEQUENCE: 65
acagaatgta gggatgggtt aagcctgca 29

<210> SEQ ID NO 66
<211> LENGTH: 23
<212> TYPE: DNA
<213> ORGANISM: homo sapiens

<400> SEQUENCE: 66
ttcaaggacc ggttcatttg gcg 23

<210> SEQ ID NO 67
<211> LENGTH: 1778
<212> TYPE: DNA
<213> ORGANISM: Homo sapiens

<400> SEQUENCE: 67
tagaagttta caatgaagtt tcttctaata ctgctcctgc aggccactgc ttctggagct 60
cttcccctga acagctctac aagcctggaa aaaaataatg tgctatttgg tgagagatac 120
ttagaaaaat tttatggcct tgagataaac aaacttccag tgacaaaaat gaaatatagt 180
ggaaacttaa tgaaggaaaa aatccaagaa atgcagcact tcttgggtct gaaagtgacc 240
gggcaactgg acacatctac cctggagatg atgcacgcac ctcgatgtgg agtccccgat 300
ctccatcatt tcagggaaat gccagggggg cccgtatgga ggaaacatta tatcacctac 360
agaatcaata attacacacc tgacatgaac cgtgaggatg ttgactacgc aatccggaaa 420
gctttccaag tatggagtaa tgttaccccc ttgaaattca gcaagattaa cacaggcatg 480
gctgacattt tggtggtttt tgcccgtgga gctcatggag acttccatgc ttttgatggc 540
aaaggtggaa tcctagccca tgcttttgga cctggatctg gcattggagg ggatgcacat 600
ttcgatgagg acgaattctg gactacacat tcaggaggca caaacttgtt cctcactgct 660

```
gttcacgaga ttggccattc cttaggtctt ggccattcta gtgatccaaa ggctgtaatg    720
ttccccacct acaaatatgt cgacatcaac acatttcgcc tctctgctga tgacatacgt    780
ggcattcagt ccctgtatgg agacccaaaa gagaaccaac gcttgccaaa tcctgacaat    840
tcagaaccag ctctctgtga ccccaatttg agttttgatg ctgtcactac cgtgggaaat    900
aagatctttt tcttcaaaga caggttcttc tggctgaagg tttctgagag accaaagacc    960
agtgttaatt taatttcttc cttatggcca accttgccat ctggcattga agctgcttat   1020
gaaattgaag ccagaaatca agtttttctt tttaaagatg acaaatactg gttaattagc   1080
aatttaagac cagagccaaa ttatcccaag agcatacatt cttttggttt tcctaacttt   1140
gtgaaaaaaa ttgatgcagc tgtttttaac ccacgttttt ataggaccta cttctttgta   1200
gataaccagt attggaggta tgatgaaagg agacagatga tggaccctgg ttatcccaaa   1260
ctgattacca agaacttcca aggaatcggg cctaaaattg atgcagtctt ctattctaaa   1320
aacaaatact actatttctt ccaaggatct aaccaatttg aatatgactt cctactccaa   1380
cgtatcacca aaacactgaa aagcaatagc tggtttggtt gttagaaatg gtgtaattaa   1440
tggtttttgt tagttcactt cagcttaata agtatttatt gcatatttgc tatgtcctca   1500
gtgtaccact acttagagat atgtatcata aaaataaaat ctgtaaacca taggtaatga   1560
ttatataaaa tacataatat ttttcaattt tgaaaactct aattgtccat tcttgcttga   1620
ctctactatt aagtttgaaa atagttacct tcaaagcaag ataattctat ttgaagcatg   1680
ctctgtaagt tgcttcctaa catccttgga ctgagaaatt atacttactt ctggcataac   1740
taaaattaag tatatatatt ttggctcaaa taaaattg                           1778
```

<210> SEQ ID NO 68
<211> LENGTH: 1840
<212> TYPE: DNA
<213> ORGANISM: Homo sapiens

<400> SEQUENCE: 68

```
tccacacaca caaaaaacct gcgcgtgagg ggggaggaaa agcagggcct ttaaaaaggc     60
aatcacaaca acttttgctg ccaggatgcc cttgctttgg ctgagaggat ttctgttggc    120
aagttgctgg attatagtga ggagttcccc caccccagga tccgaggggc acagcgcggc    180
ccccgactgt ccgtcctgtg cgctggccgc cctcccaaag gatgtaccca actctcagcc    240
agagatggtg gaggccgtca agaagcacat tttaaacatg ctgcacttga agaagagacc    300
cgatgtcacc cagccggtac ccaaggcggc gcttctgaac gcgatcagaa agcttcatgt    360
gggcaaagtc ggggagaacg ggtatgtgga gatagaggat gacattggaa ggagggcaga    420
aatgaatgaa cttatggagc agacctcgga gatcatcacg tttgccgagt caggaacagc    480
caggaagacg ctgcacttcg agatttccaa ggaaggcagt gacctgtcag tggtggagcg    540
tgcagaagtc tggctcttcc taaaagtccc caaggccaac aggaccagga ccaaagtcac    600
catccgcctc ttccagcagc agaagcaccc gcagggcagc ttggacacag gggaagaggc    660
cgaggaagtg ggcttaaagg gggagaggag tgaactgttg ctctctgaaa aagtagtaga    720
cgctcggaag agcacctggc atgtcttccc tgtctccagc agcatccagc ggttgctgga    780
ccagggcaag agctccctgg acgttcggat tgcctgtgag cagtgccagg agagtggcgc    840
cagcttggtt ctcctgggca agaagaagaa gaaagaagag gagggggaag ggaaaaagaa    900
gggcggaggt gaaggtgggg caggagcaga tgaggaaaag gagcagtcgc acagaccttt    960
```

cctcatgctg caggcccggc agtctgaaga ccaccctcat cgccggcgtc ggcggggctt 1020
ggagtgtgat ggcaaggtca acatctgctg taagaaacag ttctttgtca gtttcaagga 1080
catcggctgg aatgactgga tcattgctcc ctctggctat catgccaact actgcgaggg 1140
tgagtgcccg agccatatag caggcacgtc cgggtcctca ctgtccttcc actcaacagt 1200
catcaaccac taccgcatgc ggggccatag cccctttgcc aacctcaaat cgtgctgtgt 1260
gcccaccaag ctgagaccca tgtccatgtt gtactatgat gatggtcaaa acatcatcaa 1320
aaaggacatt cagaacatga tcgtggagga gtgtgggtgc tcatagagtt gcccagccca 1380
gggggaaagg gagcaagagt tgtccagaga agacagtggc aaaatgaaga aatttttaag 1440
gtttctgagt taaccagaaa aatagaaatt aaaaacaaaa caaaacaaaa aaaaaaacaa 1500
aaaaaaacaa aagtaaatta aaaacaaacc tgatgaaaca gatgaaacag atgaaggaag 1560
atgtggaaat cttagcctgc cttagccagg gctcagagat gaagcagtga agagacagat 1620
tgggagggaa agggagaatg gtgtaccctt tatttcttct gaaatcacac tgatgacatc 1680
agttgtttaa acggggtatt gtcctttccc cccttgaggt tcccttgtga gcttgaatca 1740
accaatctga tctgcagtag tgtggactag aacaacccaa atagcatcta gaaagccatg 1800
agtttgaaag ggcccatcac aggcactttc ctagcctaat 1840

<210> SEQ ID NO 69
<211> LENGTH: 2384
<212> TYPE: DNA
<213> ORGANISM: Homo sapiens

<400> SEQUENCE: 69
tccacacaca caaaaaaacct gcgcgtgagg ggggaggaaa agcagggcct ttaaaaaggc 60
aatcacaaca acttttgctg ccaggatgcc cttgctttgg ctgagaggat ttctgttggc 120
aagttgctgg attatagtga ggagttcccc caccccagga tccgaggggc acagcgcggc 180
ccccgactgt ccgtcctgtg cgctggccgc cctcccaaag gatgtaccca actctcagcc 240
agagatggtg gaggccgtca agaagcacat tttaaacatg ctgcacttga agaagagacc 300
cgatgtcacc cagccggtac ccaaggcggc gcttctgaac gcgatcagaa agcttcatgt 360
gggcaaagtc ggggagaacg ggtatgtgga gatagaggat gacattggaa ggagggcaga 420
aatgaatgaa cttatggagc agacctcgga gatcatcacg tttgccgagt caggaacagc 480
caggaagacg ctgcacttcg agatttccaa ggaaggcagt gacctgtcag tggtggagcg 540
tgcagaagtc tggctcttcc taaaagtccc caaggccaac aggaccagga ccaaagtcac 600
catccgcctc ttccagcagc agaagcaccc gcagggcagc ttggacacag gggaagaggc 660
cgaggaagtg ggcttaaagg gggagaggag tgaactgttg ctctctgaaa aagtagtaga 720
cgctcggaag agcacctggc atgtcttccc tgtctccagc agcatccagc ggttgctgga 780
ccagggcaag agctccctgg acgttcggat tgcctgtgag cagtgccagg agagtggcgc 840
cagcttggtt ctcctgggca agaagaagaa gaaagaagag gagggggaag ggaaaaagaa 900
gggcggaggt gaaggtgggg caggagcaga tgaggaaaag gagcagtcgc acagaccttt 960
cctcatgctg caggcccggc agtctgaaga ccaccctcat cgccggcgtc ggcggggctt 1020
ggagtgtgat ggcaaggtca acatctgctg taagaaacag ttctttgtca gtttcaagga 1080
catcggctgg aatgactgga tcattgctcc ctctggctat catgccaact actgcgaggg 1140
tgagtgcccg agccatatag caggcacgtc cgggtcctca ctgtccttcc actcaacagt 1200
catcaaccac taccgcatgc ggggccatag cccctttgcc aacctcaaat cgtgctgtgt 1260

```
gccgctgcca ccgcaccccg ccatggagcg gccgtcgctg cgcgccctgc tcctcggcgc   1320

cgctgggctg ctgctcctgc tcctgcccct ctcctcttcc tcctcttcgg acacctgcgg   1380

cccctgcgag ccggcctcct gcccgcccct gcccccgctg ggctgcctgc tgggcgagac   1440

ccgcgacgcg tgcggctgct gccctatgtg cgcccgcggc gagggcgagc cgtgcggggg   1500

tggcggcgcc ggcagggggt actgcgcgcc gggcatggag tgcgtgaaga gccgcaagag   1560

gcggaagggt aaagccgggg cagcagccgg cggtccgggt gtaagcggcg tgtgcgtgtg   1620

caagagccgc tacccggtgt gcggcagcga cggcaccacc tacccgagcg gctgccagct   1680

gcgcgccgcc agccagaggg ccgagagccg cggggagaag gccatcaccc aggtcagcaa   1740

gggcacctgc gagcaaggtc cttccatagt gacgcccccc aaggacatct ggaatgtcac   1800

tggtgcccag gtgtacttga gctgtgaggt catcggaatc ccgacacctg tcctcatctg   1860

gaacaaggta aaaaggggtc actatggagt tcaaaggaca gaactcctgc ctggtgaccg   1920

ggacaacctg gccattcaga cccggggtgg cccagaaaag catgaagtaa ctggctgggt   1980

gctggtatct cctctaagta aggaagatgc tggagaatat gagtgccatg catccaattc   2040

ccaaggacag gcttcagcat cagcaaaaat tacagtggtt gatgccttac atgaaatacc   2100

agtgaaaaaa ggtgaaggtg ccgagctata aacctccaga atattattag tctgcatggt   2160

taaaagtagt catggataac tacattacct gttcttgcct aataagtttc ttttaatcca   2220

atccactaac actttagtta tattcactgg ttttacacag agaaatacaa aataaagatc   2280

acacatcaag actatctaca aaaatttatt atatatttac agaagaaaag catgcatatc   2340

attaaacaaa taaaatactt tttatcacaa aaaaaaaaaa aaaa                    2384
```

<210> SEQ ID NO 70
<211> LENGTH: 1280
<212> TYPE: DNA
<213> ORGANISM: Homo sapiens

<400> SEQUENCE: 70

```
tgccgcagcc cccgcccgcc cgcagagctt ttgaaaggcg gcgggaggcg gcgagcgcca     60

tggccagtcc gggctgcctg ctgtgcgtgc tgggcctgct actctgcggg gcggcgagcc    120

tcgagctgtc tagaccccac ggcgacaccg ccaagaagcc catcatcgga atattaatgc    180

aaaaatgccg taataaagtc atgaaaaact atggaagata ctatattgct gcgtcctatg    240

taaagtactt ggagtctgca ggtgcgagag ttgtaccagt aaggctggat cttacagaga    300

aagactatga aatacttttc aaatctatta atggaatcct tttccctgga ggaagtgttg    360

acctcagacg ctcagattat gctaaagtgg ccaaaatatt ttataacttg tccatacaga    420

gttttgatga tggagactat tttcctgtgt ggggcacatg ccttggattt gaagagcttt    480

cactgctgat tagtggagag tgcttattaa ctgccacaga tactgttgac gtggcaatgc    540

cgctgaactt cactggaggt caattgcaca gcagaatgtt ccagaatttt cctactgagt    600

tgttgctgtc attagcagta gaacctctga ctgccaattt ccataagtgg agcctctccg    660

tgaagaattt tacaatgaat gaaaagttaa agaagttttt caatgtctta actacaaata    720

cagatggcaa gattgagttt atttcaacaa tggaaggata taagtatcca gtatatggtg    780

tccagtggca tccagagaaa gcaccttatg agtggaagaa tttggatggc atttcccatg    840

cacctaatgc tgtgaaaacc gcattttatt tagcagagtt ttttgttaat gaagctcgga    900

aaaacaacca tcattttaaa tctgaatctg aagaggagaa agcattgatt tatcagttca    960
```

gtccaattta tactggaaat atttcttcat ttcagcaatg ttacatattt gattgaaagt 1020
cttcaatttg ttaacagagc aaatttgaat aattccatga ttaaactgtt agaataactt 1080
gctactcatg gcaagattag gaagtcacag attcttttct ataatgtgcc tggctctgat 1140
tcttcattat gtatgtgact atttatataa cattagataa ttaaatagtg agacataaat 1200
agagtgcttt ttcatggaaa agccttctta tatctgaaga ttgaaaaata aatttactga 1260
aatacaaaaa aaaaaaaaaa 1280

<210> SEQ ID NO 71
<211> LENGTH: 2993
<212> TYPE: DNA
<213> ORGANISM: Homo sapiens

<400> SEQUENCE: 71
ggtggcgggt ggctggcggt tccgttaggt ctgagggagc gatggcggta cgcgcgttga 60
agctgctgac cacactgctg gctgtcgtgg ccgctgcctc ccaagccgag gtcgagtccg 120
aggcaggatg gggcatggtg acgcctgatc tgctcttcgc cgaggggacc gcagcctacg 180
cgcgcgggga ctggcccggg gtggtcctga gcatggaacg ggcgctgcgc tcccgggcag 240
ccctccgcgc ccttcgcctg cgctgccgca cccagtgtgc cgccgacttc ccgtgggagc 300
tggaccccga ctggtccccc agcccggccc aggcctcggg cgccgccgcc ctgcgcgacc 360
tgagcttctt cgggggcctt ctgcgtcgcg ctgcctgcct gcgccgctgc ctcgggccgc 420
cggccgccca ctcgctcagc gaagagatgg agctggagtt ccgcaagcgg agcccctaca 480
actacctgca ggtcgcctac ttcaagatca acaagttgga gaaagctgtt gctgcagcac 540
acaccttctt cgtgggcaat cctgagcaca tggaaatgca gcagaaccta gactattacc 600
aaaccatgtc tggagtgaag gaggccgact tcaaggatct tgagactcaa ccccatatgc 660
aagaatttcg actgggagtg cgactctact cagaggaaca gccacaggaa gctgtgcccc 720
acctagaggc ggcgctgcaa gaatactttg tggcctatga ggagtgccgt gccctctgcg 780
aagggcccta tgactacgat ggctacaact accttgagta caacgctgac ctcttccagg 840
ccatcacaga tcattacatc caggtcctca actgtaagca gaactgtgtc acggagcttg 900
cttcccaccc aagtcgagag aagccctttg aagacttcct cccatcgcat tataattatc 960
tgcagtttgc ctactataac attgggaatt atacacaggc tgttgaatgt gccaagacct 1020
atcttctctt cttccccaat gacgaggtga tgaaccaaaa tttggcctat tatgcagcta 1080
tgcttggaga agaacacacc agatccatcg gcccccgtga gagtgccaag gagtaccgac 1140
agcgaagcct actggaaaaa gaactgcttt tcttcgctta tgatgttttt ggaattccct 1200
ttgtggatcc ggattcatgg actccaggag aagtgattcc caagagattg caagagaaac 1260
agaagtcaga acgggaaaca gccgtacgca tctcccagga gattgggaac cttatgaagg 1320
aaatcgagac ccttgtggaa gagaagacca aggagtcact ggatgtgagc agactgaccc 1380
gggaaggtgg cccccctgctg tatgaaggca tcagtctcac catgaactcc aaactcctga 1440
atggttccca gcgggtggtg atggacggcg taatctctga ccacgagtgt caggagctgc 1500
agagactgac caatgtggca gcaacctcag gagatggcta ccggggtcag acctccccac 1560
atactcccaa tgaaaagttc tatggtgtca ctgtcttcaa agccctcaag ctggggcaag 1620
aaggcaaagt tcctctgcag agtgcccacc tgtactacaa cgtgacggag aaggtgcggc 1680
gcatcatgga gtcctacttc cgcctggata cgcccctcta cttttcctac tctcatctgg 1740
tgtgccgcac tgccatcgaa gaggtccagg cagagaggaa ggatgatagt catccagtcc 1800

-continued

```
acgtggacaa ctgcatcctg aatgccgaga ccctcgtgtg tgtcaaagag cccccagcct   1860

acaccttccg cgactacagc gccatccttt acctaaatgg ggacttcgat ggcggaaact   1920

tttatttcac tgaactggat gccaagaccg tgacggcaga ggtgcagcct cagtgtggaa   1980

gagccgtggg attctcttca ggcactgaaa acccacatgg agtgaaggct gtcaccaggg   2040

ggcagcgctg tgccatcgcc ctgtggttca ccctggaccc tcgacacagc gagcgggtga   2100

gagcagctcg agcgggtgag agcagctggt gctgtggtga cccgttccca gagcgccctt   2160

ggtttgcctt tctcttcccc aaatcccatt gccagtggct gagacacgaa aggagcactt   2220

gggacaccag ctccaacgcc ctgtcattat ggtcacattg ccttgtcctc cctgggcctg   2280

ctgtgaacgg gatccaggtg gggaaagagg tcaagacagg gagcgatgct gagttcttgg   2340

ttccctcctt gggccccact tcagctgtcc ttttccagag agtaggacct gctgggaagg   2400

agatgagcct ggggccatta aggaaccttc cttgtcccct gggaagtagc agctgagaga   2460

tagcgagtgt ctggagcgga ggcctctctg aatgggcagg ggtttgtcct tgcaggacag   2520

ggtgcaggca gatgacctgg tgaagatgct cttcagccca gaagagatgg tcctctccca   2580

ggagcagccc ctggatgccc agcagggccc ccccgaacct gcacaagagt ctctctcagg   2640

cagtgaatcg aagcccaagg atgagctatg acagcgtcca ggtcagacgg atgggtgact   2700

agacccatgg agaggaactc ttctgcactc tgagctggcc agcccctcgg ggctgcagag   2760

cagtgagcct acatctgcca ctcagccgag ggaccctgc tcacagcctt ctacatggtg   2820

ctactgctct tggagtggac atgaccagac accgcacccc ctggatctgg ctgagggctc   2880

aggacacagg cccagccacc cccaggggcc tccacaggcc gctgcataac agcgatacag   2940

tacttaagtg tctgtgtaga caaccaaaga ataaatgatt catggttttt ttt          2993
```

<210> SEQ ID NO 72
<211> LENGTH: 736
<212> TYPE: DNA
<213> ORGANISM: Homo sapiens

<400> SEQUENCE: 72

```
ggctctcacc ctcctctcct gcagctccag ctttgtgctc tgcctctgag gagaccatgg     60

cccggcctct gtgtaccctg ctactcctga tggctaccct ggctggggct ctggcctcga    120

gctccaagga ggagaatagg ataatcccag gtggcatcta tgatgcagac ctcaatgatg    180

agtgggtaca gcgtgccctt cacttcgcca tcagcgagta caacaaggcc accgaagatg    240

agtactacag acgcccgctg caggtgctgc gagccaggga gcagaccttt gggggggtga    300

attacttctt cgacgtagag gtgggccgca ccatatgtac caagtcccag cccaacttgg    360

acacctgtgc cttccatgaa cagccagaac tgcagaagaa acagttgtgc tctttcgaga    420

tctacgaagt tccctgggag gacagaatgt ccctggtgaa ttccaggtgt caagaagcct    480

aggggtctgt gccaggccag tcacaccgac caccacccac tcccacccac tgtagtgctc    540

ccacccctgg actggtggcc cccaccctgc gggaggcctc cccatgtgcc tgtgccaaga    600

gacagacaga gaaggctgca ggagtccttt gttgctcagc agggcgctct gccctccctc    660

cttccttctt gcttctaata gacctggtac atggtacaca cacccccacc tcctgcaatt    720

aaacagtagc atcgcc                                                    736
```

<210> SEQ ID NO 73
<211> LENGTH: 2820
<212> TYPE: DNA

<213> ORGANISM: Homo sapiens

<400> SEQUENCE: 73
ggcgggttcg cgccccgaag gctgagagct ggcgctgctc gtgccctgtg tgccagacgg 60
cggagctccg cggccggacc ccgcggcccc gctttgctgc cgactggagt ttgggggaag 120
aaactctcct gcgccccaga agatttcttc ctcggcgaag ggacagcgaa agatgagggt 180
ggcaggaaga gaaggcgctt tctgtctgcc ggggtcgcag cgcgagaggg cagtgccatg 240
ttcctctcca tcctagtggc gctgtgcctg tggctgcacc tggcgctggg cgtgcgcggc 300
gcgccctgcg aggcggtgcg catccctatg tgccggcaca tgccctggaa catcacgcgg 360
atgcccaacc acctgcacca cagcacgcag gagaacgcca tcctggccat cgagcagtac 420
gaggagctgg tggacgtgaa ctgcagcgcc gtgctgcgct tcttcttctg tgccatgtac 480
gcgcccattt gcaccctgga gttcctgcac gaccctatca agccgtgcaa gtcggtgtgc 540
caacgcgcgc gcgacgactg cgagcccctc atgaagatgt acaaccacag ctggcccgaa 600
agcctggcct gcgacgagct gcctgtctat gaccgtggcg tgtgcatttc gcctgaagcc 660
atcgtcacgg acctcccgga ggatgttaag tggatagaca tcacaccaga catgatggta 720
caggaaaggc ctcttgatgt tgactgtaaa cgcctaagcc ccgatcggtg caagtgtaaa 780
aaggtgaagc caactttggc aacgtatctc agcaaaaact acagctatgt tattcatgcc 840
aaaataaaag ctgtgcagag gagtggctgc aatgaggtca caacggtggt ggatgtaaaa 900
gagatcttca agtcctcatc acccatccct cgaactcaag tcccgctcat tacaaattct 960
tcttgccagt gtccacacat cctgccccat caagatgttc tcatcatgtg ttacgagtgg 1020
cgttcaagga tgatgcttct tgaaaattgc ttagttgaaa aatggagaga tcagcttagt 1080
aaaagatcca tacagtggga agagaggctg caggaacagc ggagaacagt tcaggacaag 1140
aagaaaacag ccgggcgcac cagtcgtagt aatcccccca aaccaaaggg aaagcctcct 1200
gctcccaaac cagccagtcc caagaagaac attaaaacta ggagtgccca gaagagaaca 1260
aacccgaaaa gagtgtgagc taactagttt ccaaagcgga gacttccgac ttccttacag 1320
gatgaggctg ggcattgcct gggacagcct atgtaaggcc atgtgcccct tgccctaaca 1380
actcactgca gtgctcttca tagacacatc ttgcagcatt tttcttaagg ctatgcttca 1440
gtttttcttt gtaagccatc acaagccata gtggtaggtt tgccctttgg tacagaaggt 1500
gagttaaagc tggtggaaaa ggcttattgc attgcattca gagtaacctg tgtgcatact 1560
ctagaagagt agggaaaata atgcttgtta caattcgacc taatatgtgc attgtaaaat 1620
aaatgccata tttcaaacaa aacacgtaat ttttttacag tatgttttat taccttttga 1680
tatctgttgt tgcaatgtta gtgatgtttt aaaatgtgat gaaaatataa tgtttttaag 1740
aaggaacagt agtggaatga atgttaaaag atctttatgt gtttatggtc tgcagaagga 1800
tttttgtgat gaaaggggat tttttgaaaa attagagaag tagcatatgg aaaattataa 1860
tgtgtttttt taccaatgac ttcagtttct gtttttagct agaaacttaa aaacaaaaat 1920
aataataaag aaaaataaat aaaaaggaga ggcagacaat gtctggattc ctgtttttttg 1980
gttacctgat ttccatgatc atgatgcttc ttgtcaacac cctcttaagc agcaccagaa 2040
acagtgagtt tgtctgtacc attaggagtt aggtactaat tagttggcta atgctcaagt 2100
attttatacc cacaagagag gtatgtcact catcttactt cccaggacat ccaccctgag 2160
aataatttga caagcttaaa aatggccttc atgtgagtgc caaattttgt ttttcttcat 2220
ttaaatattt tctttgccta aatacatgtg agaggagtta aatataaatg tacagagagg 2280
aaagttgagt tccacctctg aaatgagaat tacttgacag ttgggatact ttaatcagaa 2340
aaaaagaact tatttgcagc attttatcaa caaatttcat aattgtggac aattggaggc 2400
atttatttta aaaaacaatt ttattggcct tttgctaaca cagtaagcat gtattttata 2460
aggcattcaa taaatgcaca acgcccaaag gaaataaaat cctatctaat cctactctcc 2520
actacacaga ggtaatcact attagtattt tggcatatta ttctccaggt gtttgcttat 2580
gcacttataa aatgatttga acaaataaaa ctaggaacct gtatacatgt gtttcataac 2640
ctgcctcctt tgcttggccc tttattgaga taagttttcc tgtcaagaaa gcagaaacca 2700
tctcatttct aacagctgtg ttatattcca tagtatgcat tactcaacaa actgttgtgc 2760
tattggatac ttaggtggtt tcttcactga caatactgaa taaacatctc accggaattc 2820

<210> SEQ ID NO 74
<211> LENGTH: 2480
<212> TYPE: DNA
<213> ORGANISM: Homo sapiens

<400> SEQUENCE: 74
agtactaaca tggactaatc tgtgggagca gtttattcca gtatcaccca gggtgcagcc 60
acaccaggac tgtgttgaag ggtgtttttt ttcttttaaa tgtaatacct cctcatcttt 120
tcttcttaca cagtgtctga gaacatttac attatagata agtagtacat ggtggataac 180
ttctactttt aggaggacta ctctcttctg acagtcctag actggtcttc tacactaaga 240
caccatgaag gagtatgtgc tcctattatt cctggctttg tgctctgcca aacccttctt 300
tagcccttca cacatcgcac tgaagaatat gatgctgaag gatatggaag acacagatga 360
tgatgatgat gatgatgatg atgatgatga tgatgatgag gacaactctc tttttccaac 420
aagagagcca agaagccatt tttttccatt tgatctgttt ccaatgtgtc catttggatg 480
tcagtgctat tcacgagttg tacattgctc agatttaggt ttgacctcag tcccaaccaa 540
cattccattt gatactcgaa tgcttgatct tcaaaacaat aaaattaagg aaatcaaaga 600
aaatgatttt aaaggactca cttcacttta tggtctgatc ctgaacaaca acaagctaac 660
gaagattcac ccaaaagcct ttctaaccac aaagaagttg cgaaggctgt atctgtccca 720
caatcaacta agtgaaatac cacttaatct tcccaaatca ttagcagaac tcagaattca 780
tgaaaataaa gttaagaaaa tacaaaagga cacattcaaa ggaatgaatg ctttacacgt 840
tttggaaatg agtgcaaacc ctcttgataa taatgggata gagccagggg catttgaagg 900
ggtgacggtg ttccatatca gaattgcaga agcaaaactg acctcagttc ctaaaggctt 960
accaccaact ttattggagc ttcacttaga ttataataaa atttcaacag tggaacttga 1020
ggattttaaa cgatacaaag aactacaaag gctgggccta ggaaacaaca aaatcacaga 1080
tatcgaaaat gggagtcttg ctaacatacc acgtgtgaga gaaatacatt tggaaaacaa 1140
taaactaaaa aaaatccctt caggattacc agagttgaaa tacctccaga taatcttcct 1200
tcattctaat tcaattgcaa gagtgggagt aaatgacttc tgtccaacag tgccaaagat 1260
gaagaaatct ttatacagtg caataagttt attcaacaac ccggtgaaat actgggaaat 1320
gcaacctgca acatttcgtt gtgttttgag cagaatgagt gttcagcttg ggaactttgg 1380
aatgtaataa ttagtaattg gtaatgtcca tttaatataa gattcaaaaa tccctacatt 1440
tggaatactt gaactctatt aataatggta gtattatata tacaagcaaa tatctattct 1500
caagtggtaa gtccactgac ttattttatg acaagaaatt tcaacggaat tttgccaaac 1560

-continued

```
tattgataca taagggttga gagaaacaag catctattgc agtttctttt tgcgtacaaa   1620

tgatcttaca taaatctcat gcttgaccat tcctttcttc ataacaaaaa agtaagatat   1680

tcggtattta acactttgtt atcaagcata ttttaaaaag aactgtactg taaatggaat   1740

gcttgactta gcaaaatttg tgctctttca tttgctgtta gaaaaacaga attaacaaag   1800

acagtaatgt gaagagtgca ttacactatt cttattcttt agtaacttgg gtagtactgt   1860

aatattttta atcatcttaa agtatgattt gatataatct tattgaaatt accttatcat   1920

gtcttagagc ccgtctttat gtttaaaact aatttcttaa aataaagcct tcagtaaatg   1980

ttcattacca acttgataaa tgctactcat aagagctggt ttggggctat agcatatgct   2040

ttttttttt taattattac ctgatttaaa aatctctgta aaaacgtgta gtgtttcata   2100

aaatctgtaa ctcgcatttt aatgatccgc tattataagc ttttaatagc atgaaaattg   2160

ttaggctata taacattgcc acttcaactc taaggaatat ttttgagata tccctttgga   2220

agaccttgct tggaagagcc tggacactaa caattctaca ccaaattgtc tcttcaaata   2280

cgtatggact ggataactct gagaaacaca tctagtataa ctgaataagc agagcatcaa   2340

attaaacaga cagaaaccga aagctctata taaatgctca gagttcttta tgtatttctt   2400

attggcattc aacatatgta aaatcagaaa acagggaaat tttcattaaa aatattggtt   2460

tgaaataaaa aaaaaaaaaa                                               2480
```

<210> SEQ ID NO 75
<211> LENGTH: 1887
<212> TYPE: DNA
<213> ORGANISM: Homo sapiens

<400> SEQUENCE: 75

```
cgcgcagccc ctccggccgc gggcgcagcg ggggcgctgg tggagctgcg aagggccagg     60

tccggcgggc ggggcggcgg ctggcactgg ctccggactc tgcccggcca gggcggcggc    120

tccagccggg agggcgacgt ggagcggcca cgtggagcgg cccgggggag gctggcggcg    180

ggaggcgagg cgcgggcggc gcagcagcca ggagcgccca cggagctgga cccccagagc    240

cgcgcggcgc cgcagcagtt ccaggaagga tgttaccttt gacgatgaca gtgttaatcc    300

tgctgctgct ccccacgggt caggctgccc caaaggatgg agtcacaagg ccagactctg    360

aagtgcagca tcagctcctg cccaacccct tccagccagg ccaggagcag ctcggacttc    420

tgcagagcta cctaaaggga ctaggaagga cagaagtgca actggagcat ctgagccggg    480

agcaggttct cctctacctc tttgccctcc atgactatga ccagagtgga cagctggatg    540

gcctggagct gctgtccatg ttgacagctg ctctggcccc tggagctgcc aactctccta    600

ccaccaaccc ggtgatattg atagtggaca aagtgctcga gacgcaggac ctgaatgggg    660

atgggctcat gacccctgct gagctcatca acttcccggg agtagccctc aggcacgtgg    720

agcccggaga gccccttgct ccatctcctc aggagccaca agctgttgga aggcagtccc    780

tattagctaa aagcccatta agacaagaaa cacaggaagc ccctggtccc agagaagaag    840

caaagggcca ggtagaggcc agaagggagt ctttggatcc tgtccaggag cctgggggcc    900

aggcagaggc tgatggagat gttccagggc ccagagggga agctgagggc caggcagagg    960

ctaaaggaga tgcccctggg cccagagggg aagctggggg ccaggcagag gctgaaggag   1020

atgcccccgg gcccagaggg gaagctgggg gccaggcaga ggccagggag aatggagagg   1080

aggccaagga acttccaggg gaaacactgg agtctaagaa cacccaaaat gactttgagg   1140

tgcacattgt tcaagtggag aatgatgaga tctagatctt gaagatacag gtaccccacg   1200
```

```
aagtctcagt gccagaacat aagccctgaa gtgggcaggg gaaatgtacg ctgggacaag   1260
gaccatctct gtgcccctg  tctggtccca gtaggtatca ggtctttctg tgcagctcag   1320
ggagacccta agttaagggg cagattacca ataaagaact gaatgaattc atcccccgg    1380
gccacctctc tacccgtcca gcctgcccag accctctcag aggaacgggg ttggggaccg   1440
aaaggacagg gatgccgcct gcccagtgtt tctgggcctc acggtgctcc ggcagcagag   1500
cgcatggtgc tagccatggc cggctgcaga ggacccagtg aggaaagctc agtctatccc   1560
tgggccccaa accctcaccg gttcccctc  acctggtgtt cagacacccc atgctctcct   1620
gcagctcagg gcaggtgacc ccatccccag taatattaat catcactaga actttttgag   1680
agccttgtac acatcaggca tcatgctggg cattttatat atgattttat cctcacaata   1740
attctgtagc caagcagaat tggttccatt tgacagatga agaaattgag gcagattgcg   1800
ttaagtgctg taccctaagg tgatatgcag ctaattaaat ggcagatttg aaaaaaaaaa   1860
aaaaaaaaaa aaaaaaaaaa aaaaaaa                                       1887

<210> SEQ ID NO 76
<211> LENGTH: 1580
<212> TYPE: DNA
<213> ORGANISM: Homo sapiens

<400> SEQUENCE: 76

catcctgcca cccctagcct tgctggggac gtgaaccctc tccccgcgcc tgggaagcct     60
tcttggcacc gggacccgga gaatccccac ggaagccagt tccaaaaggg atgaaaaggg    120
ggcgtttcgg gcactgggag aagcctgtat tccagggccc ctcccagagc aggaatctgg    180
gacccaggag tgccagcctc acccacgcag atcctggcca tgagagctcc gcacctccac    240
ctctccgccg cctctggcgc ccgggctctg gcgaagctgc tgccgctgct gatggcgcaa    300
ctctgggccg cagaggcggc gctgctcccc caaaacgaca cgcgcttgga ccccgaagcc    360
tatggctccc cgtgcgcgcg cggctcgcag ccctggcagg tctcgctctt caacggcctc    420
tcgttccact gcgcgggtgt cctggtggac cagagttggg tgctgacggc cgcgcactgc    480
ggaaacaagc cactgtgggc tcgagtaggg gatgaccacc tgctgcttct tcagggagag    540
cagctccgcc ggaccactcg ctctgttgtc catcccaagt accaccaggg ctcaggcccc    600
atcctgccaa ggcgaacgga tgagcacgat ctcatgttgc tgaagctggc caggcccgta    660
gtgctggggc cccgcgtccg ggccctgcag cttccctacc gctgtgctca gcccggagac    720
cagtgccagg ttgctggctg ggcaccacg  gccgcccgga gagtgaagta caacaagggc    780
ctgacctgct ccagcatcac tatcctgagc cctaaagagt gtgaggtctt ctaccctggc    840
gtggtcacca acaacatgat atgtgctgga ctggaccggg gccaggaccc ttgccagagt    900
gactctggag gccccctggt ctgtgacgag accctccaag gcatcctctc gtggggtgtt    960
taccccctgtg gctctgccca gcatccagct gtctacaccc agatctgcaa atacatgtcc   1020
tggatcaata aagtcatacg ctccaactga tccagatgct acgctccagc tgatccagat   1080
gttatgctcc tgctgatcca gatgcccaga ggctccatcg tccatcctct tcctccccag   1140
tcggctgaac tctccccttg tctgcactgt tcaaacctct gccgccctcc acacctctaa   1200
acatctcccc tctcacctca ttcccccacc tatccccatt ctctgcctgt actgaagctg   1260
aaatgcagga agtggtggca aaggtttatt ccagagaagc caggaagccg gtcatcaccc   1320
agcctctgag agcagttact ggggtcaccc aacctgactt cctctgccac tccctgctgt   1380
```

```
gtgactttgg gcaagccaag tgccctctct gaacctcagt ttcctcatct gcaaaatggg   1440

aacaatgacg tgcctacctc ttagacatgt tgtgaggaga ctatgatata acatgtgtat   1500

gtaaatcttc atggtgattg tcatgtaagg cttaacacag tgggtggtga gttctgacta   1560

aaggttacct gttgtcgtga                                                1580


<210> SEQ ID NO 77
<211> LENGTH: 1443
<212> TYPE: DNA
<213> ORGANISM: Homo sapiens

<400> SEQUENCE: 77

accagcggca gaccacaggc agggcagagg cacgtctggg tcccctccct ccttcctatc     60

ggcgactccc aggatcctgg ccatgagagc tccgcacctc cacctctccg ccgcctctgg    120

cgcccgggct ctggcgaagc tgctgccgct gctgatggcg caactctggg ccgcagaggc    180

ggcgctgctc ccccaaaacg acacgcgctt ggaccccgaa gcctatggct ccccgtgcgc    240

gcgcggctcg cagccctggc aggtctcgct cttcaacggc ctctcgttcc actgcgcggg    300

tgtcctggtg gaccagagtt gggtgctgac ggccgcgcac tgcggaaaca agccactgtg    360

ggctcgagta ggggatgacc acctgctgct tcttcaggga gagcagctcc gccggaccac    420

tcgctctgtt gtccatccca agtaccacca gggctcaggc cccatcctgc caaggcgaac    480

ggatgagcac gatctcatgt tgctgaagct ggccaggccc gtagtgctgg ggccccgcgt    540

ccgggccctg cagcttccct accgctgtgc tcagcccgga gaccagtgcc aggttgctgg    600

ctggggcacc acggccgccc ggagagtgaa gtacaacaag ggcctgacct gctccagcat    660

cactatcctg agccctaaag agtgtgaggt cttctaccct ggcgtggtca ccaacaacat    720

gatatgtgct ggactggacc ggggccagga ccccttgccag agtgactctg gaggcccccct    780

ggtctgtgac gagaccctcc aaggcatcct ctcgtggggt gtttacccct gtggctctgc    840

ccagcatcca gctgtctaca cccagatctg caaatacatg tcctggatca ataaagtcat    900

acgctccaac tgatccagat gctacgctcc agctgatcca gatgttatgc tcctgctgat    960

ccagatgccc agaggctcca tcgtccatcc tcttcctccc cagtcggctg aactctcccc   1020

ttgtctgcac tgttcaaacc tctgccgccc tccacacctc taaacatctc ccctctcacc   1080

tcattccccc acctatcccc attctctgcc tgtactgaag ctgaaatgca ggaagtggtg   1140

gcaaaggttt attccagaga agccaggaag ccggtcatca cccagcctct gagagcagtt   1200

actggggtca cccaacctga cttcctctgc cactccctgc tgtgtgactt tgggcaagcc   1260

aagtgccctc tctgaacctc agtttcctca tctgcaaaat gggaacaatg acgtgcctac   1320

ctcttagaca tgttgtgagg agactatgat ataacatgtg tatgtaaatc ttcatggtga   1380

ttgtcatgta aggcttaaca cagtgggtgg tgagttctga ctaaaggtta cctgttgtcg   1440

tga                                                                  1443


<210> SEQ ID NO 78
<211> LENGTH: 782
<212> TYPE: DNA
<213> ORGANISM: Homo sapiens

<400> SEQUENCE: 78

aggggcctta gcgtgccgca tcgccgagat ccagcgccca gagagacacc agagaaccca     60

ccatggcccc ctttgagccc ctggcttctg gcatcctgtt gttgctgtgg ctgatagccc    120

ccagcagggc ctgcacctgt gtcccacccc acccacagac ggccttctgc aattccgacc    180
```

tcgtcatcag ggccaagttc gtggggacac cagaagtcaa ccagaccacc ttataccagc 240
gttatgagat caagatgacc aagatgtata aagggttcca agccttaggg gatgccgctg 300
acatccggtt cgtctacacc cccgccatgg agagtgtctg cggatacttc cacaggtccc 360
acaaccgcag cgaggagttt ctcattgctg gaaaactgca ggatggactc ttgcacatca 420
ctacctgcag tttcgtggct ccctggaaca gcctgagctt agctcagcgc cggggcttca 480
ccaagaccta cactgttggc tgtgaggaat gcacagtgtt tccctgttta tccatcccct 540
gcaaactgca gagtggcact cattgcttgt ggacggacca gctcctccaa ggctctgaaa 600
agggcttcca gtcccgtcac cttgcctgcc tgcctcggga gccagggctg tgcacctggc 660
agtccctgcg gtcccagata gcctgaatcc tgcccggagt ggaactgaag cctgcacagt 720
gtccaccctg ttcccactcc catctttctt ccggacaatg aaataaagag ttaccaccca 780
gc 782

<210> SEQ ID NO 79
<211> LENGTH: 3178
<212> TYPE: DNA
<213> ORGANISM: Homo sapiens

<400> SEQUENCE: 79
gttgcctgtc tctaaacccc tccacattcc cgcggtcctt cagactgccc ggagagcgcg 60
ctctgcctgc cgcctgcctg cctgccactg agggttccca gcaccatgag ggcctggatc 120
ttctttctcc tttgcctggc cgggagggcc ttggcagccc ctcagcaaga agccctgcct 180
gatgagacag aggtggtgga agaaactgtg gcagaggtga ctgaggtatc tgtgggagct 240
aatcctgtcc aggtggaagt aggagaattt gatgatggtg cagaggaaac cgaagaggag 300
gtggtggcgg aaaatccctg ccagaaccac cactgcaaac acggcaaggt gtgcgagctg 360
gatgagaaca acacccccat gtgcgtgtgc caggacccca ccagctgccc agcccccatt 420
ggcgagtttg agaaggtgtg cagcaatgac aacaagacct tcgactcttc ctgccacttc 480
tttgccacaa agtgcaccct ggagggcacc aagaagggcc acaagctcca cctggactac 540
atcgggcctt gcaaatacat ccccccttgc ctggactctg agctgaccga attccccctg 600
cgcatgcggg actggctcaa gaacgtcctg gtcaccctgt atgagaggga tgaggacaac 660
aaccttctga ctgagaagca gaagctgcgg gtgaagaaga tccatgagaa tgagaagcgc 720
ctggaggcag gagaccaccc cgtggagctg ctggcccggg acttcgagaa gaactataac 780
atgtacatct tccctgtaca ctggcagttc ggccagctgg accagcaccc cattgacggg 840
tacctctccc acaccgagct ggctccactg cgtgctcccc tcatccccat ggagcattgc 900
accacccgct tttcgagac ctgtgacctg gacaatgaca agtacatcgc cctggatgag 960
tgggccggct gcttcggcat caagcagaag gatatcgaca aggatcttgt gatctaaatc 1020
cactccttcc acagtaccgg attctctctt taaccctccc cttcgtgttt cccccaatgt 1080
ttaaaatgtt tggatggttt gttgttctgc ctggagacaa ggtgctaaca tagatttaag 1140
tgaatacatt aacggtgcta aaaatgaaaa ttctaaccca agacatgaca ttcttagctg 1200
taacttaact attaaggcct tttccacacg cattaatagt cccatttttc tcttgccatt 1260
tgtagctttg cccattgtct tattggcaca tgggtggaca cggatctgct gggctctgcc 1320
ttaaacacac attgcagctt caacttttct ctttagtgtt ctgtttgaaa ctaatactta 1380
ccgagtcaga ctttgtgttc atttcatttc agggtcttgg ctgcctgtgg gcttccccag 1440

```
gtggcctgga ggtgggcaaa gggaagtaac agacacacga tgttgtcaag gatggttttg   1500
ggactagagg ctcagtggtg ggagagatcc ctgcagaacc caccaaccag aacgtggttt   1560
gcctgaggct gtaactgaga gaaagattct ggggctgtgt tatgaaaata tagacattct   1620
cacataagcc cagttcatca ccatttcctc ctttaccttt cagtgcagtt tcttttcaca   1680
ttaggctgtt ggttcaaact tttgggagca cggactgtca gttctctggg aagtggtcag   1740
cgcatcctgc agggcttctc ctcctctgtc ttttggagaa ccagggctct tctcaggggc   1800
tctagggact gccaggctgt ttcagccagg aaggccaaaa tcaagagtga gatgtagaaa   1860
gttgtaaaat agaaaaagtg gagttggtga atcggttgtt ctttcctcac atttggatga   1920
ttgtcataag gtttttagca tgttcctcct tttcttcacc ctccccttt ttcttctatt   1980
aatcaagaga aacttcaaag ttaatgggat ggtcggatct cacaggctga gaactcgttc   2040
acctccaagc atttcatgaa aaagctgctt cttattaatc atacaaactc tcaccatgat   2100
gtgaagagtt tcacaaatcc ttcaaaataa aaagtaatga cttagaaact gccttcctgg   2160
gtgatttgca tgtgtcttag tcttagtcac cttattatcc tgacacaaaa acacatgagc   2220
atacatgtct acacatgact acacaaatgc aaacctttgc aaacacatta tgcttttgca   2280
cacacacacc tgtacacaca caccggcatg tttatacaca gggagtgtat ggttcctgta   2340
agcactaagt tagctgtttt catttaatga cctgtggttt aacccttttg atcactacca   2400
ccattatcag caccagactg agcagctata tccttttatt aatcatggtc attcattcat   2460
tcattcattc acaaaatatt tatgatgtat ttactctgca ccaggtccca tgccaagcac   2520
tggggacaca gttatggcaa agtagacaaa gcatttgttc atttggagct tagagtccag   2580
gaggaataca ttagataatg acacaatcaa atataaattg caagatgtca caggtgtgat   2640
gaagggagag taggagagac catgagtatg tgtaacagga ggacacagca ttattctagt   2700
gctgtactgt tccgtacggc agccactacc cacatgtaac tttttaagat ttaaatttaa   2760
attagttaac attcaaaacg cagctcccca atcacactag caacatttca agtgcttgag   2820
agccatgcat gattagtggt taccctattg aataggtcag aagtagaatc ttttcatcat   2880
cacagaaagt tctattggac agtgctcttc tagatcatca taagactaca gagcactttt   2940
caaagctcat gcatgttcat catgttagtg tcgtattttg agctggggtt ttgagactcc   3000
ccttagagat agagaaacag acccaagaaa tgtgctcaat tgcaatgggc cacataccta   3060
gatctccaga tgtcatttcc cctctcttat tttaagttat gttaagatta ctaaaacaat   3120
aaaagctcct aaaaaatcaa aaaaaaaaaa aaaaaaaaaa aaaaaaaaaa aaaaaaaa     3178
```

<210> SEQ ID NO 80
<211> LENGTH: 2691
<212> TYPE: DNA
<213> ORGANISM: Homo sapiens

<400> SEQUENCE: 80

```
gcttgcccgt cggtcgctag ctcgctcggt gcgcgtcgtc ccgctccatg gcgctcttcg     60
tgcggctgct ggctctcgcc ctggctctgg ccctgggccc cgccgcgacc ctggcgggtc    120
ccgccaagtc gccctaccag ctggtgctgc agcacagcag gctccggggc cgccagcacg    180
gccccaacgt gtgtgctgtg cagaaggtta ttggcactaa taggaagtac ttcaccaact    240
gcaagcagtg gtaccaaagg aaaatctgtg gcaaatcaac agtcatcagc tacgagtgct    300
gtcctggata tgaaaaggtc cctggggaga agggctgtcc agcagcccta ccactctcaa    360
acctttacga gaccctggga gtcgttggat ccaccaccac tcagctgtac acggaccgca    420
```

```
cggagaagct gaggcctgag atggaggggc ccggcagctt caccatcttc gcccctagca    480
acgaggcctg ggcctccttg ccagctgaag tgctggactc cctggtcagc aatgtcaaca    540
ttgagctgct caatgccctc cgctaccata tggtgggcag gcgagtcctg actgatgagc    600
tgaaacacgg catgaccctc acctctatgt accagaattc caacatccag atccaccact    660
atcctaatgg gattgtaact gtgaactgtg cccggctcct gaaagccgac caccatgcaa    720
ccaacggggt ggtgcacctc atcgataagg tcatctccac catcaccaac aacatccagc    780
agatcattga gatcgaggac acctttgaga cccttcgggc tgctgtggct gcatcagggc    840
tcaacacgat gcttgaaggt aacggccagt acacgctttt ggccccgacc aatgaggcct    900
tcgagaagat ccctagtgag actttgaacc gtatcctggg cgacccagaa gccctgagag    960
acctgctgaa caaccacatc ttgaagtcag ctatgtgtgc tgaagccatc gttgcggggc   1020
tgtctgtaga gaccctggag ggcacgacac tggaggtggg ctgcagcggg gacatgctca   1080
ctatcaacgg gaaggcgatc atctccaata aagacatcct agccaccaac ggggtgatcc   1140
actacattga tgagctactc atcccagact cagccaagac actatttgaa ttggctgcag   1200
agtctgatgt gtccacagcc attgaccttt tcagacaagc cggcctcggc aatcatctct   1260
ctggaagtga gcggttgacc ctcctggctc ccctgaattc tgtattcaaa gatggaaccc   1320
ctccaattga tgcccataca aggaatttgc ttcggaacca cataattaaa gaccagctgg   1380
cctctaagta tctgtaccat ggacagaccc tggaaactct gggcggcaaa aaactgagag   1440
tttttgttta tcgtaatagc ctctgcattg agaacagctg catcgcggcc cacgacaaga   1500
gggggaggta cgggaccctg ttcacgatgg accgggtgct gacccccccca atggggactg   1560
tcatggatgt cctgaaggga gacaatcgct ttagcatgct ggtagctgcc atccagtctg   1620
caggactgac ggagaccctc aaccgggaag gagtctacac agtctttgct cccacaaatg   1680
aagccttccg agccctgcca ccaagagaac ggagcagact cttgggagat gccaaggaac   1740
ttgccaacat cctgaaatac cacattggtg atgaaatcct ggttagcgga ggcatcgggg   1800
ccctggtgcg gctaaagtct ctccaaggtg acaagctgga agtcagcttg aaaaacaatg   1860
tggtgagtgt caacaaggag cctgttgccg agcctgacat catggccaca aatggcgtgg   1920
tccatgtcat caccaatgtt ctgcagcctc cagccaacag acctcaggaa agaggggatg   1980
aacttgcaga ctctgcgctt gagatcttca aacaagcatc agcgttttcc agggcttccc   2040
agaggtctgt gcgactagcc cctgtctatc aaaagttatt agagaggatg aagcattagc   2100
ttgaagcact acaggaggaa tgcaccacgg cagctctccg ccaatttctc tcagatttcc   2160
acagagactg tttgaatgtt ttcaaaacca agtatcacac tttaatgtac atgggccgca   2220
ccataatgag atgtgagcct tgtgcatgtg ggggaggagg gagagagatg tactttttaa   2280
atcatgttcc ccctaaacat ggctgttaac ccactgcatg cagaaacttg gatgtcactg   2340
cctgacattc acttccagag aggacctatc ccaaatgtgg aattgactgc ctatgccaag   2400
tccctggaaa aggagcttca gtattgtggg gctcataaaa catgaatcaa gcaatccagc   2460
ctcatgggaa gtcctggcac agtttttgta aagcccttgc acagctggag aaatggcatc   2520
attataagct atgagttgaa atgttctgtc aaatgtgtct cacatctaca cgtggcttgg   2580
aggcttttat ggggccctgt ccaggtagaa aagaaatggt atgtagagct tagatttccc   2640
tattgtgaca gagccatggt gtgtttgtaa taataaaacc aaagaaacat a            2691
```

<210> SEQ ID NO 81

<211> LENGTH: 1757
<212> TYPE: DNA
<213> ORGANISM: Homo sapiens

<400> SEQUENCE: 81
caagcttggc acgagggcag gcattgcccg agccagccga gccgccagag ccgcgggccg 60
cgcgggtgtc gcgggcccaa ccccaggatg ctcccctgcg cctcctgcct acccgggtct 120
ctactgctct gggcgctgct actgttgctc ttgggatcag cttctcctca ggattctgaa 180
gagcccgaca gctacacgga atgcacagat ggctatgagt gggacccaga cagccagcac 240
tgccgggatg tcaacgagtg tctgaccatc cctgaggcct gcaaggggga aatgaagtgc 300
atcaaccact acgggggcta cttgtgcctg ccccgctccg ctgccgtcat caacgaccta 360
cacggcgagg gacccccgcc accagtgcct cccgctcaac accccaaccc ctgcccacca 420
ggctatgagc ccgacgatca ggacagctgt gtggatgtgg acgagtgtgc ccaggccctg 480
cacgactgtc gccccagcca ggactgccat aacttgcctg gctcctatca gtgcacctgc 540
cctgatggtt accgcaagat cgggcccgag tgtgtggaca tagacgagtg ccgctaccgc 600
tactgccagc accgctgcgt gaacctgcct ggctccttcc gctgccagtg cgagccgggc 660
ttccagctgg ggcctaacaa ccgctcctgt gttgatgtga acgagtgtga catgggggcc 720
ccatgcgagc agcgctgctt caactcctat gggaccttcc tgtgtcgctg ccaccagggc 780
tatgagctgc atcgggatgg cttctcctgc agtgatattg atgagtgtag ctactccagc 840
tacctctgtc agtaccgctg cgtcaacgag ccaggccgtt tctcctgcca ctgcccacag 900
ggttaccagc tgctggccac acgcctctgc caagacattg atgagtgtga gtctggtgcg 960
caccagtgct ccgaggccca aacctgtgtc aacttccatg gggctaccg ctgcgtggac 1020 accaaccgct gcgtggagcc ctacatccag gtctctgaga accgctgtct ctgcccggcc 1080
tccaaccctc tatgtcgaga gcagccttca tccattgtgc accgctacat gaccatcacc 1140
tcggagcgga gagtacccgc tgacgtgttc cagatccagg cgacctccgt ctaccccggt 1200
gcctacaatg cctttcagat ccgtgctgga aactcgcagg gggactttta cattaggcaa 1260
atcaacaacg tcagcgccat gctggtcctc gcccggccgg tgacgggccc ccgggagtac 1320
gtgctggacc tggagatggt caccatgaat tccctcatga gctaccgggc cagctctgta 1380
ctgaggctca ccgtctttgt aggggcctac accttctgag gagcaggagg gagccaccct 1440
ccctgcagct accctagctg aggagcctgt tgtgaggggc agaatgagaa aggcccaggg 1500
gcccccattg acaggagctg ggagctctgc accacgagct tcagtcaccc cgagaggaga 1560
ggaggtaacg aggagggcgg actccaggcc ccggcccaga gatttggact tggctggctt 1620
gcaggggtcc taagaaactc cactctggac agcgccagga ggccctgggt tccattccta 1680
actctgcctc aaactgtaca tttggataag ccctagtagt tccctgggcc tgtttttcta 1740
taaaacgagg caactgg 1757

<210> SEQ ID NO 82
<211> LENGTH: 1804
<212> TYPE: DNA
<213> ORGANISM: Homo sapiens

<400> SEQUENCE: 82
gtatcactca gaatctggca gccagttccg tcctgacaga gttcacagca tatattggtg 60
gattcttgtc catagtgcat ctgctttaag aattaacgaa agcagtgtca agacagtaag 120
gattcaaacc atttgccaaa aatgagtcta agtgcattta ctctcttcct ggcattgatt 180

```
ggtggtacca gtggccagta ctatgattat gattttcccc tatcaattta tgggcaatca    240
tcaccaaact gtgcaccaga atgtaactgc cctgaaagct acccaagtgc catgtactgt    300
gatgagctga aattgaaaag tgtaccaatg gtgcctcctg gaatcaagta tctttacctt    360
aggaataacc agattgacca tattgatgaa aaggcctttg agaatgtaac tgatctgcag    420
tggctcattc tagatcacaa ccttctagaa aactccaaga taaaagggag agttttctct    480
aaattgaaac aactgaagaa gctgcatata aaccacaaca acctgacaga gtctgtgggc    540
ccacttccca aatctctgga ggatctgcag cttactcata acaagatcac aaagctgggc    600
tcttttgaag gattggtaaa cctgaccttc atccatctcc agcacaatcg gctgaaagag    660
gatgctgttt cagctgcttt taaaggtctt aaatcactcg aataccttga cttgagcttc    720
aatcagatag ccagactgcc ttctggtctc cctgtctctc ttctaactct ctacttagac    780
aacaataaga tcagcaacat ccctgatgag tatttcaagc gttttaatgc attgcagtat    840
ctgcgtttat ctcacaacga actggctgat agtggaatac ctggaaattc tttcaatgtg    900
tcatccctgg ttgagctgga tctgtcctat aacaagctta aaaacatacc aactgtcaat    960
gaaaaccttg aaaactatta cctggaggtc aatcaacttg agaagtttga cataaagagc   1020
ttctgcaaga tcctggggcc attatcctac tccaagatca agcatttgcg tttggatggc   1080
aatcgcatct cagaaaccag tcttccaccg gatatgtatg aatgtctacg tgttgctaac   1140
gaagtcactc ttaattaata tctgtatcct ggaacaatat tttatggtta tgtttttctg   1200
tgtgtcagtt ttcatagtat ccatatttta ttactgttta ttacttccat gaattttaaa   1260
atctgaggga aatgttttgt aaacatttat tttttttaaa gaaaagatga aaggcaggcc   1320
tatttcatca caagaacaca cacatataca cgaatagaca tcaaactcaa tgctttattt   1380
gtaaatttag tgttttttta tttctactgt caaatgatgt gcaaaacctt ttactggttg   1440
catggaaatc agccaagttt tataatcctt aaatcttaat gttcctcaaa gcttggatta   1500
aatacatatg gatgttactc tcttgcacca aattatcttg atacattcaa atttgtctgg   1560
ttaaaaaata ggtggtagat attgaggcca agaatattgc aaaatacatg aagcttcatg   1620
cacttaaaga agtattttta gaataagaat ttgcatactt acctagtgaa actttctag    1680
aattattttt cactctaagt catgtatgtt tctctttgat tatttgcatg ttatgtttaa   1740
taagctacta gcaaaataaa acatagcaaa tgaaaaaaaa aaaaaaaaaa aaaaaaaaaa   1800
aaaa                                                                1804
```

<210> SEQ ID NO 83
<211> LENGTH: 3290
<212> TYPE: DNA
<213> ORGANISM: Homo sapiens

<400> SEQUENCE: 83

```
agcggggccg gaccgggcgg gcggagccgg gcccgcgggg ctgctgcggg gcgatcgggc     60
cgggccgctg ccgcgccatg gactcccgtg tccagcctga gttccagcct cactgagtgg    120
ccacccccaa agtgctgcca gccgaggaag cccccagcac tgaccatgtc tattatggac    180
cacagcccca ccacgggcgt ggtcacagtc atcgtcatcc tcattgccat cgcggccctg    240
ggggccttga tcctgggctg ctggtgctac ctgcggctgc agcgcatcag ccagtcagag    300
gacgaggaga gcatcgtggg ggatggggag accaaggaac ccttcctgct ggtgcagtat    360
tcggccaagg gaccgtgcgt ggagagaaag gccaagctga tgactcccaa cggcccggaa    420
```

-continued

```
gtccacggct gagccaggat gcaaggctcc tggtcctgtt tgcagccggc caagaggcgc    480
tgggaggggc aaaaccatac ggatgcgctg ctgtctgaga ggaagggctg acacttgctg    540
gcatggcctc tgcgggcttc gtcatcgcat gcactgatgc ccggggacct ggctgtcctg    600
ggcttcccct cggcctccag gtgaggctgc ccattgcagg cactgggcag gcctgacctt    660
gctggggctc atggccctgt agcgcttttg ttacttgaat gtctagctga gcctgttttt    720
gatggagcta ctactgtaat gcgtgaacta acaaacctgt gaactgtaaa taggcccctg    780
gaagcacgtg cttaagccct tttgctgatt tttaaaaata tcatctagcg cacacgggac    840
tggtattctg gctgtactaa tgacaagctg agtcaagacc ctggagggtc ataggcttgt    900
aaaggcccac gccacactcg gcaggggtct ctcatgtgtg tccatctgcg tgtatgtcaa    960
ggaagtgaga tgccaatttg gggtcttgag gctgaccagt tggggtgctt gggtgatctc   1020
tgcttcatta gtcatgggtg gaagaaaaac cacacccccc gcacccctcc gttctttctg   1080
catagactca cttgttaaat agcagttctg ttgagagtgg agttactgca gggaagctac   1140
cggacctgcc tgggagccag tgaagggcga gtcagggcac gcgtcctgga ggctgccagc   1200
gtccttgtag cagagcagtt tcttgccgct tgggtcttca gcacgccaag ccccccacca   1260
accctccacc ccgagtgaag gcttcgctga aattgctttg gtcctcatag agcctgtggt   1320
ggctactttt ggtctgaaac ccacttggcc caggaaagag aaaaggttgt atgttttgtg   1380
ttggtgtttc ctattttctg cactggaggg gaggggactg ttgaggttct gtctttttc    1440
ttcttttcct cttccctctt cacatcactt ggcttccttt cctctctgat gaccgtccgc   1500
ctatggggtt ctgacttcac tttcctcagc gggtctccag tcccctgacc cagctctaaa   1560
ggcacttagg acccagggaa catttctcac gtgcacattc ccctaagagc caccagactg   1620
cttcctgcca gcctgtgctt gcggcaggga gccggggcag ggcagaggtg aacttgaagt   1680
tcaggacttg actctcccac aggtggtgag ctggtggctc tctggtgagc tagtgtctcc   1740
acagcctgtc tccaaggcct cccctatgta catttcagtg agctcacttt gatttttaat   1800
cccaccacaa gcacatacta attttattta tgattcaaat gtgactcgtg cctgcccatc   1860
cctgtaatag atggaaggtc agccccggct taaccacaga gcactggccc ttcatggctg   1920
agctcagagc tctggcctcc tgctcagact aaaggcacct cctctggcct cacccaagcc   1980
tcttctaaaa accatgttga atgaatccac gttctggaac cccgaggcgg gagaagtagg   2040
gagctgttcg tttaagcagc atacacctaa attgggggtt taaacattaa gtaggagctt   2100
ggggtggaag agggacagcc ggctgggcca cctgagcaga aggtggtaat gaaacacctc   2160
agctgggctc ttgggagacc ttaggaagca ggagaggcaa cacctctggc tactgatggt   2220
gtggcaagtt cagaagaggt ggtggtgggg taggcgtgat gtcagcagaa gccctgcagg   2280
ctgggtgggc aggacacgtg gtgggggcca ctgaaaccag gcctaggagg gagaacaagt   2340
tccaaaggtg ccgactggaa gaagggggta aaagtttgct ttggtgagtg agaaaaggct   2400
ggggcgtgtg atccatcccc tcacgtttca gaacttccag gctttctacc tcgactctca   2460
ccacagccag cacatacacc taggctgttt ttccttcctc cacacctgag ggacgcagca   2520
acagctagga tctgcatttt caggttccga gcctgacccc tggaactgac cagcgctcga   2580
ttgtcagcct tggcctgggg ttttgacctt gccagtgaag tttcggtttt gaagtgatta   2640
aatgtcactt cctcatcagt ttcacttctg gaggttttct tatcctactc cctggtgcca   2700
gggacgtacc tgggagtttg aatcaggccc atttgagcgt ggcagccgtg ttgggtgaag   2760
gtccggggct cggtgaggca ctgggggggt tttcgggagg aaaatgaaaa tgcttctaga   2820
```

-continued atgagtgaac cacatcatag ctctcactgt tttttcaata gctacttttt ttagcagaca 2880
ccagagccac actcaaatgg ctaagtaggt tatgacctct ctggattatt tttgaatgcc 2940
caactgttgc attcaagttt tctgactaat aagaaattaa gcattcatcc ttcgtatcac 3000
tgcagaagca acagtggggg cacagggagg gaactcttga cactgagcca ctaaaatatg 3060
gactaatttt ttggacaaat cttcaaacgg actgtgctac tgtatttgtc tcaaagctac 3120
caagtttgtg caataagtgg aagggatgtc atccttcttc aataaatgct gaatgacatt 3180
caagctgatt ttctagacca ctgagaaaat ctttatttac aataaatttc aataaaattt 3240
gcataaatat attcccaaaa aaaaaaaaaa aaaaaaagaa aaaaaaaaaa 3290

<210> SEQ ID NO 84
<211> LENGTH: 1616
<212> TYPE: DNA
<213> ORGANISM: Homo sapiens

<400> SEQUENCE: 84
ctccctgtgt tggtggagga tgtctgcagc agcatttaaa ttctgggagg gcttggttgt 60
cagcagcagc aggaggaggc agagcacagc atcgtcggga ccagactcgt ctcaggccag 120
ttgcagcctt ctcagccaaa cgccgaccaa ggaaaactca ctaccatgag aattgcagtg 180
atttgctttt gcctcctagg catcacctgt gccataccag ttaaacaggc tgattctgga 240
agttctgagg aaaagcagct ttacaacaaa tacccagatg ctgtggccac atggctaaac 300
cctgacccat ctcagaagca gaatctccta gccccacaga cccttccaag taagtccaac 360
gaaagccatg accacatgga tgatatggat gatgaagatg atgatgacca tgtggacagc 420
caggactcca ttgactcgaa cgactctgat gatgtagatg acactgatga ttctcaccag 480
tctgatgagt ctcaccattc tgatgaatct gatgaactgg tcactgattt tcccacggac 540
ctgccagcaa ccgaagtttt cactccagtt gtccccacag tagacacata tgatggccga 600
ggtgatagtg tggtttatgg actgaggtca aaatctaaga agtttcgcag acctgacatc 660
cagtaccctg atgctacaga cgaggacatc acctcacaca tggaaagcga ggagttgaat 720
ggtgcataca aggccatccc cgttgcccag gacctgaacg cgccttctga ttgggacagc 780
cgtgggaagg acagttatga aacgagtcag ctggatgacc agagtgctga aacccacagc 840
cacaagcagt ccagattata taagcggaaa gccaatgatg agagcaatga gcattccgat 900
gtgattgata gtcaggaact ttccaaagtc agccgtgaat tccacagcca tgaatttcac 960
agccatgaag atatgctggt tgtagacccc aaaagtaagg aagaagataa acacctgaaa 1020
tttcgtattt ctcatgaatt agatagtgca tcttctgagg tcaattaaaa ggagaaaaaa 1080
tacaatttct cactttgcat ttagtcaaaa gaaaaaatgc tttatagcaa aatgaaagag 1140
aacatgaaat gcttctttct cagtttattg gttgaatgtg tatctatttg agtctggaaa 1200
taactaatgt gtttgataat tagtttagtt tgtggcttca tggaaactcc ctgtaaacta 1260
aaagcttcag ggttatgtct atgttcattc tatagaagaa atgcaaacta tcactgtatt 1320
ttaatatttg ttattctctc atgaatagaa atttatgtag aagcaaacaa aatactttta 1380
cccacttaaa aagagaatat aacattttat gtcactataa tcttttgttt tttaagttag 1440
tgtatatttt gttgtgatta tctttttgtg gtgtgaataa atcttttatc ttgaatgtaa 1500
taagaatttg gtggtgtcaa ttgcttattt gttttcccac ggttgtccag caattaataa 1560
aacataacct tttttactgc ctaaaaaaaa aaaaaaaaaa aaaaaaaaaa aaaaaa 1616

<210> SEQ ID NO 85
<211> LENGTH: 11185
<212> TYPE: DNA
<213> ORGANISM: Homo sapiens

<400> SEQUENCE: 85
gctgccccga gcctttctgg ggaagaactc caggcgtgcg gacgcaacag ccgagaacat 60
taggtgttgt ggacaggagc tgggaccaag atcttcggcc agccccgcat cctcccgcat 120
cttccagcac cgtcccgcac cctccgcatc cttccccggg ccaccacgct tcctatgtga 180
cccgcctggg caacgccgaa cccagtcgcg cagcgctgca gtgaattttc cccccaaact 240
gcaataagcc gccttccaag gccaagatgt tcataaatat aaagagcatc ttatggatgt 300
gttcaacctt aatagtaacc catgcgctac ataaagtcaa agtgggaaaa agcccaccgg 360
tgaggggctc cctctctgga aaagtcagcc taccttgtca tttttcaacg atgcctactt 420
tgccacccag ttacaacacc agtgaatttc tccgcatcaa atggtctaag attgaagtgg 480
acaaaaatgg aaaagatttg aaagagacta ctgtccttgt ggcccaaaat ggaaatatca 540
agattggtca ggactacaaa gggagagtgt ctgtgcccac acatcccgag gctgtgggcg 600
atgcctccct cactgtggtc aagctgctgg caagtgatgc gggtctttac cgctgtgacg 660
tcatgtacgg gattgaagac acacaagaca cggtgtcact gactgtggat ggggttgtgt 720
ttcactacag ggcggcaacc agcaggtaca cactgaattt tgaggctgct cagaaggctt 780
gtttggacgt tggggcagtc atagcaactc cagagcagct ctttgctgcc tatgaagatg 840
gatttgagca gtgtgacgca ggctggctgg ctgatcagac tgtcagatat cccatccggg 900
ctcccagagt aggctgttat ggagataaga tgggaaaggc aggagtcagg acttatggat 960
tccgttctcc ccaggaaact tacgatgtgt attgttatgt ggatcatctg gatggtgatg 1020
tgttccacct cactgtcccc agtaaattca ccttcgagga ggctgcaaaa gagtgtgaaa 1080
accaggatgc caggctggca acagtggggg aactccaggc ggcatggagg aacggctttg 1140
accagtgcga ttacgggtgg ctgtcggatg ccagcgtgcg ccaccctgtg actgtggcca 1200
gggcccagtg tggaggtggt ctacttgggg tgagaaccct gtatcgtttt gagaaccaga 1260
caggcttccc tccccctgat agcagatttg atgcctactg ctttaaacct aaagaggcta 1320
caaccatcga tttgagtatc ctcgcagaaa ctgcatcacc cagtttatcc aaagaaccac 1380
aaatggtttc tgatagaact acaccaatca tccctttagt tgatgaatta cctgtcattc 1440
caacagagtt ccctcccgtg ggaaatattg tcagttttga acagaaagcc acagtccaac 1500
ctcaggctat cacagatagt ttagccacca aattacccac acctactggc agtaccaaga 1560
agccctggga tatggatgac tactcacctt ctgcttcagg acctcttgga aagctagaca 1620
tatcagaaat taaggaagaa gtgctccaga gtacaactgg cgtctctcat tatgctacgg 1680
attcatggga tggtgtcgtg gaagataaac aaacacaaga atcggttaca cagattgaac 1740
aaatagaagt gggtcctttg gtaacatcta tggaaatctt aaagcacatt ccttccaagg 1800
aattccctgt aactgaaaca ccattggtaa ctgcaagaat gatcctggaa tccaaaactg 1860
aaaagaaaat ggtaagcact gtttctgaat tggtaaccac aggtcactat ggattcacct 1920
tgggagaaga ggatgatgaa gacagaacac ttacagttgg atctgatgag agcaccttga 1980
tctttgacca aattcctgaa gtcattacgg tgtcaaagac ttcagaagac accatccaca 2040
ctcatttaga agacttggag tcagtctcag catccacaac tgtttcccct ttaattatgc 2100
ctgataataa tggatcatcc atggatgact gggaagagag acaaactagt ggtaggataa 2160

-continued

```
cggaagagtt tcttggcaaa tatctgtcta ctacaccttt tccatcacag catcgtacag   2220
aaatagaatt gtttccttat tctggtgata aaatattagt agagggaatt tccacagtta   2280
tttatccttc tctacaaaca gaaatgacac atagaagaga aagaacagaa acactaatac   2340
cagagatgag aacagatact tatacagatg aaatacaaga agagatcact aaaagtccat   2400
ttatgggaaa aacagaagaa gaagtcttct ctgggatgaa actctctaca tctctctcag   2460
agccaattca tgttacagag tcttctgtgg aaatgaccaa gtcttttgat ttcccaacat   2520
tgataacaaa gttaagtgca gagccaacag aagtaagaga tatggaggaa gactttacag   2580
caactccagg tactacaaaa tatgatgaaa atattacaac agtgcttttg gcccatggta   2640
ctttaagtgt tgaagcagcc actgtatcaa aatggtcatg ggatgaagat aatacaacat   2700
ccaagccttt agagtctaca gaaccttcag cctcttcaaa attgccccct gccttactca   2760
caactgtggg gatgaatgga aaggataaag acatcccaag tttcactgaa gatggagcag   2820
atgaatttac tcttattcca gatagtactc aaaagcagtt agaggaggtt actgatgaag   2880
acatagcagc ccatggaaaa ttcacaatta gatttcagcc aactacatca actggtattg   2940
cagaaaagtc aactttgaga gattctacaa ctgaagaaaa agttccacct atcacaagca   3000
ctgaaggcca agtttatgca accatggaag gaagtgcttt gggtgaagta gaagatgtgg   3060
acctctctaa gccagtatct actgttcccc aatttgcaca cacttcagag gtggaaggat   3120
tagcatttgt tagttatagt agcacccaag agcctactac ttatgtagac tcttcccata   3180
ccattcctct ttctgtaatt cccaagacag actggggagt gttagtacct tctgttccat   3240
cagaagatga agttctaggt gaaccctctc aagacatact tgtcattgat cagactcgcc   3300
ttgaagcgac tatttctcca gaaactatga gaacaacaaa aatcacagag ggaacaactc   3360
aggaagaatt cccttggaaa gaacagactg cagagaaacc agttcctgct ctcagttcta   3420
cagcttggac tcccaaggag gcagtaacac cactggatga acaagagggc gatggatcag   3480
catatacagt ctctgaagat gaattgttga caggttctga gagggtccca gttttagaaa   3540
caactccagt tggaaaaatt gatcacagtg tgtcttatcc accaggtgct gtaactgagc   3600
acaaagtgaa aacagatgaa gtggtaacac taacaccacg cattgggcca aaagtatctt   3660
taagtccagg gcctgaacaa aaatatgaaa cagaaggtag tagtacaaca ggatttacat   3720
catctttgag tccttttagt acccacatta cccagcttat ggaagaaacc actactgaga   3780
aaacatccct agaggatatt gatttaggct caggattatt tgaaaagccc aaagccacag   3840
aactcataga attttcaaca atcaaagtca cagttccaag tgatattacc actgccttca   3900
gttcagtaga cagacttcac acaacttcag cattcaagcc atcttccgcg atcactaaga   3960
aaccacctct catcgacagg gaacctggtg aagaaacaac cagtgacatg gtaatcattg   4020
gagaatcaac atctcatgtt cctcccacta cccttgaaga tattgtagcc aaggaaacag   4080
aaaccgatat tgatagagag tatttcacga cttcaagtcc tcctgctaca cagccaacaa   4140
gaccacccac tgtggaagac aaagaggcct ttggacctca ggcgcttttct acgccacagc   4200
ccccagcaag cacaaaattt caccctgaca ttaatgttta tattattgag gtcagagaaa   4260
ataagacagg tcgaatgagt gatttgagtg taattggtca tccaatagat tcagaatcta   4320
aagaagatga accttgtagt gaagaaacag atccagtgca tgatctaatg gctgaaattt   4380
tacctgaatt ccctgacata attgaaatag acctatacca cagtgaagaa aatgaagaag   4440
aagaagaaga gtgtgcaaat gctactgatg tgacaaccac cccatctgtg cagtacataa   4500
```

-continued

```
atgggaagca tctcgttacc actgtgccca aggacccaga agctgcagaa gctaggcgtg   4560
gccagtttga aagtgttgca ccttctcaga atttctcgga cagctctgaa agtgatactc   4620
atccatttgt aatagccaaa acggaattgt ctactgctgt gcaacctaat gaatctacag   4680
aaacaactga gtctcttgaa gttacatgga agcctgagac ttaccctgaa acatcagaac   4740
atttttcagg tggtgagcct gatgttttcc ccacagtccc attccatgag gaatttgaaa   4800
gtggaacagc caaaaaaggg gcagaatcag tcacagagag agatactgaa gttggtcatc   4860
aggcacatga acatactgaa cctgtatctc tgtttcctga agagtcttca ggagagattg   4920
ccattgacca agaatctcag aaaatagcct ttgcaagggc tacagaagta acatttggtg   4980
aagaggtaga aaaaagtact tctgtcacat acactcccac tatagttcca agttctgcat   5040
cagcatatgt ttcagaggaa gaagcagtta ccctaatagg aaatccttgg ccagatgacc   5100
tgttgtctac caaagaaagc tgggtagaag caactcctag acaagttgta gagctctcag   5160
ggagttcttc gattccaatt acagaaggct ctggagaagc agaagaagat gaagatacaa   5220
tgttcaccat ggtaactgat ttatcacaga gaaatactac tgatacactc attactttag   5280
acactagcag gataatcaca gaaagctttt ttgaggttcc tgcaaccacc atttatccag   5340
tttctgaaca accttctgca aaagtggtgc ctaccaagtt tgtaagtgaa acagacactt   5400
ctgagtggat ttccagtacc actgttgagg aaaagaaaag gaaggaggag gagggaacta   5460
caggtacggc ttctacattt gaggtatatt catctacaca gagatcggat caattaattt   5520
taccctttga attagaaagt ccaaatgtag ctacatctag tgattcaggt accaggaaaa   5580
gttttatgtc cttgacaaca ccaacacagt ctgaaaggga aatgacagat tctactcctg   5640
tctttacaga aacaaataca ttagaaaatt tgggggcaca gaccactgag cacagcagta   5700
tccatcaacc tggggttcag gaagggctga ccactctccc acgtagtcct gcctctgtct   5760
ttatggagca gggctctgga gaagctgctg ccgacccaga aaccaccact gtttcttcat   5820
tttcattaaa cgtagagtat gcaattcaag ccgaaaagga agtagctggc actttgtctc   5880
cgcatgtgga aactacattc tccactgagc caacaggact ggttttgagt acagtaatgg   5940
acagagtagt tgctgaaaat ataacccaaa catccaggga aatagtgatt tcagagcgat   6000
taggagaacc aaattatggg gcagaaataa ggggcttttc cacaggtttt cctttggagg   6060
aagatttcag tggtgacttt agagaatact caacagtgtc tcatcccata gcaaaagaag   6120
aaacggtaat gatggaaggc tctggagatg cagcatttag ggacacccag acttcaccat   6180
ctacagtacc tacttcagtt cacatcagtc acatatctga ctcagaagga cccagtagca   6240
ccatggtcag cacttcagcc ttcccctggg aagagtttac atcctcagct gagggctcag   6300
gtgagcaact ggtcacagtc agcagctctg ttgttccagt gcttcccagt gctgtgcaaa   6360
agttttctgg tacagcttcc tccattatcg acgaaggatt gggagaagtg ggtactgtca   6420
atgaaattga tagaagatcc accattttac caacagcaga agtggaaggt acgaaagctc   6480
cagtagagaa ggaggaagta aaggtcagtg gcacagtttc aacaaacttt ccccaaacta   6540
tagagccagc caaattatgg tctaggcaag aagtcaaccc tgtaagacaa gaaattgaaa   6600
gtgaaacaac atcagaggaa caaattcaag aagaaaagtc atttgaatcc cctcaaaact   6660
ctcctgcaac agaacaaaca atctttgatt cacagacatt tactgaaact gaactcaaaa   6720
ccacagatta ttctgtacta acaacaaaga aaacttacag tgatgataaa gaaatgaagg   6780
aggaagacac ttctttagtt aacatgtcta ctccagatcc agatgcaaat ggcttggaat   6840
cttacacaac tctccctgaa gctactgaaa agtcacattt tttcttagct actgcattag   6900
```

-continued

```
taactgaatc tataccagct gaacatgtag tcacagattc accaatcaaa aaggaagaaa   6960
gtacaaaaca ttttccgaaa ggcatgagac caacaattca agagtcagat actgagctct   7020
tattctctgg actgggatca ggagaagaag ttttacctac tctaccaaca gagtcagtga   7080
attttactga agtggaacaa atcaataaca cattatatcc ccacacttct caagtggaaa   7140
gtacctcaag tgacaaaatt gaagacttta acagaatgga aaatgtggca aaagaagttg   7200
gaccactcgt atctcaaaca gacatctttg aaggtagtgg gtcagtaacc agcacaacat   7260
taatagaaat tttaagtgac actggagcag aaggacccac ggtggcacct ctccctttct   7320
ccacggacat cggacatcct caaaatcaga ctgtcaggtg ggcagaagaa atccagacta   7380
gtagaccaca aaccataact gaacaagact ctaacaagaa ttcttcaaca gcagaaatta   7440
acgaaacaac aacctcatct actgattttc tggctagagc ttatggtttt gaaatggcca   7500
aagaatttgt tacatcagca ccaaaaccat ctgacttgta ttatgaacct tctggagaag   7560
gatctggaga agtggatatt gttgattcat ttcacacttc tgcaactact caggcaacca   7620
gacaagaaag cagcaccaca tttgtttctg atgggtccct ggaaaaacat cctgaggtgc   7680
caagcgctaa agctgttact gctgatggat tcccaacagt ttcagtgatg ctgcctcttc   7740
attcagagca gaacaaaagc tcccctgatc caactagcac actgtcaaat acagtgtcat   7800
atgagaggtc cacagacggt agtttccaag accgtttcag ggaattcgag gattccacct   7860
taaaacctaa cagaaaaaaa cccactgaaa atattatcat agacctggac aaagaggaca   7920
aggatttaat attgacaatt acagagagta ccatccttga aattctacct gagctgacat   7980
cggataaaaa tactatcata gatattgatc atactaaacc tgtgtatgaa gacattcttg   8040
gaatgcaaac agatatagat acagaggtac catcagaacc acatgacagt aatgatgaaa   8100
gtaatgatga cagcactcaa gttcaagaga tctatgaggc agctgtcaac ctttctttaa   8160
ctgaggaaac atttgagggc tctgctgatg ttctggctag ctacactcag gcaacacatg   8220
atgaatcaat gacttatgaa gatagaagcc aactagatca catgggcttt cacttcacaa   8280
ctgggatccc tgctcctagc acagaaacag aattagacgt tttacttccc acggcaacat   8340
ccctgccaat tcctcgtaag tctgccacag ttattccaga gattgaagga ataaaagctg   8400
aagcaaaagc cctggatgac atgtttgaat caagcacttt gtctgatggt caagctattg   8460
cagaccaaag tgaaataata ccaacattgg gccaatttga aaggactcag gaggagtatg   8520
aagacaaaaa acatgctggt ccttcttttc agccagaatt ctcttcagga gctgaggagg   8580
cattagtaga ccatactccc tatctaagta ttgctactac ccaccttatg gatcagagtg   8640
taacagaggt gcctgatgtg atggaaggat ccaatccccc atattacact gatacaacat   8700
tagcagtttc aacatttgcg aagttgtctt ctcagacacc atcatctccc ctcactatct   8760
actcaggcag tgaagcctct ggacacacag agatccccca gcccagtgct ctgccaggaa   8820
tagacgtcgg ctcatctgta atgtccccac aggattcttt taaggaaatt catgtaaata   8880
ttgaagcaac tttcaaacca tcaagtgagg aatacettca cataactgag cctccctctt   8940
tatctcctga cacaaaatta gaaccttcag aagatgatgg taaacctgag ttattagaag   9000
aaatggaagc ttctcccaca gaacttattg ctgtggaagg aactgagatt ctccaagatt   9060
tccaaaacaa aaccgatggt caagtttctg gagaagcaat caagatgttt cccaccatta   9120
aaacacctga ggctggaact gttattacaa ctgccgatga aattgaatta gaaggtgcta   9180
cacagtggcc acactctact tctgcttctg ccacctatgg ggtcgaggca ggtgtggtgc   9240
```

cttggctaag tccacagact tctgagaggc ccacgctttc ttcttctcca gaaataaacc 9300
ctgaaactca agcagcttta atcagagggc aggattccac gatagcagca tcagaacagc 9360
aagtggcagc gagaattctt gattccaatg atcaggcaac agtaaaccct gtggaattta 9420
atactgaggt tgcaacacca ccattttccc ttctggagac ttctaatgaa acagatttcc 9480
tgattggcat taatgaagag tcagtggaag gcacggcaat ctatttacca ggacctgatc 9540
gctgcaaaat gaacccgtgc cttaacggag gcacctgtta tcctactgaa acttcctacg 9600
tatgcacctg tgtgccagga tacagcggag accagtgtga acttgatttt gatgaatgtc 9660
actctaatcc ctgtcgtaat ggagccactt gtgttgatgg ttttaacaca ttcaggtgcc 9720
tctgccttcc aagttatgtt ggtgcacttt gtgagcaaga taccgagaca tgtgactatg 9780
gctggcacaa attccaaggg cagtgctaca aatactttgc ccatcgacgc acatgggatg 9840
cagctgaacg ggaatgccgt ctgcagggtg cccatctcac aagcatcctg tctcacgaag 9900
aacaaatgtt tgttaatcgt gtgggccatg attatcagtg gataggcctc aatgacaaga 9960
tgtttgagca tgacttccgt tggactgatg gcagcacact gcaatacgag aattggagac 10020
ccaaccagcc agacagcttc ttttctgctg gagaagactg tgttgtaatc atttggcatg 10080
agaatggcca gtggaatgat gttccctgca attaccatct cacctatacg tgcaagaaag 10140
gaacagttgc ttgcggccag ccccctgttg tagaaaatgc caagaccttt ggaaagatga 10200
aacctcgtta tgaaatcaac tccctgatta gataccactg caaagatggt ttcattcaac 10260
gtcaccttcc aactatccgg tgcttaggaa atggaagatg ggctatacct aaaattacct 10320
gcatgaaccc atctgcatac caaaggactt attctatgaa atactttaaa aattcctcat 10380
cagcaaagga caattcaata aatacatcca aacatgatca tcgttggagc cggaggtggc 10440
aggagtcgag gcgctgatcc ctaaaatggc gaacatgtgt tttcatcatt tcagccaaag 10500
tcctaacttc ctgtgccttt cctatcacct cgagaagtaa ttatcagttg gtttggattt 10560
ttggaccacc gttcagtcat tttgggttgc cgtgctccca aaacatttta aatgaaagta 10620
ttggcattca aaaagacagc agacaaaatg aaagaaaatg agagcagaaa gtaagcattt 10680
ccagcctatc taatttcttt agttttctat ttgcctccag tgcagtccat ttcctaatgt 10740
ataccagcct actgtactat ttaaaatgct caatttcagc accgatggcc atgtaaataa 10800
gatgatttaa tgttgatttt aatcctgtat ataaaataaa aagtcacaat gagtttgggc 10860
atatttaatg atgattatgg agccttagag gtctttaatc attggttcgg ctgcttttat 10920
gtagtttagg ctggaaatgg tttcacttgc tctttgactg tcagcaagac tgaagatggc 10980
ttttcctgga cagctagaaa acacaaaatc ttgtaggtca ttgcacctat ctcagccata 11040
ggtgcagttt gcttctacat gatgctaaag gctgcgaatg ggatcctgat ggaactaagg 11100
actccaatgt cgaactcttc tttgctgcat tccttttttct tcacttacaa gaaaggcctg 11160
aatggaggac ttttctgtaa ccagg 11185

<210> SEQ ID NO 86
<211> LENGTH: 2503
<212> TYPE: DNA
<213> ORGANISM: Homo sapiens

<400> SEQUENCE: 86
ggactttgaa atccaacccg gtcacctacc cgcgcgactg tgtccacgga tggcacgaaa 60
gccaagcgag tccccctgcc gagctactcg cgtccgcctc ctcccaagct gagctctgct 120
ccgcccacct gagtccttcg ccagttagga ggaaacacag ccgcttaatg aactgctgca 180

-continued

```
tcgggctggg agagaaagct cgcgggtccc accgggcctc ctacccaagt ctcagcgcgc    240
ttttcaccga ggcctcaatt ctgggatttg gcagctttgc tgtgaaagcc caatggacag    300
aggactgcag aaaatcaacc tatcctcctt caggaccaac gtacagaggt gcagttccat    360
ggtacaccat aaatcttgac ttaccaccct acaaaagatg gcatgaattg atgcttgaca    420
aggcaccaat gctaaaggtt atagtgaatt ctctgaagaa tatgataaat acattcgtgc    480
caagtggaaa agttatgcag gtggtggatg aaaaattgcc tggcctactt ggcaactttc    540
ctggcccttt tgaagaggaa atgaagggta ttgccgctgt tactgatata cctttaggag    600
agattatttc attcaatatt ttttatgaat tatttaccat ttgtacttca atagtagcag    660
aagacaaaaa aggtcatcta atacatggga gaaacatgga ttttggagta tttcttgggt    720
ggaacataaa taatgatacc tgggtcataa ctgagcaact aaaaccttta acagtgaatt    780
tggatttcca aagaaacaac aaaactgtct tcaaggcttc aagctttgct ggctatgtgg    840
gcatgttaac aggattcaaa ccaggactgt tcagtcttac actgaatgaa cgtttcagta    900
taaatggtgg ttatctgggt attctagaat ggattctggg aaagaaagat gccatgtgga    960
tagggttcct cactagaaca gttctggaaa atagcacaag ttatgaagaa gccaagaatt   1020
tattgaccaa gaccaagata ttggccccag cctactttat cctgggaggc aaccagtctg   1080
gggaaggttg tgtgattaca cgagacagaa aggaatcatt ggatgtatat gaactcgatg   1140
ctaagcaggg tagatggtat gtggtacaaa caaattatga ccgttggaaa catcccttct   1200
tccttgatga tcgcagaacg cctgcaaaga tgtgtctgaa ccgcaccagc caagagaata   1260
tctcatttga aaccatgtat gatgtcctgt caacaaaacc tgtcctcaac aagctgaccg   1320
tatacacaac cttgatagat gttaccaaag gtcaattcga aacttacctg cgggactgcc   1380
ctgacccttg tataggttgg tgagcacacg tctggcctac agaatgcggc ctctgagaca   1440
tgaagacacc atctccatgt gaccgaacac tgcagctgtc tgaccttcca aagactaaga   1500
ctcgcggcag gttctctttg agtcaaaagc ttgtcttcgt ccatctgttg acaaatgaca   1560
gaccttttt tttcccccat cagttgattt ttcttattta cagataactt ctttagggga   1620
agtaaaacag tcatctagaa ttcactgagt tttgtttcac tttgacattt ggggatctgg   1680
tgggcagtcg aaccatggtg aactccacct ccgtggaata aatggagatt cagcgtgggt   1740
gttgaatcca gcacgtctgt gtgagtaacg ggacagtaaa cactccacat tcttcagttt   1800
ttcacttcta cctacatatt tgtatgtttt tctgtataac agccttttcc ttctggttct   1860
aactgctgtt aaaattaata tatcattatc tttgctgtta ttgacagcga tataatttta   1920
ttacatatga ttagagggat gagacagaca ttcacctgta tatttctttt aatgggcaca   1980
aaatgggccc ttgcctctaa atagcacttt ttggggttca agaagtaatc agtatgcaaa   2040
gcaatctttt atacaataat tgaagtgttc ccttttttcat aattactgta cttcccagta   2100
accctaagga agttgctaac ttaaaaaact gcatcccacg ttctgttaat ttagtaaata   2160
aacaagtcaa agacttgtgg aaaataggaa gtgaacccat attttaaatt ctcataagta   2220
gcattcatgt aataaacagg tttttagttt gttcttcaga ttgataggga gttttaaaga   2280
aattttagta gttactaaaa ttatgttact gtatttttca gaaatcaaac tgcttatgaa   2340
aagtactaat agaacttgtt aacctttcta accttcacga ttaactgtga aatgtacgtc   2400
atttgtgcaa gaccgtttgt ccacttcatt ttgtataatc acagttgtgt tcctgacact   2460
caataaacag tcattggaaa gagtgccagt cagcagtcat gca                      2503
```

<210> SEQ ID NO 87
<211> LENGTH: 2341
<212> TYPE: DNA
<213> ORGANISM: Homo sapiens

<400> SEQUENCE: 87
ggctcttctt tgcctctgct ggagtccggg gagtggcgtt ggctgctaga gcgatgccgg 60
gccggagttg cgtcgcctta gtcctcctgg ctgccgccgt cagctgtgcc gtcgcgcagc 120
acgcgccgcc gtggacagag gactgcagaa aatcaaccta tcctccttca ggaccaacgt 180
acagaggtgc agttccatgg tacaccataa atcttgactt accaccctac aaaagatggc 240
atgaattgat gcttgacaag gcaccaatgc taaaggttat agtgaattct ctgaagaata 300
tgataaatac attcgtgcca agtggaaaag ttatgcaggt ggtggatgaa aaattgcctg 360
gcctacttgg caactttcct ggcccttttg aagaggaaat gaagggtatt gccgctgtta 420
ctgatatacc tttaggagag attatttcat tcaatatttt ttatgaatta tttaccattt 480
gtacttcaat agtagcagaa gacaaaaaag gtcatctaat acatgggaga aacatggatt 540
ttggagtatt tcttgggtgg aacataaata atgatacctg ggtcataact gagcaactaa 600
aacctttaac agtgaatttg gatttccaaa gaaacaacaa aactgtcttc aaggcttcaa 660
gctttgctgg ctatgtgggc atgttaacag gattcaaacc aggactgttc agtcttacac 720
tgaatgaacg tttcagtata aatggtggtt atctgggtat tctagaatgg attctgggaa 780
agaaagatgc catgtggata gggttcctca ctagaacagt tctggaaaat agcacaagtt 840
atgaagaagc caagaattta ttgaccaaga ccaagatatt ggccccagcc tactttatcc 900
tgggaggcaa ccagtctggg gaaggttgtg tgattacacg agacagaaag gaatcattgg 960
atgtatatga actcgatgct aagcagggta gatggtatgt ggtacaaaca aattatgacc 1020
gttggaaaca tcccttcttc cttgatgatc gcagaacgcc tgcaaagatg tgtctgaacc 1080
gcaccagcca agagaatatc tcatttgaaa ccatgtatga tgtcctgtca acaaaacctg 1140
tcctcaacaa gctgaccgta tacacaacct tgatagatgt taccaaaggt caattcgaaa 1200
cttacctgcg ggactgccct gacccttgta taggttggtg agcacacgtc tggcctacag 1260
aatgcggcct ctgagacatg aagacaccat ctccatgtga ccgaacactg cagctgtctg 1320
accttccaaa gactaagact cgcggcaggt tctctttgag tcaaaagctt gtcttcgtcc 1380
atctgttgac aaatgacaga cctttttttt tcccccatca gttgattttt cttatttaca 1440
gataacttct ttaggggaag taaaacagtc atctagaatt cactgagttt tgtttcactt 1500
tgacatttgg ggatctggtg ggcagtcgaa ccatggtgaa ctccacctcc gtggaataaa 1560
tggagattca gcgtgggtgt tgaatccagc acgtctgtgt gagtaacggg acagtaaaca 1620
ctccacattc ttcagttttt cacttctacc tacatatttg tatgtttttc tgtataacag 1680
ccttttcctt ctggttctaa ctgctgttaa aattaatata tcattatctt tgctgttatt 1740
gacagcgata taattttatt acatatgatt agagggatga gacagacatt cacctgtata 1800
tttcttttaa tgggcacaaa atgggccctt gcctctaaat agcacttttt ggggttcaag 1860
aagtaatcag tatgcaaagc aatcttttat acaataattg aagtgttccc tttttcataa 1920
ttactgtact tcccagtaac cctaaggaag ttgctaactt aaaaaactgc atcccacgtt 1980
ctgttaattt agtaaataaa caagtcaaag acttgtggaa aataggaagt gaacccatat 2040
tttaaattct cataagtagc attcatgtaa taaacaggtt tttagtttgt tcttcagatt 2100
gatagggagt tttaaagaaa ttttagtagt tactaaaatt atgttactgt atttttcaga 2160

-continued

```
aatcaaactg cttatgaaaa gtactaatag aacttgttaa cctttctaac cttcacgatt   2220

aactgtgaaa tgtacgtcat ttgtgcaaga ccgtttgtcc acttcatttt gtataatcac   2280

agttgtgttc ctgacactca ataaacagtc attggaaaga gtgccagtca gcagtcatgc   2340

a                                                                   2341


<210> SEQ ID NO 88
<211> LENGTH: 2039
<212> TYPE: DNA
<213> ORGANISM: Homo sapiens

<400> SEQUENCE: 88

ccggccctcg ccctgtccgc cgccaccgcc gccgccgcca gagtcgccat gcagatcccg     60

cgcgccgctc ttctcccgct gctgctgctg ctgctggcgg cgcccgcctc ggcgcagctg    120

tcccgggccg gccgctcggc gcctttggcc gccgggtgcc cagaccgctg cgagccggcg    180

cgctgcccgc cgcagccgga gcactgcgag ggcggccggg cccgggacgc gtgcggctgc    240

tgcgaggtgt gcggcgcgcc cgagggcgcc gcgtgcggcc tgcaggaggg cccgtgcggc    300

gaggggctgc agtgcgtggt gcccttcggg gtgccagcct cggccacggt gcggcggcgc    360

gcgcaggccg gcctctgtgt gtgcgccagc agcgagccgg tgtgcggcag cgacgccaac    420

acctacgcca acctgtgcca gctgcgcgcc gccagccgcc gctccgagag gctgcaccgg    480

ccgccggtca tcgtcctgca gcgcggagcc tgcggccaag ggcaggaaga tcccaacagt    540

ttgcgccata aatataactt tatcgcggac gtggtggaga agatcgcccc tgccgtggtt    600

catatcgaat tgtttcgcaa gcttccgttt tctaaacgag aggtgccggt ggctagtggg    660

tctgggttta ttgtgtcgga agatggactg atcgtgacaa atgcccacgt ggtgaccaac    720

aagcaccggg tcaaagttga gctgaagaac ggtgccactt acgaagccaa aatcaaggat    780

gtggatgaga aagcagacat cgcactcatc aaaattgacc accagggcaa gctgcctgtc    840

ctgctgcttg gccgctcctc agagctgcgg ccgggagagt tcgtggtcgc catcggaagc    900

ccgttttccc ttcaaaacac agtcaccacc gggatcgtga gcaccaccca gcgaggcggc    960

aaagagctgg ggctccgcaa ctcagacatg gactacatcc agaccgacgc catcatcaac   1020

tatggaaact cgggaggccc gttagtaaac ctggacggtg aagtgattgg aattaacact   1080

ttgaaagtga cagctggaat ctcctttgca atcccatctg ataagattaa aaagttcctc   1140

acggagtccc atgaccgaca ggccaaagga aaagccatca ccaagaagaa gtatattggt   1200

atccgaatga tgtcactcac gtccagcaaa gccaaagagc tgaaggaccg gcaccgggac   1260

ttcccagacg tgatctcagg agcgtatata attgaagtaa ttcctgatac cccagcagaa   1320

gctggtggtc tcaaggaaaa cgacgtcata atcagcatca atggacagtc cgtggtctcc   1380

gccaatgatg tcagcgacgt cattaaaagg gaaagcaccc tgaacatggt ggtccgcagg   1440

ggtaatgaag atatcatgat cacagtgatt cccgaagaaa ttgacccata ggcagaggca   1500

tgagctggac ttcatgtttc cctcaaagac tctcccgtgg atgacggatg aggactctgg   1560

gctgctggaa taggacactc aagacttttg actgccattt tgtttgttca gtggagactc   1620

cctggccaac agaatccttc ttgatagttt gcaggcaaaa caaatgtaat gttgcagatc   1680

cgcaggcaga agctctgccc ttctgtatcc tatgtatgca gtgtgctttt tcttgccagc   1740

ttgggccatt cttgcttaga cagtcagcat ttgtctcctc ctttaactga gtcatcatct   1800

tagtccaact aatgcagtcg atacaatgcg tagatagaag aagccccacg ggagccagga   1860
```

-continued

```
tgggactggt cgtgtttgtg cttttctcca agtcagcacc caaaggtcaa tgcacagaga   1920

ccccgggtgg gtgagcgctg gcttctcaaa cggccgaagt tgcctctttt aggaatctct   1980

ttggaattgg gagcacgatg actctgagtt tgagctatta aagtacttct tacacattg    2039
```

```
<210> SEQ ID NO 89
<211> LENGTH: 1387
<212> TYPE: DNA
<213> ORGANISM: Homo sapiens

<400> SEQUENCE: 89

ccgggtcgga gccccccgga gctgcgcgcg ggcttgcagc gcctcgcccg cgctgtcctc     60

ccggtgtccc gcttctccgc gccccagccg ccggctgcca gcttttcggg gccccgagtc    120

gcacccagcg aagagagcgg gcccgggaca agctcgaact ccggccgcct cgcccttccc    180

cggctccgct ccctctgccc cctcggggtc gcgcgcccac gatgctgcag ggccctggct    240

cgctgctgct gctcttcctc gcctcgcact gctgcctggg ctcggcgcgc gggctcttcc    300

tctttggcca gcccgacttc tcctacaagc gcagcaattg caagcccatc cctgccaacc    360

tgcagctgtg ccacggcatc gaataccaga acatgcggct gcccaacctg ctgggccacg    420

agaccatgaa ggaggtgctg gagcaggccg gcgcttggat cccgctggtc atgaagcagt    480

gccacccgga caccaagaag ttcctgtgct cgctcttcgc cccgtctgc ctcgatgacc     540

tagacgagac catccagcca tgccactcgc tctgcgtgca ggtgaaggac cgctgcgccc    600

cggtcatgtc cgccttcggc ttcccctggc ccgacatgct tgagtgcgac cgtttccccc    660

aggacaacga cctttgcatc cccctcgcta gcagcgacca cctcctgcca gccaccgagg    720

aagctccaaa ggtatgtgaa gcctgcaaaa ataaaaatga tgatgacaac gacataatgg    780

aaacgctttg taaaaatgat tttgcactga aaataaaagt gaaggagata acctacatca    840

accgagatac caaaatcatc ctggagacca agagcaagac catttacaag ctgaacggtg    900

tgtccgaaag ggacctgaag aaatcggtgc tgtggctcaa agacagcttg cagtgcacct    960

gtgaggagat gaacgacatc aacgcgccct atctggtcat gggacagaaa cagggtgggg   1020

agctggtgat cacctcggtg aagcggtggc agaaggggca gagagagttc aagcgcatct   1080

cccgcagcat ccgcaagctg cagtgctagt cccggcatcc tgatggctcc gacaggcctg   1140

ctccagagca cggctgacca tttctgctcc gggatctcag ctcccgttcc ccaagcacac   1200

tcctagctgc tccagtctca gcctgggcag cttccccctg ccttttgcac gtttgcatcc   1260

ccagcatttc ctgagttata aggccacagg agtggatagc tgttttcacc taaaggaaaa   1320

gcccacccga atcttgtaga aatattcaaa ctaataaaat catgaatatt tttatgaagt   1380

ttaaaaa                                                              1387
```

```
<210> SEQ ID NO 90
<211> LENGTH: 1092
<212> TYPE: DNA
<213> ORGANISM: Homo sapiens

<400> SEQUENCE: 90

tgtccctgga attctgggac actggctggg gtttgaggag agaagccagt acctacctgg     60

ctgcaggatg aagctggcca gtggcttctt ggttttgtgg ctcagccttg gggtggcct    120

ggctcagagc gacacgagcc ctgacacgga ggagtcctat tcagactggg gccttcggca    180

cctccgggga agctttgaat ccgtcaatag ctacttcgat tcttttctgg agctgctggg    240

agggaagaat ggagtctgtc agtacaggtg ccgatatgga aaggcaccaa tgcccagacc    300
```

-continued

```
tggctacaag ccccaagagc ccaatggctg cggctcctat ttcctgggtc tcaaggtacc    360

agaaagtatg gacttgggca ttccagcaat gacaaagtgc tgcaaccagc tggatgtctg    420

ttatgacact tgcggtgcca acaaatatcg ctgtgatgca aaattccgat ggtgtctcca    480

ctcgatctgc tctgacctta agcggagtct gggctttgtc tccaaagtgg aagcagcctg    540

tgattccctg gttgacactg tgttcaacac cgtgtggacc ttgggctgcc gcccctttat    600

gaatagtcag cgggcagctt gcatctgtgc agaggaggag aaggaagagt tatgaggaag    660

aagtgattcc ttcctggttt tgagtgacac cacagctgtc agccttcaag atgtcaagtc    720

ttcgagtcag cgtgactcat tcattcttcc aacagtttgg acaccacaaa gcaggagaaa    780

gggaacattt ttctacagct ggaaagtgag tcctatcctt tgaggaaatt tgaaaaaaga    840

catggagtgg tttgaaagct actcttcatt taagactgct ctccccaacc aagacacatt    900

tgcctggaaa ttcagttctt agcttaaaga ctaaaatgca agcaaaccct gcaattcctg    960

gacctgatag ttatattcat gagtgaaatt gtggggagtc cagccatttg ggaggcaatg   1020

actttctgct ggcccatgtt tcagttgcca gtaagcttct cacatttaat aaagtgtact   1080

ttttagaaca tt                                                        1092
```

```
<210> SEQ ID NO 91
<211> LENGTH: 1807
<212> TYPE: DNA
<213> ORGANISM: Homo sapiens

<400> SEQUENCE: 91

gcacgaggga agagggtgat ccgacccggg gaaggtcgct gggcagggcg agttgggaaa     60

gcggcagccc ccgccgcccc cgcagcccct tctcctcctt tctcccacgt cctatctgcc    120

tctcgctgga ggccaggccg tgcagcatcg aagacaggag gaactggagc ctcattggcc    180

ggcccggggc gccggcctcg ggcttaaata ggagctccgg gctctggctg ggacccgacc    240

gctgccggcc gcgctcccgc tgctcctgcc gggtgatgga aaaccccagc ccggccgccg    300

ccctgggcaa ggccctctgc gctctcctcc tggccactct cggcgccgcc ggccagcctc    360

ttgggggaga gtccatctgt tccgccagag ccccggccaa atacagcatc accttcacgg    420

gcaagtggag ccagacggcc ttccccaagc agtacccccct gttccgcccc cctgcgcagt    480

ggtcttcgct gctgggggcc gcgcatagct ccgactacag catgtggagg aagaaccagt    540

acgtcagtaa cgggctgcgc gactttgcgg agcgcggcga ggcctgggcg ctgatgaagg    600

agatcgaggc ggcgggggag gcgctgcaga gcgtgcacgc ggtgttttcg gcgcccgccg    660

tccccagcgg caccgggcag acgtcggcgg agctggaggt gcagcgcagg cactcgctgg    720

tctcgtttgt ggtgcgcatc gtgcccagcc ccgactggtt cgtgggcgtg gacagcctgg    780

acctgtgcga cggggaccgt tggcgggaac aggcggcgct ggacctgtac ccctacgacg    840

ccgggacgga cagcggcttc accttctcct cccccaactt cgccaccatc ccgcaggaca    900

cggtgaccga gataacgtcc tcctctccca gccacccggc caactccttc tactacccgc    960

ggctgaaggc cctgcctccc atcgccaggg tgacactggt gcggctgcga cagagcccca   1020

gggccttcat ccctcccgcc ccagtcctgc ccagcaggga caatgagatt gtagacagcg   1080

cctcagttcc agaaacgccg ctggactgcg aggtctccct gtggtcgtcc tggggactgt   1140

gcggaggcca ctgtgggagg ctcgggacca agagcaggac tcgctacgtc cgggtccagc   1200

ccgccaacaa cgggagcccc tgccccgagc tcgaagaaga ggctgagtgc gtccctgata   1260
```

actgcgtcta agaccagagc cccgcagccc ctggggcccc cggagccatg ggtgtcgggg 1320
ggctcctgtg caggctcatg ctgcaggcgg ccgaggcaca gggggtttcg cgctgctcct 1380
gaccgcggtg aggccgcgcc gaccatctct gcactgaagg gccctctggt ggccggcacg 1440
ggcattggga aacagcctcc tcctttccca accttgcttc ttaggggccc ccgtgtcccg 1500
tctgctctca gcctcctcct cctgcaggat aaagtcatcc ccaaggctcc agctactcta 1560
aattatggtc tccttataag ttattgctgc tccaggagat tgtccttcat cgtccagggg 1620
cctggctccc acgtggttgc agatacctca gacctggtgc tctaggctgt gctgagccca 1680
ctctcccgag ggcgcatcca agcgggggcc acttgagaag tgaataaatg gggcggtttc 1740
ggaagcgtca gtgtttccat gttatggatc tctctgcgtt tgaataaaga ctatctctgt 1800
tgctcac 1807

<210> SEQ ID NO 92
<211> LENGTH: 1077
<212> TYPE: DNA
<213> ORGANISM: Homo sapiens

<400> SEQUENCE: 92
cccgcccccg ccccttccga gcaaactttt ggcacccacc gcagcccagc gcgcgttcgt 60
gctccgcagg gcgcgcctct ctccgccaat gccaggcgcg cgggggagcc attaggaggc 120
gaggagagag gagggcgcag ctcccgccca gcccagccct gcccagccct gcccggaggc 180
agacgcgccg gaaccgggac gcgataaata tgcagagcgg aggcttcgcg cagcagagcc 240
cgcgcgccgc ccgctccggg tgctgaatcc aggcgtgggg acacgagcca ggcgccgccg 300
ccggagccag cggagccggg gccagagccg gagcgcgtcc gcgtccacgc agccgccggc 360
cggccagcac ccagggccct gcatgccagg tcgttggagg tggcagcgag acatgcaccc 420
ggcccggaag ctcctcagcc tcctcttcct catcctgatg ggcactgaac tcactcaaaa 480
taaaagagaa aacaaagcag agaagatggg agggccagag agcgagagga agaccacagg 540
agagaagaca ctgaacgagc ttcccttgtt ttgcctggaa gcccacgctg gctccctggc 600
tctgcccagg atgtgcagtc caaatcccaa tccagcagtg ggttatgtc gtcccgctta 660 ccctcagagc ccttctcctg gtgctgccca gacgatcagc cagtccctcc tggagaggtt 720
ctgcatggcc tctaggagag aagttttctt ggccccagga aggcctggtg gagggtggtg 780
gttgtgcact gttgctggac agatgcattc attcatgtgc acacacacac acacacatgc 840
acacacaggg gagcagatac ctgcagagaa gagccaacca ggtcctgatt agtggcaagc 900
tgccccacaa agggctatgc ctgtgtctta ttgagacacc ttggcaaaga gatggctgat 960
tctgggtggt cctggacatg gccgcaccca agggccctcc aagccttaat ggcaccctga 1020
agcctccatg cccaggccaa aagatgcttt tcctccctaa aaaaaaaaaa aaaaaaa 1077

<210> SEQ ID NO 93
<211> LENGTH: 4229
<212> TYPE: DNA
<213> ORGANISM: Homo sapiens

<400> SEQUENCE: 93
ggggccccag tggccgccgc ggagcgaggt tgcctggaga gagcgcctgg gcgcagaagg 60
gttaacgggc caccgggggc tcgcagagca ggagggtgct ctcggacggt gtgtccccca 120
ctgcactcct gaacttggag gacagggtcg ccgcgaggga cgcagagagc accctccacg 180
cccagatgcc tgcgtagttt ttgtgaccag tccgctcctg cctccccctg gggcagtaga 240

```
gggggagcga tggagaactg gactggcagg ccctggctgt atctgctgct gcttctgtcc    300
ctccctcagc tctgcttgga tcaggaggtg ttgtccggac actctcttca gacacctaca    360
gaggagggcc agggccccga aggtgtctgg ggaccttggg tccagtgggc ctcttgctcc    420
cagccctgcg gggtgggggt gcagcgcagg agccggacat gtcagctccc tacagtgcag    480
ctccacccga gtctgcccct ccctccccgg cccccaagac atccagaagc cctcctcccc    540
cggggccagg gtcccagacc ccagacttct ccagaaaccc tccccttgta caggacacag    600
tctcggggaa ggggtggccc acttcgaggt cccgcttccc acctagggag agaggagacc    660
caggagattc gagcggccag gaggtcccgg cttcgagacc ccatcaagcc aggaatgttc    720
ggttatggga gagtgccctt tgcattgcca ctgcaccgga accgcaggca ccctcggagc    780
ccacccagat ctgagctgtc cctgatctct tctagagggg aagaggctat tccgtcccct    840
actccaagag cagagccatt ctccgcaaac ggcagccccc aaactgagct ccctcccaca    900
gaactgtctg tccacacccc atccccccaa gcagaacctc taagccctga aactgctcag    960
acagaggtgg cccccagaac caggcctgcc cccctacggc atcaccccag agcccaggcc   1020
tctggcacag agccccccctc acccacgcac tccttaggag aaggtggctt cttccgtgca   1080
tcccctcagc cacgaaggcc aagttcccag ggttgggcca gtccccaggt agcagggaga   1140
cgccctgatc cttttccttc ggtccctcgg ggccgaggcc agcagggcca agggccttgg   1200
ggaacggggg ggactcctca cgggccccgc ctggagcctg accctcagca cccgggcgcc   1260
tggctgcccc tgctgagcaa cggcccccat gccagctccc tctggagcct ctttgctccc   1320
agtagcccta ttccaagatg ttctggggag agtgaacagc taagagcctg cagccaagcg   1380
ccctgccccc ctgagcagcc agacccccgg gccctgcagt gcgcagcctt taactcccag   1440
gaattcatgg gccagctgta tcagtgggag cccttcactg aagtccaggg ctcccagcgc   1500
tgtgaactga actgccggcc ccgtggcttc cgcttctatg tccgtcacac tgaaaaggtc   1560
caggatggga ccctgtgtca gcctggagcc cctgacatct gtgtggctgg acgctgtctg   1620
agccccggct gtgatgggat ccttggctct ggcaggcgtc ctgatggctg tggagtctgt   1680
gggggtgatg attctacctg tcgccttgtt tcggggaacc tcactgaccg agggggcccc   1740
ctgggctatc agaagatctt gtggattcca gcgggagcct tgcggctcca gattgcccag   1800
ctccggccta gctccaacta cctggcactt cgtggccctg gggggccggtc catcatcaat   1860
gggaactggg ctgtggatcc ccctgggtcc tacagggccg gcgggaccgt ctttcgatat   1920
aaccgtcctc ccagggagga gggcaaaggg gagagtctgt cggctgaagg ccccaccacc   1980
cagcctgtgg atgtctatat gatctttcag gaggaaaacc caggcgtttt ttatcagtat   2040
gtcatctctt cacctcctcc aatccttgag aaccccaccc cagagccccc tgtcccccag   2100
cttcagccgg agattctgag ggtggagccc ccacttgctc cggcaccccg cccagcccgg   2160
accccaggca ccctccagcg tcaggtgcgg atcccccaga tgcccgcccc gccccatccc   2220
aggacacccc tggggtctcc agctgcgtac tggaaacgag tgggacactc tgcatgctca   2280
gcgtcctgcg ggaaaggtgt ctggcgcccc attttcctct gcatctcccg tgagtcggga   2340
gaggaactgg atgaacgcag ctgtgccgcg ggtgccaggc cccccagcctc ccctgaaccc   2400
tgccacggca ccccatgccc cccatactgg gaggctggcg agtggacatc ctgcagccgc   2460
tcctgtggcc ccggcaccca gcaccgccag ctgcagtgcc ggcaggaatt tgggggggggt   2520
ggctcctcgg tgcccccgga gcgctgtgga catctccccc ggcccaacat cacccagtct   2580
```

tgccagctgc gcctctgtgg ccattgggaa gttggctctc cttggagcca gtgctccgtg 2640
cggtgcggcc ggggccagag aagccggcag gttcgctgtg ttgggaacaa cggtgatgaa 2700
gtgagcgagc aggagtgtgc gtcaggcccc ccgcagcccc ccagcagaga ggcctgtgac 2760
atggggccct gtactactgc ctggttccac agcgactgga gctccaagtg ctcagccgag 2820
tgtgggacgg gaatccagcg gcgctctgtg gtctgccttg ggagtggggc agccctcggg 2880
ccaggccagg gggaagcagg agcaggaact gggcagagct gtccaacagg aagccggccc 2940
cctgacatgc gcgcctgcag cctggggccc tgtgagagaa cttggcgctg gtacacaggg 3000
ccctggggtg agtgctcctc cgaatgtggc tctggcacac agcgtagaga catcatctgt 3060
gtatccaaac tggggacgga gttcaacgtg acttctccga gcaactgttc tcacctcccc 3120
aggccccctg ccctgcagcc ctgtcaaggg caggcctgcc aggaccgatg gttttccacg 3180
ccctggagcc catgttctcg ctcctgccaa gggggaacgc agacacggga ggtccagtgc 3240
ctgagcacca accagaccct cagcacccga tgccctcctc aactgcggcc ctccaggaag 3300
cgcccctgta acagccaacc ctgcagccag cgccctgatg atcaatgcaa ggacagctct 3360
ccacattgcc ccctggtggt acaggcccgg ctctgcgtct acccctacta cacagccacc 3420
tgttgccgct cttgcgcaca tgtcctggag cggtctcccc aggatccctc ctgaaagggg 3480
tccggggcac cttcacggtt ttctgtgcca ccatcggtca cccattgatc ggcccactct 3540 gaacccccctg gctctccagc ctgtcccagt ctcagcaggg atgtcctcca ggtgacagag 3600
ggtggcaagg tgactgacac aaagtgactt tcagggctgt ggtcaggccc atgtggtggt 3660
gtgatgggtg tgtgcacata tgcctcaggt gtgcttttgg gactgcatgg atatgtgtgt 3720
gctcaaacgt gtatcacttt tcaaaaagag gttacacaga ctgagaagga caagacctgt 3780
ttccttgaga ctttcctagg tggaaaggaa agcaagtctg cagttccttg ctaatctgag 3840
ctacttagag tgtggtctcc ccaccaactc cagttttgtg ccctaagcct catttctcat 3900
gttcagacct cacatcttct aagccgccct gtgtctctga ccccttctca tttgcctagt 3960
atctctgccc ctgcctccct aattagctag ggctggggtc agccactgcc aatcctgcct 4020
tactcaggaa ggcaggagga aagagactgc ctctccagag caaggcccag ctgggcagag 4080
ggtgaaaaag agaaatgtga gcatccgctc ccccaccacc ccgcccagcc cctagcccca 4140
ctccctgcct cctgaaatgg ttcccaccca gaactaattt attttttatt aaagatggtc 4200
atgacaaatg aaaaaaaaaa aaaaaaaaa 4229

<210> SEQ ID NO 94
<211> LENGTH: 5826
<212> TYPE: DNA
<213> ORGANISM: Homo sapiens

<400> SEQUENCE: 94
gaggaggaga cggcatccag tacagagggg ctggacttgg acccctgcag cagccctgca 60
caggagaagc ggcatataaa gccgcgctgc ccgggagccg ctcggccacg tccaccggag 120
catcctgcac tgcagggccg gtctctcgct ccagcagagc ctgcgccttt ctgactcggt 180
ccggaacact gaaaccagtc atcactgcat ctttttggca aaccaggagc tcagctgcag 240
gaggcaggat ggtctggagg ctggtcctgc tggctctgtg ggtgtggccc agcacgcaag 300
ctggtcacca ggacaaagac acgaccttcg accttttcag tatcagcaac atcaaccgca 360
agaccattgg cgccaagcag ttccgcgggc ccgaccccgg cgtgccggct taccgcttcg 420
tgcgctttga ctacatccca ccggtgaacg cagatgacct cagcaagatc accaagatca 480

```
tgcggcagaa ggagggcttc ttcctcacgg cccagctcaa gcaggacggc aagtccaggg    540
gcacgctgtt ggctctggag ggccccggtc tctcccagag gcagttcgag atcgtctcca    600
acggccccgc ggacacgctg gatctcacct actggattga cggcacccgg catgtggtct    660
ccctggagga cgtcggcctg gctgactcgc agtggaagaa cgtcaccgtg caggtggctg    720
gcgagaccta cagcttgcac gtgggctgcg acctcataga cagcttcgct ctggacgagc    780
ccttctacga gcacctgcag gcggaaaaga gccggatgta cgtggccaaa ggctctgcca    840
gagagagtca cttcaggggt ttgcttcaga acgtccacct agtgtttgaa aactctgtgg    900
aagatattct aagcaagaag ggttgccagc aaggccaggg agctgagatc aacgccatca    960
gtgagaacac agagacgctg cgcctgggtc cgcatgtcac caccgagtac gtgggcccca   1020
gctcggagag gaggcccgag gtgtgcgaac gctcgtgcga ggagctggga aacatggtcc   1080
aggagctctc ggggctccac gtcctcgtga accagctcag cgagaacctc aagagagtgt   1140
cgaatgataa ccagtttctc tgggagctca ttggtggccc tcctaagaca aggaacatgt   1200
cagcttgctg gcaggatggc cggttctttg cggaaaatga aacgtgggtg gtggacagct   1260
gcaccacgtg tacctgcaag aaatttaaaa ccatttgcca ccaaatcacc tgcccgcctg   1320
caacctgcgc cagtccatcc tttgtggaag gcgaatgctg cccttcctgc ctccactcgg   1380
tggacggtga ggagggctgg tctccgtggg cagagtggac ccagtgctcc gtgacgtgtg   1440
gctctgggac ccagcagaga ggccggtcct gtgacgtcac cagcaacacc tgcttggggc   1500
cctccatcca gacacgggct tgcagtctga gcaagtgtga cacccgcatc cggcaggacg   1560
gcggctggag ccactggtca ccttggtctt catgctctgt gacctgtgga gttggcaata   1620
tcacacgcat ccgtctctgc aactccccag tgccccagat gggggcaag aattgcaaag   1680
ggagtggccg ggagaccaaa gcctgccagg gcgccccatg cccaatcgat ggccgctgga   1740
gcccctggtc cccgtggtcg gcctgcactg tcacctgtgc cggtgggatc cgggagcgca   1800
cccgggtctg caacagccct gagcctcagt acggagggaa ggcctgcgtg gggatgtgc   1860
aggagcgtca gatgtgcaac aagaggagct gccccgtgga tggctgttta tccaacccct   1920
gcttcccggg agcccagtgc agcagcttcc ccgatgggtc ctggtcatgc ggctcctgcc   1980
ctgtgggctt cttgggcaat ggcacccact gtgaggacct ggacgagtgt gccctggtcc   2040
ccgacatctg cttctccacc agcaaggtgc ctcgctgtgt caacactcag cctggcttcc   2100
actgcctgcc ctgcccgccc cgatacagag ggaaccagcc cgtcggggtc ggcctggaag   2160
cagccaagac ggaaaagcaa gtgtgtgagc ccgaaaaccc atgcaaggac aagacacaca   2220
actgccacaa gcacgcggag tgcatctacc tgggccactt cagcgacccc atgtacaagt   2280
gcgagtgcca gacaggctac gcgggcgacg ggctcatctg cggggaggac tcggacctgg   2340
acggctggcc caacctcaat ctggtctgcg ccaccaacgc cacctaccac tgcatcaagg   2400
ataactgccc ccatctgcca aattctgggc aggaagactt tgacaaggac gggattggcg   2460
atgcctgtga tgatgacgat gacaatgacg gtgtgaccga tgagaaggac aactgccagc   2520
tcctcttcaa tccccgccag gctgactatg acaaggatga ggttggggac cgctgtgaca   2580
actgccctta cgtgcacaac cctgcccaga tcgacacaga caacaatgga gagggtgacg   2640
cctgctccgt ggacattgat ggggacgatg tcttcaatga acgagacaat tgtccctacg   2700
tctacaacac tgaccagagg gacacggatg gtgacggtgt gggggatcac tgtgacaact   2760
gcccccctggt gcacaaccct gaccagaccg acgtggacaa tgaccttgtt ggggaccagt   2820
```

-continued

```
gtgacaacaa cgaggacata gatgacgacg gccaccagaa caaccaggac aactgcccct   2880
acatctccaa cgccaaccag gctgaccatg acagagacgg ccagggcgac gcctgtgacc   2940
ctgatgatga caacgatggc gtccccgatg acagggacaa ctgccggctt gtgttcaacc   3000
cagaccagga ggacttggac ggtgatggac ggggtgatat ttgtaaagat gattttgaca   3060
atgacaacat cccagatatt gatgatgtgt gtcctgaaaa caatgccatc agtgagacag   3120
acttcaggaa cttccagatg gtccccttgg atcccaaagg gaccacccaa attgatccca   3180
actgggtcat tcgccatcaa ggcaaggagc tggttcagac agccaactcg gaccccggca   3240
tcgctgtagg ttttgacgag tttgggtctg tggacttcag tggcacattc tacgtaaaca   3300
ctgaccggga cgacgactat gccggcttcg tctttggtta ccagtcaagc agccgcttct   3360
atgtggtgat gtggaagcag gtgacgcaga cctactggga ggaccagccc acgcgggcct   3420
atggctactc cggcgtgtcc ctcaaggtgg tgaactccac cacggggacg ggcgagcacc   3480
tgaggaacgc gctgtggcac acggggaaca cgccggggca ggtgcgaacc ttatggcacg   3540
accccaggaa cattggctgg aaggactaca cggcctatag gtggcacctg actcacaggc   3600
ccaagactgg ctacatcaga gtcttagtgc atgaaggaaa acaggtcatg gcagactcag   3660
gacctatcta tgaccaaacc tacgctggcg ggcggctggg tctatttgtc ttctctcaag   3720
aaatggtcta tttctcagac ctcaagtacg aatgcagaga tatttaaaca agatttgctg   3780
catttccggc aatgccctgt gcatgccatg gtccctagac acctcagttc attgtggtcc   3840
ttgtggcttc tctctctagc agcacctcct gtcccttgac cttaactctg atggttcttc   3900
acctcctgcc agcaacccca aacccaagtg ccttcagagg ataaatatca atggaactca   3960
gagatgaaca tctaacccac tagaggaaac cagtttggtg atatatgaga ctttatgtgg   4020
agtgaaaatt gggcatgcca ttacattgct tttcttgtt tgtttaaaaa gaatgacgtt   4080
tacatataaa atgtaattac ttattgtatt tatgtgtata tggagttgaa gggaatactg   4140
tgcataagcc attatgataa attaagcatg aaaaatattg ctgaactact tttggtgctt   4200
aaagttgtca ctattcttga attagagttg ctctacaatg acacacaaat cccattaaat   4260
aaattataaa caagggtcaa ttcaaatttg aagtaatgtt ttagtaagga gagattagaa   4320
gacaacaggc atagcaaatg acataagcta ccgattaact aatcggaaca tgtaaaacag   4380
ttacaaaaat aaacgaactc tcctcttgtc ctacaatgaa agccctcatg tgcagtagag   4440
atgcagtttc atcaaagaac aaacatcctt gcaaatgggt gtgacgcggt tccagatgtg   4500
gatttggcaa aacctcattt aagtaaaagg ttagcagagc aaagtgcggt gctttagctg   4560
ctgcttgtgc cgctgtggcg tcggggaggc tcctgcctga gcttccttcc ccagctttgc   4620
tgcctgagag gaaccagagc agacgcacag gccggaaaag gcgcatctaa cgcgtatcta   4680
ggctttggta actgcggaca agttgctttt acctgatttg atgatacatt tcattaaggt   4740
tccagttata aatattttgt taatatttat taagtgacta tagaatgcaa ctccatttac   4800
cagtaactta ttttaaatat gcctagtaac acatatgtag tataatttct agaaacaaac   4860
atctaataag tatataatcc tgtgaaaata tgaggcttga taatattagg ttgtcacgat   4920
gaagcatgct agaagctgta acagaataca tagagaataa tgaggagttt atgatggaac   4980
cttaaatata taatgttgcc agcgatttta gttcaatatt tgttactgtt atctatctgc   5040
tgtatatgga attcttttaa ttcaaacgct gaaaagaatc agcatttagt cttgccaggc   5100
acacccaata atcagtcatg tgtaatatgc acaagtttgt ttttgttttt gttttttttg   5160
ttggttggtt tgtttttttg ctttaagttg catgatcttt ctgcaggaaa tagtcactca   5220
```

```
tcccactcca cataaggggt ttagtaagag aagtctgtct gtctgatgat ggataggggg   5280
caaatctttt tccccttttct gttaatagtc atcacatttc tatgccaaac aggaacaatc   5340
cataacttta gtcttaatgt acacattgca ttttgataaa attaattttg ttgtttcctt   5400
tgaggttgat cgttgtgttg ttgttttgct gcacttttta ctttttttgcg tgtggagctg   5460
tattcccgag accaacgaag cgttgggata cttcattaaa tgtagcgact gtcaacagcg   5520
tgcaggtttt ctgtttctgt gttgtggggt caaccgtaca atggtgtggg agtgacgatg   5580
atgtgaatat ttagaatgta ccatattttt tgtaaattat ttatgttttt ctaaacaaat   5640
ttatcgtata ggttgatgaa acgtcatgtg ttttgccaaa gactgtaaat atttatttat   5700
gtgttcacat ggtcaaaatt tcaccactga aaccctgcac ttagctagaa cctcattttt   5760
aaagattaac aacaggaaat aaattgtaaa aaaggttttc tatacatgaa aaaaaaaaaa   5820
aaaaaa                                                              5826
```

<210> SEQ ID NO 95
<211> LENGTH: 9645
<212> TYPE: DNA
<213> ORGANISM: Homo sapiens

<400> SEQUENCE: 95

```
atgcccaagc gcgcgcactg gggggccctc tccgtggtgc tgatcctgct ttggggccat     60
ccgcgagtgg cgctggcctg cccgcatcct tgtgcctgct acgtccccag cgaggtccac    120
tgcacgttcc gatccctggc ttccgtgccc gctggcattg ctagacacgt ggaaagaatc    180
aatttggggt ttaatagcat acaggccctg tcagaaacct catttgcagg actgaccaag    240
ttggagctac ttatgattca cggcaatgag atcccaagca tccccgatgg agctttaaga    300
gacctcagct ctcttcaggt tttcaagttc agctacaaca agctgagagt gatcacagga    360
cagaccctcc agggtctctc taacttaatg aggctgcaca ttgaccacaa caagatcgag    420
tttatccacc ctcaagcttt caacggctta acgtctctga ggctactcca tttggaagga    480
aatctcctcc accagctgca ccccagcacc ttctccacgt tcacattttt ggattatttc    540
agactctcca ccataaggca cctctactta gcagagaaca tggttagaac tcttcctgcc    600
agcatgcttc ggaacatgcc gcttctggag aatctttact tgcagggaaa tccgtggacc    660
tgcgattgtg agatgagatg gtttttggaa tgggatgcaa aatccagagg aattctgaag    720
tgtaaaaagg acaaagctta tgaaggcggt cagttgtgtg caatgtgctt cagtccaaag    780
aagttgtaca aacatgagat acacaagctg aaggacatga cttgtctgaa gccttcaata    840
gagtcccctc tgagacagaa caggagcagg agtattgagg aggagcaaga acaggaagag    900
gatggtggca gccagctcat cctggagaaa ttccaactgc cccagtggag catctctttg    960
aatatgaccg acgagcacgg gaacatggtg aacttggtct gtgacatcaa gaaaccaatg   1020
gatgtgtaca agattcactt gaaccaaacg gatcctccag atattgacat aaatgcaaca   1080
gttgccttgg actttgagtg tccaatgacc cgagaaaact atgaaaagct atggaaattg   1140
atagcatact acagtgaagt tcccgtgaag ctacacagag agctcatgct cagcaaagac   1200
cccagagtca gctaccagta caggcaggat gctgatgagg aagctcttta ctacacaggt   1260
gtgagagccc agattcttgc agaaccagaa tgggtcatgc agccatccat agatatccag   1320
ctgaaccgac gtcagagtac ggccaagaag gtgctacttt cctactacac ccagtattct   1380
caaacaatat ccaccaaaga tacaaggcag gctcggggca gaagctgggt aatgattgag   1440
```

-continued

```
cctagtggag ctgtgcaaag agatcagact gtcctggaag ggggtccatg ccagttgagc   1500
tgcaacgtga aagcttctga gagtccatct atcttctggg tgcttccaga tggctccatc   1560
ctgaaagcgc ccatggatga cccagacagc aagttctcca ttctcagcag tggctggctg   1620
aggatcaagt ccatggagcc atctgactca ggcttgtacc agtgcattgc tcaagtgagg   1680
gatgaaatgg accgcatggt atatagggta cttgtgcagt ctccctccac tcagccagcc   1740
gagaaagaca cagtgacaat tggcaagaac ccaggggagt cggtgacatt gccttgcaat   1800
gctttagcaa tacccgaagc ccaccttagc tggattcttc caaacagaag gataattaat   1860
gatttggcta acacatcaca tgtatacatg ttgccaaatg gaactctttc catcccaaag   1920
gtccaagtca gtgatagtgg ttactacaga tgtgtggctg tcaaccagca aggggcagac   1980
cattttacgg tgggaatcac agtgaccaag aaagggtctg gcttgccatc caaaagaggc   2040
agacgcccag gtgcaaaggc tctttccaga gtcagagaag acatcgtgga ggatgaaggg   2100
ggctcgggca tgggagatga agagaacact tcaaggagac ttctgcatcc aaaggaccaa   2160
gaggtgttcc tcaaaacaaa ggatgatgcc atcaatggag acaagaaagc caagaaaggg   2220
agaagaaagc tgaaactctg gaagcattcg gaaaaagaac cagagaccaa tgttgcagaa   2280
ggtcgcagag tgtttgaatc tagacgaagg ataaacatgg caaacaaaca gattaatccg   2340
gagcgctggg ctgatatttt agccaaagtc cgtgggaaaa atctccctaa gggcacagaa   2400
gtacccccgt tgattaaaac cacaagtcct ccatccttga gcctagaagt cacaccacct   2460
tttcctgctg tttctccccc ctcagcatct cctgtgcaga cagtaaccag tgctgaagaa   2520
tcctcagcag atgtacctct acttggtgaa gaagagcacg ttttgggtac catttcctca   2580
gccagcatgg ggctagaaca caaccacaat ggagttattc ttgttgaacc tgaagtaaca   2640
agcacacctc tggaggaagt tgttgatgac ctttctgaga agactgagga gataacttcc   2700
actgaaggag acctgaaggg gacagcagcc cctacactta tatctgagcc ttatgaacca   2760
tctcctactc tgcacacatt agacacagtc tatgaaaagc ccacccatga agagacggca   2820
acagagggtt ggtctgcagc agatgttgga tcgtcaccag agcccacatc cagtgagtat   2880
gagcctccat tggatgctgt ctccttggct gagtctgagc ccatgcaata ctttgaccca   2940
gatttggaga ctaagtcaca accagatgag gataagatga aagaagacac ctttgcacac   3000
cttactccaa cccccaccat ctgggttaat gactccagta catcacagtt atttgaggat   3060
tctactatag gggaaccagg tgtcccaggc caatcacatc tacaaggact gacagacaac   3120
atccaccttg tgaaaagtag tctaagcact caagacacct tactgattaa aaagggtatg   3180
aaagagatgt ctcagacact acagggagga aatatgctag agggagaccc cacacactcc   3240
agaagttctg agagtgaggg ccaagagagc aaatccatca ctttgcctga ctccacactg   3300
ggtataatga gcagtatgtc tccagttaag aagcctgcgg aaaccacagt tggtaccctc   3360
ctagacaaag acaccacaac agtaacaaca acaccaaggc aaaaagttgc tccgtcatcc   3420
accatgagca ctcacccttc tcgaaggaga cccaacggga gaaggagatt acgccccaac   3480
aaattccgcc accggcacaa gcaaaccccca cccacaactt ttgccccatc agagactttt   3540
tctactcaac caactcaagc acctgacatt aagatttcaa gtcaagtgga gagttctctg   3600
gttcctacag cttgggtgga taacacagtt aatacccccca aacagttgga aatggagaag   3660
aatgcagaac ccacatccaa gggaacacca cggagaaaac acgggaagag gccaaacaaa   3720
catcgatata ccccttctac agtgagctca agagcgtccg gatccaagcc cagcccttct   3780
ccagaaaata aacatagaaa cattgttact cccagttcag aaactatact tttgcctaga   3840
```

```
actgtttctc tgaaaactga gggcccttat gattccttag attacatgac aaccaccaga   3900
aaaatatatt catcttaccc taaagtccaa gagacacttc cagtcacata taaacccaca   3960
tcagatggaa aagaaattaa ggatgatgtt gccacaaatg ttgacaaaca taaaagtgac   4020
attttagtca ctggtgaatc aattactaat gccataccaa cttctcgctc cttggtctcc   4080
actatgggag aatttaagga agaatcctct cctgtaggct ttccaggaac tccaacctgg   4140
aatccctcaa ggacggccca gcctgggagg ctacagacag acatacctgt taccacttct   4200
ggggaaaatc ttacagaccc tccccttctt aaagagcttg aggatgtgga tttcacttcc   4260
gagtttttgt cctctttgac agtctccaca ccatttcacc aggaagaagc tggttcttcc   4320
acaactctct caagcataaa agtggaggtg gcttcaagtc aggcagaaac caccaccctt   4380
gatcaagatc atcttgaaac cactgtggct attctccttt ctgaaactag accacagaat   4440
cacaccccta ctgctgcccg gatgaaggag ccagcatcct cgtccccatc cacaattctc   4500
atgtctttgg gacaaaccac caccactaag ccagcacttc ccagtccaag aatatctcaa   4560
gcatctagag attccaagga aaatgttttc ttgaattatg tggggaatcc agaaacagaa   4620
gcaaccccag tcaacaatga aggaacacag catatgtcag ggccaaatga attatcaaca   4680
ccctcttccg accgggatgc atttaacttg tctacaaagc tggaattgga aaagcaagta   4740
tttggtagta ggagtctacc acgtggccca gatagccaac gccaggatgg aagagttcat   4800
gcttctcatc aactaaccag agtccctgcc aaacccatcc taccaacagc aacagtgagg   4860
ctacctgaaa tgtccacaca aagcgcttcc agatactttg taacttccca gtcacctcgt   4920
cactggacca acaaaccgga aataactaca tatccttctg ggggctttgcc agagaacaaa   4980
cagtttacaa ctccaagatt atcaagtaca acaattcctc tcccattgca catgtccaaa   5040
cccagcattc ctagtaagtt tactgaccga agaactgacc aattcaatgg ttactccaaa   5100
gtgtttggaa ataacaacat ccctgaggca agaaacccag ttggaaagcc tcccagtcca   5160
agaattcctc attattccaa tggaagactc cctttcttta ccaacaagac tctttctttt   5220
ccacagttgg gagtcacccg gagaccccag atacccactt ctcctgcccc agtaatgaga   5280
gagagaaaag ttattccagg ttcctacaac aggatacatt cccatagcac cttccatctg   5340
gactttggcc ctccggcacc tccgttgttg cacactccgc agaccacggg atcaccctca   5400
actaacttac agaatatccc tatggtctct tccacccaga gttctatctc ctttataaca   5460
tcttctgtcc agtcctcagg aagcttccac cagagcagct caaagttctt tgcaggagga   5520
cctcctgcat ccaaattctg gtctcttggg gaaaagcccc aaatcctcac caagtcccca   5580
cagactgtgt ccgtcaccgc tgagacagac actgtgttcc cctgtgaggc aacaggaaaa   5640
ccaaagcctt tcgttacttg gacaaaggtt tccacaggag ctcttatgac tccgaatacc   5700
aggatacaac ggtttgaggt tctcaagaac ggtaccttag tgatacggaa ggttcaagta   5760
caagatcgag gccagtatat gtgcaccgcc agcaacctgc acggcctgga caggatggtg   5820
gtcttgcttt cggtcaccgt gcagcaacct caaatcctag cctcccacta ccaggacgtc   5880
actgtctacc tgggagacac cattgcaatg gagtgtctgg ccaaagggac cccagccccc   5940
caaatttcct ggatcttccc tgacaggagg gtgtggcaaa ctgtgtcccc cgtggagagc   6000
cgcatcaccc tgcacgaaaa ccggaccctt tccatcaagg aggcgtcctt ctcagacaga   6060
ggcgtctata agtgcgtggc cagcaatgca gccggggcgg acagcctggc catccgcctg   6120
cacgtggcgg cactgccccc cgttatccac caggagaagc tggagaacat ctcgctgccc   6180
```

-continued

```
ccggggctca gcattcacat tcactgcact gccaaggctg cgcccctgcc cagcgtgcgc   6240
tgggtgctcg gggacggtac ccagatccgc ccctcgcagt tcctccacgg gaacttgttt   6300
gttttcccca acgggacgct ctacatccgc aacctcgcgc ccaaggacag cgggcgctat   6360
gagtgcgtgg ccgccaacct ggtaggctcc gcgcgcagga cggtgcagct gaacgtgcag   6420
cgtgcagcag ccaacgcgcg catcacgggc acctccccgc ggaggacgga cgtcaggtac   6480
ggaggaaccc tcaagctgga ctgcagcgcc tcgggggacc cctggccgcg catcctctgg   6540
aggctgccgt ccaagaggat gatcgacgcg ctcttcagtt ttgatagcag aatcaaggtg   6600
tttgccaatg ggaccctggt ggtgaaatca gtgacggaca aagatgccgg agattacctg   6660
tgcgtagctc gaaataaggt tggtgatgac tacgtggtgc tcaaagtgga tgtggtgatg   6720
aaaccggcca agattgaaca caaggaggag aacgaccaca aagtcttcta cgggggtgac   6780
ctgaaagtgg actgtgtggc caccgggctt cccaatcccg agatctcctg gagcctccca   6840
gacgggagtc tggtgaactc cttcatgcag tcggatgaca gcggtggacg caccaagcgc   6900
tatgtcgtct tcaacaatgg gacactctac tttaacgaag tggggatgag ggaggaagga   6960
gactacacct gctttgctga aaatcaggtc gggaaggacg agatgagagt cagagtcaag   7020
gtggtgacag cgcccgccac catccggaac aagacttact tggcggttca ggtgccctat   7080
ggagacgtgg tcactgtagc ctgtgaggcc aaaggagaac ccatgcccaa ggtgacttgg   7140
ttgtccccaa ccaacaaggt gatccccacc tcctctgaga agtatcagat ataccaagat   7200
ggcactctcc ttattcagaa agcccagcgt tctgacagcg gcaactacac ctgcctggtc   7260
aggaacagcg cgggagagga taggaagacg gtgtggattc acgtcaacgt ccagccaccc   7320
aagatcaacg gtaaccccaa ccccatcacc accgtgcggg agatagcagc cgggggcagt   7380
cggaaactga ttgactgcaa agctgaaggc atccccaccc cgagggtgtt atgggctttt   7440
cccgagggtg tggttctgcc agctccatac tatggaaacc ggatcactgt ccatggcaac   7500
ggttccctgg acatcaggag tttgaggaag agcgactccg tccagctggt atgcatggca   7560
cgcaacgagg gaggggaggc gaggttgatc gtgcagctca ctgtcctgga gcccatggag   7620
aaacccatct tccacgaccc gatcagcgag aagatcacgg ccatggcggg ccacaccatc   7680
agcctcaact gctctgccgc ggggaccccg acacccagcc tggtgtgggt ccttcccaat   7740
ggcaccgatc tgcagagtgg acagcagctg cagcgcttct accacaaggc tgacggcatg   7800
ctacacatta gcggtctctc ctcggtggac gctggggcct accgctgcgt ggcccgcaat   7860
gccgctggcc acacggagag gctggtctcc ctgaaggtgg gactgaagcc agaagcaaac   7920
aagcagtatc ataacctggt cagcatcatc aatggtgaga ccctgaagct cccctgcacc   7980
cctcccgggg ctgggcaggg acgtttctcc tggacgctcc ccaatggcat gcatctggag   8040
ggcccccaaa ccctgggacg cgtttctctt ctggacaatg gcaccctcac ggttcgtgag   8100
gcctcggtgt ttgacagggg tacctatgta tgcaggatgg agacggagta cggcccttcg   8160
gtcaccagca tccccgtgat tgtgatcgcc tatcctcccc ggatcaccag cgagcccacc   8220
ccggtcatct acacccggcc cgggaacacc gtgaaactga actgcatggc tatggggatt   8280
cccaaagctg acatcacgtg ggagttaccg gataagtcgc atctgaaggc aggggttcag   8340
gctcgtctgt atggaaacag atttcttcac ccccagggat cactgaccat ccagcatgcc   8400
acacagagag atgccggctt ctacaagtgc atggcaaaaa acattctcgg cagtgactcc   8460
aaaacaactt acatccacgt cttctgaaat gtggattcca gaatgattgc ttaggaactg   8520
acaacaaagc ggggtttgta agggaagcca ggttggggaa taggagctct taaataatgt   8580
```

-continued gtcacagtgc atggtggcct ctggtgggtt tcaagttgag gttgatcttg atctacaatt 8640
gttgggaaaa ggaagcaatg cagacacgag aaggagggct cagccttgct gagacacttt 8700
cttttgtgtt tacatcatgc caggggcttc attcagggtg tctgtgctct gactgcaatt 8760
tttcttcttt tgcaaatgcc actcgactgc cttcataagc gtccatagga tatctgagga 8820
acattcatca aaaataagcc atagacatga acaacacctc actaccccat tgaagacgca 8880
tcacctagtt aacctgctgc agtttttaca tgatagactt tgttccagat tgacaagtca 8940
tctttcagtt atttcctctg tcacttcaaa actccagctt gcccaataag gatttagaac 9000
cagagtgact gatatatata tatatatttt aattcagagt tacatacata cagctaccat 9060
tttatatgaa aaaagaaaaa catttcttcc tggaactcac tttttatata atgttttata 9120
tatatatttt ttcctttcaa atcagacgat gagactagaa ggagaaatac tttctgtctt 9180
attaaaatta ataaattatt ggtctttaca agacttggat acattacagc agacatggaa 9240
atataatttt aaaaaatttc tctccaacct ccttcaaatt cagtcaccac tgttatatta 9300
ccttctccag gaaccctcca gtggggaagg ctgcgatatt agatttcctt gtatgcaaag 9360
tttttgttga aagctgtgct cagaggaggt gagaggagag gaaggagaaa actgcatcat 9420
aactttacag aattgaatct agagtcttcc ccgaaaagcc cagaaacttc tctgcagtat 9480
ctggcttgtc catctggtct aaggtggctg cttcttcccc agccatgagt cagtttgtgc 9540
ccatgaataa tacacgacct gttatttcca tgactgcttt actgtatttt taaggtcaat 9600
atactgtaca tttgataata aaataatatt ctcccaaaaa aaaaa 9645

<210> SEQ ID NO 96
<211> LENGTH: 694
<212> TYPE: DNA
<213> ORGANISM: Homo sapiens

<400> SEQUENCE: 96
gcctccgagg agaccatggc ctggcccctg tgcaccctgc tgctcctgct ggccacccag 60
gctgtggccc tggcctggag cccccaggag gaggacagga taatcgaggg tggcatctat 120
gatgcagacc tcaatgatga gcgggtacag cgtgcccttc actttgtcat cagcgagtat 180
aacaaggcca ctgaagatga gtactacaga cgcctgctgc gggtgctacg agccagggag 240
cagatcgtgg gcggggtgaa ttacttcttc gacatagagg tgggccgaac catatgtacc 300
aagtcccagc ccaacttgga cacctgtgcc ttccatgaac agccagaact gcagaagaaa 360
cagttgtgct ctttccagat ctacgaagtt ccctgggagg acagaatgtc cctggtgaat 420
tccaggtgtc aagaagccta gggatctgtg ccagggagtc acactgacca cctcctactc 480
ccaccccttg tagtgctccc acccctggac tggtggcccc caccctgtgg gaggtctccc 540
catgcacctg cagcaggaga agacagagaa ggctgcagga ggcctttgtt gctcagcagg 600
ggactctgcc ctccctcctt ccttttgctt ctcatagccc tggtacatgg tacacacacc 660
cccacctcct gcaattaaac agtagcatca cctc 694

<210> SEQ ID NO 97
<211> LENGTH: 782
<212> TYPE: DNA
<213> ORGANISM: Homo sapiens

<400> SEQUENCE: 97
gggctccctg cctcgggctc tcaccctcct ctcctgcagc tccagctttg tgctctgcct 60

```
ctgaggagac catggcccag tatctgagta ccctgctgct cctgctggcc accctagctg    120
tggccctggc ctggagcccc aaggaggagg ataggataat cccgggtggc atctataacg    180
cagacctcaa tgatgagtgg gtacagcgtg cccttcactt cgccatcagc gagtataaca    240
aggccaccaa agatgactac tacagacgtc cgctgcgggt actaagagcc aggcaacaga    300
ccgttggggg ggtgaattac ttcttcgacg tagaggtggg ccgcaccata tgtaccaagt    360
cccagcccaa cttggacacc tgtgccttcc atgaacagcc agaactgcag aagaaacagt    420
tgtgctcttt cgagatctac gaagttccct gggagaacag aaggtccctg gtgaaatcca    480
ggtgtcaaga atcctaggga tctgtgccag gccattcgca ccagccacca cccactccca    540
ccccctgtag tgctcccacc cctggactgg tggcccccac cctgcgggag gcctccccat    600
gtgcctgcgc caagagacag acagagaagg ctgcaggagt cctttgttgc tcagcagggc    660
gctctgccct ccctccttcc ttcttgcttc taatagccct ggtacatggt acacaccccc    720
ccacctcctg caattaaaca gtagcatcgc ctccctctga aaaaaaaaaa aaaaaaaaaa    780
aa                                                                    782
```

<210> SEQ ID NO 98
<211> LENGTH: 3432
<212> TYPE: DNA
<213> ORGANISM: homo sapiens

<400> SEQUENCE: 98

```
actccagcgc gcggctacct acgcttggtg cttgctttct ccagccatcg gagaccagag     60
ccgccccctc tgctcgagaa aggggctcag cggcggcgga agcggagggg gaccaccgtg    120
gagagcgcgg tcccagcccg gccactgcgg atccctgaaa ccaaaaagct cctgctgctt    180
ctgtaccccg cctgtccctc ccagctgcgc agggcccctt cgtgggatca tcagcccgaa    240
gacagggatg gagaggcctc tgtgctccca cctctgcagc tgcctggcta tgctggccct    300
cctgtccccc ctgagcctgg cacagtatga cagctggccc cattaccccg agtacttcca    360
gcaaccggct cctgagtatc accagcccca ggcccccgcc aacgtggcca agattcagct    420
gcgcctggct gggcagaaga ggaagcacag cgagggccgg gtggaggtgt actatgatgg    480
ccagtggggc accgtgtgcg atgacgactt ctccatccac gctgcccacg tcgtctgccg    540
ggagctgggc tatgtggagg ccaagtcctg gactgccagc tcctcctacg gcaagggaga    600
agggcccatc tggttagaca atctccactg tactggcaac gaggcgaccc ttgcagcatg    660
cacctccaat ggctggggcg tcactgactg caagcacacg gaggatgtcg gtgtggtgtg    720
cagcgacaaa aggattcctg ggttcaaatt tgacaattcg ttgatcaacc agatagagaa    780
cctgaatatc caggtggagg acattcggat tcgagccatc ctctcaacct accgcaagcg    840
caccccagtg atggagggct acgtggaggt gaaggagggc aagacctgga agcagatctg    900
tgacaagcac tggacggcca agaattcccg cgtggtctgc ggcatgtttg gcttccctgg    960
ggagaggaca tacaatacca aagtgtacaa aatgtttgcc tcacggagga agcagcgcta   1020
ctggccattc tccatggact gcaccggcac agaggcccac atctccagct gcaagctggg   1080
cccccaggtg tcactggacc ccatgaagaa tgtcacctgc gagaatgggc tgccggccgt   1140
ggtgagttgt gtgcctgggc aggtcttcag ccctgacgga ccctcgagat tccggaaagc   1200
atacaagcca gagcaacccc tggtgcgact gagaggcggt gcctacatcg ggagggccg    1260
cgtggaggtg ctcaaaaatg gagaatgggg gaccgtctgc gacgacaagt gggacctggt   1320
gtcggccagt gtggtctgca gagagctggg ctttgggagt gccaaagagg cagtcactgg   1380
```

ctcccgactg gggcaaggga tcggacccat ccacctcaac gagatccagt gcacaggcaa 1440
tgagaagtcc attatagact gcaagttcaa tgccgagtct cagggctgca accacgagga 1500
ggatgctggt gtgagatgca acacccctgc catgggcttg cagaagaagc tgcgcctgaa 1560
cggcggccgc aatccctacg agggccgagt ggaggtgctg gtggagagaa acgggtccct 1620
tgtgtggggg atggtgtgtg gccaaaactg ggcatcgtg gaggccatgg tggtctgccg 1680
ccagctgggc ctgggattcg ccagcaacgc cttccaggag acctggtatt ggcacggaga 1740
tgtcaacagc aacaaagtgg tcatgagtgg agtgaagtgc tcgggaacgg agctgtccct 1800
ggcgcactgc cgccacgacg gggaggacgt ggcctgcccc cagggcggag tgcagtacgg 1860
ggccggagtt gcctgctcag aaaccgcccc tgacctggtc ctcaatgcgg agatggtgca 1920
gcagaccacc tacctggagg accggcccat gttcatgctg cagtgtgcca tggaggagaa 1980
ctgcctctcg gcctcagccg cgcagaccga ccccaccacg ggctaccgcc ggctcctgcg 2040
cttctcctcc cagatccaca acaatggcca gtccgacttc cggcccaaga acggccgcca 2100
cgcgtggatc tggcacgact gtcacaggca ctaccacagc atggaggtgt tcacccacta 2160
tgacctgctg aacctcaatg gcaccaaggt ggcagagggc cacaaggcca gcttctgctt 2220
ggaggacaca gaatgtgaag gagacatcca gaagaattac gagtgtgcca acttcggcga 2280
tcagggcatc accatgggct gctgggacat gtaccgccat gacatcgact gccagtgggt 2340
tgacatcact gacgtgcccc ctggagacta cctgttccag gttgttatta accccaactt 2400
cgaggttgca gaatccgatt actccaacaa catcatgaaa tgcaggagcc gctatgacgg 2460
ccaccgcatc tggatgtaca actgccacat aggtggttcc ttcagcgaag agacggaaaa 2520
aaagtttgag cacttcagcg ggctcttaaa caaccagctg tccccgcagt aaagaagcct 2580
gcgtggtcaa ctcctgtctt caggccacac cacatcttcc atgggacttc cccccaacaa 2640
ctgagtctga acgaatgcca cgtgccctca cccagcccgg cccccaccct gtccagaccc 2700
ctacagctgt gtctaagctc aggaggaaag ggaccctccc atcattcatg gggggctgct 2760
acctgaccct tggggcctga gaaggccttg ggggggtggg gtttgtccac agagctgctg 2820
gagcagcacc aagagccagt cttgaccggg atgaggccca cagacaggtt gtcatcagct 2880
tgtcccattc aagccaccga gctcaccaca gacacagtgg agccgcgctc ttctccagtg 2940
acacgtggac aaatgcgggc tcatcagccc ccccagagag ggtcaggccg aaccccattt 3000
ctcctcctct taggtcattt tcagcaaact tgaatatcta gacctctctt ccaatgaaac 3060
cctccagtct attatagtca catagataat ggtgccacgt gttttctgat ttggtgagct 3120
cagacttggt gcttccctct ccacaacccc caccccttgt ttttcaagat actattatta 3180
tattttcaca gacttttgaa gcacaaattt attggcattt aatattggac atctgggccc 3240
ttggaagtac aaatctaagg aaaaaccaac ccactgtgta agtgactcat cttcctgttg 3300
ttccaattct gtgggttttt gattcaacgg tgctataacc agggtcctgg gtgacagggc 3360
gctcactgag caccatgtgt catcacagac acttacacat acttgaaact tggaataaaa 3420
gaaagattta tg 3432

<210> SEQ ID NO 99
<211> LENGTH: 8448
<212> TYPE: DNA
<213> ORGANISM: Homo sapiens

<400> SEQUENCE: 99

-continued

```
gcagtggttt ctcctccttc ctcccaggaa gggccaggaa aatggccctg gtcctggaga     60
tcttcaccct gctggcctcc atctgctggg tgtcggccaa tatcttcgag taccaggttg    120
atgcccagcc ccttcgtccc tgtgagctgc agagggaaac ggcctttctg aagcaagcag    180
actacgtgcc ccagtgtgca gaggatggca gcttccagac tgtccagtgc cagaacgacg    240
gccgctcctg ctggtgtgtg ggtgccaacg gcagtgaagt gctgggcagc aggcagccag    300
gacggcctgt ggcttgtctg tcattttgtc agctacagaa acagcagatc ttactgagtg    360
gctacattaa cagcacagac acctcctacc tccctcagtg tcaggattca ggggactacg    420
cgcctgttca gtgtgatgtg cagcatgtcc agtgctggtg tgtggacgca gaggggatgg    480
aggtgtatgg gacccgccag ctggggaggc caaagcgatg tccaaggagc tgtgaaataa    540
gaaatcgtcg tcttctccac ggggtgggag ataagtcacc accccagtgt tctgcggagg    600
gagagtttat gcctgtccag tgcaaatttg tcaacaccac agacatgatg atttttgatc    660
tggtccacag ctacaacagg tttccagatg catttgtgac cttcagttcc ttccagagga    720
ggttccctga ggtatctggg tattgccact gtgctgacag ccaagggcgg gaactggctg    780
agacaggttt ggagttgtta ctggatgaaa tttatgacac catttttgct ggcctggacc    840
ttccttccac cttcactgaa accaccctgt accggatact gcagagacgg ttcctcgcag    900
ttcaatcagt catctctggc agattccgat gccccacaaa atgtgaagtg gagcggttta    960
cagcaaccag ctttggtcac ccctatgttc caagctgccg ccgaaatggc gactatcagg   1020
cggtgcagtg ccagacggaa gggccctgct ggtgtgtgga cgcccagggg aaggaaatgc   1080
atggaacccg gcagcaaggg gagccgccat cttgtgctga aggccaatct tgtgcctccg   1140
aaaggcagca ggccttgtcc agactctact ttgggacctc aggctacttc agccagcacg   1200
acctgttctc ttccccagag aaaagatggg cctctccaag agtagccaga tttgccacat   1260
cctgcccacc cacgatcaag gagctctttg tggactctgg gcttctccgc ccaatggtgg   1320
agggacagag ccaacagttt tctgtctcag aaaatcttct caaagaagcc atccgagcaa   1380
tttttccctc ccgagggctg gctcgtcttg cccttcagtt taccaccaac ccaaagagac   1440
tccagcaaaa cctttttgga gggaaatttt tggtgaatgt tggccagttt aacttgtctg   1500
gagcccttgg cacaagaggc acatttaact tcagtcaatt tttccagcaa cttggtcttg   1560
caagcttctt gaatggaggg agacaagaag atttggccaa gccactctct gtgggattag   1620
attcaaattc ttccacagga acccctgaag ctgctaagaa ggatggtact atgaataagc   1680
caactgtggg cagctttggc tttgaaatta acctacaaga gaaccaaaat gccctcaaat   1740
tccttgcttc tctcctggag cttccagaat tccttctctt cttgcaacat gctatctctg   1800
tgccagaaga tgtggcaaga gatttaggtg atgtgatgga aacggtactc gactcccaga   1860
cctgtgagca gacacctgaa aggctatttg tcccatcatg cacgacagaa ggaagctatg   1920
aggatgtcca atgcttttcc ggagagtgct ggtgtgtgaa ttcctggggc aaagagcttc   1980
caggctcaag agtcagagat ggacagccaa ggtgccccac agactgtgaa aagcaaaggg   2040
ctcgcatgca aagcctcatg ggcagccagc ctgctggctc caccttgttt gtccctgctt   2100
gtactagtga gggacatttc ctgcctgtcc agtgcttcaa ctcagagtgc tactgtgttg   2160
atgctgaggg tcaggccatt cctggaactc gaagtgcaat agggaagccc aagaaatgcc   2220
ccacgccctg tcaattacag tctgagcaag ctttcctcag gacggtgcag gccctgctct   2280
ctaactccag catgctaccc accctttccg acacctacat cccacagtgc agcaccgatg   2340
ggcagtggag acaagtgcaa tgcaatgggc ctcctgagca ggtcttcgag ttgtaccaac   2400
```

-continued

```
gatgggaggc tcagaacaag ggccaggatc tgacgcctgc caagctgcta gtgaagatca   2460
tgagctacag agaagcagct tccggaaact tcagtctctt tattcaaagt ctgtatgagg   2520
ctggccagca agatgtcttc ccggtgctgt cacaataccc ttctctgcaa gatgtcccac   2580
tagcagcact ggaagggaaa cggccccagc ccagggagaa tatcctcctg gagccctacc   2640
tcttctggca gatcttaaat ggccaactca gccaataccc ggggtcctac tcagacttca   2700
gcactccttt ggcacatttt gatcttcgga actgctggtg tgtggatgag gctggccaag   2760
aactggaagg aatgcggtct gagccaagca agctcccaac gtgtcctggc tcctgtgagg   2820
aagcaaagct ccgtgtactg cagttcatta gggaaacgga agagattgtt tcagcttcca   2880
acagttctcg gttccctctg gggggagagtt tcctggtggc caagggaatc cggctgagga   2940
atgaggacct cggccttcct ccgctcttcc cgccccggga ggctttcgcg gagtttctgc   3000
gtgggagtga ttacgccatt cgcctggcgg ctcagtctac cttaagcttc tatcagagac   3060
gccgcttttc ccggacgac tcggctggag catccgccct tctgcggtcg ggcccctaca   3120
tgccacagtg tgatgcgttt ggaagttggg agcctgtgca gtgccacgct gggactgggc   3180
actgctggtg tgtagatgag aaaggagggt tcatccctgg ctcactgact gcccgctctc   3240
tgcagattcc acagtgcccg acaacctgcg agaaatctcg aaccagtggg ctgctttcca   3300
gttggaaaca ggctagatcc caagaaaacc catctccaaa agacctgttc gtcccagcct   3360
gcctagaaac aggagaatat gccaggctgc aggcatcggg ggctggcacc tggtgtgtgg   3420
accctgcatc aggagaagag ttgcggcctg gctcgagcag cagtgcccag tgcccaagcc   3480
tctgcaatgt gctcaagagt ggagtcctct ctaggagagt cagcccaggc tatgtcccag   3540
cctgcagggc agaggatggg ggcttttccc cagtgcaatg tgaccaggcc cagggcagct   3600
gctggtgtgt catggacagc ggagaagagg tgcctgggac gcgcgtgacc gggggccagc   3660
ccgcctgtga gagcccgcgg tgtccgctgc cattcaacgc gtcggaggtg gttggtggaa   3720
caatcctgtg tgagacaatc tcgggcccca caggctctgc catgcagcag tgccaattgc   3780
tgtgccgcca aggctcctgg agcgtgtttc caccagggcc attgatatgt agcctggaga   3840
gcggacgctg ggagtcacag ctgcctcagc cccgggcctg ccaacggccc cagctgtggc   3900
agaccatcca gacccaaggg cactttcagc tccagctccc gccgggcaag atgtgcagtg   3960
ctgactacgc gggtttgctg cagactttcc aggttttcat attggatgag ctgacagccc   4020
gcggcttctg ccagatccag gtgaagactt ttggcaccct ggtttccatt cctgtctgca   4080
acaactcctc tgtgcaggtg ggttgtctga ccagggagcg tttaggagtg aatgttacat   4140
ggaaatcacg gcttgaggac atcccagtgg cttctcttcc tgacttacat gacattgaga   4200
gagccttggt gggcaaggat ctccttgggc gcttcacaga tctgatccag agtggctcat   4260
tccagcttca tctggactcc aagacgttcc cagcggaaac catccgcttc ctccaagggg   4320
accactttgg cacctctcct aggacacggt ttgggtgctc ggaaggattc taccaagtct   4380
tgacaagtga ggccagtcag gacggactgg gatgcgttaa gtgccatgaa ggaagctatt   4440
cccaagatga ggaatgcatt ccttgtcctg ttggattcta ccaagaacag gcagggagct   4500
tggcctgtgt cccatgtcct gtgggcagaa cgaccatttc tgccggagct ttcagccaga   4560
ctcactgtgt cactgactgt cagaggaacg aagcaggcct gcaatgtgac cagaatggcc   4620
agtatcgagc cagccagaag gacaggggca gtgggaaggc cttctgtgtg gacggcgagg   4680
ggcggaggct gccatggtgg gaaacagagg cccctcttga ggactcacag tgtttgatga   4740
```

-continued

```
tgcagaagtt tgagaaggtt ccagaatcaa aggtgatctt cgacgccaat gctcctgtgg   4800
ctgtcagatc caaagttcct gattctgagt tccccgtgat gcagtgcttg acagattgca   4860
cagaggacga ggcctgcagc ttcttcaccg tgtccacgac ggagccagag atttcctgtg   4920
atttctatgc ttggacaagt gacaatgttg cctgcatgac ttctgaccag aaacgagatg   4980
cactggggaa ctcaaaggcc accagctttg gaagtcttcg ctgccaggtg aaagtgagga   5040
gccatggtca agattctcca gctgtgtatt tgaaaaaggg ccaaggatcc accacaacac   5100
ttcagaaacg ctttgaaccc actggtttcc aaaacatgct ttctggattg tacaacccca   5160
ttgtgttctc agcctcagga gccaatctaa ccgatgctca cctcttctgt cttcttgcat   5220
gcgaccgtga tctgtgttgc gatggcttcg tcctcacaca ggttcaagga ggtgccatca   5280
tctgtgggtt gctgagctca cccagtgtcc tgctttgtaa tgtcaaagac tggatggatc   5340
cctctgaagc ctgggctaat gctacatgtc ctggtgtgac atatgaccag gagagccacc   5400
aggtgatatt gcgtcttgga gaccaggagt tcatcaagag tctgacaccc ttagaaggaa   5460
ctcaagacac ctttaccaat tttcagcagg tttatctctg gaaagattct gacatggggt   5520
ctcggcctga gtctatggga tgtagaaaaa acacagtgcc aaggccagca tctccaacag   5580
aagcaggttt gacaacagaa cttttctccc ctgtggacct caaccaggtc attgtcaatg   5640
gaaatcaatc actatccagc cagaagcact ggcttttcaa gcacctgttt tcagcccagc   5700
aggcaaacct atggtgcctt tctcgttgtg tgcaggagca ctctttctgt cagctcgcag   5760
agataacaga gagtgcatcc ttgtacttca cctgcaccct ctacccagag gcacaggtgt   5820
gtgatgacat catggagtcc aatacccagg gctgcagact gatcctgcct cagatgccaa   5880
aggccctgtt ccggaagaaa gttatactgg aagataaagt gaagaacttt tacactcgcc   5940
tgccgttcca aaaactgatg gggatatcca ttagaaataa agtgcccatg tctgaaaaat   6000
ctatttctaa tgggttcttt gaatgtgaac gacggtgcga tgcggaccca tgctgcactg   6060
gctttggatt tctaaatgtt tcccagttaa aggaggaga ggtgacatgt ctcactctga   6120
acagcttggg aattcagatg tgcagtgagg agaatggagg agcctggcgc attttggact   6180
gtggctctcc tgacattgaa gtccacacct atcccttcgg atggtaccag aagcccattg   6240
ctcaaaataa tgctcccagt ttttgccctt tggttgttct gccttccctc acagagaaag   6300
tgtctctgga atcgtggcag tccctggccc tctcttcagt ggttgttgat ccatccatta   6360
ggcactttga tgttgcccat gtcagcactg ctgccaccag caatttctct gctgtccgag   6420
acctctgttt gtcggaatgt tcccaacatg aggcctgtct catcaccact ctgcaaaccc   6480
aactcggggc tgtgagatgt atgttctatg ctgatactca aagctgcaca catagtctgc   6540
agggtcggaa ctgccgactt ctgcttcgtg aagaggccac ccacatctac cggaagccag   6600
gaatctctct gctcagctat gaggcatctg taccttctgt gcccatttcc acccatggcc   6660
ggctgctggg caggtcccag gccatccagg tgggtacctc atggaagcaa gtggaccagt   6720
tccttggagt tccatatgct gccccgcccc tggcagagag gcacttccag gcaccagagc   6780
ccttgaactg gacaggctcc tgggatgcca gcaagccaag ggccagctgc tggcagccag   6840
gcaccagaac atccacgtct cctggagtca gtgaagattg tttgtatctc aatgtgttca   6900
tccctcagaa tgtggcccct aacgcgtctg tgctggtgtt cttccacaac accatggaca   6960
gggaggagag tgaaggatgg ccggctatcg acggctcctt cttggctgct gttggcaacc   7020
tcatcgtggt cactgccagc taccgagtgg gtgtcttcgg cttcctgagt tctggatccg   7080
gagaggtgag tggcaactgg gggctgctgg accaggtggc ggctctgacc tgggtgcaga   7140
```

cccacatccg aggatttggc ggggaccctc ggcgcgtgtc cctggcagca gaccgtggcg 7200
gggctgatgt ggccagcatc caccttctca cggccagggc caccaactcc caacttttcc 7260
ggagagctgt gctgatggga ggctccgcac tctccccggc cgccgtcatc agccatgaga 7320
gggctcagca gcaggcaatt gctttggcaa aggaggtcag ttgccccatg tcatccagcc 7380
aagaagtggt gtcctgcctc cgccagaagc ctgccaatgt cctcaatgat gcccagacca 7440
agctcctggc cgtgagtggc cctttccact actggggtcc tgtgatcgat ggccacttcc 7500
tccgtgagcc tccagccaga gcactgaaga ggtctttatg ggtagaggtc gatctgctca 7560
ttgggagttc tcaggacgac gggctcatca acagagcaaa ggctgtgaag caatttgagg 7620
aaagtcgagg ccggaccagt agcaaaacag ccttttacca ggcactgcag aattctctgg 7680
gtggcgagga ctcagatgcc cgcgtcgagg ctgctgctac atggtattac tctctggagc 7740
actccacgga tgactatgcc tccttctccc gggctctgga gaatgccacc cgggactact 7800
ttatcatctg ccctataatc gacatggcca gtgcctgggc aaagagggcc cgaggaaacg 7860
tcttcatgta ccatgctcct gaaaactacg gccatggcag cctggagctg ctggcggatg 7920
ttcagtttgc cttggggctt cccttctacc cagcctacga ggggcagttt tctctggagg 7980
agaagagcct gtcgctgaaa atcatgcagt acttttccca cttcatcaga tcaggaaatc 8040
ccaactaccc ttatgagttc tcacggaaag tacccacatt tgcaaccccc tggcctgact 8100
ttgtaccccg tgctggtgga gagaactaca aggagttcag tgagctgctc cccaatcgac 8160
agggcctgaa gaaagccgac tgctccttct ggtccaagta catctcgtct ctgaagacat 8220
ctgcagatgg agccaagggc gggcagtcag cagagagtga agaggaggag ttgacggctg 8280
gatctgggct aagagaagat ctcctaagcc tccaggaacc aggctctaag acctacagca 8340
agtgaccagc ccttgagctc cccaaaaacc tcacccgagg ctgcccacta tggtcatctt 8400
tttctctaaa atagttactt accttcaata aagtatctac atgcggtg 8448

<210> SEQ ID NO 100
<211> LENGTH: 5025
<212> TYPE: DNA
<213> ORGANISM: Homo sapiens

<400> SEQUENCE: 100
gcagtggttt ctcctccttc ctcccaggaa gggccaggaa aatggccctg gtcctggaga 60
tcttcaccct gctggcctcc atctgctggg tgtcggccaa tatcttcgag taccaggttg 120
atgcccagcc ccttcgtccc tgtgagctgc agagggaaac ggcctttctg aagcaagcag 180
actacgtgcc ccagtgtgca gaggatggca gcttccagac tgtccagtgc cagaacgacg 240
gccgctcctg ctggtgtgtg ggtgccaacg gcagtgaagt gctgggcagc aggcagccag 300
gacggcctgt ggcttgtctg tcattttgtc agctacagaa acagcagatc ttactgagtg 360
gctacattaa cagcacagac acctcctacc tccctcagtg tcaggattca ggggactacg 420
cgcctgttca gtgtgatgtg cagcatgtcc agtgctggtg tgtggacgca gaggggatgg 480
aggtgtatgg gacccgccag ctggggaggc caaagcgatg tccaaggagc tgtgaaataa 540
gaaatcgtcg tcttctccac ggggtgggag ataagtcacc accccagtgt tctgcggagg 600
gagagtttat gcctgtccag tgcaaatttg tcaacaccac agacatgatg atttttgatc 660
tggtccacag ctacaacagg tttccagatg catttgtgac cttcagttcc ttccagagga 720
ggttccctga ggtatctggg tattgccact gtgctgacag ccaagggcgg gaactggctg 780

-continued

```
agacaggttt ggagttgtta ctggatgaaa tttatgacac catttttgct ggcctggacc    840
ttccttccac cttcactgaa accaccctgt accggatact gcagagacgg ttcctcgcag    900
ttcaatcagt catctctggc agattccgat gccccacaaa atgtgaagtg gagcggttta    960
cagcaaccag ctttggtcac ccctatgttc caagctgccg ccgaaatggc gactatcagg   1020
cggtgcagtg ccagacggaa gggccctgct ggtgtgtgga cgcccagggg aaggaaatgc   1080
atggaacccg gcagcaaggg gagccgccat cttgtgctga aggccaatct tgtgcctccg   1140
aaaggcagca ggccttgtcc agactctact ttgggacctc aggctacttc agccagcacg   1200
acctgttctc ttccccagag aaaagatggg cctctccaag agtagccaga tttgccacat   1260
cctgcccacc cacgatcaag gagctctttg tggactctgg gcttctccgc ccaatggtgg   1320
agggacagag ccaacagttt tctgtctcag aaaatcttct caaagaagcc atccgagcaa   1380
tttttccctc ccgagggctg gctcgtcttg cccttcagtt taccaccaac ccaaagagac   1440
tccagcaaaa cctttttgga gggaaatttt tggtgaatgt tggccagttt aacttgtctg   1500
gagcccttgg cacaagaggc acatttaact tcagtcaatt tttccagcaa cttggtcttg   1560
caagcttctt gaatggaggg agacaagaag atttggccaa gccactctct gtgggattag   1620
attcaaattc ttccacagga acccctgaag ctgctaagaa ggatggtact atgaataagc   1680
caactgtggg cagctttggc tttgaaatta acctacaaga gaaccaaaat gccctcaaat   1740
tccttgcttc tctcctggag cttccagaat tccttctctt cttgcaacat gctatctctg   1800
tgccagaaga tgtggcaaga gatttaggtg atgtgatgga aacggtactc gactcccaga   1860
cctgtgagca gacacctgaa aggctatttg tcccatcatg cacgacagaa ggaagctatg   1920
aggatgtcca atgcttttcc ggagagtgct ggtgtgtgaa ttcctggggc aaagagcttc   1980
caggctcaag agtcagagat ggacagccaa ggtgccccac agactgtgaa aagcaaaggg   2040
ctcgcatgca aagcctcatg ggcagccagc ctgctggctc caccttgttt gtccctgctt   2100
gtactagtga gggacatttc ctgcctgtcc agtgcttcaa ctcagagtgc tactgtgttg   2160
atgctgaggg tcaggccatt cctggaactc gaagtgcaat agggaagccc aagaaatgcc   2220
ccacgccctg tcaattacag tctgagcaag ctttcctcag gacggtgcag gccctgctct   2280
acctccctcc gcggagcagc cagacagcga gggccccggc cgggggcagg ggggacgccc   2340
cgtccggggc acccccccg gctctgagcc gcccgcgggg ccggcctcgg cccggagcgg   2400
aggaaggagt cgccgaggag cagcctgagg ccccagagtc tgagacgagc cgccgccgcc   2460
cccgccactg cggggaggag ggggaggagg agcgggagga gggacgagct ggtcgggaga   2520
agaggaaaaa aacttttgag acttttccgt tgccgctggg agccggaggc gcggggacct   2580
cttggcgcga cgctgccccg cgaggaggca ggacttgggg accccagacc gcctcccttt   2640
gccgccgggg acgcttgctc cctccctgcc ccctacacgg cgtccctcag gcgcccccat   2700
tccggaccag ccctcgggag tcgccgaccc ggcctcccgc aaagactttt ccccagacct   2760
cgggcgcacc ccctgcacgc cgccttcatc cccggcctgt ctcctgagcc cccgcgcatc   2820
ctagaccctt tctcctccag gagacggatc tctctccgac ctgccacaga tcccctattc   2880
aagaccaccc accttctggt accagatcgc gcccatctag gttatttccg tgggatactg   2940
agacaccccc ggtccaagcc tcccctccac cactgcgccc ttctccctga ggagcctcag   3000
ctttccctcg aggccctcct accttttgcc gggagacccc cagcccctgc aggggcgggg   3060
cctccccacc acaccagccc tgttcgcgct ctcggcagtg ccggggggcg ccgcctcccc   3120
catgccgccc tccgggctgc ggctgctgcc gctgctgcta ccgctgctgt ggctactggt   3180
```

gctgacgcct ggcccgccgg ccgcgggact atccacctgc aagactatcg acatggagct 3240
ggtgaagcgg aagcgcatcg aggccatccg cggccagatc ctgtccaagc tgcggctcgc 3300
cagccccccg agccaggggg aggtgccgcc cggcccgctg cccgaggccg tgctcgccct 3360
gtacaacagc acccgcgacc gggtggccgg ggagagtgca gaaccggagc ccgagcctga 3420
ggccgactac tacgccaagg aggtcacccg cgtgctaatg gtggaaaccc acaacgaaat 3480
ctatgacaag ttcaagcaga gtacacacag catatatatg ttcttcaaca catcagagct 3540
ccgagaagcg gtacctgaac ccgtgttgct ctcccgggca gagctgcgtc tgctgaggag 3600
gctcaagtta aaagtggagc agcacgtgga gctgtaccag aaatacagca acaattcctg 3660
gcgatacctc agcaaccggc tgctggcacc cagcgactcg ccagagtggt tatcttttga 3720
tgtcaccgga gttgtgcggc agtggttgag ccgtggaggg gaaattgagg gctttcgcct 3780
tagcgcccac tgctcctgtg acagcaggga taacacactg caagtggaca tcaacgggtt 3840
cactaccggc cgccgaggtg acctggccac cattcatggc atgaaccggc ctttcctgct 3900
tctcatggcc accccgctgg agagggccca gcatctgcaa agctcccggc accgccgagc 3960
cctggacacc aactattgct tcagctccac ggagaagaac tgctgcgtgc ggcagctgta 4020
cattgacttc cgcaaggacc tcggctggaa gtggatccac gagcccaagg gctaccatgc 4080
caacttctgc ctcgggccct gcccctacat ttggagcctg gacacgcagt acagcaaggt 4140
cctggccctg tacaaccagc ataacccggg cgcctcggcg gcgccgtgct gcgtgccgca 4200
ggcgctggag ccgctgccca tcgtgtacta cgtgggccgc aagcccaagg tggagcagct 4260
gtccaacatg atcgtgcgct cctgcaagtg cagctgaggt cccgccccgc cccgccccgc 4320
cccggcaggc ccggccccac cccgccccgc ccccgctgcc ttgcccatgg gggctgtatt 4380
taaggacacc gtgccccaag cccacctggg gccccattaa agatggagag aggactgcgg 4440
atctctgtgt cattgggcgc ctgcctgggg tctccatccc tgacgttccc ccactcccac 4500
tccctctctc tccctctctg cctcctcctg cctgtctgca ctattccttt gcccggcatc 4560
aaggcacagg ggaccagtgg ggaacactac tgtagttaga tctatttatt gagcaccttg 4620
ggcactgttg aagtgcctta cattaatgaa ctcattcagt caccatagca acactctgag 4680
atggcaggga ctctgataac acccatttta aaggttgagg aaacaagccc agagaggtta 4740
agggaggagt tcctgcccac caggaacctg ctttagtggg ggatagtgaa gaagacaata 4800
aaagatagta gttcaggcca ggcggggtgc tcacgcctgt aatcctagca cttttgggag 4860
gcagagatgg gaggatactt gaatccaggc atttgagacc agcctgggta acatagtgag 4920
accctatctc tacaaaacac ttttaaaaaa tgtacacctg tggtcccagc tactctggag 4980
gctaaggtgg gaggatcact tgatcctggg aggtcaaggc tgcag 5025

<210> SEQ ID NO 101
<211> LENGTH: 2208
<212> TYPE: DNA
<213> ORGANISM: Homo sapiens

<400> SEQUENCE: 101
tctttggctt tttttggcgg agctggggcg ccctccggaa gcgtttccaa ctttccagaa 60
gtttctcggg acgggcagga gggggtgggg actgccatat atagatcccg ggagcagggg 120
agcgggctaa gagtagaatc gtgtcgcggc tcgagagcga gagtcacgtc ccggcgctag 180
cccagcccga cccaggccca ccgtggtgca cgcaaaccac ttcctggcca tgcgctccct 240

-continued

```
cctgcttctc agcgccttct gcctcctgga ggcggccctg gccgccgagg tgaagaaacc    300
tgcagccgca gcagctcctg gcactgcgga gaagttgagc cccaaggcgg ccacgcttgc    360
cgagcgcagc gccggcctgg ccttcagctt gtaccaggcc atggccaagg accaggcagt    420
ggagaacatc ctggtgtcac ccgtggtggt ggcctcgtcg ctagggctcg tgtcgctggg    480
cggcaaggcg accacggcgt cgcaggccaa ggcagtgctg agcgccgagc agctgcgcga    540
cgaggaggtg cacgccggcc tgggcgagct gctgcgctca ctcagcaact ccacggcgcg    600
caacgtgacc tggaagctgg gcagccgact gtacggaccc agctcagtga gcttcgctga    660
tgacttcgtg cgcagcagca agcagcacta caactgcgag cactccaaga tcaacttccg    720
cgacaagcgc agcgcgctgc agtccatcaa cgagtgggcc gcgcagacca ccgacggcaa    780
gctgcccgag gtcaccaagg acgtggagcg cacggacggc gccctgctag tcaacgccat    840
gttcttcaag ccacactggg atgagaaatt ccaccacaag atggtggaca accgtggctt    900
catggtgact cggtcctata ccgtgggtgt catgatgatg caccggacag gcctctacaa    960
ctactacgac gacgagaagg aaaagctgca aatcgtggag atgcccctgg cccacaagct   1020
ctccagcctc atcatcctca tgccccatca cgtggagcct ctcgagcgcc ttgaaaagct   1080
gctaaccaaa gagcagctga agatctggat ggggaagatg cagaagaagg ctgttgccat   1140
ctccttgccc aagggtgtgg tggaggtgac ccatgacctg cagaaacacc tggctgggct   1200
gggcctgact gaggccattg acaagaacaa ggccgacttg tcacgcatgt caggcaagaa   1260
ggacctgtac ctggccagcg tgttccacgc caccgccttt gagttggaca cagatggcaa   1320
cccctttgac caggacatct acgggcgcga ggagctgcgc agccccaagc tgttctacgc   1380
cgaccacccc ttcatcttcc tagtgcggga cacccaaagc ggctccctgc tattcattgg   1440
gcgcctggtc cggcctaagg gtgacaagat gcgagacgag ttatagggcc tcagggtgca   1500
cacaggatgg caggaggcat ccaaaggctc ctgagacaca tgggtgctat tggggttggg   1560
ggggaggtga ggtaccagcc ttggatactc catggggtgg gggtggaaaa acagaccggg   1620
gttcccgtgt gcctgagcgg accttcccag ctagaattca ctccacttgg acatgggccc   1680
cagataccat gatgctgagc ccggaaactc cacatcctgt gggacctggg ccatagtcat   1740
tctgcctgcc ctgaaagtcc cagatcaagc ctgcctcaat cagtattcat atttatagcc   1800
aggtaccttc tcacctgtga gaccaaattg agctaggggg gtcagccagc cctcttctga   1860
cactaaaaca cctcagctgc ctccccagct ctatcccaac ctctcccaac tataaaacta   1920
ggtgctgcag cccctgggac caggcacccc cagaatgacc tggccgcagt gaggcggatt   1980
gagaaggagc tcccaggagg ggcttctggg cagactctgg tcaagaagca tcgtgtctgg   2040
cgttgtgggg atgaactttt tgttttgttt cttccttttt tagttcttca aagataggga   2100
gggaaggggg aacatgagcc tttgttgcta tcaatccaag aacttatttg tacatttttt   2160
ttttcaataa aacttttcca atgacatttt gttggagcgt ggaaaaaa                2208
```

<210> SEQ ID NO 102
<211> LENGTH: 2566
<212> TYPE: DNA
<213> ORGANISM: Homo sapiens

<400> SEQUENCE: 102

```
ggcacgagtt gtgctcctcg cttgcctgtt ccttttccac gcattttcca ggataactgt     60
gactccaggc ccgcaatgga tgccctgcaa ctagcaaatt cggcttttgc cgttgatctg    120
ttcaaacaac tatgtgaaaa ggagccactg ggcaatgtcc tcttctctcc aatctgtctc    180
```

-continued

```
tccacctctc tgtcacttgc tcaagtgggt gctaaaggtg acactgcaaa tgaaattgga    240
caggttcttc attttgaaaa tgtcaaagat ataccctttg gatttcaaac agtaacatcg    300
gatgtaaaca aacttagttc cttttactca ctgaaactaa tcaagcggct ctacgtagac    360
aaatctctga atctttctac agagttcatc agctctacga agagacccta tgcaaaggaa    420
ttggaaactg ttgacttcaa agataaattg gaagaaacga aaggtcagat caacaactca    480
attaaggatc tcacagatgg ccactttgag aacattttag ctgacaacag tgtgaacgac    540
cagaccaaaa tccttgtggt taatgctgcc tactttgttg gcaagtggat gaagaaattt    600
cctgaatcag aaacaaaaga atgtcctttc agactcaaca agacagacac caaaccagtg    660
cagatgatga acatggaggc cacgttctgt atgggaaaca ttgacagtat caattgtaag    720
atcatagagc ttccttttca aaataagcat ctcagcatgt tcatcctact acccaaggat    780
gtggaggatg agtccacagg cttggagaag attgaaaaac aactcaactc agagtcactg    840
tcacagtgga ctaatcccag caccatggcc aatgccaagg tcaaactctc cattccaaaa    900
tttaaggtgg aaaagatgat tgatcccaag gcttgtctgg aaaatctagg gctgaaacat    960
atcttcagtg aagacacatc tgatttctct ggaatgtcag agaccaaggg agtggcccta   1020
tcaaatgtta tccacaaagt gtgcttagaa ataactgaag atggtgggga ttccatagag   1080
gtgccaggag cacggatcct gcagcacaag gatgaattga atgctgacca tcccctttatt   1140
tacatcatca ggcacaacaa aactcgaaac atcattttct ttggcaaatt ctgttctcct   1200
taagtggcat agcccatgtt aagtcctccc tgacttttct gtggatgccg atttctgtaa   1260
actctgcatc cagagattca ttttctagat acaataaatt gctaatgttg ctggatcagg   1320
aagccgccag tacttgtcat atgtagcctt cacacagata gaccttttttt tttttccaat   1380
tctatctttt gtttcctttt ttcccataag acaatgacat acgcttttaa tgaaaaggaa   1440
tcacgttaga ggaaaaatat ttattcatta tttgtcaaat tgtccggggt agttggcaga   1500
aatacagtct tccacaaaga aaattcctat aaggaagatt tggaagctct tcttcccagc   1560
actatgcttt ccttctttgg gatagagaat gttccagaca ttctcgcttc cctgaaagac   1620
tgaagaaagt gtagtgcatg ggacccacga aactgccctg gctccagtga aacttgggca   1680
catgctcagg ctactatagg tccagaagtc cttatgttaa gccctggcag gcaggtgttt   1740
attaaaattc tgaattttgg ggattttcaa aagataatat tttacataca ctgtatgtta   1800
tagaacttca tggatcagat ctggggcagc aacctataaa tcaacacctt aatatgctgc   1860
aacaaaatgt agaatattca gacaaaatgg atacataaag actaagtagc ccataagggg   1920
tcaaaatttg ctgccaaatg cgtatgccac caacttacaa aaacacttcg ttcgcagagc   1980
ttttcagatt gtggaatgtt ggataaggaa ttatagacct ctagtagctg aaatgcaaga   2040
ccccaagagg aagttcagat cttaatataa attcactttc atttttgata gctgtcccat   2100
ctggtcatgt ggttggcact agactggtgg caggggcttc tagctgactc gcacagggat   2160
tctcacaata gccgatatca gaatttgtgt tgaaggaact tgtctcttca tctaatatga   2220
tagcgggaaa aggagaggaa actactgcct ttagaaaata taagtaaagt gattaaagtg   2280
ctcacgttac cttgacacat agtttttcag tctatgggtt tagttacttt agatggcaag   2340
catgtaactt atattaatag taatttgtaa agttgggtgg ataagctatc cctgttgccg   2400
gttcatggat tacttctcta taaaaaatat atatttacca aaaaattttg tgacattcct   2460
tctcccatct cttccttgac atgcattgta aataggttct tcttgttctg agattcaata   2520
```

ttgaatttct cctatgctat tgacaataaa atattattga actacc 2566

<210> SEQ ID NO 103
<211> LENGTH: 2974
<212> TYPE: DNA
<213> ORGANISM: Homo sapiens

<400> SEQUENCE: 103
ctcagggcag agggaggaag gacagcagac cagacagtca cagcagcctt gacaaaacgt 60
tcctggaact caagctcttc tccacagagg aggacagagc agacagcaga gaccatggag 120
tctccctcgg cccctcccca cagatggtgc atcccctggc agaggctcct gctcacagcc 180
tcacttctaa ccttctggaa cccgcccacc actgccaagc tcactattga atccacgccg 240
ttcaatgtcg cagaggggaa ggaggtgctt ctacttgtcc acaatctgcc ccagcatctt 300
tttggctaca gctggtacaa aggtgaaaga gtggatggca accgtcaaat tataggatat 360
gtaataggaa ctcaacaagc taccccaggg cccgcataca gtggtcgaga gataatatac 420
cccaatgcat ccctgctgat ccagaacatc atccagaatg acacaggatt ctacacccta 480
cacgtcataa agtcagatct tgtgaatgaa gaagcaactg gccagttccg ggtatacccg 540
gagctgccca agccctccat ctccagcaac aactccaaac ccgtggagga caaggatgct 600
gtggccttca cctgtgaacc tgagactcag gacgcaacct acctgtggtg ggtaaacaat 660
cagagcctcc cggtcagtcc caggctgcag ctgtccaatg gcaacaggac cctcactcta 720
ttcaatgtca caagaaatga cacagcaagc tacaaatgtg aaacccagaa cccagtgagt 780
gccaggcgca gtgattcagt catcctgaat gtcctctatg gcccggatgc ccccaccatt 840
tcccctctaa acacatctta cagatcaggg gaaaatctga acctctcctg ccacgcagcc 900
tctaacccac ctgcacagta ctcttggttt gtcaatggga ctttccagca atccacccaa 960
gagctcttta tccccaacat cactgtgaat aatagtggat cctatacgtg ccaagcccat 1020
aactcagaca ctggcctcaa taggaccaca gtcacgacga tcacagtcta tgcagagcca 1080
cccaaaccct tcatcaccag caacaactcc aaccccgtgg aggatgagga tgctgtagcc 1140
ttaacctgtg aacctgagat tcagaacaca acctacctgt ggtgggtaaa taatcagagc 1200
ctcccggtca gtcccaggct gcagctgtcc aatgacaaca ggaccctcac tctactcagt 1260
gtcacaagga atgatgtagg accctatgag tgtggaatcc agaacgaatt aagtgttgac 1320
cacagcgacc cagtcatcct gaatgtcctc tatggcccag acgaccccac catttccccc 1380
tcatacacct attaccgtcc aggggtgaac ctcagcctct cctgccatgc agcctctaac 1440
ccacctgcac agtattcttg gctgattgat gggaacatcc agcaacacac acaagagctc 1500
tttatctcca acatcactga gaagaacagc ggactctata cctgccaggc caataactca 1560
gccagtggcc acagcaggac tacagtcaag acaatcacag tctctgcgga gctgcccaag 1620
ccctccatct ccagcaacaa ctccaaaccc gtggaggaca aggatgctgt ggccttcacc 1680
tgtgaacctg aggctcagaa cacaacctac ctgtggtggg taaatggtca gagcctccca 1740
gtcagtccca ggctgcagct gtccaatggc aacaggaccc tcactctatt caatgtcaca 1800
agaaatgacg caagagccta tgtatgtgga atccagaact cagtgagtgc aaaccgcagt 1860
gacccagtca ccctggatgt cctctatggg ccggacaccc ccatcatttc ccccccagac 1920
tcgtcttacc tttcgggagc gaacctcaac ctctcctgcc actcggcctc taacccatcc 1980
ccgcagtatt cttggcgtat caatgggata ccgcagcaac acacacaagt tctctttatc 2040
gccaaaatca cgccaaataa taacgggacc tatgcctgtt ttgtctctaa cttggctact 2100

-continued

```
ggccgcaata attccatagt caagagcatc acagtctctg catctggaac ttctcctggt   2160

ctctcagctg gggccactgt cggcatcatg attggagtgc tggttggggt tgctctgata   2220

tagcagccct ggtgtagttt cttcatttca ggaagactga cagttgtttt gcttcttcct   2280

taaagcattt gcaacagcta cagtctaaaa ttgcttcttt accaaggata tttacagaaa   2340

agactctgac cagagatcga gaccatccta gccaacatcg tgaaacccca tctctactaa   2400

aaatacaaaa atgagctggg cttggtggcg cgcacctgta gtcccagtta ctcgggaggc   2460

tgaggcagga gaatcgcttg aacccgggag gtggagattg cagtgagccc agatcgcacc   2520

actgcactcc agtctggcaa cagagcaaga ctccatctca aaaagaaaag aaaagaagac   2580

tctgacctgt actcttgaat acaagtttct gataccactg cactgtctga gaatttccaa   2640

aactttaatg aactaactga cagcttcatg aaactgtcca ccaagatcaa gcagagaaaa   2700

taattaattt catgggacta aatgaactaa tgaggattgc tgattcttta aatgtcttgt   2760

ttcccagatt tcaggaaact ttttttcttt taagctatcc actcttacag caatttgata   2820

aaatatactt ttgtgaacaa aaattgagac atttacattt tctccctatg tggtcgctcc   2880

agacttggga aactattcat gaatatttat attgtatggt aatatagtta ttgcacaagt   2940

tcaataaaaa tctgctcttt gtataacaga aaaa                               2974
```

<210> SEQ ID NO 104
<211> LENGTH: 3069
<212> TYPE: DNA
<213> ORGANISM: Homo sapiens

<400> SEQUENCE: 104

```
tgtttccgct gcatccagac ttcctcaggc ggtggctgga ggctgcgcat ctggggcttt     60

aaacatacaa agggattgcc aggacctgcg gcggcggcgg cggcggcggg ggctggggcg    120

cgggggccgg accatgagcc gctgagccgg gcaaacccca ggccaccgag ccagcggacc    180

ctcggagcgc agccctgcgc cgcggaccag gctccaacca ggcggcgagg cggccacacg    240

caccgagcca gcgacccccg ggcgacgcgc ggggccaggg agcgctacga tggaggcgct    300

aatggcccgg ggcgcgctca cgggtcccct gagggcgctc tgtctcctgg gctgcctgct    360

gagccacgcc gccgccgcgc cgtcgcccat catcaagttc cccggcgatg tcgcccccaa    420

aacggacaaa gagttggcag tgcaatacct gaacaccttc tatggctgcc ccaaggagag    480

ctgcaacctg tttgtgctga aggacacact aaagaagatg cagaagttct ttggactgcc    540

ccagacaggt gatcttgacc agaataccat cgagaccatg cggaagccac gctgcggcaa    600

cccagatgtg gccaactaca acttcttccc tcgcaagccc aagtgggaca agaaccagat    660

cacatacagg atcattggct acacacctga tctggaccca gagacagtgg atgatgcctt    720

tgctcgtgcc ttccaagtct ggagcgatgt gaccccactg cggttttctc gaatccatga    780

tggagaggca gacatcatga tcaactttgg ccgctgggag catggcgatg gatacccctt    840

tgacggtaag gacggactcc tggctcatgc cttcgcccca ggcactggtg ttgggggaga    900

ctcccatttt gatgacgatg agctatggac cttgggagaa ggccaagtgg tccgtgtgaa    960

gtatggcaac gccgatgggg agtactgcaa gttccccttc ttgttcaatg gcaaggagta   1020

caacagctgc actgatactg gccgcagcga tggcttcctc tggtgctcca ccacctacaa   1080

ctttgagaag gatggcaagt acggcttctg tccccatgaa gccctgttca ccatgggcgg   1140

caacgctgaa ggacagccct gcaagtttcc attccgcttc cagggcacat cctatgacag   1200
```

-continued

```
ctgcaccact gagggccgca cggatggcta ccgctggtgc ggcaccactg aggactacga   1260

ccgcgacaag aagtatggct tctgccctga gaccgccatg tccactgttg gtgggaactc   1320

agaaggtgcc ccctgtgtct tccccttcac tttcctgggc aacaaatatg agagctgcac   1380

cagcgccggc cgcagtgacg gaaagatgtg gtgtgcgacc acagccaact acgatgacga   1440

ccgcaagtgg ggcttctgcc ctgaccaagg gtacagcctg ttcctcgtgg cagcccacga   1500

gtttggccac gccatggggc tggagcactc ccaagaccct ggggccctga tggcacccat   1560

ttacacctac accaagaact tccgtctgtc ccaggatgac atcaagggca ttcaggagct   1620

ctatggggcc tctcctgaca ttgaccttgg caccggcccc acccccacac tgggccctgt   1680

cactcctgag atctgcaaac aggacattgt atttgatggc atcgctcaga tccgtggtga   1740

gatcttcttc ttcaaggacc ggttcatttg gcggactgtg acgccacgtg acaagcccat   1800

ggggcccctg ctggtggcca cattctggcc tgagctcccg gaaaagattg atgcggtata   1860

cgaggcccca caggaggaga aggctgtgtt ctttgcaggg aatgaatact ggatctactc   1920

agccagcacc ctggagcgag ggtaccccaa gccactgacc agcctgggac tgccccctga   1980

tgtccagcga gtggatgccg cctttaactg gagcaaaaac aagaagacat acatctttgc   2040

tggagacaaa ttctggagat acaatgaggt gaagaagaaa atggatcctg gctttcccaa   2100

gctcatcgca gatgcctgga atgccatccc cgataacctg gatgccgtcg tggacctgca   2160

gggcggcggt cacagctact tcttcaaggg tgcctattac ctgaagctgg agaaccaaag   2220

tctgaagagc gtgaagtttg gaagcatcaa atccgactgg ctaggctgct gagctggccc   2280

tggctcccac aggcccttcc tctccactgc cttcgataca ccgggcctgg agaactagag   2340

aaggacccgg aggggcctgg cagccgtgcc ttcagctcta cagctaatca gcattctcac   2400

tcctacctgg taatttaaga ttccagagag tggctcctcc cggtgcccaa gaatagatgc   2460

tgactgtact cctcccaggc gccccttccc cctccaatcc caccaaccct cagagccacc   2520

cctaaagaga tcctttgata ttttcaacgc agccctgctt tgggctgccc tggtgctgcc   2580

acacttcagg ctcttctcct ttcacaacct tctgtggctc acagaaccct tggagccaat   2640

ggagactgtc tcaagagggc actggtggcc cgacagcctg gcacagggca gtgggacagg   2700

gcatggccag gtggccactc cagacccctg gcttttcact gctggctgcc ttagaacctt   2760

tcttacatta gcagtttgct ttgtatgcac tttgtttttt tctttgggtc ttgttttttt   2820

tttccactta gaaattgcat ttcctgacag aaggactcag gttgtctgaa gtcactgcac   2880

agtgcatctc agcccacata gtgatggttc ccctgttcac tctacttagc atgtccctac   2940

cgagtctctt ctccactgga tggaggaaaa ccaagccgtg gcttcccgct cagccctccc   3000

tgcccctccc ttcaaccatt ccccatggga aatgtcaaca agtatgaata aagacaccta   3060

ctgagtggc                                                           3069


<210> SEQ ID NO 105
<211> LENGTH: 3299
<212> TYPE: DNA
<213> ORGANISM: Homo sapiens

<400> SEQUENCE: 105

cggagggagc gctgggagcg agcaagcgag cgtttggagc ccgggccagc agagggggcg     60

cccggtcgct gcctgtaccg ctcccgctgg tcatctccgc cgcgctcggg ggccccggga    120

ggagcgagac cgagtcggag agtccgggag ccaagccggg cgaaacccaa ctgcggagga    180

cgcccgcccc actcagcctc ctcctgcgtc cgagccgggg agcatcgccg agcgccccac    240
```

-continued gggccggaga gctgggagca caggtcccgg cagccccagg gatggtctag gagccggcgt 300
aaggctcgct gctctgctcc ctgccggggc tagccgcctc ctgccgatcg cccggggctg 360
cgagctgcgg cggcccgggg ctgctcgccg ggcggcgcag gccggagaag ttagttgtgc 420
gcgcccttag tgcgcggaac cagccagcga gcgagggagc agcgaggcgc cgggaccatg 480
ggctggggga gccgctgctg ctgcccggga cgtttggacc tgctgtgcgt gctggcgctg 540
ctcgggggct gcctgctccc cgtgtgtcgg acgcgcgtct acaccaacca ctgggcagtc 600
aaaatcgccg gggcttcccc ggaggccaac cgtatcgcca gcaagtacgg attcatcaac 660
ataggacaga taggggccct gaaggactac taccacttct accatagcag gacgattaaa 720
aggtcagtta tctcgagcag agggacccac agtttcattt caatggaacc aaaggtggaa 780
tggatccaac agcaagtggt aaaaaagcgg acaaagaggg attatgactt cagtcgtgcc 840
cagtctacct atttcaatga tcccaagtgg cccagcatgt ggtatatgca ctgcagtgac 900
aatacacatc cctgccagtc tgacatgaat atcgaaggag cctggaagag aggctacacg 960
ggaaagaaca ttgtggtcac tatcctggat gacggaattg agagaaccca tccagatctg 1020
atgcaaaact acgatgctct ggcaagttgc gacgtgaatg ggaatgactt ggacccaatg 1080
cctcgttatg atgcaagcaa cgagaacaag catgggactc gctgtgctgg agaagtggca 1140
gccgctgcaa acaattcgca ctgcacagtc ggaattgctt tcaacgccaa gatcggagga 1200
gtgcgaatgc tggacggaga tgtcacggac atggttgaag caaaatcagt tagcttcaac 1260
ccccagcacg tgcacattta cagcgccagc tggggcccgg atgatgatgg caagactgtg 1320
gacggaccag ccccccctcac ccggcaagcc tttgaaaacg gcgttagaat ggggcggaga 1380
ggcctcggct ctgtgtttgt ttgggcatct ggaaatggtg gaaggagcaa agaccactgc 1440
tcctgtgatg gctacaccaa cagcatctac accatctcca tcagcagcac tgcagaaagc 1500
ggaaagaaac cttggtacct ggaagagtgt tcatccacgc tggccacaac ctacagcagc 1560
ggggagtcct acgataagaa aatcatcact acagatctga ggcagcgttg cacggacaac 1620
cacactggga cgtcagcctc agcccccatg gctgcaggca tcattgcgct ggccctggaa 1680
gccaatccgt ttctgacctg gagagacgta cagcatgtta ttgtcaggac ttcccgtgcg 1740
ggacatttga acgctaatga ctggaaaacc aatgctgctg gttttaaggt gagccatctt 1800
tatggatttg gactgatgga cgcagaagcc atggtgatgg aggcagagaa gtggaccacc 1860
gttccccggc agcacgtgtg tgtggagagc acagaccgac aaatcaagac aatccgccct 1920
aacagtgcag tgcgctccat ctacaaagct tcaggctgct cggataaccc caaccgccat 1980
gtcaactacc tggagcacgt cgttgtgcgc atcaccatca cccaccccag gagaggagac 2040
ctggccatct acctgacctc gccctctgga actaggtctc agcttttggc caacaggcta 2100
tttgatcact ccatggaagg attcaaaaac tgggagttca tgaccattca ttgctgggga 2160
gaaagagctg ctggtgactg ggtccttgaa gtttatgata ctccctctca gctaaggaac 2220
tttaagactc caggtaaatt gaaagaatgg tctttggtcc tctacggcac ctccgtgcag 2280
ccatattcac caaccaatga atttccgaaa gtggaacggt tccgctatag ccgagttgaa 2340
gaccccacag acgactatgg cacagaggat tatgcaggtc cctgcgaccc tgagtgcagt 2400
gaggttggct gtgacgggcc aggaccagac cactgcaatg actgtttgca ctactactac 2460
aagctgaaaa acaataccag gatctgtgtc tccagctgcc cccctggcca ctaccacgcc 2520
gacaagaagc gctgcaggaa gtgtgccccc aactgtgagt cctgctttgg gagccatggt 2580

-continued gaccaatgca tgtcctgcaa atatggatac tttctgaatg aagaaaccaa cagctgtgtt 2640
actcactgcc ctgatgggtc atatcaggat accaagaaaa atctttgccg gaaatgcagt 2700
gaaaactgca agacatgtac tgaattccat aactgtacag aatgtaggga tgggttaagc 2760
ctgcagggat cccggtgctc tgtctcctgt gaagatggac ggtatttcaa cggccaggac 2820
tgccagccct gccaccgctt ctgcgccact tgtgctgggg caggagctga tgggtgcatt 2880
aactgcacag agggctactt catggaggat gggagatgcg tgcagagctg tagtatcagc 2940
tattactttg accactcttc agagaatgga tacaaatcct gcaaaaaatg tgatatcagt 3000
tgtttgacgt gcaatggccc aggattcaag aactgtacaa gctgccctag tgggtatctc 3060
ttagacttag gaatgtgtca aatgggagcc atttgcaagg atgcaacgga agagtcctgg 3120
gcggaaggag gcttctgtat gcttgtgaaa aagaacaatc tgtgccaacg gaaggttctt 3180
caacaacttt gctgcaaaac atgtacattt caaggctgag cagccatctt agatttcttt 3240
gttcctgtag acttatagat tattccatat tattaaaaag aaaaaaaaaa gccaaaaag 3299

<210> SEQ ID NO 106
<211> LENGTH: 1664
<212> TYPE: DNA
<213> ORGANISM: Homo Sapiens

<400> SEQUENCE: 106
atgggttgtg actgcttcgt ccaggaggtg ttctgctcag atgaggagct tgccaccgtc 60
ccgctggaca tcccgccata tacgaaaaac atcatctttg tggagacctc gttcaccaca 120
ttggaaacca gagcttttgg cagtaacccc aacttgacca aggtggtctt cctcaacact 180
cagctctgcc agtttaggcc ggatgccttt ggggggctgc ccaggctgga ggacctggag 240
gtcacaggca gtagcttctt gaacctcagc accaacatct tctccaacct gacctcgctg 300
ggcaagctca ccctcaactt caacatgctg gaggctctgc ccgagggtct tttccagcac 360
ctggctgccc tggagtccct ccacctgcag gggaaccagc tccaggccct gcccaggagg 420
ctcttccagc ctctgaccca tctgaagaca ctcaacctgg cccagaacct cctggcccag 480
ctcccggagg agctgttcca cccactcacc agcctgcaga ccctgaagct gagcaacaac 540
gcgctctctg gtctccccca gggtgtgttt ggcaaactgg gcagcctgca ggagctcttc 600
ctggacagca acaacatctc ggagctgccc cctcaggtgt tctcccagct cttctgccta 660
gagaggctgt ggctgcaacg caacgccatc acgcacctgc cgctctccat ctttgcctcc 720
ctgggtaatc tgacctttct gagcttgcag tggaacatgc ttcgggtcct gcctgccggc 780
ctctttgccc acaccccatg cctggttggc ctgtctctga cccataacca gctggagact 840
gtcgctgagg gcacctttgc ccacctgtcc aacctgcgtt ccctcatgct ctcatacaat 900
gccattaccc acctcccagc tggcatcttc agagacctgg aggagttggt caaactctac 960
ctgggcagca acaaccttac ggcgctgcac ccagccctct tccagaacct gtccaagctg 1020
gagctgctca gcctctccaa gaaccagctg accacacttc cggagggcat cttcgacacc 1080
aactacaacc tgttcaacct ggccctgcac ggtaacccct ggcagtgcga ctgccacctg 1140
gcctacctct tcaactggct gcagcagtac accgatcggc tcctgaacat ccagacctac 1200
tgcgctggcc ctgcctacct caaaggccag gtggtgcccg ccttgaatga gaagcagctg 1260
gtgtgtcccg tcacccggga ccacttgggc ttccaggtca cgtggccgga cgaaagcaag 1320
gcagggggca gctgggatct ggctgtgcag gaaagggcag cccggagcca gtgcacctac 1380
agcaaccccg agggcaccgt ggtgctcgcc tgtgaccagg cccagtgtcg ctggctgaac 1440
gtccagctct ctccttggca gggctccctg ggactgcagt acaatgctag tcaggagtgg 1500
gacctgaggt cgagctgcgg ttctctgcgg ctcaccgtgt ctatcgaggc tcgggcagca 1560
gggccctagt agcagcgcat acaggagctg gggaaggggg ctttggggcc tgcccacgcg 1620
acaggtaggg gcggagggga gctgagtctc cgaagcttgg cttt 1664

<210> SEQ ID NO 107
<211> LENGTH: 3383
<212> TYPE: DNA
<213> ORGANISM: Homo sapiens

<400> SEQUENCE: 107
cgggggccgc gcgggcaaga tggtgtgcgc tcgggcggcc ctcggtcccg gcgcgctctg 60
ggccgcggcc tggggcgtcc tgctgctcac agcccctgcg ggggcgcagc gtggccggaa 120
gaaggtcgtg cacgtgctgg agggtgagtc gggctcggta gtggtacaga cagcgcctgg 180
gcaggtggta agccaccgtg gtggcaccat cgtcttgccc tgccgctacc actatgaggc 240
agccgcccac ggtcacgacg gcgtccggct caagtggaca aaggtggtgg acccgctggc 300
cttcaccgac gtcttcgtgg cactaggccc ccagcaccgg gcattcggca gctaccgtgg 360
gcgggctgag ctgcagggcg acgggcctgg ggatgcctcc ctggtcctcc gcaacgtcac 420
gctgcaagac tacgggcgct atgagtgcga agtcaccaat gagctggaag atgacgctgg 480
catggtcaag ctggacctgg aaggcgtggt ctttccctac cacccccgtg gaggccgata 540
caagctgacc ttcgcggagg cgcagcgcgc gtgcgccgag caggacggca tcctggcatc 600
tgcagaacag ctgcacgcgg cctggcgcga cggcctggac tggtgcaacg cgggctggtt 660
gcgcgacggc tcagtgcaat accccgtgaa ccggccccgg gagccctgcg gcggcctggg 720
ggggaccggg agtgcagggg gcggcggtga tgccaacggg ggcctgcgca actacgggta 780
tcgccataac gccgaggaac gctacgacgc cttctgcttc acgtccaacc tgccggggcg 840
cgtgttcttc ctgaagccgc tgcgacctgt acccttctcc ggagctgcgc gcgcgtgtgc 900
tgcgcgtggc gcggccgtgg ccaaggtggg gcagctgttc gccgcgtgga agctgcagct 960
gctagaccgc tgcaccgcgg gttggctggc cgatggcagt gcgcgctacc ccatcgtgaa 1020
cccgcgagcg cgctgcggag gccgcaggcc tggtgtgcgc agcctcggct tcccggacgc 1080
cacccgacgg ctcttcggcg tctactgcta ccgcgctcca ggagcaccgg acccggcacc 1140
tggcggctgg ggctggggct gggcgggcgg cggcggctgg gcagggggcg cgcgcgatcc 1200
tgctgcctgg acccctctgc acgtctaggc tgggagtagg cggacagcca gggcgcttga 1260
ccactggtct agagccctgt ggtcccctgg agcctggcca cgcccttgaa gccctggaca 1320
ctggccacat tccctgtggt cccttacaaa ctaactgtgc ccctggggtc cctgaagact 1380
ggctagtcct ggcagaacag tactttggag ttccctggag cctggccagc cctcacctct 1440
tctggataga ggattccccc aactccccaa ctttctccat gagggtcacg ccccctgagg 1500
acctcaggag gccagcagaa cccgcaggct cctgaagact ggccacgcct cctgagacca 1560
cttggaaaca gaccaactgc ccccgtggtc gcctggtggc tggacccccg ggattgacta 1620
gagaccggcc gtacaccttc tgcatctcac tggagactga acactagtcc cttgcggtca 1680
cgtgggacac tgggcgcctc ctcctccccc tcctcctcac ctggagagac tacaggaact 1740
tcagggtcac tccccgtggt cacatggagg ttgtgggccg aggcgcttat tttcccttat 1800
ggtgacctga gtcctggaga ctcccattct ccccctctcc ctgagagtcc cctgcagttt 1860

-continued

```
ctgggtaaca gggcacaccc ctctagtttc atgggcgagc acccccatct gccacctcag   1920
actgacacac agccagctgg ctcacttact gggggccacg tcccacccct cagatatttc   1980
tttgaaggga gagcaaaccc accctgtcct ctgacgtccc tttcccaact gtcaccaaac   2040
agaccatctt cccaggcctg gggaccggta agatccatgt cactagttat gcagagcagt   2100
tgccttgggt cccactgtca ccaaggcaac cagtcctgct gctacctgtc acctagagtc   2160
acacacccct tccctcatca ggcacaccca tgaagacagt gcctccctcc tccagctgta   2220
accatggata ccacacattt ctcatctcat tggcccccac cccagagacc tccacctcaa   2280
cttctggctg tccctaccct gactcaccgc catggagatc accctccccg aagctgtcgc   2340
cagggtgacc caacatccag ttctccggct ctcaccatgg aaacaaactg tccctgtccc   2400
caggcccact ccagttccag accaccctcc atgctccacc cccaggcggt ttggacccca   2460
ccactgttgc catggtgacc aaactctgga gtccgaggta acagaacacc tgtcccccta   2520
ggcttttcct tgtggacaac ggggccctgt tcaccaagct gttgccatag agactgtcaa   2580
cgttgtcctc atgacaacca gacttccagt tctcaggaac ttctcattgt gggccagaag   2640
tcctgggtgc ctcctactag ggctacccta ctgcacccca tcaggggcct gatggctgcc   2700
ccttccccag acagggctgg acttctggag ctgctaagcc accctccgtt tgcacgttaa   2760
ctctatgccg gatagcagct gtgcacgaga caatcttgca acacccgggc atgtttgtcg   2820
tcgtcctaca aatgaggaaa ccgagcctat ggcgtgccct ggtctgttga gatatgcaag   2880
cactgagctc ctcttttgtc ctctgagacc ccatctccat tctcacccag ttcctctctc   2940
cttccctgac ccccacccac atttccctcc ttagagatcc aggagggatg gaatgttctt   3000
taaaattcaa cacccaccag gctctaagcg gcgatctgtg ctaagaggtc aggacccagc   3060
cgaagtcctc ggcgttgaca ggcagctggg gggacatgat ccatggacaa ggccatcccg   3120
gccgtgggag accccagtcc cgaagtcttg cctgcaggag tactggggtc cccctggggc   3180
cctctttact gtcacgtcat ctctaggaaa cctatctctg agttttggga ccaggtcggt   3240
ttgggtttga attctgcctc ttcttgctca ctgtgtgacc aagtgacaaa ctccttctga   3300
acctgtgttc tcccactgta ccagggctgt tctgtggtcc ccgtgagtgc caagcataca   3360
gtaggggctc aataaatcct tgt                                           3383

<210> SEQ ID NO 108
<211> LENGTH: 17
<212> TYPE: PRT
<213> ORGANISM: homo sapiens

<400> SEQUENCE: 108

Phe Ala Ile Ser Glu Tyr Asn Lys Ala Thr Lys Asp Asp Tyr Tyr Arg
1               5                   10                  15

Arg
```

TREATMENT OF RECURRENT GASTRIC CANCER IDENTIFIED USING GENETIC BIOMARKERS

RELATED APPLICATION CLAIM OF PRIORITY

This United States non-provisional patent application is a continuation of U.S. patent application Ser. No. 10/565,068 filed Jul. 13, 2006, which is a National Phase application of International Patent Application No. PCT/US2004/022959, filed Jul. 16, 2004, which claims priority under 35 U.S.C. 119 to United States Provisional Patent Application Ser. No. 60/487,906, filed Jul. 17, 2003, titled "Markers for Detection of Gastric Cancer," listing Parry John Guilford as inventor. Each of the above applications are herein incorporated fully by reference.

FIELD OF THE INVENTION

This invention relates to detection of cancer. Specifically, this invention relates to the use of genetic and/or protein markers for detection of cancer, and more particularly to the use of genetic and/or protein markers for detection of gastric cancer.

BACKGROUND

Survival of cancer patients is greatly enhanced when the cancer is detected and treated early. In the case of gastric cancer, patients diagnosed with early stage disease have 5-year survival rates of 90%, compared to approximately 10% for patients diagnosed with advanced disease. However, the vast majority of gastric cancer patients currently present with advanced disease. Therefore, developments that lead to early diagnosis of gastric cancer can lead to an improved prognosis for the patients.

Identification of specific cancer-associated markers in biological samples, including body fluids, for example, blood, urine, peritoneal washes and stool extracts can provide a valuable approach for the early diagnosis of cancer, leading to early treatment and improved prognosis. Specific cancer markers also can provide a means for monitoring disease progression, enabling the efficacy of surgical, radiotherapeutic and chemotherapeutic treatments to be tracked. However, for a number of major cancers, the available markers suffer from insufficient sensitivity and specificity. For example, the most frequently used markers for gastric cancer, ca19-9, ca72-4 and chorioembryonic antigen (CEA) detect only about 15-50% of gastric tumors of any stage, declining to approximately 2-11% for early stage disease. Thus, there is a very high frequency of false negative tests that can lead patients and health care practitioners to believe that no disease exists, whereas in fact, the patient may have severe cancer that needs immediate attention. Moreover, these markers can give false positive signals in up to ⅓ of individuals affected by benign gastric disease.

SUMMARY OF THE INVENTION

Thus, there is an acute need for better methods for detecting the presence of cancer. Aspects of this invention provide methods, compositions and devices that can provide for detection of early stage cancer, and decreasing the frequency of false positives and false negative test results.

In certain embodiments, molecular analysis can be used to identify genes that are over-expressed in gastric tumor tissue compared to non-malignant gastric tissue. Such analyses include microarray and quantitative polymerase chain reaction (qPCR) methods. Cancer genes and proteins encoded by those genes are herein termed gastric tumor markers (GTM). It is to be understood that the term GTM does not require that the marker be specific only for gastric tumors. Rather, expression of GTM can be increased in other types of tumors, including malignant or non-malignant tumors, including gastric, bladder, colorectal, pancreatic, ovarian, skin (e.g., melanomas), liver, esophageal, endometrial and brain cancers, among others. It should be understood, however that the term GTM does not include prior the art markers, ca19-9, ca72-4 and CEA. Some GTM are sufficiently over-expressed to be diagnostic of gastric cancer with a high degree of reliability, and in other cases, over-expression of two or more GTM can provide reliable diagnosis of gastric cancer.

In certain embodiments, microarray methods can be used to detect patterns of over-expression of one or more genes associated with cancer.

In other embodiments, quantitative polymerase chain reaction (qPCR) can be used to identify the presence of markers over expressed in tumor or other biological samples.

Some of the embodiments of GTM detection disclosed herein are over expressed in a highly selective fashion in tumor cells and little, if at all, in non-tumor cells, permitting sensitive and accurate detection of cancer with measurement of only one over expressed GTM. In other embodiments, over-expression of two, three or more GTM can be detected in a sample and can provide greater certainty of diagnosis.

Selected genes that encode proteins can be secreted by or cleaved from the cell. These proteins, either alone or in combination with each other, have utility as serum or body fluid markers for the diagnosis of gastric cancer or as markers for monitoring the progression of established disease. Detection of protein markers can be carried out using methods known in the art, and include the use of monoclonal antibodies, polyclonal antisera and the like.

BRIEF DESCRIPTION OF THE FIGURES

This invention is described with reference to specific embodiments thereof and with reference to the figures, in which:

FIG. 1 depicts a table of markers and oligonucleotide sequences of markers for gastric cancer of this invention.

FIG. 2 depicts a table of results obtained of studies carried out using microarray methods.

FIG. 3 depicts a table of results obtained of studies carried out using quantitative PCR.

FIG. 4*a*: ASPN. FIG. 4*b*: SPP1. FIG. 4*c*: SPARC. FIG. 4*d*: MMP12.

FIG. 5*a*: ASPN; FIG. 5*w*: TGFBI.

FIGS. 7*a*-7*c* depicts graphs that show relative log2 expression of the markers in individual tumor samples and non-malignant samples compared to the expression of the gene for the tumor marker, CEA. CEA is the serum marker currently most used to monitor progression of gastric cancer.

FIG. 8 shows a table that complements FIG. 3. FIG. 8 summarizes expression levels determined by qPCR for the candidate tumor markers, but using the paired data (i.e., tumor ("T") and non-malignant ("N") samples from the same individual) to provide a T:N ratio. FIG. 8 also includes additional markers not included in FIG. 3, namely MMP2, CGR11, TGFB1, PCSK5, SERPINB5, SERPINH1. For comparison, the expression level of the established serum marker gene, CEACAM5 (CEA), is also shown. 27 of the 29 markers have a median T:N difference greater than or equal to CEA. Further, compared to CEA, 29/29 of the markers have a higher percentage of paired samples in which the expression in the tumor sample exceeds the expression in the normal sample. Three markers, CST1,2,4, ASPN and SFRP4 showed 100% discrimination between the paired tumor and normal samples. The gene sequences of these markers, and the location of the primers and probes used to detect them, are shown herein.

FIGS. 9*a*-9*d* depict individual and median T:N fold change data for 29 gastric cancer markers in 40 patients with paired samples.

FIGS. 10*a*-10*ad* depict graphs of tumor stage and log2 fold change in expression of CEA and other GTM of this invention. FIG. 10*a*: adlican; FIG. 10*b*: ASPN; FIG. 10*c*: CSPG2; FIG. 10*d*: CST1,2,4; FIG. 10*e*:EFEMP2; FIG. 10*f*: GGF; FIG. 10*g*: INHBA; FIG. 10*h*: IGFBP7; FIG. 10*i*: KLK10; FIG. 10*j*: LEPRE1; FIG. 10*k*: LUM; FIG. 10*l*: LOXL2; FIG. 10*m*: MMP12; FIG. 10*n*; TIMP1; FIG. 100: ASAH1; FIG. 10*p*: SPP1; FIG. 10*q*: SFRP2; FIG. 10*r*: SFRP4; FIG. 10*s*: SPARC; FIG. 10*t*: PRSS11; FIG. 10*u*: THBS2: FIG. 10*v*: TG; FIG. 10*w*: TGFBI; FIG. 10*x*: CGR11; FIG. 10*y*: SERPINH1; FIG. 10*z*: MMP2; FIG. 10*aa*: PCSK5; FIG. 10*ab*: SERPINB5; FIG. 10*ac*: TGFB1 and FIG. 10*ad*: CEA (CEACAM5).

FIGS. 11*a*-11*ad* depict graphs of tumor type (diffuse (D) or intestinal (I)) and log2 fold change in expression 29 GTM of this invention and CEA. FIG. 11*a*: adlican; FIG. 11*b*: ASPN; FIG. 11*c*: CSPG2; FIG. 11*d*: CST1,2,4; FIG. 11*e*: EFEMP2; FIG. 11*f*: GGH; FIG. 11*g*: INHBA; FIG. 11*h*: IGFBP7; FIG. 11*i*: KLK10; FIG. 11*j*: LEPRE1: FIG. 11*k*: LUM; FIG. 11*l*: LOXL2; FIG. 11*m*: MMP12; FIG. 11*n*: TIMP1; FIG. 11*o*: ASAH1; FIG. 11*p*: SPP1; FIG. 11*q*: SFRP2; FIG. 11*r*: SFRP4: FIG. 11*s*; SPARC; FIG. 11*t*: PRSS11: FIG. 11*u*: THBS2; FIG. 11*v*: TG; FIG. 11*w*: TGFBI; FIG. 11*x*: CGR11: FIG. 11*y*: SERPINH1; FIG. 11*z*: MMP2; FIG. 11*aa*: PCSK5; FIG. 11*ab*: SERPINB5; FIG. 11*ac*: TGFB1 and FIG. 11*ad*: CEA (CEACAM5).

FIG. 12 depicts a three-dimensional graph showing 3 markers, SERPINH1, CST1,2,4 and INHBA, in a series of gastric tumor samples and non-malignant gastric samples.

FIG. 13 depicts a table that shows the effect of multiple markers on the ability to accurately discriminate between tumor tissue and non-malignant tissue. The table has been derived from normal distributions derived from qPCR data.

FIG. 14 is a Western blot of 4 tumor markers derived from tumor and non-tumor tissue.

FIG. 15 is a Western blot of the tumor marker SPARC in gastric tumor tissue and in serum.

FIG. 16 is an immunoblot depicting cystatin SN in the supernatant of a gastric cell line, AGS.

DETAILED DESCRIPTION

Definitions

Figure 4A:
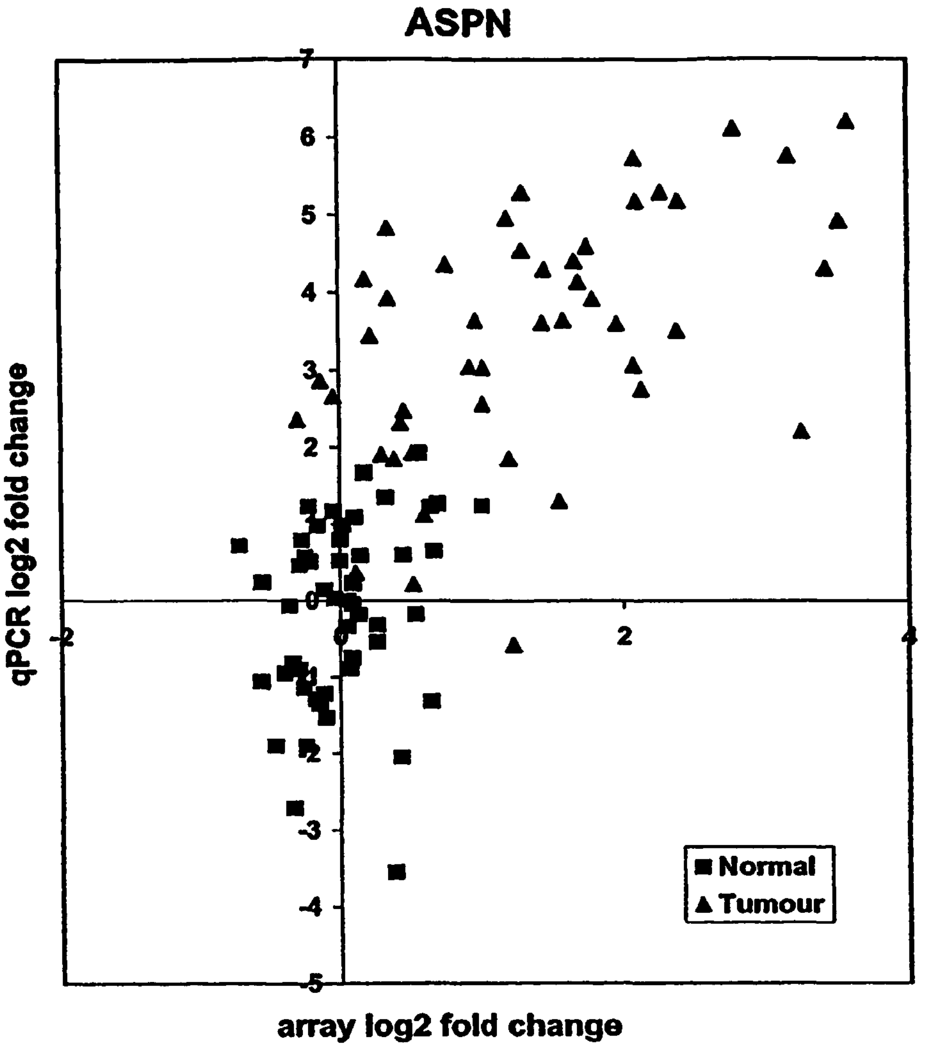
FIGS. 4*a*-4*d* depict relationships between log2 fold results obtained using array and qPCR methods, in which the data is centered on the median normal for four gastric cancer markers. Grey squares correspond to non-malignant ("normal") samples and black triangles to tumor samples.
Figure 4B:
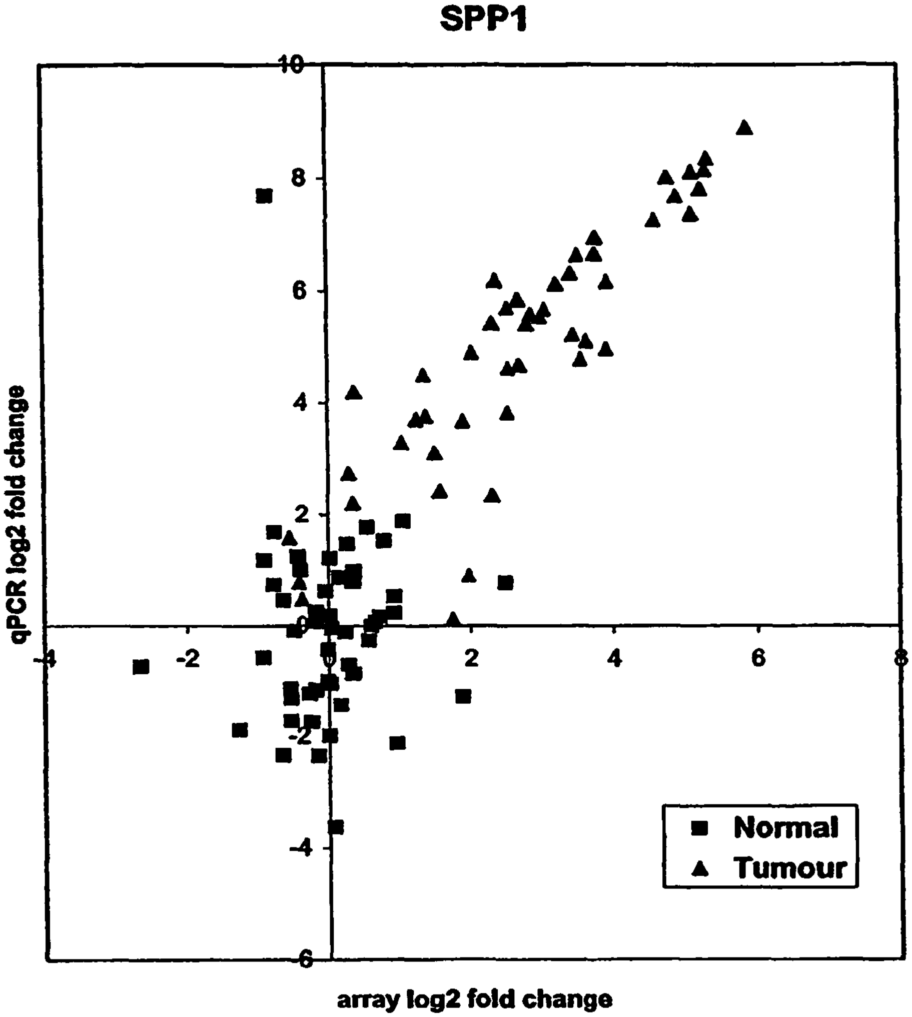
Figure 4C:
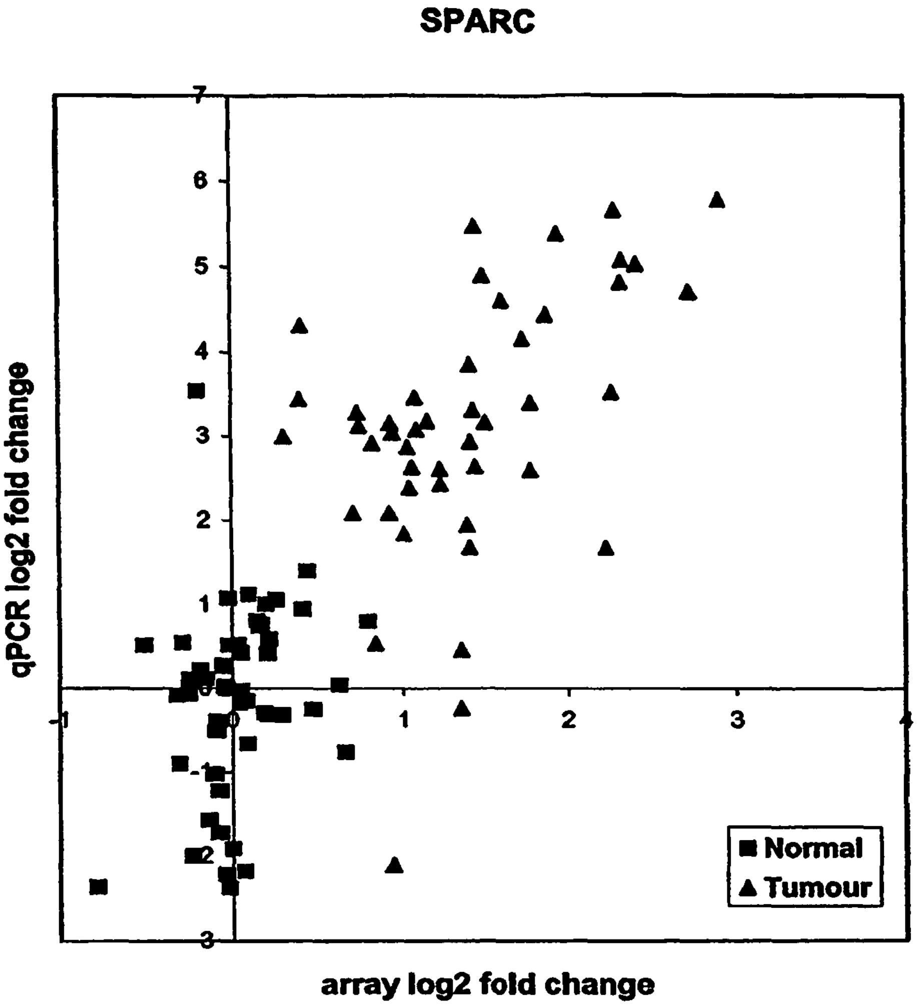
Figure 4D:
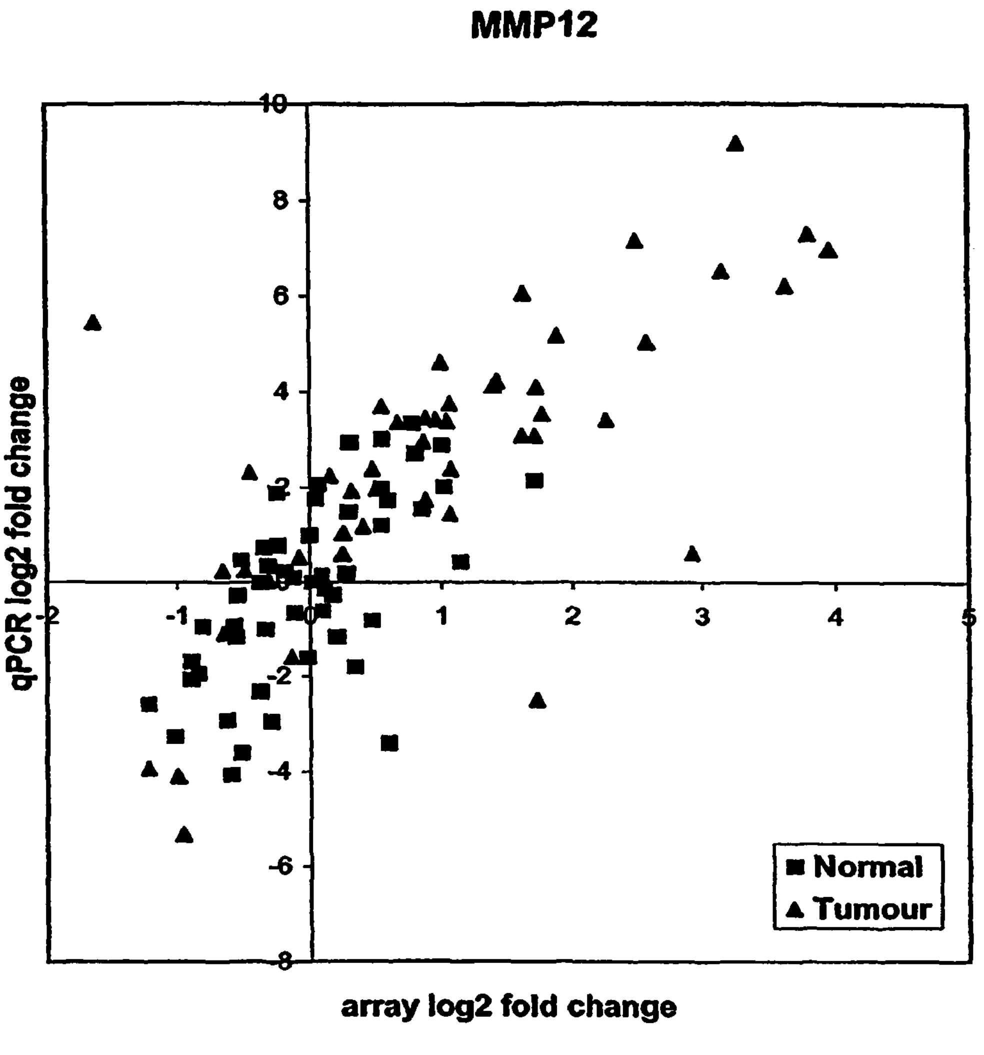

Before describing embodiments of the invention in detail, it will be useful to provide some definitions of terms as used herein.

The term "GTM" or "gastric tumor marker" or "GTM family member" means a gene, gene fragment, RNA, RNA fragment, protein or protein fragment related or other identifying molecule associated with gastric cancer that does not include molecules that are known in the prior art to be associated with gastric cancer, ca19-9, ca72-4 and CEA. Examples of GTMs are included herein below.

The term "marker" means a molecule that is associated quantitatively or qualitatively with the presence of a biological phenomenon. Examples of "markers" are GTMs, however, "markers" also includes metabolites, byproducts, whether related directly or indirectly to a mechanism underlying a condition.

The term "qPCR" means quantitative polymerase chain reaction.

The term "expression" includes production of mRNA from a gene or portion of a gene, and includes the production of a protein encoded by an RNA or gene or portion of a gene, and includes appearance of a detection material associated with expression. For example, the binding of a binding ligand, such as an antibody, to a gene or other oligonucleotide, a protein or a protein fragment and the visualization of the binding ligand is included within the scope of the term "expression." Thus, increased density of a spot on an immunoblot, such as a Western blot, is included within the term "expression" of the underlying biological molecule.

The term "CPN2" means human carboxypeptidase N, polypeptide 2, 83 kDa chain; and carboxypeptidase N.

The term "HAPLN4" means human hyaluronan glycoprotein link protein 4. The term "MMP12" means human matrix metalloproteinase 12.

The term "INHBA" means human inhibin, beta A (also includes activin A, activin AB or alpha polypeptide).

The term "IGFBP7" means human insulin-like growth factor 7.

The term "GGH" means human gamma-glutamyl hydrolase (also known as conjugase, folylpolygammaglutamyl hydrolase).

The term "LEPRE1" means human leucine proline-enriched proteoglycan (also known as leprecan 1).

The term "CST4" means human cystatin S.

The term "SFRP4" means human secreted frizzled-related protein 4.

The term "ASPN" means human asporin (also known as LRR class 1).

The term "CGREF1" or "CGR11" means human cell growth regulator with EF hand domain 1.

The term "KLK" means either human kallikrein 10, variant 1 or human kallikrein 10, variant 2, or both, unless specified otherwise.

The term "TIMP1" means human tissue inhibitor of metalloproteinase 1 (also known as erythroid potentiating activity or collagenase inhibitor).

The term "SPARC" means human secreted protein, acidic, cysteine-rich (also known as osteonectin).

The term "TGFB1" means human transforming growth factor, beta-induced, 68 kDa.

The term “EFEMP2” means human EGF-containing fibulin-like extracellular matrix protein 2.

The term “LUM” means human lumican.

The term “SNN” means human stannin.

The term “SPP1” means human secreted phosphoprotein 1 (also known as osteopontin, or bone sialoprotein I, or early T-lymphocyte activation 1).

The term “CSPG2” means human chondroitin sulfate proteoglycan 2 (also known as versican).

The term “ASAH1” means human N-acylsphingosine amidohydrolase, variant 1, or N-acylsphingosine amidohydrolase, variant 2, or both N-acylsphingosine amidohydrolase variants 1 and 2 (also known as acid ceramidase 1, variants 1 and 2).

The term “PRSS11” means human protease, serine, 11 (also known as IGF binding serine protease).

The term “SFRP2” means human secreted frizzled-related protein 2.

The term “PLA2G12B” means human phospholipase A2, group XIIB

The term “SPON2” means human spondin 2, extracellular matrix protein.

The term “OLFM1” means human olfactomedin 1.

The term “TSRC1” means human thrombospondin repeat containing 1.

The term “THBS2” means human thrombospondin 2.

The term “adlican” means DKFZp564I1922.

The term “CST2” means human cystatin SA.

The term “CST1” means human cystatin SN.

The term “LOXL2” means human lysyl oxidase-like enzyme 2.

The term “TG” means human thyroglobulin.

The term “TGFB1” means human transforming growth factor, beta1.

The term “SERPINH1” means human serine or cysteine proteinase inhibitor clade H (also known as heat shock protein 47, member 1, or collagen binding protein 1).

The term “SERPINB5” means human serine or cysteine proteinase inhibitor, clade B (also known as ovalbumin, member 5).

The term “CEACAM5” or “CEA” means human carcinoembryonic antigen-related cell adhesion molecule 5.

The term “MMP2” means human matrix metalloproteinase 2 (also known as gelatinase A, or 72 kDa gelatinase, or 72 kDa type IV collagenase).

The term “PCSK5” means human proprotein convertase subtilisin/kexin type 5.

It is to be understood that the above terms may refer to protein, DNA sequence and/or RNA sequence. It is also to be understood that the above terms also refer to non-human proteins, DNA and/or RNA having the same sequences as depicted herein.

DESCRIPTION OF EMBODIMENTS OF THE INVENTION

Markers for detection and evaluation of tumors including gastric cancer are provided that have a greater reliability in detecting gastric cancer than prior art markers. By the term “reliability” we include the absence of false positives and/or false negatives. Thus, with higher reliability of a marker, fewer false positives and/or false negatives are associated with diagnoses made using that marker Therefore, in certain embodiments, markers are provided that permit detection of gastric cancer with reliability greater than the reliability of prior art markers of about 50%. In other embodiments, markers are provided that have reliability greater than about 70%; in other embodiments, greater than about 73%, in still other embodiments, greater than about 80%, in yet further embodiments, greater than about 90%, in still others, greater than about 95%, in yet further embodiments greater than about 98%, and in certain embodiments, about 100% reliability.

Thus, we have surprisingly found numerous genes and proteins whose presence is associated with gastric tumors. Detection of gene products (e.g., oligonucleotides such as mRNA) and proteins and peptides translated from such oligonucleotides therefore can be used to diagnose tumors, such as gastric tumors. Array analysis of samples taken from patients with gastric tumors and from non-malignant tissues of the same subjects has led us to the surprising discovery that in many gastric tumors, specific patterns of over-expression of certain genes are associated with the disease.

Cancer markers can also be detected using antibodies raised against cancer markers.

By analyzing the presence and amounts of expression of a plurality of cancer markers can thus increase the sensitivity of diagnosis while decreasing the frequency of false positive and/or false negative results.

General Approaches to Cancer Detection

The following approaches are non-limiting methods that can be used to detect cancer including gastric cancer using GTM family members.

- Microarray approaches using oligonucleotide probes selective for products of GTM genes.
- Real-time quantitative PCR (qPCR) on tumor samples and normal samples using marker specific primers and probes.
- Enzyme-linked immunological assays (ELISA).
- Immunohistochemistry using anti-marker antibodies on gastric tumors and lymph node metastases.
- Immunohistochemistry using anti-marker antibodies on other tumors including but not limited to colorectal, pancreatic, ovarian, melanoma, liver, esophageal, bladder, endometrial, and brain.
- Immunodetection of marker family members in sera from gastric cancer patients taken before and after surgery to remove the tumor.
- Immunodetection of marker family members in sera from healthy individuals and individuals with non-malignant diseases such as gastritis, ulceration, gastric metaplasia and dysplasia.
- Immunodetection of marker family members in patients with other cancers including but not limited to colorectal, pancreatic, ovarian, melanoma, liver, oesophageal, bladder, endometrial, and brain.
- Detection of markers in body fluids, including serum, lymph, peritoneal fluid, cerebrospinal fluid, synovial fluid and the like.
- Immunodetection of marker family members in gastric fluid, peritoneal washes, urine and stool from gastric cancer patients. Using array methods and/or qPCR.
- Analysis of array or qPCR data using computers. Primary data is collected and fold change analysis is performed by comparison of levels of gastric tumor gene expression with expression of the same genes in non-tumor tissue. A threshold for concluding that expression is increased is provided (e.g., 1.5×increase, 2-fold increase, and in alternative embodiments, 3-fold increase, 4-fold increase or 5-fold increase). It can be appreciated that other thresholds for concluding that increased expression has occurred can be selected without departing from the scope of this invention. Further analysis of tumor gene expression includes matching those genes exhibiting increased expression with expression profiles of known gastric tumors to provide diagnosis of tumors.

In certain aspects, this invention provides methods for detecting cancer, comprising:

(a) providing a biological sample; and (b) detecting the over expression of a GTM family member in said sample.

In other aspects, the invention includes a step of detecting over expression of GTM mRNA.

In other aspects, the invention includes a step of detecting over expression of a GTM protein.

In yet further aspects, the invention includes a step of detecting over-expression of a GTM peptide.

In still further aspects, the invention includes a device for detecting a GTM, comprising:

a substrate having a GTM capture reagent thereon; and a detector associated with said substrate, said detector capable of detecting a GTM associated with said capture reagent, wherein the capture reagent includes an oligonucleotide or an antibody.

Additional aspects include kits for detecting cancer, comprising:

a substrate;

a GTM capture reagent, including one or more of a GTM-specific oligonucleotide and a GTM-specific antibody; and instructions for use.

Yet further aspects of the invention include method for detecting a GTM using qPCR, comprising:

a forward primer specific for said GTM;

a reverse primer specific for said GTM;

PCR reagents;

a reaction vial; and instructions for use.

Additional aspects of this invention comprise a kit for detecting the presence of a GTM protein or peptide, comprising:

a substrate having a capture agent for said GTM protein or peptide;

an antibody specific for said GTM protein or peptide;

a reagent capable of labeling bound antibody for said GTM protein or peptide; and instructions for use.

Additional aspects of this invention include a method for manufacturing a monoclonal antibody, comprising the steps of:

In yet further aspects, this invention includes a method for detecting gastric cancer, comprising the steps of:

providing a sample from a patient suspected of having gastric cancer;

measuring the presence of a GTM protein using an ELISA method.

As described herein, detection of tumors can be accomplished by measuring expression of one or more tumor-specific markers. We have unexpectedly found that the association between increased expression of GTMs and the presence of diagnosed gastric cancer is extremely high. The least significant association detected had a p value of about $1.6\times10^{-6}$. Many of the associations were significant at p values of less than $10^{-20}$. With such a high significance, it may not be necessary to detect increased expression in more than one GTM. However, the redundancy in the GTMs of this invention can permit detection of gastric cancers with an increased reliability.

The methods provided herein also include assays of high sensitivity. qPCR is extremely sensitive, and can be used to detect gene products in very low copy number (e.g., 1-100) in a sample. With such sensitivity, very early detection of events that are associated with gastric cancer is made possible.

Methods

The following general methods were used to evaluate the suitability of various approaches to molecular identification of markers associated with gastric tumors.

Tumor Collection

Gastric tumor samples and non-malignant gastric tissues were collected from surgical specimens resected at Seoul National University Hospital, Korea and Dunedin Hospital, New Zealand. Diagnosis of gastric cancer was made on the basis of symptoms, physical findings and histological examination of tissues.

RNA Extraction

In some embodiments, expression of genes associated with gastric tumors was analyzed by determining the changes in RNA from samples taken from tumors. Frozen surgical specimens were embedded in OCT medium. 60 μm sections were sliced from the tissue blocks using a microtome, homogenized in a TriReagent: water (3:1) mix, then chloroform extracted. Total RNA was then purified from the aqueous phase using the RNeasy™ procedure (Qiagen). RNA was also extracted from 16 cancer cell lines and pooled to serve as a reference RNA.

Microarray Slide Preparation

Epoxy coated glass slides were obtained from MWG Biotech AG, Ebersberg, Germany) and were printed with ~30,000 50mer oligonucleotides using a Gene Machines microarraying robot, according to the manufacturer's protocol. Reference numbers (MWG oligo #) for relevant oligonucleotides, and the NCBI mRNA and protein reference sequences are shown in FIG. 2. Full DNA sequences of the GTM of this invention are shown herein below.

RNA Labeling and Hybridization cDNA was transcribed from 10 μg total RNA using Superscript II reverse transcriptase (Invitrogen) in reactions containing 5-(3-aminoallyl)-2' deoxyuridine-5'-triphosphate. The reaction was then de-ionized in a Microcon column before being incubated with Cy3 or Cy5 in bicarbonate buffer for 1 hour at room temperature. Unincorporated dyes were removed using a Qiaquick column (Qiagen) and the sample concentrated to 15 ul in a SpeedVac. Cy3 and Cy5 labeled cDNAs were then mixed with Ambion ULTRA-hyb buffer, denatured at 100° C. for 2 minutes and hybridized to the microarray slides in hybridization chambers at 42° C. for 16 hours. The slides were then washed and scanned twice in an Axon 4000A scanner at two power settings to yield primary fluorescence data on gene expression.

Normalization Procedure

To compare expression of cancer genes from tumors and non-cancerous tissues, median fluorescence intensities detected by Genepix™ software were corrected by subtraction of the local background fluorescence intensities. Spots with a background corrected intensity of less than zero were excluded. To facilitate normalization, intensity ratios and overall spot intensities were log-transformed. Log-transformed intensity ratios were corrected for dye and spatial bias using local regression implemented in the LOCFIT™ package. Log-transformed intensity ratios were regressed simultaneously with respect to overall spot intensity and location. The residuals of the local regression provided the corrected log-fold changes. For quality control, ratios of each normalized microarray were plotted with respect to spot intensity and localization. The plots were subsequently visually inspected for possible remaining artifacts. Additionally, an analysis of variance (ANOVA) model was applied for the detection of pin-tip bias. All results and parameters of the normalization were inserted into a Postgres-database for statistical analysis.

Statistical Analysis

Statistically significant changes in gene expression in tumor samples vs. normal tissues were identified by measured fold changes between arrays. To accomplish this, log2 (ratios) were scaled to have the same overall standard deviation per array. This standardization procedure reduced the average within-tissue class variability. The log2 (ratios) were further shifted to have a median value of zero for each oligonucleotide to facilitate visual inspection of results. A rank-test based on fold changes was then used to improve the noise robustness. This test consisted of two steps: (i) calculation of the rank of fold change (Rfc) within arrays and ii) subtraction of the median (Rfc) for normal tissue from the median(Rfc) for tumor tissue. The difference of both median ranks defines the score of the fold change rank presented in FIG. 2. Two additional statistical tests were also performed on this standardized data: 1) Two sample student's t-test, with and without the Bonferroni adjustment and 2) the Wilcoxon test.

Statistical Analysis of Marker Combinations

To determine the value of using combinations of two or three of the markers to discriminate between tumor and non-malignant samples, the qPCR data from 40 paired samples (tumor and non-malignant samples from the same patient) were subjected to the following analysis. Normal distributions for the non-malignant and tumor samples were generated using the sample means and standard deviations. The probability that values taken from the tumor expression data would exceed a defined threshold (e.g., greater than 50%, 70%, 73%, 80%, 90%, 95%, 98%, 99% or 100%) in the non-malignant distribution was then determined (i.e., sensitivity). For combinations of markers, the probability that at least one marker exceeded the threshold was determined.

Quantitative Real-Time PCR

In other embodiments, real-time, or quantitative PCR (qPCR) can be used for absolute or relative quantitation of PCR template copy number. Taqman™ probe and primer sets were designed using Primer Express V 2.0™ (Applied Biosystems). Where possible, all potential splice variants were included in the resulting amplicon, with amplicon preference given to regions covered by the MWG-Biotech-derived microarray oligonucleotide. Alternatively, if the target gene was represented by an Assay-on-Demand™ expression assay (Applied Biosystems) covering the desired amplicons, these were used. The name of the gene, symbol, the Applied Biosystems "assay on demand" number, forward primer, reverse primer and probe sequence used for qPCR are shown in Table 1 and in FIG. 1. In the in-house designed assays, primer concentration was titrated using a SYBR green labeling protocol and cDNA made from the reference RNA Amplification was carried out on an ABI Prism™ 7000 sequence detection system under standard cycling conditions. When single amplification products were observed in the dissociation curves, standard curves were generated over a 625-fold concentration range using optimal primer concentrations and 5'FAM-3'TAMRA phosphate Taqman™ probe (Proligo) at a final concentration of 250 nM. Assays giving standard curves with regression coefficients over 0.98 were used in subsequent assays. It can be appreciated that in other embodiments, regression coefficients need not be as high. Rather, any standard curve can be used so long as the regression coefficients are sufficiently high to permit statistically significant determination of differences in expression. Such regression coefficients may be above about 0.7, above about 0.8, above about 0.9 or above about 0.95 in alternative embodiments.

Assays were performed over two 96 well plates with each RNA sample represented by a single cDNA. Each plate contained a reference cDNA standard curve, over a 625-fold concentration range, in duplicate. Analysis consisted of calculating the ΔCT (target gene CT—mean reference cDNA CT). ΔCT is directly proportional to the negative log2 fold change. Log2 fold changes relative to the median non-malignant log2 fold change were then calculated (log2 fold change—median normal log2 fold change). These fold changes were then clustered into frequency classes and graphed.

Microarray Analysis of Cancer Marker Genes

RNA from 58 gastric tumors and 58 non-malignant ("normal") gastric tissue samples were labeled with Cy5 and hybridized in duplicate or triplicate with Cy3 labeled reference RNA. After normalization, the change in expression in each of 29,718 genes was then estimated by three measures: (i) fold change: the ratio of the gene's median expression (un-standardized) in the tumor samples divided by the median level in the non-malignant samples. (ii) fold change rank and (iii) the statistical probability that the observed fold changes were significant.

Selection of Serum Markers for Gastric Malignancy

In certain embodiments, the cancer marker can be found in biological fluids, including serum. Serum markers were selected from the array data based on (i) the presence of a signal sequence characteristic of secreted proteins or cleaved from the outside of the membrane, (ii) the median level of over-expression (fold change) in tumors compared to non-malignant controls, (iii) the median change in expression rank between tumors and non-malignant controls, and (iv) the degree of overlap between the ranges of expression in the tumor and the non-malignant controls.

All 29 GTMs are known to have a signal peptide sequence at the 5' end of their coding sequences. The signal sequence targets the GTM proteins for transport to an extracellular compartment through the plasma membrane (Gunner von Heijne, Journal of Molecular Biology 173:243-251 (1984). In addition, none of the GTMs have transmembrane sequence motifs that would result in the full-length protein being retained within the plasma membrane. Consequently, all of the GTM markers of this invention are likely to be secreted into the extracellular compartment, and therefore can be in contact with the blood supply, either being taken up by capillaries, or by being transported into the lymphatic system and then into the blood supply. As a result, each of these tumor-derived markers will be present in the blood.

Next, genes were excluded if >50% of the tumor samples showed expression levels within the $95^{th}$ percentile of the non-malignant range. The variation in the degree of over-expression in the tumor samples reflects not only tumor heterogeneity but also variations in the extent of contamination of the tumor samples with "normal" tissue including muscle, stromal cells and non-malignant epithelial glands. This "normal" contamination ranged from 5 to 70% with a median of approximately 25%. Other genes were excluded because of high relative expression in hematopoietic cells, or elevated expression in metaplastic gastric tissue. It can be appreciated that depending on the degree of contamination by normal cells or cells that normally express the marker, different threshold ranges can be selected that can provide sufficient separation between a cancer source and a normal source.

GTM that we have found to be useful include genes (DNA), complementary DNA (cDNA), RNA, proteins, and protein fragments of the following markers: carboxypeptidase N, polypeptide 2, 83 kDa chain (also known as carboxypeptidase N (CPN2), matrix metalloproteinase 12 (MMP12), inhibin ("INHBA"), insulin-like growth factor 7 ("IGFBP7"), gamma-glutamyl hydrolase ("GGH"), leucine proline-enriched proteoglycan ("LEPRE1"), cystatin S ("CST4"), secreted frizzled-related protein 4 ("SFRP4"), asporin ("ASPN"), cell growth regulator with EF hand domain 1 ("CGREF1"), kallikrein (KLK10), tissue inhibitor of metalloproteinase 1 ("TIMP1"), secreted acidic cysteine-rich protein ("SPARC"), transforming growth factor, β-induced ("TGFB1"), EGF-containing fibulin-like extracellular matrix protein 2 ("EFEMP2"), lumican ("LUM"), stannin ("SNN"), secreted phosphoprotein 1 ("SPP1"), chondroitin sulfate proteoglycan 2 ("CSPG2"), N-acylsphingosine amidohydrolase ("ASAH1"), serine protease 11 ("PRSS11"), secreted frizzled-related protein 2 ("SFRP2"), phospholipase A2, group XIIB ("PLA2G12B"), spondin 2, extracellular matrix protein ("SPON2"), olfactomedin 1 ("OLFM1"), thrombospondin repeat containing 1 ("TSRC1"), thrombospondin 2 ("THBS2"), adlican, cystatin SA ("CST2"), cystatin SN (CST1), lysyl oxidase-like enzyme 2 ("LOXL2"), thyroglobulin ("TG"), transforming growth factor beta1 ("TGFB1"), serine or cysteine proteinase inhibitor clade H ("SERPINH1"), serine or cysteine proteinase inhibitor clade B ("SERPINB5"), matrix metalloproteinase 2 ("MMP2"), proprotein convertase subtilisin/kexin type 5 ("PCSK5"), and hyaluronan proteoglycan link protein 4 ("HAPLN4").

DNA sequences of GTM of this invention along with identifying information are shown herein below.

Matrix Metalloproteinase 12

>gi|4505206|ref|NM_002426.1| *Homo sapiens* matrix metalloproteinase 12 (macrophage elastase) (MMP12), mRNA|qPCR forward_primer match [758 . . . 780]| qPCR reverse_primer match [888 . . . 864]|qPCR probe match [786 . . . 815]

SEQ ID NO: 67

```
TAGAAGTTTACAATGAAGTTTCTTCTAATACTGCTCCTGCAGGCCACTGC
TTCTGGAGCTCTTCCCCTGAACAGCTCTACAAGCCTGGAAAAAAATAATG
TGCTATTTGGTGAGAGATACTTAGAAAAATTTTATGGCCTTGAGATAAAC
AAACTTCCAGTGACAAAAATGAAATATAGTGGAAACTTAATGAAGGAAAA
AATCCAAGAAATGCAGCACTTCTTGGGTCTGAAAGTGACCGGGCAACTGG
ACACATCTACCCTGGAGATGATGCACGCACCTCGATGTGGATTCCCCGAT
CTCCATCATTTCAGGGAAATGCCAGGGGGGCCCGTATGGAGGAAACATTA
TATCACCTACAGAATCAATAATTACACACCTGACATGAACCGTGAGGATG
TTGACTACGCAATCCGGAAAGCTTTCCAAGTATGGAGTAATGTTACCCCC
TTGAAATTCAGCAAGATTAACACAGGCATGGCTGACATTTTGGTGGTTTT
TGCCCGTGGAGCTCATGGAGACTTCCATGCTTTTGATGGCAAAGGTGGAA
TCCTAGCCCATGCTTTTGGACCTGGATCTGGCATTGGAGGGGATGCACAT
TTCGATGAGGACGAATTCTGGACTACACATTCAGGAGGCACAAACTTGTT
```

-continued

```
CCTCACTGCTGTTCACGAGATTGGCCATTCCTTAGGTCTTGGCCATTCTA
GTGATCCAAAGGCTGTAATGTTCCCCACCTACAAATATGTCGACATCAAC
ACATTTCGCCTCTCTGCTGATGACATACGTGGCATTCAGTCCCTGTATGG
AGACCCAAAAGAGAACCAACGCTTGCCAAATCCTGACAATTCAGAACCAG
CTCTCTGTGACCCCAATTTGAGTTTTGATGCTGTCACTACCGTGGGAAAT
AAGATCTTTTTCTTCAAAGACAGGTTCTTCTGGCTGAAGGTTTCTGAGAG
ACCAAAGACCAGTGTTAATTTAATTTCTTCCTTATGGCCAACCTTGCCAT
CTGGCATTGAAGCTGCTTATGAAATTGAAGCCAGAAATCAAGTTTTTCTT
TTTAAAGATGACAAATACTGGTTAATTAGCAATTTAAGACCAGAGCCAAA
TTATCCCAAGAGCATACATTCTTTTGGTTTTCCTAACTTTGTGAAAAAAA
TTGATGCAGCTGTTTTTAACCCACGTTTTTATAGGACCTACTTCTTTGTA
GATAACCAGTATTGGAGGTATGATGAAAGGAGACAGATGATGGACCCTGG
TTATCCCAAACTGATTACCAAGAACTTCCAAGGAATCGGGCCTAAAATTG
ATGCAGTCTTCTATTCTAAAAACAAATACTACTATTTCTTCCAAGGATCT
AACCAATTTGAATATGACTTCCTACTCCAACGTATCACCAAAACACTGAA
AAGCAATAGCTGGTTTGGTTGTTAGAAATGGTGTAATTAATGGTTTTTGT
TAGTTCACTTCAGCTTAATAAGTATTTATTGCATATTTGCTATGTCCTCA
GTGTACCACTACTTAGAGATATGTATCATAAAAATAAAATCTGTAAACCA
TAGGTAATGATTATATAAAATACATAATATTTTTCAATTTTGAAAACTCT
AATTGTCCATTCTTGCTTGACTCTACTATTAAGTTTGAAAATAGTTACCT
TCAAAGCAAGATAATTCTATTTGAAGCATGCTCTGTAAGTTGCTTCCTAA
CATCCTTGGACTGAGAAATTATACTTACTTCTGGCATAACTAAAATTAAG
TATATATATTTTGGCTCAAATAAAATTG
```

Inhibin Beta A

>gi|4504698|ref|NM_002192.1| *Homo sapiens* inhibin, beta A (activin A, activin AB alpha polypeptide) (INHBA), mRNA|qPCR assay_on_demand_context match [457 . . . 481]

SEQ ID NO: 68

```
TCCACACACACAAAAAACCTGCGCGTGAGGGGGGAGGAAAAGCAGGGCCT
TTAAAAAGGCAATCACAACAACTTTTGCTGCCAGGATGCCCTTGCTTTGG
CTGAGAGGATTTCTGTTGGCAAGTTGCTGGATTATAGTGAGGAGTTCCCC
CACCCCAGGATCCGAGGGGCACAGCGCGGCCCCCGACTGTCCGTCCTGTG
CGCTGGCCGCCCTCCCAAAGGATGTACCCAACTCTCAGCCAGAGATGGTG
GAGGCCGTCAAGAAGCACATTTTAAACATGCTGCACTTGAAGAAGAGACC
CGATGTCACCCAGCCGGTACCCAAGGCGGCGCTTCTGAACGCGATCAGAA
AGCTTCATGTGGGCAAAGTCGGGGAGAACGGGTATGTGGAGATAGAGGAT
GACATTGGAAGGAGGGCAGAAATGAATGAACTTATGGAGCAGACCTCGGA
GATCATCACGTTTGCCGAGTCAGGAACAGCCAGGAAGACGCTGCACTTCG
AGATTTCCAAGGAAGGCAGTGACCTGTCAGTGGTGGAGCGTGCAGAAGTC
TGGCTCTTCCTAAAAGTCCCCAAGGCCAACAGGACCAGGACCAAAGTCAC
CATCCGCCTCTTCCAGCAGCAGAAGCACCCGCAGGGCAGCTTGGACACAG
```

-continued

GGGAAGAGGCCGAGGAAGTGGGCTTAAAGGGGGAGAGGAGTGAACTGTTG

CTCTCTGAAAAAGTAGTAGACGCTCGGAAGAGCACCTGGCATGTCTTCCC

TGTCTCCAGCAGCATCCAGCGGTTGCTGGACCAGGGCAAGAGCTCCCTGG

ACGTTCGGATTGCCTGTGAGCAGTGCCAGGAGAGTGGCGCCAGCTTGGTT

CTCCTGGGCAAGAAGAAGAAGAAAGAAGAGGAGGGGGAAGGGAAAAAGAA

GGGCGGAGGTGAAGGTGGGGCAGGAGCAGATGAGGAAAAGGAGCAGTCGC

ACAGACCTTTCCTCATGCTGCAGGCCCGGCAGTCTGAAGACCACCCTCAT

CGCCGGCGTCGGCGGGGCTTGGAGTGTGATGGCAAGGTCAACATCTGCTG

TAAGAAACAGTTCTTTGTCAGTTTCAAGGACATCGGCTGGAATGACTGGA

TCATTGCTCCCTCTGGCTATCATGCCAACTACTGCGAGGGTGAGTGCCCG

AGCCATATAGCAGGCACGTCCGGGTCCTCACTGTCCTTCCACTCAACAGT

CATCAACCACTACCGCATGCGGGGCCATAGCCCCTTTGCCAACCTCAAAT

CGTGCTGTGTGCCCACCAAGCTGAGACCCATGTCCATGTTGTACTATGAT

GATGGTCAAAACATCATCAAAAAGGACATTCAGAACATGATCGTGGAGGA

GTGTGGGTGCTCATAGAGTTGCCCAGCCCAGGGGGAAAGGGAGCAAGAGT

TGTCCAGAGAAGACAGTGGCAAAATGAAGAAATTTTTAAGGTTTCTGAGT

TAACCAGAAAAAATAGAAATTAAAAACAAAACAAAACAAAAAAAAAAACAA

AAAAAAACAAAAGTAAATTAAAAACAAACCTGATGAAACAGATGAAACAG

ATGAAGGAAGATGTGGAAATCTTAGCCTGCCTTAGCCAGGGCTCAGAGAT

GAAGCAGTGAAGAGACAGATTGGGAGGGAAAGGGAGAATGGTGTACCCTT

TATTTCTTCTGAAATCACACTGATGACATCAGTTGTTTAAACGGGGTATT

GTCCTTTCCCCCCTTGAGGTTCCCTTGTGAGCTTGAATCAACCAATCTGA

TCTGCAGTAGTGTGGACTAGAACAACCCAAATAGCATCTAGAAAGCCATG

AGTTTGAAAGGGCCCATCACAGGCACTTTCCTAGCCTAAT

Insulin-Like Growth Factor Binding Protein 7

>gi|4504618|ref|NM_001553.1| *Homo sapiens* insulin-like growth factor binding protein 7 (IGFBP7), mRNA|qPCR forward_primer match [470 . . . 487]|qPCR reverse_primer match [567 . . . 546]|qPCR probe match [492 . . . 517]

SEQ ID NO: 69

GCCGCTGCCACCGCACCCCGCCATGGAGCGGCCGTCGCTGCGCGCCCTGC

TCCTCGGCGCCGCTGGGCTGCTGCTCCTGCTCCTGCCCCTCTCCTCTTCC

TCCTCTTCGGACACCTGCGGCCCCTGCGAGCCGGCCTCCTGCCCGCCCCT

GCCCCCGCTGGGCTGCCTGCTGGGCGAGACCCGCGACGCGTGCGGCTGCT

GCCCTATGTGCGCCCGCGGCGAGGGCGAGCCGTGCGGGGGTGGCGGCGCC

GGCAGGGGGTACTGCGCGCCGGGCATGGAGTGCGTGAAGAGCCGCAAGAG

GCGGAAGGGTAAAGCCGGGGCAGCAGCCGGCGGTCCGGGTGTAAGCGGCG

TGTGCGTGTGCAAGAGCCGCTACCCGGTGTGCGGCAGCGACGGCACCACC

TACCCGAGCGGCTGCCAGCTGCGCGCCGCCAGCCAGAGGGCCGAGAGCCG

CGGGGAGAAGGCCATCACCCAGGTCAGCAAGGGCACCTGCGAGCAAGGTC

CTTCCATAGTGACGCCCCCCAAGGACATCTGGAATGTCACTGGTGCCCAG

-continued

GTGTACTTGAGCTGTGAGGTCATCGGAATCCCGACACCTGTCCTCATCTG

GAACAAGGTAAAAAGGGGTCACTATGGAGTTCAAAGGACAGAACTCCTGC

CTGGTGACCGGGACAACCTGGCCATTCAGACCCGGGGTGGCCCAGAAAAG

CATGAAGTAACTGGCTGGGTGCTGGTATCTCCTCTAAGTAAGGAAGATGC

TGGAGAATATGAGTGCCATGCATCCAATTCCCAAGGACAGGCTTCAGCAT

CAGCAAAAATTACAGTGGTTGATGCCTTACATGAAATACCAGTGAAAAAA

GGTGAAGGTGCCGAGCTATAAACCTCCAGAATATTATTAGTCTGCATGGT

TAAAAGTAGTCATGGATAACTACATTACCTGTTCTTGCCTAATAAGTTTC

TTTTAATCCAATCCACTAACACTTTAGTTATATTCACTGGTTTTACACAG

AGAAATACAAAATAAAGATCACACATCAAGACTATCTACAAAAAATTTATT

ATATATTTACAGAAGAAAAGCATGCATATCATTAAACAAATAAAATACTT

TTTATCACAAAAAAAAAAAAAAAA

Gamma-Glutamyl Hydrolase

>gi|4503986|ref|NM_003878.1| *Homo sapiens* gamma-glutamyl hydrolase (conjugase, folylpolygammaglutamyl hydrolase) (GGH), mRNA|qPCR forward_primer match [531 . . . 547]|qPCR reverse_primer match [611 . . . 587]|qPCR probe match [549 . . . 577]

SEQ ID NO: 70

TGCCGCAGCCCCCGCCCGCCCGCAGAGCTTTTGAAAGGCGGCGGGAGGCG

GCGAGCGCCATGGCCAGTCCGGGCTGCCTGCTGTGCGTGCTGGGCCTGCT

ACTCTGCGGGGCGGCGAGCCTCGAGCTGTCTAGACCCCACGGCGACACCG

CCAAGAAGCCCATCATCGGAATATTAATGCAAAAATGCCGTAATAAAGTC

ATGAAAAACTATGGAAGATACTATATTGCTGCGTCCTATGTAAAGTACTT

GGAGTCTGCAGGTGCGAGAGTTGTACCAGTAAGGCTGGATCTTACAGAGA

AAGACTATGAAATACTTTTCAAATCTATTAATGGAATCCTTTTCCCTGGA

GGAAGTGTTGACCTCAGACGCTCAGATTATGCTAAAGTGGCCAAAATATT

TTATAACTTGTCCATACAGAGTTTTGATGATGGAGACTATTTTCCTGTGT

GGGGCACATGCCTTGGATTTGAAGAGCTTTCACTGCTGATTAGTGGAGAG

TGCTTATTAACTGCCACAGATACTGTTGACGTGGCAATGCCGCTGAACTT

CACTGGAGGTCAATTGCACAGCAGAATGTTCCAGAATTTTCCTACTGAGT

TGTTGCTGTCATTAGCAGTAGAACCTCTGACTGCCAATTTCCATAAGTGG

AGCCTCTCCGTGAAGAATTTTACAATGAATGAAAAGTTAAAGAAGTTTTT

CAATGTCTTAACTACAAATACAGATGGCAAGATTGAGTTTATTTCAACAA

TGGAAGGATATAAGTATCCAGTATATGGTGTCCAGTGGCATCCAGAGAAA

GCACCTTATGAGTGGAAGAATTTGGATGGCATTTCCCATGCACCTAATGC

TGTGAAAACCGCATTTTATTTAGCAGAGTTTTTTGTTAATGAAGCTCGGA

AAAACAACCATCATTTTAAATCTGAATCTGAAGAGGAGAAAGCATTGATT

TATCAGTTCAGTCCAATTTATACTGGAAATATTTCTTCATTTCAGCAATG

TTACATATTTGATTGAAAGTCTTCAATTTGTTAACAGAGCAAATTTGAAT

AATTCCATGATTAAACTGTTAGAATAACTTGCTACTCATGGCAAGATTAG

GAAGTCACAGATTCTTTTCTATAATGTGCCTGGCTCTGATTCTTCATTAT

-continued

GTATGTGACTATTTATATAACATTAGATAATTAAATAGTGAGACATAAAT

AGAGTGCTTTTTCATGGAAAAGCCTTCTTATATCTGAAGATTGAAAAATA

AATTTACTGAAATACAAAAAAAAAAAAAAA

Leucine Proline-Enriched Proteoglycan 1

>gi|21361917|ref|NM_022356.2| *Homo sapiens* leucine proline-enriched proteoglycan (leprecan) 1 (LEPRE1), mRNA|qPCR forward_primer match [813 . . . 836]|qPCR reverse_primer match [894 . . . 872]|qPCR probe match [841 . . . 870]

SEQ ID NO: 71

GGTGGCGGGTGGCTGGCGGTTCCGTTAGGTCTGAGGGAGCGATGGCGGTA

CGCGCGTTGAAGCTGCTGACCACACTGCTGGCTGTCGTGGCCGCTGCCTC

CCAAGCCGAGGTCGAGTCCGAGGCAGGATGGGGCATGGTGACGCCTGATC

TGCTCTTCGCCGAGGGGACCGCAGCCTACGCGCGCGGGGACTGGCCCGGG

GTGGTCCTGAGCATGGAACGGGCGCTGCGCTCCCGGGCAGCCCTCCGCGC

CCTTCGCCTGCGCTGCCGCACCCAGTGTGCCGCCGACTTCCCGTGGGAGC

TGGACCCCGACTGGTCCCCCAGCCCGGCCCAGGCCTCGGGCGCCGCCGCC

CTGCGCGACCTGAGCTTCTTCGGGGGCCTTCTGCGTCGCGCTGCCTGCCT

GCGCCGCTGCCTCGGGCCGCCGGCCGCCCACTCGCTCAGCGAAGAGATGG

AGCTGGAGTTCCGCAAGCGGAGCCCCTACAACTACCTGCAGGTCGCCTAC

TTCAAGATCAACAAGTTGGAGAAAGCTGTTGCTGCAGCACACACCTTCTT

CGTGGGCAATCCTGAGCACATGGAAATGCAGCAGAACCTAGACTATTACC

AAACCATGTCTGGAGTGAAGGAGGCCGACTTCAAGGATCTTGAGACTCAA

CCCCATATGCAAGAATTTCGACTGGGAGTGCGACTCTACTCAGAGGAACA

GCCACAGGAAGCTGTGCCCCACCTAGAGGCGGCGCTGCAAGAATACTTTG

TGGCCTATGAGGAGTGCCGTGCCCTCTGCGAAGGGCCCTATGACTACGAT

GGCTACAACTACCTTGAGTACAACGCTGACCTCTTCCAGGCCATCACAGA

TCATTACATCCAGGTCCTCAACTGTAAGCAGAACTGTGTCACGGAGCTTG

CTTCCCACCCAAGTCGAGAGAAGCCCTTTGAAGACTTCCTCCCATCGCAT

TATAATTATCTGCAGTTTGCCTACTATAACATTGGGAATTATACACAGGC

TGTTGAATGTGCCAAGACCTATCTTCTCTTCTTCCCCAATGACGAGGTGA

TGAACCAAAATTTGGCCTATTATGCAGCTATGCTTGGAGAAGAACACACC

AGATCCATCGGCCCCCGTGAGAGTGCCAAGGAGTACCGACAGCGAAGCCT

ACTGGAAAAAGAACTGCTTTTCTTCGCTTATGATGTTTTTGGAATTCCCT

TTGTGGATCCGGATTCATGGACTCCAGGAGAAGTGATTCCCAAGAGATTG

CAAGAGAAACAGAAGTCAGAACGGGAAACAGCCGTACGCATCTCCCAGGA

GATTGGGAACCTTATGAAGGAAATCGAGACCCTTGTGGAAGAGAAGACCA

AGGAGTCACTGGATGTGAGCAGACTGACCCGGGAAGGTGGCCCCCTGCTG

TATGAAGGCATCAGTCTCACCATGAACTCCAAACTCCTGAATGGTTCCCA

GCGGGTGGTGATGGACGGCGTAATCTCTGACCACGAGTGTCAGGAGCTGC

AGAGACTGACCAATGTGGCAGCAACCTCAGGAGATGGCTACCGGGGTCAG

ACCTCCCCACATACTCCCAATGAAAAGTTCTATGGTGTCACTGTCTTCAA

-continued

AGCCCTCAAGCTGGGGCAAGAAGGCAAAGTTCCTCTGCAGAGTGCCCACC

TGTACTACAACGTGACGGAGAAGGTGCGGCGCATCATGGAGTCCTACTTC

CGCCTGGATACGCCCCTCTACTTTTCCTACTCTCATCTGGTGTGCCGCAC

TGCCATCGAAGAGGTCCAGGCAGAGAGGAAGGATGATAGTCATCCAGTCC

ACGTGGACAACTGCATCCTGAATGCCGAGACCCTCGTGTGTGTCAAAGAG

CCCCCAGCCTACACCTTCCGCGACTACAGCGCCATCCTTTACCTAAATGG

GGACTTCGATGGCGGAAACTTTTATTTCACTGAACTGGATGCCAAGACCG

TGACGGCAGAGGTGCAGCCTCAGTGTGGAAGAGCCGTGGGATTCTCTTCA

GGCACTGAAAACCCACATGGAGTGAAGGCTGTCACCAGGGGGCAGCGCTG

TGCCATCGCCCTGTGGTTCACCCTGGACCCTCGACACAGCGAGCGGGTGA

GAGCAGCTCGAGCGGGTGAGAGCAGCTGGTGCTGTGGTGACCCGTTCCCA

GAGCGCCCTTGGTTTGCCTTTCTCTTCCCCAAATCCCATTGCCAGTGGCT

GAGACACGAAAGGAGCACTTGGGACACCAGCTCCAACGCCCTGTCATTAT

GGTCACATTGCCTTGTCCTCCCTGGGCCTGCTGTGAACGGGATCCAGGTG

GGGAAAGAGGTCAAGACAGGGAGCGATGCTGAGTTCTTGGTTCCCTCCTT

GGGCCCCACTTCAGCTGTCCTTTTCCAGAGAGTAGGACCTGCTGGGAAGG

AGATGAGCCTGGGGCCATTAAGGAACCTTCCTTGTCCCCTGGGAAGTAGC

AGCTGAGAGATAGCGAGTGTCTGGAGCGGAGGCCTCTCTGAATGGGCAGG

GGTTTGTCCTTGCAGGACAGGGTGCAGGCAGATGACCTGGTGAAGATGCT

CTTCAGCCCAGAAGAGATGGTCCTCTCCCAGGAGCAGCCCCTGGATGCCC

AGCAGGGCCCCCCCGAACCTGCACAAGAGTCTCTCTCAGGCAGTGAATCG

AAGCCCAAGGATGAGCTATGACAGCGTCCAGGTCAGACGGATGGGTGACT

AGACCCATGGAGAGGAACTCTTCTGCACTCTGAGCTGGCCAGCCCCTCGG

GGCTGCAGAGCAGTGAGCCTACATCTGCCACTCAGCCGAGGGGACCCTGC

TCACAGCCTTCTACATGGTGCTACTGCTCTTGGAGTGGACATGACCAGAC

ACCGCACCCCCTGGATCTGGCTGAGGGCTCAGGACACAGGCCCAGCCACC

CCCAGGGGCCTCCACAGGCCGCTGCATAACAGCGATACAGTACTTAAGTG

TCTGTGTAGACAACCAAAGAATAAATGATTCATGGTTTTTTTT

Cystatin S

>gi|19882254|ref|NM_001899.2| *Homo sapiens* cystatin S (CST4), mRNA|qPCR forward_primer match [343 . . . 361]|qPCR reverse_primer match [434 . . . 411]|qPCR probe match [382 . . . 410]

SEQ ID NO: 72

GGCTCTCACCCTCCTCTCCTGCAGCTCCAGCTTTGTGCTCTGCCTCTGAG

GAGACCATGGCCCGGCCTCTGTGTACCCTGCTACTCCTGATGGCTACCCT

GGCTGGGGCTCTGGCCTCGAGCTCCAAGGAGGAGAATAGGATAATCCCAG

GTGGCATCTATGATGCAGACCTCAATGATGAGTGGGTACAGCGTGCCCTT

CACTTCGCCATCAGCGAGTACAACAAGGCCACCGAAGATGAGTACTACAG

ACGCCCGCTGCAGGTGCTGCGAGCCAGGGAGCAGACCTTTGGGGGGGTGA

ATTACTTCTTCGACGTAGAGGTGGGCCGCACCATATGTACCAAGTCCCAG

-continued

CCCAACTTGGACACCTGTGCCTTCCATGAACAGCCAGAACTGCAGAAGAA

ACAGTTGTGCTCTTTCGAGATCTACGAAGTTCCCTGGGAGGACAGAATGT

CCCTGGTGAATTCCAGGTGTCAAGAAGCCTAGGGGTCTGTGCCAGGCCAG

TCACACCGACCACCACCCACTCCCACCCACTGTAGTGCTCCCACCCCTGG

ACTGGTGGCCCCCACCCTGCGGGAGGCCTCCCCATGTGCCTGTGCCAAGA

GACAGACAGAGAAGGCTGCAGGAGTCCTTTGTTGCTCAGCAGGGCGCTCT

GCCCTCCCTCCTTCCTTCTTGCTTCTAATAGACCTGGTACATGGTACACA

CACCCCCACCTCCTGCAATTAAACAGTAGCATCGCC

Secreted Frizzled-Related Protein 4

>gi|8400733|ref|NM_003014.2| *Homo sapiens* secreted frizzled-related protein 4 (SFRP4), mRNA|qPCR assay_on_demand_context match [1079 . . . 1103]

SEQ ID NO: 73

GGCGGGTTCGCGCCCCGAAGGCTGAGAGCTGGCGCTGCTCGTGCCCTGTG

TGCCAGACGGCGGAGCTCCGCGGCCGGACCCCGCGGCCCCGCTTTGCTGC

CGACTGGAGTTTGGGGGAAGAAACTCTCCTGCGCCCCAGAAGATTTCTTC

CTCGGCGAAGGGACAGCGAAAGATGAGGGTGGCAGGAAGAGAAGGCGCTT

TCTGTCTGCCGGGGTCGCAGCGCGAGAGGGCAGTGCCATGTTCCTCTCCA

TCCTAGTGGCGCTGTGCCTGTGGCTGCACCTGGCGCTGGGCGTGCGCGGC

GCGCCCTGCGAGGCGGTGCGCATCCCTATGTGCCGGCACATGCCCTGGAA

CATCACGCGGATGCCCAACCACCTGCACCACAGCACGCAGGAGAACGCCA

TCCTGGCCATCGAGCAGTACGAGGAGCTGGTGGACGTGAACTGCAGCGCC

GTGCTGCGCTTCTTCTTCTGTGCCATGTACGCGCCCATTTGCACCCTGGA

GTTCCTGCACGACCCTATCAAGCCGTGCAAGTCGGTGTGCCAACGCGCGC

GCGACGACTGCGAGCCCCTCATGAAGATGTACAACCACAGCTGGCCCGAA

AGCCTGGCCTGCGACGAGCTGCCTGTCTATGACCGTGGCGTGTGCATTTC

GCCTGAAGCCATCGTCACGGACCTCCCGGAGGATGTTAAGTGGATAGACA

TCACACCAGACATGATGGTACAGGAAAGGCCTCTTGATGTTGACTGTAAA

CGCCTAAGCCCCGATCGGTGCAAGTGTAAAAAGGTGAAGCCAACTTTGGC

AACGTATCTCAGCAAAAACTACAGCTATGTTATTCATGCCAAAATAAAAG

CTGTGCAGAGGAGTGGCTGCAATGAGGTCACAACGGTGGTGGATGTAAAA

GAGATCTTCAAGTCCTCATCACCCATCCCTCGAACTCAAGTCCCGCTCAT

TACAAATTCTTCTTGCCAGTGTCCACACATCCTGCCCCATCAAGATGTTC

TCATCATGTGTTACGAGTGGCGTTCAAGGATGATGCTTCTTGAAAATTGC

TTAGTTGAAAAATGGAGAGATCAGCTTAGTAAAAGATCCATACAGTGGGA

AGAGAGGCTGCAGGAACAGCGGAGAACAGTTCAGGACAAGAAGAAAACAG

CCGGGCGCACCAGTCGTAGTAATCCCCCCAAACCAAAGGGAAAGCCTCCT

GCTCCCAAACCAGCCAGTCCCAAGAAGAACATTAAAACTAGGAGTGCCCA

GAAGAGAACAAACCCGAAAAGAGTGTGAGCTAACTAGTTTCCAAAGCGGA

GACTTCCGACTTCCTTACAGGATGAGGCTGGGCATTGCCTGGGACAGCCT

ATGTAAGGCCATGTGCCCCTTGCCCTAACAACTCACTGCAGTGCTCTTCA

TAGACACATCTTGCAGCATTTTTCTTAAGGCTATGCTTCAGTTTTTCTTT

-continued

GTAAGCCATCACAAGCCATAGTGGTAGGTTTGCCCTTTGGTACAGAAGGT

GAGTTAAAGCTGGTGGAAAAGGCTTATTGCATTGCATTCAGAGTAACCTG

TGTGCATACTCTAGAAGAGTAGGGAAAATAATGCTTGTTACAATTCGACC

TAATATGTGCATTGTAAAATAAATGCCATATTTCAAACAAAACACGTAAT

TTTTTTACAGTATGTTTTATTACCTTTTGATATCTGTTGTTGCAATGTTA

GTGATGTTTTAAAATGTGATGAAAATATAATGTTTTTAAGAAGGAACAGT

AGTGGAATGAATGTTAAAAGATCTTTATGTGTTTATGGTCTGCAGAAGGA

TTTTTGTGATGAAAGGGGATTTTTTGAAAAATTAGAGAAGTAGCATATGG

AAAATTATAATGTGTTTTTTTACCAATGACTTCAGTTTCTGTTTTTAGCT

AGAAACTTAAAAACAAAAATAATAATAAAGAAAAATAAATAAAAAGGAGA

GGCAGACAATGTCTGGATTCCTGTTTTTTGGTTACCTGATTTCCATGATC

ATGATGCTTCTTGTCAACACCCTCTTAAGCAGCACCAGAAACAGTGAGTT

TGTCTGTACCATTAGGAGTTAGGTACTAATTAGTTGGCTAATGCTCAAGT

ATTTTATACCCACAAGAGAGGTATGTCACTCATCTTACTTCCCAGGACAT

CCACCCTGAGAATAATTTGACAAGCTTAAAAATGGCCTTCATGTGAGTGC

CAAATTTTGTTTTTCTTCATTTAAATATTTTCTTTGCCTAAATACATGTG

AGAGGAGTTAAATATAAATGTACAGAGAGGAAAGTTGAGTTCCACCTCTG

AAATGAGAATTACTTGACAGTTGGGATACTTTAATCAGAAAAAAAGAACT

TATTTGCAGCATTTTATCAACAAATTTCATAATTGTGGACAATTGGAGGC

ATTTATTTTAAAAAACAATTTTATTGGCCTTTTGCTAACACAGTAAGCAT

GTATTTTATAAGGCATTCAATAAATGCACAACGCCCAAAGGAAATAAAAT

CCTATCTAATCCTACTCTCCACTACACAGAGGTAATCACTATTAGTATTT

TGGCATATTATTCTCCAGGTGTTTGCTTATGCACTTATAAAATGATTTGA

ACAAATAAAACTAGGAACCTGTATACATGTGTTTCATAACCTGCCTCCTT

TGCTTGGCCCTTTATTGAGATAAGTTTTCCTGTCAAGAAAGCAGAAACCA

TCTCATTTCTAACAGCTGTGTTATATTCCATAGTATGCATTACTCAACAA

ACTGTTGTGCTATTGGATACTTAGGTGGTTTCTTCACTGACAATACTGAA

TAAACATCTCACCGGAATTC

Asporin

>gi|41350213|ref|NM_017680.3| *Homo sapiens* asporin (LRR class 1) (ASPN), mRNA|qPCR forward_primer match [798 . . . 823]|qPCR reverse_primer match [934 . . . 912]|qPCR probe match [842 . . . 875]

SEQ ID NO: 74

AGTACTAACATGGACTAATCTGTGGGAGCAGTTTATTCCAGTATCACCCA

GGGTGCAGCCACACCAGGACTGTGTTGAAGGGTGTTTTTTTTCTTTTAAA

TGTAATACCTCCTCATCTTTTCTTCTTACACAGTGTCTGAGAACATTTAC

ATTATAGATAAGTAGTACATGGTGGATAACTTCTACTTTTAGGAGGACTA

CTCTCTTCTGACAGTCCTAGACTGGTCTTCTACACTAAGACACCATGAAG

GAGTATGTGCTCCTATTATTCCTGGCTTTGTGCTCTGCCAAACCCTTCTT

TAGCCCTTCACACATCGCACTGAAGAATATGATGCTGAAGGATATGGAAG

-continued

ACACAGATGATGATGATGATGATGATGATGATGATGATGATGATGATGAG

GACAACTCTCTTTTTCCAACAAGAGAGCCAAGAAGCCATTTTTTTCCATT

TGATCTGTTTCCAATGTGTCCATTTGGATGTCAGTGCTATTCACGAGTTG

TACATTGCTCAGATTTAGGTTTGACCTCAGTCCCAACCAACATTCCATTT

GATACTCGAATGCTTGATCTTCAAAACAATAAAATTAAGGAAATCAAAGA

AAATGATTTTAAAGGACTCACTTCACTTTATGGTCTGATCCTGAACAACA

ACAAGCTAACGAAGATTCACCCAAAAGCCTTTCTAACCACAAAGAAGTTG

CGAAGGCTGTATCTGTCCCACAATCAACTAAGTGAAATACCACTTAATCT

TCCCAAATCATTAGCAGAACTCAGAATTCATGAAAATAAAGTTAAGAAAA

TACAAAAGGACACATTCAAAGGAATGAATGCTTTACACGTTTTGGAAATG

AGTGCAAACCCTCTTGATAATAATGGGATAGAGCCAGGGGCATTTGAAGG

GGTGACGGTGTTCCATATCAGAATTGCAGAAGCAAAACTGACCTCAGTTC

CTAAAGGCTTACCACCAACTTTATTGGAGCTTCACTTAGATTATAATAAA

ATTTCAACAGTGGAACTTGAGGATTTTAAACGATACAAAGAACTACAAAG

GCTGGGCCTAGGAAACAACAAAATCACAGATATCGAAAATGGGAGTCTTG

CTAACATACCACGTGTGAGAGAAATACATTTGGAAAACAATAAACTAAAA

AAAATCCCTTCAGGATTACCAGAGTTGAAATACCTCCAGATAATCTTCCT

TCATTCTAATTCAATTGCAAGAGTGGGAGTAAATGACTTCTGTCCAACAG

TGCCAAAGATGAAGAAATCTTTATACAGTGCAATAAGTTTATTCAACAAC

CCGGTGAAATACTGGGAAATGCAACCTGCAACATTTCGTTGTGTTTTGAG

CAGAATGAGTGTTCAGCTTGGGAACTTTGGAATGTAATAATTAGTAATTG

GTAATGTCCATTTAATATAAGATTCAAAAATCCCTACATTTGGAATACTT

GAACTCTATTAATAATGGTAGTATTATATATACAAGCAAATATCTATTCT

CAAGTGGTAAGTCCACTGACTTATTTTATGACAAGAAATTTCAACGGAAT

TTTGCCAAACTATTGATACATAAGGGTTGAGAGAAACAAGCATCTATTGC

AGTTTCTTTTTGCGTACAAATGATCTTACATAAATCTCATGCTTGACCAT

TCCTTTCTTCATAACAAAAAGTAAGATATTCGGTATTTAACACTTTGTT

ATCAAGCATATTTTAAAAAGAACTGTACTGTAAATGGAATGCTTGACTTA

GCAAAATTTGTGCTCTTTCATTTGCTGTTAGAAAAACAGAATTAACAAAG

ACAGTAATGTGAAGAGTGCATTACACTATTCTTATTCTTTAGTAACTTGG

GTAGTACTGTAATATTTTTAATCATCTTAAAGTATGATTTGATATAATCT

TATTGAAATTACCTTATCATGTCTTAGAGCCCGTCTTTATGTTTAAAACT

AATTTCTTAAAATAAAGCCTTCAGTAAATGTTCATTACCAACTTGATAAA

TGCTACTCATAAGAGCTGGTTTGGGGCTATAGCATATGCTTTTTTTTTTT

TAATTATTACCTGATTTAAAAATCTCTGTAAAAACGTGTAGTGTTTCATA

AAATCTGTAACTCGCATTTTAATGATCCGCTATTATAAGCTTTTAATAGC

ATGAAAATTGTTAGGCTATATAACATTGCCACTTCAACTCTAAGGAATAT

TTTTGAGATATCCCTTTGGAAGACCTTGCTTGGAAGAGCCTGGACACTAA

CAATTCTACACCAAATTGTCTCTTCAAATACGTATGGACTGGATAACTCT

GAGAAACACATCTAGTATAACTGAATAAGCAGAGCATCAAATTAAACAGA

CAGAAACCGAAAGCTCTATATAAATGCTCAGAGTTCTTTATGTATTTCTT

-continued

ATTGGCATTCAACATATGTAAAATCAGAAAACAGGGAAATTTTCATTAAA

AATATTGGTTTGAAATAAAAAAAAAAAAAA

Cell Growth Regulator with EF Hand Domain 1

>gi|33589823|ref|NM_006569.2| *Homo sapiens* cell growth regulator with EF hand domain 1 (CGREF1), mRNA|qPCR forward_primer match [378 . . . 394]|qPCR reverse_primer match [455 . . . 431]|qPCR probe match [396 . . . 415]

SEQ ID NO: 75

CGCGCAGCCCCTCCGGCCGCGGGCGCAGCGGGGGCGCTGGTGGAGCTGCG

AAGGGCCAGGTCCGGCGGGCGGGGCGGCGGCTGGCACTGGCTCCGGACTC

TGCCCGGCCAGGGCGGCGGCTCCAGCCGGGAGGGCGACGTGGAGCGGCCA

CGTGGAGCGGCCCGGGGGAGGCTGGCGGCGGGAGGCGAGGCGCGGGCGGC

GCAGCAGCCAGGAGCGCCCACGGAGCTGGACCCCCAGAGCCGCGCGGCGC

CGCAGCAGTTCCAGGAAGGATGTTACCTTTGACGATGACAGTGTTAATCC

TGCTGCTGCTCCCCACGGGTCAGGCTGCCCCAAAGGATGGAGTCACAAGG

CCAGACTCTGAAGTGCAGCATCAGCTCCTGCCCAACCCCTTCCAGCCAGG

CCAGGAGCAGCTCGGACTTCTGCAGAGCTACCTAAAGGGACTAGGAAGGA

CAGAAGTGCAACTGGAGCATCTGAGCCGGGAGCAGGTTCTCCTCTACCTC

TTTGCCCTCCATGACTATGACCAGAGTGGACAGCTGGATGGCCTGGAGCT

GCTGTCCATGTTGACAGCTGCTCTGGCCCCTGGAGCTGCCAACTCTCCTA

CCACCAACCCGGTGATATTGATAGTGGACAAAGTGCTCGAGACGCAGGAC

CTGAATGGGGATGGGCTCATGACCCCTGCTGAGCTCATCAACTTCCCGGG

AGTAGCCCTCAGGCACGTGGAGCCCGGAGAGCCCCTTGCTCCATCTCCTC

AGGAGCCACAAGCTGTTGGAAGGCAGTCCCTATTAGCTAAAAGCCCATTA

AGACAAGAAACACAGGAAGCCCCTGGTCCCAGAGAAGAAGCAAAGGGCCA

GGTAGAGGCCAGAAGGGAGTCTTTGGATCCTGTCCAGGAGCCTGGGGGCC

AGGCAGAGGCTGATGGAGATGTTCCAGGGCCCAGAGGGGAAGCTGAGGGC

CAGGCAGAGGCTAAAGGAGATGCCCCTGGGCCCAGAGGGGAAGCTGGGGG

CCAGGCAGAGGCTGAAGGAGATGCCCCCGGGCCCAGAGGGGAAGCTGGGG

GCCAGGCAGAGGCCAGGGAGAATGGAGAGGAGGCCAAGGAACTTCCAGGG

GAAACACTGGAGTCTAAGAACACCCAAAATGACTTTGAGGTGCACATTGT

TCAAGTGGAGAATGATGAGATCTAGATCTTGAAGATACAGGTACCCCACG

AAGTCTCAGTGCCAGAACATAAGCCCTGAAGTGGGCAGGGGAAATGTACG

CTGGGACAAGGACCATCTCTGTGCCCCCTGTCTGGTCCCAGTAGGTATCA

GGTCTTTCTGTGCAGCTCAGGGAGACCCTAAGTTAAGGGGCAGATTACCA

ATAAAGAACTGAATGAATTCATCCCCCCGGGCCACCTCTCTACCCGTCCA

GCCTGCCCAGACCCTCTCAGAGGAACGGGGTTGGGGACCGAAAGGACAGG

GATGCCGCCTGCCCAGTGTTTCTGGGCCTCACGGTGCTCCGGCAGCAGAG

CGCATGGTGCTAGCCATGGCCGGCTGCAGAGGACCCAGTGAGGAAAGCTC

AGTCTATCCCTGGGCCCCAAACCCTCACCGGTTCCCCCTCACCTGGTGTT

CAGACACCCCATGCTCTCCTGCAGCTCAGGGCAGGTGACCCCATCCCCAG

-continued

TAATATTAATCATCACTAGAACTTTTTGAGAGCCTTGTACACATCAGGCA

TCATGCTGGGCATTTTATATATGATTTTATCCTCACAATAATTCTGTAGC

CAAGCAGAATTGGTTCCATTTGACAGATGAAGAAATTGAGGCAGATTGCG

TTAAGTGCTGTACCCTAAGGTGATATGCAGCTAATTAAATGGCAGATTTG

AAAAAAAAAAAAAAAAAAAAAAAAAAAAAAAAAAAA

Kallikrein 10, Transcript Variant 1

>gi|22208981|ref|NM_002776.3| *Homo sapiens* kallikrein 10 (KLK10), transcript variant 1, mRNA|qPCR forward_primer match [851 . . . 874]|qPCR reverse_primer match [950 . . . 931]|qPCR probe match [890 . . . 914]

SEQ ID NO: 76

CATCCTGCCACCCCTAGCCTTGCTGGGGACGTGAACCCTCTCCCCGCGCC

TGGGAAGCCTTCTTGGCACCGGGACCCGGAGAATCCCCACGGAAGCCAGT

TCCAAAAGGGATGAAAAGGGGGCGTTTCGGGCACTGGGAGAAGCCTGTAT

TCCAGGGCCCCTCCCAGAGCAGGAATCTGGGACCCAGGAGTGCCAGCCTC

ACCCACGCAGATCCTGGCCATGAGAGCTCCGCACCTCCACCTCTCCGCCG

CCTCTGGCGCCCGGGCTCTGGCGAAGCTGCTGCCGCTGCTGATGGCGCAA

CTCTGGGCCGCAGAGGCGGCGCTGCTCCCCCAAAACGACACGCGCTTGGA

CCCCGAAGCCTATGGCTCCCCGTGCGCGCGCGGCTCGCAGCCCTGGCAGG

TCTCGCTCTTCAACGGCCTCTCGTTCCACTGCGCGGGTGTCCTGGTGGAC

CAGAGTTGGGTGCTGACGGCCGCGCACTGCGGAAACAAGCCACTGTGGGC

TCGAGTAGGGGATGACCACCTGCTGCTTCTTCAGGGAGAGCAGCTCCGCC

GGACCACTCGCTCTGTTGTCCATCCCAAGTACCACCAGGGCTCAGGCCCC

ATCCTGCCAAGGCGAACGGATGAGCACGATCTCATGTTGCTGAAGCTGGC

CAGGCCCGTAGTGCTGGGGCCCCGCGTCCGGGCCCTGCAGCTTCCCTACC

GCTGTGCTCAGCCCGGAGACCAGTGCCAGGTTGCTGGCTGGGGCACCACG

GCCGCCCGGAGAGTGAAGTACAACAAGGGCCTGACCTGCTCCAGCATCAC

TATCCTGAGCCCTAAAGAGTGTGAGGTCTTCTACCCTGGCGTGGTCACCA

ACAACATGATATGTGCTGGACTGGACCGGGGCCAGGACCCTTGCCAGAGT

GACTCTGGAGGCCCCCTGGTCTGTGACGAGACCCTCCAAGGCATCCTCTC

GTGGGGTGTTTACCCCTGTGGCTCTGCCCAGCATCCAGCTGTCTACACCC

AGATCTGCAAATACATGTCCTGGATCAATAAAGTCATACGCTCCAACTGA

TCCAGATGCTACGCTCCAGCTGATCCAGATGTTATGCTCCTGCTGATCCA

GATGCCCAGAGGCTCCATCGTCCATCCTCTTCCTCCCCAGTCGGCTGAAC

TCTCCCCTTGTCTGCACTGTTCAAACCTCTGCCGCCCTCCACACCTCTAA

ACATCTCCCCTCTCACCTCATTCCCCCACCTATCCCCATTCTCTGCCTGT

ACTGAAGCTGAAATGCAGGAAGTGGTGGCAAAGGTTTATTCCAGAGAAGC

CAGGAAGCCGGTCATCACCCAGCCTCTGAGAGCAGTTACTGGGGTCACCC

AACCTGACTTCCTCTGCCACTCCCTGCTGTGTGACTTTGGGCAAGCCAAG

TGCCCTCTCTGAACCTCAGTTTCCTCATCTGCAAAATGGGAACAATGACG

TGCCTACCTCTTAGACATGTTGTGAGGAGACTATGATATAACATGTGTAT

-continued

GTAAATCTTCATGGTGATTGTCATGTAAGGCTTAACACAGTGGGTGGTGA

GTTCTGACTAAAGGTTACCTGTTGTCGTGA

Kallikrein 10 Transcript Variant 2

>gi|22208983|ref|NM_145888.1| *Homo sapiens* kallikrein 10 (KLK10), transcript variant 2, mRNA|qPCR forward_primer match [714 . . . 737]|qPCR reverse_primer match [813 . . . 794]|qPCR probe match [753 . . . 777]

SEQ ID NO: 77

ACCAGCGGCAGACCACAGGCAGGGCAGAGGCACGTCTGGGTCCCCTCCCT

CCTTCCTATCGGCGACTCCCAGGATCCTGGCCATGAGAGCTCCGCACCTC

CACCTCTCCGCCGCCTCTGGCGCCCGGGCTCTGGCGAAGCTGCTGCCGCT

GCTGATGGCGCAACTCTGGGCCGCAGAGGCGGCGCTGCTCCCCCAAAACG

ACACGCGCTTGGACCCCGAAGCCTATGGCTCCCCGTGCGCGCGCGGCTCG

CAGCCCTGGCAGGTCTCGCTCTTCAACGGCCTCTCGTTCCACTGCGCGGG

TGTCCTGGTGGACCAGAGTTGGGTGCTGACGGCCGCGCACTGCGGAAACA

AGCCACTGTGGGCTCGAGTAGGGGATGACCACCTGCTGCTTCTTCAGGGA

GAGCAGCTCCGCCGGACCACTCGCTCTGTTGTCCATCCCAAGTACCACCA

GGGCTCAGGCCCCATCCTGCCAAGGCGAACGGATGAGCACGATCTCATGT

TGCTGAAGCTGGCCAGGCCCGTAGTGCTGGGGCCCCGCGTCCGGGCCCTG

CAGCTTCCCTACCGCTGTGCTCAGCCCGGAGACCAGTGCCAGGTTGCTGG

CTGGGGCACCACGGCCGCCCGGAGAGTGAAGTACAACAAGGGCCTGACCT

GCTCCAGCATCACTATCCTGAGCCCTAAAGAGTGTGAGGTCTTCTACCCT

GGCGTGGTCACCAACAACATGATATGTGCTGGACTGGACCGGGGCCAGGA

CCCTTGCCAGAGTGACTCTGGAGGCCCCCTGGTCTGTGACGAGACCCTCC

AAGGCATCCTCTCGTGGGGTGTTTACCCCTGTGGCTCTGCCCAGCATCCA

GCTGTCTACACCCAGATCTGCAAATACATGTCCTGGATCAATAAAGTCAT

ACGCTCCAACTGATCCAGATGCTACGCTCCAGCTGATCCAGATGTTATGC

TCCTGCTGATCCAGATGCCCAGAGGCTCCATCGTCCATCCTCTTCCTCCC

CAGTCGGCTGAACTCTCCCCTTGTCTGCACTGTTCAAACCTCTGCCGCCC

TCCACACCTCTAAACATCTCCCCTCTCACCTCATTCCCCCACCTATCCCC

ATTCTCTGCCTGTACTGAAGCTGAAATGCAGGAAGTGGTGGCAAAGGTTT

ATTCCAGAGAAGCCAGGAAGCCGGTCATCACCCAGCCTCTGAGAGCAGTT

ACTGGGGTCACCCAACCTGACTTCCTCTGCCACTCCCTGCTGTGTGACTT

TGGGCAAGCCAAGTGCCCTCTCTGAACCTCAGTTTCCTCATCTGCAAAAT

GGGAACAATGACGTGCCTACCTCTTAGACATGTTGTGAGGAGACTATGAT

ATAACATGTGTATGTAAATCTTCATGGTGATTGTCATGTAAGGCTTAACA

CAGTGGGTGGTGAGTTCTGACTAAAGGTTACCTGTTGTCGTGA

Tissue Inhibitor of Metalloproteinase 1

>gi|4507508|ref|NM_003254.1| *Homo sapiens* tissue inhibitor of metalloproteinase 1 (erythroid potentiating activity, collagenase inhibitor) (TIMP1), mRNA|qPCR forward_primer match [221 . . . 241]|qPCR reverse_primer match [359 . . . 340]|qPCR probe match [251 . . . 283]

SEQ ID NO: 78

AGGGGCCTTAGCGTGCCGCATCGCCGAGATCCAGCGCCCAGAGAGACACC

AGAGAACCCACCATGGCCCCCTTTGAGCCCCTGGCTTCTGGCATCCTGTT

GTTGCTGTGGCTGATAGCCCCCAGCAGGGCCTGCACCTGTGTCCCACCCC

ACCCACAGACGGCCTTCTGCAATTCCGACCTCGTCATCAGGGCCAAGTTC

GTGGGGACACCAGAAGTCAACCAGACCACCTTATACCAGCGTTATGAGAT

CAAGATGACCAAGATGTATAAAGGGTTCCAAGCCTTAGGGGATGCCGCTG

ACATCCGGTTCGTCTACACCCCCGCCATGGAGAGTGTCTGCGGATACTTC

CACAGGTCCCACAACCGCAGCGAGGAGTTTCTCATTGCTGGAAAACTGCA

GGATGGACTCTTGCACATCACTACCTGCAGTTTCGTGGCTCCCTGGAACA

GCCTGAGCTTAGCTCAGCGCCGGGGCTTCACCAAGACCTACACTGTTGGC

TGTGAGGAATGCACAGTGTTTCCCTGTTTATCCATCCCCTGCAAACTGCA

GAGTGGCACTCATTGCTTGTGGACGGACCAGCTCCTCCAAGGCTCTGAAA

AGGGCTTCCAGTCCCGTCACCTTGCCTGCCTGCCTCGGGAGCCAGGGCTG

TGCACCTGGCAGTCCCTGCGGTCCCAGATAGCCTGAATCCTGCCCGGAGT

GGAACTGAAGCCTGCACAGTGTCCACCCTGTTCCCACTCCCATCTTTCTT

CCGGACAATGAAATAAAGAGTTACCACCCAGC

Secreted Protein, Acidic, Cysteine-Rich

>gi|48675809|ref|NM_003 118.2| *Homo sapiens* secreted protein, acidic, cysteine-rich (osteonectin) (SPARC), mRNA|qPCR forward_primer match [788 . . . 810]|qPCR reverse_primer match [915 . . . 898]|qPCR probe match [818 . . . 839]

SEQ ID NO: 79

GTTGCCTGTCTCTAAACCCCTCCACATTCCCGCGGTCCTTCAGACTGCCC

GGAGAGCGCGCTCTGCCTGCCGCCTGCCTGCCTGCCACTGAGGGTTCCCA

GCACCATGAGGGCCTGGATCTTCTTTCTCCTTTGCCTGGCCGGGAGGGCC

TTGGCAGCCCCTCAGCAAGAAGCCCTGCCTGATGAGACAGAGGTGGTGGA

AGAAACTGTGGCAGAGGTGACTGAGGTATCTGTGGGAGCTAATCCTGTCC

AGGTGGAAGTAGGAGAATTTGATGATGGTGCAGAGGAAACCGAAGAGGAG

GTGGTGGCGGAAAATCCCTGCCAGAACCACCACTGCAAACACGGCAAGGT

GTGCGAGCTGGATGAGAACAACACCCCCATGTGCGTGTGCCAGGACCCCA

CCAGCTGCCCAGCCCCCATTGGCGAGTTTGAGAAGGTGTGCAGCAATGAC

AACAAGACCTTCGACTCTTCCTGCCACTTCTTTGCCACAAAGTGCACCCT

GGAGGGCACCAAGAAGGGCCACAAGCTCCACCTGGACTACATCGGGCCTT

GCAAATACATCCCCCCTTGCCTGGACTCTGAGCTGACCGAATTCCCCCTG

CGCATGCGGGACTGGCTCAAGAACGTCCTGGTCACCCTGTATGAGAGGGA

TGAGGACAACAACCTTCTGACTGAGAAGCAGAAGCTGCGGGTGAAGAAGA

TCCATGAGAATGAGAAGCGCCTGGAGGCAGGAGACCACCCCGTGGAGCTG

CTGGCCCGGGACTTCGAGAAGAACTATAACATGTACATCTTCCCTGTACA

CTGGCAGTTCGGCCAGCTGGACCAGCACCCCATTGACGGGTACCTCTCCC

ACACCGAGCTGGCTCCACTGCGTGCTCCCCTCATCCCCATGGAGCATTGC

ACCACCCGCTTTTTCGAGACCTGTGACCTGGACAATGACAAGTACATCGC

-continued

CCTGGATGAGTGGGCCGGCTGCTTCGGCATCAAGCAGAAGGATATCGACA

AGGATCTTGTGATCTAAATCCACTCCTTCCACAGTACCGGATTCTCTCTT

TAACCCTCCCCTTCGTGTTTCCCCCAATGTTTAAAATGTTTGGATGGTTT

GTTGTTCTGCCTGGAGACAAGGTGCTAACATAGATTTAAGTGAATACATT

AACGGTGCTAAAAATGAAAATTCTAACCCAAGACATGACATTCTTAGCTG

TAACTTAACTATTAAGGCCTTTTCCACACGCATTAATAGTCCCATTTTTC

TCTTGCCATTTGTAGCTTTGCCCATTGTCTTATTGGCACATGGGTGGACA

CGGATCTGCTGGGCTCTGCCTTAAACACACATTGCAGCTTCAACTTTTCT

CTTTAGTGTTCTGTTTGAAACTAATACTTACCGAGTCAGACTTTGTGTTC

ATTTCATTTCAGGGTCTTGGCTGCCTGTGGGCTTCCCCAGGTGGCCTGGA

GGTGGGCAAAGGGAAGTAACAGACACACGATGTTGTCAAGGATGGTTTTG

GGACTAGAGGCTCAGTGGTGGGAGAGATCCCTGCAGAACCCACCAACCAG

AACGTGGTTTGCCTGAGGCTGTAACTGAGAGAAAGATTCTGGGGCTGTGT

TATGAAAATATAGACATTCTCACATAAGCCCAGTTCATCACCATTTCCTC

CTTTACCTTTCAGTGCAGTTTCTTTTCACATTAGGCTGTTGGTTCAAACT

TTTGGGAGCACGGACTGTCAGTTCTCTGGGAAGTGGTCAGCGCATCCTGC

AGGGCTTCTCCTCCTCTGTCTTTTGGAGAACCAGGGCTCTTCTCAGGGGC

TCTAGGGACTGCCAGGCTGTTTCAGCCAGGAAGGCCAAAATCAAGAGTGA

GATGTAGAAAGTTGTAAAATAGAAAAAGTGGAGTTGGTGAATCGGTTGTT

CTTTCCTCACATTTGGATGATTGTCATAAGGTTTTTAGCATGTTCCTCCT

TTTCTTCACCCTCCCCTTTTTTCTTCTATTAATCAAGAGAAACTTCAAAG

TTAATGGGATGGTCGGATCTCACAGGCTGAGAACTCGTTCACCTCCAAGC

ATTTCATGAAAAAGCTGCTTCTTATTAATCATACAAACTCTCACCATGAT

GTGAAGAGTTTCACAAATCCTTCAAAATAAAAAGTAATGACTTAGAAACT

GCCTTCCTGGGTGATTTGCATGTGTCTTAGTCTTAGTCACCTTATTATCC

TGACACAAAAACACATGAGCATACATGTCTACACATGACTACACAAATGC

AAACCTTTGCAAACACATTATGCTTTTGCACACACACACCTGTACACACA

CACCGGCATGTTTATACACAGGGAGTGTATGGTTCCTGTAAGCACTAAGT

TAGCTGTTTTCATTTAATGACCTGTGGTTTAACCCTTTTGATCACTACCA

CCATTATCAGCACCAGACTGAGCAGCTATATCCTTTTATTAATCATGGTC

ATTCATTCATTCATTCATTCACAAAATATTTATGATGTATTTACTCTGCA

CCAGGTCCCATGCCAAGCACTGGGGACACAGTTATGGCAAAGTAGACAAA

GCATTTGTTCATTTGGAGCTTAGAGTCCAGGAGGAATACATTAGATAATG

ACACAATCAAATATAAATTGCAAGATGTCACAGGTGTGATGAAGGGAGAG

TAGGAGAGACCATGAGTATGTGTAACAGGAGGACACAGCATTATTCTAGT

GCTGTACTGTTCCGTACGGCAGCCACTACCCACATGTAACTTTTTAAGAT

TTAAATTTAAATTAGTTAACATTCAAAACGCAGCTCCCCAATCACACTAG

CAACATTTCAAGTGCTTGAGAGCCATGCATGATTAGTGGTTACCCTATTG

AATAGGTCAGAAGTAGAATCTTTTCATCATCACAGAAAGTTCTATTGGAC

AGTGCTCTTCTAGATCATCATAAGACTACAGAGCACTTTTCAAAGCTCAT

-continued

GCATGTTCATCATGTTAGTGTCGTATTTTGAGCTGGGGTTTTGAGACTCC

CCTTAGAGATAGAGAAACAGACCCAAGAAATGTGCTCAATTGCAATGGGC

CACATACCTAGATCTCCAGATGTCATTTCCCCTCTCTTATTTTAAGTTAT

GTTAAGATTACTAAAACAATAAAAGCTCCTAAAAAATCAAAAAAAAAAAA

AAAAAAAAAAAAAAAAAAAAAAAAAAA

Transforming Growth Factor, Beta-Induced

>gi|4507466|ref|NM_000358.1| *Homo sapiens* transforming growth factor, beta-induced, 68 kDa (TGIFBI), mRNA|qPCR assay_on_demand_context match [170 . . . 194]

SEQ ID NO: 80

GCTTGCCCGTCGGTCGCTAGCTCGCTCGGTGCGCGTCGTCCCGCTCCATG

GCGCTCTTCGTGCGGCTGCTGGCTCTCGCCCTGGCTCTGGCCCTGGGCCC

CGCCGCGACCCTGGCGGGTCCCGCCAAGTCGCCCTACCAGCTGGTGCTGC

AGCACAGCAGGCTCCGGGGCCGCCAGCACGGCCCCAACGTGTGTGCTGTG

CAGAAGGTTATTGGCACTAATAGGAAGTACTTCACCAACTGCAAGCAGTG

GTACCAAAGGAAAATCTGTGGCAAATCAACAGTCATCAGCTACGAGTGCT

GTCCTGGATATGAAAAGGTCCCTGGGGAGAAGGGCTGTCCAGCAGCCCTA

CCACTCTCAAACCTTTACGAGACCCTGGGAGTCGTTGGATCCACCACCAC

TCAGCTGTACACGGACCGCACGGAGAAGCTGAGGCCTGAGATGGAGGGGC

CCGGCAGCTTCACCATCTTCGCCCCTAGCAACGAGGCCTGGGCCTCCTTG

CCAGCTGAAGTGCTGGACTCCCTGGTCAGCAATGTCAACATTGAGCTGCT

CAATGCCCTCCGCTACCATATGGTGGGCAGGCGAGTCCTGACTGATGAGC

TGAAACACGGCATGACCCTCACCTCTATGTACCAGAATTCCAACATCCAG

ATCCACCACTATCCTAATGGGATTGTAACTGTGAACTGTGCCCGGCTCCT

GAAAGCCGACCACCATGCAACCAACGGGGTGGTGCACCTCATCGATAAGG

TCATCTCCACCATCACCAACAACATCCAGCAGATCATTGAGATCGAGGAC

ACCTTTGAGACCCTTCGGGCTGCTGTGGCTGCATCAGGGCTCAACACGAT

GCTTGAAGGTAACGGCCAGTACACGCTTTTGGCCCCGACCAATGAGGCCT

TCGAGAAGATCCCTAGTGAGACTTTGAACCGTATCCTGGGCGACCCAGAA

GCCCTGAGAGACCTGCTGAACAACCACATCTTGAAGTCAGCTATGTGTGC

TGAAGCCATCGTTGCGGGGCTGTCTGTAGAGACCCTGGAGGGCACGACAC

TGGAGGTGGGCTGCAGCGGGGACATGCTCACTATCAACGGGAAGGCGATC

ATCTCCAATAAAGACATCCTAGCCACCAACGGGGTGATCCACTACATTGA

TGAGCTACTCATCCCAGACTCAGCCAAGACACTATTTGAATTGGCTGCAG

AGTCTGATGTGTCCACAGCCATTGACCTTTTCAGACAAGCCGGCCTCGGC

AATCATCTCTCTGGAAGTGAGCGGTTGACCCTCCTGGCTCCCCTGAATTC

TGTATTCAAAGATGGAACCCCTCCAATTGATGCCCATACAAGGAATTTGC

TTCGGAACCACATAATTAAAGACCAGCTGGCCTCTAAGTATCTGTACCAT

GGACAGACCCTGGAAACTCTGGGCGGCAAAAAACTGAGAGTTTTTGTTTA

TCGTAATAGCCTCTGCATTGAGAACAGCTGCATCGCGGCCCACGACAAGA

GGGGGAGGTACGGGACCCTGTTCACGATGGACCGGGTGCTGACCCCCCCA

-continued

ATGGGGACTGTCATGGATGTCCTGAAGGGAGACAATCGCTTTAGCATGCT

GGTAGCTGCCATCCAGTCTGCAGGACTGACGGAGACCCTCAACCGGGAAG

GAGTCTACACAGTCTTTGCTCCCACAAATGAAGCCTTCCGAGCCCTGCCA

CCAAGAGAACGGAGCAGACTCTTGGGAGATGCCAAGGAACTTGCCAACAT

CCTGAAATACCACATTGGTGATGAAATCCTGGTTAGCGGAGGCATCGGGG

CCCTGGTGCGGCTAAAGTCTCTCCAAGGTGACAAGCTGGAAGTCAGCTTG

AAAAACAATGTGGTGAGTGTCAACAAGGAGCCTGTTGCCGAGCCTGACAT

CATGGCCACAAATGGCGTGGTCCATGTCATCACCAATGTTCTGCAGCCTC

CAGCCAACAGACCTCAGGAAAGAGGGGATGAACTTGCAGACTCTGCGCTT

GAGATCTTCAAACAAGCATCAGCGTTTTCCAGGGCTTCCCAGAGGTCTGT

GCGACTAGCCCCTGTCTATCAAAAGTTATTAGAGAGGATGAAGCATTAGC

TTGAAGCACTACAGGAGGAATGCACCACGGCAGCTCTCCGCCAATTTCTC

TCAGATTTCCACAGAGACTGTTTGAATGTTTTCAAAACCAAGTATCACAC

TTTAATGTACATGGGCCGCACCATAATGAGATGTGAGCCTTGTGCATGTG

GGGGAGGAGGGAGAGAGATGTACTTTTTAAATCATGTTCCCCCTAAACAT

GGCTGTTAACCCACTGCATGCAGAAACTTGGATGTCACTGCCTGACATTC

ACTTCCAGAGAGGACCTATCCCAAATGTGGAATTGACTGCCTATGCCAAG

TCCCTGGAAAAGGAGCTTCAGTATTGTGGGGCTCATAAAACATGAATCAA

GCAATCCAGCCTCATGGGAAGTCCTGGCACAGTTTTTGTAAAGCCCTTGC

ACAGCTGGAGAAATGGCATCATTATAAGCTATGAGTTGAAATGTTCTGTC

AAATGTGTCTCACATCTACACGTGGCTTGGAGGCTTTTATGGGGCCCTGT

CCAGGTAGAAAAGAAATGGTATGTAGAGCTTAGATTTCCCTATTGTGACA

GAGCCATGGTGTGTTTGTAATAATAAAACCAAAGAAACATA

EGF-Containing Fibulin-Like Extracellular Matrix Protein 2

>gi|8393298|ref|NM_016938.1| *Homo sapiens* EGF-containing fibulin-like extracellular matrix protein 2 (EFEMP2), mRNA|qPCR assay_on_demand_context match [1248 . . . 1272]

SEQ ID NO: 81

CAAGCTTGGCACGAGGGCAGGCATTGCCCGAGCCAGCCGAGCCGCCAGAG

CCGCGGGCCGCGCGGGTGTCGCGGGCCCAACCCCAGGATGCTCCCCTGCG

CCTCCTGCCTACCCGGGTCTCTACTGCTCTGGGCGCTGCTACTGTTGCTC

TTGGGATCAGCTTCTCCTCAGGATTCTGAAGAGCCCGACAGCTACACGGA

ATGCACAGATGGCTATGAGTGGGACCCAGACAGCCAGCACTGCCGGGATG

TCAACGAGTGTCTGACCATCCCTGAGGCCTGCAAGGGGGAAATGAAGTGC

ATCAACCACTACGGGGGCTACTTGTGCCTGCCCCGCTCCGCTGCCGTCAT

CAACGACCTACACGGCGAGGGACCCCCGCCACCAGTGCCTCCCGCTCAAC

ACCCCAACCCCTGCCCACCAGGCTATGAGCCCGACGATCAGGACAGCTGT

GTGGATGTGGACGAGTGTGCCCAGGCCCTGCACGACTGTCGCCCCAGCCA

GGACTGCCATAACTTGCCTGGCTCCTATCAGTGCACCTGCCCTGATGGTT

ACCGCAAGATCGGGCCCGAGTGTGTGGACATAGACGAGTGCCGCTACCGC

-continued

TACTGCCAGCACCGCTGCGTGAACCTGCCTGGCTCCTTCCGCTGCCAGTG
CGAGCCGGGCTTCCAGCTGGGGCCTAACAACCGCTCCTGTGTTGATGTGA
ACGAGTGTGACATGGGGGCCCCATGCGAGCAGCGCTGCTTCAACTCCTAT
GGGACCTTCCTGTGTCGCTGCCACCAGGGCTATGAGCTGCATCGGGATGG
CTTCTCCTGCAGTGATATTGATGAGTGTAGCTACTCCAGCTACCTCTGTC
AGTACCGCTGCGTCAACGAGCCAGGCCGTTTCTCCTGCCACTGCCCACAG
GGTTACCAGCTGCTGGCCACACGCCTCTGCCAAGACATTGATGAGTGTGA
GTCTGGTGCGCACCAGTGCTCCGAGGCCCAAACCTGTGTCAACTTCCATG
GGGGCTACCGCTGCGTGGACACCAACCGCTGCGTGGAGCCCTACATCCAG
GTCTCTGAGAACCGCTGTCTCTGCCCGGCCTCCAACCCTCTATGTCGAGA
GCAGCCTTCATCCATTGTGCACCGCTACATGACCATCACCTCGGAGCGGA
GAGTACCCGCTGACGTGTTCCAGATCCAGGCGACCTCCGTCTACCCCGGT
GCCTACAATGCCTTTCAGATCCGTGCTGGAAACTCGCAGGGGGACTTTTA
CATTAGGCAAATCAACAACGTCAGCGCCATGCTGGTCCTCGCCCGGCCGG
TGACGGGCCCCCGGGAGTACGTGCTGGACCTGGAGATGGTCACCATGAAT
TCCCTCATGAGCTACCGGGCCAGCTCTGTACTGAGGCTCACCGTCTTTGT
AGGGGCCTACACCTTCTGAGGAGCAGGAGGGAGCCACCCTCCCTGCAGCT
ACCCTAGCTGAGGAGCCTGTTGTGAGGGGCAGAATGAGAAAGGCCCAGGG
GCCCCCATTGACAGGAGCTGGGAGCTCTGCACCACGAGCTTCAGTCACCC
CGAGAGGAGAGGAGGTAACGAGGAGGGCGGACTCCAGGCCCCGGCCCAGA
GATTTGGACTTGGCTGGCTTGCAGGGGTCCTAAGAAACTCCACTCTGGAC
AGCGCCAGGAGGCCCTGGGTTCCATTCCTAACTCTGCCTCAAACTGTACA
TTTGGATAAGCCCTAGTAGTTCCCTGGGCCTGTTTTTCTATAAAACGAGG
CAACTGG

Lumican

>gi|21359858|ref|NM_002345.2| *Homo sapiens* lumican (LUM), mRNA|qPCR forward_primer match [61 . . . 84]|qPCR reverse_primer match [182 . . . 162]1 qPCR probe match [117 . . . 152]

SEQ ID NO: 82

GTATCACTCAGAATCTGGCAGCCAGTTCCGTCCTGACAGAGTTCACAGCA
TATATTGGTGGATTCTTGTCCATAGTGCATCTGCTTTAAGAATTAACGAA
AGCAGTGTCAAGACAGTAAGGATTCAAACCATTTGCCAAAAATGAGTCTA
AGTGCATTTACTCTCTTCCTGGCATTGATTGGTGGTACCAGTGGCCAGTA
CTATGATTATGATTTTCCCCTATCAATTTATGGGCAATCATCACCAAACT
GTGCACCAGAATGTAACTGCCCTGAAAGCTACCCAAGTGCCATGTACTGT
GATGAGCTGAAATTGAAAAGTGTACCAATGGTGCCTCCTGGAATCAAGTA
TCTTTACCTTAGGAATAACCAGATTGACCATATTGATGAAAAGGCCTTTG
AGAATGTAACTGATCTGCAGTGGCTCATTCTAGATCACAACCTTCTAGAA
AACTCCAAGATAAAAGGGAGAGTTTTCTCTAAATTGAAACAACTGAAGAA
GCTGCATATAAACCACAACAACCTGACAGAGTCTGTGGGCCCACTTCCCA

-continued

AATCTCTGGAGGATCTGCAGCTTACTCATAACAAGATCACAAAGCTGGGC
TCTTTTGAAGGATTGGTAAACCTGACCTTCATCCATCTCCAGCACAATCG
GCTGAAAGAGGATGCTGTTTCAGCTGCTTTTAAAGGTCTTAAATCACTCG
AATACCTTGACTTGAGCTTCAATCAGATAGCCAGACTGCCTTCTGGTCTC
CCTGTCTCTCTTCTAACTCTCTACTTAGACAACAATAAGATCAGCAACAT
CCCTGATGAGTATTTCAAGCGTTTTAATGCATTGCAGTATCTGCGTTTAT
CTCACAACGAACTGGCTGATAGTGGAATACCTGGAAATTCTTTCAATGTG
TCATCCCTGGTTGAGCTGGATCTGTCCTATAACAAGCTTAAAAACATACC
AACTGTCAATGAAAACCTTGAAAACTATTACCTGGAGGTCAATCAACTTG
AGAAGTTTGACATAAAGAGCTTCTGCAAGATCCTGGGGCCATTATCCTAC
TCCAAGATCAAGCATTTGCGTTTGGATGGCAATCGCATCTCAGAAACCAG
TCTTCCACCGGATATGTATGAATGTCTACGTGTTGCTAACGAAGTCACTC
TTAATTAATATCTGTATCCTGGAACAATATTTTATGGTTATGTTTTTCTG
TGTGTCAGTTTTCATAGTATCCATATTTTATTACTGTTTATTACTTCCAT
GAATTTTAAAATCTGAGGGAAATGTTTTGTAAACATTTATTTTTTTTAAA
GAAAAGATGAAAGGCAGGCCTATTTCATCACAAGAACACACACATATACA
CGAATAGACATCAAACTCAATGCTTTATTTGTAAATTTAGTGTTTTTTTA
TTTCTACTGTCAAATGATGTGCAAAACCTTTTACTGGTTGCATGGAAATC
AGCCAAGTTTTATAATCCTTAAATCTTAATGTTCCTCAAAGCTTGGATTA
AATACATATGGATGTTACTCTCTTGCACCAAATTATCTTGATACATTCAA
ATTTGTCTGGTTAAAAAATAGGTGGTAGATATTGAGGCCAAGAATATTGC
AAAATACATGAAGCTTCATGCACTTAAAGAAGTATTTTTAGAATAAGAAT
TTGCATACTTACCTAGTGAAACTTTTCTAGAATTATTTTTCACTCTAAGT
CATGTATGTTTCTCTTTGATTATTTGCATGTTATGTTTAATAAGCTACTA
GCAAAATAAAACATAGCAAATGAAAAAAAAAAAAAAAAAAAAAAAAAAAA
AAAA

Stannin

>gi|29893560|ref|NM_003498.3| *Homo sapiens* stannin (SNN), mRNA

SEQ ID NO: 83

AGCGGGGCCGGACCGGGCGGGCGGAGCCGGGCCCGCGGGGCTGCTGCGGG
GCGATCGGGCCGGGCCGCTGCCGCGCCATGGACTCCCGTGTCCAGCCTGA
GTTCCAGCCTCACTGAGTGGCCACCCCCAAAGTGCTGCCAGCCGAGGAAG
CCCCCAGCACTGACCATGTCTATTATGGACCACAGCCCCACCACGGGCGT
GGTCACAGTCATCGTCATCCTCATTGCCATCGCGGCCCTGGGGGCCTTGA
TCCTGGGCTGCTGGTGCTACCTGCGGCTGCAGCGCATCAGCCAGTCAGAG
GACGAGGAGAGCATCGTGGGGGATGGGGAGACCAAGGAACCCTTCCTGCT
GGTGCAGTATTCGGCCAAGGGACCGTGCGTGGAGAGAAAGGCCAAGCTGA
TGACTCCCAACGGCCCGGAAGTCCACGGCTGAGCCAGGATGCAAGGCTCC
TGGTCCTGTTTGCAGCCGGCCAAGAGGCGCTGGGAGGGGCAAAACCATAC
GGATGCGCTGCTGTCTGAGAGGAAGGGCTGACACTTGCTGGCATGGCCTC

-continued

TGCGGGCTTCGTCATCGCATGCACTGATGCCCGGGGACCTGGCTGTCCTG
GGCTTCCCCTCGGCCTCCAGGTGAGGCTGCCCATTGCAGGCACTGGGCAG
GCCTGACCTTGCTGGGGCTCATGGCCCTGTAGCGCTTTTGTTACTTGAAT
GTCTAGCTGAGCCTGTTTTTGATGGAGCTACTACTGTAATGCGTGAACTA
ACAAACCTGTGAACTGTAAATAGGCCCCTGGAAGCACGTGCTTAAGCCCT
TTTGCTGATTTTTAAAAATATCATCTAGCGCACACGGGACTGGTATTCTG
GCTGTACTAATGACAAGCTGAGTCAAGACCCTGGAGGGTCATAGGCTTGT
AAAGGCCCACGCCACACTCGGCAGGGGTCTCTCATGTGTGTCCATCTGCG
TGTATGTCAAGGAAGTGAGATGCCAATTTGGGGTCTTGAGGCTGACCAGT
TGGGGTGCTTGGGTGATCTCTGCTTCATTAGTCATGGGTGGAAGAAAAAC
CACACCCCCCGCACCCCTCCGTTCTTTCTGCATAGACTCACTTGTTAAAT
AGCAGTTCTGTTGAGAGTGGAGTTACTGCAGGGAAGCTACCGGACCTGCC
TGGGAGCCAGTGAAGGGCGAGTCAGGGCACGCGTCCTGGAGGCTGCCAGC
GTCGTTGTAGCAGAGCAGTTTCTTGCCGCTTGGGTCTTCAGCACGCCAAG
CCCCCCACCAACCCTCCACCCCGAGTGAAGGCTTCGCTGAAATTGCTTTG
GTCCTCATAGAGCCTGTGGTGGCTACTTTTGGTCTGAAACCCACTTGGCC
CAGGAAAGAGAAAAGGTTGTATGTTTTGTGTTGGTGTTTCCTATTTTCTG
CACTGGAGGGGAGGGGACTGTTGAGGTTCTGTCTTTTTTCTTCTTTTCCT
CTTCCCTCTTCACATCACTTGGCTTCCTTTCCTCTCTGATGACCGTCCGC
CTATGGGGTTCTGACTTCACTTTCCTCAGCGGGTCTCCAGTCCCCTGACC
CAGCTCTAAAGGCACTTAGGACCCAGGGAACATTTCTCACGTGCACATTC
CCCTAAGAGCCACCAGACTGCTTCCTGCCAGCCTGTGCTTGCGGCAGGGA
GCCGGGGCAGGGCAGAGGTGAACTTGAAGTTCAGGACTTGACTCTCCCAC
AGGTGGTGAGCTGGTGGCTCTCTGGTGAGCTAGTGTCTCCACAGCCTGTC
TCCAAGGCCTCCCCTATGTACATTTCAGTGAGCTCACTTTGATTTTTAAT
CCCACCACAAGCACATACTAATTTTATTTATGATTCAAATGTGACTCGTG
CCTGCCCATCCCTGTAATAGATGGAAGGTCAGCCCCGGCTTAACCACAGA
GCACTGGCCCTTCATGGCTGAGCTCAGAGCTCTGGCCTCCTGCTCAGACT
AAAGGCACCTCCTCTGGCCTCACCCAAGCCTCTTCTAAAAACCATGTTGA
ATGAATCCACGTTCTGGAACCCCGAGGCGGGAGAAGTAGGGAGCTGTTCG
TTTAAGCAGCATACACCTAAATTGGGGGTTTAAACATTAAGTAGGAGCTT
GGGGTGGAAGAGGGACAGCCGGCTGGGCCACCTGAGCAGAAGGTGGTAAT
GAAACACCTCAGCTGGGCTCTTGGGAGACCTTAGGAAGCAGGAGAGGCAA
CACCTCTGGCTACTGATGGTGTGGCAAGTTCAGAAGAGGTGGTGGTGGGG
TAGGCGTGATGTCAGCAGAAGCCCTGCAGGCTGGGTGGGCAGGACACGTG
GTGGGGGCCACTGAAACCAGGCCTAGGAGGGAGAACAAGTTCCAAAGGTG
CCGACTGGAAGAAGGGGGTAAAAGTTTGCTTTGGTGAGTGAGAAAAGGCT
GGGGCGTGTGATCCATCCCCTCACGTTTCAGAACTTCCAGGCTTTCTACC
TCGACTCTCACCACAGCCAGCACATACACCTAGGCTGTTTTTCCTTCCTC
CACACCTGAGGGACGCAGCAACAGCTAGGATCTGCATTTTCAGGTTCCGA
GCCTGACCCCTGGAACTGACCAGCGCTCGATTGTCAGCCTTGGCCTGGGG

-continued

TTTTGACCTTGCCAGTGAAGTTTCGGTTTTGAAGTGATTAAATGTCACTT
CCTCATCAGTTTCACTTCTGGAGGTTTTCTTATCCTACTCCCTGGTGCCA
GGGACGTACCTGGGAGTTTGAATCAGGCCCATTTGAGCGTGGCAGCCGTG
TTGGGTGAAGGTCCGGGGCTCGGTGAGGCACTGGGGGGGTTTTCGGGAGG
AAAATGAAAATGCTTCTAGAATGAGTGAACCACATCATAGCTCTCACTGT
TTTTTCAATAGCTACTTTTTTTAGCAGACACCAGAGCCACACTCAAATGG
CTAAGTAGGTTATGACCTCTCTGGATTATTTTTGAATGCCCAACTGTTGC
ATTCAAGTTTTCTGACTAATAAGAAATTAAGCATTCATCCTTCGTATCAC
TGCAGAAGCAACAGTGGGGGCACAGGGAGGGAACTCTTGACACTGAGCCA
CTAAAATATGGACTAATTTTTTGGACAAATCTTCAAACGGACTGTGCTAC
TGTATTTGTCTCAAAGCTACCAAGTTTGTGCAATAAGTGGAAGGGATGTC
ATCCTTCTTCAATAAATGCTGAATGACATTCAAGCTGATTTTCTAGACCA
CTGAGAAAATCTTTATTTACAATAAATTTCAATAAAATTTGCATAAATAT
ATTCCCAAAAAAAAAAAAAAAAAAAAAAAGAAAAAAAAAAAAAA

Secreted Phosphoprotein 1

>gi|38146097|ref|NM_000582.2| *Homo sapiens* secreted phosphoprotein 1 (osteopontin, bone sialoprotein I, early T-lymphocyte activation 1) (SPP1), mRNA 1 qPCR assay_on_demand_context match [253 . . . 277]

SEQ ID NO: 84

CTCCCTGTGTTGGTGGAGGATGTCTGCAGCAGCATTTAAATTCTGGGAGG
GCTTGGTTGTCAGCAGCAGCAGGAGGAGGCAGAGCACAGCATCGTCGGGA
CCAGACTCGTCTCAGGCCAGTTGCAGCCTTCTCAGCCAAACGCCGACCAA
GGAAAACTCACTACCATGAGAATTGCAGTGATTTGCTTTTGCCTCCTAGG
CATCACCTGTGCCATACCAGTTAAACAGGCTGATTCTGGAAGTTCTGAGG
AAAAGCAGCTTTACAACAAATACCCAGATGCTGTGGCCACATGGCTAAAC
CCTGACCCATCTCAGAAGCAGAATCTCCTAGCCCCACAGACCCTTCCAAG
TAAGTCCAACGAAAGCCATGACCACATGGATGATATGGATGATGAAGATG
ATGATGACCATGTGGACAGCCAGGACTCCATTGACTCGAACGACTCTGAT
GATGTAGATGACACTGATGATTCTCACCAGTCTGATGAGTCTCACCATTC
TGATGAATCTGATGAACTGGTCACTGATTTTCCCACGGACCTGCCAGCAA
CCGAAGTTTTCACTCCAGTTGTCCCCACAGTAGACACATATGATGGCCGA
GGTGATAGTGTGGTTTATGGACTGAGGTCAAAATCTAAGAAGTTTCGCAG
ACCTGACATCCAGTACCCTGATGCTACAGACGAGGACATCACCTCACACA
TGGAAAGCGAGGAGTTGAATGGTGCATACAAGGCCATCCCCGTTGCCCAG
GACCTGAACGCGCCTTCTGATTGGGACAGCCGTGGGAAGGACAGTTATGA
AACGAGTCAGCTGGATGACCAGAGTGCTGAAACCCACAGCCACAAGCAGT
CCAGATTATATAAGCGGAAAGCCAATGATGAGAGCAATGAGCATTCCGAT
GTGATTGATAGTCAGGAACTTTCCAAAGTCAGCCGTGAATTCCACAGCCA
TGAATTTCACAGCCATGAAGATATGCTGGTTGTAGACCCCAAAAGTAAGG
AAGAAGATAAACACCTGAAATTTCGTATTTCTCATGAATTAGATAGTGCA

-continued

TCTTCTGAGGTCAATTAAAAGGAGAAAAAATACAATTTCTCACTTTGCAT

TTAGTCAAAAGAAAAAATGCTTTATAGCAAAATGAAAGAGAACATGAAAT

GCTTTCTTTCTCAGTTTATTGGTTGAATGTGTATCTATTTGAGTCTGGAA

ATAACTAATGTGTTTGATAATTAGTTTAGTTTGTGGCTTCATGGAAACTC

CCTGTAAACTAAAAGCTTCAGGGTTATGTCTATGTTCATTCTATAGAAGA

AATGCAAACTATCACTGTATTTTAATATTTGTTATTCTCTCATGAATAGA

AATTTATGTAGAAGCAAACAAAATACTTTTACCCACTTAAAAAGAGAATA

TAACATTTTATGTCACTATAATCTTTTGTTTTTTAAGTTAGTGTATATTT

TGTTGTGATTATCTTTTTGTGGTGTGAATAAATCTTTTATCTTGAATGTA

ATAAGAATTTGGTGGTGTCAATTGCTTATTTGTTTTCCCACGGTTGTCCA

GCAATTAATAAAACATAACCTTTTTTACTGCCTAAAAAAAAAAAAAAAAA

AAAAAAAAAAAAAAAA

Chondroitin Sulfate Proteoglycan 2

>gi|21361115|ref|NM_004385.2| *Homo sapiens* chondroitin sulfate proteoglycan 2 (versican) (CSPG2), mRNA|qPCR forward_primer match [10087 . . . 10106] |qPCR reverse_primer match [10185 . . . 10163]|qPCR probe match [10139 . . . 10161]

SEQ ID NO: 85

GCTGCCCCGAGCCTTTCTGGGGAAGAACTCCAGGCGTGCGGACGCAACAG

CCGAGAACATTAGGTGTTGTGGACAGGAGCTGGGACCAAGATCTTCGGCC

AGCCCCGCATCCTCCCGCATCTTCCAGCACCGTCCCGCACCCTCCGCATC

CTTCCCCGGGCCACCACGCTTCCTATGTGACCCGCCTGGGCAACGCCGAA

CCCAGTCGCGCAGCGCTGCAGTGAATTTTCCCCCCAAACTGCAATAAGCC

GCCTTCCAAGGCCAAGATGTTCATAAATATAAAGAGCATCTTATGGATGT

GTTCAACCTTAATAGTAACCCATGCGCTACATAAAGTCAAAGTGGGAAAA

AGCCCACCGGTGAGGGGCTCCCTCTCTGGAAAAGTCAGCCTACCTTGTCA

TTTTTCAACGATGCCTACTTTGCCACCCAGTTACAACACCAGTGAATTTC

TCCGCATCAAATGGTCTAAGATTGAAGTGGACAAAAATGGAAAAGATTTG

AAAGAGACTACTGTCCTTGTGGCCCAAAATGGAAATATCAAGATTGGTCA

GGACTACAAAGGGAGAGTGTCTGTGCCCACACATCCCGAGGCTGTGGGCG

ATGCCTCCCTCACTGTGGTCAAGCTGCTGGCAAGTGATGCGGGTCTTTAC

CGCTGTGACGTCATGTACGGGATTGAAGACACACAAGACACGGTGTCACT

GACTGTGGATGGGGTTGTGTTTCACTACAGGGCGGCAACCAGCAGGTACA

CACTGAATTTTGAGGCTGCTCAGAAGGCTTGTTTGGACGTTGGGGCAGTC

ATAGCAACTCCAGAGCAGCTCTTTGCTGCCTATGAAGATGGATTTGAGCA

GTGTGACGCAGGCTGGCTGGCTGATCAGACTGTCAGATATCCCATCCGGG

CTCCCAGAGTAGGCTGTTATGGAGATAAGATGGGAAAGGCAGGAGTCAGG

ACTTATGGATTCCGTTCTCCCCAGGAAACTTACGATGTGTATTTTTTATG

TGGATCATCTGGATGGTGATGTGTTCCACCTCACTGTCCCCAGTAAATTC

ACCTTCGAGGAGGCTGCAAAAGAGTGTGAAAACCAGGATGCCAGGCTGGC

AACAGTGGGGGAACTCCAGGCGGCATGGAGGAACGGCTTTGACCAGTGCG

-continued

ATTACGGGTGGCTGTCGGATGCCAGCGTGCGCCACCCTGTGACTGTGGCC

AGGGCCCAGTGTGGAGGTGGTCTACTTGGGGTGAGAACCCTGTATCGTTT

TGAGAACCAGACAGGCTTCCCTCCCCCTGATAGCAGATTTGATGCCTACT

GCTTTAAACCTAAAGAGGCTACAACCATCGATTTGAGTATCCTCGCAGAA

ACTGCATCACCCAGTTTATCCAAAGAACCACAAATGGTTTCTGATAGAAC

TACACCAATCATCCCTTTAGTTGATGAATTACCTGTCATTCCAACAGAGT

TCCCTCCCGTGGGAAATATTGTCAGTTTTTGAACAGAAAGCCACAGTCCA

ACCTCAGGCTATCACAGATAGTTTAGCCACCAAATTACCCACACCTACTG

GCAGTACCAAGAAGCCCTGGGATATGGATGACTACTCACCTTCTGCTTCA

GGACCTCTTGGAAAGCTAGACATATCAGAAATTAAGGAAGAAGTGCTCCA

GAGTACAACTGGCGTCTCTCATTATGCTACGGATTCATGGGATGGTGTCG

TGGAAGATAAACAAACACAAGAATCGGTTACACAGATTGAACAAATAGAA

GTGGGTCCTTTGGTAACATCTATGGAAATCTTAAAGCACATTCCTTTCCA

AGGAATTCCCTGTAACTGAAACACCATTGGTAACTGCAAGAATGATCCTG

GAATCCAAAACTGAAAAGAAAATGGTAAGCACTGTTTTCTGAATTGGTAA

CCACAGGTCACTATGGATTCACCTTGGGAGAAGAGGATGATGAAGACAGA

ACACTTACAGTTGGATCTGATGAGAGCACCTTGATCTTTGACCAAATTCC

TGAAGTCATTACGGTGTCAAAGACTTCAGAAGACACCATCCACACTCATT

TAGAAGACTTGGAGTCAGTCTCAGCATCCACAACTGTTTCCCCTTTAATT

ATGCCTGATAATAATGGATCATCCATGGATGACTGGGAAGAGAGACAAAC

TAGTGGTAGGATAACGGAAGAGTTTCTTGGCAAATATCTGTCTACTACAC

CTTTTCCATCACAGCATCGTACAGAAATAGAATTGTTTCCTTATTCTGGT

GATAAAATATTAGTAGAGGGAATTTCCACAGTTATTTATCCTTCTCTACA

AACAGAAATGACACATAGAAGAGAAAGAACAGAAACACTAATACCAGAGA

TGAGAACAGATACTTATACAGATGAAATACAAGAAGAGATCACTAAAAGT

CCATTTATGGGAAAAACAGAAGAAGAAGTCTTCTCTGGGATGAAACTCTC

TACATCTCTCTCAGAGCCAATTCATGTTACAGAGTCTTCTGTGGAAATGA

CCAAGTCTTTTGATTTCCCAACATTGATAACAAAGTTAAGTGCAGAGCCA

ACAGAAGTAAGAGATATGGAGGAAGACTTTACAGCAACTCCAGGTACTAC

AAAATATGATGAAAATATTACAACAGTGCTTTTGGCCCATGGTACTTTAA

GTGTTGAAGCAGCCACTGTATCAAAATGGTCATGGGATGAAGATAATACA

ACATCCAAGCCTTTAGAGTCTACAGAACCTTCAGCCTCTTCAAAATTGCC

CCCTGCCTTACTCACAACTGTGGGGATGAATGGAAAGGATAAAGACATCC

CAAGTTTCACTGAAGATGGAGCAGATGAATTTACTCTTATTCCAGATAGT

ACTCAAAAGCAGTTAGAGGAGGTTACTGATGAAGACATAGCAGCCCATGG

AAAATTCACAATTAGATTTCAGCCAACTACATCAACTGGTATTGCAGAAA

AGTCAACTTTGAGAGATTCTACAACTGAAGAAAAAGTTCCACCTATCACA

AGCACTGAAGGCCAAGTTTATGCAACCATGGAAGGAAGTGCTTTGGGTGA

AGTAGAAGATGTGGACCTCTCTAAGCCAGTATCTACTGTTCCCCAATTTG

CACACACTTCAGAGGTGGAAGGATTAGCATTTGTTAGTTATAGTAGCACC

CAAGAGCCTACTACTTATGTAGACTCTTCCCATACCATTCCTCTTTCTGT

-continued

AATTCCCAAGACAGACTGGGGAGTGTTAGTACCTTCTGTTCCATCAGAAG

ATGAAGTTCTAGGTGAACCCTCTCAAGACATACTTGTCATTGATCAGACT

CGCCTTGAAGCGACTATTTCTCCAGAAACTATGAGAACAACAAAAATCAC

AGAGGGAACAACTCAGGAAGAATTCCCTTGGAAAGAACAGACTGCAGAGA

AACCAGTTCCTGCTCTCAGTTCTACAGCTTGGACTCCCAAGGAGGCAGTA

ACACCACTGGATGAACAAGAGGGCGATGGATCAGCATATACAGTCTCTGA

AGATGAATTGTTGACAGGTTCTGAGAGGGTCCCAGTTTTAGAAACAACTC

CAGTTGGAAAAATTGATCACAGTGTGTCTTATCCACCAGGTGCTGTAACT

GAGCACAAAGTGAAAACAGATGAAGTGGTAACACTAACACCACGCATTGG

GCCAAAAGTATCTTTAAGTCCAGGGCCTGAACAAAAATATGAAACAGAAG

GTAGTAGTACAACAGGATTTACATCATCTTTGAGTCCTTTTAGTACCCAC

ATTACCCAGCTTATGGAAGAAACCACTACTGAGAAAACATCCCTAGAGGA

TATTGATTTAGGCTCAGGATTATTTGAAAAGCCCAAAGCCACAGAACTCA

TAGAATTTTCAACAATCAAAGTCACAGTTCCAAGTGATATTACCACTGCC

TTCAGTTCAGTAGACAGACTTCACACAACTTCAGCATTCAAGCCATCTTC

CGCGATCACTAAGAAACCACCTCTCATCGACAGGGAACCTGGTGAAGAAA

CAACCAGTGACATGGTAATCATTGGAGAATCAACATCTCATGTTCCTCCC

ACTACCCTTGAAGATATTGTAGCCAAGGAAACAGAAACCGATATTGATAG

AGAGTATTTCACGACTTCAAGTCCTCCTGCTACACAGCCAACAAGACCAC

CCACTGTGGAAGACAAAGAGGCCTTTGGACCTCAGGCGCTTTCTACGCCA

CAGCCCCCAGCAAGCACAAAATTTCACCCTGACATTAATGTTTATATTAT

TGAGGTCAGAGAAAATAAGACAGGTCGAATGAGTGATTTGAGTGTAATTG

GTCATCCAATAGATTCAGAATCTAAAGAAGATGAACCTTGTAGTGAAGAA

ACAGATCCAGTGCATGATCTAATGGCTGAAATTTTACCTGAATTCCCTGA

CATAATTGAAATAGACCTATACCACAGTGAAGAAAATGAAGAAGAAGAAG

AAGAGTGTGCAAATGCTACTGATGTGACAACCACCCCATCTGTGCAGTAC

ATAAATGGGAAGCATCTCGTTACCACTGTGCCCAAGGACCCAGAAGCTGC

AGAAGCTAGGCGTGGCCAGTTTGAAAGTGTTGCACCTTCTCAGAATTTCT

CGGACAGCTCTGAAAGTGATACTCATCCATTTGTAATAGCCAAAACGGAA

TTGTCTACTGCTGTGCAACCTAATGAATCTACAGAAACAACTGAGTCTCT

TGAAGTTACATGGAAGCCTGAGACTTACCCTGAAACATCAGAACATTTTT

CAGGTGGTGAGCCTGATGTTTTCCCCACAGTCCCATTCCATGAGGAATTT

GAAAGTGGAACAGCCAAAAAAGGGGCAGAATCAGTCACAGAGAGAGATAC

TGAAGTTGGTCATCAGGCACATGAACATACTGAACCTGTATCTCTGTTTC

CTGAAGAGTCTTCAGGAGAGATTGCCATTGACCAAGAATCTCAGAAAATA

GCCTTTGCAAGGGCTACAGAAGTAACATTTGGTGAAGAGGTAGAAAAAAG

TACTTCTGTCACATACACTCCCACTATAGTTCCAAGTTCTGCATCAGCAT

ATGTTTCAGAGGAAGAAGCAGTTACCCTAATAGGAAATCCTTGGCCAGAT

GACCTGTTGTCTACCAAAGAAAGCTGGGTAGAAGCAACTCCTAGACAAGT

TGTAGAGCTCTCAGGGAGTTCTTCGATTCCAATTACAGAAGGCTCTGGAG

-continued

AAGCAGAAGAAGATGAAGATACAATGTTCACCATGGTAACTGATTTATCA

CAGAGAAATACTACTGATACACTCATTACTTTAGACACTAGCAGGATAAT

CACAGAAAGCTTTTTTGAGGTTCCTGCAACCACCATTTATCCAGTTTCTG

AACAACCTTCTGCAAAAGTGGTGCCTACCAAGTTTGTAAGTGAAACAGAC

ACTTCTGAGTGGATTTCCAGTACCACTGTTGAGGAAAAGAAAAGGAAGGA

GGAGGAGGGAACTACAGGTACGGCTTCTACATTTGAGGTATATTCATCTA

CACAGAGATCGGATCAATTAATTTTACCCTTTGAATTAGAAAGTCCAAAT

GTAGCTACATCTAGTGATTCAGGTACCAGGAAAAGTTTTATGTCCTTGAC

AACACCAACACAGTCTGAAAGGGAAATGACAGATTCTACTCCTGTCTTTA

CAGAAACAAATACATTAGAAAATTTGGGGGCACAGACCACTGAGCACAGC

AGTATCCATCAACCTGGGGTTCAGGAAGGGCTGACCACTCTCCCACGTAG

TCCTGCCTCTGTCTTTATGGAGCAGGGCTCTGGAGAAGCTGCTGCCGACC

CAGAAACCACCACTGTTTCTTCATTTTCATTAAACGTAGAGTATGCAATT

CAAGCCGAAAAGGAAGTAGCTGGCACTTTGTCTCCGCATGTGGAAACTAC

ATTCTCCACTGAGCCAACAGGACTGGTTTTGAGTACAGTAATGGACAGAG

TAGTTGCTGAAAATATAACCCAAACATCCAGGGAAATAGTGATTTCAGAG

CGATTAGGAGAACCAAATTATGGGGCAGAAATAAGGGGCTTTTCCACAGG

TTTTCCTTTGGAGGAAGATTTCAGTGGTGACTTTAGAGAATACTCAACAG

TGTCTCATCCCATAGCAAAAGAAGAAACGGTAATGATGGAAGGCTCTGGA

GATGCAGCATTTAGGGACACCCAGACTTCACCATCTACAGTACCTACTTC

AGTTCACATCAGTCACATATCTGACTCAGAAGGACCCAGTAGCACCATGG

TCAGCACTTCAGCCTTCCCCTGGGAAGAGTTTACATCCTCAGCTGAGGGC

TCAGGTGAGCAACTGGTCACAGTCAGCAGCTCTGTTGTTCCAGTGCTTCC

CAGTGCTGTGCAAAAGTTTTCTGGTACAGCTTCCTCCATTATCGACGAAG

GATTGGGAGAAGTGGGTACTGTCAATGAAATTGATAGAAGATCCACCATT

TTACCAACAGCAGAAGTGGAAGGTACGAAAGCTCCAGTAGAGAAGGAGGA

AGTAAAGGTCAGTGGCACAGTTTCAACAAACTTTCCCCAAACTATAGAGC

CAGCCAAATTATGGTCTAGGCAAGAAGTCAACCCTGTAAGACAAGAAATT

GAAAGTGAAACAACATCAGAGGAACAAATTCAAGAAGAAAAGTCATTTGA

ATCCCCTCAAAACTCTCCTGCAACAGAACAAACAATCTTTGATTCACAGA

CATTTACTGAAACTGAACTCAAAACGACAGATTATTCTGTACTAACAACA

AAGAAAACTTACAGTGATGATAAAGAAATGAAGGAGGAAGACACTTCTTT

AGTTAACATGTCTACTCCAGATCCAGATGCAAATGGCTTGGAATCTTACA

CAACTCTCCCTGAAGCTACTGAAAAGTCACATTTTTTCTTAGCTACTGCA

TTAGTAACTGAATCTATACCAGCTGAACATGTAGTCACAGATTCACCAAT

CAAAAAGGAAGAAAGTACAAAACATTTTCCGAAAGGCATGAGACCAACAA

TTCAAGAGTCAGATACTGAGCTCTTATTCTCTGGACTGGGATCAGGAGAA

GAAGTTTTACCTACTCTACCAACAGAGTCAGTGAATTTTACTGAAGTGGA

ACAAATCAATAACACATTATATCCCCACACTTCTCAAGTGGAAAGTACCT

CAAGTGACAAAATTGAAGACTTTAACAGAATGGAAAATGTGGCAAAAGAA

GTTGGACCACTCGTATCTCAAACAGACATCTTTGAAGGTAGTGGGTCAGT

-continued

AACCAGCACAACATTAATAGAAATTTTAAGTGACACTGGAGCAGAAGGAC

CCACGGTGGCACCTCTCCCTTTCTCCACGGACATCGGACATCCTCAAAAT

CAGACTGTCAGGTGGGCAGAAGAAATCCAGACTAGTAGACCACAAACCAT

AACTGAACAAGACTCTAACAAGAATTCTTCAACAGCAGAAATTAACGAAA

CAACAACCTCATCTACTGATTTTCTGGCTAGAGCTTATGGTTTTGAAATG

GCCAAAGAATTTGTTACATCAGCACCAAAACCATCTGACTTGTATTATGA

ACCTTCTGGAGAAGGATCTGGAGAAGTGGATATTGTTGATTCATTTCACA

CTTCTGCAACTACTCAGGCAACCAGACAAGAAAGCAGCACCACATTTGTT

TCTGATGGGTCCCTGGAAAAACATCCTGAGGTGCCAAGCGCTAAAGCTGT

TACTGCTGATGGATTCCCAACAGTTTCAGTGATGCTGCCTCTTCATTCAG

AGCAGAACAAAAGCTCCCCTGATCCAACTAGCACACTGTCAAATACAGTG

TCATATGAGAGGTCCACAGACGGTAGTTTCCAAGACCGTTTCAGGGAATT

CGAGGATTCCACCTTAAAACCTAACAGAAAAAAACCCACTGAAAATATTA

TCATAGACCTGGACAAAGAGGACAAGGATTTAATATTGACAATTACAGAG

AGTACCATCCTTGAAATTCTACCTGAGCTGACATCGGATAAAAATACTAT

CATAGATATTGATCATACTAAACCTGTGTATGAAGACATTCTTGGAATGC

AAACAGATATAGATACAGAGGTACCATCAGAACCACATGACAGTAATGAT

GAAAGTAATGATGACAGCACTCAAGTTCAAGAGATCTATGAGGCAGCTGT

CAACCTTTCTTTAACTGAGGAAACATTTGAGGGCTCTGCTGATGTTCTGG

CTAGCTACACTCAGGCAACACATGATGAATCAATGACTTATGAAGATAGA

AGCCAACTAGATCACATGGGCTTTCACTTCACAACTGGGATCCCTGCTCC

TAGCACAGAAACAGAATTAGACGTTTTACTTCCCACGGCAACATCCCTGC

CAATTCCTCGTAAGTCTGCCACAGTTATTCCAGAGATTGAAGGAATAAAA

GCTGAAGCAAAAGCCCTGGATGACATGTTTGAATCAAGCACTTTGTCTGA

TGGTCAAGCTATTGCAGACCAAAGTGAAATAATACCAACATTGGGCCAAT

TTGAAAGGACTCAGGAGGAGTATGAAGACAAAAAACATGCTGGTCCTTCT

TTTCAGCCAGAATTCTCTTCAGGAGCTGAGGAGGCATTAGTAGACCATAC

TCCCTATCTAAGTATTGCTACTACCCACCTTATGGATCAGAGTGTAACAG

AGGTGCCTGATGTGATGGAAGGATCCAATCCCCCATATTACACTGATACA

ACATTAGCAGTTTCAACATTTGCGAAGTTGTCTTCTCAGACACCATCATC

TCCCCTCACTATCTACTCAGGCAGTGAAGCCTCTGGACACACAGAGATCC

CCCAGCCCAGTGCTCTGCCAGGAATAGACGTCGGCTCATCTGTAATGTCC

CCACAGGATTCTTTTAAGGAAATTCATGTAAATATTGAAGCAACTTTCAA

ACCATCAAGTGAGGAATACCTTCACATAACTGAGCCTCCCTCTTTATCTC

CTGACACAAAATTAGAACCTTCAGAAGATGATGGTAAACCTGAGTTATTA

GAAGAAATGGAAGCTTCTCCCACAGAACTTATTGCTGTGGAAGGAACTGA

GATTCTCCAAGATTTCCAAAACAAAACCGATGGTCAAGTTTCTGGAGAAG

CAATCAAGATGTTTCCCACCATTAAAACACCTGAGGCTGGAACTGTTATT

ACAACTGCCGATGAAATTGAATTAGAAGGTGCTACACAGTGGCCACACTC

TACTTCTGCTTCTGCCACCTATGGGGTCGAGGCAGGTGTGGTGCCTTGGC

-continued

TAAGTCCACAGACTTCTGAGAGGCCCACGCTTTCTTCTTCTCCAGAAATA

AACCCTGAAACTCAAGCAGCTTTAATCAGAGGGCAGGATTCCACGATAGC

AGCATCAGAACAGCAAGTGGCAGCGAGAATTCTTGATTCCAATGATCAGG

CAACAGTAAACCCTGTGGAATTTAATACTGAGGTTGCAACACCACCATTT

TCCCTTCTGGAGACTTCTAATGAAACAGATTTCCTGATTGGCATTAATGA

AGAGTCAGTGGAAGGCACGGCAATCTATTTACCAGGACCTGATCGCTGCA

AAATGAACCCGTGCCTTAACGGAGGCACCTGTTATCCTACTGAAACTTCC

TACGTATGCACCTGTGTGCCAGGATACAGCGGAGACCAGTGTGAACTTGA

TTTTGATGAATGTCACTCTAATCCCTGTCGTAATGGAGCCACTTGTGTTG

ATGGTTTTAACACATTCAGGTGCCTCTGCCTTCCAAGTTATGTTGGTGCA

CTTTGTGAGCAAGATACCGAGACATGTGACTATGGCTGGCACAAATTCCA

AGGGCAGTGCTACAAATACTTTGCCCATCGACGCACATGGGATGCAGCTG

AACGGGAATGCCGTCTGCAGGGTGCCCATCTCACAAGCATCCTGTCTCAC

GAAGAACAAATGTTTGTTAATCGTGTGGGCCATGATTATCAGTGGATAGG

CCTCAATGACAAGATGTTTGAGCATGACTTCCGTTGGACTGATGGCAGCA

CACTGCAATACGAGAATTGGAGACCCAACCAGCCAGACAGCTTCTTTTCT

GCTGGAGAAGACTGTGTTGTAATCATTTGGCATGAGAATGGCCAGTGGAA

TGATGTTCCCTGCAATTACCATCTCACCTATACGTGCAAGAAAGGAACAG

TTGCTTGCGGCCAGCCCCCTGTTGTAGAAAATGCCAAGACCTTTGGAAAG

ATGAAACCTCGTTATGAAATCAACTCCCTGATTAGATACCACTGCAAAGA

TGGTTTCATTCAACGTCACCTTCCAACTATCCGGTGCTTAGGAAATGGAA

GATGGGCTATACCTAAAATTACCTGCATGAACCCATCTGCATACCAAAGG

ACTTATTCTATGAAATACTTTAAAAATTCCTCATCAGCAAAGGACAATTC

AATAAATACATCCAAACATGATCATCGTTGGAGCCGGAGGTGGCAGGAGT

CGAGGCGCTGATCCCTAAAATGGCGAACATGTGTTTTCATCATTTCAGCC

AAAGTCCTAACTTCCTGTGCCTTTCCTATCACCTCGAGAAGTAATTATCA

GTTGGTTTGGATTTTTGGACCACCGTTCAGTCATTTTGGGTTGCCGTGCT

CCCAAAACATTTTAAATGAAAGTATTGGCATTCAAAAAGACAGCAGACAA

AATGAAAGAAAATGAGAGCAGAAAGTAAGCATTTCCAGCCTATCTAATTT

CTTTAGTTTTCTATTTGCCTCCAGTGCAGTCCATTTCCTAATGTATACCA

GCCTACTGTACTATTTAAAATGCTCAATTTCAGCACCGATGGCCATGTAA

ATAAGATGATTTAATGTTGATTTTAATCCTGTATATAAAATAAAAAGTCA

CAATGAGTTTGGGCATATTTAATGATGATTATGGAGCCTTAGAGGTCTTT

AATCATTGGTTCGGCTGCTTTTATGTAGTTTAGGCTGGAAATGGTTTCAC

TTGCTCTTTGACTGTCAGCAAGACTGAAGATGGCTTTTCCTGGACAGCTA

GAAAACACAAAATCTTGTAGGTCATTGCACCTATCTCAGCCATAGGTGCA

GTTTGCTTCTACATGATGCTAAAGGCTGCGAATGGGATCCTGATGGAACT

AAGGACTCCAATGTCGAACTCTTCTTTGCTGCATTCCTTTTTCTTCACTT

ACAAGAAAGGCCTGAATGGAGGACTTTTCTGTAACCAGG

N-Acylsphingosine Amidohydrolase 1

>gi|30089929|ref|NM_004315.2| *Homo sapiens* N-acylsphingosine amidohydrolase (acid ceramidase) 1 (ASAH1), transcript variant 2, mRNA|qPCR forward_primer match [1212 . . . 1228]|qPCR reverse_primer match [1290 . . . 1266]|qPCR probe match [1233 . . . 1260]

SEQ ID NO: 86

GGACTTTGAAATCCAACCCGGTCACCTACCCGCGCGACTGTGTCCACGGA
TGGCACGAAAGCCAAGCGAGTCCCCCTGCCGAGCTACTCGCGTCCGCCTC
CTCCCAAGCTGAGCTCTGCTCCGCCCACCTGAGTCCTTCGCCAGTTAGGA
GGAAACACAGCCGCTTAATGAACTGCTGCATCGGGCTGGGAGAGAAAGCT
CGCGGGTCCCACCGGGCCTCCTACCCAAGTCTCAGCGCGCTTTTCACCGA
GGCCTCAATTCTGGGATTTGGCAGCTTTGCTGTGAAAGCCCAATGGACAG
AGGACTGCAGAAAATCAACCTATCCTCCTTCAGGACCAACGTACAGAGGT
GCAGTTCCATGGTACACCATAAATCTTGACTTACCACCCTACAAAAGATG
GCATGAATTGATGCTTGACAAGGCACCAATGCTAAAGGTTATAGTGAATT
CTCTGAAGAATATGATAAATACATTCGTGCCAAGTGGAAAAGTTATGCAG
GTGGTGGATGAAAAATTGCCTGGCCTACTTGGCAACTTTCCTGGCCCTTT
TGAAGAGGAAATGAAGGGTATTGCCGCTGTTACTGATATACCTTTAGGAG
AGATTATTTCATTCAATATTTTTTATGAATTATTTACCATTTGTACTTCA
ATAGTAGCAGAAGACAAAAAAGGTCATCTAATACATGGGAGAAACATGGA
TTTTGGAGTATTTCTTGGGTGGAACATAAATAATGATACCTGGGTCATAA
CTGAGCAACTAAAACCTTTAACAGTGAATTTGGATTTCCAAAGAAACAAC
AAAACTGTCTTCAAGGCTTCAAGCTTTGCTGGCTATGTGGGCATGTTAAC
AGGATTCAAACCAGGACTGTTCAGTCTTACACTGAATGAACGTTTCAGTA
TAAATGGTGGTTATCTGGGTATTCTAGAATGGATTCTGGGAAAGAAAGAT
GCCATGTGGATAGGGTTCCTCACTAGAACAGTTCTGGAAAATAGCACAAG
TTATGAAGAAGCCAAGAATTTATTGACCAAGACCAAGATATTGGCCCCAG
CCTACTTTATCCTGGGAGGCAACCAGTCTGGGGAAGGTTGTGTGATTACA
CGAGACAGAAAGGAATCATTGGATGTATATGAACTCGATGCTAAGCAGGG
TAGATGGTATGTGGTACAAACAAATTATGACCGTTGGAAACATCCCTTCT
TCCTTGATGATCGCAGAACGCCTGCAAAGATGTGTCTGAACCGCACCAGC
CAAGAGAATATCTCATTTGAAACCATGTATGATGTCCTGTCAACAAAACC
TGTCCTCAACAAGCTGACCGTATACACAACCTTGATAGATGTTACCAAAG
GTCAATTCGAAACTTACCTGCGGGACTGCCCTGACCCTTGTATAGGTTGG
TGAGCACACGTCTGGCCTACAGAATGCGGCCTCTGAGACATGAAGACACC
ATCTCCATGTGACCGAACACTGCAGCTGTCTGACCTTCCAAAGACTAAGA
CTCGCGGCAGGTTCTCTTTGAGTCAAAAGCTTGTCTTCGTCCATCTGTTG
ACAAATGACAGACCTTTTTTTTTCCCCCATCAGTTGATTTTTCTTATTTA
CAGATAACTTCTTTAGGGGAAGTAAAACAGTCATCTAGAATTCACTGAGT
TTTGTTTCACTTTGACATTTGGGGATCTGGTGGGCAGTCGAACCATGGTG
AACTCCACCTCCGTGGAATAAATGGAGATTCAGCGTGGGTGTTGAATCCA
GCACGTCTGTGTGAGTAACGGGACAGTAAACACTCCACATTCTTCAGTTT
TTCACTTCTACCTACATATTTGTATGTTTTTCTGTATAACAGCCTTTTCC
TTCTGGTTCTAACTGCTGTTAAAATTAATATATCATTATCTTTGCTGTTA

-continued

TTGACAGCGATATAATTTTATTACATATGATTAGAGGGATGAGACAGACA
TTCACCTGTATATTTCTTTTAATGGGCACAAAATGGGCCCTTGCCTCTAA
ATAGCACTTTTTGGGGTTCAAGAAGTAATCAGTATGCAAAGCAATCTTTT
ATACAATAATTGAAGTGTTCCCTTTTTCATAATTACTGTACTTCCCAGTA
ACCCTAAGGAAGTTGCTAACTTAAAAAACTGCATCCCACGTTCTGTTAAT
TTAGTAAATAAACAAGTCAAAGACTTGTGGAAAATAGGAAGTGAACCCAT
ATTTTAAATTCTCATAAGTAGCATTCATGTAATAAACAGGTTTTTAGTTT
GTTCTTCAGATTGATAGGGAGTTTTAAAGAAATTTTAGTAGTTACTAAAA
TTATGTTACTGTATTTTTCAGAAATCAAACTGCTTATGAAAAGTACTAAT
AGAACTTGTTAACCTTTCTAACCTTCACGATTAACTGTGAAATGTACGTC
ATTTGTGCAAGACCGTTTGTCCACTTCATTTTGTATAATCACAGTTGTGT
TCCTGACACTCAATAAACAGTCATTGGAAAGAGTGCCAGTCAGCAGTCAT
GCA

N-Acylsphingosine Amidohydrolase 1 Transcript Variant 1

>gi|30089927|ref|NM_177924.1| *Homo sapiens* N-acylsphingosine amidohydrolase (acid ceramidase) 1 (ASAH1), transcript variant 1, mRNA|qPCR forward_primer match [1050 . . . 1066]|qPCR reverse_primer match [1128 . . . 1104]|qPCR probe match [1071 . . . 1098]

SEQ ID NO: 87

GGCTCTTCTTTGCCTCTGCTGGAGTCCGGGGAGTGGCGTTGGCTGCTAGA
GCGATGCCGGGCCGGAGTTGCGTCGCCTTAGTCCTCCTGGCTGCCGCCGT
CAGCTGTGCCGTCGCGCAGCACGCGCCGCCGTGGACAGAGGACTGCAGAA
AATCAACCTATCCTCCTTCAGGACCAACGTACAGAGGTGCAGTTCCATGG
TACACCATAAATCTTGACTTACCACCCTACAAAAGATGGCATGAATTGAT
GCTTGACAAGGCACCAATGCTAAAGGTTATAGTGAATTCTCTGAAGAATA
TGATAAATACATTCGTGCCAAGTGGAAAAGTTATGCAGGTGGTGGATGAA
AAATTGCCTGGCCTACTTGGCAACTTTCCTGGCCCTTTTGAAGAGGAAAT
GAAGGGTATTGCCGCTGTTACTGATATACCTTTAGGAGAGATTATTTCAT
TCAATATTTTTTATGAATTATTTACCATTTGTACTTCAATAGTAGCAGAA
GACAAAAAAGGTCATCTAATACATGGGAGAAACATGGATTTTGGAGTATT
TCTTGGGTGGAACATAAATAATGATACCTGGGTCATAACTGAGCAACTAA
AACCTTTAACAGTGAATTTGGATTTCCAAAGAAACAACAAAACTGTCTTC
AAGGCTTCAAGCTTTGCTGGCTATGTGGGCATGTTAACAGGATTCAAACC
AGGACTGTTCAGTCTTACACTGAATGAACGTTTCAGTATAAATGGTGGTT
ATCTGGGTATTCTAGAATGGATTCTGGGAAAGAAAGATGCCATGTGGATA
GGGTTCCTCACTAGAACAGTTCTGGAAAATAGCACAAGTTATGAAGAAGC
CAAGAATTTATTGACCAAGACCAAGATATTGGCCCCAGCCTACTTTATCC
TGGGAGGCAACCAGTCTGGGGAAGGTTGTGTGATTACACGAGACAGAAAG
GAATCATTGGATGTATATGAACTCGATGCTAAGCAGGGTAGATGGTATGT
GGTACAAACAAATTATGACCGTTGGAAACATCCCTTCTTCCTTGATGATC

-continued

GCAGAACGCCTGCAAAGATGTGTCTGAACCGCACCAGCCAAGAGAATATC

TCATTTGAAACCATGTATGATGTCCTGTCAACAAAACCTGTCCTCAACAA

GCTGACCGTATACACAACCTTGATAGATGTTACCAAAGGTCAATTCGAAA

CTTACCTGCGGGACTGCCCTGACCCTTGTATAGGTTGGTGAGCACACGTC

TGGCCTACAGAATGCGGCCTCTGAGACATGAAGACACCATCTCCATGTGA

CCGAACACTGCAGCTGTCTGACCTTCCAAAGACTAAGACTCGCGGCAGGT

TCTCTTTGAGTCAAAAGCTTGTCTTCGTCCATCTGTTGACAAATGACAGA

CCTTTTTTTTTCCCCCATCAGTTGATTTTTCTTATTTACAGATAACTTCT

TTAGGGGAAGTAAAACAGTCATCTAGAATTCACTGAGTTTTGTTTCACTT

TGACATTTGGGGATCTGGTGGGCAGTCGAACCATGGTGAACTCCACCTCC

GTGGAATAAATGGAGATTCAGCGTGGGTGTTGAATCCAGCACGTCTGTGT

GAGTAACGGGACAGTAAACACTCCACATTCTTCAGTTTTTCACTTCTACC

TACATATTTGTATGTTTTTCTGTATAACAGCCTTTTCCTTCTGGTTCTAA

CTGCTGTTAAAATTAATATATCATTATCTTTGCTGTTATTGACAGCGATA

TAATTTTATTACATATGATTAGAGGGATGAGACAGACATTCACCTGTATA

TTTCTTTTAATGGGCACAAAATGGGCCCTTGCCTCTAAATAGCACTTTTT

GGGGTTCAAGAAGTAATCAGTATGCAAAGCAATCTTTTATACAATAATTG

AAGTGTTCCCTTTTTCATAATTACTGTACTTCCCAGTAACCCTAAGGAAG

TTGCTAACTTAAAAAACTGCATCCCACGTTCTGTTAATTTAGTAAATAAA

CAAGTCAAAGACTTGTGGAAAATAGGAAGTGAACCCATATTTTAAATTCT

CATAAGTAGCATTCATGTAATAAACAGGTTTTTAGTTTGTTCTTCAGATT

GATAGGGAGTTTTAAAGAAATTTTAGTAGTTACTAAAATTATGTTACTGT

ATTTTTCAGAAATCAAACTGCTTATGAAAAGTACTAATAGAACTTGTTAA

CCTTTCTAACCTTCACGATTAACTGTGAAATGTACGTCATTTGTGCAAGA

CCGTTTGTCCACTTCATTTTGTATAATCACAGTTGTGTTCCTGACACTCA

ATAAACAGTCATTGGAAAGAGTGCCAGTCAGCAGTCATGCA

Protease, Serine 11

>gi|21327712|ref|NM_002775.2| *Homo sapiens* protease, serine, 11 (IGF binding) (PRSS11), mRNA|qPCR forward_primer match [1030 . . . 1048]|qPCR reverse_primer match [1106 . . . 1083]|qPCR probe match [1080 . . . 1050]

SEQ ID NO: 88

CCGGCCCTCGCCCTGTCCGCCGCCACCGCCGCCGCCGCCAGAGTCGCCAT

GCAGATCCCGCGCGCCGCTCTTCTCCCGCTGCTGCTGCTGCTGCTGGCGG

CGCCCGCCTCGGCGCAGCTGTCCCGGGCCGGCCGCTCGGCGCCTTTGGCC

GCCGGGTGCCCAGACCGCTGCGAGCCGGCGCGCTGCCCGCCGCAGCCGGA

GCACTGCGAGGGCGGCCGGGCCCGGGACGCGTGCGGCTGCTGCGAGGTGT

GCGGCGCGCCCGAGGGCGCCGCGTGCGGCCTGCAGGAGGGCCCGTGCGGC

GAGGGGCTGCAGTGCGTGGTGCCCTTCGGGGTGCCAGCCTCGGCCACGGT

GCGGCGGCGCGCGCAGGCCGGCCTCTGTGTGTGCGCCAGCAGCGAGCCGG

TGTGCGGCAGCGACGCCAACACCTACGCCAACCTGTGCCAGCTGCGCGCC

-continued

GCCAGCCGCCGCTCCGAGAGGCTGCACCGGCCGCCGGTCATCGTCCTGCA

GCGCGGAGCCTGCGGCCAAGGGCAGGAAGATCCCAACAGTTTGCGCCATA

AATATAACTTTATCGCGGACGTGGTGGAGAAGATCGCCCCTGCCGTGGTT

CATATCGAATTGTTTCGCAAGCTTCCGTTTTCTAAACGAGAGGTGCCGGT

GGCTAGTGGGTCTGGGTTTATTGTGTCGGAAGATGGACTGATCGTGACAA

ATGCCCACGTGGTGACCAACAAGCACCGGGTCAAAGTTGAGCTGAAGAAC

GGTGCCACTTACGAAGCCAAAATCAAGGATGTGGATGAGAAAGCAGACAT

CGCACTCATCAAAATTGACCACCAGGGCAAGCTGCCTGTCCTGCTGCTTG

GCCGCTCCTCAGAGCTGCGGCCGGGAGAGTTCGTGGTCGCCATCGGAAGC

CCGTTTTCCCTTCAAAACACAGTCACCACCGGGATCGTGAGCACCACCCA

GCGAGGCGGCAAAGAGCTGGGGCTCCGCAACTCAGACATGGACTACATCC

AGACCGACGCCATCATCAACTATGGAAACTCGGGAGGCCCGTTAGTAAAC

CTGGACGGTGAAGTGATTGGAATTAACACTTTGAAAGTGACAGCTGGAAT

CTCCTTTGCAATCCCATCTGATAAGATTAAAAAGTTCCTCACGGAGTCCC

ATGACCGACAGGCCAAAGGAAAAGCCATCACCAAGAAGAAGTATATTGGT

ATCCGAATGATGTCACTCACGTCCAGCAAAGCCAAAGAGCTGAAGGACCG

GCACCGGGACTTCCCAGACGTGATCTCAGGAGCGTATATAATTGAAGTAA

TTCCTGATACCCCAGCAGAAGCTGGTGGTCTCAAGGAAAACGACGTCATA

ATCAGCATCAATGGACAGTCCGTGGTCTCCGCCAATGATGTCAGCGACGT

CATTAAAAGGGAAAGCACCCTGAACATGGTGGTCCGCAGGGGTAATGAAG

ATATCATGATCACAGTGATTCCCGAAGAAATTGACCCATAGGCAGAGGCA

TGAGCTGGACTTCATGTTTCCCTCAAAGACTCTCCCGTGGATGACGGATG

AGGACTCTGGGCTGCTGGAATAGGACACTCAAGACTTTTGACTGCCATTT

TGTTTGTTCAGTGGAGACTCCCTGGCCAACAGAATCCTTCTTGATAGTTT

GCAGGCAAAACAAATGTAATGTTGCAGATCCGCAGGCAGAAGCTCTGCCC

TTCTGTATCCTATGTATGCAGTGTGCTTTTTCTTGCCAGCTTGGGCCATT

CTTGCTTAGACAGTCAGCATTTGTCTCCTCCTTTAACTGAGTCATCATCT

TAGTCCAACTAATGCAGTCGATACAATGCGTAGATAGAAGAAGCCCCACG

GGAGCCAGGATGGGACTGGTCGTGTTTGTGCTTTTCTCCAAGTCAGCACC

CAAAGGTCAATGCACAGAGACCCCGGGTGGGTGAGCGCTGGCTTCTCAAA

CGGCCGAAGTTGCCTCTTTTAGGAATCTCTTTGGAATTGGGAGCACGATG

ACTCTGAGTTTGAGCTATTAAAGTACTTCTTACACATTG

Secreted Frizzled-Related Protein 2

>gi|42656988|ref|XM_050625.4| *Homo sapiens* secreted frizzled-related protein 2 (SFRP2), mRNA|qPCR forward_primer match [686 . . . 703]|qPCR reverse_primer match [750 . . . 728]|qPCR probe match [705 . . . 726]

SEQ ID NO: 89

CCGGGTCGGAGCCCCCCGGAGCTGCGCGCGGGCTTGCAGCGCCTCGCCCG

CGCTGTCCTCCCGGTGTCCCGCTTCTCCGCGCCCCAGCCGCCGGCTGCCA

GCTTTTCGGGGCCCCGAGTCGCACCCAGCGAAGAGAGCGGGCCCGGGACA

AGCTCGAACTCCGGCCGCCTCGCCCTTCCCCGGCTCCGCTCCCTCTGCCC

-continued

CCTCGGGGTCGCGCGCCCACGATGCTGCAGGGCCCTGGCTCGCTGCTGCT

GCTCTTCCTCGCCTCGCACTGCTGCCTGGGCTCGGCGCGCGGGCTCTTCC

TCTTTGGCCAGCCCGACTTCTCCTACAAGCGCAGCAATTGCAAGCCCATC

CCTGCCAACCTGCAGCTGTGCCACGGCATCGAATACCAGAACATGCGGCT

GCCCAACCTGCTGGGCCACGAGACCATGAAGGAGGTGCTGGAGCAGGCCG

GCGCTTGGATCCCGCTGGTCATGAAGCAGTGCCACCCGGACACCAAGAAG

TTCCTGTGCTCGCTCTTCGCCCCCGTCTGCCTCGATGACCTAGACGAGAC

CATCCAGCCATGCCACTCGCTCTGCGTGCAGGTGAAGGACCGCTGCGCCC

CGGTCATGTCCGCCTTCGGCTTCCCCTGGCCCGACATGCTTGAGTGCGAC

CGTTTCCCCCAGGACAACGACCTTTGCATCCCCCTCGCTAGCAGCGACCA

CCTCCTGCCAGCCACCGAGGAAGCTCCAAAGGTATGTGAAGCCTGCAAAA

ATAAAAATGATGATGACAACGACATAATGGAAACGCTTTGTAAAAATGAT

TTTGCACTGAAAATAAAAGTGAAGGAGATAACCTACATCAACCGAGATAC

CAAAATCATCCTGGAGACCAAGAGCAAGACCATTTACAAGCTGAACGGTG

TGTCCGAAAGGGACCTGAAGAAATCGGTGCTGTGGCTCAAAGACAGCTTG

CAGTGCACCTGTGAGGAGATGAACGACATCAACGCGCCCTATCTGGTCAT

GGGACAGAAACAGGGTGGGGAGCTGGTGATCACCTCGGTGAAGCGGTGGC

AGAAGGGGCAGAGAGAGTTCAAGCGCATCTCCCGCAGCATCCGCAAGCTG

CAGTGCTAGTCCCGGCATCCTGATGGCTCCGACAGGCCTGCTCCAGAGCA

CGGCTGACCATTTCTGCTCCGGGATCTCAGCTCCCGTTCCCCAAGCACAC

TCCTAGCTGCTCCAGTCTCAGCCTGGGCAGCTTCCCCCTGCCTTTTGCAC

GTTTGCATCCCCAGCATTTCCTGAGTTATAAGGCCACAGGAGTGGATAGC

TGTTTTCACCTAAAGGAAAAGCCCACCCGAATCTTGTAGAAATATTCAAA

CTAATAAAATCATGAATATTTTTATGAAGTTTAAAAA

Phospholipase A2, Group XIIB
>gi|45505134|ref|NM_032562.2| *Homo sapiens* phospholipase A2, group XIIB (PLA2G12B), mRNA

SEQ ID NO: 90

TGTCCCTGGAATTCTGGGACACTGGCTGGGGTTTGAGGAGAGAAGCCAGT

ACCTACCTGGCTGCAGGATGAAGCTGGCCAGTGGCTTCTTGGTTTTGTGG

CTCAGCCTTGGGGGTGGCCTGGCTCAGAGCGACACGAGCCCTGACACGGA

GGAGTCCTATTCAGACTGGGGCCTTCGGCACCTCCGGGGAAGCTTTGAAT

CCGTCAATAGCTACTTCGATTCTTTTCTGGAGCTGCTGGGAGGGAAGAAT

GGAGTCTGTCAGTACAGGTGCCGATATGGAAAGGCACCAATGCCCAGACC

TGGCTACAAGCCCCAAGAGCCCAATGGCTGCGGCTCCTATTTCCTGGGTC

TCAAGGTACCAGAAAGTATGGACTTGGGCATTCCAGCAATGACAAAGTGC

TGCAACCAGCTGGATGTCTGTTATGACACTTGCGGTGCCAACAAATATCG

CTGTGATGCAAAATTCCGATGGTGTCTCCACTCGATCTGCTCTGACCTTA

AGCGGAGTCTGGGCTTTGTCTCCAAAGTGGAAGCAGCCTGTGATTCCCTG

GTTGACACTGTGTTCAACACCGTGTGGACCTTGGGCTGCCGCCCCTTTAT

GAATAGTCAGCGGGCAGCTTGCATCTGTGCAGAGGAGGAGAAGGAAGAGT

-continued

TATGAGGAAGAAGTGATTCCTTCCTGGTTTTGAGTGACACCACAGCTGTC

AGCCTTCAAGATGTCAAGTCTTCGAGTCAGCGTGACTCATTCATTCTTCC

AACAGTTTGGACACCACAAAGCAGGAGAAAGGGAACATTTTTCTACAGCT

GGAAAGTGAGTCCTATCCTTTGAGGAAATTTGAAAAAAGACATGGAGTGG

TTTGAAAGCTACTCTTCATTTAAGACTGCTCTCCCCAACCAAGACACATT

TGCCTGGAAATTCAGTTCTTAGCTTAAAGACTAAAATGCAAGCAAACCCT

GCAATTCCTGGACCTGATAGTTATATTCATGAGTGAAATTGTGGGGAGTC

CAGCCATTTGGGAGGCAATGACTTTCTGCTGGCCCATGTTTCAGTTGCCA

GTAAGCTTCTCACATTTAATAAAGTGTACTTTTTAGAACATT

Spondin 2, Extracellular Matrix Protein
>gi|6912681|ref|NM_012445.1| *Homo sapiens* spondin 2, extracellular matrix protein (SPON2), mRNA

SEQ ID NO: 91

GCACGAGGGAAGAGGGTGATCCGACCCGGGGAAGGTCGCTGGGCAGGGCG

AGTTGGGAAAGCGGCAGCCCCCGCCGCCCCCGCAGCCCCTTCTCCTCCTT

TCTCCCACGTCCTATCTGCCTCTCGCTGGAGGCCAGGCCGTGCAGCATCG

AAGACAGGAGGAACTGGAGCCTCATTGGCCGGCCCGGGGCGCCGGCCTCG

GGCTTAAATAGGAGCTCCGGGCTCTGGCTGGGACCCGACCGCTGCCGGCC

GCGCTCCCGCTGCTCCTGCCGGGTGATGGAAAACCCCAGCCCGGCCGCCG

CCCTGGGCAAGGCCCTCTGCGCTCTCCTCCTGGCCACTCTCGGCGCCGCC

GGCCAGCCTCTTGGGGGAGAGTCCATCTGTTCCGCCAGAGCCCCGGCCAA

ATACAGCATCACCTTCACGGGCAAGTGGAGCCAGACGGCCTTCCCCAAGC

AGTACCCCCTGTTCCGCCCCCCTGCGCAGTGGTCTTCGCTGCTGGGGGCC

GCGCATAGCTCCGACTACAGCATGTGGAGGAAGAACCAGTACGTCAGTAA

CGGGCTGCGCGACTTTGCGGAGCGCGGCGAGGCCTGGGCGCTGATGAAGG

AGATCGAGGCGGCGGGGGAGGCGCTGCAGAGCGTGCACGCGGTGTTTTCG

GCGCCCGCCGTCCCCAGCGGCACCGGGCAGACGTCGGCGGAGCTGGAGGT

GCAGCGCAGGCACTCGCTGGTCTCGTTTGTGGTGCGCATCGTGCCCAGCC

CCGACTGGTTCGTGGGCGTGGACAGCCTGGACCTGTGCGACGGGGACCGT

TGGCGGGAACAGGCGGCGCTGGACCTGTACCCCTACGACGCCGGGACGGA

CAGCGGCTTCACCTTCTCCTCCCCCAACTTCGCCACCATCCCGCAGGACA

CGGTGACCGAGATAACGTCCTCCTCTCCCAGCCACCCGGCCAACTCCTTC

TACTACCCGCGGCTGAAGGCCCTGCCTCCCATCGCCAGGGTGACACTGGT

GCGGCTGCGACAGAGCCCCAGGGCCTTCATCCCTCCCGCCCCAGTCCTGC

CCAGCAGGGACAATGAGATTGTAGACAGCGCCTCAGTTCCAGAAACGCCG

CTGGACTGCGAGGTCTCCCTGTGGTCGTCCTGGGGACTGTGCGGAGGCCA

CTGTGGGAGGCTCGGGACCAAGAGCAGGACTCGCTACGTCCGGGTCCAGC

CCGCCAACAACGGGAGCCCCTGCCCCGAGCTCGAAGAAGAGGCTGAGTGC

GTCCCTGATAACTGCGTCTAAGACCAGAGCCCCGCAGCCCCTGGGGCCCC

CGGAGCCATGGGGTGTCGGGGGCTCCTGTGCAGGCTCATGCTGCAGGCGG

CCGAGGCACAGGGGGTTTCGCGCTGCTCCTGACCGCGGTGAGGCCGCGCC

-continued

```
GACCATCTCTGCACTGAAGGGCCCTCTGGTGGCCGGCACGGGCATTGGGA
AACAGCCTCCTCCTTTCCCAACCTTGCTTCTTAGGGGCCCCCGTGTCCCG
TCTGCTCTCAGCCTCCTCCTCCTGCAGGATAAAGTCATCCCCAAGGCTCC
AGCTACTCTAAATTATGGTCTCCTTATAAGTTATTGCTGCTCCAGGAGAT
TGTCCTTCATCGTCCAGGGGCCTGGCTCCCACGTGGTTGCAGATACCTCA
GACCTGGTGCTCTAGGCTGTGCTGAGCCCACTCTCCCGAGGGCGCATCCA
AGCGGGGGCCACTTGAGAAGTGAATAAATGGGGCGGTTTCGGAAGCGTCA
GTGTTTCCATGTTATGGATCTCTCTGCGTTTGAATAAAGACTATCTCTGT
TGCTCAC
```

Olfactomedin 1, Transcript Variant 3

>gi|34335282|ref|NM_058199.2| *Homo sapiens* olfactomedin 1 (OLFM1), transcript variant 3, mRNA

SEQ ID NO: 92

```
CCCGCCCCCGCCCCTTCCGAGCAAACTTTTGGCACCCACCGCAGCCCAGC
GCGCGTTCGTGCTCCGCAGGGCGCGCCTCTCTCCGCCAATGCCAGGCGCG
CGGGGGAGCCATTAGGAGGCGAGGAGAGAGGAGGGCGCAGCTCCCGCCCA
GCCCAGCCCTGCCCAGCCCTGCCCGGAGGCAGACGCGCCGGAACCGGGAC
GCGATAAATATGCAGAGCGGAGGCTTCGCGCAGCAGAGCCCGCGCGCCGC
CCGCTCCGGGTGCTGAATCCAGGCGTGGGGACACGAGCCAGGCGCCGCCG
CCGGAGCCAGCGGAGCCGGGGCCAGAGCCGGAGCGCGTCCGCGTCCACGC
AGCCGCCGGCCGGCCAGCACCCAGGGCCCTGCATGCCAGGTCGTTGGAGG
TGGCAGCGAGACATGCACCCGGCCCGGAAGCTCCTCAGCCTCCTCTTCCT
CATCCTGATGGGCACTGAACTCACTCAAAATAAAAGAGAAAACAAAGCAG
AGAAGATGGGAGGGCCAGAGAGCGAGAGGAAGACCACAGGAGAGAAGACA
CTGAACGAGCTTCCCTTGTTTTGCCTGGAAGCCCACGCTGGCTCCCTGGC
TCTGCCCAGGATGTGCAGTCCAAATCCCAATCCAGCAGTGGGGTTATGTC
GTCCCGCTTACCCTCAGAGCCCTTCTCCTGGTGCTGCCCAGACGATCAGC
CAGTCCCTCCTGGAGAGGTTCTGCATGGCCTCTAGGAGAGAAGTTTTCTT
GGCCCCAGGAAGGCCTGGTGGAGGGTGGTGGTTGTGCACTGTTGCTGGAC
AGATGCATTCATTCATGTGCACACACACACACACACATGCACACACAGGG
GAGCAGATACCTGCAGAGAAGAGCCAACCAGGTCCTGATTAGTGGCAAGC
TGCCCCACAAAGGGCTATGCCTGTGTCTTATTGAGACACCTTGGCAAAGA
GATGGCTGATTCTGGGTGGTCCTGGACATGGCCGCACCCAAGGGCCCTCC
AAGCCTTAATGGCACCCTGAAGCCTCCATGCCCAGGCCAAAAGATGCTTT
TCCTCCCTAAAAAAAAAAAAAAAAAAA
```

Thrombospondin Repeat Containing 1

>gi|38016903|ref|NM_019032.2| *Homo sapiens* thrombospondin repeat containing 1 (TSRC1), mRNA

SEQ ID NO: 93

```
GGGGCCCCAGTGGCCGCCGCGGAGCGAGGTTGCCTGGAGAGAGCGCCTGG
GCGCAGAAGGGTTAACGGGCCACCGGGGGCTCGCAGAGCAGGAGGGTGCT
```

-continued

```
CTCGGACGGTGTGTCCCCCACTGCACTCCTGAACTTGGAGGACAGGGTCG
CCGCGAGGGACGCAGAGAGCACCCTCCACGCCCAGATGCCTGCGTAGTTT
TTGTGACCAGTCCGCTCCTGCCTCCCCCTGGGGCAGTAGAGGGGGAGCGA
TGGAGAACTGGACTGGCAGGCCCTGGCTGTATCTGCTGCTGCTTCTGTCC
CTCCCTCAGCTCTGCTTGGATCAGGAGGTGTTGTCCGGACACTCTCTTCA
GACACCTACAGAGGAGGGCCAGGGCCCCGAAGGTGTCTGGGGACCTTGGG
TCCAGTGGGCCTCTTGCTCCCAGCCCTGCGGGGTGGGGGTGCAGCGCAGG
AGCCGGACATGTCAGCTCCCTACAGTGCAGCTCCACCCGAGTCTGCCCCT
CCCTCCCCGGCCCCCAAGACATCCAGAAGCCCTCCTCCCCCGGGGCCAGG
GTCCCAGACCCCAGACTTCTCCAGAAACCCTCCCCTTGTACAGGACACAG
TCTCGGGGAAGGGGTGGCCCACTTCGAGGTCCCGCTTCCCACCTAGGGAG
AGAGGAGACCCAGGAGATTCGAGCGGCCAGGAGGTCCCGGCTTCGAGACC
CCATCAAGCCAGGAATGTTCGGTTATGGGAGAGTGCCCTTTGCATTGCCA
CTGCACCGGAACCGCAGGCACCCTCGGAGCCCACCCAGATCTGAGCTGTC
CCTGATCTCTTCTAGAGGGGAAGAGGCTATTCCGTCCCCTACTCCAAGAG
CAGAGCCATTCTCCGCAAACGGCAGCCCCCAAACTGAGCTCCCTCCCACA
GAACTGTCTGTCCACACCCCATCCCCCCAAGCAGAACCTCTAAGCCCTGA
AACTGCTCAGACAGAGGTGGCCCCCAGAACCAGGCCTGCCCCCCTACGGC
ATCACCCCAGAGCCCAGGCCTCTGGCACAGAGCCCCCCTCACCCACGCAC
TCCTTAGGAGAAGGTGGCTTCTTCCGTGCATCCCCTCAGCCACGAAGGCC
AAGTTCCCAGGGTTGGGCCAGTCCCCAGGTAGCAGGGAGACGCCCTGATC
CTTTTCCTTCGGTCCCTCGGGGCCGAGGCCAGCAGGGCCAAGGGCCTTGG
GGAACGGGGGGGACTCCTCACGGGCCCCGCCTGGAGCCTGACCCTCAGCA
CCCGGGCGCCTGGCTGCCCCTGCTGAGCAACGGCCCCCATGCCAGCTCCC
TCTGGAGCCTCTTTGCTCCCAGTAGCCCTATTCCAAGATGTTCTGGGGAG
AGTGAACAGCTAAGAGCCTGCAGCCAAGCGCCCTGCCCCCCTGAGCAGCC
AGACCCCCGGGCCCTGCAGTGCGCAGCCTTTAACTCCCAGGAATTCATGG
GCCAGCTGTATCAGTGGGAGCCCTTCACTGAAGTCCAGGGCTCCCAGCGC
TGTGAACTGAACTGCCGGCCCCGTGGCTTCCGCTTCTATGTCCGTCACAC
TGAAAAGGTCCAGGATGGGACCCTGTGTCAGCCTGGAGCCCCTGACATCT
GTGTGGCTGGACGCTGTCTGAGCCCCGGCTGTGATGGGATCCTTGGCTCT
GGCAGGCGTCCTGATGGCTGTGGAGTCTGTGGGGGTGATGATTCTACCTG
TCGCCTTGTTTCGGGGAACCTCACTGACCGAGGGGGCCCCCTGGGCTATC
AGAAGATCTTGTGGATTCCAGCGGGAGCCTTGCGGCTCCAGATTGCCCAG
CTCCGGCCTAGCTCCAACTACCTGGCACTTCGTGGCCCTGGGGGCCGGTC
CATCATCAATGGGAACTGGGCTGTGGATCCCCCTGGGTCCTACAGGGCCG
GCGGGACCGTCTTTCGATATAACCGTCCTCCCAGGGAGGAGGGCAAAGGG
GAGAGTCTGTCGGCTGAAGGCCCCACCACCCAGCCTGTGGATGTCTATAT
GATCTTTCAGGAGGAAAACCCAGGCGTTTTTTATCAGTATGTCATCTCTT
CACCTCCTCCAATCCTTGAGAACCCCACCCCAGAGCCCCCTGTCCCCCAG
CTTCAGCCGGAGATTCTGAGGGTGGAGCCCCCACTTGCTCCGGCACCCCG
```

-continued

CCCAGCCCGGACCCCAGGCACCCTCCAGCGTCAGGTGCGGATCCCCCAGA
TGCCCGCCCCGCCCCATCCCAGGACACCCCTGGGGTCTCCAGCTGCGTAC
TGGAAACGAGTGGGACACTCTGCATGCTCAGCGTCCTGCGGGAAAGGTGT
CTGGCGCCCCATTTTCCTCTGCATCTCCCGTGAGTCGGGAGAGGAACTGG
ATGAACGCAGCTGTGCCGCGGGTGCCAGGCCCCCAGCCTCCCCTGAACCC
TGCCACGGCACCCCATGCCCCCCATACTGGGAGGCTGGCGAGTGGACATC
CTGCAGCCGCTCCTGTGGCCCCGGCACCCAGCACCGCCAGCTGCAGTGCC
GGCAGGAATTTGGGGGGGGTGGCTCCTCGGTGCCCCCGGAGCGCTGTGGA
CATCTCCCCCGGCCCAACATCACCCAGTCTTGCCAGCTGCGCCTCTGTGG
CCATTGGGAAGTTGGCTCTCCTTGGAGCCAGTGCTCCGTGCGGTGCGGCC
GGGGCCAGAGAAGCCGGCAGGTTCGCTGTGTTGGGAACAACGGTGATGAA
GTGAGCGAGCAGGAGTGTGCGTCAGGCCCCCCGCAGCCCCCCAGCAGAGA
GGCCTGTGACATGGGGCCCTGTACTACTGCCTGGTTCCACAGCGACTGGA
GCTCCAAGTGCTCAGCCGAGTGTGGGACGGGAATCCAGCGGCGCTCTGTG
GTCTGCCTTGGGAGTGGGGCAGCCCTCGGGCCAGGCCAGGGGGAAGCAGG
AGCAGGAACTGGGCAGAGCTGTCCAACAGGAAGCCGGCCCCCTGACATGC
GCGCCTGCAGCCTGGGGCCCTGTGAGAGAACTTGGCGCTGGTACACAGGG
CCCTGGGGTGAGTGCTCCTCCGAATGTGGCTCTGGCACACAGCGTAGAGA
CATCATCTGTGTATCCAAACTGGGGACGGAGTTCAACGTGACTTCTCCGA
GCAACTGTTCTCACCTCCCCAGGCCCCCTGCCCTGCAGCCCTGTCAAGGG
CAGGCCTGCCAGGACCGATGGTTTTCCACGCCCTGGAGCCCATGTTCTCG
CTCCTGCCAAGGGGGAACGCAGACACGGGAGGTCCAGTGCCTGAGCACCA
ACCAGACCCTCAGCACCCGATGCCCTCCTCAACTGCGGCCCTCCAGGAAG
CGCCCCTGTAACAGCCAACCCTGCAGCCAGCGCCCTGATGATCAATGCAA
GGACAGCTCTCCACATTGCCCCCTGGTGGTACAGGCCCGGCTCTGCGTCT
ACCCCTACTACACAGCCACCTGTTGCCGCTCTTGCGCACATGTCCTGGAG
CGGTCTCCCCAGGATCCCTCCTGAAAGGGGTCCGGGGCACCTTCACGGTT
TTCTGTGCCACCATCGGTCACCCATTGATCGGCCCACTCTGAACCCCCTG
GCTCTCCAGCCTGTCCCAGTCTCAGCAGGGATGTCCTCCAGGTGACAGAG
GGTGGCAAGGTGACTGACACAAAGTGACTTTCAGGGCTGTGGTCAGGCCC
ATGTGGTGGTGTGATGGGTGTGTGCACATATGCCTCAGGTGTGCTTTTGG
GACTGCATGGATATGTGTGTGCTCAAACGTGTATCACTTTTCAAAAAGAG
GTTACACAGACTGAGAAGGACAAGACCTGTTTCCTTGAGACTTTCCTAGG
TGGAAAGGAAAGCAAGTCTGCAGTTCCTTGCTAATCTGAGCTACTTAGAG
TGTGGTCTCCCCACCAACTCCAGTTTTGTGCCCTAAGCCTCATTTCTCAT
GTTCAGACCTCACATCTTCTAAGCCGCCCTGTGTCTCTGACCCCTTCTCA
TTTGCCTAGTATCTCTGCCCCTGCCTCCCTAATTAGCTAGGGCTGGGGTC
AGCCACTGCCAATCCTGCCTTACTCAGGAAGGCAGGAGGAAAGAGACTGC
CTCTCCAGAGCAAGGCCCAGCTGGGCAGAGGGTGAAAAAGAGAAATGTGA
GCATCCGCTCCCCCACCACCCCGCCCAGCCCCTAGCCCCACTCCCTGCCT

-continued

CCTGAAATGGTTCCCACCCAGAACTAATTTATTTTTTATTAAAGATGGTC
ATGACAAATGAAAAAAAAAAAAAAAAAAA

Thrombospondin 2

>gi|40317627|ref|NM_003247.2| *Homo sapiens* thrombospondin 2 (THBS2), mRNA|qPCR forward_primer match [3558 . . . 3580]|qPCR reverse_primer match [3682 . . . 3655]|qPCR probe match [3597 . . . 3623]

SEQ ID NO: 94

GAGGAGGAGACGGCATCCAGTACAGAGGGGCTGGACTTGGACCCCTGCAG
CAGCCCTGCACAGGAGAAGCGGCATATAAAGCCGCGCTGCCCGGGAGCCG
CTCGGCCACGTCCACCGGAGCATCCTGCACTGCAGGGCCGGTCTCTCGCT
CCAGCAGAGCCTGCGCCTTTCTGACTCGGTCCGGAACACTGAAACCAGTC
ATCACTGCATCTTTTTGGCAAACCAGGAGCTCAGCTGCAGGAGGCAGGAT
GGTCTGGAGGCTGGTCCTGCTGGCTCTGTGGGTGTGGCCCAGCACGCAAG
CTGGTCACCAGGACAAAGACACGACCTTCGACCTTTTCAGTATCAGCAAC
ATCAACCGCAAGACCATTGGCGCCAAGCAGTTCCGCGGGCCCGACCCCGG
CGTGCCGGCTTACCGCTTCGTGCGCTTTGACTACATCCCACCGGTGAACG
CAGATGACCTCAGCAAGATCACCAAGATCATGCGGCAGAAGGAGGGCTTC
TTCCTCACGGCCCAGCTCAAGCAGGACGGCAAGTCCAGGGGCACGCTGTT
GGCTCTGGAGGGCCCCGGTCTCTCCCAGAGGCAGTTCGAGATCGTCTCCA
ACGGCCCCGCGGACACGCTGGATCTCACCTACTGGATTGACGGCACCCGG
CATGTGGTCTCCCTGGAGGACGTCGGCCTGGCTGACTCGCAGTGGAAGAA
CGTCACCGTGCAGGTGGCTGGCGAGACCTACAGCTTGCACGTGGGCTGCG
ACCTCATAGACAGCTTCGCTCTGGACGAGCCCTTCTACGAGCACCTGCAG
GCGGAAAAGAGCCGGATGTACGTGGCCAAAGGCTCTGCCAGAGAGAGTCA
CTTCAGGGGTTTGCTTCAGAACGTCCACCTAGTGTTTGAAAACTCTGTGG
AAGATATTCTAAGCAAGAAGGGTTGCCAGCAAGGCCAGGGAGCTGAGATC
AACGCCATCAGTGAGAACACAGAGACGCTGCGCCTGGGTCCGCATGTCAC
CACCGAGTACGTGGGCCCCAGCTCGGAGAGGAGGCCCGAGGTGTGCGAAC
GCTCGTGCGAGGAGCTGGGAAACATGGTCCAGGAGCTCTCGGGGCTCCAC
GTCCTCGTGAACCAGCTCAGCGAGAACCTCAAGAGAGTGTCGAATGATAA
CCAGTTTCTCTGGGAGCTCATTGGTGGCCCTCCTAAGACAAGGAACATGT
CAGCTTGCTGGCAGGATGGCCGGTTCTTTGCGGAAAATGAAACGTGGGTG
GTGGACAGCTGCACCACGTGTACCTGCAAGAAATTTAAAACCATTTGCCA
CCAAATCACCTGCCCGCCTGCAACCTGCGCCAGTCCATCCTTTGTGGAAG
GCGAATGCTGCCCTTCCTGCCTCCACTCGGTGGACGGTGAGGAGGGCTGG
TCTCCGTGGGCAGAGTGGACCCAGTGCTCCGTGACGTGTGGCTCTGGGAC
CCAGCAGAGAGGCCGGTCCTGTGACGTCACCAGCAACACCTGCTTGGGGC
CCTCCATCCAGACACGGGCTTGCAGTCTGAGCAAGTGTGACACCCGCATC
CGGCAGGACGGCGGCTGGAGCCACTGGTCACCTTGGTCTTCATGCTCTGT
GACCTGTGGAGTTGGCAATATCACACGCATCCGTCTCTGCAACTCCCCAG
TGCCCCAGATGGGGGGCAAGAATTGCAAAGGGAGTGGCCGGGAGACCAAA

-continued

GCCTGCCAGGGCGCCCCATGCCCAATCGATGGCCGCTGGAGCCCCTGGTC

CCCGTGGTCGGCCTGCACTGTCACCTGTGCCGGTGGGATCCGGGAGCGCA

CCCGGGTCTGCAACAGCCCTGAGCCTCAGTACGGAGGGAAGGCCTGCGTG

GGGGATGTGCAGGAGCGTCAGATGTGCAACAAGAGGAGCTGCCCCGTGGA

TGGCTGTTTATCCAACCCCTGCTTCCCGGGAGCCCAGTGCAGCAGCTTCC

CCGATGGGTCCTGGTCATGCGGCTCCTGCCCTGTGGGCTTCTTGGGCAAT

GGCACCCACTGTGAGGACCTGGACGAGTGTGCCCTGGTCCCCGACATCTG

CTTCTCCACCAGCAAGGTGCCTCGCTGTGTCAACACTCAGCCTGGCTTCC

ACTGCCTGCCCTGCCCGCCCCGATACAGAGGGAACCAGCCCGTCGGGGTC

GGCCTGGAAGCAGCCAAGACGGAAAAGCAAGTGTGTGAGCCCGAAAACCC

ATGCAAGGACAAGACACACAACTGCCACAAGCACGCGGAGTGCATCTACC

TGGGCCACTTCAGCGACCCCATGTACAAGTGCGAGTGCCAGACAGGCTAC

GCGGGCGACGGGCTCATCTGCGGGGAGGACTCGGACCTGGACGGCTGGCC

CAACCTCAATCTGGTCTGCGCCACCAACGCCACCTACCACTGCATCAAGG

ATAACTGCCCCCATCTGCCAAATTCTGGGCAGGAAGACTTTGACAAGGAC

GGGATTGGCGATGCCTGTGATGATGACGATGACAATGACGGTGTGACCGA

TGAGAAGGACAACTGCCAGCTCCTCTTCAATCCCCGCCAGGCTGACTATG

ACAAGGATGAGGTTGGGGACCGCTGTGACAACTGCCCTTACGTGCACAAC

CCTGCCCAGATCGACACAGACAACAATGGAGAGGGTGACGCCTGCTCCGT

GGACATTGATGGGGACGATGTCTTCAATGAACGAGACAATTGTCCCTACG

TCTACAACACTGACCAGAGGGACACGGATGGTGACGGTGTGGGGGATCAC

TGTGACAACTGCCCCCTGGTGCACAACCCTGACCAGACCGACGTGGACAA

TGACCTTGTTGGGGACCAGTGTGACAACAACGAGGACATAGATGACGACG

GCCACCAGAACAACCAGGACAACTGCCCCTACATCTCCAACGCCAACCAG

GCTGACCATGACAGAGACGGCCAGGGCGACGCCTGTGACCCTGATGATGA

CAACGATGGCGTCCCCGATGACAGGGACAACTGCCGGCTTGTGTTCAACC

CAGACCAGGAGGACTTGGACGGTGATGGACGGGGTGATATTTGTAAAGAT

GATTTTGACAATGACAACATCCCAGATATTGATGATGTGTGTCCTGAAAA

CAATGCCATCAGTGAGACAGACTTCAGGAACTTCCAGATGGTCCCCTTGG

ATCCCAAAGGGACCACCCAAATTGATCCCAACTGGGTCATTCGCCATCAA

GGCAAGGAGCTGGTTCAGACAGCCAACTCGGACCCCGGCATCGCTGTAGG

TTTTGACGAGTTTGGGTCTGTGGACTTCAGTGGCACATTCTACGTAAACA

CTGACCGGGACGACGACTATGCCGGCTTCGTCTTTGGTTACCAGTCAAGC

AGCCGCTTCTATGTGGTGATGTGGAAGCAGGTGACGCAGACCTACTGGGA

GGACCAGCCCACGCGGGCCTATGGCTACTCCGGCGTGTCCCTCAAGGTGG

TGAACTCCACCACGGGGACGGGCGAGCACCTGAGGAACGCGCTGTGGCAC

ACGGGGAACACGCCGGGGCAGGTGCGAACCTTATGGCACGACCCCAGGAA

CATTGGCTGGAAGGACTACACGGCCTATAGGTGGCACCTGACTCACAGGC

CCAAGACTGGCTACATCAGAGTCTTAGTGCATGAAGGAAAACAGGTCATG

GCAGACTCAGGACCTATCTATGACCAAACCTACGCTGGCGGGCGGCTGGG

-continued

TCTATTTGTCTTCTCTCAAGAAATGGTCTATTTCTCAGACCTCAAGTACG

AATGCAGAGATATTTAAACAAGATTTGCTGCATTTCCGGCAATGCCCTGT

GCATGCCATGGTCCCTAGACACCTCAGTTCATTGTGGTCCTTGTGGCTTC

TCTCTCTAGCAGCACCTCCTGTCCCTTGACCTTAACTCTGATGGTTCTTC

ACCTCCTGCCAGCAACCCCAAACCCAAGTGCCTTCAGAGGATAAATATCA

ATGGAACTCAGAGATGAACATCTAACCCACTAGAGGAAACCAGTTTGGTG

ATATATGAGACTTTATGTGGAGTGAAAATTGGGCATGCCATTACATTGCT

TTTTCTTGTTTGTTTAAAAAGAATGACGTTTACATATAAAATGTAATTAC

TTATTGTATTTATGTGTATATGGAGTTGAAGGGAATACTGTGCATAAGCC

ATTATGATAAATTAAGCATGAAAAATATTGCTGAACTACTTTTGGTGCTT

AAAGTTGTCACTATTCTTGAATTAGAGTTGCTCTACAATGACACACAAAT

CCCATTAAATAAATTATAAACAAGGGTCAATTCAAATTTGAAGTAATGTT

TTAGTAAGGAGAGATTAGAAGACAACAGGCATAGCAAATGACATAAGCTA

CCGATTAACTAATCGGAACATGTAAAACAGTTACAAAAATAAACGAACTC

TCCTCTTGTCCTACAATGAAAGCCCTCATGTGCAGTAGAGATGCAGTTTC

ATCAAAGAACAAACATCCTTGCAAATGGGTGTGACGCGGTTCCAGATGTG

GATTTGGCAAAACCTCATTTAAGTAAAAGGTTAGCAGAGCAAAGTGCGGT

GCTTTAGCTGCTGCTTGTGCCGCTGTGGCGTCGGGGAGGCTCCTGCCTGA

GCTTCCTTCCCCAGCTTTGCTGCCTGAGAGGAACCAGAGCAGACGCACAG

GCCGGAAAAGGCGCATCTAACGCGTATCTAGGCTTTGGTAACTGCGGACA

AGTTGCTTTTACCTGATTTGATGATACATTTCATTAAGGTTCCAGTTATA

AATATTTTGTTAATATTTATTAAGTGACTATAGAATGCAACTCCATTTAC

CAGTAACTTATTTTAAATATGCCTAGTAACACATATGTAGTATAATTTCT

AGAAACAAACATCTAATAAGTATATAATCCTGTGAAAATATGAGGCTTGA

TAATATTAGGTTGTCACGATGAAGCATGCTAGAAGCTGTAACAGAATACA

TAGAGAATAATGAGGAGTTTATGATGGAACCTTAAATATATAATGTTGCC

AGCGATTTTAGTTCAATATTTGTTACTGTTATCTATCTGCTGTATATGGA

ATTCTTTTAATTCAAACGCTGAAAAGAATCAGCATTTAGTCTTGCCAGGC

ACACCCAATAATCAGTCATGTGTAATATGCACAAGTTTGTTTTTTGTTTT

GTTTTTGTTTGGTTGGTTTGTTTTTTTGCTTTAAGTTGCATGATCTTTCT

GCAGGAAATAGTCACTCATCCCACTCCACATAAGGGGTTTAGTAAGAGAA

GTCTGTCTGTCTGATGATGGATAGGGGGCAAATCTTTTTCCCCTTTCTGT

TAATAGTCATCACATTTCTATGCCAAACAGGAACAATCCATAACTTTAGT

CTTAATGTACACATTGCATTTTGATAAAATTAATTTTTGTTGTTTCCTTT

GAGGTTGATCGTTGTGTTGTTGTTTGCTGCACTTTTTTACTTTTTTGCGT

GTGGAGCTGTATTCCCGAGACCAACGAAGCGTTGGGATACTTCATTAAAT

GTAGCGACTGTCAACAGCGTGCAGGTTTTCTGTTTCTGTGTTGTGGGGTC

AACCGTACAATGGTGTGGGAGTGACGATGATGTGAATATTTAGAATGTAC

CATATTTTTTGTAAATTATTTATGTTTTTCTAAACAAATTTATCGTATAG

GTTGATGAAACGTCATGTGTTTTGCCAAAGACTGTAAATATTTATTTATG

TGTTCACATGGTCAAAATTTCACCACTGAAACCCTGCACTTAGCTAGAAC

-continued

CTCATTTTTAAAGATTAACAACAGGAAATAAATTGTAAAAAAGGTTTTCT

ATACATGAAAAAAAAAAAAAAAAAA

Adlican
>gi|18390318|ref|NM_015419.1| *Homo sapiens* adlican (DKFZp564I1922), mRNA|qPCR assay_on_demand_context match [694 . . . 718]

SEQ ID NO: 95

ATGCCCAAGCGCGCGCACTGGGGGGCCCTCTCCGTGGTGCTGATCCTGCT

TTGGGGCCATCCGCGAGTGGCGCTGGCCTGCCCGCATCCTTGTGCCTGCT

ACGTCCCCAGCGAGGTCCACTGCACGTTCCGATCCCTGGCTTCCGTGCCC

GCTGGCATTGCTAGACACGTGGAAAGAATCAATTTGGGGTTTAATAGCAT

ACAGGCCCTGTCAGAAACCTCATTTGCAGGACTGACCAAGTTGGAGCTAC

TTATGATTCACGGCAATGAGATCCCAAGCATCCCCGATGGAGCTTTAAGA

GACCTCAGCTCTCTTCAGGTTTTCAAGTTCAGCTACAACAAGCTGAGAGT

GATCACAGGACAGACCCTCCAGGGTCTCTCTAACTTAATGAGGCTGCACA

TTGACCACAACAAGATCGAGTTTATCCACCCTCAAGCTTTCAACGGCTTA

ACGTCTCTGAGGCTACTCCATTTGGAAGGAAATCTCCTCCACCAGCTGCA

CCCCAGCACCTTCTCCACGTTCACATTTTTGGATTATTTCAGACTCTCCA

CCATAAGGCACCTCTACTTAGCAGAGAACATGGTTAGAACTCTTCCTGCC

AGCATGCTTCGGAACATGCCGCTTCTGGAGAATCTTTACTTGCAGGGAAA

TCCGTGGACCTGCGATTGTGAGATGAGATGGTTTTTGGAATGGGATGCAA

AATCCAGAGGAATTCTGAAGTGTAAAAAGGACAAAGCTTATGAAGGCGGT

CAGTTGTGTGCAATGTGCTTCAGTCCAAAGAAGTTGTACAAACATGAGAT

ACACAAGCTGAAGGACATGACTTGTCTGAAGCCTTCAATAGAGTCCCCTC

TGAGACAGAACAGGAGCAGGAGTATTGAGGAGGAGCAAGAACAGGAAGAG

GATGGTGGCAGCCAGCTCATCCTGGAGAAATTCCAACTGCCCCAGTGGAG

CATCTCTTTGAATATGACCGACGAGCACGGGAACATGGTGAACTTGGTCT

GTGACATCAAGAAACCAATGGATGTGTACAAGATTCACTTGAACCAAACG

GATCCTCCAGATATTGACATAAATGCAACAGTTGCCTTGGACTTTGAGTG

TCCAATGACCCGAGAAAACTATGAAAAGCTATGGAAATTGATAGCATACT

ACAGTGAAGTTCCCGTGAAGCTACACAGAGAGCTCATGCTCAGCAAAGAC

CCCAGAGTCAGCTACCAGTACAGGCAGGATGCTGATGAGGAAGCTCTTTA

CTACACAGGTGTGAGAGCCCAGATTCTTGCAGAACCAGAATGGGTCATGC

AGCCATCCATAGATATCCAGCTGAACCGACGTCAGAGTACGGCCAAGAAG

GTGCTACTTTCCTACTACACCCAGTATTCTCAAACAATATCCACCAAAGA

TACAAGGCAGGCTCGGGGCAGAAGCTGGGTAATGATTGAGCCTAGTGGAG

CTGTGCAAAGAGATCAGACTGTCCTGGAAGGGGGTCCATGCCAGTTGAGC

TGCAACGTGAAAGCTTCTGAGAGTCCATCTATCTTCTGGGTGCTTCCAGA

TGGCTCCATCCTGAAAGCGCCCATGGATGACCCAGACAGCAAGTTCTCCA

TTCTCAGCAGTGGCTGGCTGAGGATCAAGTCCATGGAGCCATCTGACTCA

GGCTTGTACCAGTGCATTGCTCAAGTGAGGGATGAAATGGACCGCATGGT

-continued

ATATAGGGTACTTGTGCAGTCTCCCTCCACTCAGCCAGCCGAGAAAGACA

CAGTGACAATTGGCAAGAACCCAGGGGAGTCGGTGACATTGCCTTGCAAT

GCTTTAGCAATACCCGAAGCCCACCTTAGCTGGATTCTTCCAAACAGAAG

GATAATTAATGATTTGGCTAACACATCACATGTATACATGTTGCCAAATG

GAACTCTTTCCATCCCAAAGGTCCAAGTCAGTGATAGTGGTTACTACAGA

TGTGTGGCTGTCAACCAGCAAGGGGCAGACCATTTTACGGTGGGAATCAC

AGTGACCAAGAAAGGGTCTGGCTTGCCATCCAAAAGAGGCAGACGCCCAG

GTGCAAAGGCTCTTTCCAGAGTCAGAGAAGACATCGTGGAGGATGAAGGG

GGCTCGGGCATGGGAGATGAAGAGAACACTTCAAGGAGACTTCTGCATCC

AAAGGACCAAGAGGTGTTCCTCAAAACAAAGGATGATGCCATCAATGGAG

ACAAGAAAGCCAAGAAAGGGAGAAGAAAGCTGAAACTCTGGAAGCATTCG

GAAAAAGAACCAGAGACCAATGTTGCAGAAGGTCGCAGAGTGTTTGAATC

TAGACGAAGGATAAACATGGCAAACAAACAGATTAATCCGGAGCGCTGGG

CTGATATTTTAGCCAAAGTCCGTGGGAAAAATCTCCCTAAGGGCACAGAA

GTACCCCCGTTGATTAAAACCACAAGTCCTCCATCCTTGAGCCTAGAAGT

CACACCACCTTTTCCTGCTGTTTCTCCCCCCTCAGCATCTCCTGTGCAGA

CAGTAACCAGTGCTGAAGAATCCTCAGCAGATGTACCTCTACTTGGTGAA

GAAGAGCACGTTTTGGGTACCATTTCCTCAGCCAGCATGGGGCTAGAACA

CAACCACAATGGAGTTATTCTTGTTGAACCTGAAGTAACAAGCACACCTC

TGGAGGAAGTTGTTGATGACCTTTCTGAGAAGACTGAGGAGATAACTTCC

ACTGAAGGAGACCTGAAGGGGACAGCAGCCCCTACACTTATATCTGAGCC

TTATGAACCATCTCCTACTCTGCACACATTAGACACAGTCTATGAAAAGC

CCACCCATGAAGAGACGGCAACAGAGGGTTGGTCTGCAGCAGATGTTGGA

TCGTCACCAGAGCCCACATCCAGTGAGTATGAGCCTCCATTGGATGCTGT

CTCCTTGGCTGAGTCTGAGCCCATGCAATACTTTGACCCAGATTTGGAGA

CTAAGTCACAACCAGATGAGGATAAGATGAAAGAAGACACCTTTGCACAC

CTTACTCCAACCCCCACCATCTGGGTTAATGACTCCAGTACATCACAGTT

ATTTGAGGATTCTACTATAGGGGAACCAGGTGTCCCAGGCCAATCACATC

TACAAGGACTGACAGACAACATCCACCTTGTGAAAAGTAGTCTAAGCACT

CAAGACACCTTACTGATTAAAAAGGGTATGAAAGAGATGTCTCAGACACT

ACAGGGAGGAAATATGCTAGAGGGAGACCCCACACACTCCAGAAGTTCTG

AGAGTGAGGGCCAAGAGAGCAAATCCATCACTTTGCCTGACTCCACACTG

GGTATAATGAGCAGTATGTCTCCAGTTAAGAAGCCTGCGGAAACCACAGT

TGGTACCCTCCTAGACAAAGACACCACAACAGTAACAACAACACCAAGGC

AAAAAGTTGCTCCGTCATCCACCATGAGCACTCACCCTTCTCGAAGGAGA

CCCAACGGGAGAAGGAGATTACGCCCCAACAAATTCCGCCACCGGCACAA

GCAAACCCCACCCACAACTTTTGCCCCATCAGAGACTTTTTCTACTCAAC

CAACTCAAGCACCTGACATTAAGATTTCAAGTCAAGTGGAGAGTTCTCTG

GTTCCTACAGCTTGGGTGGATAACACAGTTAATACCCCCAAACAGTTGGA

AATGGAGAAGAATGCAGAACCCACATCCAAGGGAACACCACGGAGAAAAC

ACGGGAAGAGGCCAAACAAACATCGATATACCCCTTCTACAGTGAGCTCA

-continued

AGAGCGTCCGGATCCAAGCCCAGCCCTTCTCCAGAAAATAAACATAGAAA

CATTGTTACTCCCAGTTCAGAAACTATACTTTTGCCTAGAACTGTTTCTC

TGAAAACTGAGGGCCCTTATGATTCCTTAGATTACATGACAACCACCAGA

AAAATATATTCATCTTACCCTAAAGTCCAAGAGACACTTCCAGTCACATA

TAAACCCACATCAGATGGAAAAGAAATTAAGGATGATGTTGCCACAAATG

TTGACAAACATAAAAGTGACATTTTAGTCACTGGTGAATCAATTACTAAT

GCCATACCAACTTCTCGCTCCTTGGTCTCCACTATGGGAGAATTTAAGGA

AGAATCCTCTCCTGTAGGCTTTCCAGGAACTCCAACCTGGAATCCCTCAA

GGACGGCCCAGCCTGGGAGGCTACAGACAGACATACCTGTTACCACTTCT

GGGGAAAATCTTACAGACCCTCCCCTTCTTAAAGAGCTTGAGGATGTGGA

TTTCACTTCCGAGTTTTTGTCCTCTTTGACAGTCTCCACACCATTTCACC

AGGAAGAAGCTGGTTCTTCCACAACTCTCTCAAGCATAAAAGTGGAGGTG

GCTTCAAGTCAGGCAGAAACCACCACCCTTGATCAAGATCATCTTGAAAC

CACTGTGGCTATTCTCCTTTCTGAAACTAGACCACAGAATCACACCCCTA

CTGCTGCCCGGATGAAGGAGCCAGCATCCTCGTCCCCATCCACAATTCTC

ATGTCTTTGGGACAAACCACCACCACTAAGCCAGCACTTCCCAGTCCAAG

AATATCTCAAGCATCTAGAGATTCCAAGGAAAATGTTTTCTTGAATTATG

TGGGGAATCCAGAAACAGAAGCAACCCCAGTCAACAATGAAGGAACACAG

CATATGTCAGGGCCAAATGAATTATCAACACCCTCTTCCGACCGGGATGC

ATTTAACTTGTCTACAAAGCTGGAATTGGAAAAGCAAGTATTTGGTAGTA

GGAGTCTACCACGTGGCCCAGATAGCCAACGCCAGGATGGAAGAGTTCAT

GCTTCTCATCAACTAACCAGAGTCCCTGCCAAACCCATCCTACCAACAGC

AACAGTGAGGCTACCTGAAATGTCCACACAAAGCGCTTCCAGATACTTTG

TAACTTCCCAGTCACCTCGTCACTGGACCAACAAACCGGAAATAACTACA

TATCCTTCTGGGGCTTTGCCAGAGAACAAACAGTTTACAACTCCAAGATT

ATCAAGTACAACAATTCCTCTCCCATTGCACATGTCCAAACCCAGCATTC

CTAGTAAGTTTACTGACCGAAGAACTGACCAATTCAATGGTTACTCCAAA

GTGTTTGGAAATAACAACATCCCTGAGGCAAGAAACCCAGTTGGAAAGCC

TCCCAGTCCAAGAATTCCTCATTATTCCAATGGAAGACTCCCTTTCTTTA

CCAACAAGACTCTTTCTTTTCCACAGTTGGGAGTCACCCGGAGACCCCAG

ATACCCACTTCTCCTGCCCCAGTAATGAGAGAGAGAAAAGTTATTCCAGG

TTCCTACAACAGGATACATTCCCATAGCACCTTCCATCTGGACTTTGGCC

CTCCGGCACCTCCGTTGTTGCACACTCCGCAGACCACGGGATCACCCTCA

ACTAACTTACAGAATATCCCTATGGTCTCTTCCACCCAGAGTTCTATCTC

CTTTATAACATCTTCTGTCCAGTCCTCAGGAAGCTTCCACCAGAGCAGCT

CAAAGTTCTTTGCAGGAGGACCTCCTGCATCCAAATTCTGGTCTCTTGGG

GAAAAGCCCCAAATCCTCACCAAGTCCCCACAGACTGTGTCCGTCACCGC

TGAGACAGACACTGTGTTCCCCTGTGAGGCAACAGGAAAACCAAAGCCTT

TCGTTACTTGGACAAAGGTTTCCACAGGAGCTCTTATGACTCCGAATACC

AGGATACAACGGTTTGAGGTTCTCAAGAACGGTACCTTAGTGATACGGAA

-continued

GGTTCAAGTACAAGATCGAGGCCAGTATATGTGCACCGCCAGCAACCTGC

ACGGCCTGGACAGGATGGTGGTCTTGCTTTCGGTCACCGTGCAGCAACCT

CAAATCCTAGCCTCCCACTACCAGGACGTCACTGTCTACCTGGGAGACAC

CATTGCAATGGAGTGTCTGGCCAAAGGGACCCCAGCCCCCCAAATTTCCT

GGATCTTCCCTGACAGGAGGGTGTGGCAAACTGTGTCCCCCGTGGAGAGC

CGCATCACCCTGCACGAAAACCGGACCCTTTCCATCAAGGAGGCGTCCTT

CTCAGACAGAGGCGTCTATAAGTGCGTGGCCAGCAATGCAGCCGGGGCGG

ACAGCCTGGCCATCCGCCTGCACGTGGCGGCACTGCCCCCCGTTATCCAC

CAGGAGAAGCTGGAGAACATCTCGCTGCCCCCGGGGCTCAGCATTCACAT

TCACTGCACTGCCAAGGCTGCGCCCCTGCCCAGCGTGCGCTGGGTGCTCG

GGGACGGTACCCAGATCCGCCCCTCGCAGTTCCTCCACGGGAACTTGTTT

GTTTTCCCCAACGGGACGCTCTACATCCGCAACCTCGCGCCCAAGGACAG

CGGGCGCTATGAGTGCGTGGCCGCCAACCTGGTAGGCTCCGCGCGCAGGA

CGGTGCAGCTGAACGTGCAGCGTGCAGCAGCCAACGCGCGCATCACGGGC

ACCTCCCCGCGGAGGACGGACGTCAGGTACGGAGGAACCCTCAAGCTGGA

CTGCAGCGCCTCGGGGGACCCCTGGCCGCGCATCCTCTGGAGGCTGCCGT

CCAAGAGGATGATCGACGCGCTCTTCAGTTTTGATAGCAGAATCAAGGTG

TTTGCCAATGGGACCCTGGTGGTGAAATCAGTGACGGACAAAGATGCCGG

AGATTACCTGTGCGTAGCTCGAAATAAGGTTGGTGATGACTACGTGGTGC

TCAAAGTGGATGTGGTGATGAAACCGGCCAAGATTGAACACAAGGAGGAG

AACGACCACAAAGTCTTCTACGGGGGTGACCTGAAAGTGGACTGTGTGGC

CACCGGGCTTCCCAATCCCGAGATCTCCTGGAGCCTCCCAGACGGGAGTC

TGGTGAACTCCTTCATGCAGTCGGATGACAGCGGTGGACGCACCAAGCGC

TATGTCGTCTTCAACAATGGGACACTCTACTTTAACGAAGTGGGGATGAG

GGAGGAAGGAGACTACACCTGCTTTGCTGAAAATCAGGTCGGGAAGGACG

AGATGAGAGTCAGAGTCAAGGTGGTGACAGCGCCCGCCACCATCCGGAAC

AAGACTTACTTGGCGGTTCAGGTGCCCTATGGAGACGTGGTCACTGTAGC

CTGTGAGGCCAAAGGAGAACCCATGCCCAAGGTGACTTGGTTGTCCCCAA

CCAACAAGGTGATCCCCACCTCCTCTGAGAAGTATCAGATATACCAAGAT

GGCACTCTCCTTATTCAGAAAGCCCAGCGTTCTGACAGCGGCAACTACAC

CTGCCTGGTCAGGAACAGCGCGGGAGAGGATAGGAAGACGGTGTGGATTC

ACGTCAACGTGCAGCCACCCAAGATCAACGGTAACCCCAACCCCATCACC

ACCGTGCGGGAGATAGCAGCCGGGGGCAGTCGGAAACTGATTGACTGCAA

AGCTGAAGGCATCCCCACCCCGAGGGTGTTATGGGCTTTTCCCGAGGGTG

TGGTTCTGCCAGCTCCATACTATGGAAACCGGATCACTGTCCATGGCAAC

GGTTCCCTGGACATCAGGAGTTTGAGGAAGAGCGACTCCGTCCAGCTGGT

ATGCATGGCACGCAACGAGGGAGGGGAGGCGAGGTTGATCGTGCAGCTCA

CTGTCCTGGAGCCCATGGAGAAACCCATCTTCCACGACCCGATCAGCGAG

AAGATCACGGCCATGGCGGGCCACACCATCAGCCTCAACTGCTCTGCCGC

GGGGACCCCGACACCCAGCCTGGTGTGGGTCCTTCCCAATGGCACCGATC

TGCAGAGTGGACAGCAGCTGCAGCGCTTCTACCACAAGGCTGACGGCATG

-continued

CTACACATTAGCGGTCTCTCCTCGGTGGACGCTGGGGCCTACCGCTGCGT
GGCCCGCAATGCCGCTGGCCACACGGAGAGGCTGGTCTCCCTGAAGGTGG
GACTGAAGCCAGAAGCAAACAAGCAGTATCATAACCTGGTCAGCATCATC
AATGGTGAGACCCTGAAGCTCCCCTGCACCCCTCCCGGGGCTGGGCAGGG
ACGTTTCTCCTGGACGCTCCCCAATGGCATGCATCTGGAGGGCCCCCAAA
CCCTGGGACGCGTTTCTCTTCTGGACAATGGCACCCTCACGGTTCGTGAG
GCCTCGGTGTTTGACAGGGGTACCTATGTATGCAGGATGGAGACGGAGTA
CGGCCCTTCGGTCACCAGCATCCCCGTGATTGTGATCGCCTATCCTCCCC
GGATCACCAGCGAGCCCACCCCGGTCATCTACACCCGGCCCGGGAACACC
GTGAAACTGAACTGCATGGCTATGGGGATTCCCAAAGCTGACATCACGTG
GGAGTTACCGGATAAGTCGCATCTGAAGGCAGGGGTTCAGGCTCGTCTGT
ATGGAAACAGATTTCTTCACCCCCAGGGATCACTGACCATCCAGCATGCC
ACACAGAGAGATGCCGGCTTCTACAAGTGCATGGCAAAAAACATTCTCGG
CAGTGACTCCAAAACAACTTACATCCACGTCTTCTGAAATGTGGATTCCA
GAATGATTGCTTAGGAACTGACAACAAAGCGGGGTTTGTAAGGGAAGCCA
GGTTGGGGAATAGGAGCTCTTAAATAATGTGTCACAGTGCATGGTGGCCT
CTGGTGGGTTTCAAGTTGAGGTTGATCTTGATCTACAATTGTTGGGAAAA
GGAAGCAATGCAGACACGAGAAGGAGGGCTCAGCCTTGCTGAGACACTTT
CTTTTGTGTTTACATCATGCCAGGGGCTTCATTCAGGGTGTCTGTGCTCT
GACTGCAATTTTTCTTCTTTTGCAAATGCCACTCGACTGCCTTCATAAGC
GTCCATAGGATATCTGAGGAACATTCATCAAAAATAAGCCATAGACATGA
ACAACACCTCACTACCCCATTGAAGACGCATCACCTAGTTAACCTGCTGC
AGTTTTTACATGATAGACTTTGTTCCAGATTGACAAGTCATCTTTCAGTT
ATTTCCTCTGTCACTTCAAAACTCCAGCTTGCCCAATAAGGATTTAGAAC
CAGAGTGACTGATATATATATATATATTTTAATTCAGAGTTACATACATA
CAGCTACCATTTTATATGAAAAAAGAAAAACATTTCTTCCTGGAACTCAC
TTTTTATATAATGTTTTATATATATATATTTTTTCCTTTCAAATCAGACGAT
GAGACTAGAAGGAGAAATACTTTCTGTCTTATTAAAATTAATAAATTATT
GGTCTTTACAAGACTTGGATACATTACAGCAGACATGGAAATATAATTTT
AAAAAATTTCTCTCCAACCTCCTTCAAATTCAGTCACCACTGTTATATTA
CCTTCTCCAGGAACCCTCCAGTGGGGAAGGCTGCGATATTAGATTTCCTT
GTATGCAAAGTTTTTGTTGAAAGCTGTGCTCAGAGGAGGTGAGAGGAGAG
GAAGGAGAAAACTGCATCATAACTTTACAGAATTGAATCTAGAGTCTTCC
CCGAAAAGCCCAGAAACTTCTCTGCAGTATCTGGCTTGTCCATCTGGTCT
AAGGTGGCTGCTTCTTCCCCAGCCATGAGTCAGTTTGTGCCCATGAATAA
TACACGACCTGTTATTTCCATGACTGCTTTACTGTATTTTTAAGGTCAAT
ATACTGTACATTTGATAATAAAATAATATTCTCCCAAAAAAAAAA

Cystatin SA

>gi|19882252|ref|NM_001322.2| *Homo sapiens* cystatin SA (CST2), mRNA|qPCR forward_primer match [302 . . . 320]|qPCR reverse_primer match [393 . . . 370]|qPCR probe match [341 . . . 369]

SEQ ID NO: 96

GCCTCCGAGGAGACCATGGCCTGGCCCCTGTGCACCCTGCTGCTCCTGCT
GGCCACCCAGGCTGTGGCCCTGGCCTGGAGCCCCCAGGAGGAGGACAGGA
TAATCGAGGGTGGCATCTATGATGCAGACCTCAATGATGAGCGGGTACAG
CGTGCCCTTCACTTTGTCATCAGCGAGTATAACAAGGCCACTGAAGATGA
GTACTACAGACGCCTGCTGCGGGTGCTACGAGCCAGGGAGCAGATCGTGG
GCGGGGTGAATTACTTCTTCGACATAGAGGTGGGCCGAACCATATGTACC
AAGTCCCAGCCCAACTTGGACACCTGTGCCTTCCATGAACAGCCAGAACT
GCAGAAGAAACAGTTGTGCTCTTTCCAGATCTACGAAGTTCCCTGGGAGG
ACAGAATGTCCCTGGTGAATTCCAGGTGTCAAGAAGCCTAGGGATCTGTG
CCAGGGAGTCACACTGACCACCTCCTACTCCCACCCCTTGTAGTGCTCCC
ACCCCTGGACTGGTGGCCCCCACCCTGTGGGAGGTCTCCCCATGCACCTG
CAGCAGGAGAAGACAGAGAAGGCTGCAGGAGGCCTTTGTTGCTCAGCAGG
GGACTCTGCCCTCCCTCCTTCCTTTTGCTTCTCATAGCCCTGGTACATGG
TACACACACCCCCACCTCCTGCAATTAAACAGTAGCATCACCTC

Cystatin SN

>gi|19882250|ref|NM_001898.2| *Homo sapiens* cystatin SN (CST1), mRNA|qPCR forward_primer match [358 . . . 376]|qPCR reverse_primer match [449 . . . 426]|qPCR probe match [397 . . . 425]

SEQ ID NO: 97

GGGCTCCCTGCCTCGGGCTCTCACCCTCCTCTCCTGCAGCTCCAGCTTTG
TGCTCTGCCTCTGAGGAGACCATGGCCCAGTATCTGAGTACCCTGCTGCT
CCTGCTGGCCACCCTAGCTGTGGCCCTGGCCTGGAGCCCCAAGGAGGAGG
ATAGGATAATCCCGGGTGGCATCTATAACGCAGACCTCAATGATGAGTGG
GTACAGCGTGCCCTTCACTTCGCCATCAGCGAGTATAACAAGGCCACCAA
AGATGACTACTACAGACGTCCGCTGCGGGTACTAAGAGCCAGGCAACAGA
CCGTTGGGGGGGTGAATTACTTCTTCGACGTAGAGGTGGGCCGCACCATA
TGTACCAAGTCCCAGCCCAACTTGGACACCTGTGCCTTCCATGAACAGCC
AGAACTGCAGAAGAAACAGTTGTGCTCTTTCGAGATCTACGAAGTTCCCT
GGGAGAACAGAAGGTCCCTGGTGAAATCCAGGTGTCAAGAATCCTAGGGA
TCTGTGCCAGGCCATTCGCACCAGCCACCACCCACTCCCACCCCCTGTAG
TGCTCCCACCCCTGGACTGGTGGCCCCCACCCTGCGGGAGGCCTCCCCAT
GTGCCTGCGCCAAGAGACAGACAGAGAAGGCTGCAGGAGTCCTTTGTTGC
TCAGCAGGGCGCTCTGCCCTCCCTCCTTCCTTCTTGCTTCTAATAGCCCT
GGTACATGGTACACACCCCCCCACCTCCTGCAATTAAACAGTAGCATCGC
CTCCCTCTGAAAAAAAAAAAAAAAAAAAAAA

Lysyl Oxidase-Like Enzyme 2

>gi|4505010|ref|NM_002318.1| *Homo sapiens* lysyl oxidase-like 2 (LOXL2), mRNA|qPCR forward_primer match [2205 . . . 2223]|qPCR reverse_primer match [2286 . . . 2269]|qPCR probe match [2261 . . . 2229]

SEQ ID NO: 98

ACTCCAGCGCGCGGCTACCTACGCTTGGTGCTTGCTTTCTCCAGCCATCG
GAGACCAGAGCCGCCCCCTCTGCTCGAGAAAGGGGCTCAGCGGCGGCGGA
AGCGGAGGGGGACCACCGTGGAGAGCGCGGTCCCAGCCCGGCCACTGCGG
ATCCCTGAAACCAAAAAGCTCCTGCTGCTTCTGTACCCCGCCTGTCCCTC
CCAGCTGCGCAGGGCCCCTTCGTGGGATCATCAGCCCGAAGACAGGGATG
GAGAGGCCTCTGTGCTCCCACCTCTGCAGCTGCCTGGCTATGCTGGCCCT
CCTGTCCCCCCTGAGCCTGGCACAGTATGACAGCTGGCCCCATTACCCCG
AGTACTTCCAGCAACCGGCTCCTGAGTATCACCAGCCCCAGGCCCCCGCC
AACGTGGCCAAGATTCAGCTGCGCCTGGCTGGGCAGAAGAGGAAGCACAG
CGAGGGCCGGGTGGAGGTGTACTATGATGGCCAGTGGGGCACCGTGTGCG
ATGACGACTTCTCCATCCACGCTGCCCACGTCGTCTGCCGGGAGCTGGGC
TATGTGGAGGCCAAGTCCTGGACTGCCAGCTCCTCCTACGGCAAGGGAGA
AGGGCCCATCTGGTTAGACAATCTCCACTGTACTGGCAACGAGGCGACCC
TTGCAGCATGCACCTCCAATGGCTGGGGCGTCACTGACTGCAAGCACACG
GAGGATGTCGGTGTGGTGTGCAGCGACAAAAGGATTCCTGGGTTCAAATT
TGACAATTCGTTGATCAACCAGATAGAGAACCTGAATATCCAGGTGGAGG
ACATTCGGATTCGAGCCATCCTCTCAACCTACCGCAAGCGCACCCCAGTG
ATGGAGGGCTACGTGGAGGTGAAGGAGGGCAAGACCTGGAAGCAGATCTG
TGACAAGCACTGGACGGCCAAGAATTCCCGCGTGGTCTGCGGCATGTTTG
GCTTCCCTGGGGAGAGGACATACAATACCAAAGTGTACAAAATGTTTGCC
TCACGGAGGAAGCAGCGCTACTGGCCATTCTCCATGGACTGCACCGGCAC
AGAGGCCCACATCTCCAGCTGCAAGCTGGGCCCCCAGGTGTCACTGGACC
CCATGAAGAATGTCACCTGCGAGAATGGGCTGCCGGCCGTGGTGAGTTGT
GTGCCTGGGCAGGTCTTCAGCCCTGACGGACCCTCGAGATTCCGGAAAGC
ATACAAGCCAGAGCAACCCCTGGTGCGACTGAGAGGCGGTGCCTACATCG
GGGAGGGCCGCGTGGAGGTGCTCAAAAATGGAGAATGGGGGACCGTCTGC
GACGACAAGTGGGACCTGGTGTCGGCCAGTGTGGTCTGCAGAGAGCTGGG
CTTTGGGAGTGCCAAAGAGGCAGTCACTGGCTCCCGACTGGGGCAAGGGA
TCGGACCCATCCACCTCAACGAGATCCAGTGCACAGGCAATGAGAAGTCC
ATTATAGACTGCAAGTTCAATGCCGAGTCTCAGGGCTGCAACCACGAGGA
GGATGCTGGTGTGAGATGCAACACCCCTGCCATGGGCTTGCAGAAGAAGC
TGCGCCTGAACGGCGGCCGCAATCCCTACGAGGGCCGAGTGGAGGTGCTG
GTGGAGAGAAACGGGTCCCTTGTGTGGGGGATGGTGTGTGGCCAAAACTG
GGGCATCGTGGAGGCCATGGTGGTCTGCCGCCAGCTGGGCCTGGGATTCG
CCAGCAACGCCTTCCAGGAGACCTGGTATTGGCACGGAGATGTCAACAGC
AACAAAGTGGTCATGAGTGGAGTGAAGTGCTCGGGAACGGAGCTGTCCCT
GGCGCACTGCCGCCACGACGGGGAGGACGTGGCCTGCCCCCAGGGCGGAG
TGCAGTACGGGGCCGGAGTTGCCTGCTCAGAAACCGCCCCTGACCTGGTC
CTCAATGCGGAGATGGTGCAGCAGACCACCTACCTGGAGGACCGGCCCAT
GTTCATGCTGCAGTGTGCCATGGAGGAGAACTGCCTCTCGGCCTCAGCCG

-continued

CGCAGACCGACCCCACCACGGGCTACCGCCGGCTCCTGCGCTTCTCCTCC
CAGATCCACAACAATGGCCAGTCCGACTTCCGGCCCAAGAACGGCCGCCA
CGCGTGGATCTGGCACGACTGTCACAGGCACTACCACAGCATGGAGGTGT
TCACCCACTATGACCTGCTGAACCTCAATGGCACCAAGGTGGCAGAGGGC
CACAAGGCCAGCTTCTGCTTGGAGGACACAGAATGTGAAGGAGACATCCA
GAAGAATTACGAGTGTGCCAACTTCGGCGATCAGGGCATCACCATGGGCT
GCTGGGACATGTACCGCCATGACATCGACTGCCAGTGGGTTGACATCACT
GACGTGCCCCCTGGAGACTACCTGTTCCAGGTTGTTATTAACCCCAACTT
CGAGGTTGCAGAATCCGATTACTCCAACAACATCATGAAATGCAGGAGCC
GCTATGACGGCCACCGCATCTGGATGTACAACTGCCACATAGGTGGTTCC
TTCAGCGAAGAGACGGAAAAAAAGTTTGAGCACTTCAGCGGGCTCTTAAA
CAACCAGCTGTCCCCGCAGTAAAGAAGCCTGCGTGGTCAACTCCTGTCTT
CAGGCCACACCACATCTTCCATGGGACTTCCCCCCAACAACTGAGTCTGA
ACGAATGCCACGTGCCCTCACCCAGCCCGGCCCCCACCCTGTCCAGACCC
CTACAGCTGTGTCTAAGCTCAGGAGGAAAGGGACCCTCCCATCATTCATG
GGGGGCTGCTACCTGACCCTTGGGGCCTGAGAAGGCCTTGGGGGGGTGGG
GTTTGTCCACAGAGCTGCTGGAGCAGCACCAAGAGCCAGTCTTGACCGGG
ATGAGGCCCACAGACAGGTTGTCATCAGCTTGTCCCATTCAAGCCACCGA
GCTCACCACAGACACAGTGGAGCCGCGCTCTTCTCCAGTGACACGTGGAC
AAATGCGGGCTCATCAGCCCCCCCAGAGAGGGTCAGGCCGAACCCCATTT
CTCCTCCTCTTAGGTCATTTTCAGCAAACTTGAATATCTAGACCTCTCTT
CCAATGAAACCCTCCAGTCTATTATAGTCACATAGATAATGGTGCCACGT
GTTTTCTGATTTGGTGAGCTCAGACTTGGTGCTTCCCTCTCCACAACCCC
CACCCCTTGTTTTTCAAGATACTATTATTATATTTTCACAGACTTTTGAA
GCACAAATTTATTGGCATTTAATATTGGACATCTGGGCCCTTGGAAGTAC
AAATCTAAGGAAAAACCAACCCACTGTGTAAGTGACTCATCTTCCTGTTG
TTCCAATTCTGTGGGTTTTTGATTCAACGGTGCTATAACCAGGGTCCTGG
GTGACAGGGCGCTCACTGAGCACCATGTGTCATCACAGACACTTACACAT
ACTTGAAACTTGGAATAAAAGAAAGATTTATG

Thyroglobulin

>gi|33589851|ref|NM_003235.3| *Homo sapiens* thyroglobulin (TG), mRNA|qPCR forward_primer match [886 . . . 905]|qPCR reverse_primer match [962 . . . 941]|qPCR probe match [915 . . . 939]

SEQ ID NO: 99

GCAGTGGTTTCTCCTCCTTCCTCCCAGGAAGGGCCAGGAAAATGGCCCTG
GTCCTGGAGATCTTCACCCTGCTGGCCTCCATCTGCTGGGTGTCGGCCAA
TATCTTCGAGTACCAGGTTGATGCCCAGCCCCTTCGTCCCTGTGAGCTGC
AGAGGGAAACGGCCTTTCTGAAGCAAGCAGACTACGTGCCCCAGTGTGCA
GAGGATGGCAGCTTCCAGACTGTCCAGTGCCAGAACGACGGCCGCTCCTG
CTGGTGTGTGGGTGCCAACGGCAGTGAAGTGCTGGGCAGCAGGCAGCCAG
GACGGCCTGTGGCTTGTCTGTCATTTTGTCAGCTACAGAAACAGCAGATC

-continued

TTACTGAGTGGCTACATTAACAGCACAGACACCTCCTACCTCCCTCAGTG
TCAGGATTCAGGGGACTACGCGCCTGTTCAGTGTGATGTGCAGCATGTCC
AGTGCTGGTGTGTGGACGCAGAGGGGATGGAGGTGTATGGGACCCGCCAG
CTGGGGAGGCCAAAGCGATGTCCAAGGAGCTGTGAAATAAGAAATCGTCG
TCTTCTCCACGGGGTGGGAGATAAGTCACCACCCCAGTGTTCTGCGGAGG
GAGAGTTTATGCCTGTCCAGTGCAAATTTGTCAACACCACAGACATGATG
ATTTTTGATCTGGTCCACAGCTACAACAGGTTTCCAGATGCATTTGTGAC
CTTCAGTTCCTTCCAGAGGAGGTTCCCTGAGGTATCTGGGTATTGCCACT
GTGCTGACAGCCAAGGGCGGGAACTGGCTGAGACAGGTTTGGAGTTGTTA
CTGGATGAAATTTATGACACCATTTTTGCTGGCCTGGACCTTCCTTCCAC
CTTCACTGAAACCACCCTGTACCGGATACTGCAGAGACGGTTCCTCGCAG
TTCAATCAGTCATCTCTGGCAGATTCCGATGCCCCACAAAATGTGAAGTG
GAGCGGTTTACAGCAACCAGCTTTGGTCACCCCTATGTTCCAAGCTGCCG
CCGAAATGGCGACTATCAGGCGGTGCAGTGCCAGACGGAAGGGCCCTGCT
GGTGTGTGGACGCCCAGGGGAAGGAAATGCATGGAACCCGGCAGCAAGGG
GAGCCGCCATCTTGTGCTGAAGGCCAATCTTGTGCCTCCGAAAGGCAGCA
GGCCTTGTCCAGACTCTACTTTGGGACCTCAGGCTACTTCAGCCAGCACG
ACCTGTTCTCTTCCCCAGAGAAAAGATGGGCCTCTCCAAGAGTAGCCAGA
TTTGCCACATCCTGCCCACCCACGATCAAGGAGCTCTTTGTGGACTCTGG
GCTTCTCCGCCCAATGGTGGAGGGACAGAGCCAACAGTTTTCTGTCTCAG
AAAATCTTCTCAAAGAAGCCATCCGAGCAATTTTTCCCTCCCGAGGGCTG
GCTCGTCTTGCCCTTCAGTTTACCACCAACCCAAAGAGACTCCAGCAAAA
CCTTTTTGGAGGGAAATTTTTGGTGAATGTTGGCCAGTTTAACTTGTCTG
GAGCCCTTGGCACAAGAGGCACATTTAACTTCAGTCAATTTTTCCAGCAA
CTTGGTCTTGCAAGCTTCTTGAATGGAGGGAGACAAGAAGATTTGGCCAA
GCCACTCTCTGTGGGATTAGATTCAAATTCTTCCACAGGAACCCCTGAAG
CTGCTAAGAAGGATGGTACTATGAATAAGCCAACTGTGGGCAGCTTTGGC
TTTGAAATTAACCTACAAGAGAACCAAAATGCCCTCAAATTCCTTGCTTC
TCTCCTGGAGCTTCCAGAATTCCTTCTCTTCTTGCAACATGCTATCTCTG
TGCCAGAAGATGTGGCAAGAGATTTAGGTGATGTGATGGAAACGGTACTC
GACTCCCAGACCTGTGAGCAGACACCTGAAAGGCTATTTGTCCCATCATG
CACGACAGAAGGAAGCTATGAGGATGTCCAATGCTTTTCCGGAGAGTGCT
GGTGTGTGAATTCCTGGGGCAAAGAGCTTCCAGGCTCAAGAGTCAGAGAT
GGACAGCCAAGGTGCCCCACAGACTGTGAAAAGCAAAGGGCTCGCATGCA
AAGCCTCATGGGCAGCCAGCCTGCTGGCTCCACCTTGTTTGTCCCTGCTT
GTACTAGTGAGGGACATTTCCTGCCTGTCCAGTGCTTCAACTCAGAGTGC
TACTGTGTTGATGCTGAGGGTCAGGCCATTCCTGGAACTCGAAGTGCAAT
AGGGAAGCCCAAGAAATGCCCCACGCCCTGTCAATTACAGTCTGAGCAAG
CTTTCCTCAGGACGGTGCAGGCCCTGCTCTCTAACTCCAGCATGCTACCC
ACCCTTTCCGACACCTACATCCCACAGTGCAGCACCGATGGGCAGTGGAG

-continued

ACAAGTGCAATGCAATGGGCCTCCTGAGCAGGTCTTCGAGTTGTACCAAC
GATGGGAGGCTCAGAACAAGGGCCAGGATCTGACGCCTGCCAAGCTGCTA
GTGAAGATCATGAGCTACAGAGAAGCAGCTTCCGGAAACTTCAGTCTCTT
TATTCAAAGTCTGTATGAGGCTGGCCAGCAAGATGTCTTCCCCGGTGCTGT
CACAATACCCTTCTCTGCAAGATGTCCCACTAGCAGCACTGGAAGGGAAA
CGGCCCCAGCCCAGGGAGAATATCCTCCTGGAGCCCTACCTCTTCTGGCA
GATCTTAAATGGCCAACTCAGCCAATACCCGGGGTCCTACTCAGACTTCA
GCACTCCTTTGGCACATTTTGATCTTCGGAACTGCTGGTGTGTGGATGAG
GCTGGCCAAGAACTGGAAGGAATGCGGTCTGAGCCAAGCAAGCTCCCAAC
GTGTCCTGGCTCCTGTGAGGAAGCAAAGCTCCGTGTACTGCAGTTCATTA
GGGAAACGGAAGAGATTGTTTCAGCTTCCAACAGTTCTCGGTTCCCTCTG
GGGGAGAGTTTCCTGGTGGCCAAGGGAATCCGGCTGAGGAATGAGGACCT
CGGCCTTCCTCCGCTCTTCCCGCCCCGGGAGGCTTTCGCGGAGTTTCTGC
GTGGGAGTGATTACGCCATTCGCCTGGCGGCTCAGTCTACCITAAGCTTC
TATCAGAGACGCCGCTTTTCCCCGGACGACTCGGCTGGAGCATCCGCCCT
TCTGCGGTCGGGCCCCTACATGCCACAGTGTGATGCGTTTGGAAGTTGGG
AGCCTGTGCAGTGCCACGCTGGGACTGGGCACTGCTGGTGTGTAGATGAG
AAAGGAGGGTTCATCCCTGGCTCACTGACTGCCCGCTCTCTGCAGATTCC
ACAGTGCCCGACAACCTGCGAGAAATCTCGAACCAGTGGGCTGCTTTCCA
GTTGGAAACAGGCTAGATCCCAAGAAAACCCATCTCCAAAAGACCTGTTC
GTCCCAGCCTGCCTAGAAACAGGAGAATATGCCAGGCTGCAGGCATCGGG
GGCTGGCACCTGGTGTGTGGACCCTGCATCAGGAGAAGAGTTGCGGCCTG
GCTCGAGCAGCAGTGCCCAGTGCCCAAGCCTCTGCAATGTGCTCAAGAGT
GGAGTCCTCTCTAGGAGAGTCAGCCCAGGCTATGTCCCAGCCTGCAGGGC
AGAGGATGGGGGCTTTTCCCCAGTGCAATGTGACCAGGCCCAGGGCAGCT
GCTGGTGTGTCATGGACAGCGGAGAAGAGGTGCCTGGGACGCGCGTGACC
GGGGGCCAGCCCGCCTGTGAGAGCCCGCGGTGTCCGCTGCCATTCAACGC
GTCGGAGGTGGTTGGTGGAACAATCCTGTGTGAGACAATCTCGGGCCCCA
CAGGCTCTGCCATGCAGCAGTGCCAATTGCTGTGCCGCCAAGGCTCCTGG
AGCGTGTTTCCACCAGGGCCATTGATATGTAGCCTGGAGAGCGGACGCTG
GGAGTCACAGCTGCCTCAGCCCCGGGCCTGCCAACGGCCCCAGCTGTGGC
AGACCATCCAGACCCAAGGGCACTTTCAGCTCCAGCTCCCGCCGGGCAAG
ATGTGCAGTGCTGACTACGCGGGTTTGCTGCAGACTTTCCAGGTTTTCAT
ATTGGATGAGCTGACAGCCCGCGGCTTCTGCCAGATCCAGGTGAAGACTT
TTGGCACCCTGGTTTCCATTCCTGTCTGCAACAACTCCTCTGTGCAGGTG
GGTTGTCTGACCAGGGAGCGTTTAGGAGTGAATGTTACATGGAAATCACG
GCTTGAGGACATCCCAGTGGCTTCTCTTCCTGACTTACATGACATTGAGA
GAGCCTTGGTGGGCAAGGATCTCCTTGGGCGCTTCACAGATCTGATCCAG
AGTGGCTCATTCCAGCTTCATCTGGACTCCAAGACGTTCCCAGCGGAAAC
CATCCGCTTCCTCCAAGGGGACCACTTTGGCACCTCTCCTAGGACACGGT
TTGGGTGCTCGGAAGGATTCTACCAAGTCTTGACAAGTGAGGCCAGTCAG

-continued

GACGGACTGGGATGCGTTAAGTGCCATGAAGGAAGCTATTCCCAAGATGA

GGAATGCATTCCTTGTCCTGTTGGATTCTACCAAGAACAGGCAGGGAGCT

TGGCCTGTGTCCCATGTCCTGTGGGCAGAACGACCATTTCTGCCGGAGCT

TTCAGCCAGACTCACTGTGTCACTGACTGTCAGAGGAACGAAGCAGGCCT

GCAATGTGACCAGAATGGCCAGTATCGAGCCAGCCAGAAGGACAGGGGCA

GTGGGAAGGCCTTCTGTGTGGACGGCGAGGGGCGGAGGCTGCCATGGTGG

GAAACAGAGGCCCCTCTTGAGGACTCACAGTGTTTGATGATGCAGAAGTT

TGAGAAGGTTCCAGAATCAAAGGTGATCTTCGACGCCAATGCTCCTGTGG

CTGTCAGATCCAAAGTTCCTGATTCTGAGTTCCCCGTGATGCAGTGCTTG

ACAGATTGCACAGAGGACGAGGCCTGCAGCTTCTTCACCGTGTCCACGAC

GGAGCCAGAGATTTCCTGTGATTTCTATGCTTGGACAAGTGACAATGTTG

CCTGCATGACTTCTGACCAGAAACGAGATGCACTGGGGAACTCAAAGGCC

ACCAGCTTTGGAAGTCTTCGCTGCCAGGTGAAAGTGAGGAGCCATGGTCA

AGATTCTCCAGCTGTGTATTTGAAAAAGGGCCAAGGATCCACCACAACAC

TTCAGAAACGCTTTGAACCCACTGGTTTCCAAAACATGCTTTCTGGATTG

TACAACCCCATTGTGTTCTCAGCCTCAGGAGCCAATCTAACCGATGCTCA

CCTCTTCTGTCTTCTTGCATGCGACCGTGATCTGTGTTGCGATGGCTTCG

TCCTCACACAGGTTCAAGGAGGTGCCATCATCTGTGGGTTGCTGAGCTCA

CCCAGTGTCCTGCTTTGTAATGTCAAAGACTGGATGGATCCCTCTGAAGC

CTGGGCTAATGCTACATGTCCTGGTGTGACATATGACCAGGAGAGCCACC

AGGTGATATTGCGTCTTGGAGACCAGGAGTTCATCAAGAGTCTGACACCC

TTAGAAGGAACTCAAGACACCTTTACCAATTTTCAGCAGGTTTATCTCTG

GAAAGATTCTGACATGGGGTCTCGGCCTGAGTCTATGGGATGTAGAAAAA

ACACAGTGCCAAGGCCAGCATCTCCAACAGAAGCAGGTTTGACAACAGAA

CTTTTCTCCCCTGTGGACCTCAACCAGGTCATTGTCAATGGAAATCAATC

ACTATCCAGCCAGAAGCACTGGCTTTTCAAGCACCTGTTTTCAGCCCAGC

AGGCAAACCTATGGTGCCTTTCTCGTTGTGTGCAGGAGCACTCTTTCTGT

CAGCTCGCAGAGATAACAGAGAGTGCATCCTTGTACTTCACCTGCACCCT

CTACCCAGAGGCACAGGTGTGTGATGACATCATGGAGTCCAATACCCAGG

GCTGCAGACTGATCCTGCCTCAGATGCCAAAGGCCCTGTTCCGGAAGAAA

GTTATACTGGAAGATAAAGTGAAGAACTTTTACACTCGCCTGCCGTTCCA

AAAACTGATGGGGATATCCATTAGAAATAAAGTGCCCATGTCTGAAAAAT

CTATTTCTAATGGGTTCTTTGAATGTGAACGACGGTGCGATGCGGACCCA

TGCTGCACTGGCTTTGGATTTCTAAATGTTTCCCAGTTAAAAGGAGGAGA

GGTGACATGTCTCACTCTGAACAGCTTGGGAATTCAGATGTGCAGTGAGG

AGAATGGAGGAGCCTGGCGCATTTTGGACTGTGGCTCTCCTGACATTGAA

GTCCACACCTATCCCTTCGGATGGTACCAGAAGCCCATTGCTCAAAATAA

TGCTCCCAGTTTTTGCCCTTTGGTTGTTCTGCCTTCCCTCACAGAGAAAG

TGTCTCTGGAATCGTGGCAGTCCCTGGCCCTCTCTTCAGTGGTTGTTGAT

CCATCCATTAGGCACTTTGATGTTGCCCATGTCAGCACTGCTGCCACCAG

-continued

CAATTTCTCTGCTGTCCGAGACCTCTGTTTGTCGGAATGTTCCCAACATG

AGGCCTGTCTCATCACCACTCTGCAAACCCAACTCGGGGCTGTGAGATGT

ATGTTCTATGCTGATACTCAAAGCTGCACACATAGTCTGCAGGGTCGGAA

CTGCCGACTTCTGCTTCGTGAAGAGGCCACCCACATCTACCGGAAGCCAG

GAATCTCTCTGCTCAGCTATGAGGCATCTGTACCTTCTGTGCCCATTTCC

ACCCATGGCCGGCTGCTGGGCAGGTCCCAGGCCATCCAGGTGGGTACCTC

ATGGAAGCAAGTGGACCAGTTCCTTGGAGTTCCATATGCTGCCCCGCCCC

TGGCAGAGAGGCACTTCCAGGCACCAGAGCCCTTGAACTGGACAGGCTCC

TGGGATGCCAGCAAGCCAAGGGCCAGCTGCTGGCAGCCAGGCACCAGAAC

ATCCACGTCTCCTGGAGTCAGTGAAGATTGTTTGTATCTCAATGTGTTCA

TCCCTCAGAATGTGGCCCCTAACGCGTCTGTGCTGGTGTTCTTCCACAAC

ACCATGGACAGGGAGGAGAGTGAAGGATGGCCGGCTATCGACGGCTCCTT

CTTGGCTGCTGTTGGCAACCTCATCGTGGTCACTGCCAGCTACCGAGTGG

GTGTCTTCGGCTTCCTGAGTTCTGGATCCGGAGAGGTGAGTGGCAACTGG

GGGCTGCTGGACCAGGTGGCGGCTCTGACCTGGGTGCAGACCCACATCCG

AGGATTTGGCGGGGACCCTCGGCGCGTGTCCCTGGCAGCAGACCGTGGCG

GGGCTGATGTGGCCAGCATCCACCTTCTCACGGCCAGGGCCACCAACTCC

CAACTTTTCCGGAGAGCTGTGCTGATGGGAGGCTCCGCACTCTCCCCGGC

CGCCGTCATCAGCCATGAGAGGGCTCAGCAGCAGGCAATTGCTTTGGCAA

AGGAGGTCAGTTGCCCCATGTCATCCAGCCAAGAAGTGGTGTCCTGCCTC

CGCCAGAAGCCTGCCAATGTCCTCAATGATGCCCAGACCAAGCTCCTGGC

CGTGAGTGGCCCTTTCCACTACTGGGGTCCTGTGATCGATGGCCACTTCC

TCCGTGAGCCTCCAGCCAGAGCACTGAAGAGGTCTTTATGGGTAGAGGTC

GATCTGCTCATTGGGAGTTCTCAGGACGACGGGCTCATCAACAGAGCAAA

GGCTGTGAAGCAATTTGAGGAAAGTCGAGGCCGGACCAGTAGCAAAACAG

CCTTTTACCAGGCACTGCAGAATTCTCTGGGTGGCGAGGACTCAGATGCC

CGCGTCGAGGCTGCTGCTACATGGTATTACTCTCTGGAGCACTCCACGGA

TGACTATGCCTCCTTCTCCCGGGCTCTGGAGAATGCCACCCGGGACTACT

TTATCATCTGCCCTATAATCGACATGGCCAGTGCCTGGGCAAAGAGGGCC

CGAGGAAACGTCTTCATGTACCATGCTCCTGAAAACTACGGCCATGGCAG

CCTGGAGCTGCTGGCGGATGTTCAGTTTGCCTTGGGGCTTCCCTTCTACC

CAGCCTACGAGGGGCAGTTTTCTCTGGAGGAGAAGAGCCTGTCGCTGAAA

ATCATGCAGTACTTTTCCCACTTCATCAGATCAGGAAATCCCAACTACCC

TTATGAGTTCTCACGGAAAGTACCCACATTTGCAACCCCCTGGCCTGACT

TTGTACCCCGTGCTGGTGGAGAGAACTACAAGGAGTTCAGTGAGCTGCTC

CCCAATCGACAGGGCCTGAAGAAAGCCGACTGCTCCTTCTGGTCCAAGTA

CATCTCGTCTCTGAAGACATCTGCAGATGGAGCCAAGGGCGGGCAGTCAG

CAGAGAGTGAAGAGGAGGAGTTGACGGCTGGATCTGGGCTAAGAGAAGAT

CTCCTAAGCCTCCAGGAACCAGGCTCTAAGACCTACAGCAAGTGACCAGC

CCTTGAGCTCCCCAAAAACCTCACCCGAGGCTGCCCACTATGGTCATCTT

TTTCTCTAAAATAGTTACTTACCTTCAATAAAGTATCTACATGCGGTG

Transforming Growth Factor, Beta 1

>gi|10863872|ref|NM_000660.1| *Homo sapiens* transforming growth factor, beta 1 (Camurati-Engelmann disease) (TGFB1), mRNA|qPCR forward_primer match [1651 . . . 1668]|qPCR reverse_primer match [1539 . . . 1557]|qPCR probe match [1687 . . . 1713]

SEQ ID NO: 100

ACCTCCCTCCGCGGAGCAGCCAGACAGCGAGGGCCCCGGCCGGGGGCAGG

GGGGACGCCCCGTCCGGGGCACCCCCCCCGGCTCTGAGCCGCCCGCGGGG

CCGGCCTCGGCCCGGAGCGGAGGAAGGAGTCGCCGAGGAGCAGCCTGAGG

CCCCAGAGTCTGAGACGAGCCGCCGCCGCCCCCGCCACTGCGGGGAGGAG

GGGGAGGAGGAGCGGGAGGAGGGACGAGCTGGTCGGGAGAAGAGGAAAAA

AACTTTTGAGACTTTTCCGTTGCCGCTGGGAGCCGGAGGCGCGGGGACCT

CTTGGCGCGACGCTGGCCCGCGAGGAGGCAGGACTTGGGGACCCCAGACC

GCCTCCCTTTGCCGCCGGGGACGCTTGCTCCCTCCCTGCCCCCTACACGG

CGTCCCTCAGGCGCCCCCATTCCGGACCAGCCCTCGGGAGTCGCCGACCC

GGCCTCCCGCAAAGACTTTTCCCCAGACCTCGGGCGCACCCCCTGCACGC

CGCCTTCATCCCCGGCCTGTCTCCTGAGCCCCCGCGCATCCTAGACCCTT

TCTCCTCCAGGAGACGGATCTCTCTCCGACCTGCCACAGATCCCCTATTC

AAGACCACCCACCTTCTGGTACCAGATCGCGCCCATCTAGGTTATTTCCG

TGGGATACTGAGACACCCCCGGTCCAAGCCTCCCCTCCACCACTGCGCCC

TTCTCCCTGAGGAGCCTCAGCTTTCCCTCGAGGCCCTCCTACCTTTTGCC

GGGAGACCCCCAGCCCCTGCAGGGGCGGGGCCTCCCCACCACACCAGCCC

TGTTCGCGCTCTCGGCAGTGCCGGGGGGCGCCGCCTCCCCCATGCCGCCC

TCCGGGCTGCGGCTGCTGCCGCTGCTGCTACCGCTGCTGTGGCTACTGGT

GCTGACGCCTGGCCCGCCGGCCGCGGGACTATCCACCTGCAAGACTATCG

ACATGGAGCTGGTGAAGCGGAAGCGCATCGAGGCCATCCGCGGCCAGATC

CTGTCCAAGCTGCGGCTCGCCAGCCCCCCGAGCCAGGGGGAGGTGCCGCC

CGGCCCGCTGCCCGAGGCCGTGCTCGCCCTGTACAACAGCACCCGCGACC

GGGTGGCCGGGGAGAGTGCAGAACCGGAGCCCGAGCCTGAGGCCGACTAC

TACGCCAAGGAGGTCACCCGCGTGCTAATGGTGGAAACCCACAACGAAAT

CTATGACAAGTTCAAGCAGAGTACACACAGCATATATATGTTCTTCAACA

CATCAGAGCTCCGAGAAGCGGTACCTGAACCCGTGTTGCTCTCCCGGGCA

GAGCTGCGTCTGCTGAGGAGGCTCAAGTTAAAAGTGGAGCAGCACGTGGA

GCTGTACCAGAAATACAGCAACAATTCCTGGCGATACCTCAGCAACCGGC

TGCTGGCACCCAGCGACTCGCCAGAGTGGTTATCTTTTGATGTCACCGGA

GTTGTGCGGCAGTGGTTGAGCCGTGGAGGGGAAATTGAGGGCTTTCGCCT

TAGCGCCCACTGCTCCTGTGACAGCAGGGATAACACACTGCAAGTGGACA

TCAACGGGTTCACTACCGGCCGCCGAGGTGACCTGGCCACCATTCATGGC

ATGAACCGGCCTTTCCTGCTTCTCATGGCCACCCCGCTGGAGAGGGCCCA

GCATCTGCAAAGCTCCCGGCACCGCCGAGCCCTGGACACCAACTATTGCT

TCAGCTCCACGGAGAAGAACTGCTGCGTGCGGCAGCTGTACATTGACTTC

CGCAAGGACCTCGGCTGGAAGTGGATCCACGAGCCCAAGGGCTACCATGC

-continued

CAACTTCTGCCTCGGGCCCTGCCCCTACATTTGGAGCCTGGACACGCAGT

ACAGCAAGGTCCTGGCCCTGTACAACCAGCATAACCCGGGCGCCTCGGCG

GCGCCGTGCTGCGTGCCGCAGGCGCTGGAGCCGCTGCCCATCGTGTACTA

CGTGGGCCGCAAGCCCAAGGTGGAGCAGCTGTCCAACATGATCGTGCGCT

CCTGCAAGTGCAGCTGAGGTCCCGCCCCGCCCCGCCCCGCCCCGGCAGGC

CCGGCCCCACCCCGCCCCGCCCCCGCTGCCTTGCCCATGGGGGCTGTATT

TAAGGACACCGTGCCCCAAGCCCACCTGGGGCCCCATTAAAGATGGAGAG

AGGACTGCGGATCTCTGTGTCATTGGGCGCCTGCCTGGGGTCTCCATCCC

TGACGTTCCCCCACTCCCACTCCCTCTCTCTCCCTCTCTGCCTCCTCCTG

CCTGTCTGCACTATTCCTTTGCCCGGCATCAAGGCACAGGGGACCAGTGG

GGAACACTACTGTAGTTAGATCTATTTATTGAGCACCTTGGGCACTGTTG

AAGTGCCTTACATTAATGAACTCATTCAGTCACCATAGCAACACTCTGAG

ATGGCAGGGACTCTGATAACACCCATTTTAAAGGTTGAGGAAACAAGCCC

AGAGAGGTTAAGGGAGGAGTTCCTGCCCACCAGGAACCTGCTTTAGTGGG

GGATAGTGAAGAAGACAATAAAAGATAGTAGTTCAGGCCAGGCGGGGTGC

TCACGCCTGTAATCCTAGCACTTTTGGGAGGCAGAGATGGGAGGATACTT

GAATCCAGGCATTTGAGACCAGCCTGGGTAACATAGTGAGACCCTATCTC

TACAAAACACTTTTAAAAAATGTACACCTGTGGTCCCAGCTACTCTGGAG

GCTAAGGTGGGAGGATCACTTGATCCTGGGAGGTCAAGGCTGCAG

Serine Proteinase Inhibitor, Clade H, Member 1

>gi|32454740|ref|NM_001235.2| *Homo sapiens* serine (or cysteine) proteinase inhibitor, clade H (heat shock protein 47), member 1, (collagen binding protein 1) (SERPINH1), mRNA|qPCR assay_on_demand_context match [184 . . . 208]

SEQ ID NO: 101

TCTTTGGCTTTTTTTGGCGGAGCTGGGGCGCCCTCCGGAAGCGTTTCCAA

CTTTCCAGAAGTTTCTCGGGACGGGCAGGAGGGGGTGGGGACTGCCATAT

ATAGATCCCGGGAGCAGGGGAGCGGGCTAAGAGTAGAATCGTGTCGCGGC

TCGAGAGCGAGAGTCACGTCCCGGCGCTAGCCCAGCCCGACCCAGGCCCA

CCGTGGTGCACGCAAACCACTTCCTGGCCATGCGCTCCCTCCTGCTTCTC

AGCGCCTTCTGCCTCCTGGAGGCGGCCCTGGCCGCCGAGGTGAAGAAACC

TGCAGCCGCAGCAGCTCCTGGCACTGCGGAGAAGTTGAGCCCCAAGGCGG

CCACGCTTGCCGAGCGCAGCGCCGGCCTGGCCTTCAGCTTGTACCAGGCC

ATGGCCAAGGACCAGGCAGTGGAGAACATCCTGGTGTCACCCGTGGTGGT

GGCCTCGTCGCTAGGGCTCGTGTCGCTGGGCGGCAAGGCGACCACGGCGT

CGCAGGCCAAGGCAGTGCTGAGCGCCGAGCAGCTGCGCGACGAGGAGGTG

CACGCCGGCCTGGGCGAGCTGCTGCGCTCACTCAGCAACTCCACGGCGCG

CAACGTGACCTGGAAGCTGGGCAGCCGACTGTACGGACCCAGCTCAGTGA

GCTTCGCTGATGACTTCGTGCGCAGCAGCAAGCAGCACTACAACTGCGAG

CACTCCAAGATCAACTTCCGCGACAAGCGCAGCGCGCTGCAGTCCATCAA

CGAGTGGGCCGCGCAGACCACCGACGGCAAGCTGCCCGAGGTCACCAAGG

-continued

ACGTGGAGCGCACGGACGGCGCCCTGCTAGTCAACGCCATGTTCTTCAAG
CCACACTGGGATGAGAAATTCCACCACAAGATGGTGGACAACCGTGGCTT
CATGGTGACTCGGTCCTATACCGTGGGTGTCATGATGATGCACCGGACAG
GCCTCTACAACTACTACGACGACGAGAAGGAAAAGCTGCAAATCGTGGAG
ATGCCCCTGGCCCACAAGCTCTCCAGCCTCATCATCCTCATGCCCCATCA
CGTGGAGCCTCTCGAGCGCCTTGAAAAGCTGCTAACCAAAGAGCAGCTGA
AGATCTGGATGGGGAAGATGCAGAAGAAGGCTGTTGCCATCTCCTTGCCC
AAGGGTGTGGTGGAGGTGACCCATGACCTGCAGAAACACCTGGCTGGGCT
GGGCCTGACTGAGGCCATTGACAAGAACAAGGCCGACTTGTCACGCATGT
CAGGCAAGAAGGACCTGTACCTGGCCAGCGTGTTCCACGCCACCGCCTTT
GAGTTGGACACAGATGGCAACCCCTTTGACCAGGACATCTACGGGCGCGA
GGAGCTGCGCAGCCCCAAGCTGTTCTACGCCGACCACCCCTTCATCTTCC
TAGTGCGGGACACCCAAAGCGGCTCCCTGCTATTCATTGGGCGCCTGGTC
CGGCCTAAGGGTGACAAGATGCGAGACGAGTTATAGGGCCTCAGGGTGCA
CACAGGATGGCAGGAGGCATCCAAAGGCTCCTGAGACACATGGGTGCTAT
TGGGGTTGGGGGGGAGGTGAGGTACCAGCCTTGGATACTCCATGGGGTGG
GGGTGGAAAAACAGACCGGGGTTCCCGTGTGCCTGAGCGGACCTTCCCAG
CTAGAATTCACTCCACTTGGACATGGGCCCCAGATACCATGATGCTGAGC
CCGGAAACTCCACATCCTGTGGGACCTGGGCCATAGTCATTCTGCCTGCC
CTGAAAGTCCCAGATCAAGCCTGCCTCAATCAGTATTCATATTTATAGCC
AGGTACCTTCTCACCTGTGAGACCAAATTGAGCTAGGGGGGTCAGCCAGC
CCTCTTCTGACACTAAAACACCTCAGCTGCCTCCCCAGCTCTATCCCAAC
CTCTCCCAACTATAAAACTAGGTGCTGCAGCCCCTGGGACCAGGCACCCC
CAGAATGACCTGGCCGCAGTGAGGCGGATTGAGAAGGAGCTCCCAGGAGG
GGCTTCTGGGCAGACTCTGGTCAAGAAGCATCGTGTCTGGCGTTGTGGGG
ATGAACTTTTTGTTTTGTTTCTTCCTTTTTTAGTTCTTCAAAGATAGGGA
GGGAAGGGGGAACATGAGCCTTTGTTGCTATCAATCCAAGAACTTATTTG
TACATTTTTTTTTTCAATAAAACTTTTCCAATGACATTTTGTTGGAGCGT
GGAAAAAA

Serine Proteinase Inhibitor, Clade B, Member 5

>gi|4505788|ref|NM_002639.1| *Homo sapiens* serine (or cysteine) proteinase inhibitor, clade B (ovalbumin), member 5 (SERPINB5), mRNA|qPCR forward_primer match [36 . . . 56]|qPCR reverse_primer match [106 . . . 86]|qPCR probe match [60 . . . 80]

SEQ ID NO: 102

GGCACGAGTTGTGCTCCTCGCTTGCCTGTTCCTTTTCCACGCATTTTCCA
GGATAACTGTGACTCCAGGCCCGCAATGGATGCCCTGCAACTAGCAAATT
CGGCTTTTGCCGTTGATCTGTTCAAACAACTATGTGAAAAGGAGCCACTG
GGCAATGTCCTCTTCTCTCCAATCTGTCTCTCCACCTCTCTGTCACTTGC
TCAAGTGGGTGCTAAAGGTGACACTGCAAATGAAATTGGACAGGTTCTTC
ATTTTGAAAATGTCAAAGATATACCCTTTGGATTTCAAACAGTAACATCG

-continued

GATGTAAACAAACTTAGTTCCTTTTACTCACTGAAACTAATCAAGCGGCT
CTACGTAGACAAATCTCTGAATCTTTCTACAGAGTTCATCAGCTCTACGA
AGAGACCCTATGCAAAGGAATTGGAAACTGTTGACTTCAAAGATAAATTG
GAAGAAACGAAAGGTGAGATCAACAACTCAATTAAGGATCTCACAGATGG
CCACTTTGAGAACATTTTAGCTGACAACAGTGTGAACGACCAGACCAAAA
TCCTTGTGGTTAATGCTGCCTACTTTGTTGGCAAGTGGATGAAGAAATTT
CCTGAATCAGAAACAAAAGAATGTCCTTTCAGACTCAACAAGACAGACAC
CAAACCAGTGCAGATGATGAACATGGAGGCCACGTTCTGTATGGGAAACA
TTGACAGTATCAATTGTAAGATCATAGAGCTTCCTTTTCAAAATAAGCAT
CTCAGCATGTTCATCCTACTACCCAAGGATGTGGAGGATGAGTCCACAGG
CTTGGAGAAGATTGAAAAACAACTCAACTCAGAGTCACTGTCACAGTGGA
CTAATCCCAGCACCATGGCCAATGCCAAGGTCAAACTCTCCATTCCAAAA
TTTAAGGTGGAAAAGATGATTGATCCCAAGGCTTGTCTGGAAAATCTAGG
GCTGAAACATATCTTCAGTGAAGACACATCTGATTTCTCTGGAATGTCAG
AGACCAAGGGAGTGGCCCTATCAAATGTTATCCACAAAGTGTGCTTAGAA
ATAACTGAAGATGGTGGGGATTCCATAGAGGTGCCAGGAGCACGGATCCT
GCAGCACAAGGATGAATTGAATGCTGACCATCCCTTTATTTACATCATCA
GGCACAACAAAACTCGAAACATCATTTTCTTTGGCAAATTCTGTTCTCCT
TAAGTGGCATAGCCCATGTTAAGTCCTCCCTGACTTTTCTGTGGATGCCG
ATTTCTGTAAACTCTGCATCCAGAGATTCATTTTCTAGATACAATAAATT
GCTAATGTTGCTGGATCAGGAAGCCGCCAGTACTTGTCATATGTAGCCTT
CACACAGATAGACCTTTTTTTTTTTCCAATTCTATCTTTTGTTTCCTTTT
TTCCCATAAGACAATGACATACGCTTTTAATGAAAAGGAATCACGTTAGA
GGAAAAATATTTATTCATTATTTGTCAAATTGTCCGGGGTAGTTGGCAGA
AATACAGTCTTCCACAAAGAAAATTCCTATAAGGAAGATTTGGAAGCTCT
TCTTCCCAGCACTATGCTTTCCTTCTTTGGGATAGAGAATGTTCCAGACA
TTCTCGCTTCCCTGAAAGACTGAAGAAAGTGTAGTGCATGGGACCCACGA
AACTGCCCTGGCTCCAGTGAAACTTGGGCACATGCTCAGGCTACTATAGG
TCCAGAAGTCCTTATGTTAAGCCCTGGCAGGCAGGTGTTTATTAAAATTC
TGAATTTTGGGGATTTTCAAAAGATAATATTTTACATACACTGTATGTTA
TAGAACTTCATGGATCAGATCTGGGGCAGCAACCTATAAATCAACACCTT
AATATGCTGCAACAAAATGTAGAATATTCAGACAAAATGGATACATAAAG
ACTAAGTAGCCCATAAGGGGTCAAAATTTGCTGCCAAATGCGTATGCCAC
CAACTTACAAAAACACTTCGTTCGCAGAGCTTTTCAGATTGTGGAATGTT
GGATAAGGAATTATAGACCTCTAGTAGCTGAAATGCAAGACCCCAAGAGG
AAGTTCAGATCTTAATATAAATTCACTTTCATTTTTGATAGCTGTCCCAT
CTGGTCATGTGGTTGGCACTAGACTGGTGGCAGGGGCTTCTAGCTGACTC
GCACAGGGATTCTCACAATAGCCGATATCAGAATTTGTGTTGAAGGAACT
TGTCTCTTCATCTAATATGATAGCGGGAAAAGGAGAGGAAACTACTGCCT
TTAGAAAATATAAGTAAAGTGATTAAAGTGCTCACGTTACCTTGACACAT

-continued

AGTTTTTCAGTCTATGGGTTTAGTTACTTTAGATGGCAAGCATGTAACTT

ATATTAATAGTAATTTGTAAAGTTGGGTGGATAAGCTATCCCTGTTGCCG

GTTCATGGATTACTTCTCTATAAAAAATATATATTTACCAAAAAATTTTG

TGACATTGCTTCTCCCATCTCTTCCTTGACATGCATTGTAAATAGGTTCT

TCTTGTTCTGAGATTCAATATTGAATTTCTCCTATGCTATTGACAATAAA

ATATTATTGAACTACC

Carcinoembryonic Antigen-Related Cell Adhesion Molecule 5

>gi|11386170|ref|NM_004363.1| *Homo sapiens* carcinoembryonic antigen-related cell adhesion molecule 5 (CEACAM5), mRNA|qPCR assay_on_demand_context match [2128 . . . 2152]

SEQ ID NO: 103

CTCAGGGCAGAGGGAGGAAGGACAGCAGACCAGACAGTCACAGCAGCCTT

GACAAAACGTTCCTGGAACTCAAGCTCTTCTCCACAGAGGAGGACAGAGC

AGACAGCAGAGACCATGGAGTCTCCCTCGGCCCCTCCCCACAGATGGTGC

ATCCCCTGGCAGAGGCTCCTGCTCACAGCCTCACTTCTAACCTTCTGGAA

CCCGCCCACCACTGCCAAGCTCACTATTGAATCCACGCCGTTCAATGTCG

CAGAGGGGAAGGAGGTGCTTCTACTTGTCCACAATCTGCCCCAGCATCTT

TTTGGCTACAGCTGGTACAAAGGTGAAAGAGTGGATGGCAACCGTCAAAT

TATAGGATATGTAATAGGAACTCAACAAGCTACCCCAGGGCCCGCATACA

GTGGTCGAGAGATAATATACCCCAATGCATCCCTGCTGATCCAGAACATC

ATCCAGAATGACACAGGATTCTACACCCTACACGTCATAAAGTCAGATCT

TGTGAATGAAGAAGCAACTGGCCAGTTCCGGGTATACCCGGAGCTGCCCA

AGCCCTCCATCTCCAGCAACAACTCCAAACCCGTGGAGGACAAGGATGCT

GTGGCCTTCACCTGTGAACCTGAGACTCAGGACGCAACCTACCTGTGGTG

GGTAAACAATCAGAGCCTCCCGGTCAGTCCCAGGCTGCAGCTGTCCAATG

GCAACAGGACCCTCACTCTATTCAATGTCACAAGAAATGACACAGCAAGC

TACAAATGTGAAACCCAGAACCCAGTGAGTGCCAGGCGCAGTGATTCAGT

CATCCTGAATGTCCTCTATGGCCCGGATGCCCCCACCATTTCCCCTCTAA

ACACATCTTACAGATCAGGGGAAAATCTGAACCTCTCCTGCCACGCAGCC

TCTAACCCACCTGCACAGTACTCTTGGTTTGTCAATGGGACTTTCCAGCA

ATCCACCCAAGAGCTCTTTATCCCCAACATCACTGTGAATAATAGTGGAT

CCTATACGTGCCAAGCCCATAACTCAGACACTGGCCTCAATAGGACCACA

GTCACGACGATCACAGTCTATGCAGAGCCACCCAAACCCTTCATCACCAG

CAACAACTCCAACCCCGTGGAGGATGAGGATGCTGTAGCCTTAACCTGTG

AACCTGAGATTCAGAACACAACCTACCTGTGGTGGGTAAATAATCAGAGC

CTCCCGGTCAGTCCCAGGCTGCAGCTGTCCAATGACAACAGGACCCTCAC

TCTACTCAGTGTCACAAGGAATGATGTAGGACCCTATGAGTGTGGAATCC

AGAACGAATTAAGTGTTGACCACAGCGACCCAGTCATCCTGAATGTCCTC

TATGGCCCAGACGACCCCACCATTTCCCCCTCATACACCTATTACCGTCC

AGGGGTGAACCTCAGCCTCTCCTGCCATGCAGCCTCTAACCCACCTGCAC

-continued

AGTATTCTTGGCTGATTGATGGGAACATCCAGCAACACACACAAGAGCTC

TTTATCTCCAACATCACTGAGAAGAACAGCGGACTCTATACCTGCCAGGC

CAATAACTCAGCCAGTGGCCACAGCAGGACTACAGTCAAGACAATCACAG

TCTCTGCGGAGCTGCCCAAGCCCTCCATCTCCAGCAACAACTCCAAACCC

GTGGAGGACAAGGATGCTGTGGCCTTCACCTGTGAACCTGAGGCTCAGAA

CACAACCTACCTGTGGTGGGTAAATGGTCAGAGCCTCCCAGTCAGTCCCA

GGCTGCAGCTGTCCAATGGCAACAGGACCCTCACTCTATTCAATGTCACA

AGAAATGACGCAAGAGCCTATGTATGTGGAATCCAGAACTCAGTGAGTGC

AAACCGCAGTGACCCAGTCACCCTGGATGTCCTCTATGGGCCGGACACCC

CCATCATTTCCCCCCCAGACTCGTCTTACCTTTCGGGAGCGAACCTCAAC

CTCTCCTGCCACTCGGCCTCTAACCCATCCCCGCAGTATTCTTGGCGTAT

CAATGGGATACCGCAGCAACACACACAAGTTCTCTTTATCGCCAAAATCA

CGCCAAATAATAACGGGACCTATGCCTGTTTTGTCTCTAACTTGGCTACT

GGCCGCAATAATTCCATAGTCAAGAGCATCACAGTCTCTGCATCTGGAAC

TTCTCCTGGTCTCTCAGCTGGGGCCACTGTCGGCATCATGATTGGAGTGC

TGGTTGGGGTTGCTCTGATATAGCAGCCCTGGTGTAGTTTCTTCATTTCA

GGAAGACTGACAGTTGTTTTGCTTCTTCCTTAAAGCATTTGCAACAGCTA

CAGTCTAAAATTGCTTCTTTACCAAGGATATTTACAGAAAAGACTCTGAC

CAGAGATCGAGACCATCCTAGCCAACATCGTGAAACCCCATCTCTACTAA

AAATACAAAAATGAGCTGGGCTTGGTGGCGCGCACCTGTAGTCCCAGTTA

CTCGGGAGGCTGAGGCAGGAGAATCGCTTGAACCCGGGAGGTGGAGATTG

CAGTGAGCCCAGATCGCACCACTGCACTCCAGTCTGGCAACAGAGCAAGA

CTCCATCTCAAAAAGAAAAGAAAAGAAGACTCTGACCTGTACTCTTGAAT

ACAAGTTTCTGATACCACTGCACTGTCTGAGAATTTCCAAAACTTTAATG

AACTAACTGACAGCTTCATGAAACTGTCCACCAAGATCAAGCAGAGAAAA

TAATTAATTTCATGGGACTAAATGAACTAATGAGGATTGCTGATTCTTTA

AATGTCTTGTTTCCCAGATTTCAGGAAACTTTTTTTCTTTTAAGCTATCC

ACTCTTACAGCAATTTGATAAAATATACTTTTGTGAACAAAAATTGAGAC

ATTTACATTTTCTCCCTATGTGGTCGCTCCAGACTTGGGAAACTATTCAT

GAATATTTATATTGTATGGTAATATAGTTATTGCACAAGTTCAATAAAAA

TCTGCTCTTTGTATAACAGAAAAA

Matrix Metalloproteinase 2

>gi|11342665|ref|NM_004530.1| *Homo sapiens* matrix metalloproteinase 2 (gelatinase A, 72 kDa gelatinase, 72 kDa type IV collagenase) (MMP2), mRNA 1 qPCR forward_primer match [1713 . . . 1732]|qPCR reverse_primer match [1793 . . . 1775]|qPCR probe match [1751 . . . 1773]

SEQ ID NO: 104

TGTTTCCGCTGCATCCAGACTTCCTCAGGCGGTGGCTGGAGGCTGCGCAT

CTGGGGCTTTAAACATACAAAGGGATTGCCAGGACCTGCGGCGGCGGCGG

CGGCGGCGGGGGCTGGGGCGCGGGGGCCGGACCATGAGCCGCTGAGCCGG

GCAAACCCCAGGCCACCGAGCCAGCGGACCCTCGGAGCGCAGCCCTGCGC

-continued

CGCGGACCAGGCTCCAACCAGGCGGCGAGGCGGCCACACGCACCGAGCCA
GCGACCCCCGGGCGACGCGCGGGGCCAGGGAGCGCTACGATGGAGGCGCT
AATGGCCCGGGGCGCGCTCACGGGTCCCCTGAGGGCGCTCTGTCTCCTGG
GCTGCCTGCTGAGCCACGCCGCCGCCGCGCCGTCGCCCATCATCAAGTTC
CCCGGCGATGTCGCCCCCAAAACGGACAAAGAGTTGGCAGTGCAATACCT
GAACACCTTCTATGGCTGCCCCAAGGAGAGCTGCAACCTGTTTGTGCTGA
AGGACACACTAAAGAAGATGCAGAAGTTCTTTGGACTGCCCCAGACAGGT
GATCTTGACCAGAATACCATCGAGACCATGCGGAAGCCACGCTGCGGCAA
CCCAGATGTGGCCAACTACAACTTCTTCCCTCGCAAGCCCAAGTGGGACA
AGAACCAGATCACATACAGGATCATTGGCTACACACCTGATCTGGACCCA
GAGACAGTGGATGATGCCTTTGCTCGTGCCTTCCAAGTCTGGAGCGATGT
GACCCCACTGCGGTTTTCTCGAATCCATGATGGAGAGGCAGACATCATGA
TCAACTTTGGCCGCTGGGAGCATGGCGATGGATACCCCTTTGACGGTAAG
GACGGACTCCTGGCTCATGCCTTCGCCCCAGGCACTGGTGTTGGGGGAGA
CTCCCATTTTGATGACGATGAGCTATGGACCTTGGGAGAAGGCCAAGTGG
TCCGTGTGAAGTATGGCAACGCCGATGGGGAGTACTGCAAGTTCCCCTTC
TTGTTCAATGGCAAGGAGTACAACAGCTGCACTGATACTGGCCGCAGCGA
TGGCTTCCTCTGGTGCTCCACCACCTACAACTTTGAGAAGGATGGCAAGT
ACGGCTTCTGTCCCCATGAAGCCCTGTTCACCATGGGCGGCAACGCTGAA
GGACAGCCCTGCAAGTTTCCATTCCGCTTCCAGGGCACATCCTATGACAG
CTGCACCACTGAGGGCCGCACGGATGGCTACCGCTGGTGCGGCACCACTG
AGGACTACGACCGCGACAAGAAGTATGGCTTCTGCCCTGAGACCGCCATG
TCCACTGTTGGTGGGAACTCAGAAGGTGCCCCCTGTGTCTTCCCCTTCAC
TTTCCTGGGCAACAAATATGAGAGCTGCACCAGCGCCGGCCGCAGTGACG
GAAAGATGTGGTGTGCGACCACAGCCAACTACGATGACGACCGCAAGTGG
GGCTTCTGCCCTGACCAAGGGTACAGCCTGTTCCTCGTGGCAGCCCACGA
GTTTGGCCACGCCATGGGGCTGGAGCACTCCCAAGACCCTGGGGCCCTGA
TGGCACCCATTTACACCTACACCAAGAACTTCCGTCTGTCCCAGGATGAC
ATCAAGGGCATTCAGGAGCTCTATGGGGCCTCTCCTGACATTGACCTTGG
CACCGGCCCCACCCCCACACTGGGCCCTGTCACTCCTGAGATCTGCAAAC
AGGACATTGTATTTGATGGCATCGCTCAGATCCGTGGTGAGATCTTCTTC
TTCAAGGACCGGTTCATTTGGCGGACTGTGACGCCACGTGACAAGCCCAT
GGGGCCCCTGCTGGTGGCCACATTCTGGCCTGAGCTCCCGTGAAAAGATT
GATGCGGTATACGAGGCCCCACAGGAGGAGAAGGCTGTGTTCTTTGCAGG
GAATGAATACTGGATCTACTCAGCCAGCACCCTGGAGCGAGGGTACCCCA
AGCCACTGACCAGCCTGGGACTGCCCCCTGATGTCCAGCGAGTGGATGCC
GCCTTTAACTGGAGCAAAAACAAGAAGACATACATCTTTGCTGGAGACAA
ATTCTGGAGATACAATGAGGTGAAGAAGAAAATGGATCCTGGCTTTCCCA
AGCTCATCGCAGATGCCTGGAATGCCATCCCCGATAACCTGGATGCCGTC
GTGGACCTGCAGGGCGGCGGTCACAGCTACTTCTTCAAGGGTGCCTATTA
CCTGAAGCTGGAGAACCAAAGTCTGAAGAGCGTGAAGTTTGGAAGCATCA

-continued

AATCCGACTGGCTAGGCTGCTGAGCTGGCCCTGGCTCCCACAGGCCCTTC
CTCTCCACTGCCTTCGATACACCGGGCCTGGAGAACTAGAGAAGGACCCG
GAGGGGCCTGGCAGCCGTGCCTTCAGCTCTACAGCTAATCAGCATTCTCA
CTCCTACCTGGTAATTTAAGATTCCAGAGAGTGGCTCCTCCCGGTGCCCA
AGAATAGATGCTGACTGTACTCCTCCCAGGCGCCCCTTCCCCCTCCAATC
CCACCAACCCTCAGAGCCACCCCTAAAGAGATCCTTTGATATTTTCAACG
CAGCCCTGCTTTGGGCTGCCCTGGTGCTGCCACACTTCAGGCTCTTCTCC
TTTCACAACCTTCTGTGGCTCACAGAACCCTTGGAGCCAATGGAGACTGT
CTCAAGAGGGCACTGGTGGCCCGACAGCCTGGCACAGGGCAGTGGGACAG
GGCATGGCCAGGTGGCCACTCCAGACCCCTGGCTTTTCACTGCTGGCTGC
CTTAGAACCTTTCTTACATTAGCAGTTTGCTTTGTATGCACTTTGTTTTT
TTCTTTGGGTCTTGTTTTTTTTTTCCACTTAGAAATTGCATTTCCTGACA
GAAGGACTCAGGTTGTCTGAAGTCACTGCACAGTGCATCTCAGCCCACAT
AGTGATGGTTCCCCTGTTCACTCTACTTAGCATGTCCCTACCGAGTCTCT
TCTCCACTGGATGGAGGAAAACCAAGCCGTGGCTTCCCGCTCAGCCCTCC
CTGCCCCTCCTTCAACCATTCCCCATGGGAAATGTCAACAAGTATGAATA
AAGACACCTACTGAGTGGC

Proprotein Convertase Subtilisin/Kexin Type 5 >gi|20336245|ref|NM_006200.2| *Homo sapiens* proprotein convertase subtilisin/kexin type 5 (PCSK5), mRNA|qPCR forward_primer match [2677 . . . 2697]|qPCR reverse_primer match [2821 . . . 2801]|qPCR probe match [2737 . . . 2765]

SEQ ID NO: 105

CGGAGGGAGCGCTGGGAGCGAGCAAGCGAGCGTTTGGAGCCCGGGCCAGC
AGAGGGGGCGCCCGGTCGCTGCCTGTACCGCTCCCGCTGGTCATCTCCGC
CGCGCTCGGGGGCCCCGGGAGGAGCGAGACCGAGTCGGAGAGTCCGGGAG
CCAAGCCGGGCGAAACCCAACTGCGGAGGACGCCCGCCCCACTCAGCCTC
CTCCTGCGTCCGAGCCGGGGAGCATCGCCGAGCGCCCCACGGGCCGGAGA
GCTGGGAGCACAGGTCCCGGCAGCCCCAGGGATGGTCTAGGAGCCGGCGT
AAGGCTCGCTGCTCTGCTCCCTGCCGGGGCTAGCCGCCTCCTGCCGATCG
CCCGGGGCTGCGAGCTGCGGCGGCCCGGGGCTGCTCGCCGGGCGGCGCAG
GCCGGAGAAGTTAGTTGTGCGCGCCCTTAGTGCGCGGAACCAGCCAGCGA
GCGAGGGAGCAGCGAGGCGCCGGGACCATGGGCTGGGGGAGCCGCTGCTG
CTGCCCGGGACGTTTGGACCTGCTGTGCGTGCTGGCGCTGCTCGGGGGCT
GCCTGCTCCCCGTGTGTCGGACGCGCGTCTACACCAACCACTGGGCAGTC
AAAATCGCCGGGGGCTTCCCGGAGGCCAACCGTATCGCCAGCAAGTACGG
ATTCATCAACATAGGACAGATAGGGGCCCTGAAGGACTACTACCACTTCT
ACCATAGCAGGACGATTAAAAGGTCAGTTATCTCGAGCAGAGGGACCCAC
AGTTTGATTTCAATGGAACCAAAGGTGGAATGGATCCAACAGCAAGTGGT
AAAAAAGCGGACAAAGAGGGATTATGACTTCAGTCGTGCCCAGTCTACCT
ATTTCAATGATCCCAAGTGGCCCAGCATGTGGTATATGCACTGCAGTGAC

-continued

AATACACATCCCTGCCAGTCTGACATGAATATCGAAGGAGCCTGGAAGAG

AGGCTACACGGGAAAGAACATTGTGGTCACTATCCTGGATGACGGAATTG

AGAGAACCCATCCAGATCTGATGCAAAACTACGATGCTCTGGCAAGTTGC

GACGTGAATGGGAATGACTTGGACCCAATGCCTCGTTATGATGCAAGCAA

CGAGAACAAGCATGGGACTCGCTGTGCTGGAGAAGTGGCAGCCGCTGCAA

ACAATTCGCACTGCACAGTCGGAATTGCTTTCAACGCCAAGATCGGAGGA

GTGCGAATGCTGGACGGAGATGTCACGGACATGGTTGAAGCAAAATCAGT

TAGCTTCAACCCCCAGCACGTGCACATTTACAGCGCCAGCTGGGGCCCGG

ATGATGATGGCAAGACTGTGGACGGACCAGCCCCCCTCACCCGGCAAGCC

TTTGAAAACGGCGTTAGAATGGGGCGGAGAGGCCTCGGCTCTGTGTTTGT

TTGGGCATCTGGAAATGGTGGAAGGAGCAAAGACCACTGCTCCTGTGATG

GCTACACCAACAGCATCTACACCATCTCCATCAGCAGCACTGCAGAAAGC

GGAAAGAAACCTTGGTACCTGGAAGAGTGTTCATCCACGCTGGCCACAAC

CTACAGCAGCGGGGAGTCCTACGATAAGAAAATCATCACTACAGATCTGA

GGCAGCGTTGCACGGACAACCACACTGGGACGTCAGCCTCAGCCCCCATG

GCTGCAGGCATCATTGCGCTGGCCCTGGAAGCCAATCCGTTTCTGACCTG

GAGAGACGTACAGCATGTTATTGTCAGGACTTCCCGTGCGGGACATTTGA

ACGCTAATGACTGGAAAACCAATGCTGCTGGTTTTAAGGTGAGCCATCTT

TATGGATTTGGACTGATGGACGCAGAAGCCATGGTGATGGAGGCAGAGAA

GTGGACCACCGTTCCCCGGCAGCACGTGTGTGTGGAGAGCACAGACCGAC

AAATCAAGACAATCCGCCCTAACAGTGCAGTGCGCTCCATCTACAAAGCT

TCAGGCTGCTCGGATAACCCCAACCGCCATGTCAACTACCTGGAGCACGT

CGTTGTGCGCATCACCATCACCCACCCCAGGAGAGGAGACCTGGCCATCT

ACCTGACCTCGCCCTCTGGAACTAGGTCTCAGCTTTTGGCCAACAGGCTA

TTTGATCACTCCATGGAAGGATTCAAAAACTGGGAGTTCATGACCATTCA

TTGCTGGGGAGAAAGAGCTGCTGGTGACTGGGTCCTTGAAGTTTATGATA

CTCCCTCTCAGCTAAGGAACTTTAAGACTCCAGGTAAATTGAAAGAATGG

TCTTTGGTCCTCTACGGCACCTCCGTGCAGCCATATTCACCAACCAATGA

ATTTCCGAAAGTGGAACGGTTCCGCTATAGCCGAGTTGAAGACCCCACAG

ACGACTATGGCACAGAGGATTATGCAGGTCCCTGCGACCCTGAGTGCAGT

GAGGTTGGCTGTGACGGGCCAGGACCAGACCACTGCAATGACTGTTTGCA

CTACTACTACAAGCTGAAAAACAATACCAGGATCTGTGTCTCCAGCTGCC

CCCCTGGCCACTACCACGCCGACAAGAAGCGCTGCAGGAAGTGTGCCCCC

AACTGTGAGTCCTGCTTTGGGAGCCATGGTGACCAATGCATGTCCTGCAA

ATATGGATACTTTCTGAATGAAGAAACCAACAGCTGTGTTACTCACTGCC

CTGATGGGTCATATCAGGATACCAAGAAAAATCTTTGCCGGAAATGCAGT

GAAAACTGCAAGACATGTACTGAATTCCATAACTGTACAGAATGTAGGGA

TGGGTTAAGCCTGCAGGGATCCCGGTGCTCTGTCTCCTGTGAAGATGGAC

GGTATTTCAACGGCCAGGACTGCCAGCCCTGCCACCGCTTCTGCGCCACT

TGTGCTGGGGCAGGAGCTGATGGGTGCATTAACTGCACAGAGGGCTACTT

-continued

CATGGAGGATGGGAGATGCGTGCAGAGCTGTAGTATCAGCTATTACTTTG

ACCACTCTTCAGAGAATGGATACAAATCCTGCAAAAAATGTGATATCAGT

TGTTTGACGTGCAATGGCCCAGGATTCAAGAACTGTACAAGCTGCCCTAG

TGGGTATCTCTTAGACTTAGGAATGTGTCAAATGGGAGCCATTTGCAAGG

ATGCAACGGAAGAGTCCTGGGCGGAAGGAGGCTTCTGTATGCTTGTGAAA

AAGAACAATCTGTGCCAACGGAAGGTTCTTCAACAACTTTGCTGCAAAAC

ATGTACATTTCAAGGCTGAGCAGCCATCTTAGATTTCTTTGTTCCTGTAG

ACTTATAGATTATTCCATATTATTAAAAAGAAAAAAAAAAGCCAAAAAG

Carboxypeptidase N, polypeptide 2, 83kD
>gi|18554966|ref|XM_087358.1| *Homo sapiens* carboxypeptidase N, polypeptide 2, 83kD (CPN2), mRNA

SEQ ID NO: 106

ATGGGTTGTGACTGCTTCGTCCAGGAGGTGTTCTGCTCAGATGAGGAGCT

TGCCACCGTCCCGCTGGACATCCCGCCATATACGAAAAACATCATCTTTG

TGGAGACCTCGTTCACCACATTGGAAACCAGAGCTTTTGGCAGTAACCCC

AACTTGACCAAGGTGGTCTTCCTCAACACTCAGCTCTGCCAGTTTAGGCC

GGATGCCTTTGGGGGGCTGCCCAGGCTGGAGGACCTGGAGGTCACAGGCA

GTAGCTTCTTGAACCTCAGCACCAACATCTTCTCCAACCTGACCTCGCTG

GGCAAGCTCACCCTCAACTTCAACATGCTGGAGGCTCTGCCCGAGGGTCT

TTTCCAGCACCTGGCTGCCCTGGAGTCCCTCCACCTGCAGGGGAACCAGC

TCCAGGCCCTGCCCAGGAGGCTCTTCCAGCCTCTGACCCATCTGAAGACA

CTCAACCTGGCCCAGAACCTCCTGGCCCAGCTCCCGGAGGAGCTGTTCCA

CCCACTCACCAGCCTGCAGACCCTGAAGCTGAGCAACAACGCGCTCTCTG

GTCTCCCCCAGGGTGTGTTTGGCAAACTGGGCAGCCTGCAGGAGCTCTTC

CTGGACAGCAACAACATCTCGGAGCTGCCCCCTCAGGTGTTCTCCCAGCT

CTTCTGCCTAGAGAGGCTGTGGCTGCAACGCAACGCCATCACGCACCTGC

CGCTCTCCATCTTTGCCTCCCTGGGTAATCTGACCTTTCTGAGCTTGCAG

TGGAACATGCTTCGGGTCCTGCCTGCCGGCCTCTTTGCCCACACCCCATG

CCTGGTTGGCCTGTCTCTGACCCATAACCAGCTGGAGACTGTCGCTGAGG

GCACCTTTGCCCACCTGTCCAACCTGCGTTCCCTCATGCTCTCATACAAT

GCCATTACCCACCTCCCAGCTGGCATCTTCAGAGACCTGGAGGAGTTGGT

CAAACTCTACCTGGGCAGCAACAACCTTACGGCGCTGCACCCAGCCCTCT

TCCAGAACCTGTCCAAGCTGGAGCTGCTCAGCCTCTCCAAGAACCAGCTG

ACCACACTTCCGGAGGGCATCTTCGACACCAACTACAACCTGTTCAACCT

GGCCCTGCACGGTAACCCCTGGCAGTGCGACTGCCACCTGGCCTACCTCT

TCAACTGGCTGCAGCAGTACACCGATCGGCTCCTGAACATCCAGACCTAC

TGCGCTGGCCCTGCCTACCTCAAAGGCCAGGTGGTGCCCGCCTTGAATGA

GAAGCAGCTGGTGTGTCCCGTCACCCGGGACCACTTGGGCTTCCAGGTCA

CGTGGCCGGACGAAAGCAAGGCAGGGGGCAGCTGGGATCTGGCTGTGCAG

GAAAGGGCAGCCCGGAGCCAGTGCACCTACAGCAACCCCGAGGGCACCGT

GGTGCTCGCCTGTGACCAGGCCCAGTGTCGCTGGCTGAACGTCCAGCTCT

-continued

CTCCTTGGCAGGGCTCCCTGGGACTGCAGTACAATGCTAGTCAGGAGTGG

GACCTGAGGTCGAGCTGCGGTTCTCTGCGGCTCACCGTGTCTATCGAGGC

TCGGGCAGCAGGGCCCTAGTAGCAGCGCATACAGGAGCTGGGGAAGGGGG

CTTTGGGGCCTGCCCACGCGACAGGTAGGGGCGGAGGGGAGCTGAGTCTC

CGAAGCTTGGCTTT

Hyaluronan and proteoglycan link protein 4 >gi|30794471|ref|NM_023002.1| *Homo sapiens* hyaluronan and proteoglycan link protein 4 (HAPLN4), mRNA

SEQ ID NO: 107

CGGGGGCCGCGCGGGCAAGATGGTGTGCGCTCGGGCGGCCCTCGGTCCCG

GCGCGCTCTGGGCCGCGGCCTGGGGCGTCCTGCTGCTCACAGCCCCTGCG

GGGGCGCAGCGTGGCCGGAAGAAGGTCGTGCACGTGCTGGAGGGTGAGTC

GGGCTCGGTAGTGGTACAGACAGCGCCTGGGCAGGTGGTAAGCCACCGTG

GTGGCACCATCGTCTTGCCCTGCCGCTACCACTATGAGGCAGCCGCCCAC

GGTCACGACGGCGTCCGGCTCAAGTGGACAAAGGTGGTGGACCCGCTGGC

CTTCACCGACGTCTTCGTGGCACTAGGCCCCCAGCACCGGGCATTCGGCA

GCTACCGTGGGCGGGCTGAGCTGCAGGGCGACGGGCCTGGGGATGCCTCC

CTGGTCCTCCGCAACGTCACGCTGCAAGACTACGGGCGCTATGAGTGCGA

AGTCACCAATGAGCTGGAAGATGACGCTGGCATGGTCAAGCTGGACCTGG

AAGGCGTGGTCTTTCCCTACCACCCCCGTGGAGGCCGATACAAGCTGACC

TTCGCGGAGGCGCAGCGCGCGTGCGCCGAGCAGGACGGCATCCTGGCATC

TGCAGAACAGCTGCACGCGGCCTGGCGCGACGGCCTGGACTGGTGCAACG

CGGGCTGGTTGCGCGACGGCTCAGTGCAATACCCCGTGAACCGGCCCCGG

GAGCCCTGCGGCGGCCTGGGGGGGACCGGGAGTGCAGGGGGCGGCGGTGA

TGCCAACGGGGGCCTGCGCAACTACGGGTATCGCCATAACGCCGAGGAAC

GCTACGACGCCTTCTGCTTCACGTCCAACCTGCCGGGGCGCGTGTTCTTC

CTGAAGCCGCTGCGACCTGTACCCTTCTCCGGAGCTGCGCGCGCGTGTGC

TGCGCGTGGCGCGGCCGTGGCCAAGGTGGGGCAGCTGTTCGCCGCGTGGA

AGCTGCAGCTGCTAGACCGCTGCACCGCGGGTTGGCTGGCCGATGGCAGT

GCGCGCTACCCCATCGTGAACCCGCGAGCGCGCTGCGGAGGCCGCAGGCC

TGGTGTGCGCAGCCTCGGCTTCCCGGACGCCACCCGACGGCTCTTCGGCG

TCTACTGCTACCGCGCTCCAGGAGCACCGGACCCGGCACCTGGCGGCTGG

GGCTGGGGCTGGGCGGGCGGCGGCTGGGCAGGGGGCGCGCGCGATCC

TGCTGCCTGGACCCCTCTGCACGTCTAGGCTGGGAGTAGGCGGACAGCCA

GGGCGCTTGACCACTGGTCTAGAGCCCTGTGGTCCCCTGGAGCCTGGCCA

CGCCCTTGAAGCCCTGGACACTGGCCACATTCCCTGTGGTCCCTTACAAA

CTAACTGTGCCCCTGGGGTCCCTGAAGACTGGCTAGTCCTGGCAGAACAG

TACTTTGGAGTTCCCTGGAGCCTGGCCAGCCCTCACCTCTTCTGGATAGA

GGATTCCCCCAACTCCCCAACTTTCTCCATGAGGGTCACGCCCCCTGAGG

ACCTCAGGAGGCCAGCAGAACCCGCAGGCTCCTGAAGACTGGCCACGCCT

CCTGAGACCACTTGGAAACAGACCAACTGCCCCCGTGGTCGCCTGGTGGC

-continued

TGGACCCCCGGGATTGACTAGAGACCGGCCGTACACCTTCTGCATCTCAC

TGGAGACTGAACACTAGTCCCTTGCGGTCACGTGGGACACTGGGCGCCTC

CTCCTCCCCCTCCTCCTCACCTGGAGAGACTACAGGAACTTCAGGGTCAC

TCCCCGTGGTCACATGGAGGTTGTGGGCCGAGGCGCTTATTTTCCCTTAT

GGTGACCTGAGTCCTGGAGACTCCCATTCTCCCCCTCTCCCTGAGAGTCC

CCTGCAGTTTCTGGGTAACAGGGCACACCCCTCTAGTTTCATGGGCGAGC

ACCCCCATCTGCCACCTCAGACTGACACACAGCCAGCTGGCTCACTTACT

GGGGGCCACGTCCCACCCCTCAGATATTTCTTTGAAGGGAGAGCAAACCC

ACCCTGTCCTCTGACGTCCCTTTCCCAACTGTCACCAAACAGACCATCTT

CCCAGGCCTGGGGACCGGTAAGATCCATGTCACTAGTTATGCAGAGCAGT

TGCCTTGGGTCCCACTGTCACCAAGGCAACCAGTCCTGCTGCTACCTGTC

ACCTAGAGTCACACACCCCTTCCCTCATCAGGCACACCCATGAAGACAGT

GCCTCCCTCCTCCAGCTGTAACCATGGATACCACACATTTCTCATCTCAT

TGGCCCCCACCCCAGAGACCTCCACCTCAACTTCTGGCTGTCCCTACCCT

GACTCACCGCCATGGAGATCACCCTCCCCGAAGCTGTCGCCAGGGTGACC

CAACATCCAGTTCTCCGGCTCTCACCATGGAAACAAACTGTCCCTGTCCC

CAGGCCCACTCCAGTTCCAGACCACCCTCCATGCTCCACCCCCAGGCGGT

TTGGACCCCACCACTGTTGCCATGGTGACCAAACTCTGGAGTCCGAGGTA

ACAGAACACCTGTCCCCCTAGGCTTTTCCTTGTGGACAACGGGGCCCTGT

TCACCAAGCTGTTGCCATAGAGACTGTCAACGTTGTCCTCATGACAACCA

GACTTCCAGTTCTCAGGAACTTCTCATTGTGGGCCAGAAGTCCTGGGTGC

CTCCTACTAGGGCTACCCTACTGCACCCCATCAGGGGCCTGATGGCTGCC

CCTTCCCCAGACAGGGCTGGACTTCTGGAGCTGCTAAGCCACCCTCCGTT

TGCACGTTAACTCTATGCCGGATAGCAGCTGTGCACGAGACAATCTTGCA

ACACCCGGGCATGTTTGTCGTCGTCCTACAAATGAGGAAACCGAGCCTAT

GGCGTGCCCTGGTCTGTTGAGATATGCAAGCACTGAGCTCCTCTTTTGTC

CTCTGAGACCCCATCTCCATTCTCACCCAGTTCCTCTCTCCTTCCCTGAC

CCCCACCCACATTTCCCTCCTTAGAGATCCAGGAGGGATGGAATGTTCTT

TAAAATTCAACACCCACCAGGCTCTAAGCGGCGATCTGTGCTAAGAGGTC

AGGACCCAGCCGAAGTCCTCGGCGTTGACAGGCAGCTGGGGGGACATGAT

CCATGGACAAGGCCATCCCGGCCGTGGGAGACCCCAGTCCCGAAGTCTTG

CCTGCAGGAGTACTGGGGTCCCCCTGGGGCCCTCTTTACTGTCACGTCAT

CTCTAGGAAACCTATCTCTGAGTTTTGGGACCAGGTCGGTTTGGGTTTGA

ATTCTGCCTCTTCTTGCTCACTGTGTGACCAAGTGACAAACTCCTTCTGA

ACCTGTGTTCTCCCACTGTACCAGGGCTGTTCTGTGGTCCCCGTGAGTGC

CAAGCATACAGTAGGGGCTCAATAAATCCTTGT

Immunohistochemistry 8 uM frozen sections were cut from tissue blocks and mounted onto APES slides. The tissue was then fixed in acetone for 10 minutes before being air-dried. The slides were then soaked in 0.3% hydrogen peroxide in methanol for 10 minutes and washed in phosphate-buffered saline (PBS). Non-specific binding sites were blocked by incubating the slides in 20% serum from the appropriate animal and washing again in PBS. Primary antibody diluted in PBS containing 1% serum was then added to the slides. After incubation for 1 hour, the slides were again washed in PBS before incubating with the secondary antibody for a further 1 hour. After final washing in PBS, the secondary antibody was detected with diaminobenzidine tetrahydrochloride dissolved in Tris buffered saline (TBS), before being washed in TBS and water. The slides were then counter stained in haemotoxylin and viewed under a light microscope.

In certain embodiments, gastric tumors can be localized in situ using stains based on cancer markers of this invention. At least one marker may be forming amyloid structures that can be visualized using Congo red or equivalent, non-specific amyloid stains.

Tests for Gastric Cancer Markers in Body Fluids

In several embodiments, assays for GTM can be desirably carried out on samples obtained from blood, plasma, serum, peritoneal fluid obtained for example using peritoneal washes, or other body fluids, such as urine, lymph, cerebrospinal fluid, gastric fluid or stool samples.

In general, methods for assaying for oligonucleotides, proteins and peptides in these fluids are known in the art. Detection of oligonucleotides can be carried out using hybridization methods such as Northern blots, Southern blots or microarray methods, or qPCR. Methods for detecting proteins include such as enzyme linked immunosorbent assays (ELISA), protein chips having antibodies, suspension beads radioimmunoassay (RIA), Western blotting and lectin binding. However, for purposes of illustration, fluid levels of a GTM can be quantified using a sandwich-type enzyme-linked immunosorbent assay (ELISA). For plasma assays, a 5 uL aliquot of a properly diluted sample or serially diluted standard GTM and 75 uL of peroxidase-conjugated anti-human GTM antibody are added to wells of a microtiter plate. After a 30 minute incubation period at 30° C., the wells are washed with 0.05% Tween 20 in phosphate-buffered saline (PBS) to remove unbound antibody. Bound complexes of GTM and anti-GTM antibody are then incubated with o-phenylendiamine containing $H_2O_2$ for 15 minutes at 30° C. The reaction is stopped by adding 1 M $H_2SO_4$, and the absorbance at 492 nm is measured with a microtiter plate reader.

It can be appreciated that anti-GTM antibodies can be monoclonal antibodies or polyclonal antisera. It can also be appreciated that any other body fluid can be suitably studied.

Certain markers are known to be present in plasma or serum. These include osteopontin (Hotte et al., Cancer 95(3): 507-510 (2002)), prostate-specific antigen (Martin et al., Prostate Cancer Prostatic Dis. (Mar. 9, 2004) (Pub Med No: PMID: 15007379), thyroglobulin (Hall et al., Laryngoscope 113(1):77-81 (2003); Mazzaferri et al., J. Clin. Endocrinol. Metab. 88(4):1433-14421 (2003), matrix metalloproteinase-2 and -9 (Kuo et al., Clin. Chem. Acta. 294(1-2): 157-168 (2000), CEA and TIMP1 (Pellegrini et al., Cancer Immunol. Immunother. 49(7):388-394 (2000). Thus, because some of the above markers are also useful markers for GTM, plasma, serum or other fluid assays are already available for their detection and quantification. Because many proteins are either (1) secreted by cells, (2) sloughed from cell membranes, or (3) are lost from cells upon cell death, other GTM are also present in body fluids, such as plasma, serum and the like. Therefore, in embodiments of this invention, detection of GTM in conveniently obtained samples will be useful and desirable and can be a basis for diagnosis of gastric cancer.

Western Analysis

Proteins were extracted from gastric tissue using a TriReagent and guanidine HCl extraction method. The non-aqueous phase from the TriReagent extraction of RNA was mixed with 1.5 vols of ethanol and centrifuged to remove DNA and OCT medium. 0.5 mls of supernatant was mixed with 0.75 ml isopropanol, incubated at room temperature for 10 minutes, and then centrifuged. The pellet was washed three times in 1 ml 0.3M guanidine HCl in 95% ethanol and once in ethanol alone, then resuspended in 50 ul 1% SDS.

Proteins were quantified and electrophoresed on SDS polyacrylamide gels using standard methods. Briefly, the separated proteins were transferred to PVDF membrane using the BioRad trans-blot electrophoretic transfer cell using standard methodology. The membranes were then blocked with a solution containing non-fat milk powder for 30 minutes before being incubated with primary antibody for 2 hours at room temperature. After washing, the membrane was incubated with secondary antibody for 1 hour at room temperature. After final washes, bound antibody was visualized using the ECL detection system (Amersham Biosciences).

Detection of markers in the serum can be accomplished by providing a sample of serum using known methods and then subjecting the serum sample to analysis, either using oligonucleotide probes or antibodies directed against the protein of interest. Immunoblotting, including Western blotting analysis can be especially useful to determine whether alternatively expressed proteins are present in the serum. Additionally, other body fluids may contain markers, and include peritoneal fluid, cerebrospinal fluid and the like. It is not necessary for a marker to be secreted, in a physiological sense, to be useful. Rather, any mechanism by which a marker protein or gene enters the serum can be effective in producing a detectable, quantifiable level of the marker. Thus, normal secretion of soluble proteins from cells, sloughing of membrane proteins from plasma membranes, secretion of alternatively spliced forms of mRNA or proteins expressed therefrom, cell death (either apoptotic) can produce sufficient levels of the marker to be useful. There is increasing support for the use of serum markers as tools to diagnose and/or evaluate efficacy of therapy for a variety of cancer types.

Yoshikawa et al., (Cancer Letters, 151: 81-86 (2000) describes tissue inhibitor of matrix metalloproteinase-1 in plasma of patients with gastric cancer.

Rudland et al., (Cancer Research 62: 3417-3427 (2002) describes osteopontin as a metastasis associated protein in human breast cancer.

Buckhaults et al., (Cancer Research 61:6996-7001 (2002) describes certain secreted and cell surface genes expressed in colorectal tumors.

Kim et al., (JAMA 287(13):1671-1679 (2002) describes osteopontin as a potential diagnostic biomarker for ovarian cancer.

Hotte et al., (AJ. American Cancer Society 95(3):507-512 (2002) describes plasma osteopontin as a protein detectable in human body fluids and is associated with certain malignancies.

Martin et al., (Prostate Cancer Prostatic Dis. Mar. 9, 2004 (PMID: 15007379) (Abstract) described use of human kallikrein 2, prostate-specific antigen (PSA) and free PSA as markers for detection of prostate cancer.

Hall et al (Laryngoscope 113(1):77-81 (2003) (PMID: 12679418) (Abstract) described predictive value of serum thyroglobulin in thyroid cancer.

Mazzaferri et al., (J. Clin. Endocrinol. Metab. 88(4):1433-1441 (2003) (Abstract) describes thyroglobulin as a potential monitoring method for patients with thyroid carcinoma.

Whitley et al, (Clin. Lab. Med. 24(1):29-47 (2004) (Abstract) describes thyroglobulin as a serum marker for thyroid carcinoma.

Kuo et al (Clin. Chim Acta. 294(1-2):157-168 (2000) (Abstract) describes serum matrix metalloproteinase-2 and -9 in HCF- and HBV-infected patients.

Koopman et al., (Cancer Epidemiol. Biomarkers Prev 13(3):487-491 (2004) (Abstract) describes osteopontin as a biomarker for pancreatic adenocarcinoma.

Pellegrini et al., (Cancer Immunol. Immunother. 49(7): 388-394 (2000) (Abstract) describes measurement of soluble carcinoembryonic antigen and TIMP1 as markers for pre-invasive colorectal cancer.

Thus, we have identified numerous genes and/or proteins that are useful for developing reagents, devices and kits for detecting and evaluating gastric cancer. One or more markers of gastric can be used, either singly or in combination to provide a reliable molecular test for gastric cancer.

EXAMPLES

The examples described herein are for purposes of illustrating embodiments of the invention. Other embodiments, methods and types of analyses are within the scope of persons of ordinary skill in the molecular diagnostic arts and need not be described in detail hereon. Other embodiments within the scope of the art are considered to be part of this invention.

Example 1: Identification of Markers for Gastric Malignancy

FIG. 2 depicts a table that shows results of studies using 38 markers for gastric malignancy selected using the above criteria. The FIG. 2 includes the symbol for the gene ("symbol"), the MWG oligo number, the NCBI mRNA reference sequence number, the protein reference sequence number, the fold change between tumor and non-tumor gene expression, the fold change rank relative to other genes in the microarray analysis, the results of an original, unadjusted Student's t-test, the results of the Bonferroni-adjusted p value and the results of the 2-sample Wilcoxon test.

The median fold change (tumor: non malignant tissue) for these 34 genes ranged from 1.6 to 7 and the median change in fold change rank ranged from −16,995 to −25,783. The maximum possible change in fold change rank was −29,718. For each of the markers shown, the statistical significance of their specificity as cancer markers was found to be extremely high. The Bonferroni-adjusted p values were, in general, all below $10^{-6}$ or less, indicating that diagnosis using these markers is very highly associated with gastric cancer.

The three cystatins (CST1, CST2, and CST4) are highly homologous and represented by the same oligonucleotide on the microarray and unless otherwise stated, are referred to collectively as "CST1,2,4."

All proteins depicted in FIG. 2 were predicted to have signal peptides using the SMART package (European Molecular Biology Laboratory). The signal peptides are known to target synthesized proteins to the extracellular compartment and can therefore be secreted into the interstitial fluid, from which they can have access to the blood. In fact, some proteins of this invention have been detected in serum.

Each of the genes depicted in FIG. 2 exhibited a change in intensity rank greater than the two oligonucleotides on the array corresponding to CEA, the marker most frequently used in clinical practice to monitor gastric cancer progression.

Example 2: qPCR Analysis

More sensitive and accurate quantitation of gene expression was obtained for a subset of the genes shown in FIG. 3 using qPCR. RNA from 46 tumor and 49 non-malignant samples was analyzed for 23 genes identified by the microarray analysis (FIG. 2) and results are shown in FIG. 3. FIG. 3 includes the gene symbol, median fold change between cancer and normal tissue, and the % of tumor samples with expression levels greater than the $95^{th}$ percentile of expression levels in non-malignant samples. 12 tumor samples and 9 normal samples were excluded from the analysis because of high (>75%) normal cell contamination, a high degree of necrosis (>40%), or poor hybridization signal on the microarrays. The median fold change (tumor tissues compared to the median non-malignant tissue expression) for these 23 genes ranged from 3 to 525 fold (FIG. 3).

The level of expression of genes ASPN, CST1,2,4, LOXL2, TIMP1, SPP1, SFRP4, INHBA, THBS2 and SPARC was greater in tumors than the $95^{th}$ percentile of the non-malignant range for ≥90% of cases (FIG. 3). For the remainder of genes, the expression in tumors was greater than the $95^{th}$ percentile in >50% of samples. Each tumor over-expressed at least seven genes greater than the $95^{th}$ percentile indicating that combinations of markers will lead to comprehensive coverage of all gastric tumors.

Example 3: Validation of Array Data Using qPCR

Array data was validated using quantitative, real-time PCR (qPCR) on the tumor and non-malignant samples with probes for 24 genes. Of all 24 genes studied, 20 showed a strong correlation between the two techniques. Four of these analyses are show in FIGS. 4*a*-4*d*, which depict graphs of the relative expression for the 4 selected cancer markers detected using array and qPCR methods. For each graph in FIG. 4, the horizontal axis represents the array log2 fold change in gene expression, and the vertical axis represents the qPCR log2 fold change in gene expression. We found that there was a strong correlation between the two methods, as indicated by the co-variant relationship between the methods. The strong correlation indicates that both microarray fold change analysis and qPCR are suitable methods for detecting changes in the expression of gastric cancer marker genes and therefore can be used as an accurate, sensitive screening method. It can also be appreciated from FIGS. 4*a*-4*d* that qPCR can be more sensitive at detecting changes in expression than are array methods. Thus, in situations in which early detection is especially desirable, qPCR may be especially useful.

Figure 5A:
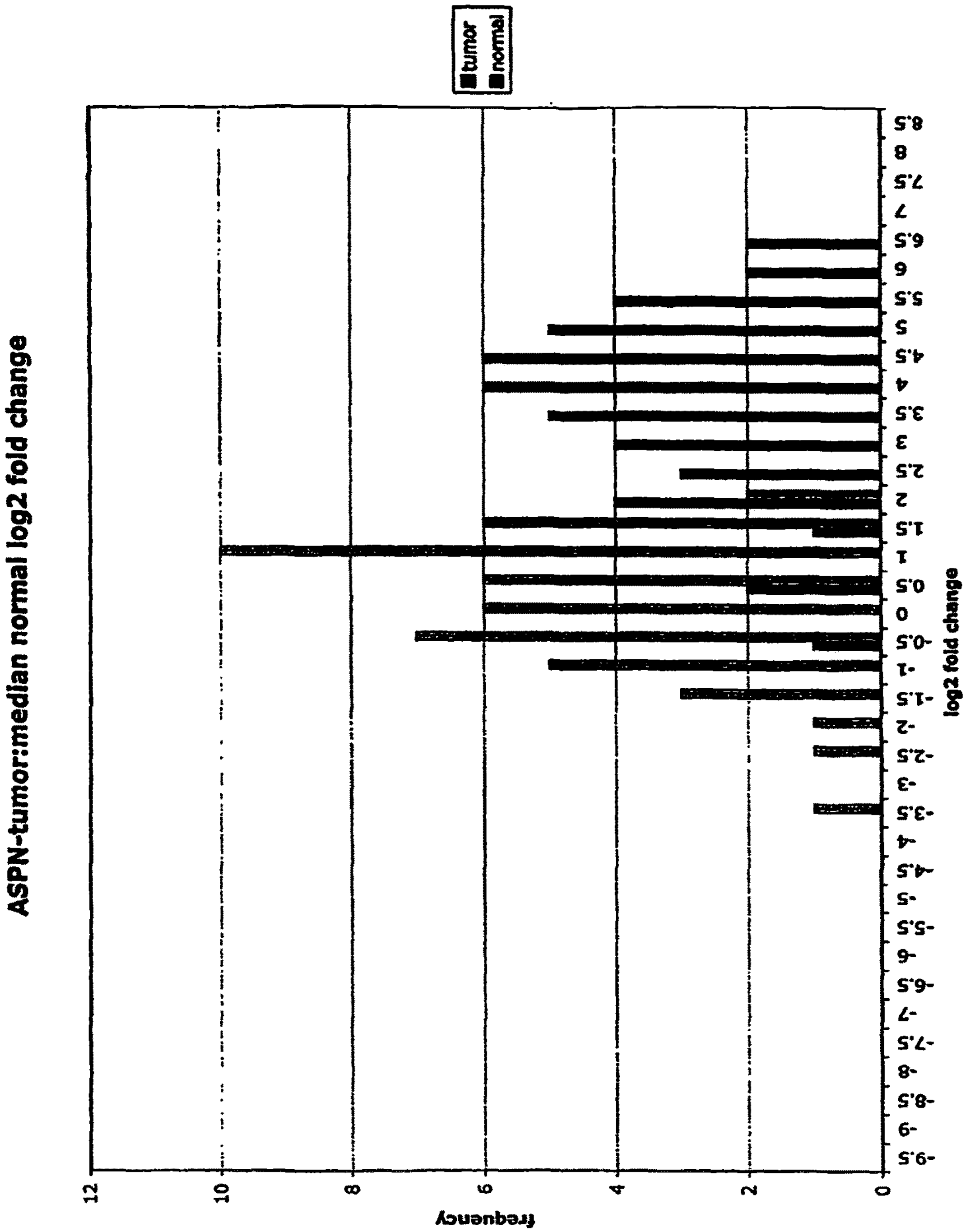
FIGS. 5*a*-5*w* depict histograms showing the relative frequency vs. log2 fold change data obtained from quantitative PCR studies of various tumor markers.
Figure 5B:
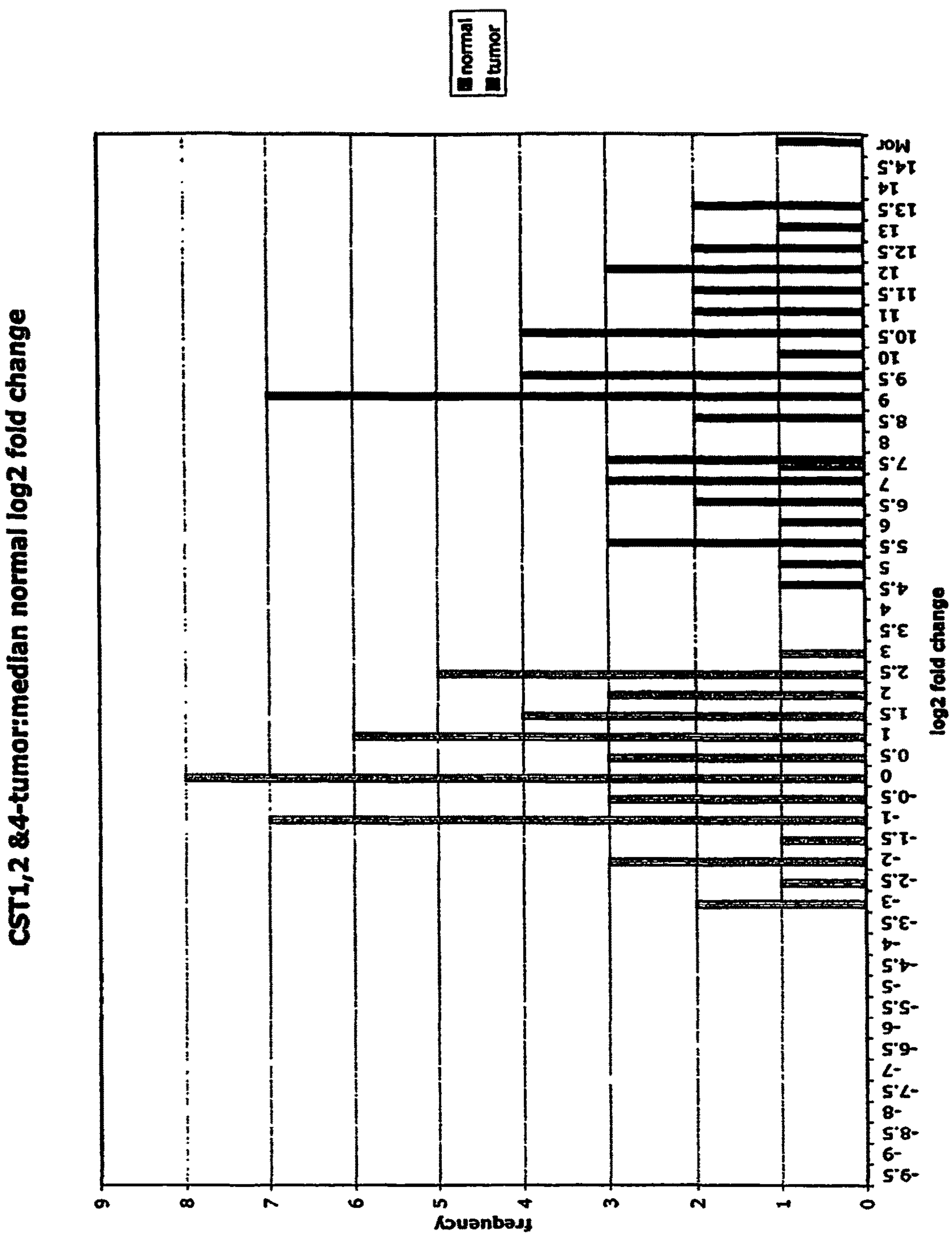
FIG. 5*b*: CST1,2 & 4.
Figure 5C:
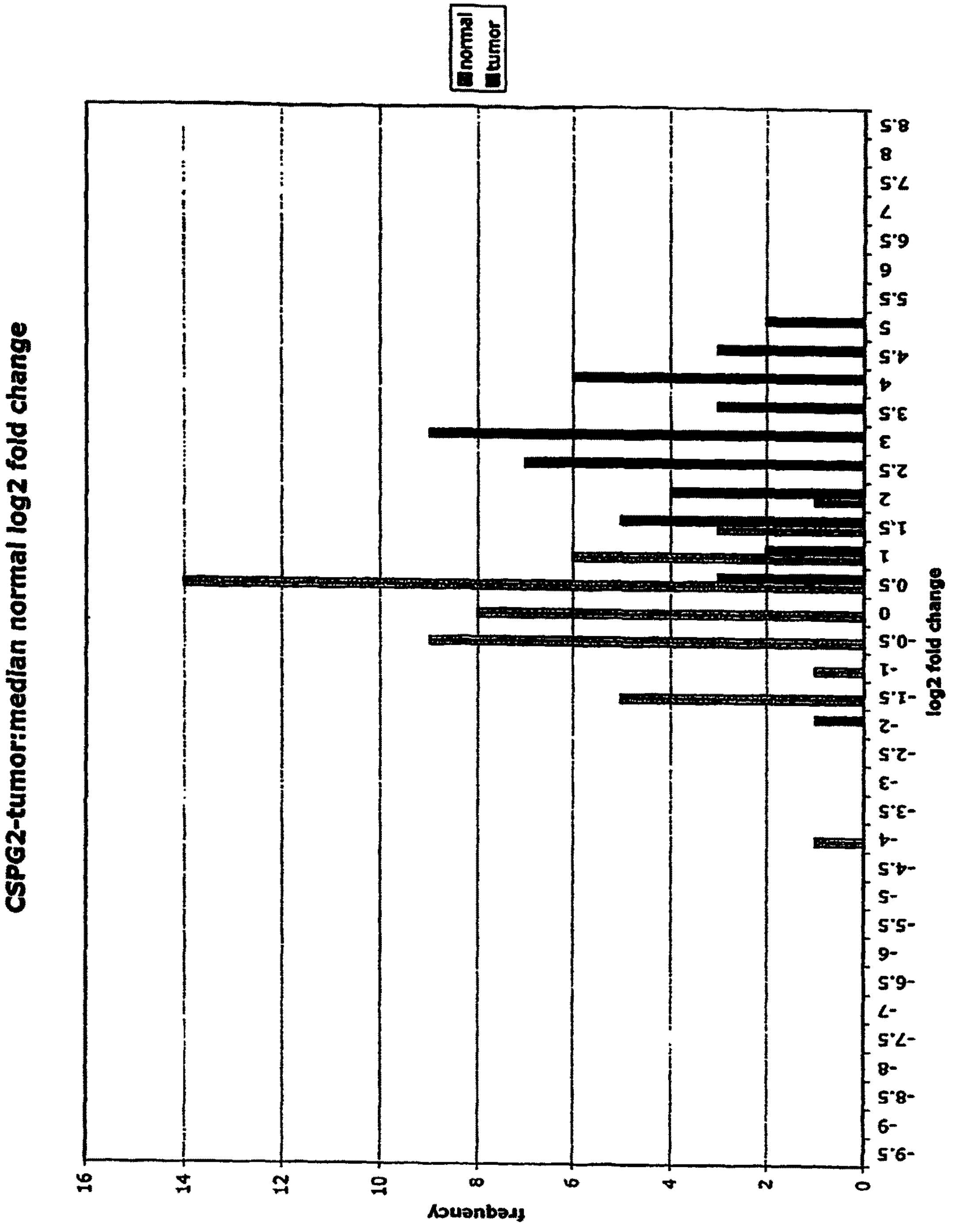
FIG. 5*c*: CSPG2.
Figure 5D:
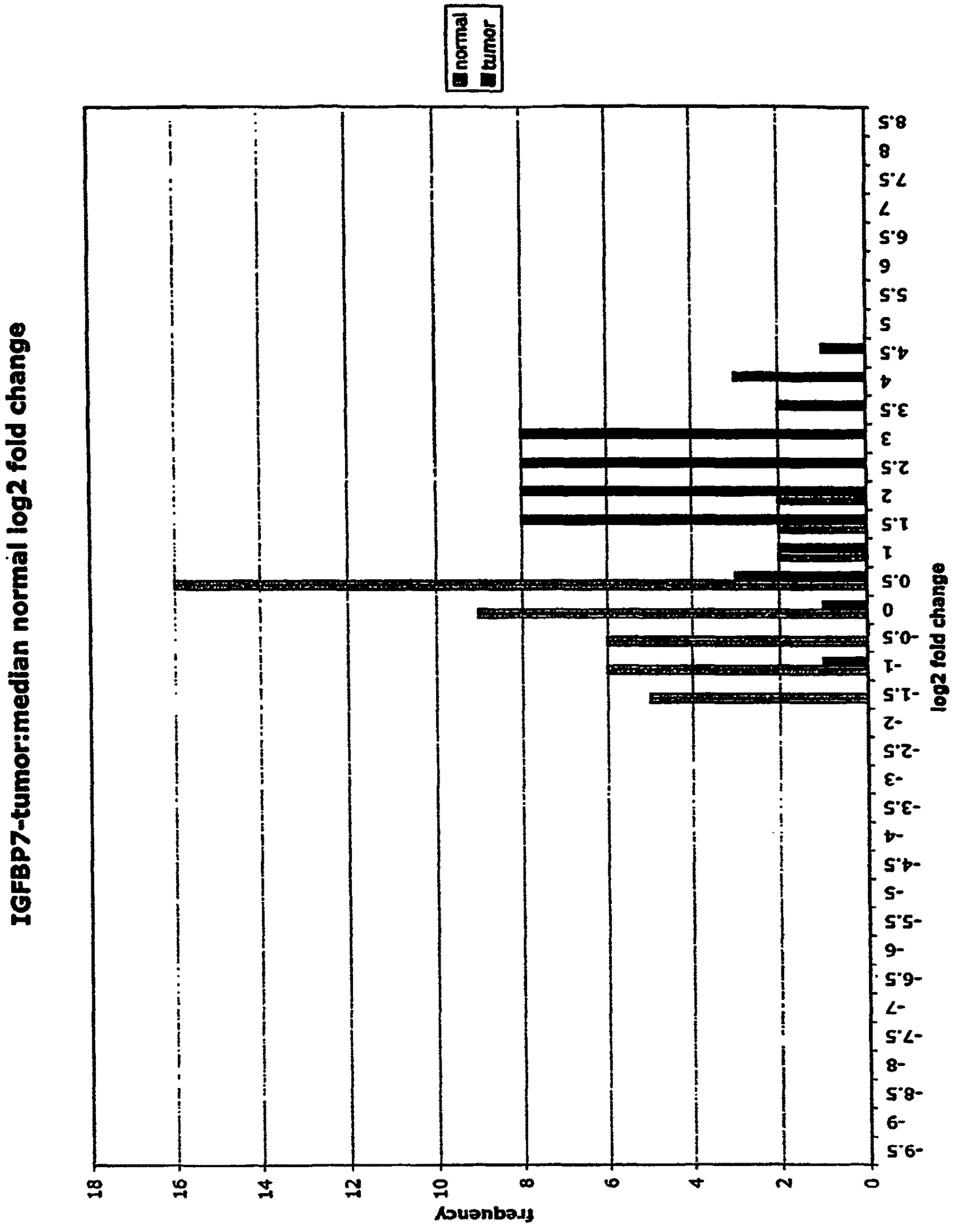
FIG. 5*d*: IGFBP7.
Figure 5E:
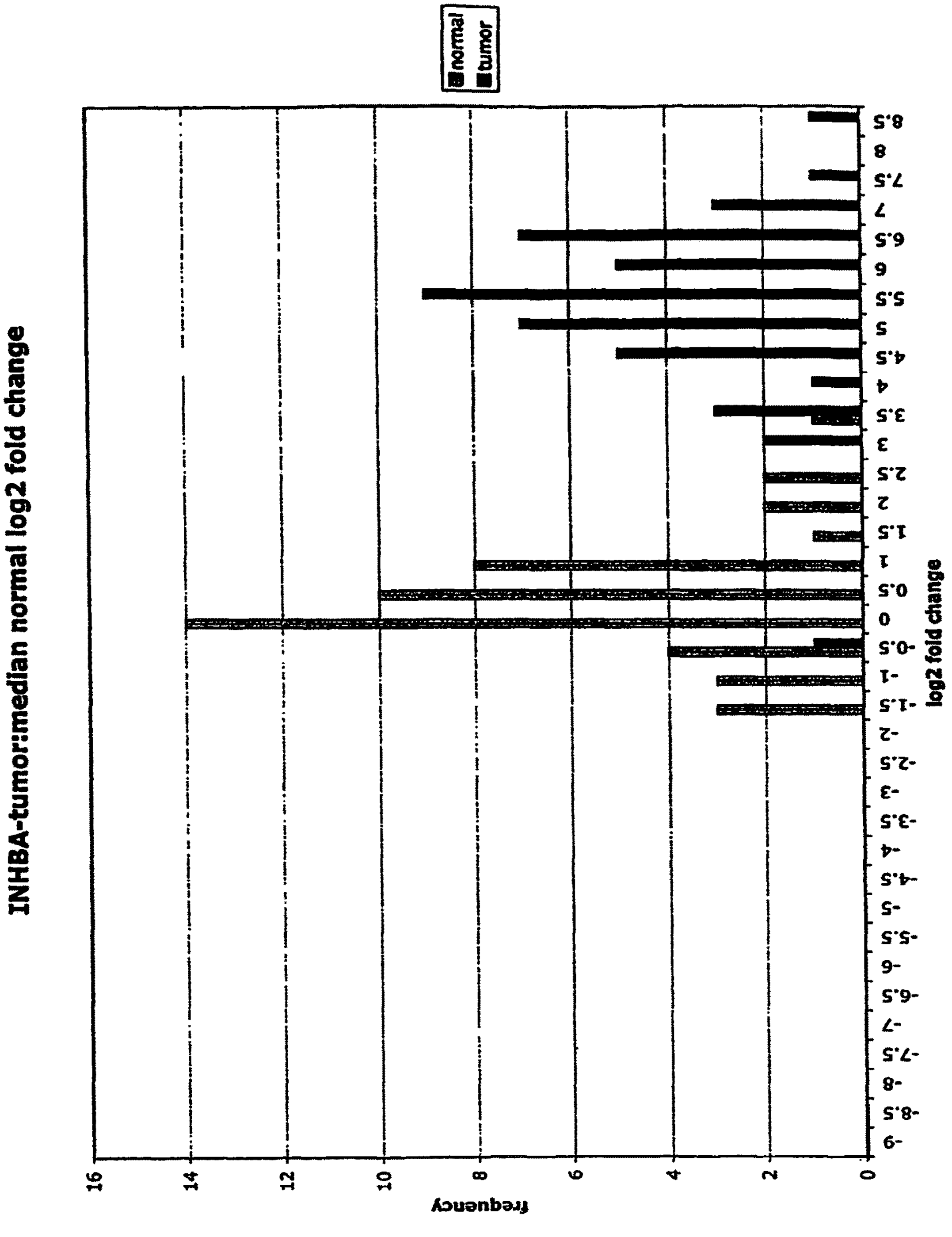
FIG. 5*e*: INHBA.
Figure 5F:
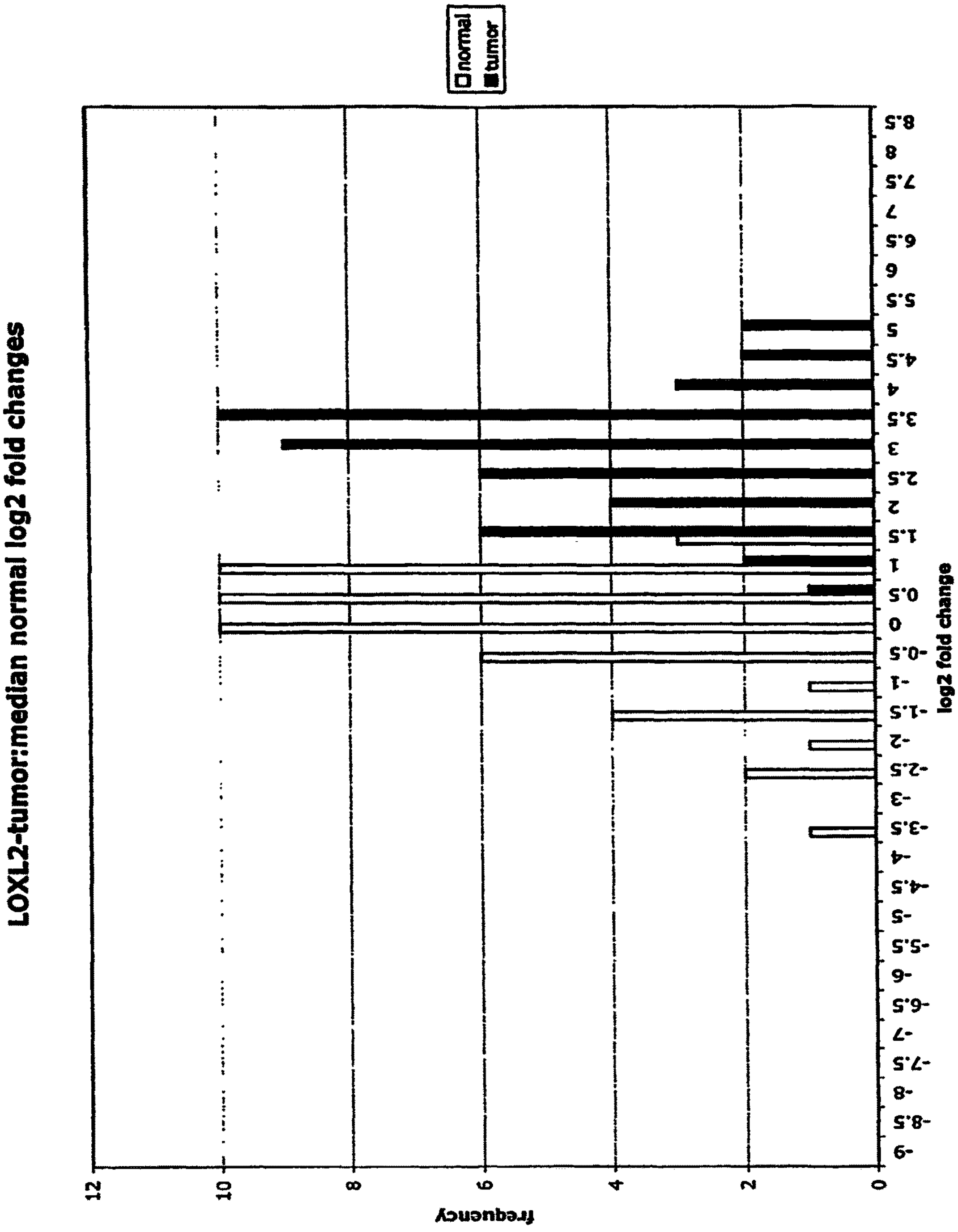
FIG. 5*f*: LOXL2.
Figure 5G:
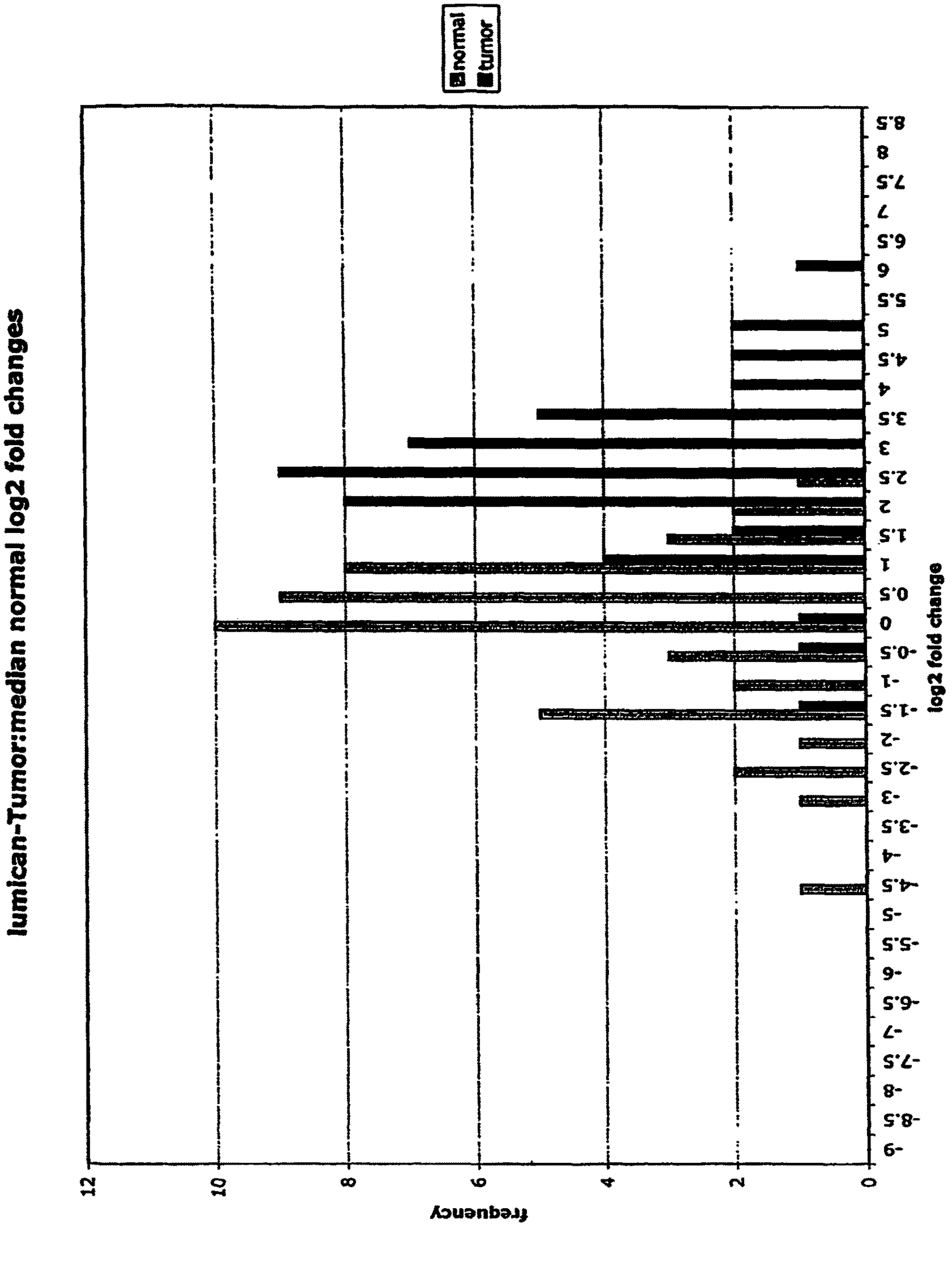
FIG. 5*g*: LUM.
Figure 5H:
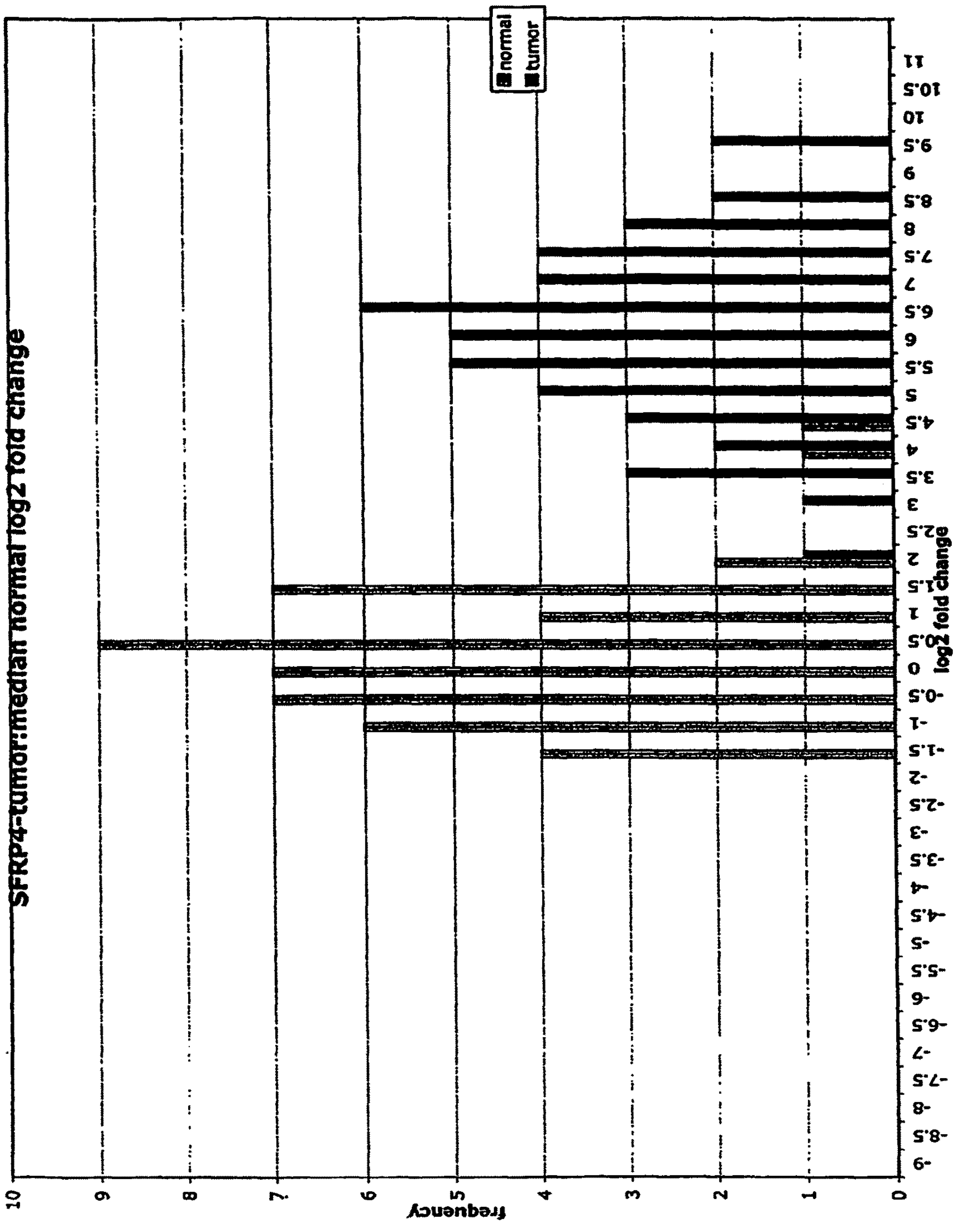
FIG. 5*h*: SFRP4.
Figure 5I:
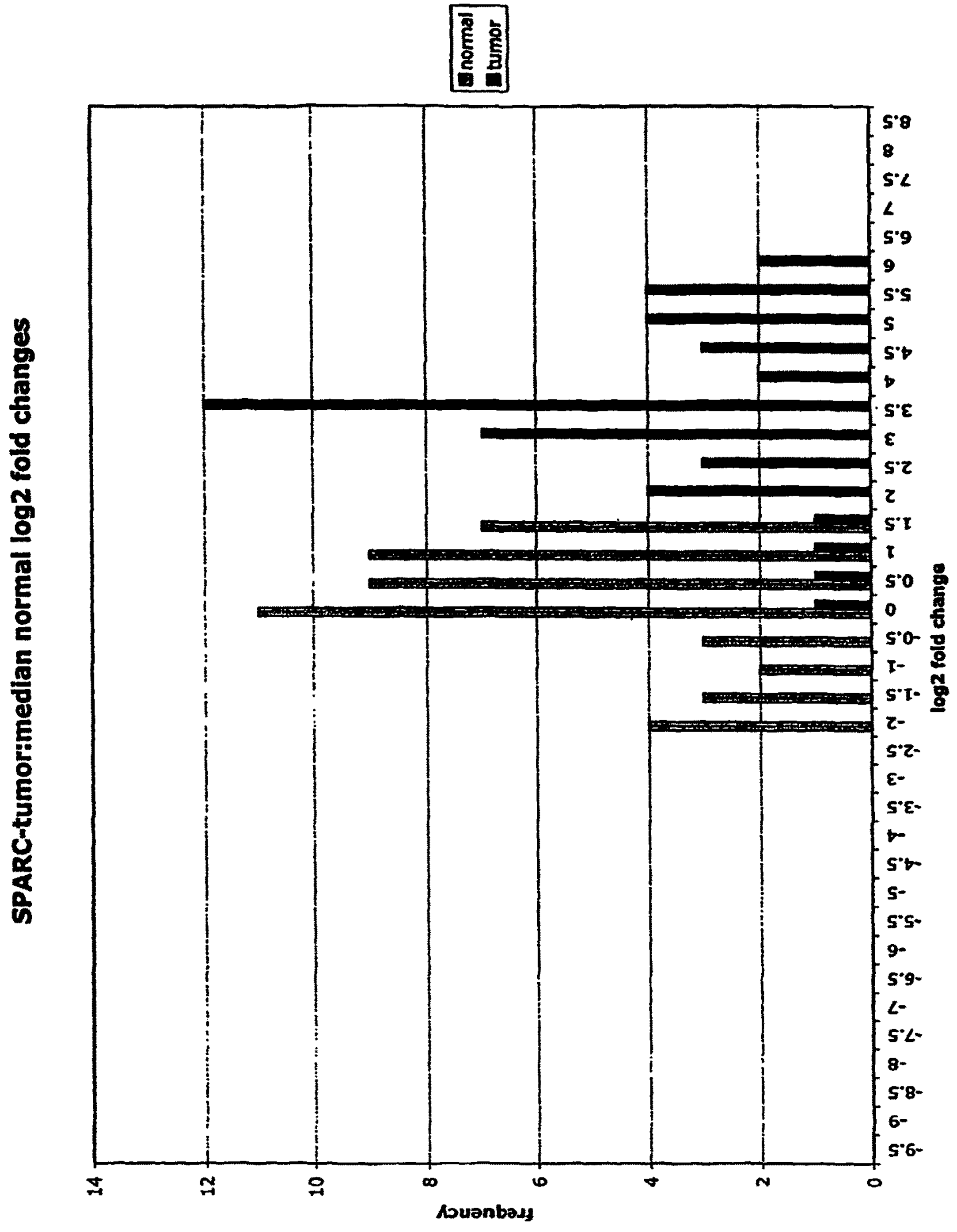
FIG. 5*i*: SPARC.
Figure 5J:
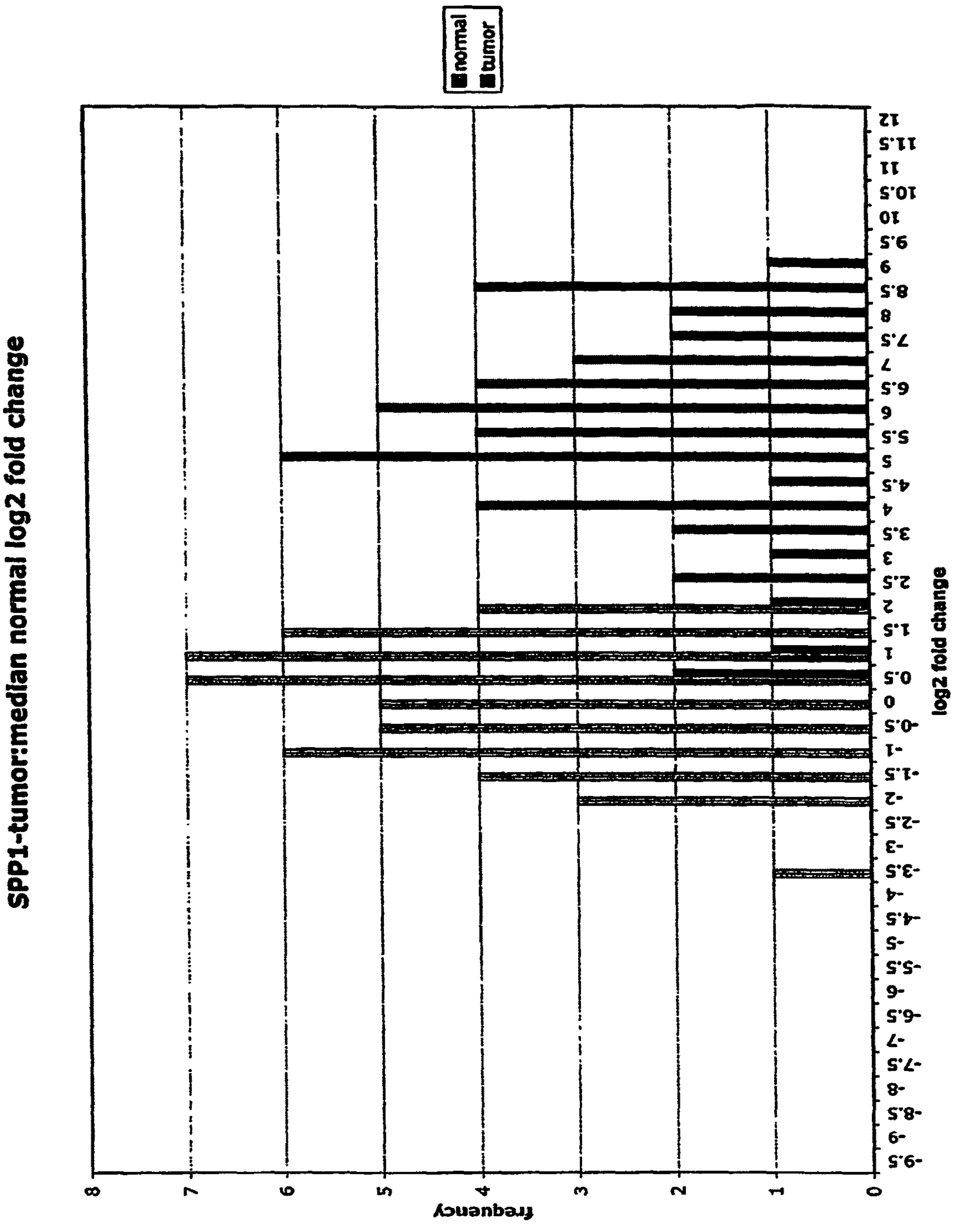
FIG. 5*j*: SPP1.
Figure 5K:
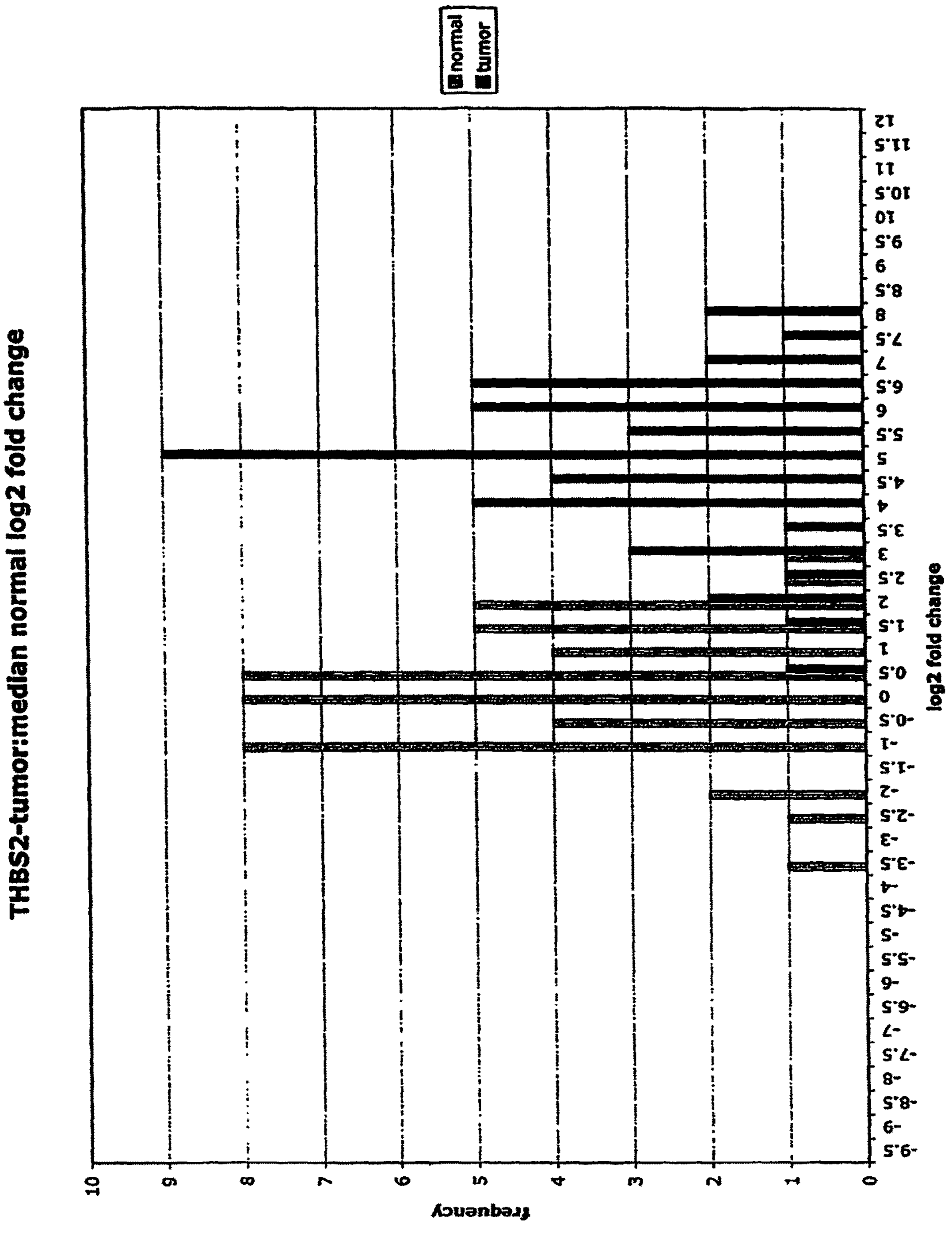
FIG. 5*k*: THBS2.
Figure 5:
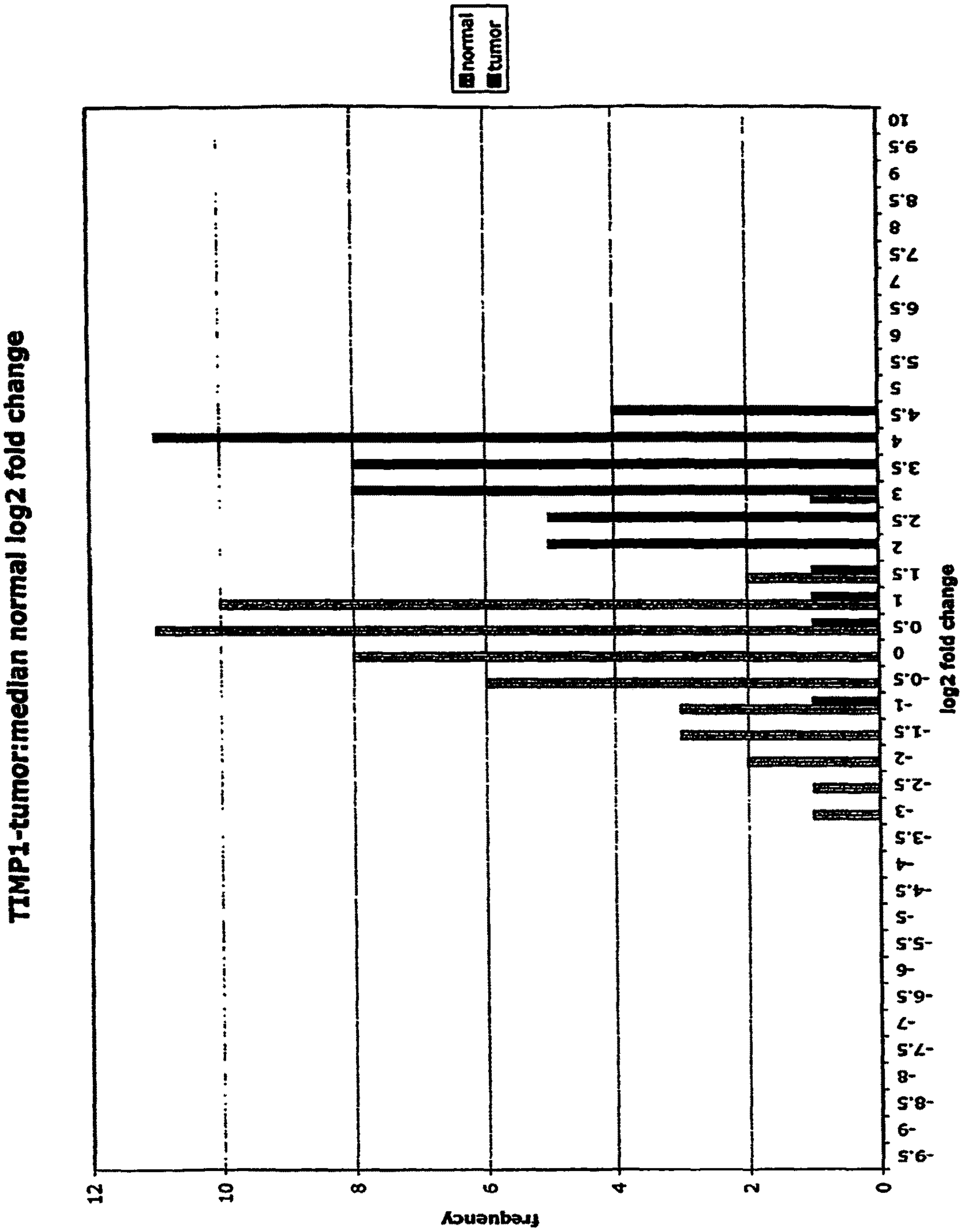
FIG. 5*l*: TIMP1.
FIG. 5*m*: adlican.
FIG. 5*n*: PRS11.
FIG. 5*o*: ASAH1.
FIG. 5*p*: SFRP2.
FIG. 5*q*: GGH.
FIG. 5*r*: MMP12.
FIG. 5*s*: KLK10.
FIG. 5*t*: LEPRE1.
FIG. 5*u*: TG.
FIG. 5*v*: EFEMP2
Figure 5M:
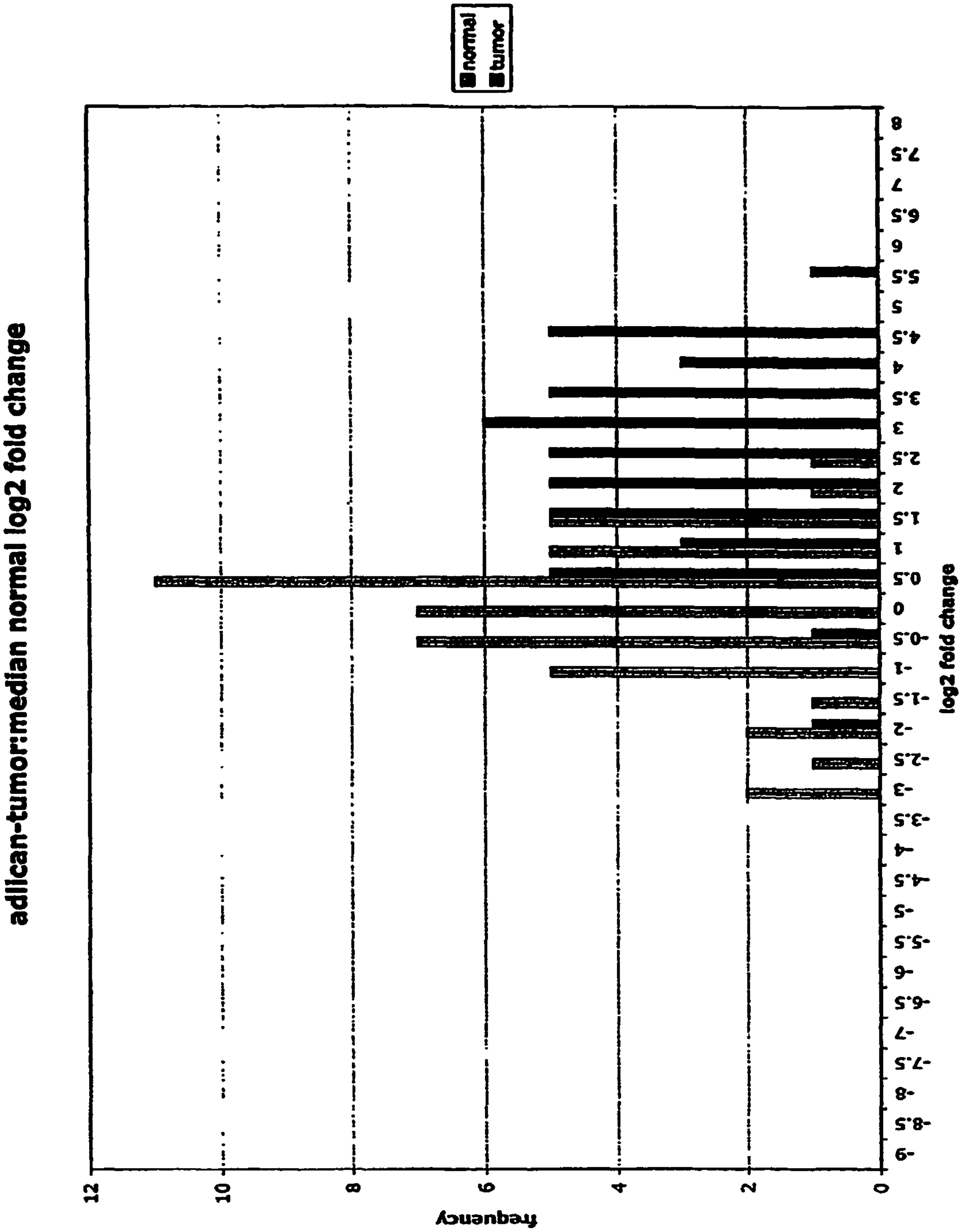
Figure 5N:
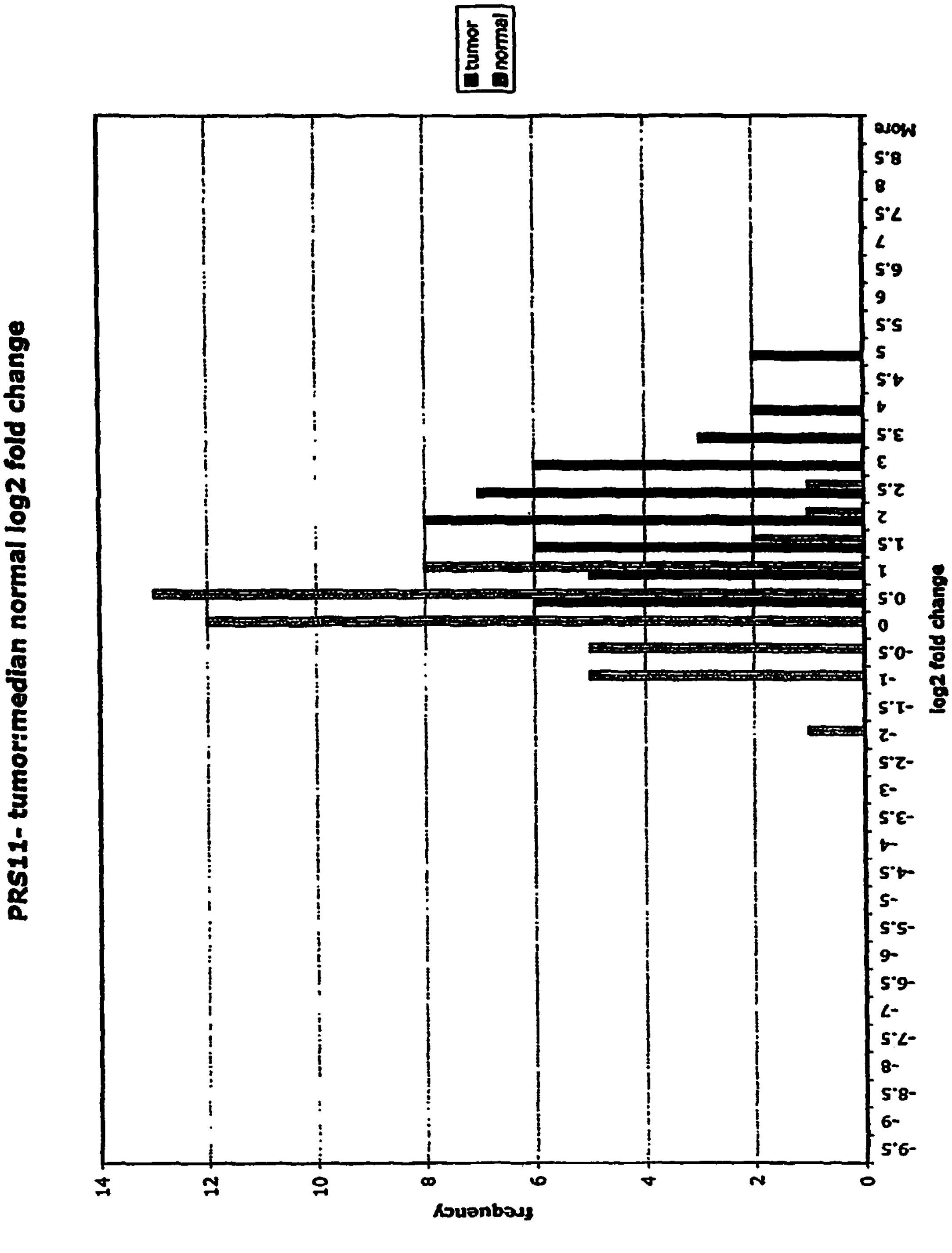
Figure 5O:
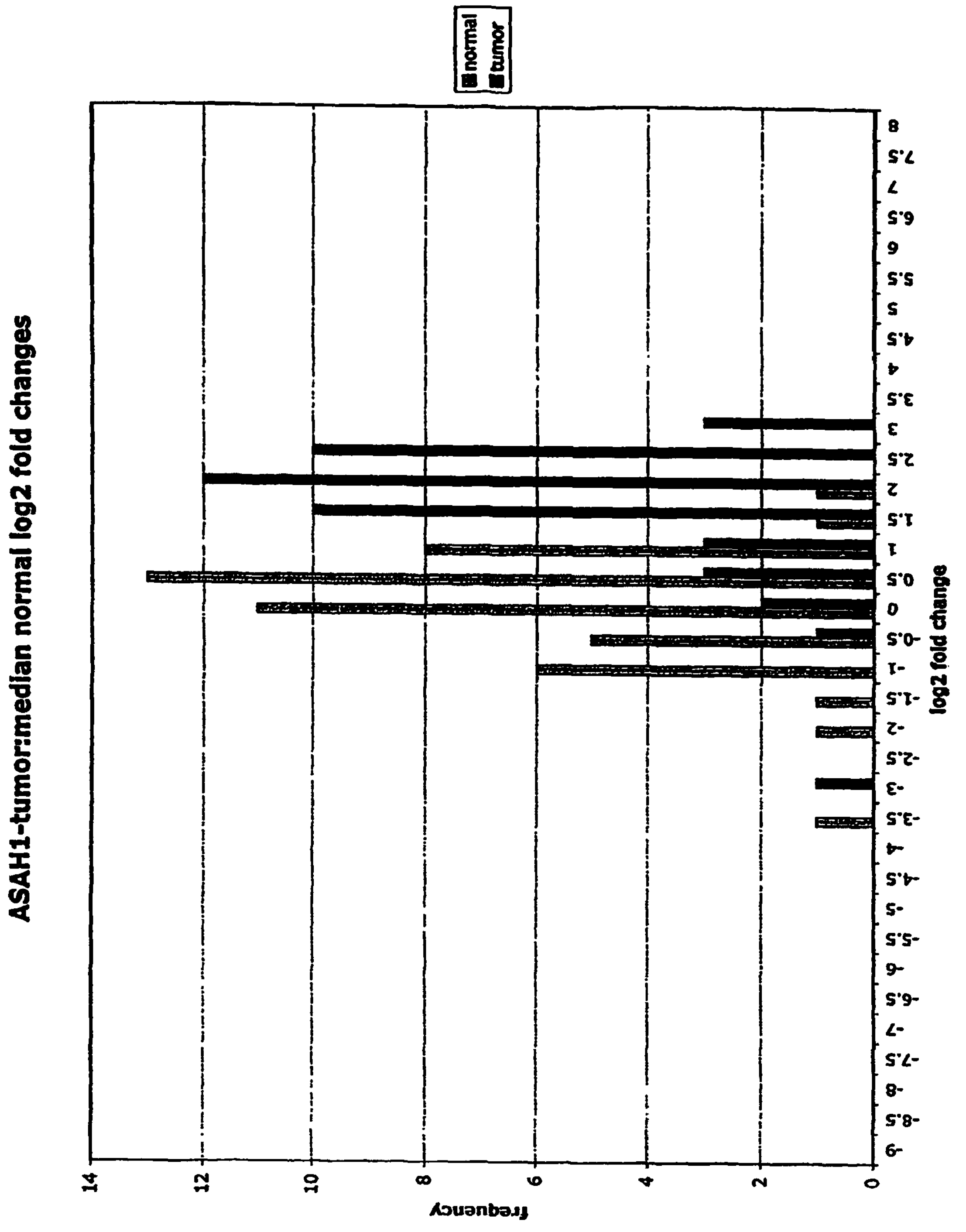
Figure 5P:
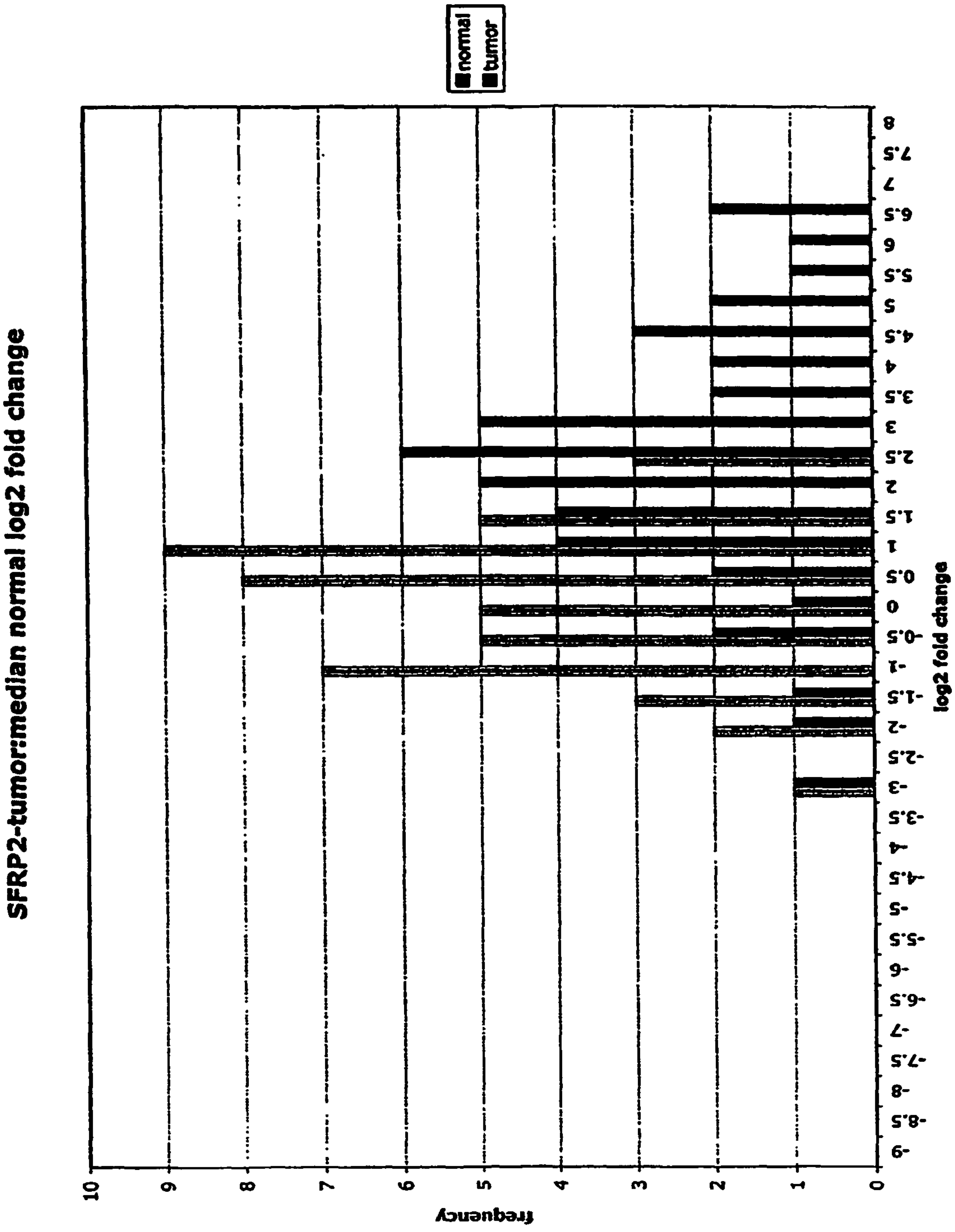
Figure 5Q:
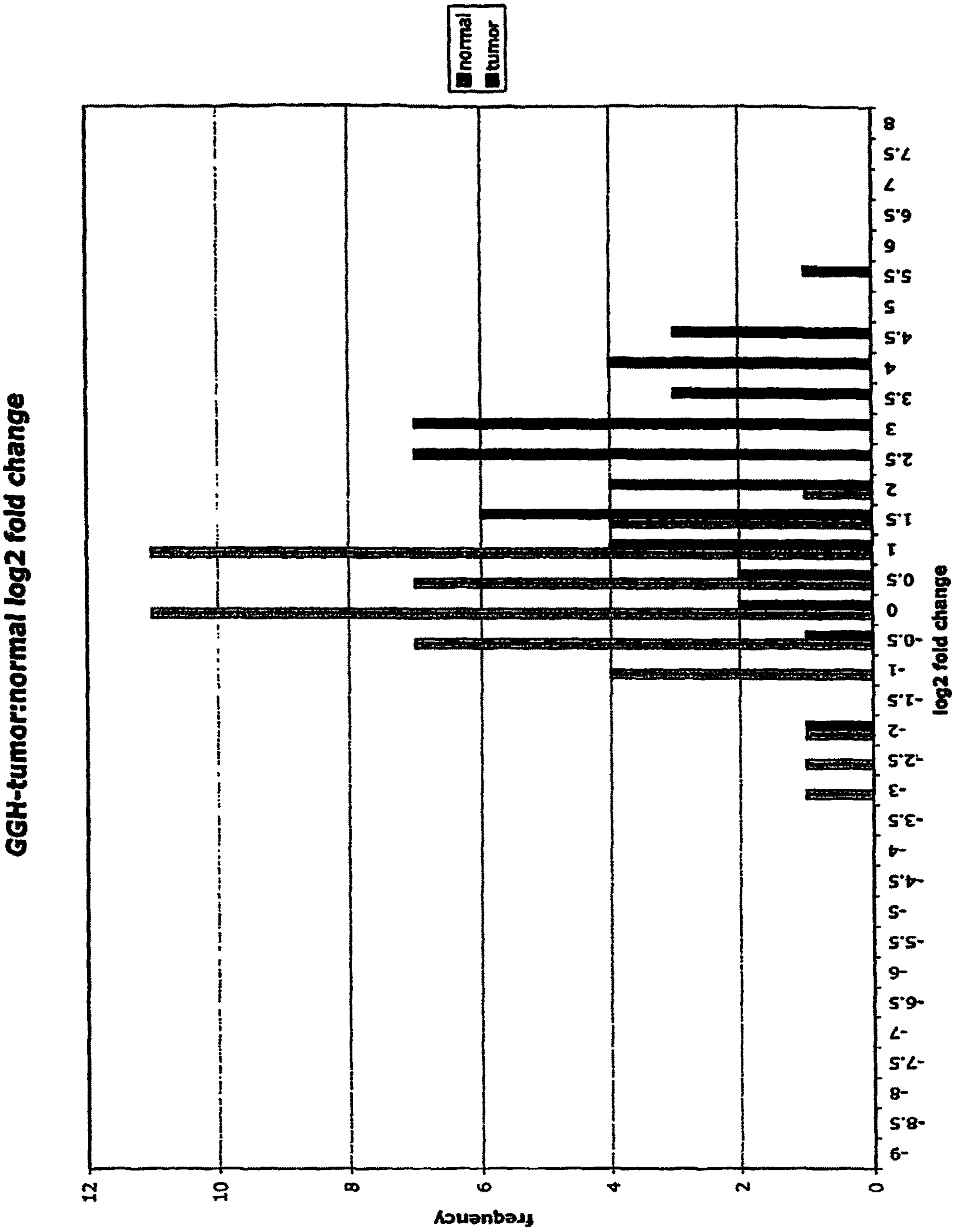
Figure 5R:
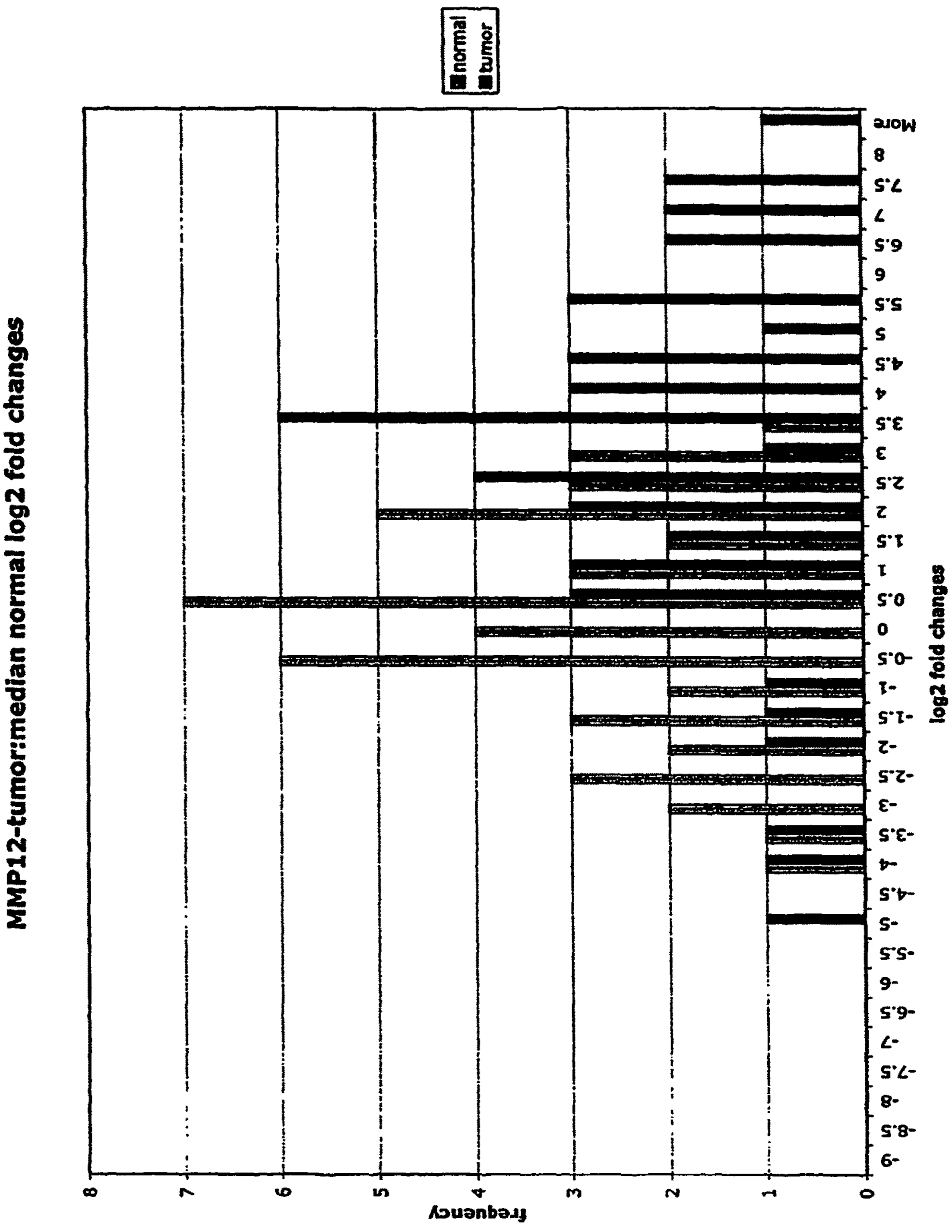
Figure 5S:
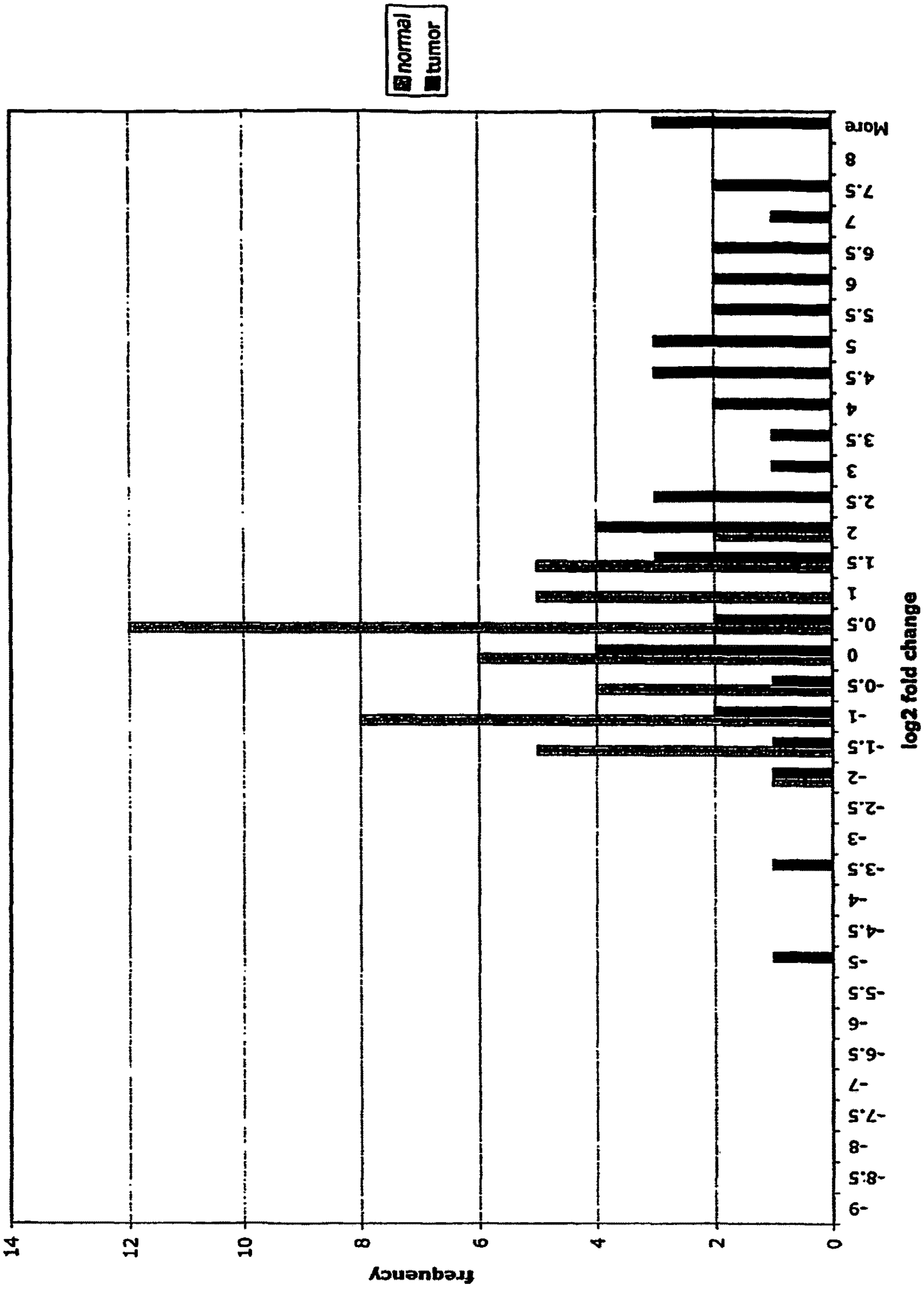
Figure 5T:
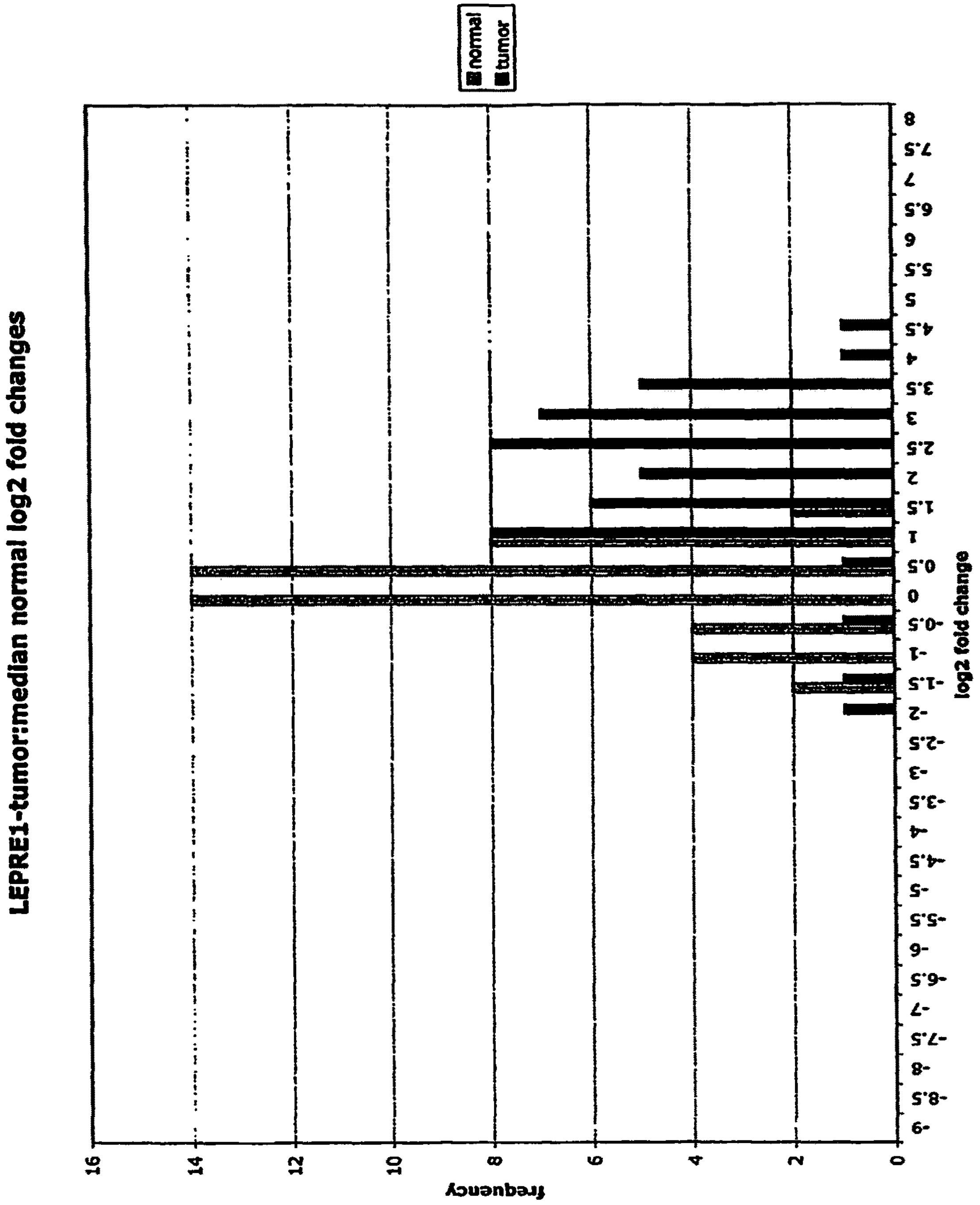
Figure 5U:
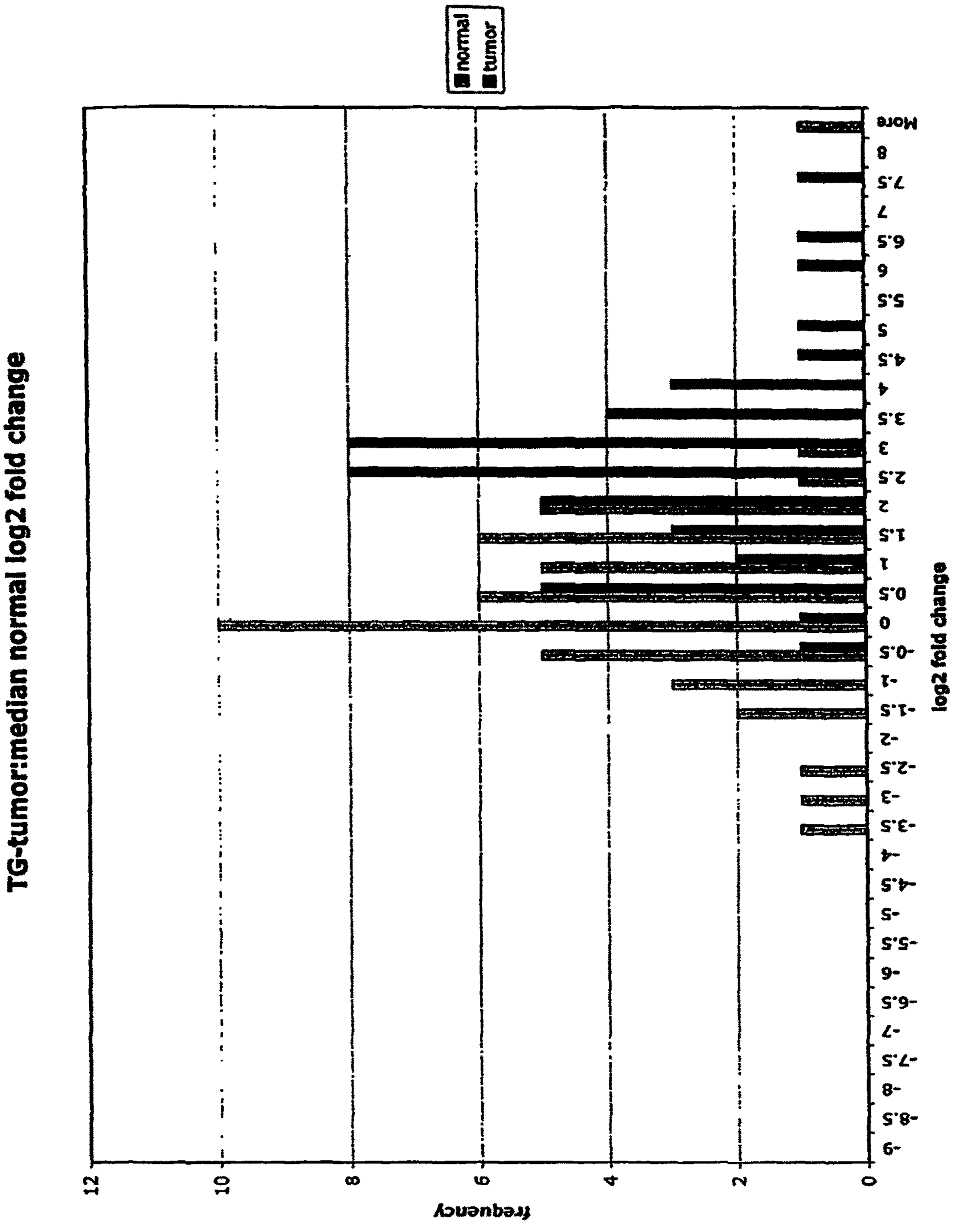
Figure 5V:
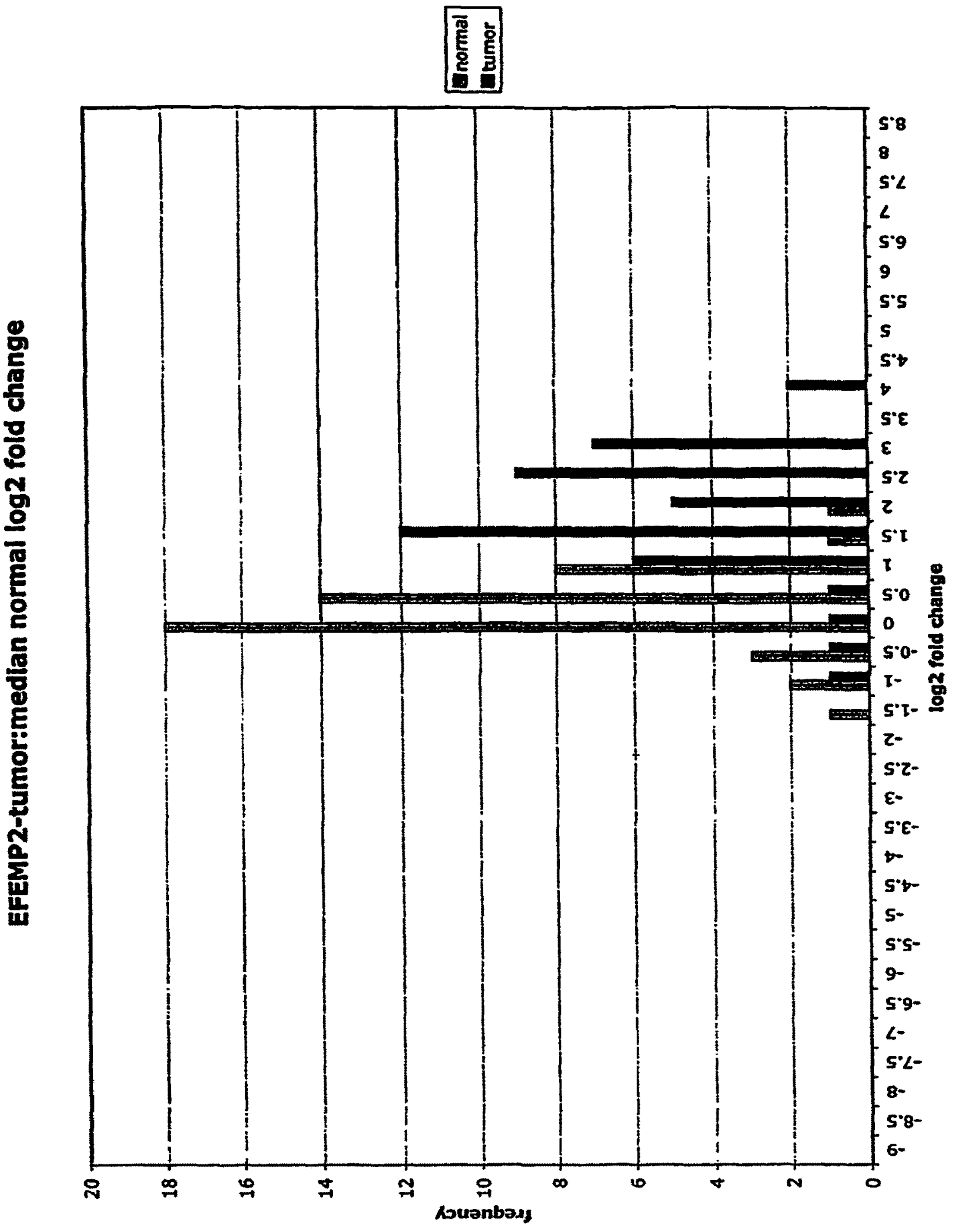
Figure 5W:
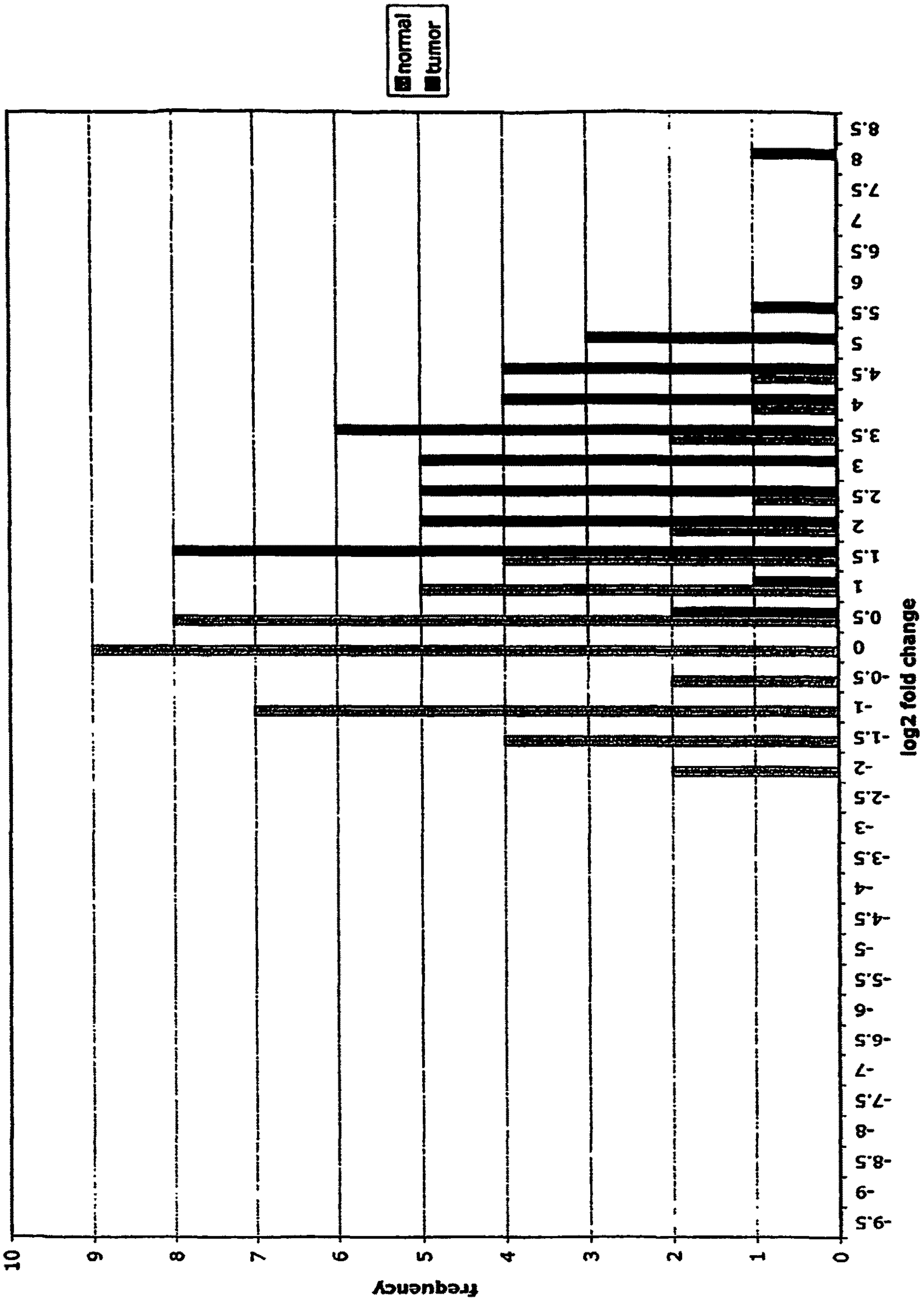

FIGS. 5*a*-5*w* depict histograms comparing frequency of observation of expression of each of a series of 23 genes (vertical axis) and the log2 fold change in expression for that gene (horizontal axis), for both normal tissue (open bars) and tumor tissues (black bars). We found surprisingly that for each of these 23 genes, there was substantial separation in the frequency distributions between normal and tumor tissue, as reflected by the low degree of overlap between the frequency distribution curves. For example, FIG. 5*b* depicts the results for CST 1, 2, 4, for which there was only one normal sample observed to have an expression level in the tumor range. In other cases (e.g., FIG. 5*n*; for PRS11) each frequency distribution curve was relatively narrow and there was a degree of overlap. However, even for this marker, the median log2 fold change showed a substantial separation of the amount of gene expression. In other cases, (e.g., FIG. 5*a*; ASPN), although there was some overlap, there was a clear separation of the median log2 fold expression between normal and tumor samples.

Figure 6:
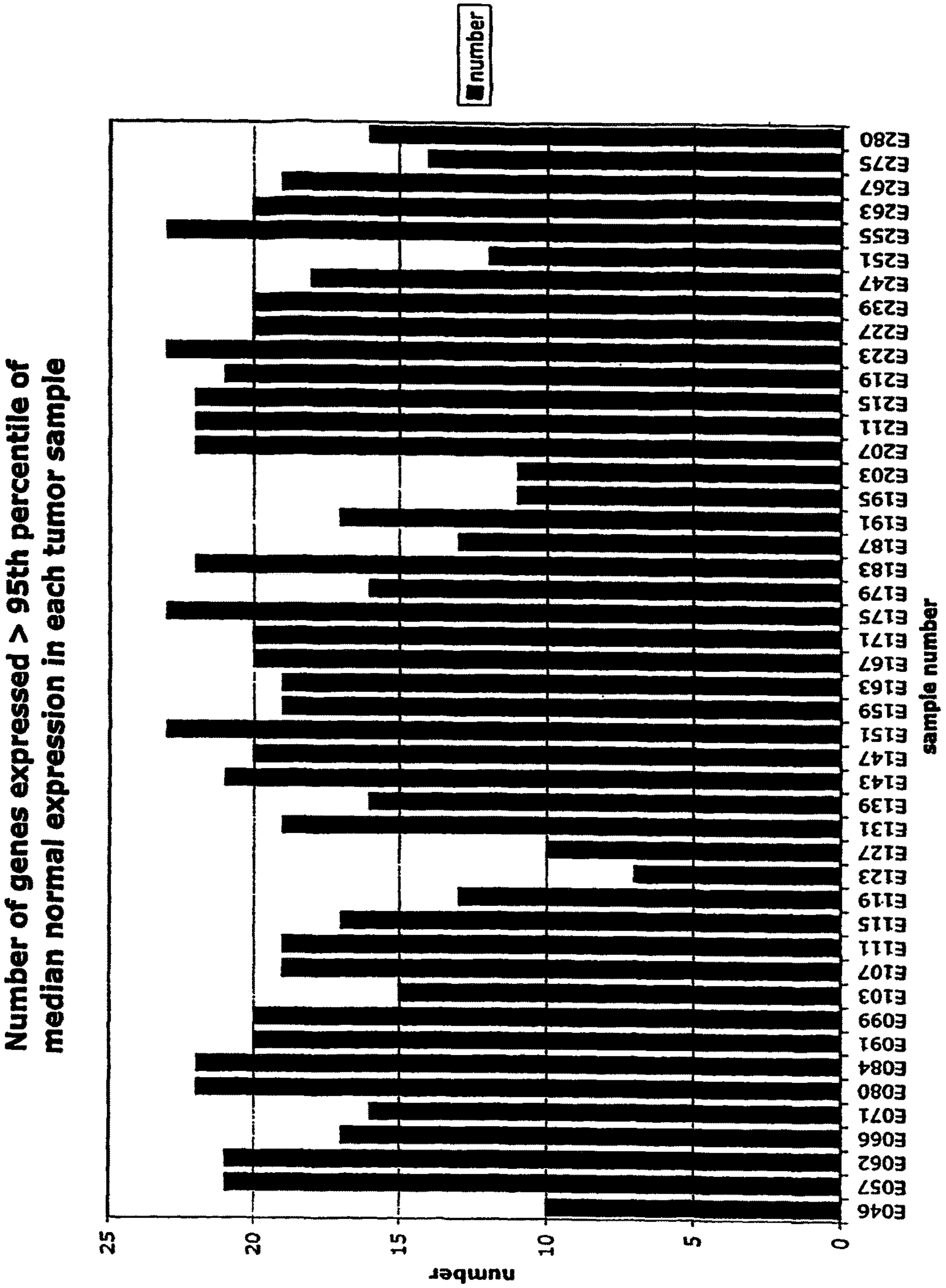
FIG. 6 is a histogram showing the number of markers with a higher expression than the $95^{th}$ percentile of the median normal expression. Results are based on qPCR data and are shown separately for each tumor sample.

FIG. 6 depicts a histogram of the number of genes exhibiting a significantly increased expression ("over-expression") in tumor samples compared to normal samples (vertical axis) and the individual samples tested. In each case, the tumor sample exhibited multiple genes with elevated expression levels. The lowest number of genes having increased expression was 7, found in sample E123. This finding indicates that, in situations in which multiple genes are over-expressed relative to normal tissue, the reliability of cancer detection can be very high, making diagnosis of cancer more certain. However, in some cases, elevation of expression of a single marker gene is sufficient to lead to the diagnosis of cancer.

Our previous comparison with the serum marker most frequently used currently for detection of gastric cancer, CEA, was based on difference in intensity rank of array data between tumors and normal samples. This comparison was verified using qPCR data for the markers and CEA.

Figure 7B:
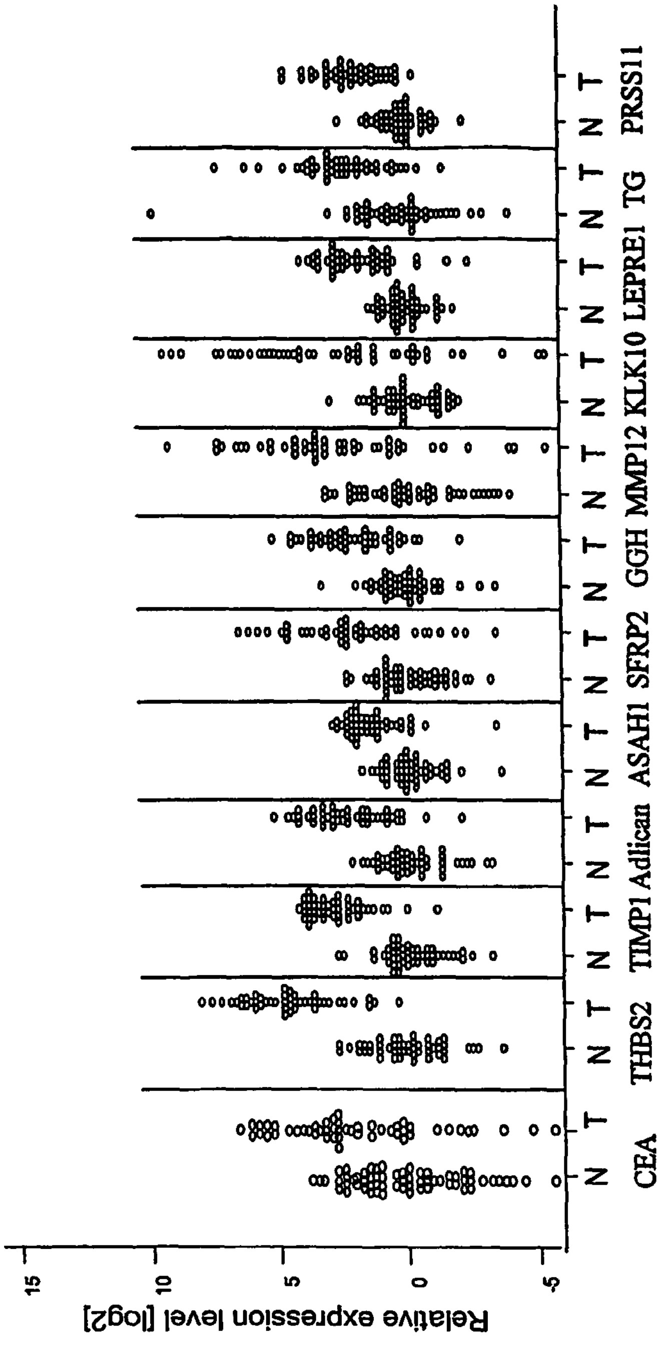
Figure 7C:
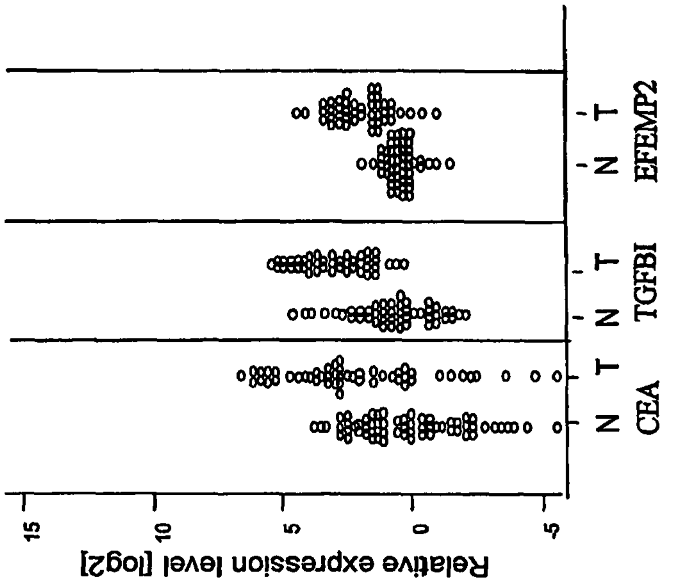
Figure 9B:
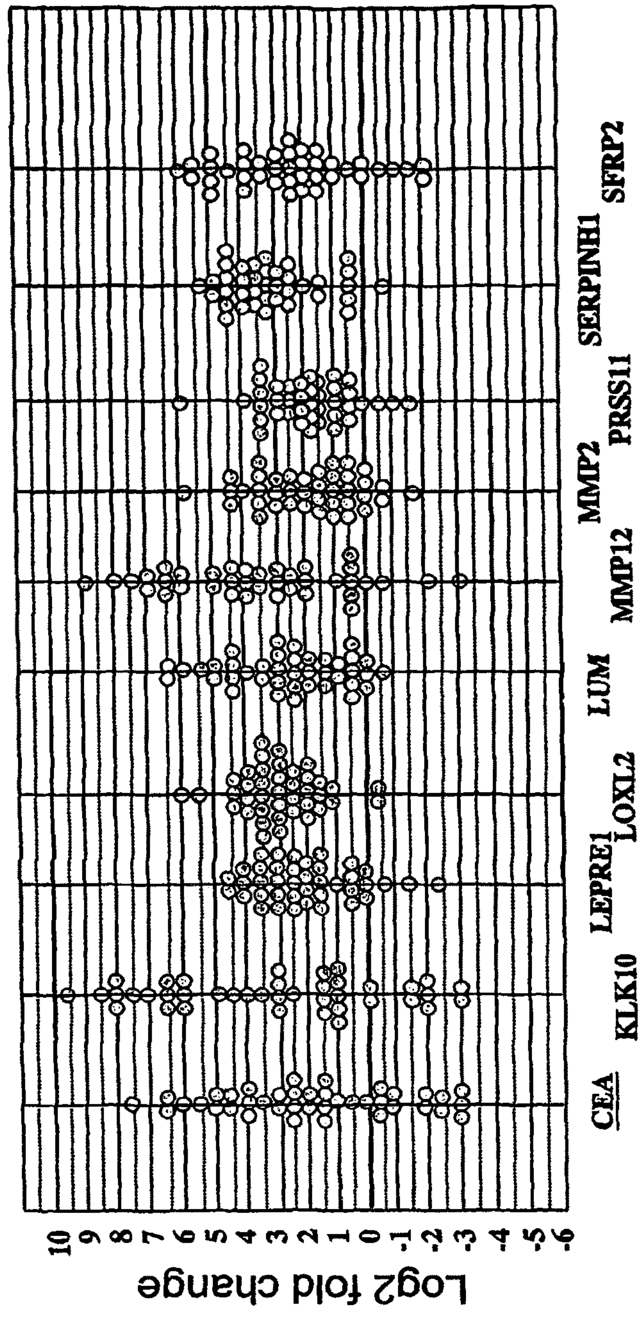
Figure 9C:
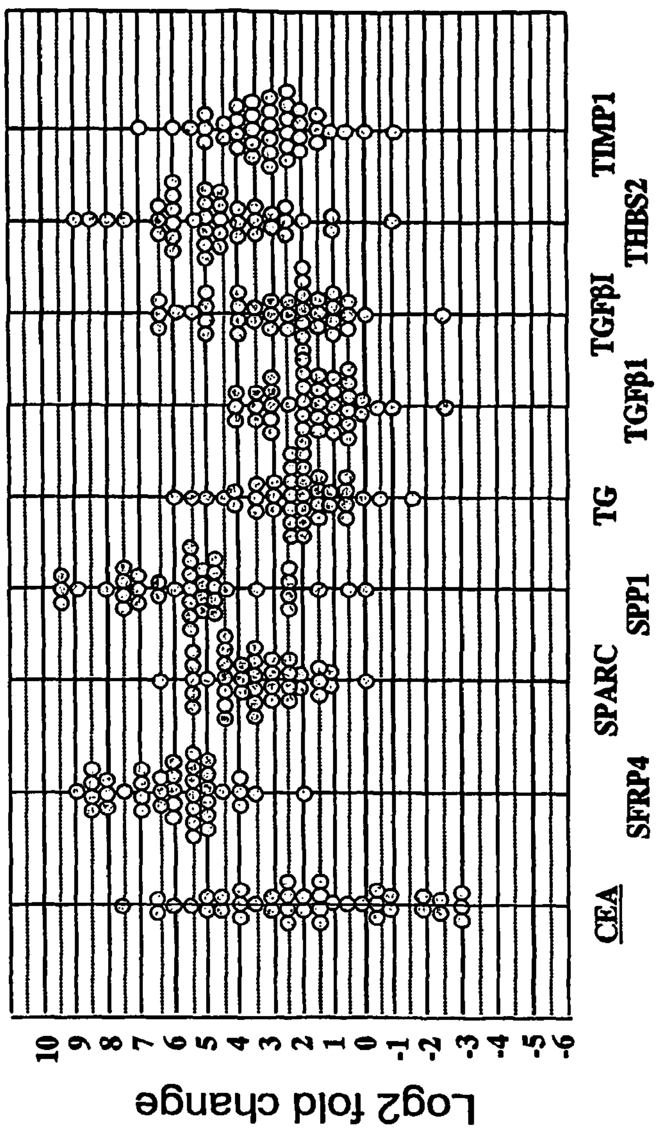
Figure 9D:
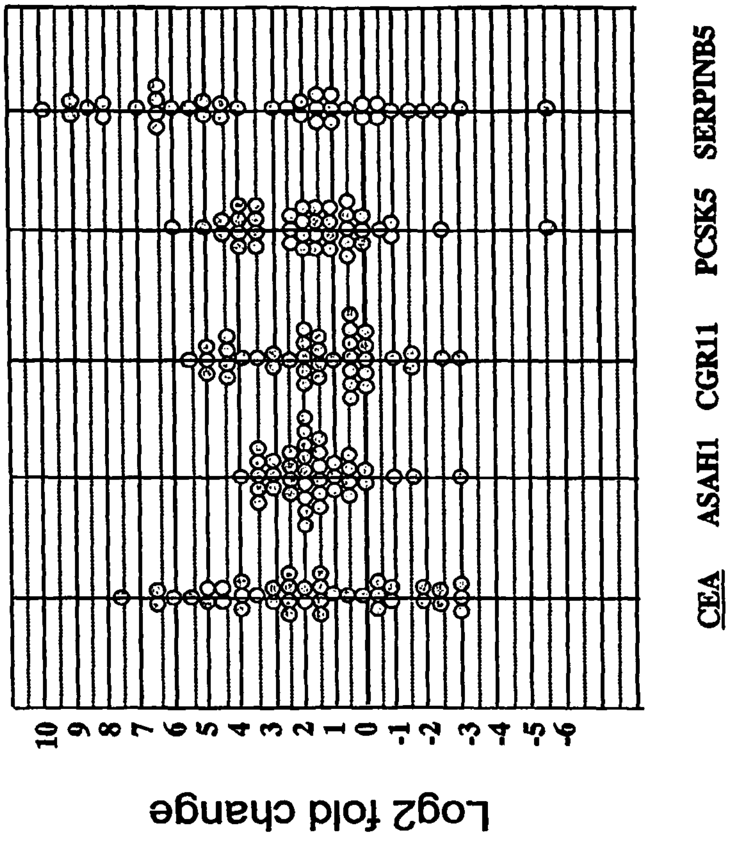

FIGS. 7*a*-7*c* depict graphs of the relative log2 expression (compared to a reference RNA preparation) of markers in individual tumor samples and non-malignant samples compared to the expression of the gene for the tumor marker, CEA. CEA is the serum marker currently most used to monitor progression of gastric cancer. The zero point is defined to be the median normal expression for each marker. It can be seen that there is extensive overlap between the expression of the CEA gene (CEACAM5) in tumor samples and normal samples. This overlap is markedly less in the gastric cancer markers ASPN, CSPG2, CST1,2,4, IGFBP7, INHBA, LOXL2, LUM, SFRP4, SPARC, SPP1, THBS2, TIMP1, adlican, LEPRE1, and EFEMP2. For the other markers in FIGS. 7*b*-7*c*, ASAH1, SFRP2, GGH, MMP12, KLK10, TG, PRSS11 and TGFBI, the overlap between the tumor expression range and the non-malignant tissue expression range is greater than the overlap for the above markers, but still less than that of CEA, indicating that all of the herein described new markers are quantitatively better than CEA, and therefore can provide more reliable diagnosis.

To minimize effects of variable tissue handling, tumor: normal (non-malignant) fold changes were calculated using qPCR data from tumor and non-malignant tissue samples derived from the same patient. Such paired analysis corrects for differences in background levels of gene expression in different individuals and minimizes the effects of tissue handling on RNA quality. For example, if the resected stomach was at room temperature for an hour, the transcripts from the normal and tumor samples will be degraded to the same extent.

FIG. 8 summarizes the T:N expression levels determined by qPCR for the markers, but used paired data (i.e., tumor and non-malignant samples) from the same individual. FIG. 8 also includes expression data for six genes that were not included in FIG. 3. The additionally studied genes are MMP2, CGR11, TGFB1, PCSK5, SERPINB5, and SERPINH1. Identifying information and probes are shown in FIGS. 1 and 2. FIG. 8 shows the median T:N fold change and the maximum T:N fold change for 29 gastric cancer markers in these 40 patients with "paired" samples. 27 of the 29 markers have a median T:N difference greater than or equal to the prior art marker, CEA. 29/29 of the markers have a higher percentage of paired samples in which the expression in the tumor sample exceeds the expression in the normal sample.

FIGS. 9*a*-9*d* depict scatter dot plots of data from tumor and normal tissue from the same individuals. Each point represents the fold-change, within patient, in expression of the markers in tumor tissue relative to the expression in non-malignant tissue. All of the markers studied have better discrimination of tumor from non-tumor tissue than CEA. Three markers, CST1,2,4, ASPN and SFRP4 showed 100% discrimination between the paired tumor and normal samples. That is, for those markers, every tumor tissue had greater expression than did the corresponding non-tumor tissue from the same individual. In many other markers, for example, Adlican, CSPG2, EFEMP2, IGFBP7, INHBA, LOXL2, LUM, SERPINH1, SPARC, SPP1, TGFbI, THBS2 and TIMP1, each had only 2 or 3 individual points for which tumor tissue expression was less than that of the non-tumor tissue. Thus, for those markers, the likelihood that any one pair of tumor and non-tumor tissue would produce a false negative is relatively low (e.g., 3 of 40 or 7.5%; 2 of 40 or 5%, 1 of 40 or 2.5%). Thus, even if the other markers listed immediately above were used, use of multiple samples from an individual patient would produce reliable diagnostic information.

The gene sequences of these markers, and the location of the primers and probes used to detect them, are shown herein above.

To determine if over-expression of the marker genes is independent of the stage of the gastric tumors, the paired T:N log2 fold changes were plotted against the tumor stage (FIGS. 10*a*-10*ad*). No stage dependency of expression on tumor stage was observed for 26 of the markers listed in FIG. 8. These markers were similarly over-expressed in early stage as well as late stage tumors. However, KLK10 showed more consistent over-expression in stage 1 and stage 2 tumors, and PCSK5 and SERPINB5 showed more consistent over-expression in stage 4 tumors. KLK10, PCSK5 and SERPINB5 therefore can be used in determining the stage of gastric tumors.

In a similar analysis, paired T:N log2 fold changes were plotted against the Lauren classification of the tumor (either diffuse type or intestinal type). FIGS. 11*a*-11*ad* show that each of the 29 GTMs discriminated between tumor and non-tumor tissue, regardless of whether the type of tumor was intestinal (I) or diffuse (D).

Example 4: Use of Multiple Markers

As described above, certain markers exhibit an ability to discriminate tumor from non-tumor tissue in 100% of the samples. Other markers, also described above, can be used in combination to achieve very high degrees of discrimination of tumor tissue from non-tumor tissue. FIG. 12 depicts a 3-dimensional plot of the expression of 3 markers, SERPINH1, CST1,2,4 and INHBA, expressed as log2 T:N fold changes for a series of gastric tumor samples and non-malignant gastric samples. There is complete separation between the two groups of samples.

The reliability of successful discrimination of tumor and non-tumor samples using marker combinations is further illustrated by a statistical analysis summarized in FIG. 13. This analysis compared the normal distributions of data generated using the qPCR gene expression from paired tumor and non-malignant samples, shows the effect of increasing the numbers of markers used to discriminate between tumor and non-malignant samples on test sensitivity (with a fixed specificity of 95%). Although few of the 29 markers (as shown in FIG. 8) have a sensitivity of greater than 90, 95, or 99% when used alone in this analysis, the combination of two or three markers enabled high sensitivity to be reached with large numbers of combinations. For example, 50 combinations of three markers would discriminate between tumor and non-malignant samples with a sensitivity of >99% and specificity of >95%.

Example 5: Detection of Gastric Tumor Marker Proteins

In yet further embodiments, GTM proteins can be detected as a basis for diagnosis. In certain situations, the concentration of mRNA in a particular sample, such as a sample containing no cells, it may be difficult to use either microarray or qPCR methods to detect elevations in gene expression. Thus, in certain embodiments, detection of GTM proteins can be accomplished using antibodies directed against either the entire protein, a fragment of the protein (peptide) or the protein core. Methods for detecting and quantifying expression of proteins and peptides are known in the art and can include methods relying on specific antibodies raised against the protein or peptide. Monoclonal antibodies and polyclonal antisera can be made using methods that are well known in the art and need not be described herein further.

To demonstrate that GTM proteins can be used to discriminate tumor from non-tumor tissue, commercial antibodies were obtained against SPARC (R&D Systems; cat # AF941), THBS2 (Santa Cruz Biotechnology Inc; cat # sc-7655), CSPG2 (Calbiochem; cat #428060) and IGFBP7 (R&D Systems; cat # AF1334). An additional polyclonal antibody was raised in rabbits (Alpha Diagnostic International Inc; San Antonio) against the cystatin SN peptide sequence 50-66 (C) FAISEYNKATKDDYYRR. SEQ ID NO: 108.

These antibodies were used in either immunohistochemistry or Western analysis of tumor and non-malignant gastric tissue. Each of these markers showed strong tumor:normal differences at the protein level. This confirmed that the over-expression observed at the RNA level for these genes also occurred at the protein level.

FIG. 14 shows a Western blot analyses of total protein extracted from two pairs of tumor and non-malignant tissues using antibodies against the proteins encoded by SPARC, CST1 (cystatin SN), IGFBP7 and THBS2. For each marker, the signal is significantly higher in the tumor samples than the non-malignant samples.

The antibody raised against cystatin SN detected three major bands, corresponding to molecular weights of approximately 34, 45 and 65 kDa respectively. The lowest molecular weight band is shown in FIG. 14. The protein species were larger than the control cystatin SN protein, suggesting that the protein produced by tumors has undergone post-translational modifications or multimerization. Regardless of the mechanism responsible for the differences in molecular weights of CST proteins, FIG. 14 demonstrated that CST expression was low in the non-tumor tissue, but was easily observed in blots of tumor-derived proteins.

FIG. 14 also showed that SPARC protein is expressed substantially to a greater degree in tumor tissue than in non-tumor tissue. The SPARC protein had gel mobility slower than the form of this protein that was detected in serum (FIG. 15), also indicating the occurrence of different post-translational modifications in proteins produced by malignant gastric cells. Regardless of the mechanism(s) responsible for any such modification, the finding that SPARC is over-expressed in tumor tissue relative to non-malignant tissue indicates that SPARC is a useful protein marker.

Similarly, IGFBP7 and THBS2 show over-expression in tumor tissue relative to non-malignant tissue.

Immunohistochemical analysis of tumor and non-malignant tissue was carried out using antibodies against the proteins encoded by CSPG2 (versican) and CST1 (cystatin SN) Immunohistochemical analysis of tissue with antibodies against versican identified strong staining in the extracellular matrix of tumor tissue, but not non-malignant tissue. With the anti-cystatin SN antibodies, strong staining was observed in the area around the outside of the tumor cells. In non-malignant cells, the staining with this antibody was weaker, and observed only on the mucosal surface of the tissue and the lining of the gastric pits. This demonstrated that in non-malignant cells, cystatin SN protein is directed out of the cell onto the mucosal surface and not into the extracellular spaces. Therefore, not only is the cystatin SN protein being produced in higher amounts in tumor tissue than non-malignant tissue, but, unlike the protein produced by the non-malignant tissue, the tumor cystatin SN is in direct contact with the tissue vasculature. To extend these observations, cystatin SN was immunoprecipitated from the supernatant of the gastric cancer cell line, AGS with a monoclonal antibody (R&D Systems; cat # MAB1285) (FIG. 16). Large amounts of cystatin SN were detected in the supernatant, confirming that this protein is produced by, and secreted from, gastric epithelial cells.

Example 6: Analysis of Tumor Markers in Serum

For a marker to be useful for rapid screening, it is desirable for the marker to be present in the serum in sufficient levels for detection. Certain proteins described in FIG. 8 can be secreted into the blood at detectable levels from gastric cancers. One marker known to be secreted from gastric tumors into blood in detectable levels is TIMP1. However, if a protein is secreted or shed from any surface of a cell other than a mucosal surface, it will have contact with the interstitial fluid. From there, it can pass either directly into the blood supply through a capillary or via the lymph system. Thus, any shed GTM will be present in blood. Osteopontin, thyroglobulin, and members of the MMP and kallikrein families have previously been described to be elevated in the serum of patients with a range of epithelial cancers, but not gastric cancer. TIMP1 has, however, previously been observed to be elevated in the serum of gastric cancer patients. These findings suggest that the selection criteria for markers in this study, namely over-expression of secreted proteins in tumor tissue but not non-malignant tissue, can be effectively used to detect markers in the serum, and thus can be of substantial use clinically, without the need for tissue or organ biopsies.

From FIG. 15, it is apparent that the serum SPARC has a different molecular weight (depicted here in the Western blot) with the tumor SPARC having a lower molecular weight than the SPARC produced by blood cells. Thus, even though SPARC is produced by tumor and non-tumor blood cells, the presence of tumor SPARC can be determined using molecular size, such as determined using Western analysis, or with an antibody specific for the glycosylated protein produced by the tumor cells.

In another study, we detected cystatin SN in the supernatant of a gastric cancer cell line, AGS. FIG. 16 depicts a Western analysis of media alone or a supernatant from AGS cells in culture. The right hand lane of FIG. 16 shows a dense band corresponding to cystatin SN protein.

Thus, we conclude from FIG. 10 that GTM of this invention are suitable for diagnosing gastric cancers at early, middle or late stages of progression of the disease.

Although certain marker proteins can be glycosylated, variations in the pattern of glycosylation can, in certain circumstances, lead to mis-detection of forms of GTMs that lack usual glycosylation patterns. Thus, in certain embodiments of this invention, GTM immunogens can include deglycosylated GTM or deglycosylated GTM fragments. Deglycosylation can be accomplished using one or more glycosidases known in the art. Alternatively, GTM cDNA can be expressed in glycosylation-deficient cell lines, such as prokaryotic cell lines, including *E. coli*, thereby producing non-glycosylated proteins or peptides. It can also be appreciated that the level and quality of glycosylation can be sensitive to the presence of essential precursors for sugar side-chains. Thus, in the absence of an essential sugar, "normal" glycosylation may not occur, but rather, shorter or missing side chain sugars may be found. Such "glycosylation variants" can be used as immunogens to produce antibodies specific for different types of marker genes.

Additionally, certain GTMs may form homo- or heterodimers or other types of multimeric forms. For example, inhibin beta A is a 47 kDa protein that can form homodimers of 97 kDa molecular weight (activin A) and 92 kDa heterodimers with the 45 kDa protein inhibin beta B (the heterodimers are known as activin AB). Thus, it can be appreciated that Western analysis or other type of assay that provides molecular weight need not be limited to only detection of a monomeric form of a GTM. Rather, one can readily appreciate that any form of a GTM can be detected, regardless of the molecular weight. Thus, detection of a multimeric form of a GTM can be readily used to diagnose the presence of gastric cancer. Further, for those GTM that are selective for stage (1-4) or type of gastric tumor (diffuse or intestinal), detection of a multimeric form can provide suitable target for evaluating stage or type of gastric cancer.

Once an antibody or antiserum against a GTM is produced, such antibody preparations can be used for in a variety of ways. First, enzyme-linked immunosorbent assay (ELISA) or radioimmunoassay (RIA) methods can be used to quantify GTM proteins or peptides Immunodetection can be accomplished in tissue samples using immunohistochemistry. These methods are all known in the art and need not be described further herein.

Example 7: Vectors Containing GTM Oligonucleotides

Other embodiments of this invention include vectors useful for in vitro expression of marker genes or portions thereof ("marker peptides") or fragments of marker gene products. For example, vectors can be made having oligonucleotides for encoding GTMs therein. Many such vectors can be based on standard vectors known in the art. This invention also includes vectors that can be used to transfect a variety of cell lines to prepare GTM-producing cell lines, which can be used to produce desired quantities of GTMs for development of specific antibodies or other reagents for detection of GTMs or for standardizing developed assays for GTMs.

It is to be understood that to manufacture such vectors, an oligonucleotide containing the entire open reading frame or a portion of such an open reading frame encoding a portion of the protein to be expressed can be inserted into a vector containing a promoter region, one or more enhancer regions operably linked to the oligonucleotide sequence, with an initiation codon, an open reading frame, and a stop codon. Methods for producing expression vectors are known in the art and need not be repeated herein.

It can also be appreciated that one or more selectable markers can be inserted into an expression vector to permit the expansion of cell lines selected to contain the expression vector of interest. Moreover, one can also insert leader sequences known in the art, in frame, to direct secretion, internal storage or membrane insertion of the protein or protein fragment in the expressing cell.

Example 8: Cells Transfected with GTM-Containing Vectors

In still further embodiments, cells are provided that can express GTMs, GTM fragments or peptide markers. Both prokaryotic and eukaryotic cells can be so used. For example, *E. coli* (a prokaryotic cell) can be use to produce large quantities of GTMs lacking in mature glycosylation (if the particular GTM normally is glycosylated). COS cells, 293 cells and a variety of other eukaryotic cells can be used to produce GTMs that are glycosylated, or have proper folding and therefore, three-dimensional structure of the native form of the GTM protein. Methods for transfecting such cells are known in the art and need not be described further herein.

Example 9: Kits

Based on the discoveries of this invention, several types of test kits can be produced. First, kits can be made that have a detection device pre-loaded with a detection molecule (or "capture reagent"). In embodiments for detection of GTM mRNA, such devices can comprise a substrate (e.g., glass, silicon, quartz, metal, etc) on which oligonucleotides as capture reagents that hybridize with the mRNA to be detected. In some embodiments, direct detection of mRNA can be accomplished by hybridizing mRNA (labeled with cy3, cy5, radiolabel or other label) to the oligonucleotides on the substrate. In other embodiments, detection of mRNA can be accomplished by first making complementary DNA (cDNA) to the desired mRNA. Then, labeled cDNA can be hybridized to the oligonucleotides on the substrate and detected.

Regardless of the detection method employed, comparison of test GTM expression with a standard measure of expression is desirable. For example, RNA expression can be standardized to total cellular DNA, to expression of constitutively expressed RNAs (for example, ribosomal RNA) or to other relatively constant markers.

Antibodies can also be used in kits as capture reagents. In some embodiments, a substrate (e.g., a multiwell plate) can have a specific GTM capture reagent attached thereto. In some embodiments, a kit can have a blocking reagent included. Blocking reagents can be used to reduce non-specific binding. For example, non-specific oligonucleotide binding can be reduced using excess DNA from any convenient source that does not contain GTM oligonucleotides, such as salmon sperm DNA. Non-specific antibody binding can be reduced using an excess of a blocking protein such as serum albumin. It can be appreciated that numerous methods for detecting oligonucleotides and proteins are known in the art, and any strategy that can specifically detect GTM associated molecules can be used and be considered within the scope of this invention.

In embodiments relying upon antibody detection, GTM proteins or peptides can be expressed on a per cell basis, or on the basis of total cellular, tissue, or fluid protein, fluid volume, tissue mass (weight). Additionally, GTM in serum can be expressed on the basis of a relatively high-abundance serum protein such as albumin.

In addition to a substrate, a test kit can comprise capture reagents (such as probes), washing solutions (e.g., SSC, other salts, buffers, detergents and the like), as well as detection moieties (e.g., cy3, cy5, radiolabels, and the like). Kits can also include instructions for use and a package.

Although this invention is described with reference to specific embodiments thereof, it can be appreciated that other embodiments involving the use of the disclosed markers can be used without departing from the scope of this invention.

INDUSTRIAL APPLICABILITY

Methods for detecting GTM family members include detection of nucleic acids using microarray and/or real time PCR methods and detection of proteins and peptides. The compositions and methods of this invention are useful in the manufacture of diagnostic devices and kits, diagnosis of disease, evaluating efficacy of therapy, and for producing reagents suitable for measuring expression of GTM family members in biological samples.

We claim:

1. A method for detecting specific cancer markers to determine the efficacy of surgical, radiotherapeutic, and/or chemotherapeutic treatments in a patient having gastric cancer and treating said patient, comprising:

(a) providing a sample containing one or more nucleic acids;

(b) detecting, using quantitative polymerase chain reaction (qPCR) expression of cystatin SN (CST-1,2,4), inhibin beta A (INHBA), asporin (ASPN), and secreted frizzled-related protein 4 ("SFRP4"), wherein CST1-1,2,4 is detected using a forward primer having the sequence of SEQ ID NO. 3, and wherein ASPN is detected using a forward primer having the sequence of SEQ ID NO.1;

c) calculating the ratios of expression of said CST-1,2,4, INHBA, ASPN, and SFRP4 in said tissue sample compared to expression of said CST-1,2,4, INHBA, ASPN, and SFRP4 from non-tumor tissue, by calculating the ΔCT (target gene CT—mean reference cDNA CT), where ΔCT is directly proportional to the negative log2 fold change, relative to the median non-malignant log2 fold change, where the median ratios of expression in said tissue sample to the level of expression in said non-tumor tissue are greater than 525, 34, 12, and 56, respectively, thereby indicating the presence of gastric cancer after treatment; and (d) treating the patient with surgery, radiotherapy, or chemotherapy.

2. The method of claim 1, said CST-1,2,4 having the amino acid sequence of SEQ ID NO. 108, using a reverse primer having the sequence of SEQ ID NO. 25 and probe having the sequence of SEQ ID NO. 47.

3. The method of claim 1, further comprising detecting expression of one or more of osteopontin (SPP1), serum proteinase inhibitor, Clade H heat shock protein 47 member 1 (collagen binding protein 1), (SERPINH1), matrix metalloproteinase 12 (MMP12), insulin-like growth factor 7 (IGFBP7), gamma-glutamyl hydrolase (GGH), leucine proline-enriched proteoglycan (LEPRE1), cystatin S (CST4), cell growth regulator with EF hand domain 1 (CGREF1), kallikrein, tissue inhibitor of metalloproteinase 1 (TIMP1), secreted acidic cysteine-rich protein (SPARC), transforming growth factor (TGFB1), EGF-containing fibulin-like extracellular matrix protein 2 (EFEMP2), lumican (LUM), stannin (SNN), chondroitin sulfate proteoglycan 2 (CSPG2), carboxypeptidase N (CPN2), N-acylsphingosine amidohydrolase (ASAH1), serine protease 11 (PRSS11), secreted frizzled-related protein 2 (SFRP2), phospholipase A2, group XIIB (PLA2G12B), sporadin 2 (SPON2), olfactomedin 1 (OLFM1), thrombospondin repeat containing 1 (TSRC1), thrombospondin 2 (THBS2), adlican, cystatin SA (CST2), lysyl oxidase-like enzyme 2 (LOXL2), thyroglobulin (TG), transforming growth factor beta 1 (TGFB1), serine or cysteine proteinase inhibitor clade B (SERPINB5), matrix metalloproteinase 2 (MMP2), proprotein convertase subtilisin/kexin type 5 (PCSK5), kallikrein 10 (KLK10), hyaluronin and proteoglycan link protein 4 (HAPLN4), and transmembrane 6 superfamily member 2 (TM6SF2).

4. The method of claim 1, wherein said step of detecting is carried out by detecting messenger ribonucleic acid (mRNA).

5. The method of claim 1, wherein said step of detecting is carried out by detecting complementary deoxyribonucleic acid (cDNA).

6. A method for detecting specific cancer markers to determine the efficacy of surgical, radiotherapeutic, and/or chemotherapeutic treatments in a patient having gastric cancer and treating said patient, comprising:

(a) providing a sample containing one or more nucleic acids;

(b) detecting, using quantitative polymerase chain reaction (qPCR) expression of cystatin SN (CST-1,2,4), inhibin beta A (INHBA), secreted frizzled-related protein 4 (SFRP4), and serum proteinase inhibitor, Clade H heat shock protein 47) member 1 (collagen binding protein 1), (SERPINH1), wherein CST-1,2,4 is detected using a forward primer having the sequence of SEQ ID NO. 3, asporin (ASPN) is detected using a forward primer having the sequence of SEQ ID NO. 1, human secreted frizzled-related protein 2 (SFRP2), thrombospondin repeat containing 1 (TSRC1), thrombospondin 2 (THBS2), lysyl oxidase-like enzyme 2 (LOXL2), serine or cysteine proteinase inhibitor clade B (SERPINB5), and human cell growth regulator with EF hand domain 1 $(CGR11)_1$ wherein ASPN is dete c) calculating the ratios of expression of said CST-1,2,4, INHBA, ASPN, and SFRP4 in said tissue sample compared to expression of said CST-1,2,4, INHBA, ASPN, and SFRP4 from non-tumor tissue, by calculating the ΔCT (target gene CT—mean reference cDNA CT), where ΔCT is directly proportional to the negative log2 fold change, relative to the median non-malignant log2 fold change, where the ratios of expression in said tissue sample to the level of expression in said non-tumor tissue are greater than 525, 34, 12, and 56, respectively, thereby indicating the presence of gastric cancer after treatment; and (d) treating the patient with surgery, radiotherapy, or chemotherapy.

7. The method of claim 6, further comprising: detecting expression of adlican, chondroitin sulfate proteoglycan 2 (CSPG2), cystatin SA (CST2), cystatin S (CST4), human EGF-containing fibulin-like extracellular matrix protein 2 (EFEMP2), gamma-glutamyl hydrolase (GGH), insulin-like growth factor 7 (IGFBP7), kallikrein 10 (KLK10), leucine proline-enriched proteoglycan (LEPRE1), lumican (LUM), lysyl oxidase-like enzyme 2 (LOXL2), matrix metalloproteinase 2 (MMP12), tissue inhibitor of metalloproteinase 1 (TIMP1), N-acylsphingosine amidohydrolase (ASAH1), secreted acidic cysteine-rich protein (SPARC), serine protease 11 (PRSS11), thyroglobulin (TG), and transforming growth factor beta 1 (TGFB1).

8. The method of claim 3, wherein said step of detecting is carried out by detecting messenger ribonucleic acid (mRNA).

9. The method of claim 3, wherein said step of detecting is carried out by detecting complementary deoxyribonucleic acid (cDNA).

10. The method of claim 6, wherein said step of detecting is carried now abandoned out by detecting messenger ribonucleic acid (mRNA).

11. The method of claim 6, wherein said step of detecting is carried out by detecting complementary deoxyribonucleic acid (cDNA).

12. The method of claim 1, wherein said step of detecting is carried out by detecting messenger ribonucleic acid (mRNA).

13. The method of claim 1, wherein said step of detecting is carried out by detecting complementary deoxyribonucleic acid (cDNA).

* * * * *

UNITED STATES PATENT AND TRADEMARK OFFICE
CERTIFICATE OF CORRECTION

PATENT NO. : 10,689,707 B2
APPLICATION NO. : 15/252869
DATED : June 23, 2020
INVENTOR(S) : Parry John Guilford and Andrew John Holyoake Page 1 of 1

It is certified that error appears in the above-identified patent and that said Letters Patent is hereby corrected as shown below:

In the Claims

On Column 207 Line 65, please replace "cystatin SN (CST-1,2,4)" with
--cystatin SN (CST-1), cystatin SA (CST-2), cystatin S (CST-4), collectively (CST1,2,4)--

On Column 209 Line 51, please replace "cystatin SN (CST-1,2,4)" with
--cystatin SN (CST-1), cystatin SA (CST-2), cystatin S (CST-4), collectively (CST1,2,4)--

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*